(12) United States Patent
Itoh et al.

(10) Patent No.: US 7,402,595 B2
(45) Date of Patent: Jul. 22, 2008

(54) JNK INHIBITOR

(75) Inventors: Fumio Itoh, Tsukuba (JP); Hiroyuki Kimura, Sakai (JP); Hideki Igata, Osaka (JP); Tomohiro Kawamoto, Takatsuki (JP); Mitsuru Sasaki, Takatsuki (JP); Shuji Kitamura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 417 days.

(21) Appl. No.: 10/504,132

(22) PCT Filed: Feb. 12, 2003

(86) PCT No.: PCT/JP03/01429

§ 371 (c)(1), (2), (4) Date: Aug. 11, 2004

(87) PCT Pub. No.: WO03/068750

PCT Pub. Date: Aug. 21, 2003

(65) Prior Publication Data

US 2005/0148624 A1 Jul. 7, 2005

(30) Foreign Application Priority Data

Feb. 13, 2002 (JP) .............................. 2002-035073
Aug. 29, 2002 (JP) .............................. 2002-251997

(51) Int. Cl.
*C07D 217/02* (2006.01)
*A61K 31/47* (2006.01)

(52) U.S. Cl. ...................................... 514/309; 546/141

(58) Field of Classification Search ................ 546/141; 514/309
See application file for complete search history.

(56) References Cited

U.S. PATENT DOCUMENTS

| 5,198,462 | A | 3/1993 | Natsugari et al. |
| 5,482,967 | A | 1/1996 | Natsugari et al. |
| 5,523,305 | A | 6/1996 | Natsugari et al. |
| 5,527,811 | A | 6/1996 | Natsugari et al. |
| 5,585,385 | A | 12/1996 | Natsugari et al. |
| 6,486,155 | B1 | 11/2002 | Pamukcu et al. |
| 2002/0103229 | A1 | 8/2002 | Bhagwat et al. |
| 2004/0082607 | A1 | 4/2004 | Oi et al. |

FOREIGN PATENT DOCUMENTS

| JP | 2000/72675 | 3/2000 |
| JP | 2000/72751 | 3/2000 |
| WO | WO 98/38168 | 9/1998 |
| WO | WO 00/00491 | 1/2000 |
| WO | WO 02/081475 | 10/2002 |

OTHER PUBLICATIONS

Unverferth et al, Arch. Pharm. (Weinheim), vol. 324, pp. 809-814, 1991.*
Ukita et al, J. of Med. Chem. vol. 44, pp. 2204-2218, 2001.*

* cited by examiner

*Primary Examiner*—Zinna N Davis
(74) *Attorney, Agent, or Firm*—Wenderoth, Lind & Ponack, L.L.P.

(57) ABSTRACT

A JNK inhibitor containing a compound having an isoquinolinone skeleton or a salt thereof, such as a compound represented by the formula

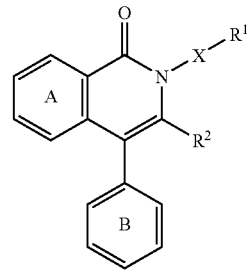

wherein ring A and ring B are each an optionally substituted benzene ring, X is —O—, —N=, —NR$^3$— or —CHR$^3$—, R$^2$ is an acyl group, an optionally esterified or thioesterified carboxyl group, an optionally substituted carbamoyl group or an optionally substituted amino group and the like, a broken line shows a single bond or a double bond, and R$^1$ is a hydrogen atom, an optionally substituted hydrocarbon group, an optionally substituted heterocyclic group and the like, and the like.

29 Claims, No Drawings

```
SEQUENCE LISTING

<160> NUMBER OF SEQ ID NOS: 8

<210> SEQ ID NO 1
<211> LENGTH: 62
<212> TYPE: DNA
<213> ORGANISM: Artificial Sequence
<220> FEATURE:
<223> OTHER INFORMATION: Primer

<400> SEQUENCE: 1
acaactcgag ataacatatg gctcatcatc atcatcatca tagcagaagc aagcgtgaca        60
ac                                                                      62

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
tcccgggtac ctcactgctg cacctgtgct aa                                     32

<210> SEQ ID NO 3
<211> LENGTH: 62
<212> TYPE: DNA
<213> ORGANISM: Artificial Sequence
<220> FEATURE:
<223> OTHER INFORMATION: Primer

<400> SEQUENCE: 3
accagaattc ataacatatg gctcatcatc atcatcatca tgcggcgtcc tccctggaac        60
ag                                                                      62

<210> SEQ ID NO 4
<211> LENGTH: 31
```

-continued

```
<212> TYPE: DNA
<213> ORGANISM: Artificial Sequence
<220> FEATURE:
<223> OTHER INFORMATION: Primer

<400> SEQUENCE: 4
accctctaga caagcagcta cctgaagaag g                               31

<210> SEQ ID NO 5
<211> LENGTH: 44
<212> TYPE: DNA
<213> ORGANISM: Artificial Sequence
<220> FEATURE:
<223> OTHER INFORMATION: Primer

<400> SEQUENCE: 5
ggccgcctgg tggacgacaa agccaaggac cggagcgccg gctg                 44

<210> SEQ ID NO 6
<211> LENGTH: 44
<212> TYPE: DNA
<213> ORGANISM: Artificial Sequence
<220> FEATURE:
<223> OTHER INFORMATION: Primer

<400> SEQUENCE: 6
cagccggcgc tccggtcctt ggctttgtcg tccaccaggc ggcc                 44

<210> SEQ ID NO 7
<211> LENGTH: 34
<212> TYPE: DNA
<213> ORGANISM: Artificial Sequence
<220> FEATURE:
<223> OTHER INFORMATION: Primer

<400> SEQUENCE: 7
aaaagaattc atgactgcaa agatggaaac gacc                            34

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
aaaagcggcc gctcacaggc gctccagctc gggcgacgc                       39
```

JNK INHIBITOR

This application is the National Phase filing of International Patent Application No. PCT/JP03/01429, filed Feb. 12, 2003.

TECHNICAL FIELD

The present invention relates to a c-Jun N-terminal kinase (JNK) inhibitor having an isoquinolinone skeleton, which is useful as a pharmaceutical agent, a novel isoquinoline derivative having JNK inhibitory activity, a production method thereof and use thereof.

BACKGROUND ART

Mammalian cells respond to extracellular stimulation as a result of the activation of a signal cascade via a mitogen activated protein kinase (MAPK) family member. There are three kinds of MAPK, c-Jun N-terminal kinase (JNK) (alternative name: stress activated protein kinase (SAPK)), p38MAP kinase and extracellular signal regulated kinase (ERK), and they are activated by various signals such as growth factors, cytokines, ultraviolet radiation, stress inducers and the like. Since MAPK is a serine/threonine kinase, it is activated by phosphorylation of both threonine and tyrosine of the Thr-X-Tyr sequence in the activation loop. MAPK controls expression of a particular gene by phosphorylation-activation of various transcription factors, and mediates a specific response to an extracellular stimulation.

There have been identified three genes of JNK: jnk1, jnk2 and jnk3, and at least 10 kinds of isoforms are present in mammals (*EMBO Journal*, vol. 15, pp. 2760-2770 (1996)). While Jnk1 and jnk2 express in many tissues, jnk3 specifically expresses in the brain. Thus, JNK3 has a potential to be particularly involved in nervous function. The JNK signal transduction system of stress response MAP kinase family system is activated by changes in osmotic pressure, DNA damage, anisomycine, heat shock, ultraviolet radiation, ischemia, inflammatory cytokines and the like and various stress stimulations relating to apoptosis induction, it is considered to constitute a major intracellular information transduction path responsible for stress response (*Biochemica et Biophysica Acta*, vol. 1333, pp. F85-F104 (1997)). The activated JNK activates various transcription factors such as c-Jun, ATF-2, Elk1, p53, cell death domain protein (DENN) and the like and cell death (apoptosis) signal, thereby suppressing transcription activity of particular gene, or induces apoptosis to respond to environmental changes such as various stresses and the like (*Proceedings of the National Academy of Sciences of the United States of America*, vol. 95, pp. 2586-2591 (1998)). Chronic activation of JNK is seen in various clinical conditions and diseases such as cancer, cell death, allergy, asthma, heart disease, autoimmune disease, ischemic disease, inflammation, neurodegenerative disease and the like, which suggests close involvement of activation of JNK in the onset and aggravation of these diseases. [In the present specification, these clinical conditions or diseases, in which such activation of JNK is involved, are referred to as a "JNK-related clinical condition or disease".]

As for the relationship between JNK and various JNK-related clinical conditions or diseases, for example, it is known that JNK is activated by dilation stimulation or ischemia and transduces stress signals in cardiac myocytes. JNK is also activated by catecholamine, angiotensin II or endothelin and controls expression of factors (BNP/ANP, TNF-α, TGF-β, MMPs and the like) involved in cardiac hypertrophy and fibrosis (*Journal of Biological Chemistry*, vol. 270, pp. 29710-29717, *FASEB Journal*, vol. 10, pp. 631-636 (1996), *Circulation Research*, vol. 80, pp. 139-146 (1997)). Recently, it has been reported that JNK activity in the hearts of cardiac failure patients increases after the onset of myocardial infarction and an MKK7 (JNK selective kinase) heart excessive expression mouse develops cardiac failure, which suggests involvement of JNK in the progression process of cardiac failure (*Journal of Molecular and Cellular Cardiology*, vol. 31, pp. 1429-1434 (1999)). In addition, it has been reported that JNK inhibition by dominant negative MKK7 suppresses cardiac hypertrophy without affecting the blood pressure in a pressure burden cardiac hypertrophy model (*Journal of Clinical Investigation*, vol. 104, pp. 391-398 (1999)). Furthermore, it has been reported that dominant negative MKK7 lowers JNK activity and suppress cardiac myocyte death in an ischemia-reperfusion model. Therefore, JNK inhibitors are possibly effective for the treatment of ischemic heart disease, cardiac failure, post-myocardial infarction and cardiac hypertrophy.

By activating the IL-2 promoter, JNK plays a key role in the T-Cell activation. From a recent experiment using knock out mouse, JNK is reported to also play a key role in the differentiation of the Th1 and Th2 cells. Therefore, JNK inhibitors are possibly effective for the treatment of pathologic immunity disease (*Journal of Immunology*, vol. 162, pp. 3176-3187, 1999, *European Journal of Immunology*, vol. 28, pp. 3867-3877, 1998, *Journal of Experimental Medicine*, vol. 186, pp. 941-953, 1997, *European Journal of Immunology*, vol. 26, pp. 989-994, 1996, *Current Biology*, vol. 9, pp. 116-125, 1999).

It is reported that since JNK is activated in synovial cell in rheumatics and JNK controls the expression of MMP gene in IL-1-stimulated synovial cell, JNK is deeply involved in the articular destruction of rheumatics (*Journal of Clinical Investigation*, vol. 108, pp. 73-81, 2001). This suggests the possibility of JNK inhibitor to be effective for the treatment of rheumatic diseases.

In view of resistance to apoptosis of nerve cells due to the administration of a large amount of kainic acid in JNK3 knock out mouse, JNK3 plays an important role in the expression of glutamate type neurotoxicity (*Nature*, vol. 389, pp. 865-870, 1997). In addition, JNK3 is activated in nerve cells in the state of low oxygen or ischemia to cause apoptosis. From these, a JNK inhibitor is possibly effective for the treatment of neurodegenerative diseases such as Alzheimer's disease, Parkinson's syndrome and Huntington's chorea or ischemia or hemorrhagic cerebral apoplexy.

Furthermore, from an experiment using a JNK1 deletion mouse, JNK is reported to be an important mediator involved in obesity and insulin resistance (*Nature*, vol. 420, pp. 333-336 (2002)).

As a compound having a JNK inhibitory action, for example, indolinone derivatives are disclosed in WO99/35906, WO99/35909 and WO99/35921, uracil derivatives are disclosed in WO00/75118, isoxazole derivatives are disclosed in WO01/12621, thiophenesulfonamide derivatives are disclosed in WO01/23378, WO01/23379 and WO01/23382, pyrazoloanthrone derivatives are disclosed in WO01/12609 and pyrimidylimidazole derivatives are disclosed in WO01/91749. However, an isoquinolinone derivative having a JNK inhibitory action has not been reported.

On the other hand, isoquinolinone derivatives are disclosed in JP-A-10-298164, JP-A-2000-72675, JP-A-2000-72751, JP-A-5-132463, JP-A-6-321906, JP-A-7-010844, JP-A-7-076573, WO02/062764 and the like.

OBJECT OF THE INVENTION

The above-mentioned compounds having JNK inhibitory action are associated with problems in terms of effectiveness, safety such as risk of side effects, and the like as evidence in the fact that their JNK inhibitory actions are not necessarily sufficient, their selectivity of inhibition from other kinases are insufficient and the like. In addition, due to the insufficient physical properties (stability, solubility etc.), oral absorbability, transfer to a target tissue and the like, practically satisfactory results as a pharmaceutical agent have not been necessarily achieved, and the development of a superior JNK inhibitor as a pharmaceutical agent effective for a JNK-related clinical condition or disease has been desired.

SUMMARY OF THE INVENTION

The present invention provides a JNK inhibitor having an isoquinolinone skeleton, which is useful and safe as an agent for the prophylaxis or treatment of a JNK-related clinical condition or disease.

The present inventors have conducted various intensive studies and, as a result, found that compounds having an isoquinolinone skeleton or a salt thereof unexpectedly have a superior JNK specific inhibitory activity based on their specific chemical structure, further have superior properties such as stability and the like as a pharmaceutical product, and can be a safe and useful pharmaceutical agent as an agent for the prophylaxis or treatment of JNK-related clinical conditions or diseases in mammals and, based on these findings, completed the present invention.

Accordingly, the present invention relates to (1) a JNK inhibitor comprising a compound having an isoquinolinone skeleton or a salt thereof;
(2) the inhibitor of the aforementioned (1), wherein the compound having an isoquinolinone skeleton is a compound having a 1-isoquinolinone skeleton;
(3) the inhibitor of the aforementioned (2), wherein the compound having a 1-isoquinolinone skeleton has an optionally substituted benzene ring at the 4-position;
(4) the inhibitor of the aforementioned (1), wherein the compound having an isoquinolinone skeleton is a compound represented by the formula

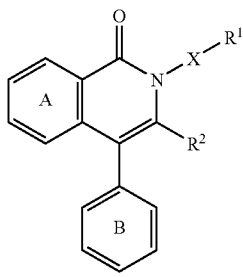

wherein
ring A and ring B are each an optionally substituted benzene ring;
X is —O—, —N=, —NR$^3$— or —CHR$^3$— wherein R$^3$ is a hydrogen atom or an optionally substituted hydrocarbon group, or may be bonded with R$^1$ to optionally form a 3 to 8-membered ring;
R$^2$ is a hydrocarbon group optionally having substituent(s) selected from an optionally substituted hydroxy group, an optionally substituted thiol group, a substituted sulfinyl group, a substituted sulfonyl group and an optionally esterified carboxyl group, an acyl group, an optionally esterified or thioesterified carboxyl group, an optionally substituted carbamoyl group or an optionally substituted amino group; and
a broken line shows a single bond or a double bond, when X is —O—, —NR$^3$— or —CHR$^3$—, then R$^1$ is a hydrogen atom, an optionally substituted hydrocarbon group or an optionally substituted heterocyclic group, and when X is —N=, then R$^1$ is an optionally substituted divalent hydrocarbon group or an optionally substituted divalent heterocyclic group;

(5) the inhibitor of the aforementioned (4), wherein the ring A is a benzene ring represented by the formula

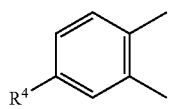

wherein R$^4$ is a hydrogen atom, a halogen atom, a cyano group, an optionally substituted hydrocarbon group, an optionally substituted heterocyclic group, an optionally substituted hydroxy group, an optionally substituted thiol group, a substituted sulfinyl group, a substituted sulfonyl group, an optionally substituted amino group, an optionally substituted carbamoyl group or an optionally esterified carboxyl group;

(6) the inhibitor of the aforementioned (5), wherein R$^4$ is a halogen atom or a $C_{1-4}$ alkyl group;
(7) the inhibitor of the aforementioned (4), wherein X is —CHR$^3$— (R$^3$ is as defined in the aforementioned (4));
(8) the inhibitor of the aforementioned (4), wherein R$^1$ is an optionally substituted aromatic hydrocarbon group or an optionally substituted aromatic heterocyclic group;
(9) the inhibitor of the aforementioned (4), wherein R$^2$ is an optionally esterified or thioesterified carboxyl group or an optionally substituted carbamoyl group;
(10) the inhibitor of the aforementioned (4), wherein R$^2$ is an acyl group;
(11) the inhibitor of the aforementioned (10), wherein the acyl group is R$^4$CO (R$^4$ is a hydrogen atom, an optionally substituted hydrocarbon group or an optionally substituted heterocyclic group);
(12) the inhibitor of the aforementioned (11), wherein R$^4$ is a $C_{1-7}$ alkyl group or a group represented by the formula

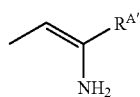

wherein R$^{A'}$ is a $C_{1-5}$ alkyl group or optionally esterified carboxyl group;
(13) the inhibitor of the aforementioned (4), wherein R$^2$ is a methoxycarbonyl group, a pyridylmethyloxycarbonyl group, a dimethylcarbamoyl group, a pyridylmethylcarbamoyl group, a hydroxymethyl group, a pyridylthiocarbonyl group, an amino group, an acetyl group, a propionyl group, a butyryl group, a valeryl group or a (2Z)-3-aminobut-2-enoyl group;
(14) the inhibitor of the aforementioned (1), which is an agent for the prophylaxis or treatment of a JNK-related clinically pathological condition or disease;

(15) a method of inhibiting JNK in a mammal, which comprises administering an effective amount of a compound having an isoquinolinone skeleton or a salt thereof to the mammal;

(16) a method of inhibiting JNK in a mammal, which comprises administering an effective amount of the compound of the aforementioned (4) or a salt thereof to the mammal;

(17) use of a compound having an isoquinolinone skeleton or a salt thereof for the production of a JNK inhibitor;

(18) use of the compound of the aforementioned (4) or a salt thereof for the production of a JNK inhibitor;

(19) a compound represented by the formula

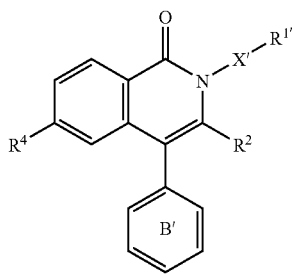

wherein ring B' is a benzene ring optionally having not more than two substituent(s);

X' is —CH$_2$—;

R$^{1'}$ is an optionally substituted phenyl group or an optionally substituted heterocyclic group bonded via a ring-constituting carbon atom;

R$^2$ is a hydrocarbon group optionally having substituent(s) selected from an optionally substituted hydroxy group, an optionally substituted thiol group, a substituted sulfinyl group, a substituted sulfonyl group and an optionally esterified carboxyl group, an acyl group, an optionally esterified or thioesterified carboxyl group, an optionally substituted carbamoyl group or an optionally substituted amino group; and R$^4$ is a hydrogen atom, a halogen atom, a cyano group, an optionally substituted hydrocarbon group, an optionally substituted heterocyclic group, an optionally substituted hydroxy group, an optionally substituted thiol group, a substituted sulfinyl group, a substituted sulfonyl group, an optionally substituted amino group, an optionally substituted carbamoyl group or an optionally esterified carboxyl group, or a salt thereof;

(20) the compound of the aforementioned (19) wherein R$^4$ is not a hydrogen atom;

(21) the compound of the aforementioned (19) wherein R$^4$ is a halogen atom, an optionally substituted alkyl group or an optionally substituted amino group;

(22) the compound of the aforementioned (19) wherein R$^4$ is a halogen atom or a C$_{1-4}$alkyl group;

(23) the compound of the aforementioned (19) wherein the ring B' is a benzene ring optionally having substituent(s) at a meta and/or para position(s);

(24) the compound of the aforementioned (19) wherein the ring B' is a non-substituted benzene ring;

(25) the compound of the aforementioned (19) wherein R$^2$ is a hydrocarbon group substituted by an optionally substituted hydroxy group, an optionally esterified or thioesterified carboxyl group, an optionally substituted carbamoyl group, an optionally substituted amino group or an acyl group;

(26) the compound of the aforementioned (19) wherein R$^2$ is a lower alkyl group substituted by a hydroxy group, an optionally esterified or thioesterified carboxyl group, a carbamoyl group optionally substituted by a lower alkyl group, an amino group optionally substituted by a lower alkyl group or an acyl group;

(27) the compound of the aforementioned (19) wherein R$^2$ is an optionally esterified or thioesterified carboxyl group;

(28) the compound of the aforementioned (19) wherein R$^2$ is a carboxyl group optionally esterified or thioesterified by an alkyl optionally substituted by substituent(s) selected from an optionally substituted phenyl group and an optionally substituted pyridyl group;

(29) the compound of the aforementioned (19) wherein R$^2$ is an acyl group;

(30) the compound of the aforementioned (19) wherein R$^2$ is R$^A$CO (R$^A$ is a hydrogen atom, an optionally substituted hydrocarbon group or an optionally substituted heterocyclic group);

(31) the compound of the aforementioned (30) wherein R$^A$ is a C$_{1-7}$ alkyl group or a group represented by the formula

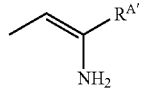

wherein R$^{A'}$ is a C$_{1-5}$ alkyl group or an optionally esterified carboxyl group;

(32) the compound of the aforementioned (19) wherein R$^2$ is a methoxycarbonyl group, a pyridylmethyloxycarbonyl group, a dimethylcarbamoyl group, a pyridylmethylcarbamoyl group, a hydroxymethyl group, a pyridylthiocarbonyl group, an amino group, an acetyl group, a propionyl group, a butyryl group, a valeryl group or a (2Z)-3-aminobut-2-enoyl group;

(33) the compound of the aforementioned (19) wherein R$^{1'}$ is a phenyl group having substituent(s) at the meta and/or para position(s)

(34) the compound of the aforementioned (19) wherein R$^{1'}$ is an optionally substituted nitrogen-containing heterocyclic group bonded via a ring-constituting carbon atom;

(35) the compound of the aforementioned (34) wherein the nitrogen-containing heterocyclic group is a nitrogen-containing heterocyclic group comprising carbon atom(s) and nitrogen atom(s);

(36) the compound of the aforementioned (34) wherein the nitrogen-containing heterocyclic group is an aromatic nitrogen-containing heterocyclic group;

(37) the compound of the aforementioned (34) wherein the nitrogen-containing heterocyclic group is a 2-, 3- or 4-piperidinyl group;

(38) the compound of the aforementioned (34) wherein the nitrogen-containing heterocyclic group is a 4-piperidinyl group;

(39) the compound of the aforementioned (19) wherein R$^{1'}$ is a 4-piperidinyl group substituted by an acyl group;

(40) a compound selected from the group consisting of 6-chloro-2-methylamino-1-oxo-4-phenyl-1,2-dihydroisoquinoline-3-carboxylic acid methyl ester, 6-bromo-2-methylamino-1-oxo-4-phenyl-1,2-dihydroisoquinoline-3-carboxylic acid methyl ester, 6-fluoro-2-methylamino-1- oxo-4-phenyl-1,2-dihydroisoquinoline-3-carboxylic acid methyl ester, 6-chloro-2-methylamino-1-oxo-4-(4-tolyl)-1,2-dihydroisoquinoline-3-carboxylic acid methyl ester, 6-chloro-2-methylamino-1-oxo-4-(4-tolyl)-1,2-dihydroisoquinoline-3-carboxylic acid ethyl ester, and 6-chloro-2-dimethylamino-1-oxo-4-phenyl-1,2-dihydroisoquinoline-3-carboxylic acid methyl ester, or a salt thereof;

(41) a compound selected from the group consisting of 2-(benzo[1,3]dioxol-5-ylmethyl)-6-bromo-1-oxo-4-phenyl-1,2-dihydroisoquinoline-3-carboxylic acid methyl ester, 6-bromo-1-oxo-4-phenyl-2-(4-sulfamoylbenzyl)-1,2-dihydroisoquinoline-3-carboxylic acid methyl ester, 6-bromo-2-(4-methanesulfonylbenzyl)-1-oxo-4-phenyl-1,2-dihydroisoquinoline-3-carboxylic acid methyl ester, 6-bromo-2-(2,3-dihydrobenzofuran-5-ylmethyl)-1-oxo-4-phenyl-1,2-dihydroisoquinoline-3-carboxylic acid methyl ester, 6-bromo-2-(4-carboxybenzyl)-1-oxo-4-phenyl-1,2-dihydroisoquinoline-3-carboxylic acid methyl ester, 2-(1-acetylpiperidine-4-ylmethyl)-6-bromo-1-oxo-4-phenyl-1,2-dihydroisoquinoline-3-carboxylic acid methyl ester, 6-bromo-2-[4-(3-carboxypropionylamino)benzyl]-1-oxo-4-phenyl-1,2-dihydroisoquinoline-3-carboxylic acid methyl ester, 6-bromo-2-(4-carbamoylbenzyl)-1-oxo-4-phenyl-1,2-dihydroisoquinoline-3-carboxylic acid methyl ester, 6-bromo-1-oxo-4-phenyl-2-[4-(2-(pyrrolidin-1-yl)ethylcarbamoyl)benzyl]-1,2-dihydroisoquinoline-3-carboxylic acid methyl ester, 2-(benzo[1,3]dioxol-5-ylmethyl)-6-methyl-1-oxo-4-phenyl-1,2-dihydroisoquinoline-3-carboxylic acid methyl ester, 6-amino-2-(benzo[1,3]dioxol-5-ylmethyl)-1-oxo-4-phenyl-1,2-dihydroisoquinoline-3-carboxylic acid methyl ester, 2-(benzo[1,3]dioxol-5-ylmethyl)-6-bromo-1-oxo-4-phenyl-1,2-dihydroisoquinoline-3-carboxylic acid pyridin-3-ylmethyl ester, N,N-dimethyl-2-(benzo[1,3]dioxol-5-ylmethyl)-6-bromo-1-oxo-4-phenyl-1,2-dihydroisoquinoline-3-carboxamide, 6-bromo-2-(4-methanesulfonylbenzyl)-4-phenyl-3-propionyl-2H-isoquinolin-1-one, 3-butyryl-6-chloro-2-(4-methanesulfonylbenzyl)-4-phenyl-2H-isoquinolin-1-one, 2-(4-carboxybenzyl)-6-chloro-4-(3-hydroxymethylphenyl)-1-oxo-1,2-dihydroisoquinoline-3-carboxylic acid methyl ester, 6-bromo-2-[4-(N',N'-diethylhydrazinocarbonyl)benzyl]-1-oxo-4-phenyl-1,2-dihydroisoquinoline-3-carboxylic acid methyl ester, 4-(6-chloro-3-butyryl-1-oxo-4-phenyl-1H-isoquinolin-2-ylmethyl)benzenesulfonamide, 4-(6-bromo-1-oxo-4-phenyl-3-propionyl-1H-isoquinolin-2-ylmethyl)benzoic acid, 4-(6-chloro-1-oxo-4-phenyl-3-propionyl-1H-isoquinolin-2-ylmethyl)benzoic acid, 6-bromo-4-phenyl-3-propionyl-2-[4-(1H-tetrazol-5-yl)benzyl]-2H-isoquinolin-1-one, 3-[(2Z)-3-aminobut-2-enoyl]-6-bromo-2-(4-methanesulfonylbenzyl)-4-phenyl-2H-isoquinolin-1-one, 3-[(2Z)-3-aminopent-2-enoyl]-6-bromo-2-(4-methanesulfonylbenzyl)-4-phenyl-2H-isoquinolin-1-one, 3-amino-2-(benzo[1,3]dioxol-5-ylmethyl)-6-bromo-4-phenyl-2H-isoquinolin-1-one, and 6-bromo-2-(4-methanesulfonylbenzyl)-1-oxo-4-phenyl-1,2-dihydroisoquinoline-3-carbothioic acid S-pyridin-2-yl ester or a salt thereof;

(42) a prodrug of the compound of the aforementioned (19) or (40);

(43) a pharmaceutical preparation comprising the compound of the aforementioned (19), (40) or (42);

(44) the pharmaceutical preparation of the aforementioned (43), which is a JNK inhibitor;

(45) the pharmaceutical preparation of the aforementioned (43), which is an agent for the prophylaxis or treatment of chronic or acute cardiac failure, cardiac hypertrophy, dilated, hypertrophic or restrictive cardiomyopathy, acute myocardial infarction, post-myocardial infarction, acute or chronic myocarditis, diastolic dysfunction of the left ventricle, systolic dysfunction of the left ventricle, hypertension and nephropathy and nephritis as complications thereof, endothelial dysfunction, arteriosclerosis or post-angioplasty restenosis;

(46) the pharmaceutical preparation of the aforementioned (43), which is an agent for the prophylaxis or treatment of chronic rheumatoid arthritis, osteoarthritis, gout, chronic obstructive pulmonary disease, asthma, bronchitis, cystic fibrosis, inflammatory bowel disease, irritable colon syndrome, mucous colitis, ulcerative colitis, Crohn's disease, gastritis, esophagitis, multiple sclerosis, eczema, dermatitis, hepatitis, glomerulonephritis, diabetes, diabetic nephropathy, diabetic retinopathy, diabetic neuropathy, obesity, psoriasis or cancer;

(47) the pharmaceutical preparation of the aforementioned (43), which is an agent for the prophylaxis or treatment of Alzheimer's disease, Huntington's chorea, Parkinson's syndrome, epilepsy, amyotrophic lateral sclerosis, peripheral neuropathy, neurodegenerative disease or spinal injury;

(48) the pharmaceutical preparation of the aforementioned (43), which is an agent for the prophylaxis or treatment of cerebral apoplexy, cerebrovascular disorder, an ischemic disorder of an organ selected from the heart, kidney, liver and brain, ischemia-reperfusion injury, organ failure, endotoxin shock or rejection in transplantation;

(49) a production method of a compound represented by the formula

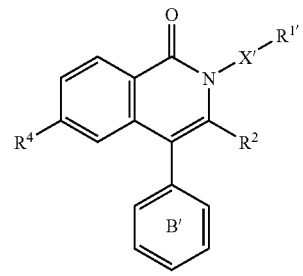

wherein each symbol is as defined above, or a salt thereof, which comprises (1) reacting a compound represented by the formula

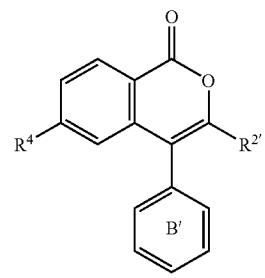

wherein $R^{2'}$ is an optionally esterified carboxyl group or an acyl group, and other symbols are as defined above, or a salt thereof with an amino compound represented by the formula $H_2N-X'-R^{1'}$ wherein the symbols in the formula are as defined above, or a salt thereof, or (2) reacting a compound represented by the formula

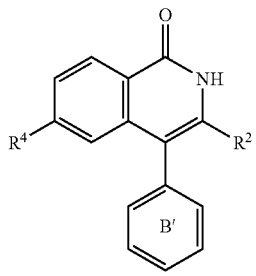

wherein the symbols in the formula are as defined above, or a salt thereof with a compound represented by the formula $L-X'-R^{1'}$ wherein L is a leaving group, and other symbols are as defined above, or a salt thereof, or (3) subjecting a compound represented by the formula

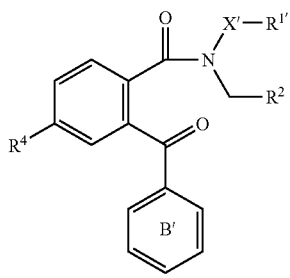

wherein the symbols in the formula are as defined above, or a salt thereof to an intramolecular cyclization reaction, or (4) reacting a compound represented by the formula

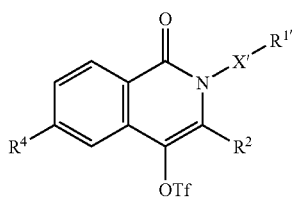

wherein OTf is a triflate group and other symbols are as defined above, or a salt thereof with a compound represented by the formula

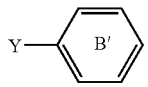

wherein Y is an atomic group capable of a crosscoupling reaction and other symbols are as defined above, or a salt thereof;

(50) a method for the prophylaxis or treatment of chronic or acute cardiac failure, cardiac hypertrophy, dilated, hypertrophic or restrictive cardiomyopathy, acute myocardial infarction, post-myocardial infarction, acute or chronic myocarditis, diastolic dysfunction of the left ventricle, systolic dysfunction of the left ventricle, hypertension and nephropathy and nephritis as complications thereof, endothelial dysfunction, arteriosclerosis or post-angioplasty restenosis, which comprises administering an effective amount of a compound of the aforementioned (19), (40) or (42) to a mammal;

(51) a method for the prophylaxis or treatment of chronic rheumatoid arthritis, osteoarthritis, gout, chronic obstructive pulmonary disease, asthma, bronchitis, cystic fibrosis, inflammatory bowel disease, irritable colon syndrome, mucous colitis, ulcerative colitis, Crohn's disease, gastritis, esophagitis, multiple sclerosis, eczema, dermatitis, hepatitis, glomerulonephritis, diabetes, diabetic nephropathy, diabetic retinopathy, diabetic neuropathy, obesity, psoriasis or cancer, which comprises administering an effective amount of a compound of the aforementioned (19), (40) or (42) to a mammal;

(52) a method for the prophylaxis or treatment of Alzheimer's disease, Huntington's chorea, Parkinson's syndrome, epilepsy, amyotrophic lateral sclerosis, peripheral neuropathy, neurodegenerative disease or spinal injury, which comprises administering an effective amount of a compound of the aforementioned (19), (40) or (42) to a mammal;

(53) a method for the prophylaxis or treatment of cerebral apoplexy, cerebrovascular disorder, an ischemic disorder of an organ selected from the heart, kidney, liver and brain, ischemia-reperfusion injury, organ failure, endotoxin shock or rejection in transplantation, which comprises administering an effective amount of a compound of the aforementioned (19), (40) or (42) to a mammal;

(54) use of a compound of the aforementioned (19), (40) or (42) for the production of an agent for the prophylaxis or treatment of chronic or acute cardiac failure, cardiac hypertrophy, dilated, hypertrophic or restrictive cardiomyopathy, acute myocardial infarction, post-myocardial infarction, acute or chronic myocarditis, diastolic dysfunction of the left ventricle, systolic dysfunction of the left ventricle, hypertension and nephropathy and nephritis as complications thereof, endothelial dysfunction, arteriosclerosis or post-angioplasty restenosis;

(55) use of a compound of the aforementioned (19), (40) or (42) for the production of an agent for the prophylaxis or treatment of chronic rheumatoid arthritis, osteoarthritis, gout, chronic obstructive pulmonary disease, asthma, bronchitis, cystic fibrosis, inflammatory bowel disease, irritable colon syndrome, mucous colitis, ulcerative colitis, Crohn's disease, gastritis, esophagitis, multiple sclerosis, eczema, dermatitis, hepatitis, glomerulonephritis, diabetes, diabetic nephropathy, diabetic retinopathy, diabetic neuropathy, obesity, psoriasis or cancer;

(56) use of a compound of the aforementioned (19), (40) or (42) for the production of an agent for the prophylaxis or treatment of Alzheimer's disease, Huntington's chorea, Parkinson's syndrome, epilepsy, amyotrophic lateral sclerosis, peripheral neuropathy, neurodegenerative disease or spinal injury;

(57) use of a compound of the aforementioned (19), (40) or (42) for the production of an agent for the prophylaxis or treatment of cerebral apoplexy, cerebrovascular disorder, an ischemic disorder of an organ selected from the heart, kidney, liver and brain, ischemia-reperfusion injury, organ failure, endotoxin shock or rejection in transplantation; and the like.

The term "halogen atom" used in the present specification means, for example, fluorine, chlorine, bromine, iodine and the like.

As the term "acyl group" used in the present specification, an acyl group obtained by removing an OH group from carboxylic acid such as $R^A$COOH and the like, sulfonic acid such as $R^A$SO$_3$H and the like, sulfinic acid such as $R^A$SO$_2$H and the like, phosphoric acid such as $R^A$OPO(OR$^B$)OH wherein $R^A$ is a hydrogen atom, an optionally substituted hydrocarbon group or an optionally substituted heterocyclic group, and $R^B$ is a hydrogen atom or an optionally substituted hydrocarbon group, and the like, is used, and $R^A$CO, $R^A$SO$_2$, $R^A$SO, $R^A$OPO(OR$^B$) (the symbols in the formula are as defined above) and the like are concretely used.

The "hydrocarbon group" of the "optionally substituted hydrocarbon group" used in the present specification means, for example, an alkyl group, a cycloalkyl group, an alkenyl group, a cycloalkenyl group, an alkynyl group, an aralkyl group, an aryl group and the like, and the "cyclic hydrocarbon group" of the "optionally substituted cyclic hydrocarbon group" used in the present specification means, for example, a cycloalkyl group, a cycloalkenyl group, an aryl group and the like.

As the "alkyl group", for example, a linear or branched $C_{1-15}$ alkyl group such as methyl, ethyl, propyl, isopropyl, butyl, isobutyl, sec-butyl, tert-butyl, pentyl, hexyl, heptyl, octyl, nonyl, decyl, undecyl, tridecyl, tetradecyl, pentadecyl and the like, and the like, preferably a $C_{1-6}$ alkyl group, more preferably a $C_{1-7}$ alkyl group, further preferably a $C_{1-6}$ alkyl group, and particularly preferably a $C_{1-4}$ alkyl group are used.

As the "cycloalkyl group", for example, a "$C_{3-10}$ cycloalkyl group" such as cyclopropyl, cyclobutyl, cyclopentyl, cyclohexyl, cycloheptyl, cyclooctyl, adamantyl and the like, and the like are used, more preferably a $C_{3-8}$ cycloalkyl group is used, and further preferably a $C_{5-7}$ cycloalkyl group is used.

As the "alkenyl group", for example, a "$C_{2-18}$ alkenyl group" such as vinyl, allyl, isopropenyl, 3-butenyl, 3-octenyl, 9-octadecenyl and the like, and the like are used, more preferably a $C_{2-6}$ alkenyl group is used, further preferably a $C_{2-4}$ alkenyl group is used.

As the "cycloalkenyl group", for example, a "$C_{3-10}$ cycloalkenyl group" such as cyclopropenyl, cyclobutenyl, cyclopentenyl, cyclohexenyl, cycloheptenyl, cyclooctenyl and the like, and the like are used, more preferably a $C_{3-8}$ cycloalkenyl group is used, further preferably a $C_{5-7}$ cycloalkenyl group is used.

As the "alkynyl group", for example, a "$C_{2-8}$ alkynyl group" such as ethynyl, 1-propynyl, propargyl, 1-butynyl, 2-butynyl, 1-pentynyl, 2-pentynyl, 3-pentynyl and the like, and the like are used, more preferably a $C_{2-6}$ alkynyl group is used, further preferably a $C_{2-4}$ alkynyl group is used.

As the "aralkyl group", a $C_{7-16}$ aralkyl group and the like are used, and concretely, for example, a phenyl-$C_{1-6}$ alkyl group such as benzyl, phenethyl, 3-phenylpropyl, 4-phenylbutyl and the like, and, for example, a naphthyl-$C_{1-6}$ alkyl group such as (1-naphthyl)methyl, 2-(1-naphthyl)ethyl, 2-(2-naphthyl)ethyl and the like, and the like can be mentioned.

As the "aryl group", for example, an aromatic monocyclic, bicyclic or tricyclic $C_{6-14}$ aryl group such as phenyl, 1-naphthyl, 2-naphthyl, phenanthryl, anthryl and the like, a biphenyl group, a tolyl group and the like are used, and preferably, a $C_{6-10}$ aryl group such as phenyl, naphthyl and the like, more preferably phenyl, is used.

As the substituent that the "hydrocarbon group" (including "cyclic hydrocarbon group" of the "optionally substituted cyclic hydrocarbon group") of the "optionally substituted hydrocarbon group" may have, for example, (i) a nitro group, (ii) a hydroxy group, an oxo group, (iii) a cyano group, (iv) a carbamoyl group, (v) a mono- or di-$C_{1-4}$alkyl-carbamoyl group (e.g., N-methylcarbamoyl, N-ethylcarbamoyl, N,N-dimethylcarbamoyl, N,N-diethylcarbamoyl and the like; said alkyl group is optionally substituted by halogen atom, hydroxy group, $C_{1-4}$ alkoxy group and the like), a mono- or di-$C_{2-4}$ alkenyl-carbamoyl group (e.g., N-allylcarbamoyl and the like; said alkenyl group is optionally substituted by halogen atom, hydroxy group, $C_{1-4}$ alkoxy group and the like), a mono- or di-phenyl-carbamoyl group, a mono- or di-benzyl-carbamoyl group, a $C_{1-4}$ alkoxy-carbonyl-carbamoyl group, a $C_{1-4}$ alkylsulfonyl-carbamoyl group, a $C_{1-4}$ alkoxy-carbamoyl group, an amino-carbamoyl group, a mono- or di-$C_{1-4}$ alkylamino-carbamoyl group, a mono- or di-phenylamino-carbamoyl group, (vi) a carboxyl group, (vii) a $C_{1-4}$ alkoxy-carbonyl group (e.g., methoxycarbonyl, ethoxycarbonyl, propoxycarbonyl, isopropoxycarbonyl and the like), (viii) a sulfo group, (ix) a halogen atom (e.g., fluorine, chlorine, bromine, iodine and the like), (x) an optionally halogenated $C_{1-4}$ alkoxy group (e.g., methoxy, ethoxy, propoxy, isopropoxy and the like), a $C_{1-4}$ alkoxy group optionally substituted by hydroxy group, a $C_{1-4}$ alkoxy group optionally substituted by carboxyl group, a $C_{1-4}$ alkoxy group optionally substituted by $C_{1-4}$ alkoxy-carbonyl group, a $C_{1-4}$ alkoxy-$C_{1-4}$ alkoxy group, a $C_{1-4}$ alkoxy-$C_{1-4}$ alkoxy-$C_{1-4}$ alkoxy group, (xi) a phenoxy group, a phenoxy-$C_{1-4}$ alkyl group, a phenoxy-$C_{1-4}$ alkoxy group, a $C_{1-4}$ alkylcarbonyl-oxy group, a carbamoyloxy group, a mono- or di-$C_{1-4}$ alkyl-carbamoyloxy group, (xii) an optionally halogenated phenyl group, an optionally halogenated phenyl-$C_{1-4}$ alkyl group, an optionally halogenated phenyl-$C_{2-4}$ alkenyl group, an optionally halogenated phenoxy group (e.g., o-, m- or p-chlorophenoxy, o-, m- or p-bromophenoxy and the like), a pyridyloxy group, a $C_{3-10}$ cycloalkyl group, a $C_{3-10}$ cycloalkyl-$C_{1-4}$ alkoxy group, a $C_{3-10}$ cycloalkyl-$C_{1-4}$ alkyl group, (xiii) an optionally halogenated $C_{1-4}$ alkyl group (e.g., methyl, ethyl, propyl, isopropyl, butyl and the like), an optionally halogenated $C_{2-6}$ alkenyl group (e.g., vinyl, allyl, 2-butenyl, 3-butenyl and the like), an optionally halogenated $C_{1-4}$ alkylthio group (e.g., methylthio, ethylthio, n-propylthio, isopropylthio, n-butylthio and the like), a $C_{1-4}$ alkyl group optionally substituted by hydroxy group, a $C_{1-4}$ alkylthio group optionally substituted by hydroxy group, (xiv) a mercapto group, a thioxo group, (xv) a benzyloxy group or benzylthio group optionally substituted by a substituent(s) selected from a halogen atom, carboxyl group and $C_{1-4}$ alkoxy-carbonyl group, (xvi) an optionally halogenated phenylthio group, a pyridylthio group, a phenylthio-$C_{1-4}$ alkyl group, a pyridylthio $C_{1-4}$ alkyl group, (xvii) an optionally halogenated $C_{1-4}$ alkylsulfinyl group (e.g., methylsulfinyl, ethylsulfinyl and the like), a phenylsulfinyl group, a phenylsulfinyl-$C_{1-4}$ alkyl group, (xviii) an optionally halogenated $C_{1-4}$ alkylsulfonyl group (e.g., methylsulfonyl, ethylsulfonyl and the like), a phenylsulfonyl group, a phenylsulfonyl-$C_{1-4}$ alkyl group, (xix) an amino group, an aminosulfonyl group, a mono- or di-$C_{1-4}$ alkylaminosulfonyl group (e.g., methylaminosulfonyl, ethylaminosulfonyl, N,N-dimethylaminosulfonyl, N,N-diethylaminosulfonyl and the like; said alkyl group is optionally substituted by halogen atom, hydroxy group, $C_{1-4}$ alkoxy group and the like), (xx) a $C_{1-10}$ acyl-amino group (e.g., $C_{1-6}$ alkanoylamino (e.g., formylamino, acetylamino, trifluoroacetylamino, propionylamino, pivaloylamino etc.), benzoylamino, $C_{1-6}$ alkylsulfonylamino (e.g., methanesulfonylamino, trifluoromethanesulfonylamino etc.), $C_{6-10}$ arylsulfonylamino (e.g., benzenesulfonylamino, toluenesulfonylamino etc.); $C_{1-10}$ acyl is optionally substituted by halogen atom, hydroxy group, carboxyl group and the like), benzyloxycarbonylamino, an optionally halogenated $C_{1-6}$ alkoxycarbonylamino, a carbamoylamino group, a mono- or di-$C_{1-4}$ alkylcarbamoylamino group, (xxi) a mono- or di-$C_{1-4}$ alkylamino group (e.g., methylamino, ethylamino, dimethylamino, diethylamino and the like; said alkyl group is optionally substituted by halogen atom, hydroxy group, $C_{1-4}$ alkoxy group and the like), phenylamino, benzylamino, (xxii) a 4 to 6-membered cyclic amino group (e.g., 1-azetidinyl, 1-pyrrolidinyl, piperidino, morpholino, thiomorpholino, 1-piperazinyl and the like), a 4 to 6-membered cyclic amino-carbonyl group (e.g., 1-azetidinylcarbonyl, 1-pyrrolidinylcarbonyl, piperidinocarbonyl, morpholinocarbonyl, thiomorpholinocarbonyl, 1-piperazinylcarbonyl and the like), a 4 to 6-membered cyclic amino-carbonyl-oxy group (e.g., 1-pyrrolidinylcarbonyloxy, piperidinocarbonyloxy, morpholinocarbonyloxy, thiomorpholinocarbonyloxy, 1-piperazinylcarbonyloxy and the like), a 4 to 6-membered cyclic amino-carbonyl-amino group (e.g., 1-pyrrolidinylcarbonylamino, piperidinocarbonylamino, morpholinocarbonylamino, thiomorpholinocarbonylamino, 1-piperazinylcarbonylamino and the like), a 4 to 6-membered cyclic amino-sulfonyl group (e.g., 1-pyrrolidinylsulfonyl, piperidinosulfonyl, morpholinosulfonyl, thiomorpholinosulfonyl, 1-piperazinylsulfonyl and the like), a 4 to 6-membered cyclic amino-$C_{1-4}$ alkyl group, (xxiii) a $C_{1-6}$ acyl group optionally substituted by a substituent(s) selected from halogen atom, carboxyl group and $C_{1-4}$ alkoxy-carbonyl group (e.g., formyl, optionally halogenated $C_{2-6}$ alkanoyl such as acetyl and the like, and the like) or a benzoyl group, (xxiv) a benzoyl group optionally substituted by halogen atom, (xxv) a 5 to 10-membered heterocyclic group (e.g., 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 1,2,3- or 1,2,4-triazolyl, 1H- or 2H-tetrazolyl, 2-, 3- or 4-pyridyl, 2-, 4- or 5-pyrimidyl, 3- or 4-pyridazinyl, quinolyl, isoquinolyl, indolyl and the like; said heterocyclic group is optionally substituted by $C_{1-4}$ alkyl group and the like), (xxvi) a 5 to 10-membered heterocycle-carbonyl group (e.g., 2- or 3-thienylcarbonyl, 2- or 3-furylcarbonyl, 3-, 4- or 5-pyrazolylcarbonyl, 2-, 4- or 5-thiazolylcarbonyl, 3-, 4- or 5-isothiazolylcarbonyl, 2-, 4- or 5-oxazolylcarbonyl, 1,2,3- or 1,2,4-triazolylcarbonyl, 1H- or 2H-tetrazolylcarbonyl, 2-, 3- or 4-pyridylcarbonyl, 2-, 4- or 5-pyrimidylcarbonyl, 3- or 4-pyridazinylcarbonyl, quinolylcarbonyl, isoquinolylcarbonyl, indolylcarbonyl and the like; said heterocyclic group is optionally substituted by $C_{1-4}$ alkyl group and the like), (xxvii) a hydroxyimino group, a $C_{1-4}$ alkoxyimino group, an aryl group (e.g., 1- or 2-naphthyl and the like) and (xxviii) an optionally halogenated linear or branched $C_{1-4}$ alkylenedioxy group (e.g., methylenedioxy, ethylenedioxy, propylenedioxy, tetrafluoroethylenedioxy and the like) and the like are used. The "hydrocarbon group" may have 1 to 5 of these substituent(s) at substitutable position(s), and when it has 2 or more substituent(s), the substituent(s) may be the same or different.

As the aryl group having an oxo group, for example, benzoquinonyl, naphthoquinolyl, anthraquinonyl and the like can be mentioned.

When the "hydrocarbon group" is a cycloalkyl group, a cycloalkenyl group, an aryl group or an aralkyl group, for example, it is optionally substituted by a $C_{1-10}$ alkyl group (e.g., methyl, ethyl, propyl, isopropyl, decyl and the like), a $C_{2-10}$ alkenyl group (e.g., vinyl, allyl, 2-butenyl, 3-butenyl and the like), a phenyl-$C_{2-4}$ alkenyl group (e.g., phenylethenyl and the like), a mono- or di-$C_{1-6}$ alkenyl-carbamoyl group (e.g., N-vinylcarbamoyl and the like), a $C_{6-14}$ aryl group (e.g., phenyl, 1-naphthyl, 2-naphthyl), a $C_{7-20}$ aralkyl group (e.g., benzyl, 2-phenylethyl, 3-phenylpropyl, 4-phenylbutyl, 5-phenylpentyl, 6-phenylhexyl, 2-(1-naphthyl)ethyl, 2-(2-naphthyl)ethyl and the like), a styryl group, an oxo group and the like. 1 to 4 "substituent(s)" of the "hydrocarbon group" may be present at the substitutable positions.

In addition, when the "hydrocarbon group" is a cyclic group such as a cycloalkyl group, a cycloalkenyl group, an aralkyl group, an aryl group and the like, it may have a substituent(s) such as optionally halogenated $C_{1-4}$alkylenedioxy group, optionally halogenated $C_{2-5}$alkyleneoxy group and the like, or these cyclic groups may be fused to form a bicyclic or tricyclic fused hydrocarbon group. Such a fused hydrocarbon group may have a group similar to the substituent that the aforementioned "alkyl group" and "cycloalkyl group" may have.

As the "hydrocarbon group" of the "optionally substituted hydrocarbon group", a $C_{1-8}$ alkyl group, a $C_{2-8}$ alkenyl group, a $C_{2-8}$ alkynyl group, a $C_{3-8}$ cycloalkyl group, a phenyl group, a naphthyl group and the like are preferable, a $C_{1-4}$ alkyl group, a $C_{2-4}$ alkenyl group, a $C_{2-4}$ alkynyl group, a phenyl group and the like are more preferable, and a $C_{1-4}$ alkyl group, a phenyl group and the like are particularly preferable.

As the "heterocyclic group" of the term "optionally substituted heterocyclic group" used in the present specification, for example, aromatic heterocyclic group, saturated or unsaturated non-aromatic heterocyclic group (aliphatic heterocyclic group) and the like, which contain at least one (preferably 1 to 4, more preferably 1 or 2) of 1 to 3 kinds of hetero atoms (preferably 1 or 2 kinds) selected from oxygen atom, sulfur atom and nitrogen atom and the like as a ring-constituting atom (ring atom) can be mentioned.

As the "aromatic heterocyclic group", for example, a 5 or 6-membered aromatic monocyclic heterocyclic groups (e.g., furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like, and for example, a 8 to 16-membered (preferably 8 to 12-membered) aromatic fused heterocycle group (preferably a heterocycle wherein 1 or 2 (preferably 1) of the aforementioned 5 or 6-membered aromatic monocyclic heterocyclic groups is/are condensed with 1 or 2 (preferably 1) benzene ring, or a heterocycle wherein the same or different 2 or 3 (preferably 2) heterocycles of the aforementioned 5 or 6-membered aromatic monocyclic heterocyclic groups are condensed, more preferably a heterocycle wherein the aforementioned 5 or 6-membered aromatic monocyclic heterocyclic group is condensed with a benzene ring) such as benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenazinyl, phenoxathiinyl, thianthrenyl, phenathridinyl, phenathrolinyl, indolizinyl, pyrrolo[1,2-b]pyridazinyl, pyrazolo[1,5-a]pyridyl, imidazo[1,2-a]pyridyl, imidazo [1,5-a]pyridyl, imidazo[1,2-b]pyridazinyl, imidazo[1,2-a] pyrimidinyl, 1,2,4-triazolo[4,3-a]pyridyl, 1,2,4-triazolo[4,3-b]pyridazinyl, benzo[1,2,5]thiadiazolyl, benzo[1,2,5] oxadiazolyl and the like) and the like can be mentioned.

As the "non-aromatic heterocyclic group", for example, a 3 to 8-membered (preferably 5 or 6-membered) saturated or unsaturated (preferably saturated) non-aromatic monocyclic heterocyclic group (aliphatic monocyclic heterocyclic group) such as oxiranyl, azetidinyl, oxetanyl, thietanyl, pyrrolidinyl, tetrahydrofuryl, thiolanyl, piperidinyl (preferably 1-piperidinyl or 4-piperidinyl), tetrahydropyranyl, morpholinyl, thiomorpholinyl, piperazinyl and the like, a heterocyclic group wherein 1 or 2 (preferably 1) of the aforementioned non-aromatic monocyclic heterocyclic groups is/are condensed with 1 or 2 (preferably 1) benzene ring, such as 2,3-dihydroindolyl, 1,3-dihydroisoindolyl and the like, a heterocyclic group wherein 1 or 2 (preferably 1) of the aforementioned non-aromatic monocyclic heterocyclic groups is/are condensed with 1 or 2 (preferably 1) heterocyclic group of the aforementioned 5 or 6-membered aromatic monocyclic heterocyclic groups, or a non-aromatic heterocyclic group wherein a part or all of the double bonds of the aforementioned aromatic monocyclic heterocyclic group or aromatic fused heterocycle group is/are saturated, such as 1,2,3,4-tetrahydroquinolyl, 1,2,3,4-tetrahydroisoquinolyl and the like, and the like can be mentioned.

As the "heterocyclic group" of the "optionally substituted heterocyclic group", 5 or 6-membered aromatic monocyclic heterocyclic group and the like are preferable, and as the substituent that the "heterocyclic group", of the "optionally substituted heterocyclic group" may have, groups similar to the substituent(s) that the "hydrocarbon group" of the "optionally substituted hydrocarbon group" may have and the like can be mentioned.

As the terms "optionally substituted divalent hydrocarbon group" and "optionally substituted divalent heterocyclic group" used in the present specification, a divalent group formed by removing one of the hydrogen atoms attached to the carbon atom of the binding site of the aforementioned "optionally substituted hydrocarbon group" and "optionally substituted heterocyclic group" and the like can be mentioned.

As the terms "optionally substituted amino group", "optionally substituted hydroxy group" and "optionally substituted thiol group" used in the present specification, "amino group", "hydroxy group" and "thiol group" and the like each optionally having substituent(s) such as "optionally substituted hydrocarbon group", "acyl group", "optionally substituted alkoxycarbonyl group", "an optionally substituted carbamoyl group", "optionally substituted heterocyclic group" and the like can be mentioned. Of these, "amino group", "hydroxy group" and "thiol group" and the like optionally having substituent(s) such as a lower alkyl (e.g., $C_{1-6}$ alkyl such as methyl, ethyl, propyl, isopropyl, butyl, isobutyl, tert-butyl, pentyl, hexyl and the like etc.) optionally substituted by a substituent(s) selected from a halogen atom (e.g., fluorine, chlorine, bromine, iodine etc.), optionally halogenated $C_{1-6}$alkoxy (e.g., methoxy, ethoxy, trifluoromethoxy, 2,2,2-trifluoroethoxy, trichloromethoxy, 2,2,2-trichloroethoxy etc.), optionally substituted phenyl (preferably phenyl optionally substituted by a substituent(s) selected from optionally halogenated $C_{1-4}$ alkyl, optionally halogenated $C_{1-4}$ alkoxy, carboxyl and halogen atom, and the like) and a 5 to 10-membered heterocyclic group (e.g., 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 1,2,3- or 1,2,4-triazolyl, 1H- or 2H-tetrazolyl, 2-, 3- or 4-pyridyl, 2-, 4- or 5-pyrimidyl, 3- or 4-pyridazinyl, quinolyl, isoquinolyl, indolyl and the like; said heterocyclic group is optionally substituted by $C_{1-4}$ alkyl group and the like); acyl ($C_{1-6}$ alkanoyl (e.g., formyl, acetyl, propionyl, pivaloyl etc.), benzoyl, $C_{1-6}$ alkylsulfonyl (e.g., methanesulfonyl etc.), benzenesulfonyl etc.), optionally halogenated $C_{1-6}$ alkoxycarbonyl (e.g., methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl etc.), $C_{1-6}$ alkoxycarbonyl optionally substituted by phenyl (e.g., benzyloxycarbonyl etc.), an optionally substituted carbamoyl group (e.g., carbamoyl group optionally substituted by 1 or 2 substituent(s) such as lower ($C_{1-6}$) alkyl group, phenyl group and the like, such as carbamoyl, N-methylcarbamoyl, N,N-dimethylcarbamoyl, phenylcarbamoyl and the like, and the like), a heterocyclic group (group similar to that of the "heterocyclic group" of the aforementioned "optionally substituted heterocyclic group" and the like) and the like can be mentioned.

In addition, two substituent(s) of the N,N-disubstituted amino may form a cyclic amino group together with a nitrogen atom, and as the cyclic amino group in such case, for example, a 3 to 8-membered (preferably 5 or 6-membered) cyclic amino group, such as 1-azetidinyl, 1-pyrrolidinyl, piperidino, morpholino, thiomorpholino (sulfur atom may be oxidized), 1-piperazinyl and 1-piperazinyl optionally having lower alkyl (e.g., $C_{1-6}$ alkyl such as methyl, ethyl, propyl, isopropyl, butyl, tert-butyl, pentyl, hexyl and the like etc.), aralkyl (e.g., $C_{7-10}$ aralkyl such as benzyl, phenethyl and the like etc.), aryl (e.g., $C_{6-10}$ aryl such as phenyl, 1-naphthyl, 2-naphthyl and the like etc.) and the like at the 4-position and the like can be mentioned.

The terms used in the present specification "substituted sulfinyl group" and "substituted sulfonyl group" are a sulfinyl group or a sulfonyl group substituted by a substituent(s) such as an optionally substituted hydroxy group, an optionally substituted amino group, an optionally substituted hydrocarbon group, an optionally substituted heterocyclic group and the like. As the hydrocarbon group and heterocyclic group which are the substituent(s) of the "substituted sulfinyl group" and "substituted sulfonyl group", groups similar to the "hydrocarbon group" of the aforementioned "optionally substituted hydrocarbon group" and the "heterocyclic group" of the "optionally substituted heterocyclic group" and the like are used. In addition, as the "optionally substituted hydroxy group" and "optionally substituted amino group" which are the substituent(s) of the "substituted sulfinyl group" and "substituted sulfonyl group", groups similar to the aforementioned "optionally substituted hydroxy group" and "optionally substituted amino group" and the like are used, and as preferable substituent(s) that may substitute the hydroxy group and amino group, for example, a $C_{1-6}$ alkyl group, a $C_{3-8}$ cycloalkyl group, a $C_{2-4}$ alkenyl group, a $C_{6-10}$ aryl group, an acyl group, an amino group, a heterocyclic group (group similar to the "heterocyclic group" of the aforementioned "optionally substituted heterocyclic group" and the like), and the like can be mentioned. As the substituent that may substitute the hydrocarbon group and heterocyclic group that are the substituent(s) of the "substituted sulfinyl group" and "substituted sulfonyl group", groups similar to the substituent(s) that the "hydrocarbon group" of the aforementioned "optionally substituted hydrocarbon group" and the "heterocycle" of the "optionally substituted heterocycle" may have and the like are used.

As the terms used in the present specification "an optionally substituted carbamoyl group", unsubstituted carbamoyl, N-monosubstituted carbamoyl and N,N-disubstituted carbamoyl can be mentioned.

As the substituent of the "carbamoyl group" of the "optionally substituted carbamoyl group", groups similar to the substituent(s) of the "amino group" of the aforementioned "optionally substituted amino group" and the like ("optionally substituted hydrocarbon group", "acyl group", "optionally substituted alkoxycarbonyl group", "an optionally substituted carbamoyl group" (preferably a carbamoyl group optionally substituted by 1 or 2 substituent(s) such as lower ($C_{1-6}$)alkyl group, phenyl group and the like, which is exemplified by carbamoyl, N-methylcarbamoyl, N,N-dimethylcarbamoyl, phenylcarbamoyl and the like, and the like), "an optionally substituted heterocyclic group" and the like) and the like can be mentioned. The "carbamoyl group" may have the aforementioned "optionally substituted amino group" (i.e., "optionally substituted carbazoyl group"), or the aforementioned "optionally substituted hydroxy group" (i.e., "optionally substituted N-hydroxycarbamoyl group") and the like. Two substituent(s) of N,N-disubstituted carbamoyl may form a cyclic amino together with the nitrogen atom, in which case the cyclic aminocarbonyl is, for example, a 3 to 8-membered (preferably 5 or 6-membered) cyclic aminocarbonyl and the like, such as 1-azetidinylcarbonyl, 1-pyrrolidinylcarbonyl, piperidinocarbonyl, morpholinocarbonyl, thiomorpholinocarbonyl (sulfur atom may be oxidized), 1-piperazinylcarbonyl and 1-piperazinylcarbonyl optionally having, at the 4-position, a lower alkyl (e.g., $C_{1-6}$ alkyl such as methyl, ethyl, propyl, isopropyl, butyl, tert-butyl, pentyl, hexyl and the like etc.), aralkyl (e.g., $C_{7-10}$ aralkyl such as benzyl, phenethyl and the like etc.), aryl (e.g., $C_{6-10}$ aryl such as phenyl, 1-naphthyl, 2-naphthyl and the like etc.), acyl group (e.g., formyl, acetyl, benzoyl, methylsulfonyl, benzenesulfonyl etc.), optionally halogenated $C_{1-6}$alkoxycarbonyl group (e.g., methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl etc.), a $C_{1-6}$alkoxycarbonyl group optionally substituted by phenyl (e.g., benzyloxycarbonyl etc.) and the like, and the like.

As the term used in the present specification "an optionally esterified carboxyl group", a group represented by the formula —$COOR^C$ ($R^C$ is a hydrogen atom or an optionally substituted hydrocarbon group or an optionally substituted heterocyclic group) and the like can be mentioned. Of these, free carboxyl, lower alkoxycarbonyl, aryloxycarbonyl, aralkyloxycarbonyl, heterocyclyloxycarbonyl, heterocyclylmethyloxycarbonyl and the like are preferably used.

As the "lower alkoxycarbonyl", for example, $C_{1-6}$ alkoxycarbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and the like, and the like can be mentioned. Of these, $C_{1-3}$ alkoxycarbonyls such as methoxycarbonyl, ethoxycarbonyl, propoxycarbonyl and the like, and the like are preferable.

The "lower alkoxycarbonyl" may have a substituent at the "lower alkyl" moiety of the "lower alkoxy", and as such substituent, groups similar to the groups mentioned as the substituent(s) of the "hydrocarbon group" of the aforementioned "optionally substituted hydrocarbon group", and the like are used in a similar number.

As the "aryloxycarbonyl", for example, $C_{7-12}$ aryloxycarbonyl such as phenoxycarbonyl, 1-naphthoxycarbonyl, 2-naphthoxycarbonyl and the like, and the like are preferable.

As the "aralkyloxycarbonyl", for example, $C_{7-15}$ aralkyloxycarbonyl such as benzyloxycarbonyl, phenethyloxycarbonyl and the like, and the like (preferably $C_{6-10}$ aryl-$C_{1-4}$ alkoxy-carbonyl and the like) are preferable.

As the heterocycle of the "heterocyclyloxycarbonyl" and "heterocyclylmethyloxycarbonyl", those similar to the "heterocyclic group" of the aforementioned "optionally substituted heterocyclic group" are used and, for example, pyridyl, quinolyl, indolyl, piperidinyl, tetrahydropyranyl and the like are preferably used.

The "aryloxycarbonyl", "aralkyloxycarbonyl", "heterocyclyloxycarbonyl" and "heterocyclylmethyloxycarbonyl" may have a substituent, and as the substituent, groups similar to the groups mentioned as the substituent(s) of the "hydrocarbon group" of the aforementioned "optionally substituted hydrocarbon group" and the like are used in a similar number.

As the terms used in the present specification "optionally thioesterified carboxyl group", a group represented by the formula —$COSR^C$ ($R_C$ is as defined above) and the like can be mentioned. Of these, lower alkylthio-carbonyl, arylthio-carbonyl, aralkylthio-carbonyl, heterocyclylthio-carbonyl and the like are preferably used.

As the "lower alkylthio-carbonyl", for example, a group wherein the "lower alkoxy" moiety of the aforementioned "lower alkoxycarbonyl" is converted to "lower alkylthio" and the like is used, and particularly, $C_{1-3}$alkylthio-carbonyl such as methylthio-carbonyl, ethylthio-carbonyl, propylthio-carbonyl and the like, and the like are preferable.

The "lower alkylthio-carbonyl" may have substituent(s) at the "lower alkyl" moiety of the "lower alkylthio", and as such substituent(s), groups similar to the groups mentioned as the substituent(s) of the "hydrocarbon group" of the aforementioned "optionally substituted hydrocarbon group" and the like are used in a similar number.

As the "arylthio-carbonyl", for example, $C_{7-12}$ arylthio-carbonyls such as phenylthio-carbonyl, 1-naphthylthio-carbonyl, 2-naphthylthio-carbonyl and the like, and the like are preferable.

As the "aralkylthio-carbonyl", for example, $C_{7-15}$aralkylthio-carbonyls such as benzylthio-carbonyl, phenethylthio-carbonyl and the like, and the like (preferably $C_{6-10}$aryl-$C_{1-4}$alkylthio-carbonyl and the like) are preferable.

As the heterocycle of the "heterocyclylthio-carbonyl", those similar to the "heterocyclic group" of the aforementioned "optionally substituted heterocyclic group" and the like are used and, for example, pyridyl, quinolyl, indolyl, piperidinyl, tetrahydropyranyl and the like are preferably used.

The "arylthio-carbonyl", "aralkylthio-carbonyl" and "heterocyclylthio-carbonyl" may have substituent(s) and as such substituent(s), groups similar to the groups mentioned as the substituent(s) of the "hydrocarbon group" of the aforementioned "optionally substituted hydrocarbon group" and the like are used in a similar number.

As the terms used in the present specification "a compound having an isoquinolinone skeleton", 1-isoquinolinone is preferably used, and as 1-isoquinolinone, any compound having a skeleton represented by the formula

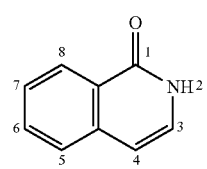

can be used, which may be one having 1 to 6 substituent(s) at any position(s) from the 2-position to the 8-position. Particularly, one having a substituent (preferably optionally substituted benzene ring) at the 4-position (with or without substituent(s) at other substitutable positions) is preferable, and further, one having substituents from the 2-position to the 4-position (with or without substituent(s) at other substitutable positions) is preferable, and specifically, one having substituents from the 2-position to the 4-position and the 6-position (with or without substituent(s) at other substitutable positions) is preferable.

Of the "compounds having an isoquinolinone skeleton", a compound represented by the formula (I)

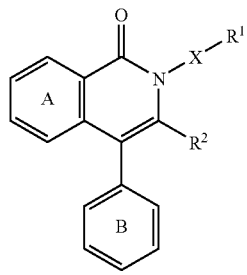

wherein ring A and ring B are each an optionally substituted benzene ring, X is —O—, —N=, —NR$^3$— or —CHR$^3$— (R$^3$ is a hydrogen atom or an optionally substituted hydrocarbon group, or may be bonded with R$^1$ to optionally form a 3 to 8-membered ring), R$^2$ is a hydrocarbon group optionally having substituent(s) selected from an optionally substituted hydroxy group, an optionally substituted thiol group, a substituted sulfinyl group, a substituted sulfonyl group and an optionally esterified carboxyl group, an acyl group, an optionally esterified or a thioesterified carboxyl group, an optionally substituted carbamoyl group or an optionally substituted amino group, and a broken line shows a single bond or a double bond, when X is —O—, —NR$^3$— or —CHR$^3$—, then R$^1$ is a hydrogen atom, an optionally substituted (monovalent) hydrocarbon group or an optionally substituted (monovalent) heterocyclic group, and when X is —N=, then R$^1$ is an optionally substituted divalent hydrocarbon group or an optionally substituted divalent heterocyclic group is preferable, particularly, a compound represented by the formula (I')

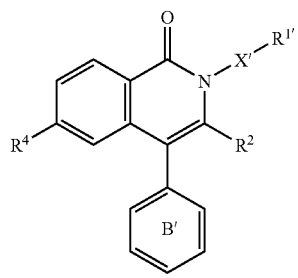

wherein ring B' is a benzene ring optionally having not more than two substituent(s), X' is —CH$_2$—, R$^{1'}$ is an optionally substituted phenyl group or an optionally substituted heterocyclic group bonded via a ring-constituting carbon atom, R$^2$ is a hydrocarbon group optionally having substituent(s) selected from an optionally substituted hydroxy group, an optionally substituted thiol group, a substituted sulfinyl group, a substituted sulfonyl group and an optionally esterified carboxyl group, an acyl group, an optionally esterified or thioesterified carboxyl group, an optionally substituted carbamoyl group or an optionally substituted amino group, R$^4$ is a hydrogen atom, a halogen atom, a cyano group, an optionally substituted hydrocarbon group, an optionally substituted heterocyclic group, an optionally substituted hydroxy group, an optionally substituted thiol group, a substituted sulfinyl group, a substituted sulfonyl group, an optionally substituted amino group, an optionally substituted carbamoyl group or an optionally esterified carboxyl group is preferably used.

In the aforementioned formula, ring A and ring B each show an "optionally substituted benzene ring".

As the substituent that ring A and ring B (including ring B') each may have, a group similar to the substituent that the "hydrocarbon group" of the "optionally substituted hydrocarbon group" may have, as well as a halogen atom, a cyano group, an optionally substituted hydrocarbon group, an optionally substituted heterocyclic group, an optionally substituted hydroxy group, an optionally substituted thiol group, a substituted sulfinyl group, a substituted sulfonyl group, an optionally substituted amino group, an optionally substituted carbamoyl group, an optionally esterified carboxyl group and the like can be mentioned. Of these, a halogen atom (e.g., fluorine, chlorine, bromine, iodine and the like), a C$_{1-4}$ alkyl group (e.g., methyl, ethyl, propyl, isopropyl, butyl and the like), a hydroxy-C$_{1-4}$ alkyl group, a C$_{1-4}$ alkoxy-C$_{1-4}$alkyl group, a C$_{2-4}$ alkenyl group (e.g., vinyl, propenyl, allyl and the like), an optionally substituted phenyl group (preferably phenyl optionally substituted by a substituent(s) selected from optionally halogenated C$_{1-4}$ alkyl group, optionally halogenated C$_{1-4}$alkoxy group, carboxyl group and halogen atom and the like), a C$_{5-7}$ cycloalkyl-amino group, a C$_{1-4}$ alkoxy group (e.g., methoxy, ethoxy, propoxy, isopropoxy and the like), a C$_{1-4}$ alkylthio group (e.g., methylthio, ethylthio, propylthio, isopropylthio and the like), a hydroxy group, a carboxyl group, a cyano group, nitro group, an amino group, a mono- or di-C$_{1-4}$ alkylamino group (e.g., methylamino, ethylamino, dimethylamino, diethylamino and the like), a formyl group, a mercapto group, a C$_{1-4}$ alkyl-carbonyl group (e.g., acetyl, propionyl, butyryl and the like), a C$_{1-4}$ alkoxy-carbonyl group (e.g., methoxycarbonyl, ethoxycarbonyl, propoxycarbonyl and the like), a sulfo group (—SO$_3$H), a C$_{1-4}$alkyl-sulfonyl group (e.g., methylsulfonyl, ethylsulfonyl, propylsulfonyl and the like), a carbamoyl group and a mono- or di-C$_{1-4}$ alkyl or a C$_{5-7}$ cycloalkyl-carbamoyl group (e.g., N-methylcarbamoyl, N-ethylcarbamoyl, N,N-dimethylcarbamoyl, N,N-diethylcarbamoyl and the like) and the like are preferably used. 1 to 3 of these substituent(s) may be present at the substitutable positions of the ring A or ring B.

In the aforementioned formula, as ring A, a benzene ring represented by the formula

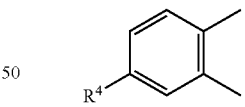

wherein R$^4$ is a hydrogen atom, a halogen atom, a cyano group, an optionally substituted hydrocarbon group, an optionally substituted heterocyclic group, an optionally substituted hydroxy group, an optionally substituted thiol group, a substituted sulfinyl group, a substituted sulfonyl group, an optionally substituted amino group, an optionally substituted carbamoyl group or an optionally esterified carboxyl group. (That is, 5-position, 7-position and 8-position of 1-isoquinolinone skeleton are unsubstituted, and substituent R$^4$ is present at the 6-position) are preferably used.

In the aforementioned formula, for R$^4$, a halogen atom, a cyano group, an optionally substituted hydrocarbon group, an optionally substituted heterocyclic group, an optionally substituted hydroxy group, an optionally substituted thiol group, a substituted sulfinyl group, a substituted sulfonyl group, an optionally substituted amino group, an optionally substituted carbamoyl group, an optionally esterified carboxyl group and the like are preferable. Of these, a halogen atom, an optionally substituted alkyl group ($C_{1-6}$ alkyl group that may have groups similar to the substituent(s) that the "alkyl group" as the "hydrocarbon group" of the "optionally substituted hydrocarbon group" may have and the like), an optionally substituted amino group and the like are preferable. Particularly, a halogen atom, a $C_{1-4}$ alkyl group and the like are preferable, and a halogen atom, a methyl group and the like are particularly preferably used.

In the aforementioned formula, as the ring B, a benzene ring optionally having not more than 2 substituents is preferable. In addition, as ring B (including ring B'), a benzene ring optionally having substituent(s) at the meta and/or para position(s) is preferable, and an unsubstituted benzene ring is more preferable.

In the aforementioned formula, X is —O—, —N=, —NR$^3$— or —CHR$^3$— (R$^3$ is a hydrogen atom or an optionally substituted hydrocarbon group, or may be bonded with R to form a 3 to 8-membered ring (e.g., a 3 to 8-membered "cyclic hydrocarbon" or a "heterocycle", preferably a 5 or 6-membered "cyclic hydrocarbon" or a "heterocycle" among the "cyclic hydrocarbon" or "heterocycle" constituting the aforementioned "cyclic hydrocarbon group" or "heterocyclic group"), and X may be —O— or —N=, or X may be —NR$^3$— or —CHR$^3$—, but as X, —CHR$^3$— is preferably used.

In the aforementioned formula, for R$^3$, a hydrogen atom or a $C_{1-8}$ alkyl group is preferably, and particularly, a hydrogen atom is preferably used.

In the aforementioned formula (I), R$^1$ is preferably an optionally substituted cyclic hydrocarbon group, an optionally substituted heterocyclic group and the like. Of these, an optionally substituted aromatic hydrocarbon group, an optionally substituted aromatic heterocyclic group and the like are preferable, and particularly, a substituted aromatic hydrocarbon group and the like are preferably used.

In the aforementioned formula, R$^2$ is a hydrocarbon group optionally having substituent(s) selected from an optionally substituted hydroxy group, an optionally substituted thiol group, a substituted sulfinyl group, a substituted sulfonyl group and an optionally esterified carboxyl group, an acyl group, an optionally esterified or a thioesterified carboxyl group, an optionally substituted carbamoyl group or an optionally substituted amino group, and R$^2$ may be an optionally esterified or thioesterified carboxyl group or an optionally substituted carbamoyl group, or R$^2$ may be a hydrocarbon group optionally having substituent(s) selected from an optionally substituted hydroxy group, an optionally substituted thiol group, a substituted sulfinyl group, a substituted sulfonyl group and an optionally esterified carboxyl group, an acyl group, an optionally substituted carbazoyl group, an optionally substituted N-hydroxycarbamoyl group or an optionally substituted amino group. When R$^2$ is an optionally esterified carboxyl group, R$^2$ is preferably a carboxyl group optionally esterified by an alkyl optionally substituted by a substituent(s) selected from an optionally substituted phenyl group (phenyl group that may have groups similar to the substituent(s) that the "phenyl group" as the "hydrocarbon group" of the "optionally substituted hydrocarbon group" may have and the like, and the like) and an optionally substituted pyridyl group (pyridyl group that may have groups similar to the substituent(s) that the "pyridyl group" as the "heterocyclic group" of the "optionally substituted heterocyclic group" may have and the like, and the like), when R$^2$ is an optionally substituted carbamoyl group, it is preferably a carbamoyl group optionally substituted by an alkyl optionally substituted by substituent(s) selected from an optionally substituted phenyl group (phenyl group that may have groups similar to the substituent(s) that the "phenyl group" as the "hydrocarbon group" of the "optionally substituted hydrocarbon group" may have and the like, and the like) and an optionally substituted pyridyl group (pyridyl group that may have groups similar to the substituent(s) that the "pyridyl group" as the "heterocyclic group" of the "optionally substituted heterocyclic group" may have and the like, and the like). When R$^2$ is an optionally thioesterified carboxyl group, it is preferably a carboxyl group optionally thioesterified by an optionally substituted pyridyl group (pyridyl group that may have groups similar to the substituent(s) that the "pyridyl group" as the "heterocyclic group" of the "optionally substituted heterocyclic group" may have and the like, and the like). In addition, when R$^2$ is a hydrocarbon group optionally having substituent(s) selected from an optionally substituted hydroxy group, an optionally substituted thiol group, a substituted sulfinyl group, a substituted sulfonyl group and an optionally esterified carboxyl group, it is preferably a 1-hydroxy $C_{1-8}$alkyl group, an $C_{2-4}$alkenyl group substituted by an optionally esterified carboxyl group (preferably vinyl group and the like) and the like.

For R$^2$, an acyl group is particularly preferable. When R$^2$ is an acyl group, R$^4$CO (R$^4$ is a hydrogen atom, an optionally substituted hydrocarbon group or an optionally substituted heterocyclic group) is preferable for R$^2$. For R$^4$CO, for example, formyl, acetyl, propionyl, butyryl, isobutyryl, valeryl, isovaleryl, pivaloyl, hexanoyl, cyclobutanecarbonyl, cyclopentanecarbonyl, cyclohexanecarbonyl, crotonyl, benzoyl, nicotinoyl, isonicotinoyl, trifluoroacetyl, (2Z)-3-aminobut-2-enoyl, (2Z)-3-aminopent-2-enoyl, (2Z)-3-aminooct-2-enoyl, (2Z)-3-amino-4-methylpent-2-enoyl, (2Z)-3-amino-3-ethoxycarbonylprop-2-enoyl, (2Z)-3-amino-3-phenylprop-2-enoyl, (2Z)-3-amino-3-pyridin-3-ylprop-2-enoyl, (2Z)-3-amino-3-pyridin-4-ylprop-2-enoyl, (2Z)-3-amino-3-(1,3-thiazol-4-yl)prop-2-enoyl, (2Z)-3-amino-3-isoxazol-4-ylprop-2-enoyl, (2Z)-3-amino-3-isoxazole-5-ylprop-2-enoyl, (2Z)-3-amino-4-phenylbut-2-enoyl, (2Z)-3-amino-3-(2-thienyl)prop-2-enoyl, (2Z)-3-amino-3-(2-furyl)prop-2-enoyl, (2Z)-3-amino-3-(3-thienyl)prop-2-enoyl, (2Z)-3-amino-3-(3-furyl)prop-2-enoyl, (2Z)-3-amino-3-pyrazin-2-ylprop-2-enoyl, (2Z)-3-amino-3-(1H-imidazol-4-yl)prop-2-enoyl and the like can be mentioned, and R$^4$CO wherein R$^4$ is a lower ($C_{1-7}$)alkyl, such as acetyl, propionyl, butyryl, valeryl and the like, or R$^4$CO wherein R$^4$ is a group represented by the formula

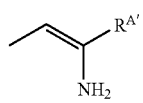

wherein R$^{4'}$ is a $C_{1-5}$alkyl group or an optionally esterified carboxyl group, such as (2Z)-3-aminobut-2-enoyl, (2Z)-3-aminopent-2-enoyl and the like, are more preferable.

For R$^2$, a methoxycarbonyl group, a benzyloxycarbonyl group, a dimethylcarbamoyl group, a hydroxymethyl group, an acetyl group, a propionyl group, a butyryl group, a valeryl group, a pyridylmethyloxycarbonyl group, a pyridylmethylcarbamoyl group, a pyridylthiocarbonyl group, an amino group or (2Z)-3-aminobut-2-enoyl group and the like are preferably used, and of these, a methoxycarbonyl group, a pyridylmethyloxycarbonyl group, a dimethylcarbamoyl group, a pyridylmethylcarbamoyl group, a hydroxymethyl group, a pyridylthiocarbonyl group, an amino group, an acetyl group, a propionyl group, a butyryl group, a valeryl group or a (2Z)-3-aminobut-2-enoyl group and the like are particularly preferable.

When X is —CH$_2$—, R$^2$ is preferably a hydrocarbon group substituted by an optionally substituted hydroxy group, acyl group, an optionally esterified or thioesterified carboxyl group, an optionally substituted carbamoyl group, an optionally substituted amino group and the like (preferably a lower (C$_{1-6}$)alkyl group substituted by hydroxy group, R$^4$CO, an optionally esterified or thioesterified carboxyl group, a carbamoyl group optionally substituted by lower(C$_{1-6}$)alkyl group, an amino group optionally substituted by lower(C$_{1-6}$)alkyl group and the like), and of these, an acyl group, an optionally esterified or thioesterified carboxyl group, (preferably R$^4$CO wherein R$^4$ is a lower (C$_{1-7}$)alkyl group or a group represented by the formula

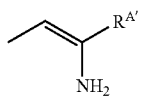

wherein the symbols in the formula are as defined above, a carboxyl group optionally esterified by an alkyl optionally substituted by substituent(s) selected from an optionally substituted phenyl group and an optionally substituted pyridyl group, a carboxyl group optionally thioesterified by optionally substituted pyridyl group and the like) and the like are preferable. When X is —CH$_2$—, for R$^2$, a methoxycarbonyl group, a dimethylcarbamoyl group, an amino group, a hydroxymethyl group, an acetyl group, a propionyl group, a butyryl group, a valeryl group, a pyridylmethyloxycarbonyl group, a pyridylmethylcarbamoyl group, a pyridylthiocarbonyl group or a (2Z)-3-aminobut-2-enoyl group and the like are preferably used.

As a compound represented by the formula (I), a compound wherein X is —NH— or —NCH$_3$—, R$^1$ is an alkyl group;

a compound wherein X is —CH$_2$—, and R$^1$ is an optionally substituted phenyl group (a phenyl group that may have groups similar to the substituent(s) that the "phenyl group" as the "hydrocarbon group" of the "optionally substituted hydrocarbon group" may have and the like);

a compound wherein X is —CH$_2$—, and R$^1$ is a phenyl group having substituent at the meta or para-position (a phenyl group that may have groups similar to the substituent(s) that the "phenyl group" as the "hydrocarbon group" of the "optionally substituted hydrocarbon group" may have and the like);

a compound wherein X is —CH$_2$—, and R$^1$ is an optionally substituted 4-piperidinyl group (a piperidinyl group that may have groups similar to the substituent(s) that the "piperidinyl group" as the "heterocyclic group" of the "optionally substituted heterocyclic group" may have and the like);

a compound wherein X is —CH$_2$—, and R$^1$ is an acyl group (optionally halogenated C$_{1-6}$alkanoyl such as formyl, acetyl and the like, benzoyl optionally substituted by halogen atom, carboxyl group and the like, optionally halogenated C$_{1-6}$alkylsulfinyl, optionally halogenated C$_{1-4}$alkylsulfonyl and the like; preferably, optionally halogenated C$_{2-6}$alkanoyl, optionally halogenated C$_{1-4}$alkylsulfonyl and the like), C$_{1-6}$alkoxycarbonyl (e.g., methoxycarbonyl, ethoxycarbonyl etc.), a 4-piperidinyl group substituted by carbamoyl and the like; a compound wherein ring A is a benzene ring represented by the formula

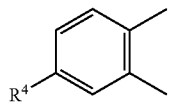

wherein R$^4$ is a hydrogen atom, a halogen atom, a cyano group, an optionally substituted hydrocarbon group, an optionally substituted heterocyclic group, an optionally substituted hydroxy group, an optionally substituted thiol group, a substituted sulfinyl group, a substituted sulfonyl group, an optionally substituted amino group, an optionally substituted carbamoyl group or an optionally esterified carboxyl group, ring B is a benzene ring optionally having not more than 2 substituent(s), and X is —NR$^3$— or —CHR$^3$— (R$^3$ is as defined above) (more preferably, a compound wherein R$^2$ is an optionally esterified or thioesterified carboxyl group or an optionally substituted carbamoyl group); and the like are preferable.

In the aforementioned formula (I'), R$^{1'}$ is an "optionally substituted phenyl group" (a phenyl group that may have groups similar to the substituent(s) that the "phenyl group" as the "hydrocarbon group" of the "optionally substituted hydrocarbon group" may have and the like) or "an optionally substituted heterocyclic group bonded via a ring-constituting carbon atom" (in the "optionally substituted heterocyclic group", one where the bond of the "heterocyclic group" is present on the ring-constituting carbon atom).

As the "optionally substituted phenyl group" for R$^{1'}$, a phenyl group having a substituent at the meta and/or para-position (a phenyl group that may have those similar to the substituent(s) that the "phenyl group" as the "hydrocarbon group" of the "optionally substituted hydrocarbon group" may have and the like) and the like are preferable, and as the heterocyclic group of the "optionally substituted heterocyclic group bonded via a ring-constituting carbon atom" for R$^{1'}$, a nitrogen-containing heterocyclic group is preferable, and particularly, a nitrogen-containing heterocyclic group comprising carbon atom(s) and nitrogen atom(s) is preferable. Moreover, the nitrogen-containing heterocyclic group may be any of an aromatic nitrogen-containing heterocyclic group and a non-aromatic nitrogen-containing heterocyclic group. In the case of a non-aromatic nitrogen-containing heterocyclic group, a saturated nitrogen-containing heterocyclic group is preferable and a 2-, 3- or 4-piperidinyl group is preferable, particularly, a 4-piperidinyl group is preferably used. As the "optionally substituted heterocyclic group bonded via a ring-constituting carbon atom" for R$^{1'}$, a 4-piperidinyl group substituted by an acyl group (formyl, C$_{2-6}$alkanoyl optionally substituted by halogen atom or carboxyl group, such as acetyl and the like, benzoyl optionally substituted by halogen atom or carboxyl group, C$_{1-4}$alkylsulfinyl optionally substituted by halogen atom or carboxyl group, C$_{1-4}$alkylsulfonyl optionally substituted by halogen atom or carboxyl group, and the like; preferably, C$_{2-6}$alkanoyl optionally substituted by halogen atom or carboxyl group, C$_{1-4}$alkylsulfonyl optionally substituted by halogen atom or carboxyl group, and the like) and the like are preferable.

As the substituent of the "optionally substituted phenyl group" for R$^{1'}$ (including "optionally substituted phenyl group" as an example of the "optionally substituted hydrocarbon group" for $R^1$), a halogen atom (e.g., fluorine, chlorine, bromine, iodine and the like), a $C_{1-4}$alkyl group (e.g., methyl, ethyl, propyl, isopropyl, butyl and the like; $C_{1-4}$alkyl is optionally substituted by halogen atom, hydroxy group, carboxyl group and the like), a $C_{1-4}$alkoxy-$C_{1-4}$alkyl group ($C_{1-4}$alkoxy is optionally substituted by halogen atom, hydroxy group, carboxyl group and the like), a $C_{2-4}$alkenyl group (e.g., vinyl, propenyl, allyl and the like; $C_{2-4}$alkenyl is optionally substituted by halogen atom, hydroxy group, carboxyl group and the like), an optionally substituted phenyl group (preferably phenyl optionally substituted by a substituent(s) selected from optionally halogenated $C_{1-4}$alkyl group, optionally halogenated $C_{1-4}$alkoxy group, carboxyl group and halogen atom and the like), a $C_{5-7}$cycloalkyl-amino group ($C_{5-7}$cycloalkyl is optionally substituted by halogen atom, hydroxy group, carboxyl group and the like), a $C_{1-4}$alkoxy group (e.g., methoxy, ethoxy, propoxy, isopropoxy and the like; $C_{1-4}$alkoxy is optionally substituted by halogen atom, hydroxy group, carboxyl group and the like), a $C_{1-4}$alkylthio group (e.g., methylthio, ethylthio, propylthio, isopropylthio and the like; $C_{1-4}$alkylthio is optionally substituted by halogen atom, hydroxy group, carboxyl group and the like), a hydroxy group, a carboxyl group, a cyano group, a nitro group, an amino group, a mono- or di-$C_{1-4}$alkylamino group (e.g., methylamino, ethylamino, dimethylamino, diethylamino and the like; $C_{1-4}$alkyl is optionally substituted by halogen atom, hydroxy group, carboxyl group and the like), a $C_{1-10}$acyl-amino group (e.g., $C_{1-6}$alkanoylamino (e.g., formylamino, acetylamino, trifluoroacetylamino, propionylamino, pivaloylamino etc.), benzoylamino, $C_{1-6}$alkylsulfonylamino (e.g., methanesulfonylamino, trifluoromethanesulfonylamino etc.), $C_{6-10}$arylsulfonylamino (e.g., benzenesulfonylamino, toluenesulfonylamino etc.) and the like; $C_{1-10}$acyl is optionally substituted by halogen atom, hydroxy group, carboxyl group and the like), a formyl group, a mercapto group, a $C_{1-4}$alkyl-carbonyl group (e.g., acetyl, propionyl, butyryl and the like; $C_{1-4}$alkyl is optionally substituted by halogen atom, hydroxy group, carboxyl group and the like), a $C_{1-4}$alkoxy-carbonyl group (e.g., methoxycarbonyl, ethoxycarbonyl, propoxycarbonyl and the like; $C_{1-4}$alkoxy is optionally substituted by halogen atom, hydroxy group, carboxyl group and the like), a sulfo group (—$SO_3H$), a $C_{1-4}$alkyl-sulfonyl group (e.g., methylsulfonyl, ethylsulfonyl, propylsulfonyl and the like; $C_{1-4}$alkyl is optionally substituted by halogen atom, hydroxy group, carboxyl group and the like), a $C_{1-4}$alkyl-sulfinyl group (e.g., methylsulfinyl, ethylsulfinyl, propylsulfinyl and the like; $C_{1-4}$alkyl is optionally substituted by halogen atom, hydroxy group, carboxyl group and the like), a carbamoyl group and a mono- or di-$C_{1-4}$alkyl or $C_{5-7}$cycloalkyl-carbamoyl group (e.g., N-methylcarbamoyl, N-ethylcarbamoyl, N,N-dimethylcarbamoyl, N,N-diethylcarbamoyl and the like; $C_{1-4}$alkyl and $C_{5-7}$cycloalkyl are each optionally substituted by halogen atom, hydroxy group, carboxyl group and the like), a cyclic amino-carbonyl group (e.g., 1-pyrrolidinylcarbonyl, 1-piperidinocarbonyl, 4-morpholinocarbonyl and the like; cyclic amino is optionally substituted by halogen atom, hydroxy group, carboxyl group and the like), a sulfamoyl group and a mono- or di-$C_{1-4}$alkyl or $C_{5-7}$cycloalkyl-sulfamoyl group (e.g., N-methylsulfamoyl, N-ethylsulfamoyl, N,N-dimethylsulfamoyl, N,N-diethylsulfamoyl and the like; $C_{1-4}$alkyl and $C_{5-7}$cycloalkyl are each optionally substituted by halogen atom, hydroxy group, carboxyl group and the like), cyclic amino-sulfonyl group (e.g., 1-pyrrolidinylsulfonyl, 1-piperidinosulfonyl, 4-morpholinosulfonyl and the like; cyclic amino is optionally substituted by halogen atom, hydroxy group, carboxyl group and the like), a carbazoyl(N-aminocarbamoyl) group and a (mono- or di-(N-$C_{1-4}$alkylamino) or (N-$C_{5-7}$cycloalkylamino))carbamoyl group (e.g., (N-methylamino)carbamoyl, (N-ethylamino)carbamoyl, (N,N-dimethylamino)carbamoyl, (N,N-diethylamino)carbamoyl and the like; $C_{1-4}$alkyl and $C_{5-7}$cycloalkyl are each optionally substituted by halogen atom, hydroxy group, carboxyl group and the like), N-(cyclic amino)carbamoyl group (e.g., N-(1-pyrrolidinyl)carbamoyl, N-(1-piperidino)carbamoyl, N-(4-morpholino)carbamoyl and the like; cyclic amino is optionally substituted by halogen atom, hydroxy group, carboxyl group and the like), a 5 to 10-membered heterocyclic group (e.g., 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 1,2,3- or 1,2,4-triazolyl, 1H- or 2H-tetrazolyl, 1,2,4- or 1,3,4-oxadiazolyl, 5-oxo-4H-1,2,4-oxadiazolyl, 5-thioxo-4H-1,2,4-oxadiazolyl, 1,2,4- or 1,3,4-thiadiazolyl, 5-oxo-4H-1,2,4-thiadiazolyl, 5-thioxo-4H-1,2,4-thiadiazolyl, 2-oxo-3H-1,2,3,5-oxathiadiazolyl, 2,4-dioxothiazolidin-5-yl, 2-, 3- or 4-pyridyl, 2-, 4- or 5-pyrimidyl, 3- or 4-pyridazinyl, quinolyl, isoquinolyl, indolyl and the like; the heterocyclic group is optionally substituted by halogen atom, hydroxy group, carboxyl group and the like) and the like are preferably used, and 1 to 3 of these substituent(s) may be present at substitutable positions of the phenyl group, and when 2 or more substituent(s) are present, they may be the same or different. In addition, an optionally halogenated linear or branched $C_{1-4}$alkylenedioxy group (e.g., methylenedioxy, ethylenedioxy, propylenedioxy, tetrafluoroethylenedioxy and the like) and the like are also preferable as substituent(s) that phenyl may have.

As the substituent that the "optionally substituted phenyl group" for $R^{1'}$ (including "optionally substituted phenyl group" as an example of the "optionally substituted hydrocarbon group" for $R^1$) may have, i) a $C_{1-4}$alkoxy group optionally substituted by halogen atom, hydroxy group or carboxyl group, ii) a carboxyl group, iii) a $C_{1-4}$alkoxy-carbonyl group optionally substituted by halogen atom, hydroxy group or carboxyl group, iv) a $C_{1-4}$alkyl-sulfonyl group optionally substituted by halogen atom, hydroxy group or carboxyl group, v) a carbamoyl group, vi-1) a mono- or di-$C_{1-4}$alkyl-carbamoyl group ($C_{1-4}$alkyl is optionally substituted by halogen atom, hydroxy group or carboxyl group), vi-2) a mono- or di-$C_{5-7}$cycloalkyl-carbamoyl group ($C_{5-7}$cycloalkyl is optionally substituted by halogen atom, hydroxy group or carboxyl group), vi-3) a cyclic amino-carbonyl group (cyclic amino is optionally substituted by halogen atom, hydroxy group, carboxyl group and the like), vii) a sulfamoyl group, viii-1) a mono- or di-$C_{1-4}$alkyl-sulfamoyl group ($C_{1-4}$alkyl is optionally substituted by halogen atom, hydroxy group or carboxyl group), viii-2) a mono- or di-$C_{5-7}$cycloalkyl-sulfamoyl group ($C_{5-7}$cycloalkyl is optionally substituted by halogen atom, hydroxy group or carboxyl group), viii-3) a cyclic amino-sulfonyl group (cyclic amino is optionally substituted by halogen atom, hydroxy group, carboxyl group and the like), ix-1) a carbazoyl group, ix-2) a mono- or di-(N-$C_{1-4}$alkylamino)-carbamoyl group ($C_{1-4}$alkyl is optionally substituted by halogen atom, hydroxy group or carboxyl group), ix-3) a mono- or di-(N-$C_{5-7}$cycloalkylamino)-carbamoyl group ($C_{5-7}$cycloalkyl is optionally substituted by halogen atom, hydroxy group or carboxyl group), ix-4) a cyclic amino-carbamoyl group (cyclic amino is optionally substituted by halogen atom, hydroxy group, carboxyl group and the like), or x) a $C_{1-4}$alkylenedioxy group optionally substituted by halogen atom, hydroxy group or carboxyl group and the like are particularly preferable.

As the "optionally substituted phenyl group" for $R^{1'}$ (including "optionally substituted phenyl group" as an example of the "optionally substituted hydrocarbon group" for R¹), a group represented by the formula

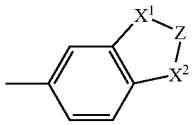

wherein X¹ and X² are each independently —O—, —S—, —N(R')— (R' is a hydrogen atom or a substituent) or methylene, and Z is optionally substituted alkylene, is also used preferably.

For combination of X¹ and X², a case where both X¹ and X² are —O—, a case where X¹ is —O—, —S— or —N(R')— (preferably —O—) and X² is methylene, a case where X¹ is methylene and X² is —O—, —S— or —N(R')— (preferably —O—) and the like are preferable.

As the substituent for R', the groups similar to the substituent(s) that the amino group of the aforementioned "optionally substituted amino group" may have and the like are used.

As the alkylene of the "optionally substituted alkylene" for Z, for example, $C_{1-4}$alkylene (e.g., methylene, ethylene, propylene and the like) and the like are used.

As the substituent that alkylene of the "optionally substituted alkylene" for Z may have, the groups similar to the substituent(s) that the "hydrocarbon group" of the aforementioned "optionally substituted hydrocarbon group" may have and the like are used in a similar number. As the substituent that the alkylene may have, halogen atom, $C_{1-4}$alkyl group (e.g., methyl, ethyl, propyl, isopropyl, butyl and the like; the $C_{1-4}$alkyl is optionally substituted by halogen atom, hydroxy group, carboxyl group and the like), optionally substituted phenyl (preferably, phenyl optionally substituted by a substituent(s) selected from optionally halogenated $C_{1-4}$alkyl group, optionally halogenated $C_{1-4}$alkoxy group, carboxyl group and halogen atom and the like), oxo group and the like are preferable.

As Z, methylene, ethylene and the like are particularly preferable.

As a compound represented by the formula (I), 2-(benzo[1,3]dioxol-5-ylmethyl)-6-bromo-1-oxo-4-phenyl-1,2-dihydroisoquinoline-3-carboxylic acid methyl ester, 6-bromo-1-oxo-4-phenyl-2-(4-sulfamoylbenzyl)-1,2-dihydroisoquinoline-3-carboxylic acid methyl ester, 6-bromo-2-(4-methanesulfonylbenzyl)-1-oxo-4-phenyl-1,2-dihydroisoquinoline-3-carboxylic acid methyl ester, 6-bromo-2-(2,3-dihydrobenzofuran-5-ylmethyl)-1-oxo-4-phenyl-1,2-dihydroisoquinoline-3-carboxylic acid methyl ester, 6-bromo-2-(4-carboxybenzyl)-1-oxo-4-phenyl-1,2-dihydroisoquinoline-3-carboxylic acid methyl ester, 2-(1-acetylpiperidin-4-ylmethyl)-6-bromo-1-oxo-4-phenyl-1,2-dihydroisoquinoline-3-carboxylic acid methyl ester, 6-bromo-2-[4-(3-carboxypropionylamino)benzyl]-1-oxo-4-phenyl-1,2-dihydroisoquinoline-3-carboxylic acid methyl ester, 6-bromo-2-(4-carbamoylbenzyl)-1-oxo-4-phenyl-1,2-dihydroisoquinoline-3-carboxylic acid methyl ester, 6-bromo-1-oxo-4-phenyl-2-[4-(2-(pyrrolidin-1-yl)ethylcarbamoyl)benzyl]-1,2-dihydroisoquinoline-3-carboxylic acid methyl ester, 2-(benzo[1,3]dioxol-5-ylmethyl)-6-methyl-1-oxo-4-phenyl-1,2-dihydroisoquinoline-3-carboxylic acid methyl ester, 6-amino-2-(benzo[1,3]dioxol-5-ylmethyl)-1-oxo-4-phenyl-1,2-dihydroisoquinoline-3-carboxylic acid methyl ester, 2-(benzo[1,3]dioxol-5-ylmethyl)-6-bromo-1-oxo-4-phenyl-1,2-dihydroisoquinoline-3-carboxylic acid pyridin-3-ylmethyl ester, N,N-dimethyl-2-(benzo[1,3]dioxol-5-ylmethyl)-6-bromo-1-oxo-4-phenyl-1,2-dihydroisoquinoline-3-carboxamide, 6-bromo-2-(4-methanesulfonylbenzyl)-4-phenyl-3-propionyl-2H-isoquinolin-1-one, 3-butyryl-6-chloro-2-(4-methanesulfonylbenzyl)-4-phenyl-2H-isoquinolin-1-one, 2-(4-carboxybenzyl)-6-chloro-4-(3-hydroxymethylphenyl)-1-oxo-1,2-dihydroisoquinoline-3-carboxylic acid methyl ester, 6-bromo-2-[4-(N',N'-diethylhydrazinocarbonyl)benzyl]-1-oxo-4-phenyl-1,2-dihydroisoquinoline-3-carboxylic acid methyl ester, 4-(6-chloro-3-butyryl-1-oxo-4-phenyl-1H-isoquinoline-2-ylmethyl)benzenesulfonamide, 4-(6-bromo-1-oxo-4-phenyl-3-propionyl-1H-isoquinolin-2-ylmethyl)benzoic acid, 4-(6-chloro-1-oxo-4-phenyl-3-propionyl-1H-isoquinolin-2-ylmethyl)benzoic acid, 6-bromo-4-phenyl-3-propionyl-2-[4-(1H-tetrazol-5-yl)benzyl]-2H-isoquinolin-1-one, 3-[(2Z)-3-aminobut-2-enoyl]-6-bromo-2-(4-methanesulfonylbenzyl)-4-phenyl-2H-isoquinolin-1-one, 3-[(2Z)-3-aminopent-2-enoyl]-6-bromo-2-(4-methanesulfonylbenzyl)-4-phenyl-2H-isoquinolin-1-one, 3-amino-2-(benzo[1,3]dioxol-5-ylmethyl)-6-bromo-4-phenyl-2H-isoquinolinon-1-one, 6-bromo-2-(4-methanesulfonylbenzyl)-1-oxo-4-phenyl-1,2-dihydroisoquinoline-3-carbothioic acid S-pyridin-2-ylester and the like are particularly preferably used.

A prodrug of a compound represented by the above-mentioned formula (I) or a salt thereof [hereinafter sometimes to be referred to as Compound (I)] and a compound represented by the above-mentioned formula (I') or a salt thereof [hereinafter sometimes to be referred to as Compound (I'); since Compound (I') is encompassed in Compound (I), it may be described as Compound (I) as a general name of Compound (I) and Compound (I')] refers to a compound capable of being converted to Compound (I) by reactions due to an enzyme, gastric juice and the like, under physiological conditions in vivo, i.e., a compound capable of being converted to Compound (I) upon enzymatic oxidation, reduction, hydrolysis and the like, or a compound capable of being converted to Compound (I) upon hydrolysis and the like by gastric juice and the like. Examples of the prodrugs of Compound (I) include compounds derived by acylation, alkylation or phosphorylation of the amino group in Compound (I) (e.g., compounds derived by eicosanoylation, alanylation, pentylaminocarbonylation, (5-methyl-2-oxo-1,3-dioxolen-4-yl) methoxycarbonylation, tetrahydrofuranylation, pyrrolidylmethylation, pivaloyloxymethylation or tert-butylation of the amino group in Compound (I), etc.); compounds derived by acylation, alkylation, phosphorylation or boration of the hydroxy group in Compound (I) (e.g., compounds derived by acetylation, palmitoylation, propanoylation, pivaloylation, succinylation, fumarylation, alanylation or dimethylaminomethylcarbonylation of the hydroxy group in Compound (I), etc.); compounds derived by esterification or amidation of the carboxyl group in Compound (I) (e.g., compounds derived by ethyl esterification, phenylesterification, carboxymethyl esterification, dimethylaminomethyl esterification, pivaloyloxymethyl esterification, ethoxycarbonyloxyethyl esterification, phthalidylesterification, (5-methyl-2-oxo-1,3-dioxolen-4-yl)methyl esterification, cyclohexyloxycarbonylethyl esterification or methylamidation of the carboxyl group in Compound (I), etc.), and the like. These compounds can be produced from Compound (I) by methods known per se.

The prodrug of Compound (I) may be one capable of being converted to Compound (I) under physiological conditions, as described in "Iyakuhin No Kaihatsu (Development of Drugs)", vol. 7, Molecular Designing, published by Hirokawa Shoten, 1990, pages 163-198.

As the salts of Compound (I), pharmacologically acceptable salts and the like can be mentioned, such as addition salt with an acid (e.g., trichloroacetic acid, acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydroiodic acid, sulfamic acid, sulfuric acid and the like), metal salts such as sodium, potassium, magnesium, calcium and the like, organic salts such as trimethylamine, triethylamine, pyridine, picoline, dicyclohexylamine, N-methylpyrrolidine, N-methylpiperidine, N-methylmorpholine and the like, and the like.

When an optically active form of Compound (I) is desired, for example, it can be obtained using an optically active starting material, or by separation of a racemic form of the compound by conventional methods.

The Compound (I) and a salt thereof can be produced by, for example, the following Methods A-D. Each compound described in the following reaction formulas may form a salt as long as the reaction is not inhibited, and as such salt, those similar to the salts of Compound (I) can be mentioned.

Method A

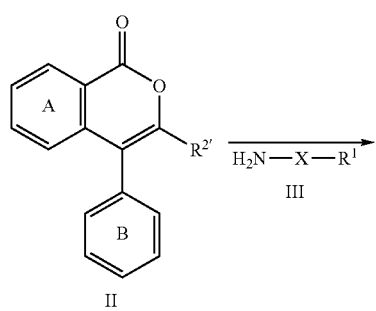

Method B

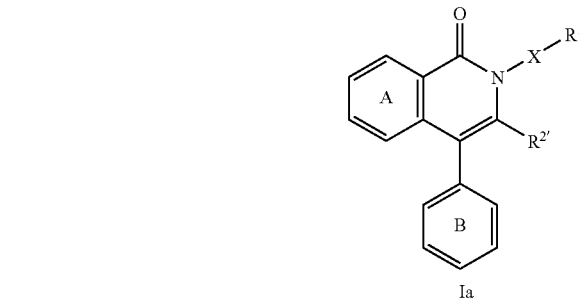

-continued

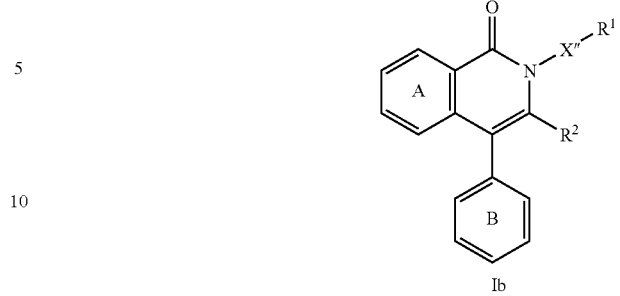

Method C

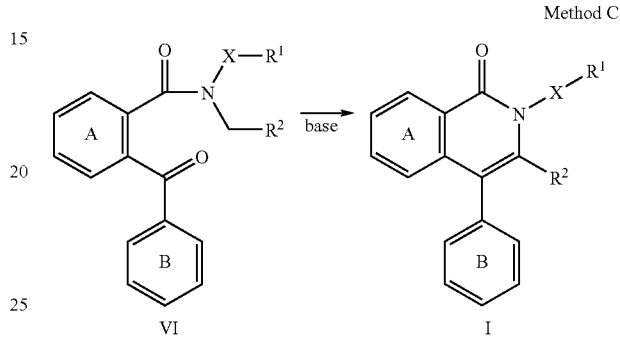

Method D

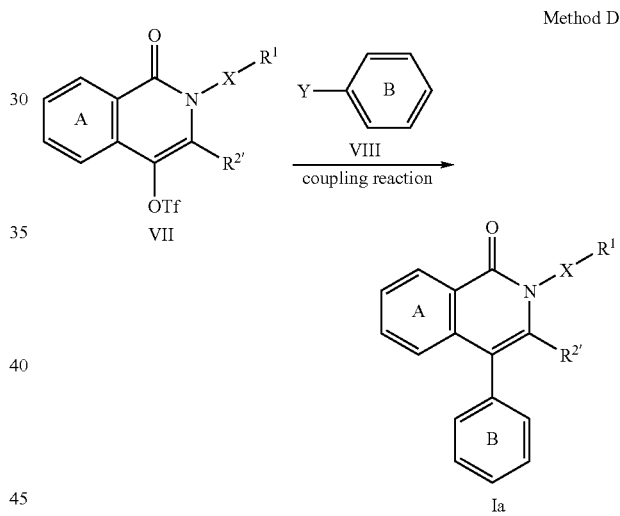

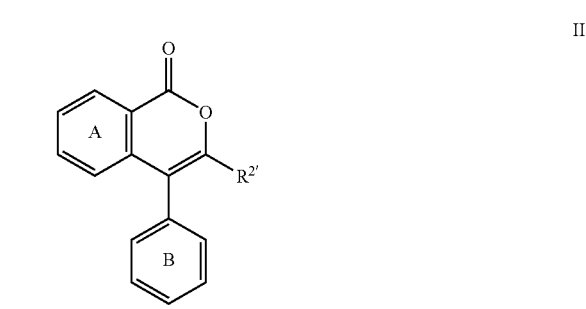

Method A

When $R^2$ of Compound (I) is an optionally esterified carboxyl group or an acyl group, compound (Ia) can be produced by reacting compound (II) represented by the formula (II)

wherein $R^{2'}$ is an optionally esterified carboxyl group or an acyl group, and other symbols are as defined above, or a salt thereof with amino compound (III) represented by the formula (III) H₂N—X ... R¹ wherein the symbols in the formula are as defined above, or a salt thereof, and then conducting dehydration.

This reaction is carried out in a solvent or without a solvent, and a solvent that does not inhibit the reaction is appropriately selected. As such solvent for example, alcohols such as methanol, ethanol, propanol, isopropanol, butanol, tert-butanol and the like; ethers such as dioxane, tetrahydrofuran, diethyl ether, tert-butylmethyl ether, diisopropyl ether, ethylene glycol-dimethyl ether and the like; esters such as ethyl formate, ethyl acetate, n-butyl acetate and the like; halogenated hydrocarbons such as dichloromethane, chloroform, carbon tetrachloride, trichloroethylene, 1,2-dichloroethane and the like; hydrocarbons such as n-hexane, benzene, toluene and the like; amides such as formamide, N,N-dimethylformamide, N,N-dimethylacetamide and the like; ketones such as acetone, methyl ethyl ketone, methylisobutyl ketone and the like; nitriles such as acetonitrile, propionitrile and the like; and the like; as well as dimethyl sulfoxide, sulfolane, hexamethylphosphoramide, water and the like are used alone or as a mixed solvent.

This reaction is preferably carried out in the presence of a base, and as such base, for example, inorganic bases such as sodium carbonate, potassium carbonate, sodium hydrogen carbonate and the like, and amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine and the like are used.

For the reaction, about 1 to about 20 mol, preferably about 1 to about 5 mol, of compound (III) is used relative to 1 mol of compound (II).

The reaction temperature is about −20° C. to about 150° C., preferably about 10° C. to about 80° C.

While the reaction time varies depending on the kind of compound (II) or (III), the kind of solvent, reaction temperature and the like, it is generally about 1 min to about 72 hr, preferably about 15 min to about 24 hr.

The dehydration step of this reaction may be completed by the reaction step of compound (II) and compound (III) depending on the conditions, but generally, an acid is used for dehydration. As such acid, organic acids such as acetic acid, trifluoroacetic acid, methanesulfonic acid, p-toluenesulfonic acid and the like, mineral acids such as hydrochloric acid, sulfuric acid, nitric acid, phosphoric acid, hydrobromic acid, perchloro acid and the like, Lewis acids such as aluminum chloride, zinc chloride, boron trifluoride etherate, titanium tetrachloride and the like, and the like are used.

For a solvent to be used for the dehydration step, a solvent that does not inhibit the reaction is appropriately selected, and as such solvent, a solvent used for the reaction of compound (II) with compound (III) is used.

The reaction temperature is about −20° C. to about 200° C., preferably about 0° C. to about 120° C.

While the reaction time varies depending on the reaction conditions, it is generally about 1 min to about 72 hr, preferably about 15 min to about 15 hr.

Method B

When X of Compound (I) is —CHR³—, compound (Ib) can be produced by reacting compound (IV) represented by the formula (IV)

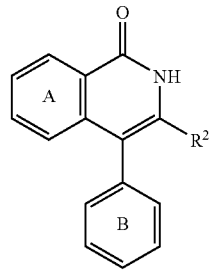

wherein the symbols in the formula are as defined above, with compound (V) represented by the formula (V) L-X" ... R¹ [for the symbols in the formula, L is a leaving group (e.g., halogen atom (e.g., chlorine, bromine, iodine etc.), a group represented by the formula $R^L$—SO₂—O— wherein $R^L$ is a lower alkyl group optionally substituted by a halogen atom or a phenyl group optionally having substituent(s) and the like) and the like], X" is —CHR³—, and other symbols are as defined above].

This method can be performed by alkylation reaction of compound (IV) or a salt thereof using compound (V) or a salt thereof (inorganic acid, organic acid etc.).

In the aforementioned formula, as the lower alkyl group of the "lower alkyl group optionally substituted by a halogen atom" represented by $R^L$, for example, a $C_{1-6}$ alkyl group such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl and the like can be mentioned. Particularly, a $C_{1-4}$alkyl group such as methyl, ethyl, propyl, isopropyl, butyl, isobutyl and the like are preferable. As the "lower alkyl group substituted by a halogen atom (e.g., fluorine, chlorine, bromine, iodine etc.)" represented by $R^L$, for example, trichloromethyl, trifluoromethyl and the like can be mentioned.

As the substituent of the phenyl group represented by $R^L$, for example, a lower alkyl group (group similar to the aforementioned lower alkyl group represented by $R^L$), a lower alkoxy group (e.g., a $C_{1-6}$ alkoxy group such as methoxy, ethoxy, propoxy, isopropoxy, butoxy and the like), a halogen atom (e.g., fluorine, chlorine, bromine, iodine etc.), a nitro group, a cyano group and the like are used.

This reaction is generally carried out in a solvent in the presence of a base. As a base to be used for the reaction, for example, hydrogenated alkali metals such as potassium hydride, sodium hydride and the like, metal alkoxides having 1 to 6 carbon atoms such as lithium ethoxide, lithium tert-butoxide, sodium methoxide, sodium ethoxide, potassium tert-butoxide and the like, inorganic bases such as lithium hydroxide, potassium hydroxide, sodium hydroxide, sodium carbonate, potassium carbonate, cesium carbonate, sodium hydrogen carbonate and the like, organic amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine, 1,5-diazabicyclo[4.3.0]non-5-ene, 1,4-diazabicyclo[2.2.2]octane, 1,8-diazabicyclo[5.4.0]-7-undecene and the like, 2-tert-butylimino-2-diethylamino-1,3-dimethyl-perhydro-1,3,2-diazaphosphorin and resins thereof and the like are used.

As such solvent, a solvent that does not inhibit the reaction is appropriately selected. As such solvent for example, alcohols such as methanol, ethanol, propanol, isopropanol, butanol, tert-butanol and the like, ethers such as dioxane, tetrahydrofuran, diethyl ether, tert-butylmethyl ether, diisopropyl ether, ethylene glycol-dimethyl ether and the like, esters such as ethyl formate, ethyl acetate, n-butyl acetate and the like, halogenated hydrocarbons such as dichloromethane, chloroform, carbon tetrachloride, trichloroethylene, 1,2-dichloroethane and the like, hydrocarbons such as n-hexane, benzene, toluene and the like, amides such as formamide, N,N-dimethylformamide, N,N-dimethylacetamide and the like, nitriles such as acetonitrile, propionitrile and the like, and the like, as well as dimethyl sulfoxide, sulfolane, hexamethylphosphoramide, water and the like are used alone or as a mixed solvent.

For the reaction, about 1 to about 5 mol, preferably about 1 to about 2 mol, of compound (V) is used relative to 1 mol of compound (IV).

The reaction temperature is about −50° C. to about 150° C., preferably about −20° C. to about 100° C.

While the reaction time varies depending on the kind of compound (IV) or (V), the kind of solvent and base, reaction temperature and the like, it is generally about 1 min to about 100 hr, preferably about 15 min to about 48 hr.

Method C

The Compound (I) or a salt thereof can be produced by intramolecular cyclization of compound (VI) represented by the formula (VI)

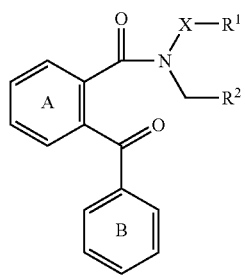

VI wherein the symbols in the formula are as defined above, or a salt thereof.

This cyclization reaction is carried out by treating compound (VI) with a base.

The reaction of this method is generally carried out in a solvent, and a solvent that does not inhibit the reaction is appropriately selected. As such solvent for example, alcohols such as methanol, ethanol, propanol, isopropanol, butanol, tert-butanol and the like, ethers such as dioxane, tetrahydrofuran, diethyl ether, tert-butylmethyl ether, diisopropyl ether, ethylene glycol-dimethyl ether and the like, esters such as ethyl formate, ethyl acetate, n-butyl acetate and the like, halogenated hydrocarbons such as dichloromethane, chloroform, carbon tetrachloride, trichloroethylene, 1,2-dichloroethane and the like, hydrocarbons such as n-hexane, benzene, toluene and the like, amides such as formamide, N,N-dimethylformamide, N,N-dimethylacetamide and the like, nitriles such as acetonitrile, propionitrile and the like and the like, as well as dimethyl sulfoxide, sulfolane, hexamethylphosphoramide, water and the like are used alone or as a mixed solvent.

In addition, as a base to be used for this reaction, for example, hydrogenated alkali metals such as potassium hydride, sodium hydride and the like, metal alkoxides having 1 to 6 carbon atoms such as lithium ethoxide, lithium tert-butoxide, sodium methoxide, sodium ethoxide, potassium tert-butoxide and the like, inorganic bases such as lithium hydroxide, potassium hydroxide, sodium hydroxide, sodium carbonate, potassium carbonate, sodium hydrogen carbonate and the like, organic amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine, 1,5-diazabicyclo[4.3.0]non-5-ene, 1,4-diazabicyclo[2.2.2]octane, 1,8-diazabicyclo[5.4.0]-7-undecene and the like, organic lithiums such as methyllithium, n-butyllithium, sec-butyllithium, tert-butyllithium and the like, lithium amides such as lithium diisopropylamide and the like, and the like are used.

For the reaction, about 0.01 to about 100 mol, preferably about 0.1 to about 3 mol, of a base is used relative to 1 mol of compound (VI).

The reaction temperature is about −80° C. to about 200° C., preferably about −20° C. to about 100° C.

While the reaction time varies depending on the kind of compound (VI), the kind of basic catalyst, the kind of solvent, reaction temperature and the like, it is generally about 1 min to about 72 hr, preferably about 15 min to about 24 hr.

Method D

The Compound (I) can be produced by reacting compound (VII) represented by the formula (VII)

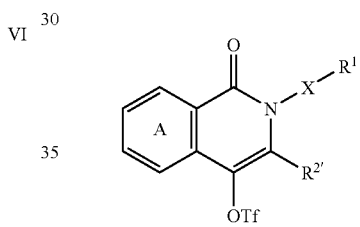

VII wherein OTf is a triflate group and other symbols are as defined above, or a salt thereof with compound (VIII) represented by the formula (VIII)

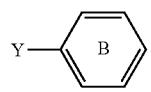

VIII wherein Y is an atomic group capable of crosscoupling reaction (e.g., atomic group bonded by boron, tin, magnesium and the like, etc.) and other symbols are as defined above, or a salt thereof.

According to this method, Compound (I) is produced by crosscoupling reaction (e.g., Suzuki coupling reaction, Stille coupling reaction etc.) of compound (VII) or a salt thereof with compound (VIII) or a salt thereof in the presence of a metal catalyst.

This reaction is generally carried out in the presence of a base, and as such base, for example, hydrogenated alkali metals (e.g., sodium hydride, potassium hydride and the like), alkali metal hydroxides (e.g., lithium hydroxide, sodium hydroxide, potassium hydroxide and the like), alkaline earth metal hydroxides (e.g., magnesium hydroxide, calcium hydroxide and the like), alkali metal carbonates (e.g., sodium carbonate, potassium carbonate and the like), inorganic bases such as alkali metal hydrogen carbonates (e.g., sodium hydrogen carbonate, potassium hydrogen carbonate and the like), and the like, metal alkoxides having 1 to 6 carbon atoms (e.g., sodium methoxide, sodium ethoxide, sodium tert-butoxide and the like), organic bases such as trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2]octane, 1,8-diazabicyclo[5.4.0]-7-undecene and the like, organic lithiums such as methyllithium, n-butyllithium, sec-butyllithium, tert-butyllithium and the like, lithium amides such as lithiumdiisopropylamide and the like, and the like are used.

This reaction is generally carried out in a solvent, and a solvent that does not inhibit the reaction is appropriately selected. As such solvent, alcohols such as methanol, ethanol, propanol, isopropanol, butanol, tert-butanol and the like, ethers such as dioxane, tetrahydrofuran, diethyl ether, tert-butylmethyl ether, diisopropyl ether, ethylene glycol-dimethyl ether and the like, esters such as ethyl formate, ethyl acetate, n-butyl acetate and the like, halogenated hydrocarbons such as dichloromethane, chloroform, carbon tetrachloride, trichloroethylene, 1,2-dichloroethane and the like, hydrocarbons such as n-hexane, benzene, toluene and the like, amides such as formamide, N,N-dimethylformamide, N,N-dimethylacetamide and the like, nitrites such as acetonitrile, propionitrile and the like, and the like, as well as dimethyl sulfoxide, sulfolane, hexamethylphosphoramide, water and the like are used alone or as a mixed solvent.

This crosscoupling reaction can be generally accelerated by the use of a metal catalyst. As such metal catalyst, a metal complex having various ligands is used, and, for example, palladium compounds [e.g., palladium acetate, tetrakis(triphenylphosphine)palladium, bis(triphenylphosphine)palladium chloride, dichloro bis(triethylphosphine)palladium, tris (dibenzylidene-acetone)dipalladium-2,2'-bis (diphenylphosphino)-1,1'-binaphthyl, complex of palladium (II)acetate and 1,1'-bis(diphenylphosphino)ferrocene and the like], nickel compounds [e.g., tetrakis(triphenylphosphine) nickel, bis(triethylphosphine)nickel chloride, bis(triphenylphosphine)nickel chloride and the like], rhodium compounds [e.g., tri(triphenylphosphine)rhodium chloride and the like], cobalt compounds, platinum compounds and the like are used. Of these, palladium and nickel compounds are preferable. The amount of these catalysts to be used is about 1-0.000001 mol, preferably about 0.1-0.0001 mol, relative to 1 mol of compound (VII).

For the reaction, about 0.8-10 mol, preferably about 0.9-2 mol, of compound (VIII) and about 1-about 20 mol, preferably about 1-about 5 mol, of a base are used relative to 1 mol of compound (VII).

The reaction temperature is about −10° C.-about 250° C., preferably about 0° C.-about 150° C.

While the reaction time varies depending on the kind of compound (VII), compound (VIII), metal catalyst, base and solvent, reaction temperature and the like, it is generally about 1 min to about 200 hr, preferably about 5 min to about 100 hr.

Method E

While compound (Ic) represented by the formula (Ic)

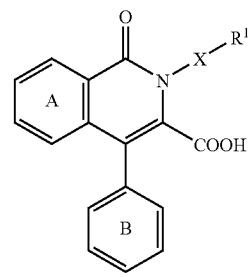

Ic wherein the symbols in the formula are as defined above, wherein $R^2$ of Compound (I) is a carboxyl group, is produced by the aforementioned Method A, various derivatives can be produced by modifying the carboxyl group of compound (Ic) by a method known per se or a method analogous thereto.

For example, 1) by esterifying compound (Ic), compound (Id) represented by the formula

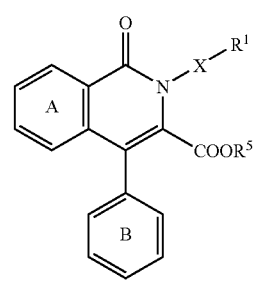

Id wherein $R^5$ is a hydrocarbon group optionally having substituent(s) or a heterocyclic group optionally having substituent(s), and other symbols are as defined above, can be produced.

For this esterification reaction, a method known per se or a method analogous thereto can be used. For example, a method comprising reacting compound (Ic) with a compound represented by $R^5$-Q [Q is a leaving group (e.g., halogen atom (e.g., chlorine, bromine, iodine and the like), a group represented by the formula $R^Q$—$SO_2$—O— wherein $R^Q$ is a group similar to the aforementioned $R^L$ such as a lower alkyl group optionally substituted by a halogen atom or a phenyl group optionally having substituent(s) and the like, and the like) and the like]] in the presence of a base, a method comprising reacting compound (Ic) with alcohols represented by $R^5$—OH in the presence of an acid catalyst, a method comprising condensation using a condensation agent [for example, carbodiimides (DCC, WSC, DIC etc.), phosphoric acid derivatives (e.g., diethyl cyanophosphorate, diphenyl azidophosphorate, BOP-Cl etc.) and the like], or a method comprising Mitsunobu reaction using a reagent such as triphenylphosphine and diethyl azodicarboxylate and the like, a method comprising reacting a reactive derivative (e.g., acid halide, active ester, acid azide etc.) of compound (Ic) with alcohols represented by $R^5$—OH in the presence of a base, and the like can be used.

2) By reducing compound (Ic), compound (Ie) represented by the formula (Ie)

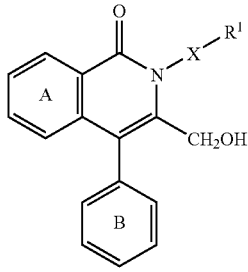

Ie wherein the symbols in the formula are as defined above, can be produced.

For this reduction reaction, a method known per se or a method analogous thereto can be used. For example, a method comprising reducing compound (Ic) or a reactive derivative thereof (e.g., acid halide, acid anhydride, active ester, ester, acid imidazolide, acid azide etc.) with a reduction agent (e.g., sodium borohydride, lithium aluminum hydride, diisobutyl aluminum hydride, diborane etc.) and the like can be used.

3) By amidating compound (Ic), compound (If) represented by the formula (If)

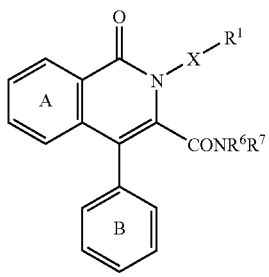

If wherein $R^6$ and $R^7$ are each a hydrogen atom, an optionally substituted hydrocarbon group, an optionally substituted heterocyclic group, an optionally substituted amino group or an optionally substituted hydroxy group and other symbols are as defined above, can be produced.

For this amidation reaction, a method known per se or a method analogous thereto can be used. For example, a method comprising use of compound (Ic) and amine with a condensation agents [e.g., carbodiimides (DCC, WSC, DIC etc.), phosphoric acid derivatives (e.g., diethyl cyanophosphate, DPPA, BOP-Cl etc.) and the like], or a method comprising reacting a reactive derivative (e.g., acid halide, acid anhydride, active ester, ester, acid imidazolide, acid azide etc.) of compound (Ic) with amine and the like can be used.

4) By converting a carboxyl group of compound (Ic) to an amino group, compound (Ig) represented by the formula (Ig)

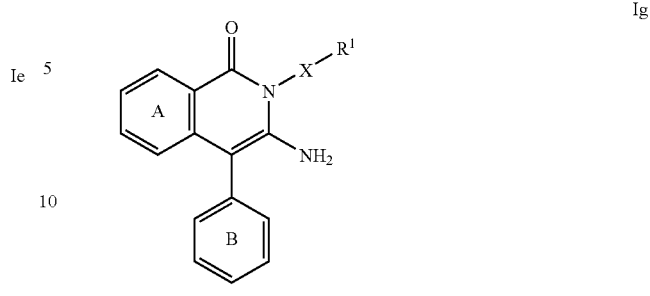

Ig wherein the symbols in the formula are as defined above, can be produced.

For this conversion reaction, a method known per se such as Curtius rearrangement, Hofmann reaction and Schmidt reaction or a method analogous thereto can be used. For example, a method comprising converting compound (Ic) or a reactive derivative thereof (e.g., acid halide, acid anhydride, active ester, ester, acid imidazolide etc.) to an acid azide form, producing an isocyanate form by thermal rearrangement, directly hydrolyzing the isocyanate or reacting the isocyanate with alcohols and removing the resulting carbamate type protective group of the amine can be used.

Method F

For the substituent $R^4$ at the 6-position of isoquinolinone of compound (Ih) represented by the formula (Ih)

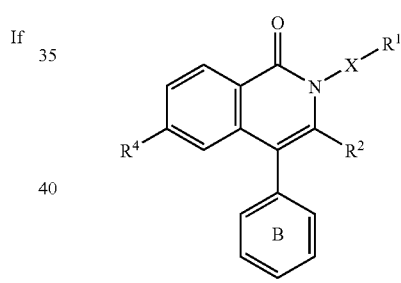

Ih wherein the symbols in the formula are as defined above, compounds having various substituent(s) $R^4$ can be produced by converting the halogen atom at the 6-position of isoquinolinone of compound (Ii) represented by the formula (Ii)

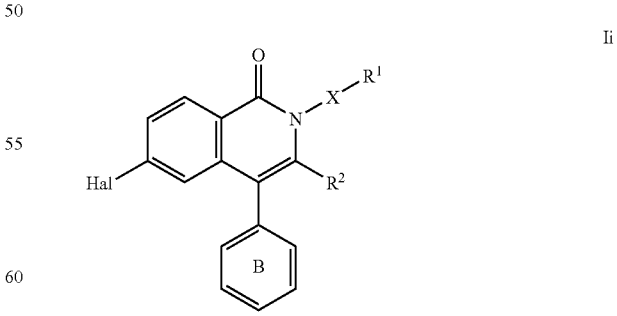

Ii wherein Hal is a halogen atom and other symbols are as defined above.

For this conversion reaction, a method known per se such as nucleophilic addition reaction using amine, alkoxide and thiolate and various coupling reactions (Suzuki coupling reaction, Heck reaction, Stille coupling reaction, Buchwald amination reaction, carbonyl insertion reaction using carbon monoxide etc.) using a metal catalyst or a method analogous thereto can be used. For example, when the halogen atom of compound (Ii) is fluorine, it is suitable for nucleophilic addition reaction, when the halogen atom is iodine, bromine or chlorine atom, it is suitable for a coupling reaction. As the metal catalyst and solvent used for this coupling reaction, those similar to the ones used in the aforementioned Method D can be used.

As substituent $R^4$ that can be introduced by this coupling reaction, for example, an optionally substituted alkyl group (e.g., methyl, ethyl, butyl etc.), an optionally substituted alkenyl group (e.g., vinyl, propenyl, allyl, 2-methoxycarbonylvinyl, stryryl etc.), an optionally substituted alkynyl group (e.g., ethynyl, 1-propynyl, propargyl etc.), an optionally substituted aryl group (e.g., phenyl, naphthyl etc.), an optionally substituted heterocyclic group (e.g., pyridyl, thienyl, furyl, imidazolyl group, triazolyl group etc.), a cyano group, an optionally substituted alkoxycarbonyl group (e.g., methoxycarbonyl group, ethoxycarbonyl group etc.), an optionally substituted carbamoyl group (e.g., carbamoyl group, methylcarbamoyl group etc.), optionally substituted various amino groups (e.g., amino group, methylamino group, dimethylamino group, benzylamino group, 1-piperidino group, anilino group, pyridylamino group etc.), an optionally substituted phenoxy group, an optionally substituted phthalimid-1-yloxy group and the like can be mentioned.

Method G

Compound (I) wherein X is —O—, —NH— or —N═ can be produced by reacting compound (Ij) represented by the formula (Ij)

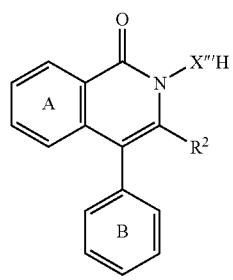

Ij wherein X''' is O or NH and other symbols are as defined above, with T-$R^1$ or O═$R^1$ wherein T is a leaving group (a group similar to the leaving group represented by the aforementioned L and the like) or a hydroxy group and other symbols are as defined above.

Compound (I) wherein X is —O— or —NH— can be produced by, for example, reacting compound (Ij) with a compound represented by $R^1$-T' [T' is a leaving group (e.g., halogen atom (e.g., chlorine, bromine, iodine and the like), a group represented by the formula $R^T$—SO$_2$—O— wherein $R^T$ is a group similar to the aforementioned $R^L$ such as a lower alkyl group optionally substituted by a halogen atom, a phenyl group optionally having substituent(s) and the like, and the like] in the presence of a base, or subjecting compound (Ij) and alcohols represented by $R^5$—OH to Mitsunobu reaction using triphenylphosphine and a reagent such as diethyl azodicarboxylate and the like. Moreover, Compound (I) wherein X is —NH— can be produced by reacting compound (Ij) wherein X''' is NH with a carbonyl compound represented by O═R to synthesize a hydrazone compound and reducing a C═N double bond using a reduction agent (e.g., sodium cyanoborohydride, sodium borohydride, sodium triacetoxyborohydride, triethylsilane, catalytic reduction and the like).

Method H

When the substituent(s) of $R^1$, $R^2$, $R^3$, ring A and ring B of Compound (I) have a functional group capable of converting the substituent(s) (e.g., carboxyl group, amino group, hydroxy group, carbonyl group, thiol group, ester group, sulfo group, halogen atom and the like), various compounds can be produced by converting functional groups by methods known per se or methods analogous thereto.

In the case of a carboxyl group, for example, reactions such as esterification, reduction, amidation, conversion to optionally protected amino group and the like, shown in the aforementioned Method E, afford conversion. In the case of an amino group, for example, reactions such as amidation, sulfonylation, nitrosation, alkylation, arylation, imidation and the like afford conversion. In the case of a hydroxy group, reactions such as esterification, carbamoylation, sulfonylation, alkylation, arylation, oxidation, halogenation and the like afford conversion. In the case of a carbonyl group, reactions such as reduction, oxidation, imination (including oximation, hydrazonation), (thio)ketalation, alkylidenation, thiocarbonylation and the like afford conversion. In the case of a thiol group, reactions such as alkylation, oxidation and the like afford conversion. In the case of an ester group, reactions such as reduction, hydrolysis and the like afford conversion. In the case of a sulfo group, reactions such as sulfonamidation, reduction and the like afford conversion. In the case of a halogen atom, reactions such as various nucleophilic substitution reactions, various coupling reactions and the like afford conversion.

The starting compounds (II), (IV), (VI) and (VII) used for the aforementioned production methods A to D can be produced by, for example, a method known per se shown in the following or a method analogous thereto.

Method I

An isocoumarin compound (II) represented by the formula (II)

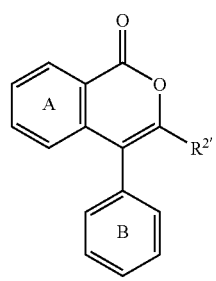

II wherein the symbols in the formula are as defined above, or a salt thereof can be produced by a method described in, for example, *J. Med. Chem.*, 38: 3106-20 (1995) and the like, by reacting compound (IX) represented by the formula (IX)

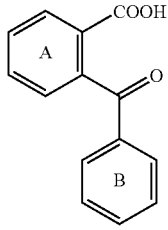

wherein the symbols in the formula are as defined above, or a salt thereof with compound (X) represented by the formula (X)

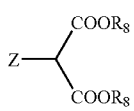

wherein Z is a leaving group (e.g., halogen atom (e.g., chlorine, bromine, iodine and the like), a group represented by the formula $R^Z$—$SO_2$—O— wherein $R^Z$ is a group similar to the aforementioned $R^L$ such as a lower alkyl group optionally substituted by a halogen atom or a phenyl group optionally having substituent(s) and the like, and the like) and $R^8$ is a lower ($C_{1-6}$)alkyl group (e.g., methyl, ethyl, propyl, butyl, tert-butyl group etc.), or a salt thereof in the presence of a base and subsequently applying dehydration and decarbonization under acidic conditions to give isocoumarin compound (II) wherein the 3-position is a carboxyl group. Where desired, the carboxylic acid thereof is esterified to give a 3-position esterified form.

Method J

A compound (IV) represented by the formula (IV)

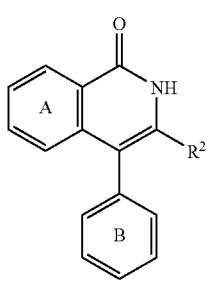

wherein the symbols in the formula are as defined above, or a salt thereof can be produced by reacting compound (II) represented by the formula (II)

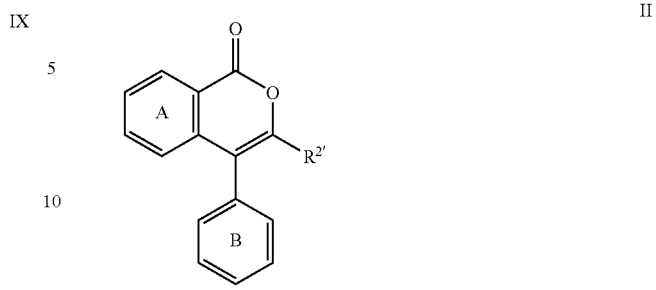

wherein the symbols are as defined above, or a salt thereof with ammonia and then dehydrating under acidic conditions.

Method K

A compound (VI) represented by the formula (VI)

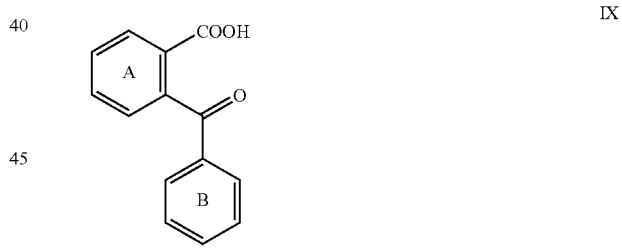

wherein the symbols are as defined above, or a salt thereof can be produced by reacting compound (IX) represented by the formula (IX)

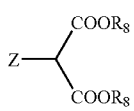

wherein the symbols in the formula are as defined above, or a salt thereof or a reactive derivative thereof (e.g., acid halide, acid anhydride, active ester, ester, acid imidazolide, acid azide etc.) with compound (XI) represented by the formula (XI)

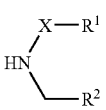

wherein the symbols are as defined above, or a salt thereof.

This reaction is an amidation reaction, and the reactive derivative of compound (IX), reaction conditions, reaction solvent, reaction time and the like follow the methods explained in the aforementioned method E-3.

Method L

A compound (VII) represented by the formula (VII)

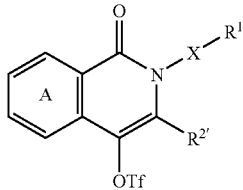

wherein the symbols are as defined above, or a salt thereof can be produced by, for example, the following method.

A compound (XII) represented by the formula (XII)

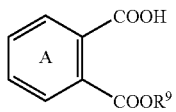

wherein $R^9$ is an optionally substituted hydrocarbon group or an optionally substituted heterocycle and other symbols are as defined above, or a salt thereof or a reactive derivative thereof (e.g., acid halide, acid anhydride, active ester, ester, acid imidazolide, acid azide etc.) is reacted with compound (XI) represented by the formula (XI)

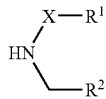

wherein the symbols are as defined above, or a salt thereof to give amide compound (XIII) represented by the formula (XIII)

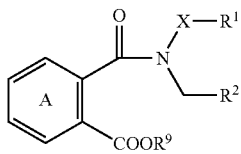

wherein the symbols in the formula are as defined above, or a salt thereof.

This reaction is an amidation reaction and the reactive derivative of compound (XII), reaction conditions, reaction solvent, reaction time and the like follow the methods explained in the aforementioned method E-3.

The obtained compound (XIII) or a salt thereof is subjected to an intramolecular cyclization reaction by a method similar to the aforementioned Method C to give compound (XIV) represented by the formula (XIV)

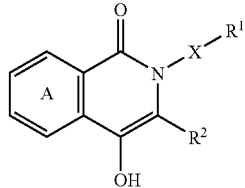

wherein the symbols in the formula are as defined above, or a salt thereof.

The Compound (VII) or a salt thereof can be produced by reacting compound (XIV) or a salt thereof in the presence of a base with triflateing reagent (e.g., trifluoromethanesulfonic acid anhydride, bis(trifluoromethanesulfonyl)aniline etc.).

As the base to be used in this reaction, for example, hydrogenated alkali metals (e.g., sodium hydride, potassium hydride and the like), alkali metal hydroxides (e.g., lithium hydroxide, sodium hydroxide, potassium hydroxide and the like), alkaline earth metal hydroxides (e.g., magnesium hydroxide, calcium hydroxide and the like), inorganic bases such as alkali metal carbonates (e.g., sodium carbonate, potassium carbonate and the like), alkali metal hydrogen carbonates (e.g., sodium hydrogen carbonate, potassium hydrogen carbonate and the like), and the like, metal alkoxides having 1 to 6 carbon atoms (e.g., sodium methoxide, sodium ethoxide, sodium tert-butoxide and the like), organic bases such as trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2]octane, 1,8-diazabicyclo[5.4.0]-7-undecene and the like, organic lithiums such as methyllithium, n-butyllithium, sec-butyllithium, tert-butyllithium and the like, lithium amides such as lithiumdiisopropylamide and the like, and the like are preferably used.

This reaction is generally carried out in a solvent, and a solvent that does not inhibit the reaction is appropriately selected. As such solvent, alcohols such as methanol, ethanol, propanol, isopropanol, butanol, tert-butanol and the like, ethers such as dioxane, tetrahydrofuran, diethyl ether, tert-butylmethyl ether, diisopropyl ether, ethylene glycol-dimethyl ether and the like, esters such as ethyl formate, ethyl acetate, n-butyl acetate and the like, halogenated hydrocarbons such as dichloromethane, chloroform, carbon tetrachloride, trichloroethylene, 1,2-dichloroethane and the like, hydrocarbons such as n-hexane, benzene, toluene and the like, amides such as formamide, N,N-dimethylformamide, N,N-dimethylacetamide and the like, nitriles such as acetonitrile, propionitrile and the like, and the like, as well as dimethyl sulfoxide, sulfolane, hexamethylphosphoramide, water and the like are used alone or as a mixed solvent.

Method M

Of the compounds wherein $R^2$ of Compound (I) is an acyl group, compound (Ik) represented by the formula (Ik)

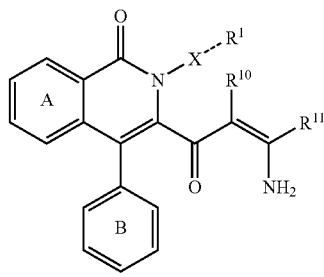

wherein $R^{10}$ is a hydrogen atom or an optionally substituted hydrocarbon group, $R^{11}$ is an optionally substituted hydrocarbon group, an optionally substituted heterocyclic group or an optionally esterified carboxyl group, and other symbols are as defined above, can be produced from compound (Im) represented by the formula (Im)

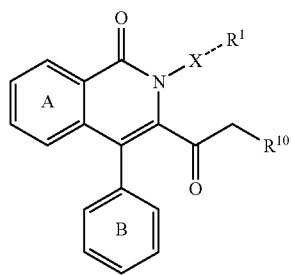

wherein the symbols in the formula are as defined above, which is produced by the aforementioned methods A-C, according to a method known per se or a method analogous thereto.

For example, compound (Im) is halogenated using a method known per se or a method analogous thereto to convert to compound (In) represented by the formula (In)

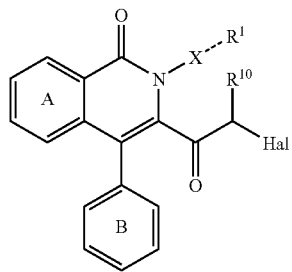

wherein the symbols in the formula are as defined above, and then compound (In) is reacted with compound (XV) represented by the formula (XV)

$R^{11}CSNH_2$ (XV)

wherein the symbols in the formula are as defined above, whereby compound (Ik) can be produced.

The halogenation is achieved by treating compound (Im) with halogens or metal halide. This reaction is carried out in the presence of a base or a basic salt on demand.

The amount of the halogens or metal halide to be used is about 1 to about 10 mol, preferably about 1 to about 3 mol, relative to 1 mol of compound (Im).

As the "halogens", bromine, chlorine, iodine and the like are used.

As the "metal halide", halogenated copper such as copper (II) bromide, copper(II) chloride and the like, and the like are used.

The amount of a base to be used is about 1 to about 10 mol, preferably about 1 to about 3 mol, relative to 1 mol of compound (Im).

As the "base", for example, inorganic bases such as sodium hydroxide, potassium hydroxide, lithium hydroxide, sodium carbonate, potassium carbonate, cesium carbonate, sodium hydrogen carbonate, sodium acetate and the like, organic bases such as pyridine, lutidine, triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like are used. This reaction is advantageously carried out without solvent or in a solvent inert to the reaction. While the solvent is not particularly limited as long as the reaction proceeds, for example, ethers, esters, aromatic hydrocarbons, aliphatic hydrocarbons, amides, halogenated hydrocarbons, nitriles, sulfoxides, organic acids, water, aromatic amines and the like are used alone or as a mixed solvent.

The reaction temperature is about −20 to about 150° C., preferably about 0 to about 100° C. The reaction time is generally about 5 min to about 72 hr, preferably about 10 min to about 24 hr.

While compound (In) can be used in the next reaction in the form of a reaction mixture or as a crude product, it can be isolated from the reaction mixture according to conventional methods, and easily purified by separation means such as recrystallization, distillation, chromatography and the like.

Where desired, the reaction of compound (In) with compound (XV) is carried out in the presence of a base.

The amount of compound (XV) to be used is about 0.5 to about 10 mol, preferably about 0.8 to about 5 mol, relative to 1 mol of compound (In).

The amount of a base to be used is about 1 to about 30 mol, preferably about 1 to about 10 mol, relative to 1 mol of compound (In).

As the "base", for example, inorganic bases such as sodium carbonate, potassium carbonate, cesium carbonate, sodium hydrogen carbonate, sodium acetate and the like, organic bases such as pyridine, lutidine, triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like are used.

This reaction is advantageously carried out without solvent or in a solvent inert- to the reaction. While the solvent is not particularly limited as long as the reaction proceeds, for example, halogenated hydrocarbons, aliphatic hydrocarbons, aromatic hydrocarbons, ethers, amides, alcohols, nitriles and the like are used alone or as a mixed solvent.

The reaction temperature is about −5 to about 200° C., preferably about 5 to about 150° C. The reaction time is generally about 5 min to about 72 hr, preferably about 0.5 to about 48 hr.

Method N

For compound (XV) used in Method M, a commercially available product may be purchased, or it can be produced according to a method known per se shown below or a method analogous thereto.

For example, compound (XV) can be obtained by treating compound (XVI) represented by the formula (XVI)

$R^{11}CN$ (XVI)

wherein the symbols in the formula are as defined above, with hydrogen sulfide or ammonium sulfide in the presence of a base.

The amount of hydrogen sulfide or ammonium sulfide to be used is about 1 to about 30 mol relative to 1 mol of compound (XVI).

The amount of a base to be used is about 1 to about 30 mol, preferably about 1 to about 10 mol, relative to 1 mol of compound (XVI).

As the "base", for example, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, ammonia or a mixture of two or more of these and the like are used.

This reaction is advantageously carried out without solvent or in a solvent inert to the reaction. While the solvent is not particularly limited as long as the reaction proceeds, for example, alcohols, halogenated hydrocarbons, aliphatic hydrocarbons, aromatic hydrocarbons, ethers, aromatic amines, amides, sulfoxides, water and the like are used alone or as a mixed solvent.

This reaction is carried out at atmospheric pressure or under pressurization. The reaction temperature is generally about −20 to about 80° C., preferably about −10 to about 50° C. The reaction time is generally about 5 min to about 72 hr, preferably about 0.5 to about 48 hr.

While compound (XV) can be used in the next reaction in the form of a reaction mixture or as a crude product, it can be isolated from the reaction mixture according to conventional methods, and easily purified by separation means such as recrystallization, distillation, chromatography and the like.

The compound (XV) can be also obtained by reacting compound (XVII) represented by the formula (XVII)

$$R^{11}CONH_2 \quad (XVII)$$

wherein the symbols in the formula are as defined above, with a sulfurization reagent such as phosphorus pentasulfide, a Lawesson reagent and the like.

The amount of sulfurization reagent to be used is about 0.5 to about 10 mol, preferably about 0.5 to about 3 mol, relative to 1 mol of compound (XVII).

This reaction is advantageously carried out without solvent or in a solvent inert to the reaction. While the solvent is not particularly limited as long as the reaction proceeds, for example, ethers, aromatic hydrocarbons, aliphatic hydrocarbons, aromatic amine, halogenated hydrocarbons and the like are used alone or as a mixed solvent.

The reaction time is generally 10 min to about 50 hr, preferably about 30 min to about 12 hr. The reaction temperature is generally about 0 to about 150° C., preferably about 20 to about 120° C.

While compound (XV) can be used in the next reaction in the form of a reaction mixture or as a crude product, it can be isolated from the reaction mixture according to conventional methods, and easily purified by separation means such as recrystallization, distillation, chromatography and the like.

For the starting compounds (VIII), (IX), (X), (XI), (XII), (XVI) and (XVII) used in the aforementioned production methods A to N, commercially available products may be purchased, or they can be produced according to a method known per se or a method analogous thereto.

When a compound is obtained in a free form by each of the aforementioned reactions of the present invention, it may be converted to a salt according to conventional methods, and when it is obtained as a salt, it can be also converted to a free form or other salts according to conventional methods.

In addition, when, in each of the aforementioned reactions of the production method of Compound (I) and each reaction of the synthesis of the starting compound, the starting compound has an amino group, a carboxyl group or a hydroxy group as a substituent, a protective group generally used in the peptide chemistry and the like may be introduced into these groups. After reaction, the protective group can be removed as necessary to give the object compound.

As an amino-protecting group, for example, formyl, $C_{1-6}$ alkylcarbonyl (e.g., acetyl, ethylcarbonyl and the like), phenylcarbonyl, $C_{1-6}$alkyl-oxycarbonyl (e.g., methoxycarbonyl, ethoxycarbonyl, tert-butoxycarbonyl (Boc) and the like), allyloxycarbonyl (Aloc), phenyloxycarbonyl, fluorenylmethyloxycarbonyl (Fmoc), $C_{7-10}$ aralkyl-carbonyl (e.g., benzylcarbonyl and the like), $C_{7-10}$ aralkyl-oxycarbonyl (e.g., benzyloxycarbonyl(Z) and the like), $C_{7-10}$ aralkyl (e.g., benzyl and the like), trityl, phthaloyl, N,N-dimethylaminomethylene and the like, each of which may have substituent(s), are used. As substituent(s) thereof, phenyl group, halogen atom (e.g., fluorine, chlorine, bromine, iodine and the like), $C_{1-6}$ alkyl-carbonyl (e.g., methylcarbonyl, ethylcarbonyl, butylcarbonyl and the like), nitro group and the like are used, and the number of substituent(s) is 1 to about 3.

As a carboxyl-protecting group, for example, $C_{1-6}$alkyl (e.g., methyl, ethyl, n-propyl, i-propyl, n-butyl, tert-butyl and the like), allyl, benzyl, phenyl, trityl or trialkylsilyl and the like are used. As substituent(s) thereof, halogen atom (e.g., fluorine, chlorine, bromine, iodine and the like), formyl, $C_{1-6}$alkyl-carbonyl (e.g., acetyl, ethylcarbonyl, butylcarbonyl and the like), nitro group and the like, each of which may have substituent(s), are used, and the number of substituent(s) is 1 to about 3.

As a hydroxy-protecting group, for example, $C_{1-6}$alkyl (e.g., methyl, ethyl, n-propyl, i-propyl, n-butyl, tert-butyl and the like), $C_{7-10}$aralkyl (e.g., benzyl and the like), formyl, $C_{1-6}$alkyl-carbonyl (e.g., acetyl, ethylcarbonyl and the like), benzoyl, $C_{7-10}$aralkyl-carbonyl (e.g., benzylcarbonyl and the like), tetrahydropyranyl, furanyl or silyl and the like, each of which may have substituent(s), are used. As substituent(s) thereof, halogen atom (e.g., fluorine, chlorine, bromine, iodine and the like), $C_{1-6}$alkyl (e.g., methyl, ethyl, n-propyl and the like), phenyl, $C_{7-10}$aralkyl (e.g., benzyl and the like), $C_{1-6}$alkoxy (e.g., methoxy, ethoxy, n-propoxy and the like), nitro group and the like are used, and the number of substituent(s) is 1 to about 4.

As a protecting group-removal method, methods known per se or methods analogous thereto are used, for example, methods employing treating with an acid, a base, reduction, ultraviolet rays, hydrazine, phenylhydrazine, sodium N-methyldithiocarbamate, tetrabutylammonium fluoride, palladium acetate and the like are used.

The Compound (I) thus obtained can be isolated and purified from a reaction mixture by a means known per se, such as extraction, concentration, neutralization, filtration, distillation, recrystallization, column chromatography, thin layer chromatography, preparative high performance liquid chromatography (HPLC), middle pressure preparative liquid chromatography (middle pressure preparative LC) and the like.

A salt of Compound (I) can be produced according to a method known per se, and, for example, when Compound (I) is a basic compound, by adding an inorganic acid or organic acid, or when Compound (I) is an acidic compound, by adding an organic base or an inorganic base.

When Compound (I) has optical isomers, each of such optical isomers and a mixture thereof are naturally encompassed in the scope of the present invention, and where desired, these isomers can be optically separated or individually produced according to a method known per se.

In addition, Compound (I) may be a hydrate, and both hydrate and non-hydrate are encompassed in the scope of the present invention. Furthermore, Compound (I) may be labeled with an isotope (e.g., $^3$H, $^{14}$C, $^{35}$S, $^{125}$I and the like) and the like.

Since JNK inhibitor having an isoquinolinone skeleton of the present invention shows selective inhibition of JNK, shows lower toxicity, and a fewer side effects, it is useful as a safe pharmaceutical product. The JNK inhibitor having an isoquinolinone skeleton of the present invention shows superior JNK selective inhibitory action in mammals (e.g., mouse, rat, hamster, rabbit, cat, dog, bovine, sheep, monkey, human etc.), and also superior in (oral) absorbability, (metabolism) stability and the like, and therefore, can be used as an agent for the prophylaxis or treatment of a JNK-related clinically pathological condition or disease, such as cardiovascular diseases (e.g., chronic or acute cardiac failure, cardiac hypertrophy, dilated/hypertrophic/restrictive cardiomyopathy, acute myocardial infarction, post-myocardial infarction, acute or chronic myocarditis, diastolic dysfunction of the left ventricle, systolic dysfunction of the left ventricle, hypertension and nephropathy and nephritis as complications thereof, diabetic nephropathy, endothelial dysfunction, arteriosclerosis or post-coronary angioplasty restenosis and the like), inflammatory diseases (e.g., chronic rheumatoid arthritis, osteoarthritis, gout, bronchitis, cystic fibrosis, inflammatory bowel disease, irritable colon syndrome, mucous colitis, ulcerative colitis, Crohn's disease, gastritis, esophagitis, multiple sclerosis, eczema, dermatitis, hepatitis, glomerulonephritis and the like), neurodegenerative diseases (e.g., asthma, chronic obstructive pulmonary disease, allergic disease, obesity, diabetes, diabetic retinopathy, diabetic neuropathy, psoriasis, cancer, Alzheimer's disease, Huntington's chorea, Parkinson's syndrome, epilepsy, amyotrophic lateral sclerosis, peripheral neuropathy and the like), spinal injury, cerebral apoplexy, cerebrovascular disorder, ischemic disorder of organ selected from heart, kidney, liver and brain, ischemia reperfusion injury, autoimmune disease, organ failure, endotoxin shock or rejection after organ transplantation and the like. Preferably, it is an agent for the prophylaxis or treatment of chronic or acute cardiac failure, cardiac hypertrophy, post-myocardial infarction, myocarditis, chronic rheumatoid arthritis, osteoarthritis, inflammatory bowel disease, asthma, ischemia injury, organ failure, cerebral apoplexy, cerebrovascular disorder, rejection after organ transplantation and the like.

When the compound of the present invention is applied to each of the above-mentioned diseases, it can be used in appropriate combination with a pharmaceutical agent or a treatment method generally employed for such diseases. For cardiac failure, for example, it can be used concurrently with angiotensin converting enzyme (ACE) inhibitors (e.g., alacepril, captopril, cilazapril, delapril, enalapril, lisinopril, temocapril, trandolapril, quinapril, imidapril, benazepril, perendopril and the like), angiotensin II receptor antagonists (e.g., losartan, candesartan cillexetil, valsartan, termisartan, irbesartan, forasartan and the like), β receptor antagonists (e.g., propranolol, nadolol, timolol, nipradilol, bunitorolol, indenolol, penbutolol, carteolol, carvedilol, pindolol, acebutolol, atenolol, bisoprolol, metoprolol, labetalol, amosulalol, arotinolol and the like), Ca antagonists (e.g., manidipine, nicardipine, nilvadipine, nisoldipine, nitrendipine, benidipine, amlodipine, aranidipine and the like), diuretics (e.g., thiazide diuretics such as benzylhydrochlorothiazide, cyclopentiazide, ethiazide, hydrochlorothiazide, hydroflumethiazide, methyclothiazide, penfluthiazide, polythiazide, trichlormethiazide and the like; loop diuretics such as chlorthalidone, clofenamide, indapamide, mefruside, meticrane, sotolazone, tribamide, quinetazone, metolazone, furosemide, mefruside and the like; potassium retention diuretics such as spironolactone, triamterene and the like; and the like), digitalis preparations (e.g., digitoxin, digoxin, methyldigoxin, lanatoside C, proscillaridin and the like), ANP or BNP preparations, Ca sensitizers (e.g., pimobendan and the like), anticoagulants (e.g., warfarin, sodium citrate, activated protein C, tissue factor pathway inhibitor, antithrombin III, dalteparin sodium, aragatroban, gabexate, sodium ozagrel, ethyl icosapentate, beraprost sodium, alprostadil, pentoxifyline, tisokinase, streptokinase and the like), antiarrhythmic drugs (e.g., sodium channel blockers such as quinidine, procainamide, disopyramide, ajmaline, cibenzoline, lidocain, diphenylhydantoin, mexiletine, propafenone, flecainide, pilsicainide, phenyloin and the like; potassium channel blockers such as amiodarone and the like; calcium channel blockers such as verapamil, diltiazem and the like; and the like), PDE inhibitors (e.g., amrinone, milrinone, olprinone hydrochloride and the like), therapeutic drugs for diabetes (e.g., sulfonylureas such as tolbutamide, chlorpropamide, glyclopyramide, acetohexamide, tolazamide, glibenclamide, glybuzole and the like; biguanides such as metformin hydrochloride, buformin hydrochloride and the like; α-glucosidase inhibitors such as voglibose, acarbose and the like, insulin sensitizers such as pioglitazone, troglitazone and the like; insulin, glucagon; therapeutic drugs for diabetic complications such as epalrestat and the like; and the like), anti-obesity drugs and the like, and is also applicable when an implantable artificial heart, an implantable defibrillator, a ventricular pacing, Batista operation, heart transplantation or cell transplantation is performed. In addition, after acute myocardial infarction or during myocardial infarction prognosis, for example, the compound can be used in combination with antithrombotics (e.g., anticoagulants such as heparin sodium, heparin calcium, warfarin and the like; thrombolytic agents such as urokinase and the like; anti-platelet drugs such as aspirin, sulfinpyrazone (anturan), dipyridamole (persantin), ticropidine (panaldine), cilostazol (pletal), clopidogrel and the like; and the like), angiotensin converting enzyme inhibitors, angiotensin II receptor antagonists, β receptor antagonists, therapeutic drugs for diabetes, therapeutic drugs for hyperlipidemia (e.g., HMG-CoA reductase inhibitors such as pravastatine, fluvastatine, cerivastatine, atorvastatine and the like; fibrate drugs such as sinfibrate, clofibrate aluminum, clinofibrate, fenofibrate and the like; and the like), coronary vessel reconstructive surgery such as PTCA, CABG and the like; and the like. Furthermore, in chronic rheumatoid arthritis, for example, the compound can be used in combination with non-steroidal antiinflammatory agents (e.g., acetaminophen, phenacetin, ethenzamide, sulpyrine, antipyrine, migrenine, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizole, tiaramide hydrochloride, zaltoprofen, gabexate mesilate, camostat mesilate, ulinastatine, colchicine, probenecid, sulfinpyrazone, benzbromarone, allopurinol, sodium aurothiomalate, sodium hyaluronate, sodium salicylate, morphine hydrochloride, salicylic acid, atropine, scopolamine, morphine, pethidine, levorphanol, ketoprofen, naproxen, oxymorphone or a salt thereof and the like), immunomodulators or immunosuppressants (e.g., methotrexate, cyclosporine, tacrolimus, gusperimus, azathioprine, antilymphocyte serum, dried sulfonated immunoglobulin, erythropoietin, colony stimulating factor, interleukin, interferon and the like), steroids (e.g., dexamethasone, hexestrol, methimazole, betamethasone, triamcinolone, triamcinoloneacetonide, fluocinonide, fluocinoloneacetonide, prednisolone, methylprednisolone, cortisone acetate, hydrocortisone, fluorometholone, beclometasone dipropionate, estriol and the like), p38 MAP kinase inhibitors, anti-TNF-α drugs (e.g., etanercept, infliximab, D2E7, CDP-571, PASS TNF-α, soluble TNF-α receptor, TNF-α binding protein, anti-TNF-α antibody and the like), cyclooxygenase inhibitors (e.g., salicylic acid derivatives such as celecoxib, rofecoxib, aspirin and the like, MK-663, valdecoxib, SC-57666, tiracoxib, S-2474, diclofenac, indomethacin, loxoprofen and the like) and the like.

Moreover, it is possible to use the compound of the present invention in combination with biological products (e.g.: antibody, vaccine preparation and the like) when applying to the above-mentioned respective diseases, and it is also possible to apply the compound in combination with a gene therapy and the like as a combination therapy. As antibody and vaccine preparation, for example, vaccine preparation to angiotensin II, vaccine preparation to CETP, CETP antibody, TNF α antibody, antibody to other cytokine, amiloid β vaccine preparation, type 1 diabetes vaccine (DIAPEP-277 of Peptor Ltd. and the like), anti-HIV antibody, HIV vaccine preparation and the like, antibody and vaccine preparation to cytokine, renin-angiotensin enzyme and products thereof, antibody and vaccine preparation to enzyme and protein involved in blood lipid metabolism, antibody and vaccine preparation to enzyme and protein involved in blood coagulation-fibrinolytic system, antibody and vaccine preparation to protein involved in glucose metabolism and insulin resistance and the like can be mentioned. In addition, a combined use with biological products involved in growth factors such as GH, IGF and the like is possible. As a gene therapy, for example, a treatment method using a gene relating to cytokine, renin-angiotensin enzyme and products thereof, G protein, G protein-coupled receptor and phosphorylation enzyme thereof, a therapeutic method using a DNA decoy such as NFκB decoy and the like, a therapeutic method using antisense, a therapeutic method using a gene relating to enzyme and protein involved in blood lipid metabolism (e.g., gene relating to metabolism, excretion and absorption of cholesterol or triglyceride or HDL-cholesterol or blood phospholipid, and the like), a therapeutic method using a gene relating to enzyme and protein (e.g., growth factors such as HGF, VEGF and the like, and the like) involved in angiogenetic therapy aiming at obstruction of peripheral vessel and the like, a therapeutic method using a gene relating protein involved in glucose metabolism and insulin resistance, antisense to cytokine such as TNF-α and the like, and the like can be mentioned. In addition, it is possible to use the compound in combination with various organ regeneration methods such as heart regeneration, kidney regeneration, pancreas regeneration, blood vessel regeneration and the like, cell transplantation therapy using bone marrow cells (bone marrow mononuclear cell, bone marrow mesenchymal stem cell and the like), and artificial organs (artificial blood vessels and cardiac muscle cell sheet) using tissue engineering.

Compound (I) or a salt thereof of the present invention can be administered orally or parenterally as it is or after mixing with a pharmacologically acceptable carrier.

The dosage form of the preparation of the present invention containing Compound (I) or a salt thereof for oral administration is, for example, tablet (including sugar-coated tablet, film-coated tablet), pill, granule, powder, capsule (including soft capsule, microcapsule), syrup, emulsion, suspension and the like, and the dosage form for parenteral administration is, for example, injection, injecting agent, instillation, suppository and the like. In addition, it is effective to make a sustained release preparation by combining with a suitable base (e.g., polymer of butyric acid, polymer of glycolic acid, copolymer of butyric acid-glycolic acid, a mixture of polymer of butyric acid and polymer of glycolic acid, polyglycerol fatty acid ester etc.).

While the content of Compound (I) or a salt thereof in the preparation of the present invention varies depending on the form of preparation, it is generally 2 to 85 wt %, preferably 5 to 70 wt %, relative to the entire preparation.

As a method to produce Compound (I) or a salt thereof in the above-mentioned dosage form, a known production method generally used in the pertinent field can be applied. When the above-mentioned dosage form is produced, suitable amounts of an excipients, a binder, a disintegrant, a lubricant, a sweetening agent, a surfactant, a suspending agent, an emulsifier and the like generally used in the pertinent field are appropriately added as necessary, and produced.

When Compound (I) or a salt thereof is prepared into a tablet, for example, it can be produced by adding an excipient, a binder, a disintegrant, a lubricant and the like, and when a pill and a granule are to be prepared, they can be produced by adding an excipient, a binder, a disintegrant and the like. When a powder and a capsule are to be prepared, they can be produced by adding an excipient and the like, and when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, cane sugar, crystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose sodium solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fruit sugar, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, carboxymethyl cellulose sodium, methyl cellulose, bentonite and the like.

Examples of the emulsifier include gum arabic, tragacanth, gelatin, polysorbate 80 and the like.

Furthermore, when Compound (I) or a salt thereof is produced in the above-mentioned dosage form, a suitable amount of a coloring agent, a preservative, an aromatic, a corrigent, a stabilizer, viscous agents and the like typically used in the purification field can be added on demand.

A preparation containing Compound (I) or a salt thereof of the present invention is stable and low toxic, and can be used safely. While the daily dose varies depending on the condition and body weight of patients, the kind of compound, administration route and the like, in the case of, for example, oral administration to patients with cardiac failure (cardiomyopathy), post-myocardial infarction, myocarditis, rheumatism and the like, the daily dose to an adult (body weight about 60 kg) is about 1 to 1000 mg, preferably about 3 to 300 mg, more preferably about 10 to 200 mg, as an active ingredient (Compound (I) or a salt thereof), which is given in a single administration or administered in 2 or 3 portions a day.

When Compound (I) or a salt thereof of the present invention is administered parenterally, it is generally administered in the form of a liquid (e.g., injection). While the dose varies depending on the subject of administration, target organ, symptom, administration method and the like, it is, for example, about 0.01 mg-about 100 mg, preferably about 0.01-about 50 mg, more preferably about 0.01-about 20 mg, in the form of an injection, relative to 1 kg of body weight, which is preferably given by intravenous injection. As the injection, intravenous injection as well as subcutaneous injection, intracutaneous injection, intramuscular injection, instillation and the like are mentioned, and as a sustained release preparation, iontophoresis transdermal agent and the like are mentioned. Such injections are prepared by methods known per se, or by dissolving, suspending or emulsifying Compound (I) or a salt thereof of the present invention in a sterilized solution or oily liquid. As an aqueous solution for injection, isotonic solutions containing physiological saline, glucose or other auxiliary drugs (e.g., D-sorbitol, D-mannitol, sodium chloride and the like) and the like can be mentioned, and they can be used in combination with suitable dissolution aids, such as alcohols (e.g., ethanol), polyalcohols (e.g., propylene glycol, polyethylene glycol), anionic surfactants (e.g., polysorbate 80, HCO-50) and the like. As an oily liquid, sesame oil, soybean oil and the like can be mentioned, which may be used in combination with dissolution aids such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like. A prepared injection is generally filled in an ampoule.

When the compound of the present invention and other pharmaceutical agent are used in combination, the mode of administration of the compound of the present invention and the combination drug is not particularly limited, as long as the compound of the present invention and the combination drug are combined. As the mode of such administration, for example, (1) administration of a single preparation obtained by simultaneous formulation of the compound of the present invention and a combination drug, (2) simultaneous administration of two kinds of preparations obtained by separate formulation of the compound of the present invention and a combination drug, by a single administration route, (3) time staggered administration of two kinds of preparations obtained by separate formulation of the compound of the present invention and a combination drug, by the same administration route, (4) simultaneous administration of two kinds of preparations obtained by separate formulation of the compound of the present invention and a combination drug, by different administration routes, (5) time staggered administration of two kinds of preparations obtained by separate formulation of the compound of the present invention and a combination drug, by different administration routes, such as administration in the order of the compound of the present invention and then the combination drug, or administration in a reversed order, and the like can be mentioned. The dose of the combination drug can be appropriately determined based on the dose employed in clinical situations. The mixing ratio of the compound of the present invention and a combination drug can be appropriately determined depending on the administration subject, administration route, target disease, symptom, combination and the like. When the subject of administration is human, for example, a combination drug can be used in 0.01-100 parts by weight relative to 1 part by weight of the compound of the present invention.

The present invention is further explained in detail by referring to the following Examples, Preparation Examples and Experimental Examples, which are mere working examples not to be construed as limitative and may be changed without departing from the scope of the present invention.

The elution by column chromatography in Examples was performed under observation by TLC (Thin Layer Chromatography). In the TLC observation, 60F254, produced by Merck, or NH produced by FUJI SILYSIA CHEMICAL LTD., was used as a TLC plate, and as a developing solvent, the solvent used as an elution solvent in column chromatography, and as a detection method, a UV detector was employed. As column silica gel, Kiesel-Gel 60 (70 to 230 mesh) or Kiesel-Gel 60 (230 to 400 mesh), also produced by Merck, were used. NMR spectra were determined with tetramethylsilane as the internal or external standard, using the Varian GEMINI 200 (200 MHz) or Mercury 300 spectrometer; chemical shift is shown by δ values and coupling constant is shown by Hz. IR spectrum was measured using Shimadzu FTIR-8200 spectrometer.

In Examples, HPLC was measured under the following conditions and purity and the like was determined.

measurement tool: LC-10Avp system, Shimadzu Corporation (unless particularly noted. Gradient cycle B method) or Agilent 1100 system (this tool was used for purity determination by LCMS)

column: CAPSEL PAK C18UG120 S-3 μm, 2.0×50 mm solvent:
  Solution A; 0.1% trifluoroacetic acid-containing water,
  Solution B; 0.1% trifluoroacetic acid-containing acetonitrile gradient cycle: (Method A) 0.00 min (Solution A/Solution B=90/10), 2.00 min (Solution A/Solution B=5/95), 2.75 min (Solution A/Solution B=5/95), 2.76 min (Solution A/Solution B=90/10), 3.45 min (Solution A/Solution B=90/10) or (Method B) 0.00 min (Solution A/Solution B=90/10), 4.00 min (Solution A/Solution B=5/95), 5.50 min (Solution A/Solution B=5/95), 5.51 min (Solution A/Solution B=90/10), 8.00 min (Solution A/Solution B=90/10)

injection amount: 10 μl, flow rate: 0.5 ml/min, detection method: UV 220 nm

In Examples, mass spectrum (MS) was measured under the following conditions.

measurement tool: Micromass Ltd., platform II, Waters Corporation ZQ, Waters Corporation ZMD or JEOL Ltd. JMS-AX505W ionization method: Atmospheric Pressure Chemical Ionization (APCI) or Electron Spray Ionization (ESI) or Fast Atom Bombardment (FAB)

For purification of compounds in Reference Examples and Examples, column chromatography and the following preparative HPLC tool or medium pressure preparative LC tool were used.

1) preparative HPLC apparatus: Gilson, Inc., high throughput purification system column: YMC Combiprep ODS-A S-5 μm, 50×20 mm solvent:
  Solution A; 0.1% trifluoroacetic acid-containing water,
  Solution B; 0.1% trifluoroacetic acid-containing acetonitrile gradient cycle: 0.00 min (Solution A/Solution B=90/10), 1.20 min (Solution A/Solution B=90/10), 4.75 min (Solution A/Solution B=0/100), 7.30 min (Solution A/Solution B=0/100), 7.40 min (Solution A/Solution B=90/10), 7.50 min (Solution A/Solution B=90/10)

flow rate: 25 ml/min, detection method: UV 220 nm 2) medium pressure preparative LC tool: Moritex high through-put purification system (purif 8) column: YAMAZEN CORPORATION HI-FLASH™ COLUMN (silica gel: 40 μm, 60° C.), 26×100 mm or 20×65 mm flow rate: 20 ml/min detection method: UV 254 nm In a mixed solvent, the numerical values in parentheses show volume mixing ratio of each solvent. In addition, % in solutions shows number of grams in 100 ml of solution. In Reference Examples and Examples, the symbols mean the following.

s: singlet
d: doublet
t: triplet
q: quartet
dd: double doublet
m: multiplet
br: broad
brs: broad singlet
J: coupling constant
$CDCl_3$: deuterated chloroform
$DMSO-d_6$: dimethyl sulfoxide-$d_6$
$^1$H-NMR: proton nuclear magnetic resonance
WSC: water-soluble carbodiimide
THF: tetrahydrofuran
DMF: dimethylformamide
DMSO: dimethyl sulfoxide The sequence number in the sequence listing of the present specification shows the following sequence.

[SEQ ID; No 1]
A base sequence of primer JNK1-U is shown.

[SEQ ID; No 2]
A base sequence of primer JNK1-L is shown.

[SEQ ID; No 3]
A base sequence of primer MKK7-U is shown.

[SEQ ID; No 4]
A base sequence of primer MKK7-L is shown.

[SEQ ID; No 5]
A base sequence of primer CAM7-U is shown.

[SEQ ID; No 6]
A base sequence of primer CAM7-L is shown.

[SEQ ID; No 7]
A base sequence of primer cJUN-U is shown.

[SEQ ID; No 8]
A base sequence of primer cJUN-L is shown.

REFERENCE EXAMPLE 1

6-chloro-4-phenylisocoumarin-3-carboxylic acid

To a solution of 4-chlorophthalic anhydride (25 g) in benzene (200 ml) was added aluminum chloride (36.5 g), and the mixture was stirred at room temperature for 1 hr. and subsequently refluxed for 30 min. After cooling the reaction mixture, it was diluted with ethyl acetate (200 ml) and poured into ice water. Conc. hydrochloric acid (20 ml) was added and the mixture was stirred at room temperature for 30 min. After separating the organic layer, the layer was washed successively with 4N hydrochloric acid, water and brine, dried over sodium sulfate and concentrated until the crystals precipitated. The crystals were collected by filtration and washed with isopropyl ether to give 4-chloro-2-benzoylbenzoic acid (16 g) as colorless crystals.

$^1$H-NMR ($CDCl_3$) δ: 7.35 (1H, d, J=2.2 Hz), 7.37-7.47 (2H, m), 7.50-7.58 (2H, m), 7.66-7.73 (2H, m), 8.02 (1H, d, J=8.4 Hz).

To a solution of 4-chloro-2-benzoylbenzoic acid (13 g) in acetone (200 ml) was added potassium carbonate (6.9 g), and the mixture was stirred at room temperature for 10 min. to allow precipitation of potassium salt. Then diethyl bromomalonate (13.15 g) and DMF (10 ml) were added, and the mixture was stirred at room temperature for 20 hrs. The reaction mixture was concentrated, and ethyl acetate (100 ml) and water (100 ml) were added to the residue. The mixture was stirred at room temperature for 30 min. After separating the organic layer, the layer was washed with water and brine, dried over sodium sulfate and concentrated. A mixed solution of acetic acid (100 ml) and conc. hydrochloric acid (100 ml) was added to the obtained residue, and the mixture was stirred for 20 hrs at 120° C. After cooling, the reaction mixture was concentrated, and the residue was dissolved in ethyl acetate, washed with water and brine, dried over sodium sulfate and concentrated. The obtained residue was crystallized from isopropyl ether and collected by filtration to give the title compound (9.78 g) as colorless crystals.

$^1$H-NMR ($CDCl_3$) δ: 7.07 (1H, d, J=1.8 Hz), 7.20-7.28 (2H, m), 7.45-7.54 (3H, m), 7.60 (1H, dd, J=1.8, 8.4 Hz), 8.34 (1H, d, J=8.4 Hz).

REFERENCE EXAMPLE 2

6-chloro-4-phenylisocoumarin-3-carboxylic acid methyl ester

To a solution of 6-chloro-4-phenylisocoumarin-3-carboxylic acid (9 g) in methanol (200 ml) was added sulfuric acid (20 ml) and the mixture was refluxed for 2 hrs. The reaction mixture was concentrated, and the residue was neutralized with aqueous sodium hydrogen carbonate and extracted with ethyl acetate. The organic layer was washed with water and brine, dried over sodium sulfate and concentrated. The residue was crystallized from isopropyl ether to give the title compound (8.7 g) as colorless crystals.

$^1$H-NMR ($CDCl_3$) δ: 3.72 (3H, s), 7.08 (1H, d, J=2.2 Hz), 7.22-7.30 (2H, m), 7.48-7.55 (3H, m), 7.59 (1H, dd, J=2.2, 8.4 Hz), 8.35 (1H, d, J=8.4 Hz).

REFERENCE EXAMPLE 3

6-bromo-4-phenylisocoumarin-3-carboxylic acid

To a solution of 4-bromophthalic acid anhydride (100 g) in benzene (500 ml) was added aluminum chloride (118 g), and the mixture was stirred at room temperature for 1 hr. and subsequently refluxed for 30 min. After cooling the reaction mixture, it was diluted with ethyl acetate (200 ml) and poured into ice water. Conc. hydrochloric acid (50 ml) was added and the mixture was stirred at room temperature for 30 min. After separating the organic layer, the layer was washed successively with 4N hydrochloric acid, water and brine, dried over sodium sulfate and concentrated until crystals precipitated. The crude crystals were collected by filtration, and recrystallized from toluene/ethyl acetate (10:1) to give 4-bromo-2-benzoylbenzoic acid (59 g) as colorless crystals.

$^1$H-NMR ($CDCl_3$) δ: 7.40-7.47 (2H, m), 7.51 (1H, d, J=1.8 Hz), 7.57 (1H, m), 7.68-7.73 (3H, m), 7.94 (1H, d, J=8.7 Hz).

To a solution of 4-bromo-2-benzoylbenzoic acid (57.6 g) in acetone (500 ml) was added potassium carbonate (26.1 g), and the mixture was stirred at room temperature for 10 min. to allow precipitation of potassium salt. Then diethyl bromomalonate (54.2 g) and DMF (25 ml) were added, and the mixture was stirred at room temperature for 20 hrs. The reaction mixture was concentrated, and ethyl acetate (200 ml) and water (200 ml) were added to the residue. The mixture was stirred at room temperature for 30 min. After separating the organic layer, the layer was washed with water and brine, dried over sodium sulfate and concentrated. A mixed solution of acetic acid (200 ml) and conc. hydrochloric acid (200 ml) was added to the obtained residue, and the mixture was stirred at 120° C. for 15 hrs. After cooling, the reaction mixture was concentrated, and the residue was dissolved in ethyl acetate, washed with water and brine, dried over sodium sulfate and concentrated. The obtained residue was crystallized from isopropyl ether and collected by filtration to give the title compound (53 g) as colorless crystals.

$^1$H-NMR (CDCl$_3$) δ: 7.18-7.30 (3H, m), 7.46-7.56 (3H, m), 7.77 (1H, dd, J=1.8, 8.4 Hz), 8.26 (1H, d, J=8.4 Hz).

REFERENCE EXAMPLE 4

6-bromo-4-phenylisocoumarin-3-carboxylic acid methyl ester

To a solution of 6-bromo-4-phenylisocoumarin-3-carboxylic acid (10 g) in methanol (200 ml) was added sulfuric acid (20 ml) and the mixture was refluxed for 2 hrs. The reaction mixture was concentrated, and the residue was neutralized with aqueous sodium hydrogen carbonate and extracted with ethyl acetate. The organic layer was washed with water and brine, dried over sodium sulfate and concentrated. The residue was crystallized from isopropyl ether to give the title compound (9.76 g) as colorless crystals.

$^1$H-NMR (CDCl$_3$) δ: 3.72 (3H, s), 7.22-7.30 (3H, m), 7.50-7.57 (3H, m), 7.75 (1H, dd, J=1.8, 8.4 Hz), 8.26 (1H, d, J=8.4 Hz).

REFERENCE EXAMPLE 5

6-chloro-4-(4-tolyl)isocoumarin-3-carboxylic acid

In the same manner as in Reference Example 1 and using toluene, the title compound was synthesized.

$^1$H-NMR (CDCl$_3$) δ: 2.46 (3H, s), 7.07-7.17 (3H, m), 7.29 (2H, d, J=8.0 Hz), 7.61 (1H, dd, J=1.8, 8.4 Hz), 8.34 (1H, d, J=8.4 Hz).

REFERENCE EXAMPLE 6

6-chloro-4-(4-tolyl)isocoumarin 3-carboxylic acid methyl ester

In the same manner as in Reference Example 2,6-chloro-4-(4-tolyl)isocoumarin-3-carboxylic acid was esterified to synthesize the title compound.

$^1$H-NMR (CDCl$_3$) δ: 2.46 (3H, s), 3.73 (3H, s), 7.08-7.17 (3H, m), 7.32 (2H, d, J=8.2 Hz), 7.57 (1H, dd, J=1.8, 8.0 Hz), 8.34 (1H, d, J=8.0 Hz).

REFERENCE EXAMPLE 7

6-bromo-1-oxo-4-phenyl-1,2-dihydroisoquinoline-3-carboxylic acid methyl ester

To a solution of 6-bromo-4-phenylisocoumarin-3-carboxylic acid (15 g) in methanol (100 ml) was added 12% ammonia-methanol solution (60 ml) and the mixture was stirred at room temperature for 24 hrs. The reaction mixture was concentrated, and 1N hydrochloric acid was added to the obtained residue. The mixture was extracted with ethyl acetate. The organic layer was dried and concentrated and 4N hydrochloric acid ethyl acetate solution (30 ml) was added to the obtained oily substance. The mixture was stirred at room temperature for 2 hrs. and the reaction mixture was concentrated. The obtained crystal was washed with water and dried under reduced pressure to give 6-bromo-1-oxo-4-phenyl-1,2-dihydroisoquinoline-3-carboxylic acid as colorless crystals.

To the obtained 6-bromo-1-oxo-4-phenyl-1,2-dihydroisoquinoline-3-carboxylic acid were added methanol (400 ml) solution and sulfuric acid (40 ml) and the mixture was refluxed for 20 hrs. The reaction mixture was concentrated, and the residue was neutralized with aqueous potassium carbonate solution and extracted with chloroform. The organic layer was washed with water and brine, dried over sodium sulfate and concentrated to give the title compound (6.51 g) as colorless crystals.

$^1$H-NMR (CDCl$_3$) δ: 3.64 (3H, s), 7.20-7.27 (2H, m), 7.32 (1H, d, J=1.8 Hz), 7.45-7.55 (3H, m), 7.71 (1H, dd, J=1.8, 8.4 Hz), 8.37 (1H, d, J=8.4 Hz), 9.35 (1H, brs).

REFERENCE EXAMPLE 8

2-benzyl-6-chloro-4-hydroxy-1-oxo-1,2-dihydroisoquinoline-3-carboxylic acid methyl ester To a solution (50 ml) of 4-chloro phthalic anhydride (12.1 g) in methanol was added sodium methoxide (3.6 g) and the mixture was stirred at room temperature for 12 hrs. The solvent was under reduced pressure, and the residue was partitioned between ethyl acetate and 1N hydrochloric acid. The organic layer was dried over magnesium sulfate and concentrated under reduced pressure to give 4-chlorophthalic acid 1- and 2-methyl ester mixture. In addition, to a mixture of methyl bromoacetate (10.1 g), triethylamine (9.7 ml) and THF (70 ml) was added dropwise a solution (35 ml) of benzylamine (7.1 g) in THF at 0° C. with stirring and the mixture was stirred for 1 hr. The mixture was further stirred at room temperature for 1 hr. and the solvent was evaporated under reduced pressure. The residue was partitioned between ethyl acetate and water, and the organic layer was dried over magnesium sulfate and concentrated under reduced pressure to dryness. Then, to a mixture of this product, 4-chlorophthalic acid 1- and 2-methyl ester mixture (mentioned above) and acetonitrile (70 ml) were added 1-ethyl-3-(3-dimethylaminopropyl)carbodiimide hydrochloride (16.5 g) and 4-hydroxybenzotriazole.monohydrate (11.2 g), and the mixture was stirred at room temperature for 12 hrs. The solvent was removed under reduced pressure, and the residue was partitioned between ethyl acetate and 1N hydrochloric acid. The organic layer was dried and concentrated to dryness. This product was dissolved in methanol (100 ml) and 28% sodium methoxide-methanol solution (26 g) was added at room temperature with stirring. The mixture was stirred at room temperature for 1 hr. The reaction mixture was concentrated, and the residue was partitioned between ethyl acetate and 1N hydrochloric acid. The organic layer was dried and concentrated. The residue was purified by silica gel column chromatography (hexane/ethyl acetate=4/1) and recrystallized from hexane/ethyl acetate to give the title compound (4.5 g) as yellow crystals.

$^1$H-NMR (CDCl$_3$) δ: 3.81 (3H, s), 5.61 (2H, s), 7.00-7.10 (2H, m), 7.16-7.32 (3H, m), 7.66 (1H, dd, J=1.8, 8.4 Hz), 8.14 (1H, d, J=1.8 Hz), 8.44 (1H, dd, J=0.3, 8.4 Hz), 11.02 (1H, s).

REFERENCE EXAMPLE 9

2-benzyl-6-chloro-1-oxo-4-trifluoromethanesulfonyloxy-1,2-dihydroisoquinoline-3-carboxylic acid methyl ester To a solution (45 ml) of 2-benzyl-6-chloro-4-hydroxy-1-oxo-1,2-dihydroisoquinoline-3-carboxylic acid methyl ester (4.5 g) in DMF was added sodium hydride (630 mg) at 0° C. with stirring, and the mixture was stirred for 30 min. Then, N-phenyltrifluoromethanesulfonimide (5.6 g) was added and the mixture was stirred at room temperature for 3 hrs. The solvent was concentrated under reduced pressure. The residue was partitioned between ethyl acetate and water, and the organic layer was dried over magnesium sulfate and concentrated under reduced pressure. The residue was purified by medium pressure preparative LC (hexane/ethyl acetate=4/1-1/1) to give the title compound (3.0 g) as colorless crystals.
$^1$H-NMR (CDCl$_3$) δ: 3.69 (3H, s), 5.51 (2H, s), 7.14-7.19 (2H, m), 7.23-7.35 (3H, m), 7.64 (1H, dd, J=2.1, 8.4 Hz), 7.76 (1H, d, J=2.1 Hz), 8.46 (1H, d, J=8.4 Hz).

REFERENCE EXAMPLE 10

6-fluoro-1-oxo-4-phenyl-1H-isocoumarin-3-carboxylic acid methyl ester

A mixture of 6-fluoro-1-oxo-4-phenyl-1H-isocoumarin-3-carboxylic acid and 7-fluoro-1-oxo-4-phenyl-1H-isocoumarin-3-carboxylic acid (86:14, 600 mg), conc. sulfuric acid (0.6 ml) and methanol (6 ml) were heated under reflux for 2 hr. The reaction mixture was concentrated under reduced pressure and water was added. The mixture was extracted with ethyl acetate. The organic layer was washed with water, saturated aqueous sodium hydrogen carbonate solution and saturated brine, dried over anhydrous sodium sulfate and concentrated under reduced pressure. The residue was purified by recrystallization (ethyl acetate-hexane) to give the title compound (410 mg).
$^1$H-NMR (CDCl$_3$)δ: 3.73 (3H, s), 6.78 (1H, dd, J=2.4, 9.8 Hz), 7.20-7.40 (3H, m), 7.44-7.60 (3H, m), 8.45 (1H, dd, J=5.6, 8.8 Hz).

REFERENCE EXAMPLE 11

6-chloro-4-hydroxy-2-(4-methoxycarbonylbenzyl)-1-oxo-1,2-dihydroisoquinoline-3-carboxylic acid methyl ester The present compound was synthesized according to the method shown in Reference Example 8 and using 4-chloro phthalic anhydride and 4-(aminomethyl)benzoic acid methyl ester hydrochloride.
$^1$H-NMR (CDCl$_3$) δ: 3.75 (3H, s), 3.89 (3H, s), 5.59 (2H, s), 7.15 (2H, d, J=8.7 Hz), 7.68 (1H, dd, J=2.1, 8.7 Hz), 7.96 (2H, d, J=8.7 Hz), 8.17 (1H, d, J=2.1 Hz), 8.43 (1H, d, J=8.7 Hz), 11.19 (1H, s).

REFERENCE EXAMPLE 12

6-chloro-2-(4-methoxycarbonylbenzyl)-1-oxo-4-trifluoromethanesulfonyloxy-1,2-dihydroisoquinoline-3-carboxylic acid methyl ester The present compound was synthesized according to the method shown in Reference Example 9 and using 6-chloro-4-hydroxy-2-(4-methoxycarbonyl-benzyl)-1-oxo-1,2-dihydroisoquinoline-3-carboxylic acid methyl ester.
$^1$H-NMR (CDCl$_3$) δ: 3.71 (3H, s), 3.90 (3H, s), 5.54 (2H, s), 7.23 (2H, d, J=8.4 Hz), 7.65 (1H, d, J=8.4 Hz), 7.78 (1H, s), 7.98 (2H, d, J=8.4 Hz), 8.45 (1H, d, J=8.4 Hz).

REFERENCE EXAMPLE 13

6-chloro-4-hydroxy-2-(4-methanesulfonylbenzyl)-1-oxo-1,2-dihydroisoquinoline-3-carboxylic acid methyl ester The present compound was synthesized according to the method shown in Reference Example 8 and using 4-chloro phthalic anhydride and 4-(methanesulfonyl)benzylamine.
$^1$H-NMR (CDCl$_3$) δ: 3.03 (3H, s), 3.76 (3H, s), 5.55 (2H, s), 7.32 (2H, d, J=8.7 Hz), 7.69 (1H, dd, J=2.1, 8.7 Hz), 7.88 (2H, d, J=8.7 Hz), 8.19 (1H, d, J=2.1 Hz), 8.40 (1H, d, J=8.7 Hz), 11.29 (1H, s).

REFERENCE EXAMPLE 14

6-chloro-2-(4-methanesulfonylbenzyl)-1-oxo-4-trifluoromethanesulfonyloxy-1,2-dihydroisoquinoline-3-carboxylic acid methyl ester The present compound was synthesized according to the method shown in Reference Example 9 and using 6-chloro-4-hydroxy-2-(4-methanesulfonylbenzyl)-1-oxo-1,2-dihydroisoquinoline-3-carboxylic acid methyl ester.
$^1$H-NMR (CDCl$_3$) δ: 3.02 (3H, s), 3.79 (3H, s), 5.49 (2H, s), 7.40 (2H, d, J=8.4 Hz), 7.65 (1H, dd, J=1.8, 8.4 Hz), 7.79 (1H, d, J=1.8 Hz), 7.89 (2H, d, J=8.4 Hz), 8.42 (1H, d, J=8.4 Hz).

REFERENCE EXAMPLE 15

1-(4-methanesulfonylbenzylamino)pentan-2-ol

A solution (50 ml) of 4-methanesulfonylbenzylamine (5.0 g) and 1,2-epoxypentane (2.8 g) in methanol was stirred at room temperature for 96 hrs. The reaction mixture was concentrated under reduced pressure, and the obtained residue was purified by silica gel column chromatography (ethyl acetate-ethyl acetate:methanol=10:1) to give the title compound (2.5 g).
$^1$H-NMR (CDCl$_3$)δ: 0.84-1.04 (3H, m), 1.24-1.60 (4H, m), 1.80-2.30 (2H, br), 2.49 (1H, dd, J=9.0, 11.9 Hz), 2.75 (1H, dd, J=3.2, 11.9 Hz), 3.05 (3H, s), 3.54-3.76 (1H, m), 3.87 (1H, d, J=14.5 Hz), 3.95 (1H, d, J=14.5 Hz), 7.54 (2H, d, J=8.4 Hz), 7.90 (2H, d, J=8.4 Hz).

REFERENCE EXAMPLE 16

1-(4-methanesulfonylbenzylamino)hexan-2-ol

A solution (50 ml) of 4-methanesulfonylbenzylamine (5.0 g) and 1,2-epoxyhexane (3.25 g) in methanol was stirred at room temperature for 96 hrs. The reaction-mixture was concentrated under reduced pressure, and the obtained residue was purified by silica gel column chromatography (ethyl acetate-ethyl acetate:methanol=10:1) to give the title compound (2.9 g).
$^1$H-NMR (CDCl$_3$)δ: 0.90-1.00 (3H, m), 1.16-1.56 (6H, m), 1.84-2.36 (2H, br), 2.49 (1H, dd, J=8.8, 11.6 Hz), 2.75 (1H, dd, J=2.8, 11.6 Hz), 3.05 (3H, s), 3.54-3.76 (1H, m), 3.87 (1H, d, J=14.5 Hz), 3.95 (1H, d, J=14.5 Hz), 7.54 (2H, d, J=8.0 Hz), 7.90 (2H, d, J=8.0 Hz).

REFERENCE EXAMPLE 17

1-(4-methanesulfonylbenzylamino)butan-2-ol

A solution (6 ml) of 4-methanesulfonylbenzylamine (3.0 g) and 1,2-epoxybutane (1.1 g) in 2-propanol was heated under reflux for 12 hrs. The reaction mixture was concentrated under reduced pressure, and the obtained residue was purified by silica gel column chromatography (ethyl acetate-ethyl acetate:methanol=10:1) to give the title compound (1.7 g).

$^1$H-NMR (CDCl$_3$)δ: 0.96 (3H, t, J=7.2 Hz), 1.34-1.60 (2H, m), 2.49 (1H, dd, J=9.2, 12.0 Hz), 2.77 (1H, dd, J=2.9, 12.0 Hz), 3.06 (3H, s), 3.48-3.70 (1H, m), 3.87 (1H, d, J=14.3 Hz), 3.96 (1H, d, J=14.3 Hz), 7.54 (2H, d, J=8.5 Hz), 7.91 (2H, d, J=8.5 Hz), 2H unconfirmed.

REFERENCE EXAMPLE 18

1-(4-methanesulfonylbenzylamino)-3-phenylpropan-2-ol

A solution (60 ml) of 4-methanesulfonylbenzylamine (5.8 g) and (2,3-epoxypropyl)benzene (5.0 g) in 2-propanol was heated under reflux for 12 hrs. The reaction mixture was concentrated under reduced pressure, and the obtained residue was purified by silica gel column chromatography (ethyl acetate-ethyl acetate:methanol=10:1) to give the title compound (4.5 g).

$^1$H-NMR (CDCl$_3$)δ: 2.09 (2H, br s), 2.57 (1H, dd, J=8.7, 12.0 Hz), 2.68-2.86 (3H, m), 3.04 (3H, s), 3.83 (1H, d, J=13.8 Hz), 3.84-3.98 (1H, m), 3.90 (1H, d, J=13.8 Hz), 7.14-7.36 (5H, m), 7.50 (2H, d, J=8.4 Hz), 7.87 (2H, d, J=8.4 Hz).

REFERENCE EXAMPLE 19

4-[(2-hydroxypropylamino)methyl]benzoic acid ethyl ester

To a solution (100 ml) of 4-formylbenzoic acid methyl ester (10.0 g) and (±)-1-amino-2-propanol (4.6 g) in THF was added anhydrous magnesium sulfate (11.2 g) at room temperature and the mixture was stirred for 3 hrs. The reaction mixture was filtered, and methanol (100 ml) was added to the filtrate under ice-cooling. Sodium borohydride (4.6 g) was added and the mixture was stirred for 1 hr. The reaction mixture was allowed to warm to room temperature and stirred for 12 hrs. and concentrated under reduced pressure. To the residue was added saturated aqueous sodium hydrogen carbonate, and the mixture was extracted with methylene chloride. The organic layer was dried over anhydrous sodium sulfate and the solvent was evaporated under reduced pressure. The obtained crystal was washed with diisopropyl ether to give the title compound (8.5 g).

$^1$H-NMR (CDCl$_3$)δ: 1.14 (3H, d, J=6.3 Hz), 2.45 (1H, dd, J=9.0, 12.0 Hz), 2.69 (1H, dd, J=3.3, 12.0 Hz), 3.70-3.96 (3H, m), 3.90 (3H, s), 7.37 (2H, d, J=8.6 Hz), 7.98 (2H, d, J=8.6 Hz), 2H unconfirmed.

REFERENCE EXAMPLE 20

Hexanethioacid amide

A mixture of hexanenitrile (3.0 g), 20% aqueous ammonium sulfide solution (20 ml) and pyridine (10 ml) was stirred at 35° C. for 24 hrs. To the reaction mixture were added water and saturated brine, and the mixture was extracted with ethyl acetate. The organic layer was washed with saturated brine and dried over anhydrous sodium sulfate. The solvent was evaporated under reduced pressure, and the crystal was washed with hexane to give the title compound (0.73 g).

$^1$H-NMR (CDCl$_3$) δ: 0.74-1.08 (3H, m), 1.12-1.54 (4H, m), 1.56-1.94 (2H, m), 2.66 (2H, t, J=7.6 Hz), 6.20-8.40 (2H, br).

REFERENCE EXAMPLE 21 thioisobutylamide

In the same manner as in Reference Example 20 and using isobutyronitrile, the title compound was synthesized.

oily substance.

$^1$H-NMR (CDCl$_3$) δ: 1.28 (6H, d, J=6.9 Hz), 2.66 (1H, septet, J=6.9 Hz), 6.60-7.20 (1H, br), 7.40-8.00 (1H, br).

EXAMPLE 1

6-chloro-2-methylamino-1-oxo-4-phenyl-1,2-dihydroisoquinoline-3-carboxylic acid methyl ester To a solution of 6-chloro-4-phenylisocoumarin-3-carboxylic acid methyl ester (1.3 g) in methanol (15 ml) was added methylhydrazine (3.0 g) and the mixture was stirred at room temperature for 1 hr. The reaction mixture was concentrated, and the obtained residue was dissolved in methanol (15 ml). Sulfuric acid (1.5 ml) was added and the mixture was refluxed for 2 hrs. The reaction mixture was concentrated, and the residue was neutralized with aqueous sodium hydrogen carbonate and extracted with ethyl acetate. The organic layer was washed with water and brine, dried over sodium sulfate and concentrated. The residue was purified by silica gel column chromatography (hexane/ethyl acetate=4/1) and crystallized from isopropyl ether to give the title compound (980 mg) as colorless crystals.

$^1$H-NMR (CDCl$_3$) δ: 2.88 (3H, d, J=6.0 Hz), 3.63 (3H, s), 5.67 (1H, q, J=6.0 Hz), 7.25 (1H, d, J=2.0 Hz), 7.30-7.38 (2H, m), 7.42-7.52 (4H, m), 8.43 (1H, d, J=8.0 Hz).

IR (KBr): 3289, 1744, 1661, 1597, 1373, 1248, 1229 cm$^{-1}$.

In the same manner as in Example 1, isocoumarin-3-carboxylic acid ester derivative was reacted with methylhydrazine to give the compounds of Examples 2-5.

EXAMPLE 2

6-chloro-2-methylamino-1-oxo-4-(4-tolyl)-1,2-dihydroisoquinoline-3-carboxylic acid methyl ester $^1$H-NMR (CDCl$_3$) δ: 2.43 (3H, s), 2.88 (3H, d, J=5.8 Hz), 3.65 (3H, s), 5.66 (1H, q, J=5.8 Hz), 7.17-7.32 (5H, m), 7.48 (1H, dd, J=2.0, 8.8 Hz), 8.42 (1H, d, J=8.8 Hz).

EXAMPLE 3

6-chloro-2-methylamino-1-oxo-4-(4-tolyl)-1,2-dihydroisoquinoline-3-carboxylic acid ethyl ester $^1$H-NMR (CDCl$_3$) δ: 1.06 (3H, t, J=7.0 Hz), 2.42 (3H, s), 2.88 (3H, d, J=5.8 Hz), 4.12 (2H, q, J=7.0 Hz), 5.67 (1H, q, J=5.8 Hz), 7.19-7.31 (5H, m), 7.47 (1H, dd, J=2.0, 8.8 Hz), 8.42 (1H, d, J=8.8 Hz).

EXAMPLE 4

6-fluoro-2-methylamino-1-oxo-4-phenyl-1,2-dihydroisoquinoline-3-carboxylic acid methyl ester $^1$H-NMR (CDCl$_3$) δ: 2.88 (3H, d, J=6.0 Hz), 3.63 (3H, s), 5.67 (1H, q, J=6.0 Hz), 6.92 (1H, dd, J=2.6, 10.2 Hz), 7.24 (1H, dt, J=2.6, 8.8 Hz), 7.30-7.39 (2H, m), 7.40-7.50 (3H, m), 8.51 (1H, dd, J=5.8, 8.8 Hz).

EXAMPLE 5

6-bromo-2-methylamino-1-oxo-4-phenyl-1,2-dihydroisoquinoline-3-carboxylic acid methyl ester $^1$H-NMR (CDCl$_3$) δ: 2.88 (3H, d, J=6.0 Hz), 3.62 (3H, s), 5.67 (1H, q, J=6.0 Hz), 7.30-7.38 (2H, m), 7.40-7.51 (4H, m), 7.64 (1H, dd, J=2.0, 8.8 Hz), 8.43 (1H, d, J=8.8 Hz).

EXAMPLE 6

2-amino-6-chloro-1-oxo-4-phenyl-1,2-dihydroisoquinoline-3-carboxylic acid methyl ester (6a) and 2-acetylamino-6-chloro-1-oxo-4-phenyl-1,2-dihydroisoquinoline-3-carboxylic acid methyl ester (6b)

To a solution of 6-chloro-4-phenylisocoumarin-3-carboxylic acid methyl ester (314 mg) in methanol (10 ml) was added hydrazine monohydrate (500 mg) and the mixture was stirred at room temperature for 1 hr. The reaction mixture was concentrated, and to the obtained residue was added 4N hydrochloric acid ethyl acetate solution (15 ml), and the mixture was stirred at room temperature for 2 days. The reaction mixture was concentrated, and the residue was neutralized with aqueous sodium hydrogen carbonate, and extracted with ethyl acetate. The organic layer was washed with water and brine, dried over sodium sulfate and concentrated. The residue was purified by silica gel column chromatography (hexane/ethyl acetate=1/1) and crystallized from isopropyl ether to give the title compound 6a (70 mg) as colorless crystals.

$^1$H-NMR (CDCl$_3$) δ: 3.62 (3H, s), 5.15 (2H, s), 7.26 (1H, d, J=2.0 Hz), 7.29-7.37 (2H, m), 7.43-7.54 (4H, m), 8.43 (1H, d, J=8.4 Hz).

IR (KBr): 1744, 1661, 1599, 1435, 1246 cm$^{-1}$.

The compound was further purified by silica gel column chromatography (hexane/ethyl acetate=1/3) and crystallized from isopropyl ether to give the title compound 6b (72 mg) as colorless crystals.

$^1$H-NMR (CDCl$_3$) δ: 2.05 (1/6×3H, s), 2.22 (5/6×3H, s), 3.50 (5/6×3H, s), 3.59 (1/6×3H, s), 6.71 (1/6×1H, s), 7.23 (1H, d, J=2.2 Hz), 7.28-7.40 (2H, m), 7.42-7.54 (3H, m), 7.90 (5/6×1H, s), 8.40 (1H, d, J=8.6 Hz).

IR (KBr): 1740, 1676, 1597, 1373, 1233 cm$^{-1}$. MS: 371 (M+1).

EXAMPLE 7

6-chloro-2-methylamino-1-oxo-4-phenyl-1,2-dihydroisoquinoline-3-carboxylic acid

In the same manner as in Reference Example 6, 6-chloro-4-phenylisocoumarin-3-carboxylic acid and methylhydrazine were reacted to give the title compound.

$^1$H-NMR (DMSO-d$_6$) δ: 2.94 (3H, s), 6.31 (1H, s), 6.86 (1H, d, J=2.4 Hz), 7.10-7.15 (2H, m), 7.22 (1H, t, J=7.5 Hz), 7.28-7.38 (3H, m), 7.77 (1H, d, J=8.4 Hz).

EXAMPLE 8

6-chloro-2-dimethylamino-1-oxo-4-phenyl-1,2-dihydroisoquinoline-3-carboxylic acid methyl ester A mixture of 6-chloro-2-methylamino-1-oxo-4-phenyl-1,2-dihydroisoquinoline-3-carboxylic acid methyl ester (800 mg), potassium carbonate (400 mg), methyl iodide (20 ml) and DMF (20 ml) was stirred at 80° C. for 3 days. The reaction mixture was concentrated, and ethyl acetate was added to the obtained residue. The mixture was washed with water and brine, dried over sodium sulfate and concentrated. The residue was purified by silica gel column chromatography (hexane/ethyl acetate=4/1) and crystallized from isopropyl ether to give the title compound (469 mg) as colorless crystals.

$^1$H-NMR (CDCl$_3$) δ: 3.10 (6H, s), 3.62 (3H, s), 7.20 (1H, d, J=2.0 Hz), 7.30-7.36 (2H, m), 7.42-7.50 (4H, m), 8.39 (1H, d, J=8.4 Hz).

IR (KBr): 1746, 1669, 1597, 1435, 1377, 1238, 1225 cm$^{-1}$.

EXAMPLE 9

6-chloro-2-(methylphenylamino)-1-oxo-4-phenyl-1,2-dihydroisoquinoline-3-carboxylic acid methyl ester Under an argon atmosphere, a solution (10 ml) of 6-chloro-2-methylamino-1-oxo-4-phenyl-1,2-dihydroisoquinoline-3-carboxylic acid methyl ester (100 mg), triphenyl bismuth diacetate (162 mg) and copper(II) pivalate (85 mg) in dichloromethane was stirred at room temperature for 24 hrs. Subsequently, to the reaction mixture was added 4N hydrochloric acid, and the mixture was stirred at room temperature for 30 min. The reaction mixture was neutralized with aqueous sodium hydrogen carbonate and the resulting insoluble material was removed by filtration, and the filtrate was extracted with dichloromethane. The organic layer was washed with aqueous sodium hydrogen carbonate and brine, dried over sodium sulfate and concentrated. The obtained residue was purified by silica gel column chromatography (hexane/ethyl acetate=4/1) to give the title compound (70 mg) as colorless crystals.

$^1$H-NMR (CDCl$_3$) δ: 3.47 (3H, s), 3.49 (3H, s), 6.84 (2H, d, J=8.4 Hz), 6.94 (1H, t, J=7.5 Hz), 7.23-7.32 (3H, m), 7.38 (1H, m), 7.43-7.53 (5H, m), 8.34 (1H, d, J=9.0 Hz).

EXAMPLE 10

2-benzyl-6-bromo-1-oxo-4-phenyl-1,2-dihydroisoquinoline-3-carboxylic acid

To a solution of 6-bromo-4-phenyl-3-isocoumarincarboxylic acid (1.00 g) in methanol (20 ml) was added benzylamine (3.16 ml) and the mixture was stirred at room temperature for 2 hrs. The solvent was evaporated under reduced pressure and 1N hydrochloric acid was added. The mixture was extracted with ethyl acetate. The extract was washed successively with 1N hydrochloric acid and saturated brine and magnesium sulfate was added to dry the mixture. The solvent was evaporated under reduced pressure, and 4N hydrogen chloride-ethyl acetate solution (17 ml) was added to the obtained residue, and the mixture was stirred at room temperature for 18 hrs. The solvent was evaporated under reduced pressure, and addition of water allowed crystal precipitation. The obtained crystals were collected by filtration, washed successively with water and ether and dried under reduced pressure at 50° C. to give the title compound (921 mg, 73%).

$^1$H-NMR (DMSO-$d_6$) δ: 5.28 (2H, s), 7.15-7.40 (8H, m), 7.45-7.55 (3H, m), 7.77 (1H, dd, J=1.8, 8.4 Hz), 8.26 (1H, d, J=8.4 Hz). LCMS (ESI+): 97% (2.19 min); 434 (M+H), 436. (Method A)

In the same manner as in Example 10, the compounds of Examples 11-18 were synthesized.

EXAMPLE 11

6-bromo-2-butyl-1-oxo-4-phenyl-1,2-dihydroisoquinoline-3-carboxylic acid yield: 1.82 g (79%).
$^1$H-NMR (DMSO-$d_6$) δ: 0.80-1.00 (3H, m), 1.60-1.80 (2H, m), 3.98 (2H, t, J=6.6 Hz), 7.15 (1H, s), 7.20-7.40 (2H, m), 7.45-7.60 (3H, m), 7.75 (1H, d, J=8.4 Hz), 8.25 (1H, d, J=8.8 Hz). LCMS (ESI+): 96% (2.17 min); 400 (M+H), 402. (Method A)

EXAMPLE 12

6-bromo-2-cyclohexylmethyl-1-oxo-4-phenyl-1,2-dihydroisoquinoline-3-carboxylic acid yield: 2.11 g (83%).
$^1$H-NMR (DMSO-$d_6$) δ: 0.80-1.30 (6H, m), 1.50-1.80 (4H, m), 1.80-2.00 (1H, m), 3.93 (2H, d, J=7.2 Hz), 7.14 (1H, d, J=1.8 Hz), 7.30-7.40 (2H, m), 7.45-7.60 (3H, m), 7.74 (1H, dd, J=1.8, 8.4 Hz), 8.25 (1H, d, J=8.4 Hz). LCMS (ESI+): 96% (2.32 min); 440 (M+H), 442. (Method A)

EXAMPLE 13

6-bromo-2-(2-methoxyethyl)-1-oxo-4-phenyl-1,2-dihydroisoquinoline-3-carboxylic acid yield: 1.10 g (48%).
$^1$H-NMR (DMSO-$d_6$) δ: 3.26 (3H, s), 3.62 (2H, t, J=6.6 Hz), 4.20 (2H, t, J=6.6 Hz), 7.14 (1H, d, J=1.8 Hz), 7.30-7.40 (2H, m), 7.45-7.55 (3H, m), 7.78 (1H, dd, J=1.8, 8.8 Hz), 8.25 (1H, d, J=8.8 Hz). LCMS (ESI+): 91% (3.01 min); 402 (M+H), 404. (Method B)

EXAMPLE 14

6-bromo-1-oxo-2-(2-phenethyl)-4-phenyl-1,2-dihydroisoquinoline-3-carboxylic acid yield: 1.87 g (72%).
$^1$H-NMR (DMSO-$d_6$) δ: 2.95-3.10 (2H, m), 4.05-4.20 (2H, m), 7.17 (1H, d, J=1.8 Hz), 7.20-7.40 (7H, m), 7.45-7.55 (3H, m), 7.78 (1H, dd, J=1.8, 8.8 Hz), 8.28 (1H, d, J=8.8 Hz). LCMS (ESI+): 99% (3.70 min); 448 (M+H), 450. (Method B)

EXAMPLE 15

2-(benzo[1,3]dioxol-5-ylmethyl)-6-bromo-1-oxo-4-phenyl-1,2-dihydroisoquinoline-3-carboxylic acid yield: 2.28 g (91%).
$^1$H-NMR (DMSO-$d_6$) δ: 5.18 (2H, s), 5.98 (2H, s), 6.75 (1H, d, J=8.0 Hz), 6.84 (1H, s), 6.85 (1H, d, J=8.0 Hz), 7.16 (1H, d, J=1.4 Hz), 7.35-7.40 (2H, m), 7.45-7.55 (3H, m), 7.76 (1H, dd, J=1.8, 8.4 Hz), 8.25 (1H, d, J=8.4 Hz). LCMS (ESI+): 90% (2.19 min); 478 (M+H), 480. (Method A)

EXAMPLE 16

6-bromo-2-(indan-1-yl)-1-oxo-4-phenyl-1,2-dihydroisoquinoline-3-carboxylic acid yield: 0.886 g (37%).
$^1$H-NMR (DMSO-$d_6$) δ: 2.55-2.70 (2H, m), 2.90-3.15 (2H, m), 5.55 (1H, m), 7.00-7.35 (5H, m), 7.40-7.55 (5H, m), 7.69 (1H, dd, J=1.8, 8.4 Hz), 8.07 (1H, d, J=8.4 Hz).
MS (ESI+): 460 (M+H), 462.

EXAMPLE 17

6-bromo-1-oxo-4-phenyl-2-(thiophen-2-ylmethyl)-1,2-dihydroisoquinoline-3-carboxylic acid yield: 1.11 g (58%).
$^1$H-NMR (DMSO-$d_6$) δ: 5.41 (2H, s), 6.96 (1H, dd, J=3.6, 4.8 Hz), 7.03 (1H, d, J=3.6 Hz), 7.15 (1H, d, J=1.8 Hz), 7.30-7.40 (2H, m), 7.45-7.55 (4H, m), 7.78 (1H, dd, J=1.8, 8.7 Hz), 8.29 (1H, d, J=8.7 Hz). LCMS (ESI+): 96% (2.27 min); 440 (M+H), 442. (Method A)

EXAMPLE 18

6-bromo-1-oxo-4-phenyl-2-(3-phenylpropyl)-1,2-dihydroisoquinoline-3-carboxylic acid yield: 1.21 g (60%).
$^1$H-NMR (DMSO-$d_6$) δ: 2.06 (2H, m), 2.66 (2H, t, J=7.2 Hz), 4.01 (2H, t, J=7.8 Hz), 7.10-7.40 (7H, m), 7.45-7.55 (4H, m), 7.74 (1H, dd, J=1.8, 8.7 Hz), 8.24 (1H, d, J=8.7 Hz). LCMS (ESI+): 92% (2.43 min); 462 (M+H), 464. (Method A)

EXAMPLE 19

2-benzyl-6-bromo-1-oxo-4-phenyl-1,2-dihydroisoquinoline-3-carboxylic acid methyl ester A mixture of 2-benzyl-6-bromo-1-oxo-4-phenyl-1,2-dihydroisoquinoline-3-carboxylic acid (150 mg), potassium carbonate (95 mg), methyl iodide (43 μl) and N,N-dimethylformamide (DMF) (5 ml) was stirred at room temperature for 3 hrs. After diluting with water, the mixture was extracted with ether and the extract was washed with saturated brine and dried over magnesium sulfate. The solvent was evaporated under reduced pressure and ethyl acetate and n-hexane was added to the residue and the mixture was crystallized to give the title compound (96 mg, 62%).

$^1$H-NMR (CDCl$_3$) δ: 3.19 (3H, s), 5.42 (2H, s), 7.20-7.30 (7H, m), 7.35-7.50 (4H, m), 7.66 (1H, dd, J=2.0, 8.8 Hz), 8.41 (1H, d, J=8.4 Hz). LCMS (ESI+): 98% (2.44 min); 448 (M+H), 450. (Method A)

In the same manner as in Example 19, the compounds of Examples 20-27 were synthesized.

EXAMPLE 20

6-bromo-2-butyl-1-oxo-4-phenyl-1,2-dihydroisoquinoline-3-carboxylic acid methyl ester yield: 111 mg (71%).
$^1$H-NMR (CDCl$_3$) δ: 0.95 (3H, t, J=7.0 Hz), 1.30-1.45 (2H, m), 1.70-1.85 (2H, m), 3.50 (3H, s), 3.95-4.05 (2H, m), 7.25-7.40 (3H, m)7.40-7.50 (3H, m), 7.63 (1H, dd, J=1.8, 8.4 Hz), 8.36 (1H, d, J=8.8 Hz). LCMS (ESI+): 99% (2.46 min); 414 (M+H), 416. (Method A)

EXAMPLE 21

6-bromo-2-cyclohexylmethyl-1-oxo-4-phenyl-1,2-dihydroisoquinoline-3-carboxylic acid methyl ester yield: 117 mg (76%).
$^1$H-NMR (CDCl$_3$) δ: 0.95-1.30 (6H, m), 1.60-1.90 (5H, m), 3.46 (3H, s), 3.96 (2H, d, J=7.4 Hz), 7.25-7.40 (3H, m), 7.40-7.50 (3H, m), 7.63 (1H, dd, J=11.8, 8.4 Hz), 8.36 (1H, d, J=8.4 Hz). LCMS (ESI+): 99% (2.62 min); 454 (M+H), 456. (Method A)

EXAMPLE 22

6-bromo-2-(2-methoxyethyl)-1-oxo-4-phenyl-1,2-dihydroisoquinoline-3-carboxylic acid methyl ester yield: 251 mg (81%).
$^1$H-NMR (CDCl$_3$) δ: 3.32 (3H, s), 3.44 (3H, s), 3.69 (2H, t, J=6.0 Hz), 4.34 (2H, t, J=6.0 Hz), 7.25-7.32 (2H, m), 7.34 (1H, d, J=1.8 Hz), 7.40-7.50 (3H, m), 7.63 (1H, dd, J=1.8, 8.8 Hz), 8.36 (1H, d, J=8.8 Hz). LCMS (ESI+): 96% (2.28 min); 416 (M+H), 418. (Method A)

EXAMPLE 23

6-bromo-1-oxo-2-(2-phenethyl)-4-phenyl-1,2-dihydroisoquinoline-3-carboxylic acid methyl ester yield: 254 mg (82%).
$^1$H-NMR (CDCl$_3$) δ: 3.12 (2H, t, J=8.1 Hz), 3.50 (3H, s), 4.16 (2H, t, J=8.1 Hz), 7.20-7.35 (7H, m), 7.38 (1H, d, J=1.8 Hz), 7.45-7.50 (3H, m), 7.66 (1H, dd, J=1.8, 8.4 Hz), 8.39 (1H, d, J=8.4 Hz). LCMS (ESI+): 97% (2.60 min); 462 (M+H), 464. (Method A)

EXAMPLE 24

2-(benzo[1,3]dioxol-5-ylmethyl)-6-bromo-1-oxo-4-phenyl-1,2-dihydroisoquinoline-3-carboxylic acid methyl ester yield: 194 mg (54%).
$^1$H-NMR (CDCl$_3$) δ: 3.27 (3H, s), 5.32 (2H, s), 5.91 (2H, s), 6.60-6.75 (2H, m), 6.84 (1H, s), 6.79 (1H, s), 7.25-7.30 (2H, m), 7.37 (1H, d, J=1.2 Hz), 7.40-7.45 (3H, m), 7.65 (1H, dd, J=1.2, 8.4 Hz), 8.40 (1H, d, J=8.4 Hz). LCMS (ESI+): 97% (2.46 min); 492 (M+H), 494. (Method A)

EXAMPLE 25

6-bromo-2-(indan-1-yl)-1-oxo-4-phenyl-1,2-dihydroisoquinoline-3-carboxylic acid methyl ester yield: 191 mg (62%).
$^1$H-NMR (CDCl$_3$) δ: 2.60-2.80 (3H, m), 2.95-3.15 (2H, m), 3.35 (3H, m), 7.15-7.40 (7H, m), 7.45 (3H, m), 7.62 (1H, d, J=8.4 Hz), 8.32 (1H, d, J=8.4 Hz).
MS (ESI+): 97% (2.59 min); 474 (M+H), 476.

EXAMPLE 26

6-bromo-1-oxo-4-phenyl-2-(thiophen-2-ylmethyl)-1,2-dihydroisoquinoline-3-carboxylic acid methyl ester yield: 265 mg (86%).
$^1$H-NMR (CDCl$_3$) δ: 3.38 (3H, s), 5.53 (2H, s), 6.91 (1H, dd, J=3.4, 5.0 Hz), 7.02 (1H, d, J=3.4 Hz), 7.20-7.30 (4H, m), 7.35 (1H, d, J=1.8 Hz), 7.40-7.50 (2H, m), 7.65 (1H, dd, J=1.8, 8.4 Hz), 8.40 (1H, d, J=8.4 Hz). LCMS (ESI+): 98% (2.57 min); 454 (M+H), 456. (Method A)

EXAMPLE 27

6-bromo-1-oxo-4-phenyl-2-(3-phenylpropyl)-1,2-dihydroisoquinoline-3-carboxylic acid methyl ester yield: 252 mg (82%).
$^1$H-NMR (CDCl$_3$) δ: 2.05-2.25 (2H, m), 2.74 (2H, t, J=7.2 Hz), 3.74 (3H, s), 3.95-4.10 (2H, m), 7.15-7.40 (8H, m), 7.45-7.50 (3H, m), 7.65 (1H, dd, J=1.8, 8.4 Hz), 8.37 (1H, d, J=8.4 Hz). LCMS (ESI+): 98% (2.72 min); 476 (M+H), 478. (Method A)

EXAMPLE 28

2-benzyl-6-bromo-1-oxo-4-phenyl-1,2-dihydroisoquinoline-3-carboxylic acid benzyl ester A mixture of 2-benzyl-6-bromo-1-oxo-4-phenyl-1,2-dihydroisoquinoline-3-carboxylic acid (150 mg), potassium carbonate (95 mg), benzylbromide (81 μl) and DMF (5 ml) was stirred at room temperature for 3 hrs. After diluting with water, the mixture was extracted with ether. The extract was washed with saturated brine and dried over magnesium sulfate. The solvent was evaporated under reduced pressure and ethyl acetate and n-hexane was added to the residue. The mixture was crystallized to give the title compound (152 mg, 84%).
$^1$H-NMR (CDCl$_3$) δ: 4.57 (2H, s), 5.43 (2H, s), 6.72 (2H, dd, J=1.8, 8.0 Hz), 7.10-7.30 (10H, m), 7.30-7.40 (4H, m), 7.64 (1H, dd, J=2.0, 8.8 Hz), 8.39 (1H, d, J=8.4 Hz). LCMS (ESI+): 94% (2.60 min); 524 (M+H), 526. (Method A)

In the same manner as in Example 28, the compounds of Examples 29 and 30 were synthesized.

EXAMPLE 29

6-bromo-2-butyl-1-oxo-4-phenyl-1,2-dihydroisoquinoline-3-carboxylic acid benzyl ester yield: 153 mg (83%).
$^1$H-NMR (CDCl$_3$) δ: 0.87 (3H, t, J=7.2 Hz), 1.20-1.35 (2H, m), 1.60-1.75 (2H, m), 3.90-4.00 (2H, m), 4.91 (2H, s), 7.05-7.15 (2H, m)7.25-7.35 (6H, m), 7.40-7.45 (3H, m), 7.61 (1H, dd, J=1.8, 8.4 Hz), 8.34 (1H, d, J=8.4 Hz). LCMS (ESI+): 97% (2.65 min); 490 (M+H), 492. (Method A)

EXAMPLE 30

6-bromo-2-cyclohexylmethyl-1-oxo-4-phenyl-1,2-dihydroisoquinoline-3-carboxylic acid benzyl ester yield: 146 mg (81%).
$^1$H-NMR (CDCl$_3$) δ: 0.80-1.20 (6H, m), 1.45-1.80 (5H, m), 3.91 (2H, d, J=7.4 Hz), 4.86 (2H, s), 7.05-7.20 (2H, m), 7.25-7.35 (6H, m), 7.40-7.45 (3H, m), 7.61 (1H, dd, J=1.8, 8.4 Hz), 8.34 (1H, d, J=8.4 Hz). LCMS (ESI+): 99% (2.77 min); 530 (M+H), 532. (Method A)

EXAMPLE 31

2-benzyl-6-bromo-3-hydroxymethyl-4-phenyl-2H-isoquinolin-1-one

To a solution of 2-benzyl-6-bromo-1-oxo-4-phenyl-1,2-dihydroisoquinoline-3-carboxylic acid (150 mg) in tetrahydrofuran (THF) (5 ml) were added oxalyl chloride (60 µl) and DMF (0.1 ml), and the mixture was stirred at room temperature for 1 hr. The solvent was concentrated under reduced pressure. A solution of the residue in THF (3 ml) was added dropwise to a suspension of sodium borohydride (39 mg) in 1,2-dimethoxyethane. The mixture was stirred under ice-cooling for 1 hr. and poured into 1N hydrochloric acid and the mixture was extracted with ethyl acetate. The extract was washed successively with saturated aqueous sodium hydrogen carbonate and saturated brine, and dried over magnesium sulfate. The solvent was concentrated under reduced pressure and the residue was purified by silica gel column chromatography (n-hexane/ethyl acetate=4/1) to give the title compound (33 mg, 23%).
$^1$H-NMR (CDCl$_3$) δ: 1.69 (1H, t, J=6.0 Hz), 4.29 (2H, d, J=6.0 Hz), 5.70 (2H, s), 7.15-7.35 (8H, m), 7.45-7.55 (3H, m), 7.59 (1H, dd, J=1.8, 8.4 Hz), 8.38 (1H, d, J=8.4 Hz). LCMS (ESI+): 94% (2.22 min); 420 (M+H), 422. (Method A)

In the same manner as in Example 31, the compounds of Examples 32-34 were synthesized.

EXAMPLE 32

6-bromo-2-butyl-3-hydroxymethyl-4-phenyl-2H-isoquinolin-1-one yield: 17 mg.
$^1$H-NMR (CDCl$_3$) δ: 0.99 (3H, t, J=7.2 Hz), 1.40-1.60 (2H, m), 1.65-1.80 (2H, m), 4.31 (2H, t, J=8.0 Hz), 4.42 (2H, s), 7.14 (1H, d, J=1.8 Hz) 7.25-7.30 (2H, m), 7.45-7.60 (4H, m), 8.30 (1H, d, J=8.4 Hz). LCMS (ESI+): 99% (2.25 min); 386 (M+H), 388. (Method A)

EXAMPLE 33

6-bromo-2-cyclohexylmethyl-3-hydroxymethyl-4-phenyl-2H-isoquinolin-1-one yield: 10 mg.
$^1$H-NMR (CDCl$_3$) δ: 1.00-1.30 (4H, m), 1.60-2.00 (7H, m), 4.22 (2H, d, J=6.8 Hz), 4.45 (2H, s), 7.12 (1H, d, J=1.8 Hz), 7.25-7.35 (2H, m), 7.40-7.55 (4H, m), 8.27 (1H, d, J=8.8 Hz). LCMS (ESI+): 98% (2.46 min); 426 (M+H), 428. (Method A)

EXAMPLE 34

6-bromo-3-hydroxymethyl-2-(2-phenethyl)-4-phenyl-2H-isoquinolin-1-one yield: 17 mg.
$^1$H-NMR (CDCl$_3$) δ: 3.15 (2H, t, J=7.6 Hz), 4.23 (2H, s), 4.52 (2H, t, J=7.6 Hz), 7.16 (1H, d, J=1.8 Hz), 7.20-7.40 (7H, m), 7.45-7.55 (3H, m), 7.59 (1H, dd, J=1.8, 8.4 Hz), 8.38 (1H, d, J=8.4 Hz). LCMS (ESI+): 99% (2.34 min); 434 (M+H), 436. (Method A)

EXAMPLE 35

6-bromo-2-(3-methoxycarbonylbenzyl)-1-oxo-4-phenyl-1,2-dihydroisoquinoline-3-carboxylic acid methyl ester To a solution of 6-bromo-1-oxo-4-phenyl-1,2-dihydroisoquinoline-3-carboxylic acid methyl ester (1.30 g) in dimethylformamide (20 ml) was added sodium hydride (oil, 216 mg), and the mixture was stirred at room temperature for 20 min. 3-Bromomethylbenzoic acid methyl ester (990 mg) was added and the mixture was stirred at room temperature for 5 hrs. The solvent was evaporated under reduced pressure and 1N hydrochloric acid was added, and the mixture was extracted with ethyl acetate. The extract was washed with saturated brine and dried by adding sodium sulfate. The solvent was evaporated under reduced pressure, and the obtained residue was purified by silica gel column chromatography (n-hexane/ethyl acetate=19/1→4/1) to give the title compound (719 mg, 39%).
$^1$H-NMR (CDCl$_3$) δ: 3.23 (3H, s), 3.89 (3H, s), 5.44 (2H, s), 7.26-7.53 (8H, m), 7.99 (1H, dd, J=1.8, 8.4 Hz), 7.91-7.95 (2H, m), 8.40 (1H, d, J=8.7 Hz).

EXAMPLE 36

6-bromo-1-oxo-4-phenyl-2-(pyridin-4-ylmethyl)-1,2-dihydroisoquinoline-3-carboxylic acid methyl ester In the same manner as in Example 35 and using 4-chloromethylpyridine hydrochloride, the title compound was obtained.
yield: 12 mg (3%)
$^1$H-NMR (CDCl$_3$) δ: 3.24 (3H, s), 5.35 (2H, s), 7.16-7.48 (9H, m), 7.68 (1H, dd, J=1.8, 8.7 Hz), 8.38 (1H, d, J=8.7 Hz), 8.54 (2H, d, J=6.0 Hz)

EXAMPLE 37

6-bromo-2-(2-fluorobenzyl)-1-oxo-4-phenyl-1,2-dihydroisoquinoline-3-carboxylic acid methyl ester 6-Bromo-1-oxo-4-phenyl-1,2-dihydroisoquinoline-3-carboxylic acid methyl ester (54 mg), 2-fluorobenzylbromide (34 mg) and 2-tert-butylimino-2-diethylamino-1,3-dimethyl-perhydro-1,3,2-diazaphosphorine resin (2.2 mmol/g, 110 mg) were suspended in dimethylformamide (2 ml), and the suspension was shaken at room temperature for 15 hr. using a shaking machine. After filtration, the solvent was evaporated under reduced pressure, and the obtained residue was purified by preparative HPLC to give the title compound (11 mg, 15%).
$^1$H-NMR (CDCl$_3$) δ: 3.30 (3H, s), 5.48 (2H, s), 7.00-7.60 (10H, m), 7.69 (1H, dd, J=1.8, 8.4 Hz), 8.43 (1H, d, J=8.4 Hz). LCMS (ESI+): 100% (4.05 min); 466 (M+1), 468. (Method B)

In the same manner as in Example 37, the compounds of Examples 38-80 were synthesized by reaction with various halides.

EXAMPLE 38

6-bromo-2-(3-fluorobenzyl)-1-oxo-4-phenyl-1,2-dihydroisoquinoline-3-carboxylic acid methyl ester yield: 52 mg (74%)
$^1$H-NMR (CDCl$_3$) δ: 3.23 (3H, s), 5.38 (2H, s), 6.90-7.05 (3H, m) 7.25-7.47 (7H, m), 7.67 (1H, dd, J=1.8, 8.7 Hz), 8.39 (1H, d, J=8.7 Hz). LCMS (ESI+): 98% (4.08 min); 466 (M+1), 468. (Method B)

EXAMPLE 39

6-bromo-2-(4-fluorobenzyl)-1-oxo-4-phenyl-1,2-dihydroisoquinoline-3-carboxylic acid methyl ester yield: 13 mg (19%)
$^1$H-NMR (CDCl$_3$) δ: 3.24 (3H, s), 5.37 (2H, s), 6.95-7.01 (2H, m), 7.24-7.47 (8H, m), 7.66 (1H, dd, J=1.8, 8.7 Hz), 8.39 (1H, d, J=8.7 Hz).

EXAMPLE 40

6-bromo-2-(2,4-difluorobenzyl)-1-oxo-4-phenyl-1,2-dihydroisoquinoline-3-carboxylic acid methyl ester yield: 10 mg (13%). LCMS (ESI+): 97% (4.11 min); 484 (M+1), 486. (Method B)

EXAMPLE 41

6-bromo-2-(3,5-difluorobenzyl)-1-oxo-4-phenyl-1,2-dihydroisoquinoline-3-carboxylic acid methyl ester yield: 47 mg (65%). LCMS (ESI+): 98% (4.13 min); 484 (M+1), 486. (Method B)

EXAMPLE 42

6-bromo-2-(2,6-difluorobenzyl)-1-oxo-4-phenyl-1,2-dihydroisoquinoline-3-carboxylic acid methyl ester yield: 3 mg (4%)
$^1$H-NMR (CDCl$_3$) δ: 3.28 (3H, s), 5.58 (2H, s), 6.80-6.90 (2H, m), 7.20-7.50 (7H, m), 7.67 (1H, dd, J=1.8, 8.4 Hz), 8.41 (1H, d, J=8.4 Hz). LCMS (ESI+): 98% (3.99 min); 484 (M+1), 486. (Method B)

EXAMPLE 43

6-bromo-2-(2-chlorobenzyl)-1-oxo-4-phenyl-1,2-dihydroisoquinoline-3-carboxylic acid methyl ester yield: 4 mg (6%). LCMS (ESI+): 97% (4.19 min); 482 (M+1), 484. (Method B)

EXAMPLE 44

6-bromo-2-(3,4-dichlorobenzyl)-1-oxo-4-phenyl-1,2-dihydroisoquinoline-3-carboxylic acid methyl ester yield: 52 mg (67%). LCMS (ESI+): 100% (2.67 min); 415 (M+1), 517. (Method A)

EXAMPLE 45

6-bromo-2-(3-bromobenzyl)-1-oxo-4-phenyl-1,2-dihydroisoquinoline-3-carboxylic acid methyl ester yield: 59 mg (75%). LCMS (ESI+): 99% (4.28 min); 526 (M+1), 528. (Method B)

EXAMPLE 46

6-bromo-1-oxo-4-phenyl-2-(2-trifluoromethylbenzyl)-1,2-dihydroisoquinoline-3-carboxylic acid methyl ester yield: 1 mg (2%). LCMS (ESI+): 92% (4.23 min); 516 (M+1), 518. (Method B)

EXAMPLE 47

6-bromo-1-oxo-4-phenyl-2-(3-trifluoromethylbenzyl)-1,2-dihydroisoquinoline-3-carboxylic acid methyl ester yield: 37 mg (48%). LCMS (ESI+): 100% (4.26 min); 516 (M+1), 518. (Method B)

EXAMPLE 48

6-bromo-1-oxo-4-phenyl-2-(4-trifluoromethylbenzyl)-1,2-dihydroisoquinoline-3-carboxylic acid methyl ester yield: 24 mg (31%)
$^1$H-NMR (CDCl$_3$) δ: 3.25 (3H, s), 5.41 (2H, s), 7.25-7.58 (10H, m), 7.67 (1H, dd, J=1.8, 8.4 Hz), 8.38 (1H, d, J=8.4 Hz). LCMS (ESI+): 100% (4.27 min); 516 (M+1), 518. (Method B)

EXAMPLE 49

6-bromo-1-oxo-4-phenyl-2-(4-trifluoromethoxybenzyl)-1,2-dihydroisoquinoline-3-carboxylic acid methyl ester yield: 48 mg (60%). LCMS (ESI+): 99% (2.63 min); 532 (M+1), 533. (Method A)

EXAMPLE 50

6-bromo-2-(2-methylbenzyl)-1-oxo-4-phenyl-1,2-dihydroisoquinoline-3-carboxylic acid methyl ester yield: 6 mg (8%). LCMS (ESI+): 95% (4.16 min); 462 (M+1), 464. (Method B)

EXAMPLE 51

6-bromo-2-(4-methylbenzyl)-1-oxo-4-phenyl-1,2-dihydroisoquinoline-3-carboxylic acid methyl ester yield: 11 mg (15%). LCMS (ESI+): 98% (4.20 min); 462 (M+1), 464. (Method B)

EXAMPLE 52

6-bromo-2-(3,4-dimethylbenzyl)-1-oxo-4-phenyl-1,
2-dihydroisoquinoline-3-carboxylic acid methyl
ester yield: 36 mg (50%). LCMS (ESI+): 98% (4.31 min); 476 (M+1), 478. (Method B)

EXAMPLE 53

6-bromo-2-(4-tert-butylbenzyl)-1-oxo-4-phenyl-1,2-
dihydroisoquinoline-3-carboxylic acid methyl ester yield: 49 mg (64%). LCMS (ESI+): 99% (4.55 min); 504 (M+1), 506. (Method B)

EXAMPLE 54

6-bromo-2-(3-methoxybenzyl)-1-oxo-4-phenyl-1,2-
dihydroisoquinoline-3-carboxylic acid methyl ester yield: 46 mg (64%). LCMS (ESI+): 97% (4.02 min); 478 (M+1), 480. (Method B)

EXAMPLE 55

6-bromo-2-(4-methoxybenzyl)-1-oxo-4-phenyl-1,2-
dihydroisoquinoline-3-carboxylic acid methyl ester yield: 10 mg (14%). LCMS (ESI+): 96% (4.03 min); 478 (M+1), 480. (Method B)

EXAMPLE 56

6-bromo-2-(2-nitrobenzyl)-1-oxo-4-phenyl-1,2-dihydroisoquinoline-3-carboxylic acid methyl ester yield: 10 mg (13%). LCMS (ESI+): 93% (3.97 min); 493 (M+1), 495. (Method B)

EXAMPLE 57

6-bromo-2-(3-nitrobenzyl)-1-oxo-4-phenyl-1,2-dihydroisoquinoline-3-carboxylic acid methyl ester yield: 26 mg (35%). LCMS (ESI+): 99% (3.99 min); 493 (M+1), 495. (Method B)

EXAMPLE 58

6-bromo-2-(4-nitrobenzyl)-1-oxo-4-phenyl-1,2-dihydroisoquinoline-3-carboxylic acid methyl ester yield: 1 mg (2%). LCMS (ESI+): 99% (3.86 min); 473 (M+1), 475. (Method B)

EXAMPLE 59

6-bromo-2-(4-cyanobenzyl)-1-oxo-4-phenyl-1,2-
dihydroisoquinoline-3-carboxylic acid methyl ester yield: 24 mg (33%). LCMS (ESI+): 93% (3.99 min); 493 (M+1), 495. (Method B)

EXAMPLE 60

2-(biphenyl-2-ylmethyl)-6-bromo-1-oxo-4-phenyl-1,
2-dihydroisoquinoline-3-carboxylic acid methyl
ester yield: 5 mg (6%). LCMS (ESI+): 100% (4.36 min); 524 (M+1), 526. (Method B)

EXAMPLE 61

2-(biphenyl-4-ylmethyl)-6-bromo-1-oxo-4-phenyl-1,
2-dihydroisoquinoline-3-carboxylic acid methyl
ester yield: 52 mg (72%). LCMS (ESI+): 99% (4.43 min); 524 (M+1), 526. (Method B)

EXAMPLE 62

6-bromo-2-(naphthalen-1-ylmethyl)-1-oxo-4-phenyl-
1,2-dihydroisoquinoline-3-carboxylic acid methyl
ester yield: 9 mg (11%). LCMS (ESI+): 99% (4.26 min); 498 (M+1), 500. (Method B)

EXAMPLE 63

6-bromo-2-(naphthalen-2-ylmethyl)-1-oxo-4-phenyl-
1,2-dihydroisoquinoline-3-carboxylic acid methyl
ester yield: 57 mg (76%). LCMS (ESI+): 99% (4.30 min); 498 (M+1), 500. (Method B)

EXAMPLE 64

6-bromo-1-oxo-2-(3-phenoxybenzyl)-4-phenyl-1,2-
dihydroisoquinoline-3-carboxylic acid methyl ester yield: 55 mg (68%). LCMS (ESI+): 99% (4.39 min); 540 (M+1), 542. (Method B)

EXAMPLE 65

2-(4-benzoylbenzyl)-6-bromo-1-oxo-4-phenyl-1,2-
dihydroisoquinoline-3-carboxylic acid methyl ester yield: 29 mg (34%). LCMS (ESI+): 100% (2.58 min); 552 (M+1), 554. (Method A)

EXAMPLE 66

6-bromo-2-(a-methoxycarbonylbenzyl)-1-oxo-4-
phenyl-1,2-dihydroisoquinoline-3-carboxylic acid
methyl ester yield: 44 mg (58%). LCMS (ESI+): 99% (4.27 min); 506 (M+1), 508. (Method B)

EXAMPLE 67

6-bromo-2-(2-oxo-2-phenethyl)-1-oxo-4-phenyl-1,2-dihydroisoquinoline-3-carboxylic acid methyl ester yield: 11 mg (15%). LCMS (ESI+): 98% (4.10 min); 476 (M+1), 478. (Method B)

EXAMPLE 68

6-bromo-2-[2-(4-chlorophenyl)-2-oxoethyl]-1-oxo-4-phenyl-1,2-dihydroisoquinoline-3-carboxylic acid methyl ester yield: 8 mg (10%). LCMS (ESI+): 93% (4.01 min); 510 (M+1), 412. (Method B)

EXAMPLE 69

6-bromo-2-[2-(4-methoxyphenyl)-2-oxoethyl]-1-oxo-4-phenyl-1,2-dihydroisoquinoline-3-carboxylic acid methyl ester yield: 6 mg (8%). LCMS (ESI+): 97% (3.81 min); 506 (M+1), 508. (Method B)

EXAMPLE 70

6-bromo-2-[2-(4-nitrophenyl)-2-oxoethyl]-1-oxo-4-phenyl-1,2-dihydroisoquinoline-3-carboxylic acid methyl ester yield: 7 mg (9%). LCMS (ESI+): 99% (3.85 min); 521 (M+1), 523. (Method B)

EXAMPLE 71

6-bromo-2-[2-(4-cyanophenyl)-2-oxoethyl]-1-oxo-4-phenyl-1,2-dihydroisoquinoline-3-carboxylic acid methyl ester yield: 8 mg (11%). LCMS (ESI+): 92% (3.76 min); 501 (M+1), 503. (Method B)

EXAMPLE 72

6-bromo-2-(3,5-dimethylisoxazol-4-ylmethyl)-1-oxo-4-phenyl-1,2-dihydroisoquinoline-3-carboxylic acid methyl ester yield: 8 mg (11%)
$^1$H-NMR (CDCl$_3$): δ: 2.08 (3H, s), 2.26 (3H, s), 3.13 (3H, s), 5.34 (2H, s), 7.20-7.30 (2H, m), 7.39-7.50 (3H, m), 7.71 (1H, dd, J=2.2, 8.4 Hz), 8.42 (1H, d, J=8.4 Hz). LCMS (ESI+): 96% (3.74 min); 467 (M+1), 469. (Method B)

EXAMPLE 73

2-(1H-benzimidazol-2-ylmethyl)-6-bromo-1-oxo-4-phenyl-1,2-dihydroisoquinoline-3-carboxylic acid methyl ester trifluoroacetate yield: 6 mg (6%). LCMS (ESI+): 90% (3.85 min); 488 (M+1), 490. (Method A)

EXAMPLE 74

6-bromo-1-oxo-4-phenyl-2-(pyridin-2-ylmethyl)-1,2-dihydroisoquinoline-3-carboxylic acid methyl ester trifluoroacetate yield: 32 mg (38%). LCMS (ESI+): 97% (2.99 min); 449 (M+1), 451. (Method A)

EXAMPLE 75

6-bromo-1-oxo-4-phenyl-2-(pyridin-3-ylmethyl)-1,2-dihydroisoquinoline-3-carboxylic acid methyl ester trifluoroacetate yield: 64 mg (76%). LCMS (ESI+): 90% (2.78 min); 449 (M+1), 451. (Method A)

EXAMPLE 76

6-bromo-1-oxo-4-phenyl-2-(quinolin-2-ylmethyl)-1,2-dihydroisoquinoline-3-carboxylic acid methyl ester trifluoroacetate yield: 35 mg (38%). LCMS (ESI+): 98% (3.59 min); 449 (M+1), 451. (Method B)

EXAMPLE 77

6-bromo-1-oxo-4-phenyl-2-(thiazol-4-ylmethyl)-1,2-dihydroisoquinoline-3-carboxylic acid methyl ester yield: 17 mg (25%). LCMS (ESI+): 98% (3.53 min); 455 (M+1), 457. (Method B)

EXAMPLE 78

6-bromo-2-[4-(4-chlorobenzoyl)benzyl]-1-oxo-4-phenyl-1,2-dihydroisoquinoline-3-carboxylic acid methyl ester yield: 48 mg (55%). LCMS (ESI+): 100% (4.43 min); 586 (M+1), 588. (Method B)

EXAMPLE 79

6-bromo-1-oxo-2-(4-phenoxybenzyl)-4-phenyl-1,2-dihydroisoquinoline-3-carboxylic acid methyl ester yield: 6 mg (8%). LCMS (ESI+): 91% (4.44 min); 540 (M+1), 542. (Method B)

EXAMPLE 80

2-(3-benzoylbenzyl)-6-bromo-1-oxo-4-phenyl-1,2-dihydroisoquinoline-3-carboxylic acid methyl ester yield: 54 mg (65%). LCMS (ESI+): 99% (4.20 min); 552 (M+1), 554. (Method B)

EXAMPLE 81

6-bromo-2-(4-methoxycarbonylbenzyl)-1-oxo-4-phenyl-1,2-dihydroisoquinoline-3-carboxylic acid methyl ester To a solution of 6-bromo-4-phenyl-3-isocoumarincarboxylic acid methyl ester (3.60 g) in methanol (50 ml) was added 4-aminomethylbenzoic acid methyl ester (3.16 ml) and the mixture was stirred at room temperature for 18 hrs. The solvent was evaporated under reduced pressure and 1N hydrochloric acid was added, and the mixture was extracted with ethyl acetate. The extract was washed with saturated brine and dried by adding sodium sulfate. The solvent was evaporated under reduced pressure, and the obtained residue was dissolved in methanol (100 ml). Conc. sulfuric acid (10 ml) was added, and the mixture was heated under reflux for 3 hr. The solvent was evaporated under reduced pressure, water was added under ice-cooling and the mixture was neutralized with potassium carbonate. The solution was extracted with ethyl acetate and the extract was washed with saturated brine. Sodium sulfate was added to dry the mixture. The obtained residue was recrystallized from methanol to give the title compound (3.39 g, 67%).

$^1$H-NMR (CDCl$_3$) δ: 3.18 (3H, s), 3.89 (3H, s), 5.45 (2H, s), 7.24-7.47 (8H, m), 7.67 (1H, dd, J=1.8, 8.4 Hz), 7.97 (2H, d, J=8.4 Hz), 8.40 (1H, d, J=8.4 Hz).

EXAMPLE 82

6-chloro-2-(4-methoxycarbonylbenzyl)-1-oxo-4-phenyl-1,2-dihydroisoquinoline-3-carboxylic acid methyl ester In the same manner as in Example 81, the title compound was synthesized.

yield: 3.26 g (71%)

$^1$H-NMR (CDCl$_3$) δ: 3.21 (3H, s), 3.91 (3H, s), 5.48 (2H, s), 7.24-7.57 (9H, m), 7.99 (2H, d, J=8.4 Hz), 8.50 (1H, d, J=8.6 Hz).

EXAMPLE 83

6-bromo-2-(3,5-dimethoxybenzyl)-1-oxo-4-phenyl-1,2-dihydroisoquinoline-3-carboxylic acid methyl ester To a solution of 6-bromo-4-phenyl-3-isocoumarincarboxylic acid methyl ester (539 mg) in methanol (10 ml) was added 3,5-dimethoxybenzylamine (1.25 g), and the mixture was stirred at room temperature for 12 hrs. The solvent was evaporated under reduced pressure and 1N hydrochloric acid was added. The mixture was extracted with ethyl acetate. The extract was washed with saturated brine and dried by adding sodium sulfate. The solvent was evaporated under reduced pressure, and 4N hydrogen chloride ethyl acetate solution (5 ml) was added to the obtained residue. The mixture was stirred at room temperature for 10 hrs. The solvent was evaporated under reduced pressure, water was added and the mixture was extracted with ethyl acetate. The extract was washed successively with saturated aqueous sodium hydrogen carbonate solution and saturated brine and dried by adding sodium sulfate. The obtained residue was purified by silica gel column chromatography (n-hexane/ethyl acetate=19/1→4/1) to give the title compound (555 mg, 73%).

$^1$H-NMR (CDCl$_3$) δ: 3.25 (3H, s), 3.74 (6H, s), 5.34 (2H, s), 6.33 (1H, t, J=2.1 Hz), 6.40 (2H, d, J=2.1 Hz), 7.26-7.47 (6H, m), 7.65 (1H, dd, J=1.8, 8.7 Hz), 8.39 (1H, d, J=8.7 Hz).

In the same manner as in Example 83, the compounds of Examples 84-101 were synthesized using various amines.

EXAMPLE 84

6-bromo-2-(3,4-dimethoxybenzyl)-1-oxo-4-phenyl-1,2-dihydroisoquinoline-3-carboxylic acid methyl ester yield: 179 mg (35%)

$^1$H-NMR (CDCl$_3$) δ: 3.25 (3H, s), 3.83 (6H, s), 5.35 (2H, s), 6.75-6.88 (3H, m), 7.26-7.48 (6H, m), 7.65 (1H, dd, J=1.8, 8.4 Hz), 8.40 (1H, d, J=8.4 Hz).

EXAMPLE 85

6-bromo-1-oxo-4-phenyl-2-(1,2,3,4-tetrahydronaphthalen-1-yl)-1,2-dihydroisoquinoline-3-carboxylic acid methyl ester yield: 125 mg (26%)

$^1$H-NMR (CDCl$_3$) δ: 1.81 (1H, m), 2.00-3.67 (8H, m), 4.96 (1/2H, s), 6.83 (1/2H, s), 7.08-7.70 (11H, m), 8.28 (1H, s). LCMS (ESI+): 98% (2.57 min); 488 (M+1), 490. (A)

EXAMPLE 86

6-bromo-2-(2,5-dimethoxybenzyl)-1-oxo-4-phenyl-1,2-dihydroisoquinoline-3-carboxylic acid methyl ester yield: 148 mg (29%)

$^1$H-NMR (CDCl$_3$) δ: 3.25 (3H, s), 3.69 (3H, s), 3.48 (3H, s), 5.35 (2H, s), 6.63 (1H, m), 6.69-6.78 (2H, m), 7.26-7.48 (6H, m), 7.65 (1H, dd, J=1.8, 8.4 Hz), 8.39 (1H, d, J=8.4 Hz).

EXAMPLE 87

6-bromo-2-(2-methoxybenzyl)-1-oxo-4-phenyl-1,2-dihydroisoquinoline-3-carboxylic acid methyl ester yield: 60 mg (12%)

$^1$H-NMR (CDCl$_3$) δ: 3.22 (3H, s), 3.80 (3H, s), 5.39 (2H, s), 6.82-6.89 (2H, m), 7.04 (1H, m), 7.19-7.48 (7H, m), 7.66 (1H, dd, J=1.8, 8.7 Hz), 8.37 (1H, d, J=8.7 Hz).

EXAMPLE 88

6-bromo-2-(2,4-dimethoxybenzyl)-1-oxo-4-phenyl-1,2-dihydroisoquinoline-3-carboxylic acid methyl ester yield: 78 mg (15%)

$^1$H-NMR (CDCl$_3$) δ: 3.25 (3H, s), 3.75 (3H, s), 3.76 (3H, s), 5.32 (2H, s), 6.37-6.40 (2H, m), 7.01 (1H, d, J=9.3 Hz), 7.26-7.44 (6H, m), 7.63 (1H, dd, J=1.8, 8.7 Hz), 8.39 (1H, d, J=8.7 Hz).

EXAMPLE 89

6-bromo-2-(2,3-dimethoxybenzyl)-1-oxo-4-phenyl-1,2-dihydroisoquinoline-3-carboxylic acid methyl ester yield: 139 mg (27%)

$^1$H-NMR (CDCl$_3$) δ: 3.25 (3H, s), 3.69 (3H, s), 3.77 (3H, s), 5.35 (2H, s), 6.62-6.78 (3H, m), 7.26-7.48 (6H, m), 7.64 (1H, dd, J=1.8, 8.4 Hz), 8.39 (1H, d, J=8.4 Hz).

EXAMPLE 90

6-bromo-2-cyclopropylmethyl-1-oxo-4-phenyl-1,2-dihydroisoquinoline-3-carboxylic acid methyl ester yield: 125 mg (30%)

$^1$H-NMR (CDCl$_3$) δ: 0.45-0.57 (4H, m), 1.24 (1H, m), 3.48 (3H, s), 4.00 (2H, d, J=6.9 Hz), 7.29-7.51 (6H, m), 7.63 (1H, dd, J=1.8, 8.4 Hz), 8.37 (1H, d, J=8.4 Hz).

EXAMPLE 91

2-(1-benzylpyrrolidin-3-yl)-6-bromo-1-oxo-4-phenyl-1,2-dihydroisoquinoline-3-carboxylic acid methyl ester yield: 30 mg (6%)

$^1$H-NMR (CDCl$_3$) δ: 2.26 (1H, m), 2.54 (1H, m), 2.98-3.17 (4H, m), 3.48 (3H, s), 3.70-3.80 (2H, m), 4.36 (1H, m), 7.20-7.48 (11H, m), 7.63 (1H, dd, J=1.8, 8.4 Hz), 8.33 (1H, d, J=8.4 Hz).

EXAMPLE 92

2-(1-benzylpiperidin-4-yl)-6-bromo-1-oxo-4-phenyl-1,2-dihydroisoquinoline-3-carboxylic acid methyl ester yield: 112 mg (21%)

$^1$H-NMR (CDCl$_3$) δ: 1.70-1.80 (2H, m), 1.95-2.07 (2H, m), 2.95-3.08 (4H, m), 3.51-3.68 (6H, m), 7.20-7.50 (11H, m), 7.60 (1H, dd, J=1.8, 8.7 Hz), 8.32 (1H, d, J=8.7 Hz).

EXAMPLE 93

6-bromo-1-oxo-4-phenyl-2-(4-sulfamoylbenzyl)-1,2-dihydroisoquinoline-3-carboxylic acid methyl ester yield: 193 mg (37%)

$^1$H-NMR (CDCl$_3$) δ: 3.26 (3H, s), 4.75 (2H, s), 5.40 (2H, s), 7.26-7.31 (2H, m), 7.39-7.50 (6H, m), 7.68 (1H, dd, J=2.1, 8.7 Hz), 7.86 (2H, d, J=8.1 Hz), 8.37 (1H, d, J=8.7 Hz).

EXAMPLE 94

6-bromo-2-(4-methanesulfonylbenzyl)-1-oxo-4-phenyl-1,2-dihydroisoquinoline-3-carboxylic acid methyl ester yield: 329 mg (63%)

$^1$H-NMR (CDCl$_3$) δ: 3.02 (3H, s), 3.26 (3H, s), 5.42 (2H, s), 7.26-7.51 (8H, m), 7.69 (1H, dd, J=1.8, 8.7 Hz), 7.87-7.91 (2H, m), 8.38 (1H, d, J=8.7 Hz).

EXAMPLE 95

6-bromo-1-oxo-4-phenyl-2-(1-phenylethyl)-1,2-dihydroisoquinoline-3-carboxylic acid methyl ester yield: 85 mg (18%)

$^1$H-NMR (CDCl$_3$) δ: 2.04 (3H, d, J=6.9 Hz), 3.12 (3H, s), 5.85 (2H, d, J=6.9 Hz), 7.21-7.46 (11H, m), 7.60 (1H, dd, J=1.8, 8.7 Hz), 8.31 (1H, d, J=8.7 Hz).

EXAMPLE 96

6-bromo-2-(indan-2-yl)-1-oxo-4-phenyl-1,2-dihydroisoquinoline-3-carboxylic acid methyl ester yield: 148 mg (31%)

$^1$H-NMR (CDCl$_3$) δ: 3.24 (2H, dd, J=9.3, 15.6 Hz), 3.48 (3H, s), 4.01 (2H, dd, J=8.1, 15.6 Hz), 4.65 (1H, m), 7.17-7.50 (2H, m), 7.61 (1H, dd, J=1.8, 8.7 Hz), 8.31 (1H, d, J=8.7 Hz).

EXAMPLE 97

2-(4-aminobenzyl)-6-bromo-1-oxo-4-phenyl-1,2-dihydroisoquinoline-3-carboxylic acid methyl ester yield: 1.03 g (74%)

$^1$H-NMR (CDCl$_3$) δ: 3.24 (3H, s), 3.62 (2H, s), 5.31 (2H, s), 6.58 (2H, d, J=8.7 Hz), 7.07 (2H, d, J=8.7 Hz), 7.26-7.48 (6H, m), 7.64 (1H, dd, J=1.8, 8.4 Hz), 8.40 (1H, d, J=8.4 Hz).

EXAMPLE 98

2-(3-aminobenzyl)-6-bromo-1-oxo-4-phenyl-1,2-dihydroisoquinoline-3-carboxylic acid methyl ester yield: 615 mg (44%)

$^1$H-NMR (CDCl$_3$) δ: 3.22 (3H, s), 3.62 (2H, s), 5.34 (2H, s), 6.53-6.61 (3H, m), 7.25-7.46 (6H, m), 7.65 (1H, dd, J=1.8, 8.7 Hz), 8.41 (1H, d, J=8.7 Hz).

EXAMPLE 99

6-bromo-1-oxo-4-phenyl-2-(3,4,5-trimethoxybenzyl)-1,2-dihydroisoquinoline-3-carboxylic acid methyl ester yield: 310 mg (63%).

$^1$H-NMR (CDCl$_3$) δ: 3.26 (3H, s), 3.80 (3H, s), 3.81 (6H, s), 5.33 (2H, s), 6.53 (2H, s), 7.23-7.31 (2H, m), 7.38 (1H, d, J=1.8 Hz), 7.40-7.49 (3H, m), 7.66 (1H, dd, J=1.8, 8.8 Hz), 8.40 (1H, d, J=8.8 Hz).

EXAMPLE 100

6-bromo-2-(2,3-dihydrobenzofuran-5-ylmethyl)-1-oxo-4-phenyl-1,2-dihydroisoquinoline-3-carboxylic acid methyl ester yield: 187 mg (46%).

$^1$H-NMR (CDCl$_3$) δ: 3.14 (2H, t, J=8.6 Hz), 3.26 (3H, s), 4.53 (2H, t, J=8.6 Hz), 5.33 (2H, s), 6.67 (1H, d, J=8.2 Hz), 6.99 (1H, dd, J=1.8, 8.0 Hz), 7.16 (1H, d, J=1.8 Hz), 7.23-7.30 (2H, m), 7.35-7.48 (4H, m), 7.65 (1H, dd, J=2.0, 8.8 Hz), 8.40 (1H, d, J=8.8 Hz).

EXAMPLE 101

6-bromo-2-(5-methylpyrazin-2-ylmethyl)-1-oxo-4-phenyl-1,2-dihydroisoquinoline-3-carboxylic acid methyl ester yield: 91 mg (23%).
$^1$H-NMR (CDCl$_3$) δ: 2.52 (3H, s), 3.33 (3H, s), 5.49 (2H, s), 7.25-7.34 (2H, m), 7.36-7.49 (3H, m), 7.66 (1H, dd, J=1.8, 8.4 Hz), 8.35 (1H, s), 8.38 (1H, d, J=8.4 Hz), 8.48 (1H, s).

EXAMPLE 102

6-bromo-2-(4-carboxybenzyl)-1-oxo-4-phenyl-1,2-dihydroisoquinoline-3-carboxylic acid methyl ester To a mixture of 6-bromo-2-(4-methoxycarbonylbenzyl)-1-oxo-4-phenyl-1,2-dihydroisoquinoline-3-carboxylic acid methyl ester (2.00 g) in methanol (10 ml) and tetrahydrofuran (20 ml) was added 8N aqueous sodium hydroxide solution (1 ml) and the mixture was stirred at room temperature for 12 hrs. The solvent was evaporated under reduced pressure and water was added. The mixture was acidified with 1N hydrochloric acid and extracted with ethyl acetate. The extract was washed with saturated brine and dried by adding sodium sulfate. The solvent was evaporated under reduced pressure and the obtained residue was recrystallized from methanol to give the title compound (1.29 g, 65%).
$^1$H-NMR (CDCl$_3$) δ: 3.21 (3H, s), 5.46 (2H, s), 7.25-7.49 (8H, m), 7.68 (1H, dd, J=1.8, 8.7 Hz), 8.02 (2H, d, J=7.0 Hz), 8.40 (1H, d, J=8.4H).

EXAMPLE 103

6-bromo-2-(3-carboxybenzyl)-1-oxo-4-phenyl-1,2-dihydroisoquinoline-3-carboxylic acid methyl ester In the same manner as in Example 102, the title compound was synthesized.
yield: 238 mg (97%)
$^1$H-NMR (CDCl$_3$) δ: 3.25 (3H, s), 5.45 (2H, s), 7.26-7.60 (8H, m), 7.70 (1H, dd, J=1.8, 8.4 Hz), 7.98-8.01 (2H, m), 8.41 (1H, d, J=8.4 Hz).

EXAMPLE 104

2-(3,5-dimethoxybenzyl)-1-oxo-4-phenyl-1,2-dihydroisoquinoline-3-carboxylic acid methyl ester To a solution of 6-bromo-2-(3,5-dimethoxybenzyl)-1-oxo-4-phenyl-1,2-dihydroisoquinoline-3-carboxylic acid methyl ester (153 mg) in methanol (5 ml) was added palladium carbon (10%, 15 mg), and hydrogen gas was filled. The mixture was stirred at room temperature for 15 hrs. and filtered through celite. The solvent was evaporated under reduced pressure, and the obtained residue was recrystallized from methanol to give the title compound (113 mg, 88%).
$^1$H-NMR (CDCl$_3$) δ: 3.25 (3H, s), 3.74 (6H, s), 5.38 (2H, s), 6.33 (1H, m), 6.42 (2H, m), 7.24-7.62 (8H, m), 8.55 (1H, m).

EXAMPLE 105

2-(4-carboxybenzyl)-1-oxo-4-phenyl-1,2-dihydroisoquinoline-3-carboxylic acid methyl ester In the same manner as in Example 104, the title compound was synthesized.
yield: 106 mg (25%)
$^1$H-NMR (CDCl$_3$) δ: 3.21 (3H, s), 5.50 (2H, s), 7.26-7.66 (10H, m), 8.03 (2H, d, J=8.1 Hz), 8.56 (1H, m).

EXAMPLE 106

6-bromo-2-(1-tert-butoxycarbonylpiperidin-2-ylmethyl)-1-oxo-4-phenyl-1,2-dihydroisoquinoline-3-carboxylic acid methyl ester To a solution of 6-bromo-4-phenyl-3-isocoumarincarboxylic acid methyl ester (539 mg) in methanol (10 ml) was added 2-aminomethylpiperidine-1-carboxylic acid tert-butyl ester (1.07 g), and the mixture was stirred at room temperature for 12 hrs. The solvent was evaporated under reduced pressure, 1N hydrochloric acid was added, and the mixture was extracted with ethyl acetate. The extract was washed with saturated brine and dried by adding sodium sulfate. The solvent was evaporated under reduced pressure, and 4N hydrogen chloride-ethyl acetate solution (5 ml) was added to the obtained residue. The mixture was stirred at room temperature for 10 hrs. The solvent was evaporated under reduced pressure, and 1N aqueous sodium hydroxide solution (10 ml), tetrahydrofuran (10 ml) and di-tert-butyl carbonate (437 mg) were added. The mixture was stirred at room temperature for 12 hrs. The solvent was evaporated under reduced pressure, and the obtained residue was extracted with ethyl acetate. The extract was washed with saturated brine and dried by adding sodium sulfate. The obtained residue was purified by silica gel column chromatography (n-hexane/ethyl acetate=9/1→4/1) to give the title compound (64 mg, 12%).
$^1$H-NMR (CDCl$_3$) δ: 1.11 (9H, s), 0.87-1.80 (6H, m), 2.81 (1H, m), 3.40 (3H, s), 3.90-4.25 (2H, m), 4.40-4.75 (2H, m), 7.20-7.60 (6H, m), 7.61 (1H, d, J=8.6 Hz), 8.44 (1H, d, J=8.6 Hz).

In the same manner as in Example 106, the compounds of Examples 107 and 108 were obtained.

EXAMPLE 107

6-bromo-2-(1-tert-butoxycarbonylpiperidin-3-ylmethyl)-1-oxo-4-phenyl-1,2-dihydroisoquinoline-3-carboxylic acid methyl ester yield: 153 mg (28%)
$^1$H-NMR (CDCl$_3$) δ: 1.10-1.65 (2H, m), 1.38 (9H, s), 1.68-2.08 (3H, m), 2.50-2.81 (2H, m), 3.46 (3H, s), 3.79-4.05 (4H, m), 7.20-7.56 (6H, m), 7.63 (1H, d, J=8.8 Hz), 8.34 (1H, d, J=8.8 Hz).

EXAMPLE 108

6-bromo-2-(1-tert-butoxycarbonylpiperidin-4-ylmethyl)-1-oxo-4-phenyl-1,2-dihydroisoquinoline-3-carboxylic acid methyl ester yield: 142 mg (26%)
$^1$H-NMR (CDCl$_3$) δ: 1.11-1.64 (4H, m), 1.43 (9H, s), 2.03 (1H, m), 2.50-2.72 (2H, m), 3.46 (3H, s), 4.83-4.20 (4H, m), 7.25-7.50 (6H, m), 7.63 (1H, dd, J=1.8, 8.8 Hz), 8.34 (1H, d, J=8.8 Hz).

EXAMPLE 109

6-bromo-1-oxo-4-phenyl-2-(piperidin-2-ylmethyl)-1,2-dihydroisoquinoline-3-carboxylic acid methyl ester hydrochloride 4N Hydrogen chloride ethyl acetate solution (5 ml) was added to 6-bromo-2-(1-tert-butoxycarbonylpiperidin-2-ylmethyl)-1-oxo-4-phenyl-1,2-dihydroisoquinoline-3-carboxylic acid methyl ester (44 mg), and the mixture was stirred at room temperature for 2 hrs. The solvent was evaporated under reduced pressure, and the obtained residue was crystallized from isopropyl ether to give the title compound (21 mg, 53%).

$^1$H-NMR (CDCl$_3$) δ: 1.52 (1H, m), 1.80-2.16 (5H, m), 2.98 (1H, m), 3.57 (3H, s), 3.60-3.78 (2H, m), 4.19 (1H, m), 4.72 (1H, m), 7.20-7.50 (6H, m), 7.63 (1H, d, J=7.2 Hz), 8.27 (1H, d, J=7.2 Hz).

In the same manner as in Example 109, the compounds of Examples 110 and 111 were obtained.

EXAMPLE 110

6-bromo-1-oxo-4-phenyl-2-(piperidin-3-ylmethyl)-1,2-dihydroisoquinoline-3-carboxylic acid methyl ester hydrochloride yield: 93 mg (79%)
$^1$H-NMR (CDCl$_3$) δ: 1.44 (1H, m), 1.80-2.00 (3H, m), 2.47 (1H, m), 2.75-2.97 (2H, m), 3.32-3.42 (2H, m), 3.50 (3H, s), 3.96 (1H, m), 4.19 (1H, m), 7.23-7.49 (6H, m), 7.67 (1H, dd, J=1.8, 8.7 Hz), 8.31 (1H, d, J=8.7 Hz).

EXAMPLE 111

6-bromo-1-oxo-4-phenyl-2-(piperidin-4-ylmethyl)-1,2-dihydroisoquinoline-3-carboxylic acid methyl ester hydrochloride yield: 96 mg (89%)
$^1$H-NMR (CDCl$_3$) δ: 0.60-2.00 (4H, m), 2.26 (1H, m), 2.75-2.90 (2H, m), 3.38-3.58 (2H, m), 3.50 (3H, s), 3.90-4.00 (2H, m), 7.25-7.52 (6H, m), 7.65 (1H, m), 8.31 (1H, d, J=8.7 Hz).

EXAMPLE 112

2-(1-acetylpiperidin-4-ylmethyl)-6-bromo-1-oxo-4-phenyl-1,2-dihydroisoquinoline-3-carboxylic acid methyl ester To a solution of 6-bromo-1-oxo-4-phenyl-2-(piperidin-4-ylmethyl)-1,2-dihydroisoquinoline-3-carboxylic acid methyl ester hydrochloride (49 mg) in tetrahydrofuran (5 ml) were added triethylamine (0.03 ml) and acetic anhydride (0.05 ml) and the mixture was stirred at room temperature for 16 hrs. The solvent was evaporated under reduced pressure, water was added and the mixture was extracted with ethyl acetate. The extract was washed with saturated brine and dried by adding sodium sulfate. The solvent was evaporated under reduced pressure, and the obtained residue was purified by preparative HPLC to give the title compound (18 mg, 36%).

$^1$H-NMR (CDCl$_3$) δ: 1.10-1.40 (2H, m), 1.60-1.80 (2H, m), 2.06 (3H, s), 2.16 (1H, m), 2.50 (1H, m), 2.98 (1H, m), 3.46 (3H, s), 3.72-3.94 (2H, m), 4.06 (1H, m), 4.61 (1H, m), 7.23-7.58 (6H, m), 7.64 (1H, dd, J=2.2, 8.8 Hz), 8.34 (1H, d, J=8.8 Hz).

In the same manner as in Example 112, an amine compound was acylated to give the compounds of Examples 113-116.

EXAMPLE 113

6-bromo-2-(1-methanesulfonylpiperidin-4-ylmethyl)-1-oxo-4-phenyl-1,2-dihydroisoquinoline-3-carboxylic acid methyl ester yield: 22 mg (41%)
$^1$H-NMR (CDCl$_3$) δ: 1.20-1.85 (4H, m), 2.04 (1H, m), 2.55-2.80 (2H, m), 2.75 (3H, s), 3.46 (3H, s), 3.70-4.07 (4H, m), 7.20-7.72 (7H, m), 8.34 (1H, d, J=8.8 Hz).

EXAMPLE 114

2-(3-acetylaminobenzyl)-6-bromo-1-oxo-4-phenyl-1,2-dihydroisoquinoline-3-carboxylic acid methyl ester yield: 200 mg (45%)
$^1$H-NMR (CDCl$_3$) δ: 2.13 (3H, s), 3.27 (3H, s), 5.37 (2H, s), 6.44 (1H, s), 6.82 (1H, d, J=7.8 Hz), 7.19-7.50 (7H, m), 7.57-7.67 (2H, m), 8.39 (1H, d, J=8.4 Hz).

EXAMPLE 115

2-(4-acetylaminobenzyl)-6-bromo-1-oxo-4-phenyl-1,2-dihydroisoquinoline-3-carboxylic acid methyl ester yield: 53 mg (52%)
$^1$H-NMR (CDCl$_3$) δ: 2.15 (3H, s), 3.23 (3H, s), 5.37 (2H, s), 7.20-7.47 (11H, m), 7.66 (1H, m), 8.39 (1H, d, J=8.7 Hz).

EXAMPLE 116

2-(1-acetylpiperidin-3-ylmethyl)-6-bromo-1-oxo-4-phenyl-1,2-dihydroisoquinoline-3-carboxylic acid methyl ester yield: 41 mg (55%)
$^1$H-NMR (CDCl$_3$) δ: 1.21-1.54 (2H, m), 1.60-1.89 (2H, m), 1.90-2.06 (3H, m), 2.56 (1H, m), 2.98 (1H, m), 3.46-3.49 (3H, m), 3.68 (1H, m), 3.90 (1H, m), 4.15 (1H, m), 4.44 (1H, m), 7.27-7.54 (6H, m), 7.65 (1H, m), 8.35 (1H, m).

EXAMPLE 117

6-bromo-2-(1-methylcarbamoylpiperidin-4-ylmethyl)-1-oxo-4-phenyl-1,2-dihydroisoquinoline-3-carboxylic acid methyl ester To a solution of 6-bromo-1-oxo-4-phenyl-2-(piperidin-4-ylmethyl)-1,2-dihydroisoquinoline-3-carboxylic acid methyl ester hydrochloride (100 mg) in tetrahydrofuran (5 ml) were added triethylamine (0.06 ml) and methylisocyanate (0.018 ml), and the mixture was stirred at room temperature for 24 hrs. The solvent was evaporated under reduced pressure, water was added and the mixture was extracted with ethyl acetate. The extract was washed with saturated brine and dried by adding sodium sulfate. The solvent was evaporated under reduced pressure, and the obtained residue was purified by preparative HPLC to give the title compound (34 mg, 33%).

¹H-NMR (CDCl₃) δ: 1.18-1.33 (2H, m), 1.60-1.75 (2H, m), 2.08 (1H, m), 2.67-2.77 (5H, m), 3.46 (3H, s), 3.88-4.00 (4H, m), 4.39 (1H, s), 7.26-7.51 (6H, m), 7.64 (1H, dd, J=1.8, 8.4 Hz), 8.34 (1H, d, J=8.4 Hz).

In the same manner as in Example 117, the compounds of Example 118 and Example 119 were obtained.

EXAMPLE 118

6-bromo-2-[3-(3-methylureido)benzyl]-1-oxo-4-phenyl-1,2-dihydroisoquinoline-3-carboxylic acid methyl ester yield: 94 mg (60%)
¹H-NMR (CDCl₃) δ: 2.79 (3H, d, J=4.8 Hz), 3.27 (3H, s), 4.80 (1H, d, J=4.8 Hz), 5.34 (2H, s), 6.44 (1H, s), 6.82 (1H, d, J=7.2 Hz), 7.09 (1H, s), 7.20-7.50 (8H, m), 7.65 (1H, dd, J=1.8, 8.7 Hz), 8.36 (1H, d, J=8.7 Hz).

EXAMPLE 119

6-bromo-2-[4-(3-methylureido)benzyl]-1-oxo-4-phenyl-1,2-dihydroisoquinoline-3-carboxylic acid methyl ester yield: 99 mg (63%)
¹H-NMR (CDCl₃) δ: 2.81 (3H, d, J=3.2 Hz), 3.27 (3H, s), 4.74 (1H, d, J=3.2 Hz), 5.33 (2H, s), 6.37 (1H, s), 7.16-7.47 (10H, m), 7.65 (1H, dd, J=1.8, 8.7 Hz), 8.37 (1H, d, J=8.7 Hz).

EXAMPLE 120

6-bromo-2-[1-(3-carboxypropionyl)piperidin-4-ylmethyl]-1-oxo-4-phenyl-1,2-dihydroisoquinoline-3-carboxylic acid methyl ester To a solution of 6-bromo-1-oxo-4-phenyl-2-(piperidin-4-ylmethyl)-1,2-dihydroisoquinoline-3-carboxylic acid methyl ester hydrochloride (100 mg) in tetrahydrofuran (5 ml) were added triethylamine (0.14 ml) and succinic anhydride (30 mg), and the mixture was stirred at room temperature for 24 hrs. The solvent was evaporated under reduced pressure, water was added and the mixture was extracted with ethyl acetate. The extract was washed with saturated brine and dried by adding sodium sulfate. The solvent was evaporated under reduced pressure, and the obtained residue was crystallized from isopropyl ether to give the title compound (96 mg, 81%).

¹H-NMR (CDCl₃) δ: 1.18-1.40 (2H, m), 1.65-1.80 (2H, m), 2.21 (1H, m), 2.52-2.70 (5H, m), 3.00 (1H, m), 3.47 (3H, s), 3.80-3.93 (2H, m), 4.07 (1H, m), 4.61 (1H, m), 7.26-7.64 (6H, m), 7.66 (1H, dd, J=2.1, 8.7 Hz), 8.34 (1H, d, J=8.7 Hz).

In the same manner as in Example 120, the compounds of Example 121 and Example 122 were obtained.

EXAMPLE 121

6-bromo-2-[1-(4-carboxybutyryl)piperidin-4-ylmethyl]-1-oxo-4-phenyl-1,2-dihydroisoquinoline-3-carboxylic acid methyl ester yield: 96 mg (81%)
¹H-NMR (CDCl₃) δ: 1.16-1.40 (2H, m), 1.65-1.80 (2H, m), 1.90-2.00 (2H, m), 2.18 (1H, m), 2.39-2.60 (5H, m), 2.97 (1H, m), 3.47 (3H, s), 3.80-3.92 (2H, m), 4.08 (1H, m), 4.63 (1H, m), 7.26-7.52 (6H, m), 7.65 (1H, dd, J=1.8, 8.7 Hz), 8.34 (1H, d, J=8.7 Hz).

EXAMPLE 122

6-bromo-2-[4-(3-carboxypropionylamino)benzyl]-1-oxo-4-phenyl-1,2-dihydroisoquinoline-3-carboxylic acid methyl ester yield: 85 mg (54%)
¹H-NMR (CDCl₃) δ: 2.59-2.80 (4H, m), 3.24 (3H, s), 5.35 (2H, s), 6.37 (1H, s), 7.18-7.58 (9H, m), 7.60-7.75 (2H, m), 8.38 (1H, d, J=8.4 Hz).

EXAMPLE 123

6-bromo-2-(4-carbamoylbenzyl)-1-oxo-4-phenyl-1,2-dihydroisoquinoline-3-carboxylic acid methyl ester To a solution of 6-bromo-2-(4-carboxybenzyl)-1-oxo-4-phenyl-1,2-dihydroisoquinoline-3-carboxylic acid methyl ester (246 mg) in tetrahydrofuran (5 ml) were added oxalylchloride (0.06 ml) and dimethylformamide (1 drop), and the mixture was stirred at room temperature for 1 hr. The solvent was evaporated under reduced pressure, dissolved in chloroform (5 ml) and a mixed solution of saturated aqueous ammonia (5 ml) and chloroform (5 ml) was added dropwise. The mixture was stirred at room temperature for 2 hrs. and extracted with dichloromethane. The extract was washed with saturated brine and dried by adding sodium sulfate. The solvent was evaporated under reduced pressure, and methanol was added to the obtained residue. The mixture was crystallized to give the title compound (116 mg, 47%).

¹H-NMR (CDCl₃) δ: 3.22 (3H, s), 5.43 (2H, s), 5.67 (1H, s), 6.03 (1H, s), 7.26-7.48 (8H, m), 7.67 (1H, dd, J=1.8, 8.7 Hz), 7.75 (2H, d, J=8.4 Hz), 8.39 (1H, d, J=8.7 Hz).

In the same manner as in Example 123, the compounds of Examples 124-143 were synthesized.

EXAMPLE 124

6-bromo-2-[4-(N',N'-dimethylhydrazinocarbonyl)benzyl]-1-oxo-4-phenyl-1,2-dihydroisoquinoline-3-carboxylic acid methyl ester yield: 95 mg (36%)
¹H-NMR (CDCl₃) δ: 2.68 (6H, s), 3.21 (3H, s), 5.41 (2H, s), 6.69 (1H, s), 7.24-7.47 (8H, m), 7.60-7.70 (3H, m), 8.38 (1H, d, J=8.8 Hz).

EXAMPLE 125

6-bromo-1-oxo-4-phenyl-2-[4-(N'-phenylhydrazinocarbonyl)benzyl]-1,2-dihydroisoquinoline-3-carboxylic acid methyl ester yield: 38 mg (22%)
¹H-NMR (CDCl₃) δ: 3.25 (3H, s), 5.43 (2H, s), 6.29 (1H, d, J=3.9 Hz), 6.87-6.96 (3H, m), 7.26-7.49 (10H, m), 7.67 (1H, dd, J=1.8, 8.7 Hz), 7.79 (2H, d, J=8.4 Hz), 7.88 (1H, d, J=3.9 Hz), 8.39 (1H, d, J=8.4 Hz).

EXAMPLE 126

6-bromo-2-(4-methylcarbamoylbenzyl)-1-oxo-4-phenyl-1,2-dihydroisoquinoline-3-carboxylic acid methyl ester yield: 115 mg (46%)
$^1$H-NMR (CDCl$_3$) δ: 2.99 (3H, d, J=4.8 Hz), 3.20 (3H, s), 5.43 (2H, s), 6.14 (1H, s), 7.26-7.48 (8H, m), 7.65-7.71 (3H, m), 8.39 (1H, d, J=8.7 Hz).

EXAMPLE 127

6-bromo-1-oxo-4-phenyl-2-(4-dimethylcarbamoylbenzyl)-1,2-dihydroisoquinoline-3-carboxylic acid methyl ester yield: 108 mg (42%)
$^1$H-NMR (CDCl$_3$) δ: 2.94 (3H, s), 3.09 (3H, s), 3.22 (3H, s), 5.42 (2H, s), 7.24-7.48 (10H, m), 7.67 (1H, dd, J=1.8, 8.7 Hz), 8.40 (1H, d, J=8.4 Hz).

EXAMPLE 128

6-bromo-2-(4-methoxycarbamoylbenzyl)-1-oxo-4-phenyl-1,2-dihydroisoquinoline-3-carboxylic acid methyl ester yield: 52 mg (50%)
$^1$H-NMR (CDCl$_3$) δ: 3.24 (3H, s), 3.88 (3H, s), 5.43 (2H, s), 6.72 (1H, s), 7.23-7.52 (8H, m), 7.62-7.76 (3H, m), 8.41 (1H, d, J=8.6 Hz).

EXAMPLE 129

6-bromo-2-[4-(2-hydroxyethylcarbamoyl)benzyl]-1-oxo-4-phenyl-1,2-dihydroisoquinoline-3-carboxylic acid methyl ester yield: 39 mg (36%)
$^1$H-NMR (CDCl$_3$) δ: 3.24 (3H, s), 3.56-3.65 (2H, m), 3.78-3.85 (2H, m), 5.43 (2H, s), 6.60-6.80 (2H, m), 7.23-7.50 (8H, m), 7.65-7.76 (3H, m), 8.40 (1H, d, J=8.8 Hz).

EXAMPLE 130

6-bromo-1-oxo-4-phenyl-2-[4-(piperidin-1-ylcarbamoyl)benzyl]-1,2-dihydroisoquinoline-3-carboxylic acid methyl ester yield: 77 mg (67%)
$^1$H-NMR (CDCl$_3$) δ: 1.39-1.60 (2H, m), 1.68-1.84 (4H, m), 2.80-2.90 (4H, m), 3.25 (3H, s), 5.43 (2H, s), 6.69 (1H, s), 7.27-7.52 (8H, m), 7.65-7.73 (3H, m), 8.41 (1H, d, J=8.4 Hz).

EXAMPLE 131

6-bromo-2-[4-(morpholin-4-ylcarbamoyl)benzyl]-1-oxo-4-phenyl-1,2-dihydroisoquinoline-3-carboxylic acid methyl ester yield: 66 mg (57%)
$^1$H-NMR (CDCl$_3$) δ: 2.89-3.00 (2H, m), 3.26 (3H, s), 3.80-3.94 (4H, m), 5.43 (2H, s), 6.79 (1H, s), 7.27-7.49 (8H, m), 7.65-7.75 (3H, m), 8.41 (1H, d, J=8.4 Hz).

EXAMPLE 132

6-bromo-2-{4-[N'-(4-fluorophenyl)hydrazinocarbonyl]benzyl}-1-oxo-4-phenyl-1,2-dihydroisoquinoline-3-carboxylic acid methyl ester yield: 30 mg (25%)
$^1$H-NMR (CDCl$_3$) δ: 3.25 (3H, s), 5.42 (2H, s), 6.23 (1H, m), 6.83-7.00 (3H, m), 7.25-7.48 (10H, m), 7.64-7.82 (3H, m), 8.38 (1H, d, J=8.8 Hz).

EXAMPLE 133

6-bromo-2-[4-(2-hydroxypropylcarbamoyl)benzyl]-1-oxo-4-phenyl-1,2-dihydroisoquinoline-3-carboxylic acid methyl ester yield: 63 mg (57%)
$^1$H-NMR (CDCl$_3$) δ: 1.23 (3H, d, J=6.3 Hz), 2.50 (1H, m), 3.21 (3H, s), 3.26 (1H, m), 4.00 (1H, m), 5.42 (2H, s), 6.59 (1H, m), 7.23-7.50 (8H, m), 7.62-7.76 (3H, m), 8.39 (1H, d, J=8.4 Hz).

EXAMPLE 134

6-bromo-2-[4-(methoxycarbonylmethylcarbamoyl)benzyl]-1-oxo-4-phenyl-1,2-dihydroisoquinoline-3-carboxylic acid methyl ester yield: 135 mg (80%)
$^1$H-NMR (CDCl$_3$) δ: 3.21 (3H, s), 3.80 (3H, s), 4.23 (2H, d, J=5.1 Hz), 5.44 (2H, s), 6.60 (1H, m), 7.26-7.49 (8H, m), 7.67 (1H, dd, J=1.8, 8.4 Hz), 7.75 (1H, d, J=8.7 Hz), 8.40 (1H, d, J=8.4 Hz).

EXAMPLE 135

6-bromo-2-[4-(3-methoxycarbonylpropylcarbamoyl)benzyl]-1-oxo-4-phenyl-1,2-dihydroisoquinoline-3-carboxylic acid methyl ester yield: 175 mg (99%)
$^1$H-NMR (CDCl$_3$) δ: 1.95 (2H, m), 2.44 (2H, t, J=6.6 Hz), 3.20 (3H, s), 3.49 (2H, dd, J=6.6, 12.3 Hz), 3.66 (3H, s), 5.44 (2H, s), 6.54 (1H, m), 7.26-7.48 (8H, m), 7.66-7.73 (3H, m), 8.40 (1H, d, J=8.7 Hz).

EXAMPLE 136

6-bromo-2-[4-(2-methoxyethylcarbamoyl)benzyl]-1-oxo-4-phenyl-1,2-dihydroisoquinoline-3-carboxylic acid methyl ester yield: 47 mg (43%)
$^1$H-NMR (CDCl$_3$) δ: 3.21 (3H, s), 3.37 (3H, s), 3.52-3.65 (4H, m), 5.43 (2H, s), 6.47 (1H, m), 7.26-7.48 (8H, m), 7.65-7.72 (3H, m), 8.39 (1H, d, J=8.7 Hz).

EXAMPLE 137

6-bromo-2-[4-(3-methoxypropylcarbamoyl)benzyl]-1-oxo-4-phenyl-1,2-dihydroisoquinoline-3-carboxylic acid methyl ester yield: 95 mg (84%)
$^1$H-NMR (CDCl$_3$) δ: 1.82-1.90 (2H, m), 3.20 (3H, s), 3.36 (3H, s), 3.52-3.58 (4H, m), 5.43 (2H, s), 6.91 (1H, m), 7.26-7.46 (8H, m), 7.63-7.72 (3H, m), 8.40 (1H, d, J=8.4 Hz).

EXAMPLE 138

6-bromo-2-[4-(carbamoylmethylcarbamoyl)benzyl]-1-oxo-4-phenyl-1,2-dihydroisoquinoline-3-carboxylic acid methyl ester yield: 57 mg (52%)
$^1$H-NMR (CDCl$_3$) δ: 3.21 (3H, s), 4.14 (2H, d, J=4.8 Hz), 5.44 (2H, s), 6.86 (1H, m), 7.26-7.47 (10H, m), 7.65 (1H, dd, J=1.8, 8.7 Hz), 7.76 (2H, d, J=8.1 Hz), 8.40 (1H, d, J=8.7 Hz).

EXAMPLE 139

6-bromo-2-[4-(morpholin-4-ylcarbonyl)benzyl]-1-oxo-4-phenyl-1,2-dihydroisoquinoline-3-carboxylic acid methyl ester yield: 97 mg (79%)
$^1$H-NMR (CDCl$_3$) δ: 3.25 (3H, s), 3.30-3.82 (8H, m), 5.39 (2H, s), 7.26-7.50 (10H, m), 7.65 (1H, dd, J=1.8, 8.7 Hz), 8.38 (1H, d, J=8.7 Hz).

EXAMPLE 140

6-bromo-2-[4-(2-dimethylaminoethylcarbamoyl)benzyl]-1-oxo-4-phenyl-1,2-dihydroisoquinoline-3-carboxylic acid methyl ester yield: 74 mg (66%)
$^1$H-NMR (CDCl$_3$) δ: 2.24 (6H, s), 2.49 (2H, t, J=6.0 Hz), 3.22 (3H, s), 3.48 (1H, dd, J=6.0, 11.1 Hz), 5.42 (2H, s), 6.78 (1H, m), 7.26-7.47 (8H, m), 7.65-7.74 (3H, m), 8.39 (1H, d, J=8.7 Hz).

EXAMPLE 141

6-bromo-1-oxo-4-phenyl-2-[4-(2-(pyrrolidin-1-yl)ethylcarbamoyl)benzyl]-1,2-dihydroisoquinoline-3-carboxylic acid methyl ester yield: 72 mg (61%)
$^1$H-NMR (CDCl$_3$) δ: 1.70-1.84 (4H, m), 2.45-2.60 (4H, m), 2.67 (2H, t, J=6.0 Hz), 3.22 (3H, s), 3.51 (1H, dd, J=6.0, 11.1 Hz), 5.42 (2H, s), 6.80 (1H, m), 7.26-7.49 (8H, m), 7.65-7.73 (3H, m), 8.39 (1H, d, J=8.7 Hz).

EXAMPLE 142

6-bromo-1-oxo-4-phenyl-2-[4-(pyrrolidin-1-ylcarbamoyl)benzyl]-1,2-dihydroisoquinoline-3-carboxylic acid methyl ester yield: 56 mg (50%)
$^1$H-NMR (CDCl$_3$) δ: 1.85-2.00 (4H, m), 2.95-3.05 (4H, m), 3.24 (3H, s), 5.43 (2H, s), 6.76 (1H, s), 7.26-7.50 (8H, m), 7.63-7.73 (3H, m), 8.41 (1H, d, J=8.6 Hz).

EXAMPLE 143

6-bromo-1-oxo-4-phenyl-2-[4-(N'-(pyridin-2-yl)hydrazinocarbonyl)benzyl]-1,2-dihydroisoquinoline-3-carboxylic acid methyl ester yield: 43 mg (37%)
$^1$H-NMR (CDCl$_3$) δ: 3.23 (3H, s), 5.43 (2H, s), 6.72-6.82 (2H, m), 7.07 (1H, s), 7.26-7.55 (10H, m), 7.67 (1H, dd, J=1.8, 8.7 Hz), 7.84 (1H, d, J=8.1 Hz), 8.16 (1H, m), 8.39 (1H, d, J=8.7 Hz).

EXAMPLE 144

6-bromo-2-[4-(carboxymethylcarbamoyl)benzyl]-1-oxo-4-phenyl-1,2-dihydroisoquinoline-3-carboxylic acid methyl ester To a mixed solution of 6-bromo-2-[4-(methoxycarbonylmethylcarbamoyl)benzyl]-1-oxo-4-phenyl-1,2-dihydroisoquinoline-3-carboxylic acid methyl ester (100 mg) in methanol (3 ml) and tetrahydrofuran (3 ml) was added 8N aqueous sodium hydroxide solution (0.05 ml), and the mixture was stirred at room temperature for 12 hrs. The solvent was evaporated under reduced pressure, water was added and the mixture was acidified with 1N hydrochloric acid and extracted with dichloromethane. The extract was washed with saturated brine and dried by adding sodium sulfate. The solvent was evaporated under reduced pressure, and methanol was added to the obtained residue. The mixture was crystallized to give the title compound (15 mg, 15%).
$^1$H-NMR (CDCl$_3$) δ: 3.26 (3H, s), 4.20-4.24 (2H, m), 5.45 (2H, s), 6.98 (1H, m), 7.28-7.51 (8H, m), 7.68-7.78 (3H, m), 8.02 (2H, d, J=7.0 Hz), 8.39 (1H, d, J=8.8 Hz).

EXAMPLE 145

6-bromo-2-[4-(3-carboxypropylcarbamoyl)benzyl]-1-oxo-4-phenyl-1,2-dihydroisoquinoline-3-carboxylic acid methyl ester In the same manner as in Example 144, ester was hydrolyzed to give the title compound.
yield: 52 mg (51%)
$^1$H-NMR (CDCl$_3$) δ: 1.85-1.98 (2H, m), 2.40-2.45 (2H, m), 3.21 (3H, s), 3.41-3.52 (2H, m), 5.40 (2H, s), 6.95 (1H, m), 7.26-7.29 (4H, m), 7.40-7.49 (4H, m), 7.64-7.73 (3H, m), 8.36 (1H, d, J=8.4 Hz).

EXAMPLE 146

6-bromo-2-(4-methylsulfamoylbenzyl)-1-oxo-4-phenyl-1,2-dihydroisoquinoline-3-carboxylic acid methyl ester A mixture of 6-bromo-2-(4-sulfamoylbenzyl)-1-oxo-4-phenyl-1,2-dihydroisoquinoline-3-carboxylic acid methyl ester (264 mg), potassium carbonate (152 mg), methyl iodide (34 μl) and dimethylformamide (DMF) (5 ml) was stirred at room temperature for 5 hrs. The solvent was evaporated under reduced pressure, and the residue was extracted with ethyl acetate. The extract was washed with saturated brine, dried over sodium sulfate. The solvent was evaporated under reduced pressure and the residue was purified by preparative HPLC to give the title compound (83 mg, 31%).
$^1$H-NMR (CDCl$_3$) δ: 2.64 (3H, d, J=5.7 Hz), 3.24 (3H, s), 4.32 (1H, m), 5.42 (2H, s), 7.26-7.50 (8H, m), 7.68 (1H, dd, J=1.8, 8.4 Hz), 7.78-7.81 (2H, m), 8.38 (1H, d, J=8.4 Hz).

EXAMPLE 147

6-bromo-2-(4-dimethylsulfamoylbenzyl)-1-oxo-4-phenyl-1,2-dihydroisoquinoline-3-carboxylic acid methyl ester A mixture of 6-bromo-2-(4-sulfamoylbenzyl)-1-oxo-4-phenyl-1,2-dihydroisoquinoline-3-carboxylic acid methyl ester (235 mg), potassium carbonate (152 mg), methyl iodide (90 µl) and dimethylformamide (DMF) (5 ml) was stirred at room temperature for 5 hrs. The solvent was evaporated under reduced pressure, and the residue was extracted with ethyl acetate. The extract was washed with saturated brine and dried over sodium sulfate. The solvent was evaporated under reduced pressure and the residue was purified by preparative HPLC to give the title compound (142 mg, 58%).
$^1$H-NMR (CDCl$_3$) δ: 2.68 (6H, s), 3.23 (3H, s), 5.44 (2H, s), 7.27-7.31 (2H, m), 7.40-7.51 (6H, m), 7.65-7.74 (3H, m), 8.38 (1H, d, J=8.7 Hz).

EXAMPLE 148

2-(benzo[1,3]dioxol-5-ylmethyl)-1-oxo-4-phenyl-1,2-dihydroisoquinoline-3,6-dicarboxylic acid dimethyl ester A mixture of 2-(benzo[1,3]dioxol-5-ylmethyl)-6-bromo-1-oxo-4-phenyl-1,2-dihydroisoquinoline-3-carboxylic acid methyl ester (300 mg), palladium(II) acetate (7 mg), 1,1'-bis(diphenylphosphino)ferrocene (17 mg), triethylamine (0.22 ml), DMF (10 ml) and methanol (10 ml) was stirred at 100° C. for 6 hrs. under 5 atm carbon monoxide. The reaction mixture was concentrated, and water was added to the residue. The mixture was extracted with ethyl acetate. The organic layer was washed with water and saturated brine, dried over anhydrous sodium sulfate, and concentrated under reduced pressure. The obtained residue was purified by silica gel column chromatography (ethyl acetate) and the obtained crystals were washed with diisopropyl ether to give the title compound (250 mg).
$^1$H-NMR (CDCl$_3$) δ: 3.28 (3H, s), 3.88 (3H, s), 5.35 (2H, s), 5.91 (2H, s), 6.64-6.88 (3H, m), 7.20-7.58 (5H, m), 7.94 (1H, d, J=1.4 Hz), 8.15 (1H, dd, J=1.4, 8.5 Hz), 8.61 (1H, d, J=8.5 Hz).

EXAMPLE 149

2-(benzo[1,3]dioxol-5-ylmethyl)-1-oxo-4,6-diphenyl-1,2-dihydroisoquinoline-3-carboxylic acid methyl ester A mixture of 2-(benzo[1,3]dioxol-5-ylmethyl)-6-bromo-1-oxo-4-phenyl-1,2-dihydroisoquinoline-3-carboxylic acid methyl ester (300 mg), phenylboronic acid (100 mg), tetrakis(triphenylphosphine)palladium(0) (35 mg), toluene (6 ml), ethanol (0.8 ml) and 2M aqueous sodium carbonate solution (0.8 ml) was heated under reflux under a nitrogen atmosphere for 6 hrs. To the reaction mixture were further added dihydroxyphenylborane (100 mg), tetrakis(triphenylphosphine)palladium(0) (35 mg), ethanol (0.8 ml) and 2M aqueous sodium carbonate solution (0.8 ml), and the mixture was heated under reflux for 6 hrs. Water was added to the reaction mixture, and the mixture was extracted with ethyl acetate. The organic layer was washed with water and saturated brine. The solvent was dried over anhydrous sodium sulfate and was concentrated under reduced pressure. The obtained residue was purified by silica gel column chromatography (hexane-hexane:ethyl acetate=2:1) and recrystallized (ethyl acetate-hexane) to give the title compound (260 mg).
$^1$H-NMR (CDCl$_3$) δ: 3.28 (3H, s), 5.36 (2H, s), 5.91 (2H, s), 6.66-6.88 (3H, m), 7.26-7.58 (11H, m), 7.79 (1H, dd, J=1.8, 8.4 Hz), 8.61 (1H, d, J=8.4 Hz).

EXAMPLE 150

2-(benzo[1,3]dioxol-5-ylmethyl)-1-oxo-4-phenyl-6-thiophen-3-yl-1,2-dihydroisoquinoline-3-carboxylic acid methyl ester A mixture of 2-(benzo[1,3]dioxol-5-ylmethyl)-6-bromo-1-oxo-4-phenyl-1,2-dihydroisoquinoline-3-carboxylic acid methyl ester (300 mg), 3-thiopheneboronic acid (120 mg), tetrakis(triphenylphosphine)palladium(0) (35 mg), toluene (6 ml), ethanol (0.8 ml) and 2M aqueous sodium carbonate solution (0.8 ml) was heated under reflux under a nitrogen atmosphere for 6 hrs. Water was added to the reaction mixture, and the mixture was extracted with ethyl acetate. The organic layer was washed with water and saturated brine. The solvent was dried over anhydrous sodium sulfate and concentrated under reduced pressure. The obtained residue was purified by silica gel column chromatography (hexane-hexane:ethyl acetate=2:1) and recrystallized (ethyl acetate-hexane) to give the title compound (260 mg).
$^1$H-NMR (CDCl$_3$) δ: 3.28 (3H, s), 5.35 (2H, s), 5.91 (2H, s), 6.64-6.88 (3H, m), 7.20-7.56 (9H, m), 7.79 (1H, dd, J=1.8, 8.4 Hz), 8.57 (1H, d, J=8.4 Hz).

EXAMPLE 151

2-(benzo[1,3]dioxol-5-ylmethyl)-6-methyl-1-oxo-4-phenyl-1,2-dihydroisoquinoline-3-carboxylic acid methyl ester A mixture of 2-(benzo[1,3]dioxol-5-ylmethyl)-6-bromo-1-oxo-4-phenyl-1,2-dihydroisoquinoline-3-carboxylic acid methyl ester (300 mg), methylboronic acid (180 mg), tetrakis(triphenylphosphine)palladium(0) (70 mg), potassium carbonate (250 mg), toluene (6 ml) and THF (4 ml) was stirred at 100° C. for 12 hrs. under a nitrogen atmosphere. Water was added to the reaction mixture, and the mixture was extracted with ethyl acetate. The organic layer was washed with water and saturated brine. The solvent was dried over anhydrous sodium sulfate and concentrated under reduced pressure. The obtained residue was purified by silica gel column chromatography (hexane-hexane:ethyl acetate=2:1) and recrystallized (ethyl acetate-hexane) to give the title compound (200 mg).
$^1$H-NMR (CDCl$_3$) δ: 2.37 (3H, s), 3.26 (3H, s), 5.33 (2H, s), 5.90 (2H, s), 6.62-6.88 (3H, m), 7.00 (1H, s), 7.20-7.52 (6H, m), 8.44 (1H, d, J=8.0 Hz).

EXAMPLE 152

2-(benzo[1,3]dioxol-5-ylmethyl)-6-cyano-1-oxo-4-phenyl-1,2-dihydroisoquinoline-3-carboxylic acid methyl ester A mixture of 2-(benzo[1,3]dioxol-5-ylmethyl)-6-bromo-1-oxo-4-phenyl-1,2-dihydroisoquinoline-3-carboxylic acid methyl ester (300 mg), zinc cyanide (50 mg), tetrakis(triphenylphosphine)palladium(0) (35 mg) and 1-methyl-2-pyrrolidone (3 ml) was stirred at 100° C. for 2 hrs. under an argon atmosphere. Water was added to the reaction mixture, and the mixture was extracted with a mixture of ethyl acetate and THF. The organic layer was washed with aqueous ammonia, water and saturated brine, dried over anhydrous sodium sulfate, and concentrated under reduced pressure. The obtained residue was purified by silica gel column chromatography (ethyl acetate). The solvent was evaporated under reduced pressure, and the obtained crystals were washed with a mixture of ethyl acetate and diethyl ether to give the title compound (210 mg).

$^1$H-NMR (CDCl$_3$) δ: 3.29 (3H, s), 5.33 (2H, s), 5.92 (2H, s), 6.66-6.86 (3H, m), 7.20-7.56 (5H, m), 7.56 (1H, d, J=1.4 Hz), 7.74 (1H, dd, J=1.4, 8.4 Hz), 8.63 (1H, d, J=8.4 Hz).

EXAMPLE 153

2-(benzo[1,3]dioxol-5-ylmethyl)-6-benzylamino-1-oxo-4-phenyl-1,2-dihydroisoquinoline-3-carboxylic acid methyl ester Palladium(II) acetate (15 mg) and rac-2,2'-bis(diphenylphosphino)-1,1'-binaphthyl (130 mg) were added to toluene (20 ml) at room temperature, and the mixture was stirred for 5 min. under a nitrogen atmosphere. To the reaction mixture were added 2-(benzo[1,3]dioxol-5-ylmethyl)-6-bromo-1-oxo-4-phenyl-1,2-dihydroisoquinoline-3-carboxylic acid methyl ester (1.0 g) and benzylamine (0.33 ml) at room temperature, and the mixture was stirred for 10 min under a nitrogen atmosphere. To the reaction mixture was further added sodium tert-butoxide (270 mg) at room temperature, and heated under reflux under a nitrogen atmosphere for 4 hrs. Water was added to the reaction mixture, and the mixture was extracted with ethyl acetate. The organic layer was washed with water and saturated brine, and dried over anhydrous sodium sulfate. The solvent was evaporated under reduced pressure, and the obtained residue was purified by silica gel column chromatography (hexane-hexane:ethyl acetate=2:1) to give the title compound (1 g).

$^1$H-NMR (CDCl$_3$) δ: 3.22 (3H, s), 4.21 (2H, d, J=5.4 Hz), 4.63 (1H, t, J=5.4 Hz), 5.28 (2H, s), 5.88 (2H, s), 6.18 (1H, d, J=2.6 Hz), 6.62-6.92 (3H, m), 6.81 (1H, dd, J=2.6, 8.8 Hz), 7.10-7.50 (10H, m), 8.31 (1H, d, J=8.8 Hz).

EXAMPLE 154

2-(benzo[1,3]dioxol-5-ylmethyl)-1-oxo-4-phenyl-6-piperidin-1-yl-1,2-dihydroisoquinoline-3-carboxylic acid methyl ester In the same manner as in Example 153 and using piperidine, the title compound was synthesized.

Crystals (ethyl acetate-hexane).

$^1$H-NMR (CDCl$_3$) δ: 1.59 (6H, s), 3.08-3.34 (4H, m), 3.24 (3H, s), 5.30 (2H, s), 5.90 (2H, s), 6.45 (1H, d, J=2.4 Hz), 6.62-6.84 (3H, m), 7.13 (1H, dd, J=2.4, 9.2 Hz), 7.22-7.50 (5H, m), 8.36 (1H, d, J=9.2 Hz).

EXAMPLE 155

2-(benzo[1,3]dioxol-5-ylmethyl)-6-morpholin-4-yl-1-oxo-4-phenyl-1,2-dihydroisoquinoline-3-carboxylic acid methyl ester In the same manner as in Example 153 and using morpholine, the title compound (amorphous powder) was synthesized.

$^1$H-NMR (CDCl$_3$) δ: 3.04-3.24 (4H, m), 3.25 (3H, s), 3.72-3.88 (4H, m), 5.30 (2H, s), 5.90 (2H, s), 6.48 (1H, d, J=2.6 Hz), 6.64-6.86 (3H, m), 7.12 (1H, dd, J=2.6, 9.2 Hz), 7.22-7.54 (5H, m), 8.41 (1H, d, J=9.2 Hz).

EXAMPLE 156

6-amino-2-(benzo[1,3]dioxol-5-ylmethyl)-1-oxo-4-phenyl-1,2-dihydroisoquinoline-3-carboxylic acid methyl ester A mixture of 2-(benzo[1,3]dioxol-5-ylmethyl)-6-benzylamino-1-oxo-4-phenyl-1,2-dihydroisoquinoline-3-carboxylic acid methyl ester (670 mg), 10% palladium carbon (200 mg), methanol (10 ml) and THF (10 ml) was stirred at room temperature at 4-5 atm hydrogen pressure for 48 hrs. Palladium carbon was filtered off and the filtrate was concentrated. The residue was purified by silica gel column chromatography (ethyl acetate) and recrystallized (ethyl acetate-hexane) to give the title compound (400 mg).

$^1$H-NMR (CDCl$_3$) δ: 3.24 (3H, s), 4.04 (2H, s), 5.29 (2H, s), 5.90 (2H, s), 6.29 (1H, d, J=2.4 Hz), 6.64-6.94 (3H, m), 6.84 (1H, dd, J=2.4, 8.6 Hz), 7.14-7.52 (5H, m), 8.33 (1H, d, J=8.6 Hz).

EXAMPLE 157

2-(benzo[1,3]dioxol-5-ylmethyl)-1-oxo-4-phenyl-1,2-dihydroisoquinoline-3,6-dicarboxylic acid 3-methyl ester To a solution of 2-(benzo[1,3]dioxol-5-ylmethyl)-1-oxo-4-phenyl-1,2-dihydroisoquinoline-3,6-dicarboxylic acid dimethyl ester (300 mg) in THF (3 ml) were added methanol (3 ml) and 8N-aqueous sodium hydroxide solution (0.16 ml) at room temperature, and the mixture was stirred for 12 hrs. The reaction mixture was concentrated under reduced pressure, and 1N-hydrochloric acid was added to the residue. The aqueous layer of the mixture was acidified, and extracted with ethyl acetate. The organic layer was washed with water and saturated brine, dried over anhydrous sodium sulfate, and concentrated under reduced pressure. The obtained residue was crystallized from ethyl acetate-hexane to give the title compound (230 mg).

$^1$H-NMR (CDCl$_3$) δ: 3.28 (3H, s), 5.35 (2H, s), 5.91 (2H, s), 6.64-6.88 (3H, m), 7.20-7.58 (5H, m), 8.00 (1H, d, J=1.6 Hz), 8.18 (1H, dd, J=1.6, 8.4 Hz), 8.64 (1H, d, J=8.4 Hz).

EXAMPLE 158

6-bromo-2-(6-bromo-benzo[1,3]dioxol-5-ylmethyl)-1-oxo-4-phenyl-1,2-dihydroisoquinoline-3-carboxylic acid methyl ester To a solution of 2-(benzo[1,3]dioxol-5-ylmethyl)-6-bromo-1-oxo-4-phenyl-1,2-dihydroisoquinoline-3-carboxylic acid methyl ester (300 mg) in THF (6 ml) were added acetic acid (3 ml) and sodium acetate (100 mg) at room temperature, and bromine (0.04 ml) was added dropwise under ice-cooling. The reaction mixture was stirred at room temperature for 1 hr., sodium acetate (100 mg) was added, and bromine (0.04 ml) was added dropwise at room temperature. The reaction mixture was further stirred at room temperature for 1 hr., and bromine (0.04 ml) was added dropwise. The mixture was stirred for 1 hr. The reaction mixture was concentrated under reduced pressure, water was added to the residue and crystals were collected by filtration. The crystals were further washed with ethyl acetate to give the title compound (250 mg).

$^1$H-NMR (CDCl$_3$) δ: 3.34 (3H, s), 5.29 (2H, s), 5.93 (2H, s), 6.49 (1H, s), 7.00 (1H, s), 7.20-7.56 (6H, m), 7.68 (1H, dd, J=2.0, 8.8 Hz), 8.39 (1H, d, J=8.8 Hz).

EXAMPLE 159

2-(benzo[1,3]dioxol-5-ylmethyl)-1-oxo-4-phenyl-1,2-dihydroisoquinoline-3-carboxylic acid methyl ester A mixture of 2-benzo[1,3]dioxol-5-ylmethyl-6-bromo-1-oxo-4-phenyl-1,2-dihydroisoquinoline-3-carboxylic acid methyl ester (300 mg), 10% palladium carbon (300 mg), methanol (6 ml) and THF (6 ml) was stirred at room temperature under 1 atm hydrogen pressure for 12 hrs. Palladium carbon was filtered off, and the filtrate was concentrated. The residue was purified by silica gel column chromatography (ethyl acetate) and recrystallized (ethyl acetate-hexane) to give the title compound (230 mg).

$^1$H-NMR (CDCl$_3$) δ: 3.27 (3H, s), 5.35 (2H, s), 5.91 (2H, s), 6.66-6.86 (3H, m), 7.20-7.66 (8H, m), 8.48-8.62 (1H, m).

EXAMPLE 160

6-bromo-2-(2,3-dihydrobenzofuran-5-ylmethyl)-1-oxo-4-phenyl-1,2-dihydroisoquinoline-3-carboxylic acid A mixture of 6-bromo-1-oxo-4-phenyl-1H-isochromen-3-carboxylic acid (2.3 g), 5-aminomethyl-2,3-dihydrobenzo[b]furan (2.0 g), triethylamine (2.3 ml) and methanol (23 ml) was stirred at 50° C. for 24 hrs. The reaction mixture was concentrated, 1N-hydrochloric acid was added and the mixture was extracted with ethyl acetate. The organic layer was washed with water and saturated brine, dried over anhydrous sodium sulfate, and concentrated under reduced pressure. 4N-Hydrochloric acid-ethyl acetate solution (8 ml) was added to the residue at room temperature, and the mixture was stirred for 12 hrs. The reaction mixture was concentrated under reduced pressure and the obtained crystals were washed with diethyl ether to give the title compound (1.98 g).

$^1$H-NMR (DMSO-d$_6$) δ: 3.12 (2H, t, J=8.8 Hz), 4.48 (2H, t, J=8.8 Hz), 5.19 (2H, s), 6.67 (1H, d, J=8.2 Hz), 7.01 (1H, d, J=8.2 Hz), 7.17 (2H, s), 7.24-7.64 (5H, m), 7.76 (1H, dd, J=1.8, 8.6 Hz), 8.26 (1H, d, J=8.6 Hz).

EXAMPLE 161

2-(2,3-dihydrobenzofuran-5-ylmethyl)-1-oxo-4-phenyl-1,2-dihydroisoquinoline-3-carboxylic acid A mixture of 6-bromo-2-(2,3-dihydrobenzofuran-5-ylmethyl)-1-oxo-4-phenyl-1,2-dihydroisoquinoline-3-carboxylic acid (350 mg), 10% palladium carbon (150 mg), methanol (5 ml) and THF (5 ml) was stirred at room temperature under 1 atm hydrogen pressure for 12 hrs. Palladium carbon was filtered off, and the filtrate was concentrated. The obtained crystals were washed with diethyl ether to give the title compound (190 mg).

$^1$H-NMR (CDCl$_3$) δ: 3.07 (2H, t, J=8.8 Hz), 4.46 (2H, t, J=8.8 Hz), 5.00-6.00 (1H, br), 5.28 (2H, s), 6.57 (1H, d, J=8.4 Hz), 6.90-7.06 (1H, m), 7.08-7.68 (9H, m), 8.34-8.54 (1H, m).

EXAMPLE 162

2-(2,3-dihydrobenzofuran-5-ylmethyl)-1-oxo-4-phenyl-1,2-dihydroisoquinoline-3-carboxylic acid methyl ester A mixture of 6-bromo-2-(2,3-dihydrobenzofuran-5-ylmethyl)-1-oxo-4-phenyl-1,2-dihydroisoquinoline-3-carboxylic acid methyl ester (400 mg), 10% palladium carbon (150 mg), methanol (6 ml) and THF (6 ml) was stirred at room temperature under 1 atm hydrogen pressure for 12 hrs. Palladium carbon was filtered off, and the filtrate was concentrated. The obtained residue was crystallized from ethyl acetate-hexane to give the title compound (310 mg).

$^1$H-NMR (CDCl$_3$) δ: 3.14 (2H, t, J=8.8 Hz), 3.26 (3H, s), 4.52 (2H, t, J=8.8 Hz), 5.36 (2H, s), 6.66 (1H, d, J=8.2 Hz), 6.92-7.10 (1H, m), 7.12-7.68 (9H, m), 8.48-8.66 (1H, m).

EXAMPLE 163

2-(2,3-dihydrobenzofuran-5-ylmethyl)-6-methyl-1-oxo-4-phenyl-1,2-dihydroisoquinoline-3-carboxylic acid methyl ester A mixture of 6-bromo-2-(2,3-dihydrobenzofuran-5-ylmethyl)-1-oxo-4-phenyl-1,2-dihydroisoquinoline-3-carboxylic acid methyl ester (300 mg), methylboronic acid (180 mg), tetrakis(triphenylphosphine)palladium(0) (70 mg), potassium carbonate (250 mg), toluene (6 ml) and THF (3 ml) was stirred at 100° C. under a nitrogen atmosphere for 12 hrs. Water was added to the reaction mixture, and the mixture was extracted with ethyl acetate. The organic layer was washed with water and saturated brine. The solvent was dried over anhydrous sodium sulfate and concentrated under reduced pressure. The obtained residue was purified by silica gel column chromatography (hexane-hexane:ethyl acetate=2:1) and recrystallized (ethyl acetate-hexane) to give the title compound (230 mg).

$^1$H-NMR (CDCl$_3$) δ: 2.36 (3H, s), 3.13 (2H, t, J=8.7 Hz), 3.25 (3H, s), 4.52 (2H, t, J=8.7 Hz), 5.35 (2H, s), 6.66 (1H, d, J=8.0 Hz), 6.94-7.06 (2H, m), 7.12-7.22 (1H, m), 7.24-7.54 (6H, m), 8.45 (1H, d, J=8.4 Hz).

EXAMPLE 164

2-(2,3-dihydrobenzofuran-5-ylmethyl)-6-fluoro-1-oxo-4-phenyl-1,2-dihydroisoquinoline-3-carboxylic acid A mixture of 6-fluoro-1-oxo-4-phenyl-1H-isochromen-3-carboxylic acid (1 g), 5-aminomethyl-2,3-dihydrobenzo[b]furan (1.1 g), triethylamine (1 ml) and methanol (10 ml) was stirred at 50° C. for 36 hrs. The reaction mixture was concentrated, 1N-hydrochloric acid was added and the mixture was extracted with ethyl acetate. The organic layer was washed with water and saturated brine, dried over anhydrous sodium sulfate, and concentrated under reduced pressure. To the residue was added 4N-hydrochloric acid-ethyl acetate solution (5 ml) at room temperature and the mixture was stirred for 12 hrs. The reaction mixture was concentrated under reduced pressure and the residue was purified by recrystallization (ethyl acetate-hexane) to give the title compound (1.2 g).

$^1$H-NMR (CDCl$_3$) δ: 2.94-3.24 (2H, m), 4.34-4.64 (2H, m), 5.12-5.40 (2H, m), 6.48-7.70 (10H, m), 8.38 (1H, J=5.8, 9.0 Hz).

EXAMPLE 165

2-(2,3-dihydrobenzofuran-5-ylmethyl)-6-fluoro-1-oxo-4-phenyl-1,2-dihydroisoquinoline-3-carboxylic acid methyl ester 2-(2,3-Dihydrobenzofuran-5-ylmethyl)-6-fluoro-1-oxo-4-phenyl-1,2-dihydroisoquinoline-3-carboxylic acid (800 mg) was dissolved in DMF (8 ml), and methyl iodide (0.24 ml) and potassium carbonate (530 mg) were added at room temperature. The mixture was stirred for 12 hrs. Water was added to the reaction mixture, and crystals were collected by filtration and washed with water. After drying the crystals, recrystallization (ethyl acetate) gave the title compound (500 mg).

$^1$H-NMR (CDCl$_3$) δ: 3.14 (2H, t, J=8.8 Hz), 3.27 (3H, s), 4.53 (2H, t, J=8.8 Hz), 5.33 (2H, s), 6.67 (1H, d, J=8.4 Hz), 6.87 (1H, dd, J=2.5, 9.9 Hz), 6.94-7.08 (1H, m), 7.12-7.54 (7H, m), 8.57 (1H, dd, J=6.0, 8.8 Hz).

EXAMPLE 166

2-benzyl-1-oxo-4-phenyl-1,2-dihydroisoquinoline-3,6-dicarboxylic acid dimethyl ester A mixture of 2-benzyl-6-bromo-1-oxo-4-phenyl-1,2-dihydroisoquinoline-3-carboxylic acid methyl ester (300 mg), palladium(II) acetate (8 mg), 1,1'-bis(diphenylphosphino)ferrocene (20 mg), triethylamine (0.23 ml), DMF (3 ml) and methanol (3 ml) was stirred at 50° C. under 1 atm carbon monoxide for 24 hrs. Water was added to the reaction mixture, and the mixture was extracted with ethyl acetate. The organic layer was washed with water and saturated brine, dried over anhydrous sodium sulfate, and concentrated under reduced pressure. The obtained residue was purified by silica gel column chromatography (hexane-hexane:ethyl acetate=2:1) and recrystallized (ethyl acetate-hexane) to give the title compound (180 mg).

$^1$H-NMR (CDCl$_3$) δ: 3.20 (3H, s), 3.88 (3H, s), 5.45 (2H, s), 7.14-7.54 (10H, m), 7.94-8.00 (1H, m), 8.16 (1H, dd, J=1.4, 8.4 Hz), 8.58-8.68 (1H, m).

EXAMPLE 167

2-benzyl-6-cyano-1-oxo-4-phenyl-1,2-dihydroisoquinoline-3-carboxylic acid methyl ester A mixture of 2-benzyl-6-bromo-1-oxo-4-phenyl-1,2-dihydroisoquinoline-3-carboxylic acid methyl ester (300 mg), zinc cyanide (50 mg), tetrakis(triphenylphosphine)palladium(0) (35 mg) and 1-methyl-2-pyrrolidone (6 ml) was stirred at 100° C. under an argon atmosphere for 2 hrs. Water was added to the reaction mixture, and the mixture was extracted with a mixture of ethyl acetate and THF. The organic layer was washed with aqueous ammonia, water and saturated brine, dried over anhydrous sodium sulfate, and concentrated under reduced pressure. The obtained residue was purified by silica gel column chromatography (ethyl acetate) and recrystallized (ethyl acetate-hexane) to give the title compound (230 mg).

$^1$H-NMR (CDCl$_3$) δ: 3.22 (3H, s), 5.44 (2H, s), 7.16-7.52 (10H, m), 7.54-7.62 (1H, m), 7.75 (1H, dd, J=1.4, 8.4 Hz), 8.58-8.72 (1H, m).

EXAMPLE 168

2-benzyl-6-methyl-1-oxo-4-phenyl-1,2-dihydroisoquinoline-3-carboxylic acid methyl ester A mixture of 2-benzyl-6-bromo-1-oxo-4-phenyl-1,2-dihydroisoquinoline-3-carboxylic acid methyl ester (300 mg), methylboronic acid (200 mg), tetrakis(triphenylphosphine)palladium(0) (80 mg), potassium carbonate (280 mg), toluene (6 ml) and THF (3 ml) was stirred at 100° C. under a nitrogen atmosphere for 12 hrs. Water was added to the reaction mixture, and the mixture was extracted with ethyl acetate. The organic layer was washed with water and saturated brine. The solvent was dried over anhydrous sodium sulfate and the residue was concentrated under reduced pressure. The obtained residue was purified by silica gel column chromatography (hexane-hexane:ethyl acetate=2:1) and recrystallized (ethyl acetate-hexane) to give the title compound (210 mg).

$^1$H-NMR (CDCl$_3$) δ: 2.37 (3H, s), 3.18 (3H, s), 5.44 (2H, s), 7.01 (1H, s), 7.14-7.54 (11H, m), 8.45 (1H, d, J=8.2 Hz).

EXAMPLE 169

2-benzyl-6-butyl-1-oxo-4-phenyl-1,2-dihydroisoquinoline-3-carboxylic acid methyl ester A mixture of 2-benzyl-6-bromo-1-oxo-4-phenyl-1,2-dihydroisoquinoline-3-carboxylic acid methyl ester (300 mg), n-butylboronic acid (340 mg), tetrakis(triphenylphosphine)palladium(0) (80 mg), potassium carbonate (280 mg), toluene (6 ml) and THF (3 ml) was stirred at 100° C. under a nitrogen atmosphere for 12 hrs. Water was added to the reaction mixture, and the mixture was extracted with ethyl acetate. The organic layer was washed with water and saturated brine. The solvent was dried over anhydrous sodium sulfate and concentrated under reduced pressure. The obtained residue was purified by silica gel column chromatography (hexane-hexane:ethyl acetate=2:1) and crystallized from hexane to give the title compound (210 mg).

$^1$H-NMR (CDCl$_3$) δ: 0.88 (3H, t, J=7.3 Hz), 1.14-1.66 (4H, m), 2.61 (2H, t, J=7.7 Hz), 3.18 (3H, s), 5.44 (2H, s), 6.94-7.06 (1H, m), 7.14-7.50 (11H, m), 8.47 (1H, d, J=8.4 Hz).

EXAMPLE 170

2-benzyl-1-oxo-4-phenyl-1,2-dihydroisoquinoline-3-carboxylic acid methyl ester A mixture of 2-benzyl-6-bromo-1-oxo-4-phenyl-1,2-dihydroisoquinoline-3-carboxylic acid methyl ester (400 mg), 10% palladium carbon (100 mg), methanol (5 ml) and THF (5 ml) was stirred at room temperature under 1 atm hydrogen pressure for 12 hrs. Palladium carbon was filtered off, and the filtrate was concentrated. The obtained residue was purified by silica gel column chromatography (ethyl acetate) and recrystallized (ethyl acetate-hexane) to give the title compound (230 mg).

$^1$H-NMR (CDCl$_3$) δ: 3.19 (3H, s), 5.46 (2H, s), 7.14-7.68 (13H, m), 8.50-8.66 (1H, m).

EXAMPLE 171

2-benzyl-6-fluoro-1-oxo-4-phenyl-1,2-dihydroisoquinoline-3-carboxylic acid

A mixture of 6-fluoro-4-phenylisocoumarin-3-carboxylic acid (300 mg), benzylamine (230 mg), triethylamine (0.3 ml) and methanol (3 ml) was stirred at 50° C. for 36 hrs. The reaction mixture was concentrated, 1N-hydrochloric acid was added and the mixture was extracted with ethyl acetate. The organic layer was washed with water and saturated brine, dried over anhydrous sodium sulfate, and concentrated under reduced pressure. 4N-Hydrochloric acid-ethyl acetate solution (3 ml) was added to the residue at room temperature, and the mixture was stirred for 12 hrs. The reaction mixture was concentrated under reduced pressure and the obtained crystals were washed with (diisopropyl ether) to give the title compound, 2-benzyl-6-fluoro-1-oxo-4-phenyl-1,2-dihydroisoquinoline-3-carboxylic acid (300 mg).
$^1$H-NMR (DMSO-$d_6$) δ: 5.28 (2H, m), 6.72 (1H, dd, J=2.6, 10.2 Hz), 7.12-7.72 (11H, m), 8.41 (1H, dd, J=6.0, 9.0 Hz).

EXAMPLE 172

2-benzyl-6-fluoro-1-oxo-4-phenyl-1,2-dihydroisoquinoline-3-carboxylic acid methyl ester 2-Benzyl-6-fluoro-1-oxo-4-phenyl-1,2-dihydroisoquinoline-3-carboxylic acid (400 mg) was dissolved in DMF (4 ml) and methyl iodide (0.14 ml) and potassium carbonate (300 mg) were added at room temperature. The mixture was stirred for 12 hrs. Water was added to the reaction mixture, and the mixture was extracted with ethyl acetate. The organic layer was washed with water and saturated brine. The solvent was dried over anhydrous sodium sulfate and evaporated under reduced pressure. The residue was crystallized from ethyl acetate-hexane to give the title compound (200 mg).
$^1$H-NMR (CDCl$_3$) δ: 3.20 (3H, s), 5.43 (2H, s), 6.88 (1H, dd, J=2.5, 9.9 Hz), 7.12-7.54 (11H, m), 8.57 (1H, dd, J=5.8, 8.8 Hz).

EXAMPLE 173

2-benzyl-6-methoxy-1-oxo-4-phenyl-1,2-dihydroisoquinoline-3-carboxylic acid

To a solution of sodium methoxide in methanol (28%, 4 ml) was added 2-benzyl-6-fluoro-1-oxo-4-phenyl-1,2-dihydroisoquinoline-3-carboxylic acid (350 mg), and the mixture was heated under reflux for 6 hrs. To the reaction mixture were added water and 10% hydrochloric acid to acidify the aqueous layer of the mixture and the mixture was extracted with ethyl acetate. The organic layer was washed with water and saturated brine and dried over anhydrous sodium sulfate. The solvent was evaporated under reduced pressure. The obtained residue was crystallized from ethyl acetate to give the title compound (260 mg).
$^1$H-NMR (DMSO-$d_6$) δ: 3.69 (3H, s), 5.26 (2H, m), 6.46 (1H, d, J=2.6 Hz), 7.12-7.58 (11H, m), 8.27 (1H, d, J=8.8 Hz).

EXAMPLE 174

2-benzyl-6-benzyloxy-1-oxo-4-phenyl-1,2-dihydroisoquinoline-3-carboxylic acid

Sodium hydride (60% in oil, 400 mg) was added to benzyl alcohol (6 ml) under ice-cooling, and the mixture was allowed to warm to room temperature and stirred for 30 min. To the reaction mixture was added 2-benzyl-6-fluoro-1-oxo-4-phenyl-1,2-dihydroisoquinoline-3-carboxylic acid (310 mg) and the mixture was stirred at 120° C. for 6 hrs. To the reaction mixture were added water and 10% hydrochloric acid to acidify the aqueous layer of the mixture and the mixture was extracted with ethyl acetate. The organic layer was washed with water and saturated brine and dried over anhydrous sodium sulfate. The solvent was evaporated under reduced pressure and the obtained residue was crystallized from diisopropyl ether-hexane and the crystals were collected by filtration. Recrystallization (ethyl acetate-hexane) gave the title compound (250 mg).
$^1$H-NMR (CDCl$_3$) δ: 4.96 (2H, s), 5.30 (2H, s), 6.60 (1H, d, J=1.6 Hz), 7.04-7.46 (16H, m), 8.34 (1H, d, J=6.0 Hz).

EXAMPLE 175

2-benzyl-6-methoxy-1-oxo-4-phenyl-1,2-dihydroisoquinoline-3-carboxylic acid methyl ester 2-Benzyl-6-methoxy-1-oxo-4-phenyl-1,2-dihydroisoquinoline-3-carboxylic acid (160 mg) was dissolved in DMF (3 ml), and methyl iodide (0.06 ml) and potassium carbonate (120 mg) were added at room temperature. The mixture was stirred for 12 hrs. Water was added to the reaction mixture, and the mixture was extracted with ethyl acetate. The organic layer was washed with water and saturated brine. The solvent was dried over anhydrous sodium sulfate and evaporated under reduced pressure, and the obtained residue was crystallized from ethyl acetate-hexane to give the title compound (120 mg).
$^1$H-NMR (CDCl$_3$) δ: 3.18 (3H, s), 3.73 (3H, s), 5.42 (2H, s), 6.60 (1H, d, J=2.6 Hz), 7.12 (1H, dd, J=2.4, 9.0), 7.14-7.50 (10H, m), 8.49 (1H, d, J=8.8 Hz).

EXAMPLE 176

2-benzyl-6-benzyloxy-1-oxo-4-phenyl-1,2-dihydroisoquinoline-3-carboxylic acid methyl ester 2-Benzyl-6-benzyloxy-1-oxo-4-phenyl-1,2-dihydroisoquinoline-3-carboxylic acid (150 mg) was dissolved in DMF (3 ml) and methyl iodide (0.04 ml) and potassium carbonate (90 mg) were added at room temperature. The mixture was stirred for 12 hrs. Water was added to the reaction mixture, and the mixture was extracted with ethyl acetate. The organic layer was washed with water and saturated brine. The solvent was dried over anhydrous sodium sulfate and evaporated under reduced pressure, and the obtained residue was crystallized from hexane to give the title compound (140 mg).
$^1$H-NMR (CDCl$_3$) δ: 3.17 (3H, s), 4.98 (2H, s), 5.41 (2H, s), 6.65 (1H, d, J=2.0 Hz), 7.12-7.54 (16H, m), 8.48 (1H, d, J=8.8 Hz).

EXAMPLE 177

2-benzyl-1-oxo-4-phenyl-1,2-dihydroisoquinoline-3,6-dicarboxylic acid 3-methyl ester To a solution of 2-benzyl-1-oxo-4-phenyl-1,2-dihydroisoquinoline-3,6-dicarboxylic acid dimethyl ester (1.75 g) in THF (10 ml) were added methanol (10 ml) and 8N-aqueous sodium hydroxide solution (1 ml) at room temperature, and the mixture was stirred for 12 hrs. The reaction mixture was concentrated under reduced pressure and water was added, after which conc. hydrochloric acid (1 ml) was added. The mixture was extracted with ethyl acetate. The organic layer was washed with water and saturated brine, dried over anhydrous sodium sulfate, and concentrated under reduced pressure. The obtained residue was crystallized from ethyl acetate-hexane to give the title compound (1.67 g).

$^1$H-NMR (CDCl$_3$) δ: 3.21 (3H, s), 5.46 (2H, s), 7.16-7.56 (10H, m), 7.94-8.06 (1H, m), 8.19 (1H, dd, J=1.8, 8.4 Hz), 8.65 (1H, d, J=8.4 Hz). 1H unconfirmed.

EXAMPLE 178

2-benzyl-6-hydroxymethyl-1-oxo-4-phenyl-1,2-dihydroisoquinoline-3-carboxylic acid methyl ester To a solution of 2-benzyl-1-oxo-4-phenyl-1,2-dihydroisoquinoline-3,6-dicarboxylic acid 3-methyl ester (300 mg) in THF (3 ml) was added dropwise a solution (1M, 1.5 ml) of borane complex in THF under ice-cooling, and the mixture was allowed to warm to room temperature and stirred for 4 hrs. To the reaction mixture was further added dropwise a solution (1M, 3 ml) of borane complex in THF at room temperature, and the mixture was stirred for 1 hr. To the reaction mixture were added water and 10% hydrochloric acid under ice-cooling, and the mixture was extracted with ethyl acetate. The organic layer was washed with water, saturated aqueous sodium hydrogen carbonate, water and saturated brine, dried over anhydrous sodium sulfate, and concentrated under reduced pressure. The obtained residue was crystallized from ethyl acetate-hexane to give the title compound (280 mg).

$^1$H-NMR (CDCl$_3$) δ: 1.91 (1H, br s), 3.19 (3H, s), 4.71 (2H, br s), 5.44 (2H, s), 7.10-7.50 (11H, m), 7.52-7.64 (1H, m), 8.52 (1H, d, J=8.0 Hz).

EXAMPLE 179

6-bromo-2-(4-tert-butoxycarbonylbenzyl)-1-oxo-4-phenyl-1,2-dihydroisoquinoline-3-carboxylic acid methyl ester To a solution of 6-bromo-2-(4-carboxybenzyl)-1-oxo-4-phenyl-1,2-dihydroisoquinoline-3-carboxylic acid methyl ester (300 mg) and 2,2,2-trichloroacetoimidate tert-butyl ester (400 mg) in methylene chloride (6 ml) was added dropwise a catalytic amount of boron trifluoride diethyl etherate at room temperature and the mixture was stirred for 1 hr. To the reaction mixture was added 10% aqueous potassium carbonate solution, and the mixture was concentrated under reduced pressure and extracted with ethyl acetate. The organic layer was washed with water and saturated brine, dried over anhydrous sodium sulfate, and concentrated under reduced pressure. The residue was purified by basic silica gel column chromatography (ethyl acetate) and the obtained crystals were washed with methanol to give the title compound (260 mg).

$^1$H-NMR (CDCl$_3$) δ: 1.56 (9H, s), 3.21 (3H, s), 5.44 (2H, s), 7.20-7.52 (8H, m), 7.62-7.74 (1H, m), 7.91 (2H, d, J=8.4 Hz), 8.40 (1H, d, J=8.4 Hz).

EXAMPLE 180

2-(4-tert-butoxycarbonylbenzyl)-6-methyl-1-oxo-4-phenyl-1,2-dihydroisoquinoline-3-carboxylic acid methyl ester A mixture of 6-bromo-2-(4-tert-butoxycarbonylbenzyl)-1-oxo-4-phenyl-1,2-dihydroisoquinoline-3-carboxylic acid methyl ester (500 mg), methylboronic acid (270 mg), tetrakis(triphenylphosphine)palladium(0) (110 mg), potassium carbonate (380 mg), toluene (6 ml) and THF (4 ml) was stirred at 100° C. for 6 hrs. under a nitrogen atmosphere. Water was added to the reaction mixture, and the mixture was extracted with ethyl acetate. The organic layer was washed with water and saturated brine. The solvent was dried over anhydrous sodium sulfate, and concentrated under reduced pressure. The obtained residue was purified by silica gel column chromatography (hexane-hexane:ethyl acetate=2:1) and recrystallized (ethyl acetate-hexane) to give the title compound (380 mg).

$^1$H-NMR (CDCl$_3$) δ: 1.56 (9H, s), 2.38 (3H, s), 3.19 (3H, s), 5.46 (2H, s), 7.02 (1H, s), 7.20-7.50 (8H, m), 7.90 (2H, d, J=8.4 Hz), 8.44 (1H, d, J=8.2 Hz).

EXAMPLE 181

2-(4-carboxybenzyl)-6-methyl-1-oxo-4-phenyl-1,2-dihydroisoquinoline-3-carboxylic acid methyl ester To a 4N-hydrochloric acid-ethyl acetate solution (6 ml) was added 2-(4-tert-butoxycarbonylbenzyl)-6-methyl-1-oxo-4-phenyl-1,2-dihydroisoquinoline-3-carboxylic acid methyl ester (220 mg) at room temperature, and the mixture was stirred for 6 hrs. The reaction mixture was concentrated under reduced pressure, and the obtained residue was crystallized from ethyl acetate-hexane to give the title compound (180 mg).

$^1$H-NMR (CDCl$_3$) δ: 2.38 (3H, s), 3.19 (3H, s), 5.48 (2H, s), 7.03 (1H, s), 7.22-7.52 (8H, m), 8.02 (2H, d, J=8.4 Hz), 8.45 (1H, d, J=8.0 Hz).

EXAMPLE 182

2-(benzo[2,1,3]thiadiazol-5-ylmethyl)-6-bromo-1-oxo-4-phenyl-1,2-dihydroisoquinoline-3-carboxylic acid methyl ester To a solution of 6-bromo-1-oxo-4-phenyl-1,2-dihydroisoquinoline-3-carboxylic acid methyl ester (600 mg) in DMF (6 ml) was added sodium hydride (60% in oil, 74 mg) under ice-cooling, and the mixture was allowed to warm to room temperature and stirred for 1 hr. To the reaction mixture was added 5-bromomethylbenzo[2,1,3]thiadiazole (460 mg) at room temperature, and the mixture was stirred for 2 hrs. Water was added to the reaction mixture and crystals were collected by filtration, washed with ethyl acetate. The filtrate was extracted with ethyl acetate, and the organic layer was washed with water and saturated brine and dried. The solvent was evaporated under reduced pressure and the obtained residue was crystallized from ethyl acetate. The crystals were collected by filtration, combined with the crystals obtained earlier, and subjected to silica gel column chromatography (THF) and further to recrystallization (THF-ethyl acetate) to give the title compound (450 mg).

$^1$H-NMR (CDCl$_3$) δ: 3.22 (3H, s), 5.55 (2H, s), 7.20-7.54 (6H, m), 7.58 (1H, dd, J=1.4, 9.2 Hz), 7.68 (1H, dd, J=2.2, 8.6 Hz), 7.81 (1H, s), 7.95 (1H, d, J=9.2 Hz), 8.40 (1H, d, J=8.6 Hz).

EXAMPLE 183

6-bromo-2-(6-chloropyridin-3-ylmethyl)-1-oxo-4-phenyl-1,2-dihydroisoquinoline-3-carboxylic acid methyl ester To a solution of 6-bromo-1-oxo-4-phenyl-1,2-dihydroisoquinoline-3-carboxylic acid methyl ester (290 mg) in DMF (3 ml) was added sodium hydride (60% in oil, 36 mg) under ice-cooling, and the mixture was allowed to warm to room temperature and stirred for 1 hr. To the reaction mixture was added 2-chloro-5-chloromethylpyridine (160 mg) at room temperature, and the mixture was stirred for 2 hrs. Water was added to the reaction mixture, and the mixture was extracted with ethyl acetate. The organic layer was washed with water and saturated brine, and dried. The solvent was evaporated under reduced pressure and the obtained residue was crystallized from ethyl acetate to give the title compound (120 mg).
$^1$H-NMR (CDCl$_3$) δ: 3.32 (3H, s), 5.33 (2H, s), 7.20-7.54 (7H, m), 7.62-7.76 (2H, m), 8.28-8.44 (2H, m).

EXAMPLE 184

6-chloro-2-methoxy-1-oxo-4-phenyl-1,2-dihydroisoquinoline-3-carboxylic acid methyl ester 6-Chloro-1-oxo-4-phenyl-1H-isochromen-3-carboxylic acid (150 mg) was dissolved in methanol (3.0 ml) and O-methylhydroxylamine hydrochloride (420 mg) and sodium methoxide (270 mg) were added. The mixture was stirred at room temperature for 12 hrs. and concentrated under reduced pressure. The residue was partitioned between ethyl acetate and 1N hydrochloric acid, and the organic layer was dried over magnesium sulfate and concentrated under reduced pressure to dryness. Then, 4N hydrochloric acid ethyl acetate solution (3 ml) was added to the residue and the mixture was stirred at room temperature for 12 hrs. Water was added to wash the reaction mixture, and the organic layer was dried over magnesium sulfate and concentrated under reduced pressure to give 6-chloro-2-methoxy-1-oxo-4-phenyl-1,2-dihydroisoquinoline-3-carboxylic acid.

Then to a mixture of this product, potassium carbonate (210 mg) and DMF (3.0 ml) was added methyl iodide (62 μl) at room temperature with stirring, and the mixture was stirred for 1 hr. The reaction mixture was concentrated under reduced pressure, and the residue was partitioned between ethyl acetate and 1N hydrochloric acid. The organic layer was dried over magnesium sulfate and concentrated under reduced pressure. The residue was purified by medium pressure preparative LC (hexane/ethyl acetate=4/1-1/1) and crystallized from methanol to give the title compound (66 mg) as colorless crystals.
IR (KBr) cm$^{-1}$: 1742, 1680, 1377, 1246. $^1$H-NMR (CDCl$_3$) δ: 3.61 (3H, s), 4.20 (3H, s), 7.26 (1H, m), 7.30-7.38 (2H, m), 7.44-7.56 (4H, m), 8.47 (1H, d, J=8.4 Hz). HPLC analysis: purity 100% (retention time: 4.30 min). MS (ESI+): 344 (M+H), 346.

EXAMPLE 185

2-butoxy-6-chloro-1-oxo-4-phenyl-1,2-dihydroisoquinoline-3-carboxylic acid methyl ester A mixture of 6-chloro-1-oxo-4-phenyl-1H-isochromen-3-carboxylic acid (210 mg), O-n-butylhydroxylamine (620 mg) and ethanol (8.4 ml) was stirred for 12 hrs. at 90° C. in a sealed tube. After cooling, the reaction mixture was concentrated under reduced pressure to give 2-butoxy-6-chloro-1-oxo-4-phenyl-1,2-dihydroisoquinoline-3-carboxylic acid.

Then to a mixture of this product, potassium carbonate (290 mg) and DMF (3.0 ml) was added methyl iodide (87 μl) at room temperature with stirring, and the mixture was stirred for 1 hr. The reaction mixture was concentrated under reduced pressure, and the residue was partitioned between ethyl acetate and 1N hydrochloric acid. The organic layer was dried over magnesium sulfate and concentrated under reduced pressure. The residue was purified by medium pressure preparative LC (hexane/ethyl acetate=4/1-1/1) and crystallized from hexane/ethyl acetate to give the title compound (120 mg) as colorless crystals.
$^1$H-NMR (CDCl$_3$) δ: 0.98 (3H, t, J=7.5 Hz), 1.40-1.56 (2H, m), 1.66-1.80 (2H, m), 3.61 (3H, m), 4.44 (2H, t, J=6.6 Hz), 7.26 (1H, m), 7.30-7.38 (2H, m), 7.42-7.57 (4H, m), 8.45 (1H, d, J=8.7 Hz).

EXAMPLE 186

2-butoxy-6-chloro-3-hydroxymethyl-4-phenyl-2H-isoquinolin-1-one

2-Butoxy-6-chloro-1-oxo-4-phenyl-1,2-dihydroisoquinoline-3-carboxylic acid (370 mg) was dissolved in THF(6.0 ml), and oxalyl chloride (170 μl) and DMF (1 drop) were added at 0° C. with stirring. The mixture was stirred at room temperature for 2 hrs. and concentrated under reduced pressure. Toluene was added to the residue and they were boiled together several times to give 2-butoxy-6-chloro-1-oxo-4-phenyl-1,2-dihydroisoquinoline-3-carbonyl chloride.

Then, to a solution (3.0 ml) of sodium borohydride (130 mg) in 1,2-dichloroethane was added a solution (3.0 ml) of the above-mentioned acid chloride in THF at 0° C. with stirring, and the mixture was stirred at room temperature for 1 hr. To the reaction mixture were added 5% aqueous potassium hydrogensulfate solution and ethyl acetate for partitioning. The organic layer was dried over magnesium sulfate and concentrated under reduced pressure. The residue was purified by medium pressure preparative LC (hexane/ethyl acetate=4/1-1/1) and crystallized from hexane/ethyl acetate to give the title compound (180 mg) as colorless crystals.
$^1$H-NMR (CDCl$_3$) δ: 1.02 (3H, t, J=7.2 Hz), 1.48-1.63 (2H, m), 1.81-1.93 (2H, m), 2.31 (1H, t, J=7.2 Hz), 4.42-4.50 (4H, m), 7.10 (1H, d, J=1.8 Hz), 7.28-7.34 (2H, m), 7.44 (1H, dd, J=2.1, 8.7 Hz), 7.48-7.56 (3H, m), 8.43 (1H, q, J=8.7 Hz). HPLC analysis (Agilent 1100 system): purity 95% (retention time 3.53 min). MS (ESI+): 358 (M+H), 360.

EXAMPLE 187

2-benzyloxy-6-chloro-1-oxo-4-phenyl-1,2-dihydroisoquinoline-3-carboxylic acid A mixture of 6-chloro-1-oxo-4-phenyl-1H-isochromen-3-carboxylic acid (300 mg), O-benzylhydroxylamine (620 mg) and ethanol (6.0 ml) was stirred at 90° C. for 12 hrs. in a sealed tube. After cooling, the reaction mixture was concentrated under reduced pressure and the residue was washed with ethyl acetate/diethyl ether=1/10 to give the title compound (360 mg) as a colorless powder.
$^1$H-NMR (CDCl$_3$) δ: 5.22 (2H, s), 7.12 (1H, d, J=2.1 Hz), 7.15-7.56 (11H, m), 8.28 (1H, d, J=8.7 Hz). HPLC analysis: purity 95% (retention time: 4.37 min).
MS (ESI+): 406 (M+H), 408.

EXAMPLE 188

6-chloro-1-oxo-4-phenyl-2-propoxy-1,2-dihydroisoquinoline-3-carboxylic acid

The present compound was synthesized by a method similar to that in Example 187 and using 6-chloro-1-oxo-4-phenyl-1H-isochromen-3-carboxylic acid and O-n-butylhydroxylamine. A colorless powder (280 mg).

HPLC analysis: purity 95% (retention time: 4.05 min). MS (ESI+): 358 (M+H), 360.

EXAMPLE 189

2-benzyloxy-6-chloro-1-oxo-4-phenyl-1,2-dihydroisoquinoline-3-carboxylic acid methyl ester To a mixture of 2-benzyloxy-6-chloro-1-oxo-4-phenyl-1,2-dihydroisoquinoline-3-carboxylic acid (120 mg), potassium carbonate (120 mg) and DMF (2.4 ml) was added methyl iodide (37 μl) at room temperature with stirring, and the mixture was stirred for 1 hr. The reaction mixture was concentrated under reduced pressure, and the residue was partitioned between ethyl acetate and 1N hydrochloric acid. The organic layer was dried over magnesium sulfate and concentrated under reduced pressure. The residue was purified by medium pressure preparative LC (hexane/ethyl acetate=9/1-1/1) and crystallized from hexane/ethyl acetate to give the title compound (75 mg) as colorless crystals.

$^1$H-NMR (CDCl$_3$) δ: 3.55 (3H, s), 5.43 (2H, s), 7.27 (1H, m), 7.30-7.60 (11H, m), 8.50 (1H, d, J=8.7 Hz). HPLC analysis (Agilent 1100 system): purity 98% (retention time: 4.06 min). MS (ESI+): 420 (M+H), 422.

EXAMPLE 190

2-benzyloxy-6-chloro-3-hydroxymethyl-4-phenyl-2H-isoquinolin-1-one

2-Benzyloxy-6-chloro-1-oxo-4-phenyl-1,2-dihydroisoquinoline-3-carboxylic acid (240 mg) was dissolved in THF (4.8 ml), and oxalyl chloride (100 μl) and DMF (1 drop) were added at 0° C. with stirring. The mixture was stirred at room temperature for 2 hrs. and concentrated under reduced pressure. Toluene was added to the residue and they were boiled together several times to give 2-benzyloxy-6-chloro-1-oxo-4-phenyl-1,2-dihydroisoquinoline-3-carbonyl chloride.

Then, to a solution (4.0 ml) of sodium borohydride (78 mg) in 1,2-dichloroethane was added a THF solution (4.0 ml) of the above-mentioned acid chloride at 0° C. with stirring, and the mixture was stirred at room temperature for 1 hr. To the reaction mixture were added 5% aqueous potassium hydrogensulfate solution and ethyl acetate for partitioning. The organic layer was dried over magnesium sulfate and concentrated under reduced pressure. The residue was purified by medium pressure preparative LC (hexane/ethyl acetate=4/1-1/1) and crystallized from hexane/ethyl acetate to give the title compound (150 mg) as colorless crystals.

$^1$H-NMR (CDCl$_3$) δ: 2.25 (1H, t, J=6.9 Hz), 4.38 (2H, d, J=6.9 Hz), 5.47 (2H, s), 7.11 (1H, d, J=2.1 Hz), 7.24-7.35 (2H, m), 7.39-7.63 (9H, m), 8.48 (1H, t, J=8.7 Hz). HPLC analysis (Agilent 1100 system): purity 95% (retention time: 3.59 min).

MS (ESI+): 392 (M+H), 394.

EXAMPLE 191

6-chloro-1-oxo-4-phenyl-2-propoxy-1,2-dihydroisoquinoline-3-carboxylic acid methyl ester The present compound was synthesized by a method similar to that in Example 189 and using 2-propoxy-6-chloro-1-oxo-4-phenyl-1,2-dihydroisoquinoline-3-carboxylic acid (100 mg) as a starting material. A colorless powder (41 mg).

$^1$H-NMR (CDCl$_3$) δ: 1.02 (3H, t, J=7.5 Hz), 1.70-1.86 (2H, m), 3.61 (3H, s), 4.40 (2H, t, J=6.6 Hz), 7.26 (1H, m), 7.30-7.39 (2H, m), 7.42-7.56 (4H, m), 8.45 (1H, d, J=8.7 Hz). HPLC analysis (Agilent 1100 system): purity 98% (retention time: 3.86 min). MS (ESI+): 372 (M+H), 374.

EXAMPLE 192

6-chloro-3-hydroxymethyl-4-phenyl-2-propoxy-2H-isoquinolin-1-one

The present compound was synthesized by a method similar to that in Example 190 and using 2-propoxy-6-chloro-1-oxo-4-phenyl-1,2-dihydroisoquinoline-3-carboxylic acid (160 mg) as a starting material. A colorless powder (112 mg).

$^1$H-NMR (CDCl$_3$) δ: 1.10 (3H, t, J=7.5 Hz), 1.82-2.00 (2H, m), 2.34 (1H, t, J=6.9 Hz), 4.35-4.50 (4H, m), 7.11 (1H, d, J=2.1 Hz), 7.28-7.38 (2H, m), 7.44 (1H, dd, J=2.1, 8.7 Hz), 7.48-7.58 (3H, m), 8.44 (1H, d, J=8.7 Hz). HPLC analysis (Agilent 1100 system): purity 98% (retention time: 3.29 min). MS (ESI+): 344 (M+H), 346.

EXAMPLE 193

6-chloro-1-oxo-4-phenyl-2-(pyridin-2-ylamino)-1,2-dihydroisoquinoline-3-carboxylic acid methyl ester A mixture of 6-chloro-1-oxo-4-phenyl-1H-isochromen-3-carboxylic acid (200 mg), pyridin-2-ylhydrazine (180 mg) and 1,3-dimethyl-2-imidazolidinone (4.0 ml) was stirred at 100° C. for 12 hrs. After cooling the reaction mixture, the residue was partitioned between 1N hydrochloric acid and ethyl acetate. The organic layer was dried over magnesium sulfate and concentrated under reduced pressure.

Then, to a mixture of this product, potassium carbonate (110 mg) and DMF (3.0 ml) was added methyl iodide (46 μl) at room temperature with stirring, and the mixture was stirred for 1 hr. The reaction mixture was concentrated under reduced pressure, and the residue was partitioned between ethyl acetate and 1N hydrochloric acid. The organic layer was dried over magnesium sulfate and concentrated under reduced pressure. The residue was purified by medium pressure preparative LC (hexane/ethyl acetate=4/1-3/7) to give the title compound (46 mg) as pale-yellow crystals.

IR (KBr) cm$^{-1}$: 1744, 1680, 1597. $^1$H-NMR (CDCl$_3$) δ: 3.51 (3H, s), 6.69 (1H, d, J=8.4 Hz), 6.93 (1H, dd, J=4.8, 7.2 Hz), 7.30 (1H, d, J=1.8 Hz), 7.32-7.62 (8H, m), 8.27 (1H, dd, J=2.1, 5.4 Hz), 8.38 (1H, d, J=8.7 Hz). HPLC analysis: purity 96% (retention time: 3.52 min). MS (ESI+): 406 (M+H), 408.

EXAMPLE 194

2-[(benzyloxycarbonyl)(methyl)amino]-6-chloro-1-oxo-4-phenyl-1,2-dihydroisoquinoline-3-carboxylic acid To a solution (76 ml) of 6-chloro-2-methylamino-1-oxo-4-phenyl-1,2-dihydroisoquinoline-3-carboxylic acid (3.8 g)

in THF were added triethylamine (4.0 ml) and benzyl chloroformate (3.6 ml) at 0° C. with stirring, and the mixture was stirred at room temperature for 1 hr. To the reaction mixture was added saturated aqueous sodium hydrogen carbonate and the mixture was extracted with ethyl acetate. The organic layer was dried over magnesium sulfate and concentrated under reduced pressure. The residue was purified by silica gel column chromatography (hexane/ethyl acetate=2/1-dichloromethane/methanol/acetic acid=50/10/1) to give the title compound (2.5 g) as yellow powder.

$^1$H-NMR (CDCl$_3$) δ: 3.42 (3H, d, J=6.3 Hz), 5.05-5.32 (2H, m), 7.17-7.55 (12H, m), 8.41 (1H, m).

EXAMPLE 195

(6-chloro-3-hydroxymethyl-1-oxo-4-phenyl-1H-isoquinolin-2-yl)methylcarbamic acid benzyl ester 2-[(Benzyloxycarbonyl)(methyl)amino]-6-chloro-1-oxo-4-phenyl-1,2-dihydroisoquinoline-3-carboxylic acid (300 mg) was dissolved in THF (6.0 ml), and oxalyl chloride (122 μl) and DMF (1 drop) were added at 0° C. with stirring, and the mixture was stirred at room temperature for 2 hrs. and concentrated under reduced pressure. Toluene was added to the residue and they were boiled together several times and dried to give 2-[(benzyloxycarbonyl)(methyl)amino]-6-chloro-1-oxo-4-phenyl-1,2-dihydroisoquinoline-3-carbonyl chloride.

Then, to a solution (4.0 ml) of sodium borohydride (81 mg) in 1,2-dichloroethane was added THF solution (4.0 ml) of the above-mentioned acid chloride at 0° C. with stirring, and the mixture was stirred at room temperature for 1 hr. To the reaction mixture were added 5% aqueous potassium hydrogensulfate solution and ethyl acetate to allow partitioning, and the organic layer was dried over magnesium sulfate and concentrated under reduced pressure. The residue was purified by medium pressure preparative LC (hexane/ethyl acetate=5/1-2/3) to give the title compound (120 mg) as a colorless powder.

$^1$H-NMR (CDCl$_3$) δ: 2.11 (1H, m), 3.46 (3H, s), 4.20-4.38 (2H m), 5.02-5.34 (2H, m), 7.08 (1H, m), 7.16-7.58 (11H, m), 8.41 (1H, m). HPLC analysis (Agilent 1100 system): purity 98% (retention time: 3.60 min). MS (ESI+): 449 (M+H), 451.

EXAMPLE 196

3-bromomethyl-6-chloro-2-methylamino-4-phenyl-2H-isoquinolin-1-one

To (6-chloro-3-hydroxymethyl-1-oxo-4-phenyl-1H-isoquinolin-2-yl)methylcarbamic acid benzyl ester (80 mg) was added 25% hydrogen bromide acetic acid solution (4.0 ml), and the mixture was stirred at room temperature for 1 hr. The reaction mixture was diluted with ethyl acetate, washed with water, saturated aqueous sodium hydrogen carbonate and saturated brine, and the organic layer was dried over magnesium sulfate, concentrated under reduced pressure. The residue was purified by medium pressure preparative LC (hexane/ethyl acetate=9/1-1/1) to give the title compound (16 mg) as a colorless powder.

$^1$H-NMR (CDCl$_3$) δ: 2.96 (3H, d, J=5.7 Hz), 4.47 (2H, s), 5.65 (1H, q, J=5.7 Hz), 7.01 (1H, d, J=1.8 Hz), 7.33-7.41 (2H, m), 7.44 (1H, dd, J=1.8, 8.4 Hz), 7.48-7.60 (3H, m), 8.41 (1H, d, J=9.3 Hz). Anal. Calcd for C$_{17}$H$_{14}$BrClN$_2$O: C, 54.07; H, 3.74; N, 7.42. Found: C, 53.98; H, 3.71; N, 7.20. HPLC analysis: purity 96% (retention time: 4.79 min). MS (FAB): 377 (M+H), 379.

EXAMPLE 197 acetic acid 6-chloro-2-methylamino-1-oxo-4-phenyl-1,2-dihydroisoquinolin-3-ylmethyl ester In the reaction of Example 196, the title compound was obtained as a side product. Colorless powder (5 mg).

$^1$H-NMR (CDCl$_3$) δ: 2.07 (3H, s), 2.85 (3H, d, J=5.7 Hz), 4.99 (2H, s), 5.70 (1H, q, J=5.7 Hz), 7.10 (1H, d, J=2.1 Hz), 7.24-7.32 (2H, m), 7.42-7.54 (4H, m), 8.43 (1H, d, J=8.7 Hz). HPLC analysis: purity 96% (retention time: 4.34 min). MS (FAB): 357 (M+H), 359.

EXAMPLE 198

6-chloro-2-ethyl-1-oxo-4-phenyl-1,2-dihydroisoquinoline-3-carboxylic acid methyl ester A mixture of 6-chloro-1-oxo-4-phenyl-1H-isochromen-3-carboxylic acid (200 mg), ethylamine hydrochloride (540 mg), sodium methoxide (360 mg) and 1,3-dimethyl-2-imidazolidinone (4.0 ml) was stirred at 100° C. for 12 hrs. After cooling the reaction mixture, the residue was partitioned between 1N hydrochloric acid and ethyl acetate, and the organic layer was dried over magnesium sulfate and concentrated under reduced pressure.

Then, to a mixture of this product, potassium carbonate (110 mg) and DMF (3.0 ml) was added methyl iodide (46 μl) at room temperature with stirring, and the mixture was stirred for 1 hr. The reaction mixture was concentrated under reduced pressure, and the residue was partitioned between ethyl acetate and 1N hydrochloric acid, and the organic layer was dried over magnesium sulfate and concentrated under reduced pressure. The residue was purified by medium pressure preparative LC (hexane/ethyl acetate=9/1-1/1) to give the title compound (24 mg) as colorless crystals.

$^1$H-NMR (CDCl$_3$) δ: 1.39 (3H, t, J=7.2 Hz), 3.52 (3H, s), 4.07 (2H, q, J=7.2 Hz), 7.19 (1H, d, J=1.5 Hz), 7.28-7.34 (2H, m), 7.42-7.51 (4H, m), 8.45 (1H, d, J=9.0 Hz). HPLC analysis: purity 93% (retention time: 4.55 min). MS (ESI+): 342 (M+H), 344.

EXAMPLE 199

6-chloro-2-methylamino-1-oxo-4-phenyl-1,2-dihydroisoquinoline-3-carboxylic acid benzyl ester To a mixture of 2-[(benzyloxycarbonyl)(methyl)amino]-6-chloro-1-oxo-4-phenyl-1,2-dihydroisoquinoline-3-carboxylic acid (190 mg), triphenylphosphine (130 mg), benzyl alcohol (52 μl) and THF (6.0 ml) was added diethyl azodicarboxylate (86 μl) at 0° C. with stirring, and the mixture was stirred at room temperature for 2 hrs. The reaction mixture was concentrated under reduced pressure, the residue was purified by medium pressure preparative LC (hexane/ethyl acetate=9/1-3/2) to give 2-[(benzyloxycarbonyl)(methyl)amino]-6-chloro-1-oxo-4-phenyl-1,2-dihydroisoquinoline-3-carboxylic acid benzyl ester as a colorless powder.

Then, 25% hydrogen bromide-acetic acid solution (4.0 ml) as added to this product, and the mixture was stirred at room temperature for 1 hr. The reaction mixture was diluted with ethyl acetate, washed successively with water, saturated aqueous sodium hydrogen carbonate and saturated brine, and the organic layer was dried over magnesium sulfate and concentrated under reduced pressure. The residue was purified by medium pressure preparative LC (hexane/ethyl acetate=9/1-3/2) to give the title compound (30 mg) as a colorless powder.

IR (KBr) cm$^{-1}$: 1740, 1661, 1597, 1385, 1221, 1177, 1157. $^1$H-NMR (CDCl$_3$) δ: 2.85 (3H, d, J=5.7 Hz), 5.05 (2H, s), 5.65 (1H, q, J=5.7 Hz), 7.05-7.12 (2H, m), 7.22-7.36 (6H, m), 7.36-7.50 (4H, m), 8.42 (1H, d, J=8.4 Hz). HPLC analysis: purity 96% (retention time: 4.92 min). MS (ESI+): 419 (M+H), 421.

EXAMPLE 200

2-[(benzyloxycarbonyl)(methyl)amino]-6-chloro-1-oxo-4-phenyl-1,2-dihydroisoquinoline-3-carboxylic acid 3-tert-butoxycarbonylaminopropyl ester To a mixture of 2-[(benzyloxycarbonyl)(methyl)amino]-6-chloro-1-oxo-4-phenyl-1,2-dihydroisoquinoline-3-carboxylic acid (200 mg), triphenylphosphine (140 mg), (3-hydroxypropyl)carbamic acid tert-butyl ester (92 mg) and THF (4.0 ml), 0° C. with stirring, diethyl azodicarboxylate (90 μl) was added, and the mixture was stirred at room temperature for 2 hrs. The reaction mixture was concentrated under reduced pressure, and the residue was purified by medium pressure preparative LC (hexane/ethyl acetate=5/1-3/2) to give the title compound (150 mg) as a colorless powder.
$^1$H-NMR (CDCl$_3$) δ: 1.30-1.50 (2H, m), 1.43 (9H, s), 2.58-2.80 (2H, m), 3.40 and 3.43 (total 3H, s for each), 3.80-3.96 (2H, m), 4.34 (1H, m), 5.00-5.40 (2H, m), 7.10-7.55 (12H, m), 8.43 (1H, m). HPLC analysis: purity 99% (retention time: 5.05 min).
MS (ESI+): 520 (M−Boc), 522.

EXAMPLE 201

2-[(benzyloxycarbonyl)(methyl)amino]-6-chloro-1-oxo-4-phenyl-1,2-dihydroisoquinoline-3-carboxylic acid 3-aminopropyl ester To 2-[(benzyloxycarbonyl)(methyl)amino]-6-chloro-1-oxo-4-phenyl-1,2-dihydroisoquinoline-3-carboxylic acid 2-tert-butoxycarbonylaminopropyl ester (26 mg), trifluoroacetic acid (2.0 ml) was added, and the mixture was stirred at room temperature for 1 hr. The reaction mixture was concentrated, added saturated aqueous sodium hydrogen carbonate to the residue and the mixture was extracted with dichloromethane, and the organic layer was dried over magnesium sulfate and concentrated under reduced pressure. The residue was purified by silica gel column chromatography (dichloromethane/methanol=10/1) to give the title compound (8 mg) as a pale-yellow powder.
$^1$H-NMR (CDCl$_3$) δ: 1.30-1.42 (2H, m), 2.26-2.46 (2H, m), 3.41 and 3.43 (total 3H, s for each), 3.86-4.00 (2H, m), 5.02-5.36 (2H, m), 7.10-7.54 (12H, m), 8.43 (1H, m). MS (ESI+): 520 (M+H), 522.

EXAMPLE 202

6-chloro-2-methylamino-1-oxo-4-phenyl-1,2-dihydroisoquinoline-3-carboxylic acid 3-aminopropyl ester To 2-[(benzyloxycarbonyl)(methyl)amino]-6-chloro-1-oxo-4-phenyl-1,2-dihydroisoquinoline-3-carboxylic acid 2-tert-butoxycarbonylaminopropyl ester (100 mg) was added 25% hydrogen bromide.acetic acid solution (2.0 ml), and the mixture was stirred at room temperature for 1 hr. The reaction mixture was concentrated, the residue was diluted with ethyl acetate and washed successively with water, saturated aqueous sodium hydrogen carbonate and saturated brine, and the organic layer was dried over magnesium sulfate, concentrated under reduced pressure. The residue was purified by silica gel column chromatography (dichloromethane/methanol=10/1) to give the title compound (30 mg) as a colorless powder.
$^1$H-NMR (CDCl$_3$) δ: 1.92-2.08 (2H, m), 2.72-2.96 (5H, s), 4.12-4.26 (2H, m), 6.02 (1H, q, J=5.7 Hz), 7.22 (1H, d, J=1.8 Hz), 7.30-7.38 (2H, m), 7.40-7.58 (4H, m), 8.36 (1H, d, J=8.4 Hz). HPLC analysis (Agilent 1100 system): purity 97% (retention time: 2.36 min). MS (ESI+): 386 (M+H), 388.

EXAMPLE 203

2-[(benzyloxycarbonyl)(methyl)amino]-6-chloro-1-oxo-4-phenyl-1,2-dihydroisoquinoline-3-carboxylic acid 2-tert-butoxycarbonylaminoethyl ester The present compound was synthesized by a method similar to that in Example 200 and using 2-[(benzyloxycarbonyl)(methyl)amino]-6-chloro-1-oxo-4-phenyl-1,2-dihydroisoquinoline-3-carboxylic acid (200 mg) and (2-hydroxyethyl)carbamic acid tert-butyl ester. A colorless powder (120 mg).
$^1$H-NMR (CDCl$_3$) δ: 1.43 and 1.44 (total 9H, s for each), 2.76-3.02 (2H, m), 3.41 and 3.43 (total 3H, s for each), 3.76-4.22 (2H, m), 5.00-5.36 (3H, m), 7.00-7.56 (12H, m), 8.43 (1H, m). HPLC analysis (Agilent 1100 system): purity 99% (retention time: 4.18 min). MS (ESI+): 506 (M−Boc), 508.

EXAMPLE 204

6-chloro-2-methylamino-1-oxo-4-phenyl-1,2-dihydroisoquinoline-3-carboxylic acid 2-aminoethyl ester The present compound was synthesized by a method similar to that in Example 202 and using 2-[(benzyloxycarbonyl)(methyl)amino]-6-chloro-1-oxo-4-phenyl-1,2-dihydroisoquinoline-3-carboxylic acid 2-tert-butoxycarbonylaminoethyl ester (100 mg) as a starting material. colorless powder (32 mg).
$^1$H-NMR (CDCl$_3$) δ: 2.83 (3H, s), 3.12-3.36 (2H, m), 4.36-4.50 (2H, m), 6.37 (1H, m), 7.21 (1H, d, J=2.4 Hz), 7.26-7.36 (2H, m), 7.38-7.52 (4H, m), 8.32 (1H, d, J=8.7 Hz). HPLC analysis (Agilent 1100 system): purity 95% (retention time: 2.32 min). MS (ESI+): 372 (M+H), 374.

EXAMPLE 205

2-[(benzyloxycarbonyl)(methyl)amino]-6-chloro-1-oxo-4-phenyl-1,2-dihydroisoquinoline-3-carboxylic acid 2-phenoxyethyl ester The present compound was synthesized by a method similar to that in Example 200 using 2-[(benzyloxycarbonyl)(methyl)amino]-6-chloro-1-oxo-4-phenyl-1,2-dihydroisoquinoline-3-carboxylic acid (150 mg) and 2-phenoxyethanol. A colorless powder (78 mg).
$^1$H-NMR (CDCl$_3$) δ: 3.42 and 3.44 (total 3H, s for each), 3.64-3.80 (2H, m), 4.10-4.36 (2H, m), 5.02-5.24 (2H, m), 6.72-6.80 (2H, m), 6.98 (1H, m), 7.16-7.46 (13H, m), 7.49 (1H, m), 8.42 (1H, m). HPLC analysis (Agilent 1100 system): purity 95% (retention time: 4.36 min). MS (ESI+): 583 (M+H), 585.

EXAMPLE 206

6-chloro-2-methylamino-1-oxo-4-phenyl-1,2-dihydroisoquinoline-3-carboxylic acid 2-phenoxyethyl ester The present compound was synthesized by a method similar to that in Example 202 and using 2-[(benzyloxycarbonyl)(methyl)amino]-6-chloro-1-oxo-4-phenyl-1,2-dihydroisoquinoline-3-carboxylic acid 2-phenoxyethyl ester (60 mg). A colorless powder (33 mg).

$^1$H-NMR (CDCl$_3$) δ: 2.88 (3H, d, J=5.7 Hz), 3.89 (2H, t, J=4.5 Hz), 4.42 (2H, t, J=4.5 Hz), 5.64 (1H, q, J=5.7 Hz), 6.81 (2H, d, J=7.5 Hz), 6.98 (1H, t, J=7.5 Hz), 7.20-7.52 (9H, m), 8.43 (1H, d, J=8.4 Hz). HPLC analysis (Agilent 1100 system): purity 97% (retention time: 4.08 min). MS (ESI+): 449 (M+H), 451.

EXAMPLE 207

6-chloro-2-methylamino-1-oxo-4-phenyl-1,2-dihydroisoquinoline-3-carboxylic acid pyridin-4-ylmethyl ester To a mixture of 2-[(benzyloxycarbonyl)(methyl)amino]-6-chloro-1-oxo-4-phenyl-1,2-dihydroisoquinoline-3-carboxylic acid (150 mg), triphenylphosphine (120 mg), 4-pyridinemethanol (51 mg) and THF (3.0 ml) was added diethyl azodicarboxylate toluene solution (40%, 210 μl) at 0° C. with stirring and the mixture was stirred at room temperature for 2 hrs. The reaction mixture was concentrated under reduced pressure and the residue was purified by medium pressure preparative LC (hexane/ethyl acetate=1/1-1/3) to give 2-[(benzyloxycarbonyl)(methyl)amino]-6-chloro-1-oxo-4-phenyl-1,2-dihydroisoquinoline-3-carboxylic acid pyridin-4-ylmethyl ester.

Then, this product was dissolved in 25% hydrogen bromide-acetic acid solution (2.0 ml) and the mixture was stirred at room temperature for 1 hr. The reaction mixture was concentrated, and the residue was diluted with ethyl acetate, washed successively with water, saturated aqueous sodium hydrogen carbonate and saturated brine. The organic layer was dried over magnesium sulfate and concentrated under reduced pressure. The residue was purified by medium pressure preparative LC (hexane/ethyl acetate=1/1-ethyl acetate) to give the title compound (15 mg) as colorless crystals.

IR (KBr) cm$^{-1}$: 1744, 1663, 1599, 1385, 1223, 1177, 1157.
$^1$H-NMR (CDCl$_3$) δ: 2.87 (3H, d, J=5.7 Hz), 5.07 (2H, s), 5.68 (1H, q, J=5.7 Hz), 6.90 (2H, d, J=5.7 Hz), 7.24 (1H, t, J=2.1 Hz), 7.28-7.36 (2H, m), 7.38-7.54 (4H, m), 8.44 (1H, d, J=8.4 Hz), 8.49 (2H, d, J=6.0 Hz). HPLC analysis (Agilent 1100 system): purity 99% (retention time: 2.51 min). MS (ESI+): 420 (M+H), 422.

EXAMPLE 208

6-chloro-2-methylamino-1-oxo-4-phenyl-1,2-dihydroisoquinoline-3-carboxylic acid pyridin-3-ylmethyl ester The present compound was synthesized by a method similar to that in Example 207 and using 2-[(benzyloxycarbonyl)(methyl)amino]-6-chloro-1-oxo-4-phenyl-1,2-dihydroisoquinoline-3-carboxylic acid (150 mg) and 3-pyridinemethanol. A colorless powder (12 mg).

IR (KBr) cm$^{-1}$: 1746, 1663, 1599, 1385, 1225, 1177.
$^1$H-NMR (CDCl$_3$) δ: 2.84 (3H, d, J=5.7 Hz), 5.07 (2H, s), 5.64 (1H, q, J=5.7 Hz), 7.17-7.23 (2H, m), 7.25-7.32 (2H, m), 7.33-7.44 (4H, m), 7.49 (1H, dd, J=2.1, 8.4 Hz), 8.39 (1H, d, J=1.8 Hz), 8.42 (1H, d, J=9.3 Hz), 8.56 (1H, dd, J=1.8, 4.8 Hz). HPLC analysis (Agilent 1100 system): purity 99% (retention time: 2.54 min). MS (ESI+): 420 (M+H), 422.

EXAMPLE 209

6-chloro-2-methylamino-1-oxo-4-phenyl-1,2-dihydroisoquinoline-3-carboxylic acid 2-(4-methylthiazol-5-yl)ethyl ester The present compound was synthesized by a method similar to that in Example 207 and using 2-[(benzyloxycarbonyl)(methyl)amino]-6-chloro-1-oxo-4-phenyl-1,2-dihydroisoquinoline-3-carboxylic acid (150 mg) and 2-(4-methylthiazol-5-yl)ethanol. A colorless powder (41 mg).

$^1$H-NMR (CDCl$_3$) δ: 2.34 (3H, s), 2.80 (2H, t, J=6.9 Hz), 2.85 (3H, d, J=5.7 Hz), 4.16 (2H, t, J=6.9 Hz), 5.64 (1H, q, J=5.7 Hz), 7.24 (1H, d, J=1.5 Hz), 7.26-7.34 (2H, m), 7.40-7.46 (3H, m), 7.50 (1H, dd, J=2.1, 8.7 Hz), 8.43 (1H, d, J=8.7 Hz), 8.57 (1H, s). HPLC analysis (Agilent 1100 system): purity 98% (retention time: 3.26 min). MS (ESI+): 454 (M+H), 456.

EXAMPLE 210

6-chloro-1-oxo-2-pentylideneamino-4-phenyl-1,2-dihydroisoquinoline-3-carboxylic acid methyl ester A mixture of 2-amino-6-chloro-1-oxo-4-phenyl-1,2-dihydroisoquinoline-3-carboxylic acid methyl ester (210 mg), triethylamine (130 μl), valeraldehyde (81 μl) and methanol (4.2 ml) was stirred at 70° C. for 3.5 hrs. After cooling, the reaction mixture was concentrated under reduced pressure. The residue was purified by medium pressure preparative LC (hexane/ethyl acetate=9/1-1/1) to give the title compound (200 mg) as colorless crystals.

$^1$H-NMR (CDCl$_3$) δ: 0.95 (3H, t, J=7.2 Hz), 1.37-1.52 (2H, m), 1.58-1.70 (2H, m), 2.48-2.58 (2H, m), 7.23 (1H, m), 7.30-7.38 (2H, m), 7.42-7.52 (4H, m), 8.43 (1H, d, J=8.7 Hz), 8.72 (1H, t, J=5.4 Hz). Anal. Calcd for C$_{22}$H$_{21}$N$_2$O$_3$Cl: C, 66.58; H, 5.33; N, 7.06. Found: C, 66.82; H, 5.44; N, 7.02.

EXAMPLE 211

6-chloro-1-oxo-2-pentylamino-4-phenyl-1,2-dihydroisoquinoline-3-carboxylic acid methyl ester To a mixture of 6-chloro-1-oxo-2-pentylidenamino-4-phenyl-1,2-dihydroisoquinoline-3-carboxylic acid methyl ester (120 mg), acetic acid (76 μl) and methanol (5.0 ml) was added sodium cyano borohydride (80 mg) and the mixture was stirred at room temperature for 1 hr. The reaction mixture was concentrated under reduced pressure and saturated aqueous sodium hydrogen carbonate was added to the residue. The mixture was extracted with dichloromethane, and after drying, the organic layer was concentrated under reduced pressure. The residue was subjected to medium pressure preparative LC (hexane/ethyl acetate=9/1-1/1) to give the title compound (78 mg) as colorless crystals.

$^1$H-NMR (CDCl$_3$) δ: 0.91 (3H, t, J=6.9 Hz), 1.30-1.42 (4H, m), 1.48-1.62 (2H, m), 3.04-3.22 (2H, m), 3.62 (3H, s), 5.49 (1H, t, J=6.9 Hz), 7.25 (1H, d, J=1.8 Hz), 7.30-7.38 (2H, m), 7.42-7.52 (4H, m), 8.42 (1H, d, J=8.7 Hz). HPLC analysis: purity 98% (retention time: 5.24 min). MS (ESI+): 399 (M+H), 401.

EXAMPLE 212

6-chloro-2-isobutylidenamino-1-oxo-4-phenyl-1,2-dihydroisoquinoline-3-carboxylic acid methyl ester The present compound was synthesized by a method similar to that in Example 210 and using 2-amino-6-chloro-1-oxo-4-phenyl-1,2-dihydroisoquinoline-3-carboxylic acid methyl ester (210 mg) and isobutylaldehyde. A colorless powder (80 mg).

$^1$H-NMR (CDCl$_3$) δ: 1.21 (6H, d, J=6.9 Hz), 2.76 (1H, m), 3.57 (3H, s), 7.22 (1H, d, J=2.1 Hz), 7.31-7.38 (2H, m), 7.42-7.52 (4H, m), 8.42 (1H, d, J=8.7 Hz), 8.75 (1H, d, J=5.1 Hz).

EXAMPLE 213

6-chloro-2-(3-methylbutylidenamino)-1-oxo-4-phenyl-1,2-dihydroisoquinoline-3-carboxylic acid methyl ester The present compound was synthesized by a method similar to that in Example 210 and using 2-amino-6-chloro-1-oxo-4-phenyl-1,2-dihydroisoquinoline-3-carboxylic acid methyl ester (210 mg) and isovaleraldehyde. A colorless powder (95 mg).

$^1$H-NMR (CDCl$_3$) δ: 1.05 (6H, d, J=6.6 Hz), 2.06 (1H, m), 2.41 (2H, dd, J=5.7, 6.9 Hz), 3.54 (3H, s), 7.23 (1H, d, J=1.5 Hz), 7.30-7.38 (2H, m), 7.42-7.51 (4H, m), 8.43 (1H, q, J=8.7 Hz), 8.68 (1H, t, J=6.0 Hz).

EXAMPLE 214

6-chloro-2-[(furan-2-ylmethylene)amino]-1-oxo-4-phenyl-1,2-dihydroisoquinoline-3-carboxylic acid methyl ester The present compound was synthesized by a method similar to that in Example 210 and using 2-amino-6-chloro-1-oxo-4-phenyl-1,2-dihydroisoquinoline-3-carboxylic acid methyl ester (210 mg) and furan-2-carbaldehyde. A colorless powder (125 mg).

$^1$H-NMR (CDCl$_3$) δ: 3.62 (3H, s), 6.55 (1H, dd, J=1.8, 3.6 Hz), 6.95 (1H, dd, J=0.9, 3.6 Hz), 7.24 (1H, m), 7.36-7.40 (2H, m), 7.42-7.54 (4H, m), 7.61 (1H, m), 8.45 (1H, d, J=8.4 Hz), 9.59 (1H, s).

EXAMPLE 215

6-chloro-2-[(furan-3-ylmethylene)amino]-1-oxo-4-phenyl-1,2-dihydroisoquinoline-3-carboxylic acid methyl ester The present compound was synthesized by a method similar to that in Example 210 and using 2-amino-6-chloro-1-oxo-4-phenyl-1,2-dihydroisoquinoline-3-carboxylic acid methyl ester (210 mg) and furan-3-carbaldehyde. A colorless powder (130 mg).

$^1$H-NMR (CDCl$_3$) δ: 3.59 (3H, s), 6.76 (1H, m), 7.24 (1H, m), 7.30-7.40 (2H, m), 7.40-7.56 (5H, m), 7.86 (1H, s), 8.46 (1H, d, J=9.0 Hz), 9.60 (1H, s).

EXAMPLE 216

6-chloro-2-ethylidenamino-1-oxo-4-phenyl-1,2-dihydroisoquinoline-3-carboxylic acid methyl ester The present compound was synthesized by a method similar to that in Example 210 and using 2-amino-6-chloro-1-oxo-4-phenyl-1,2-dihydroisoquinoline-3-carboxylic acid methyl ester (210 mg) and formaldehyde. A colorless powder (130 mg).

$^1$H-NMR (CDCl$_3$) δ: 2.23 (3H, d, J=5.4 Hz), 3.55 (3H, s), 7.23 (1H, d, J=1.8 Hz), 7.30-7.38 (2H, m), 7.40-7.54 (4H, m), 8.43 (1H, d, J=8.4 Hz), 8.73 (1H, m).

EXAMPLE 217

6-chloro-1-oxo-4-phenyl-2-propylidenamino-1,2-dihydroisoquinoline-3-carboxylic acid methyl ester The present compound was synthesized by a method similar to that in Example 210 and using 2-amino-6-chloro-1-oxo-4-phenyl-1,2-dihydroisoquinoline-3-carboxylic acid methyl ester (210 mg) and propionaldehyde. A colorless powder (120 mg).

$^1$H-NMR (CDCl$_3$) δ: 1.20 (3H, t, J=7.5 Hz), 2.50-2.62 (2H, m), 3.56 (3H, s), 7.23 (1H, d, J=2.1 Hz), 7.30-7.40 (2H, m), 7.40-7.54 (4H, m), 8.43 (1H, d, J=9.0 Hz), 8.81 (1H, m).

EXAMPLE 218

6-chloro-2-isobutylamino-1-oxo-4-phenyl-1,2-dihydroisoquinoline-3-carboxylic acid methyl ester The present compound was synthesized by a method similar to that in Example 211 and using 6-chloro-2-isobutylidenamino-1-oxo-4-phenyl-1,2-dihydroisoquinoline-3-carboxylic acid methyl ester (55 mg). A colorless powder (35 mg).

$^1$H-NMR (CDCl$_3$) δ: 0.99 (6H, d, J=6.6 Hz), 1.83 (1H, m), 2.78-3.20 (2H, m), 3.62 (3H, s), 5.53 (1H, m), 7.25 (1H, d, J=2.1 Hz), 7.30-7.38 (2H, m), 7.42-7.52 (4H, m), 8.42 (1H, d, J=8.4 Hz). HPLC analysis (Agilent 1100 system): purity 95% (retention time: 4.15 min). MS (ESI+): 385 (M+H), 387.

EXAMPLE 219

6-chloro-2-(3-methylbutylamino)-1-oxo-4-phenyl-1,2-dihydroisoquinoline-3-carboxylic acid methyl ester The present compound was synthesized by a method similar to that in Example 211 and using 6-chloro-2-(3-methylbutylidenamino)-1-oxo-4-phenyl-1,2-dihydroisoquinoline-3-carboxylic acid methyl ester (60 mg). A colorless powder (38 mg).

$^1$H-NMR (CDCl$_3$) δ: 0.93 (6H, d, J=6.6 Hz), 1.38-1.49 (2H, m), 1.70 (1H, m), 3.06-3.26 (2H, m), 3.62 (3H, s), 5.47 (1H, m), 7.25 (1H, d, J=1.5 Hz), 7.30-7.38 (2H, m), 7.40-7.52 (4H, m), 8.42 (1H, d, J=8.4 Hz). HPLC analysis (Agilent 1100 system): purity 97% (retention time: 4.31 min). MS (ESI+): 399 (M+H), 401.

EXAMPLE 220

6-chloro-2-ethylamino-1-oxo-4-phenyl-1,2-dihydroisoquinoline-3-carboxylic acid methyl ester The present compound was synthesized by a method similar to that in Example 211 and using 6-chloro-2-ethylidenamino-1-oxo-4-phenyl-1,2-dihydroisoquinoline-3-carboxylic acid methyl ester (100 mg). A colorless powder (67 mg).
$^1$H-NMR (CDCl$_3$) δ: 1.15 (3H, t, J=7.4 Hz), 3.10-3.28 (2H, m), 3.62 (3H, s), 5.46 (1H, t, J=7.0 Hz), 7.25 (1H, m), 7.30-7.38 (2H, m), 7.41-7.54 (4H, m), 8.42 (1H, d, J=8.8 Hz). HPLC analysis (Agilent 1100 system): purity 100% (retention time: 3.75 min). MS (ESI+): 357 (M+H), 359.

EXAMPLE 221

6-chloro-1-oxo-4-phenyl-2-propylamino-1,2-dihydroisoquinoline-3-carboxylic acid methyl ester The present compound was synthesized by a method similar to that in Example 211 and using 6-chloro-1-oxo-4-phenyl-2-propylidenamino-1,2-dihydroisoquinoline-3-carboxylic acid methyl ester (50 mg). A colorless powder (13 mg). HPLC analysis (Agilent 1100 system): 98% (retention time: 3.96 min). MS (ESI+): 371 (M+H), 373.

EXAMPLE 222

2-[(benzyloxycarbonyl)(methyl)amino]-6-chloro-1-oxo-4-phenyl-1,2-dihydroisoquinoline-3-carboxylic acid 4-methoxybenzyl ester The present compound was synthesized by a method similar to that in Example 200 and using 2-[(benzyloxycarbonyl)(methyl)amino]-6-chloro-1-oxo-4-phenyl-1,2-dihydroisoquinoline-3-carboxylic acid (200 mg) and 4-methoxybenzyl alcohol. A colorless powder (110 mg). HPLC analysis (Agilent 1100 system): purity 96% (retention time: 4.30 min). MS (ESI+): 583 (M+H), 585.

EXAMPLE 223

2-[(benzyloxycarbonyl)(methyl)amino]-6-chloro-1-oxo-4-phenyl-1,2-dihydroisoquinoline-3-carboxylic acid 4-fluorobenzyl ester The present compound was synthesized by a method similar to that in Example 200 and using 2-[(benzyloxycarbonyl)(methyl)amino]-6-chloro-1-oxo-4-phenyl-1,2-dihydroisoquinoline-3-carboxylic acid (200 mg) and 4-fluorobenzyl alcohol. A colorless powder (145 mg). HPLC analysis (Agilent 1100 system): purity 98% (retention time: 4.33 min). MS (ESI+): 571 (M+H), 573.

EXAMPLE 224

6-chloro-2-methylamino-1-oxo-4-phenyl-1,2-dihydroisoquinoline-3-carboxylic acid cyclohexylmethyl ester The present compound was synthesized by a method similar to that in Example 207 and using 2-[(benzyloxycarbonyl)(methyl)amino]-6-chloro-1-oxo-4-phenyl-1,2-dihydroisoquinoline-3-carboxylic acid (200 mg) and 4-cyclohexylmethylalcohol.
$^1$H-NMR (CDCl$_3$) δ: 0.68-0.86 (2H, m), 1.00-1.22 (3H, m), 1.30-1.54 (3H, m), 1.54-1.70 (3H, m), 2.88 (3H, d, J=6.0 Hz), 3.84 (2H, d, J=6.3 Hz), 5.67 (1H, q, J=6.0 Hz), 7.25 (1H, d, J=1.5 Hz), 7.33-7.40 (2H, m), 7.42-7.52 (4H, m), 8.43 (1H, d, J=8.4 Hz). A colorless powder. (46 mg). MS (ESI+): 425 (M+H), 427.

EXAMPLE 225

6-chloro-2-methylamino-1-oxo-4-phenyl-1,2-dihydroisoquinoline-3-carboxylic acid 4-fluorobenzyl ester The present compound was synthesized by a method similar to that in Example 202 and using 2-[(benzyloxycarbonyl)(methyl)amino]-6-chloro-1-oxo-4-phenyl-1,2-dihydroisoquinoline-3-carboxylic acid 4-fluorobenzyl ester (80 mg). A colorless powder (33 mg).
$^1$H-NMR (CDCl$_3$) δ: 2.84 (3H, t, J=6.0 Hz), 5.02 (2H, s), 5.64 (1H, q, J=6.0 Hz), 6.88-7.10 (1H, m), 7.22 (1H, d, J=1.8 Hz), 7.24-7.52 (6H, m), 8.42 (1H, d, J=8.4 Hz). HPLC analysis: purity 99% (5.02 min). MS (ESI+): 437 (M+H), 439.

EXAMPLE 226

6-chloro-2-(4-methoxybenzyl)-1-oxo-4-phenyl-1,2-dihydroisoquinoline-3-carboxylic acid A mixture of 6-chloro-1-oxo-4-phenyl-1H-isochromen-3-carboxylic acid (300 mg), 4-methoxybenzylamine (684 mg) and methanol (3.0 ml) was stirred at room temperature for 12 hrs. The reaction mixture was concentrated, and the residue was partitioned between 1N hydrochloric acid and ethyl acetate. The organic layer was dried over magnesium sulfate and concentrated under reduced pressure. Then, 4N hydrochloric acid ethyl acetate solution (3.0 ml) was added to the residue and the mixture was stirred for 12 hrs. at room temperature. The reaction mixture was concentrated under reduced pressure and dried to give the title compound (360 mg) as a pale-yellow powder.
$^1$H-NMR (CDCl$_3$) δ: 3.74 (3H, s), 5.33 (2H, s), 6.78 (2H, d, J=8.8 Hz), 7.12-7.54 (10H, m), 8.42 (1H, d, J=8.4 Hz). HPLC analysis (254 nm): purity 97% (retention time: 4.27 min). HPLC analysis (Agilent 1100 system): purity 94% (retention time: 3.42 min). MS (ESI+): 420 (M+H), 422.

EXAMPLE 227

6-chloro-2-(4-methoxybenzyl)-1-oxo-4-phenyl-1,2-dihydroisoquinoline-3-carboxylic acid methyl ester The present compound was synthesized by a method similar to that in Example 189 and using 6-chloro-2-(4-methoxybenzyl)-1-oxo-4-phenyl-1,2-dihydroisoquinoline-3-carboxylic acid (50 mg). Colorless crystals (23 mg).
$^1$H-NMR (CDCl$_3$) δ: 3.25 (3H, s), 3.70 (3H, s), 5.35 (2H, s), 6.81 (2H, d, J=8.7 Hz), 7.18-7.30 (5H, m), 7.38-7.46 (3H, m), 7.49 (1H, dd, J=2.1, 8.7 Hz), 8.48 (1H, q, J=8.4 Hz). HPLC analysis: purity 99% (retention time: 4.87 min). MS (ESI+): 434 (M+H), 436.

EXAMPLE 228

6-chloro-2-methylamino-1-oxo-4-phenyl-1,2-dihydroisoquinoline-3-carboxylic acid 2-pyridin-4-ylethyl ester The present compound was synthesized by a method similar to that in Example 207 and using 2-[(benzyloxycarbonyl)(methyl)amino]-6-chloro-1-oxo-4-phenyl-1,2-dihydroisoquinoline-3-carboxylic acid (200 mg) and 2-pyridineethanol. Colorless oil (78 mg).

$^1$H-NMR (CDCl$_3$) δ: 2.85 (3H, s), 2.96 (2H, t, J=6.0 Hz), 4.38 (2H, t, J=6.0 Hz), 7.23 (1H, d, J=2.1 Hz), 7.24-7.34 (2H, m), 7.38-7.56 (6H, m), 8.43 (1H, d, J=8.7 Hz), 8.76 (2H, d, J=6.6 Hz). HPLC analysis: purity 100% (retention time: 3.26 min).

EXAMPLE 229

6-chloro-2-methylamino-1-oxo-4-phenyl-1,2-dihydroisoquinoline-3-carboxylic acid (pyridin-4-ylmethyl)amide 2-[(Benzyloxycarbonyl)(methyl)amino]-6-chloro-1-oxo-4-phenyl-1,2-dihydroisoquinoline-3-carboxylic acid (320 mg) was dissolved in THF (6.0 ml), and oxalyl chloride (130 μl) and DMF (1 drop) were added at 0° C. with stirring, and the mixture was stirred at room temperature for 2 hrs. and concentrated under reduced pressure. Toluene was added to the residue and they were boiled together several times and dried to give 2-[(benzyloxycarbonyl)(methyl)amino]-6-chloro-1-oxo-4-phenyl-1,2-dihydroisoquinoline-3-carbonyl chloride.

Then, to a mixture of this product, triethylamine (210 μl) and dichloromethane (6.4 ml) was added 4-picolylamine (120 μl), and the mixture was stirred at room temperature for 2 hrs. the reaction mixture was washed with water, dried over magnesium sulfate and concentrated under reduced pressure. The residue was purified by medium pressure preparative LC (hexane/ethyl acetate=1/3-ethyl acetate) to give [6-chloro-1-oxo-4-phenyl-3-[(pyridin-4-ylmethyl)carbamoyl]-1H-isoquinolin-2-yl]methylcarbamic acid benzyl ester.

Then, this product was dissolved in 25% hydrogen bromide-acetic acid solution (2.0 ml) and the mixture was stirred at room temperature for 1 hr. The reaction mixture was concentrated, and the residue was diluted with ethyl acetate, washed successively with water, saturated aqueous sodium hydrogen carbonate and saturated brine. The organic layer was dried over magnesium sulfate and concentrated under reduced pressure. The residue was purified by medium pressure preparative LC (hexane/ethyl acetate=1/1-1/3) to give the title compound (10 mg) as a colorless powder.

$^1$H-NMR (CDCl$_3$) δ: 2.92 (3H, d, J=5.7 Hz), 4.36 (2H, d, J=6.0 Hz), 5.75 (1H, q, J=5.7 Hz), 6.05 (1H, t, J=5.7 Hz), 6.66 (2H, d, J=6.0 Hz), 7.21 (1H, d, J=1.5 Hz), 7.36-7.42 (2H, m), 7.44-7.56 (4H, m), 8.34-8.44 (3H, m). HPLC analysis (Agilent 1100 system): purity 94% (retention time: 2.08 min). MS (ESI+): 419 (M+H), 421.

EXAMPLE 230

2-(benzo[1,3]dioxol-5-ylmethyl)-6-chloro-1-oxo-4-phenyl-1,2-dihydroisoquinoline-3-carboxylic acid The present compound was synthesized by a method similar to that in Example 226 and using 6-chloro-1-oxo-4-phenyl-1H-isochromen-3-carboxylic acid (400 mg) and piperonylamine.

beige solid (500 mg).

$^1$H-NMR (CDCl$_3$) δ: 5.34 (2H, s), 5.92 (2H, s), 6.68-6.85 (3H, m), 7.16 (1H, s), 7.28-7.40 (2H, m), 7.40-7.55 (4H, m), 8.46 (1H, d, J=8.4 Hz). HPLC analysis: purity 94% (retention time: 4.33 min). MS (ESI+): 434 (M+H), 436.

EXAMPLE 231

2-(benzo[1,3]dioxol-5-ylmethyl)-6-chloro-1-oxo-4-phenyl-1,2-dihydroisoquinoline-3-carboxylic acid methyl ester The present compound was synthesized by a method similar to that in Example 189 and using 2-(benzo[1,3]dioxol-5-ylmethyl)-6-chloro-1-oxo-4-phenyl-1,2-dihydroisoquinoline-3-carboxylic acid (250 mg). A colorless powder (210 mg).

$^1$H-NMR (CDCl$_3$) δ: 3.27 (3H, s), 5.32 (2H, s), 5.92 (2H, s), 6.68-6.76 (2H, m), 6.80 (1H, d, J=0.9 Hz), 7.20 (1H, d, J=2.1 Hz), 7.24-7.32 (2H, m), 7.38-7.48 (3H, m), 7.50 (1H, dd, J=2.1, 8.7 Hz), 8.48 (1H, d, J=8.7 Hz). HPLC analysis (Agilent 1100 system): purity 98% (retention time: 3.93 min). MS (ESI+): 448 (M+H), 450.

EXAMPLE 232

2-(benzo[1,3]dioxol-5-ylmethyl)-6-bromo-1-oxo-4-phenyl-1,2-dihydroisoquinoline-3-carboxylic acid pyridin-3-ylmethyl ester The present compound was synthesized by a method similar to that in Example 200 and using 2-(benzo[1,3]dioxol-5-ylmethyl)-6-bromo-1-oxo-4-phenyl-1,2-dihydroisoquinoline-3-carboxylic acid (300 mg) and 3-pyridinemethanol. Colorless crystals (288 mg).

$^1$H-NMR (CDCl$_3$) δ: 4.60 (2H, s), 5.38 (2H, s), 5.89 (2H, s), 6.62-6.76 (3H, m), 7.03 (1H, dt, J=1.8, 7.8 Hz), 7.14 (1H, m), 7.18-7.28 (2H, m), 7.30-742 (4H, m), 7.60 (1H, dd, J=1.8, 8.4 Hz), 8.08 (1H, d, J=1.8 Hz), 8.40 (1H, d, J=8.4 Hz), 8.51 (1H, dd, J=1.8, 7.8 Hz). HPLC analysis (Agilent 1100 system): purity 98% (retention time: 2.97 min). MS (ESI+): 569 (M+H), 571.

EXAMPLE 233

2-(benzo[1,3]dioxol-5-ylmethyl)-6-bromo-1-oxo-4-phenyl-1,2-dihydroisoquinoline-3-carboxylic acid pyridin-4-ylmethyl ester The present compound was synthesized by a method similar to that in Example 200 and using 2-(benzo[1,3]dioxol-5-ylmethyl)-6-bromo-1-oxo-4-phenyl-1,2-dihydroisoquinoline-3-carboxylic acid (300 mg) and 4-pyridinemethanol. Colorless crystals (246 mg).

$^1$H-NMR (CDCl$_3$) δ: 4.58 (2H, s), 5.38 (2H, s), 5.84 (2H, s), 6.58-6.74 (5H, m), 7.22-7.30 (2H, m), 7.32-7.42 (4H, m), 7.68 (1H, dd, J=1.8, 8.4 Hz), 8.38-8.48 (3H, m). HPLC analysis (Agilent 1100 system): purity 100% (retention time: 2.86 min).

MS (ESI+): 569 (M+H), 571.

EXAMPLE 234

2-(benzo[1,3]dioxol-5-ylmethyl)-6-bromo-1-oxo-4-phenyl-1,2-dihydroisoquinoline-3-carboxylic acid benzyl ester The present compound was synthesized by a method similar to that in Example 200 and using 2-(benzo[1,3]dioxol-5-ylmethyl)-6-bromo-1-oxo-4-phenyl-1,2-dihydroisoquinoline-3-carboxylic acid (300 mg) and benzyl alcohol. Colorless crystals (278 mg).

$^1$H-NMR (CDCl$_3$) δ: 4.63 (2H, s), 5.33 (2H, s), 5.86 (2H, s), 6.62-6.84 (5H, m), 7.16-7.32 (5H, m), 7.32-7.44 (4H, m), 7.64 (1H, dd, J=2.1, 8.4 Hz), 8.39 (1H, d, J=8.4 Hz). HPLC analysis (Agilent 1100 system): purity 95% (retention time: 4.32 min). MS (ESI+): 568 (M+H), 570.

EXAMPLE 235

[2-(benzo[1,3]dioxol-5-ylmethyl)-6-bromo-1-oxo-4-phenyl-1,2-dihydroisoquinolin-3-yl]carbamic acid benzyl ester To a mixture of 2-(benzo[1,3]dioxol-5-ylmethyl)-6-bromo-1-oxo-4-phenyl-1,2-dihydroisoquinoline-3-carboxylic acid (220 mg), triethylamine (91 μl) and toluene (4.4 ml) was added diphenylphosphorylazide (185 μl) at room temperature with stirring, and the mixture was stirred at room temperature for 1 hr. and at 80° C. for 1 hr. After cooling, benzyl alcohol (79 μl) was added to the reaction mixture, and the mixture was further stirred at 80° C. for 12 hrs. After cooling the reaction mixture, the solvent was evaporated under reduced pressure and the residue was purified by medium pressure preparative LC (hexane/ethyl acetate=4/1-1/1) to give the title compound (160 mg) as pale-yellow crystals.

$^1$H-NMR (CDCl$_3$) δ: 5.04 (2H, s), 5.91 (2H, s), 6.62-6.80 (3H, m), 7.12-7.48 (13H, m), 7.61 (1H, dd, J=1.8, 8.4 Hz), 8.38 (1H, d, J=8.4 Hz). MS (ESI+): 583 (M+H), 585.

EXAMPLE 236

[2-(benzo[1,3]dioxol-5-ylmethyl)-6-bromo-1-oxo-4-phenyl-1,2-dihydroisoquinolin-3-yl]carbamic acid methyl ester The present compound was synthesized by a method similar to that in Example 235 and using 2-(benzo[1,3]dioxol-5-ylmethyl)-6-bromo-1-oxo-4-phenyl-1,2-dihydroisoquinoline-3-carboxylic acid (220 mg) and methanol. A colorless powder (130 mg).

$^1$H-NMR (CDCl$_3$) δ: 3.60 (3H, s), 5.84 (1H, s), 5.93 (2H, s), 6.70-6.79 (2H, m), 6.83 (1H, d, J=1.2 Hz), 7.18-7.26 (2H, m), 7.30 (1H, d, J=1.8 Hz), 7.39-7.50 (3H, m), 7.62 (1H, dd, J=1.8, 8.7 Hz), 8.39 (1H, d, J=8.7 Hz). HPLC analysis (Agilent 1100 system): purity 94% (retention time: 3.50 min). MS (ESI+): 507 (M+H), 509.

EXAMPLE 237

2-(benzo[1,3]dioxol-5-ylmethyl)-6-bromo-3-hydroxymethyl-4-phenyl-2H-isoquinolin-1-one The present compound was synthesized by a method similar to that in Example 195 and using 2-(benzo[1,3]dioxol-5-ylmethyl)-6-bromo-1-oxo-4-phenyl-1,2-dihydroisoquinoline-3-carboxylic acid (300 mg). Colorless crystals (230 mg).

$^1$H-NMR (CDCl$_3$) δ: 1.65 (1H, d, J=6.0 Hz), 4.33 (2H, d, J=6.0 Hz), 5.59 (2H, s), 5.92 (2H, s), 6.64-6.78 (3H, m), 7.19 (1H, d, J=2.1 Hz), 7.24-7.34 (2H, m), 7.44-7.56 (3H, m), 7.59 (1H, dd, J=1.8, 8.7 Hz), 8.37 (1H, d, J=8.7 Hz). HPLC analysis (Agilent 1100 system): purity 97% (retention time: 3.53 min).

MS (ESI+): 464 (M+H), 466.

EXAMPLE 238

2-(benzo[1,3]dioxol-5-ylmethyl)-6-bromo-1-oxo-4-phenyl-1,2-dihydroisoquinoline-3-carboxylic acid propyl ester The present compound was synthesized by a method similar to that in Example 200 and using 2-(benzo[1,3]dioxol-5-ylmethyl)-6-bromo-1-oxo-4-phenyl-1,2-dihydroisoquinoline-3-carboxylic acid (300 mg) and propanol. Colorless crystals (190 mg).

$^1$H-NMR (CDCl$_3$) δ: 0.56 (3H, t, J=7.5 Hz), 1.01-1.15 (2H, m), 3.62 (2H, t, J=6.6 Hz), 5.33 (2H, s), 5.90 (2H, s), 6.68-677 (2H, m), 6.80 (1H, m), 7.24-7.32 (2H, m), 7.37 (1H, d, J=1.8 Hz), 7.40-7.48 (3H, m), 7.65 (1H, dd, J=1.8, 8.7 Hz), 8.39 (1H, d, J=8.7 Hz). HPLC analysis (Agilent 1100 system): purity 96% (retention time: 4.27 min). MS (ESI+): 520 (M+H), 522.

EXAMPLE 239

2-(benzo[1,3]dioxol-5-ylmethyl)-6-bromo-1-oxo-4-phenyl-1,2-dihydroisoquinoline-3-carboxylic acid furan-2-ylmethyl ester The present compound was synthesized by a method similar to that in Example 200 and using 2-(benzo[1,3]dioxol-5-ylmethyl)-6-bromo-1-oxo-4-phenyl-1,2-dihydroisoquinoline-3-carboxylic acid (300 mg) and furan-2-ylmethanol. A colorless powder (190 mg).

$^1$H-NMR (CDCl$_3$) δ: 4.67 (2H, s), 5.28 (2H, s), 5.91 (2H, s), 6.12 (1H, d, J=3.3 Hz), 6.26 (1H, dd, J=1.8, 3.3 Hz), 6.68 (2H, s), 6.77 (1H, s), 7.20-7.28 (2H, m), 7.29 (1H, m), 7.33 (1H, m), 7.36-7.42 (3H, m), 7.64 (1H, dd, J=1.8, 8.7 Hz), 8.37 (1H, d, J=8.7 Hz). HPLC analysis (Agilent 1100 system): purity 99% (retention time: 4.13 min). MS (ESI+): 558 (M+H), 560.

EXAMPLE 240

2-(benzo[1,3]dioxol-5-ylmethyl)-3-benzyloxymethyl-6-bromo-4-phenyl-2H-isoquinolin-1-one To a solution (2.5 ml) of 2-(benzo[1,3]dioxol-5-ylmethyl)-6-bromo-3-hydroxymethyl-4-phenyl-2H-isoquinolin-1-one (250 mg) in THF was added sodium hydride (26 mg) at 0° C. with stirring. The mixture was stirred at room temperature for 10 min., benzylbromide (71 μl) was added, and the mixture was further stirred for 2 hrs. To the reaction mixture was added water and the mixture was extracted with ethyl acetate. The organic layer was dried over magnesium sulfate and concentrated under reduced pressure. The residue was purified by medium pressure preparative LC (hexane/ethyl acetate=9/1-1/1) to give the title compound (210 mg) as colorless crystals.

$^1$H-NMR (CDCl$_3$) δ: 4.12 (2H, s), 4.35 (2H, s), 5.47 (2H, s), 5.90 (2H, s), 6.64 (1H, dd, J=1.8, 7.8 Hz), 6.57 (1H, d, J=1.8 Hz), 6.67 (1H, d, J=7.8 Hz), 7.19-7.26 (3H, m), 7.28-7.36 (5H, m), 7.43-7.50 (3H, m), 7.60 (1H, dd, J=1.8, 8.7 Hz), 8.38 (1H, d, J=8.7 Hz). HPLC analysis (Agilent 1100 system): purity 97% (retention time: 4.41 min). MS (ESI+): 554 (M+H), 566.

EXAMPLE 241

2-(benzo[1,3]dioxol-5-ylmethyl)-6-bromo-3-butoxymethyl-4-phenyl-2H-isoquinolin-1-one The present compound was synthesized by a method similar to that in Example 240 and using 2-(benzo[1,3]dioxol-5-ylmethyl)-6-bromo-3-hydroxymethyl-4-phenyl-2H-isoquinolin-1-one (250 mg) and n-butylbromide. Colorless crystals (120 mg).

$^1$H-NMR (CDCl$_3$) δ: 0.89 (3H, t, J=7.2 Hz), 1.24-1.54 (4H, m), 3.27 (2H, t, J=6.3 Hz), 4.08 (2H, s), 5.54 (2H, s), 5.92 (2H, s), 6.64-6.78 (3H, m), 7.23-7.34 (3H, m), 7.44-7.54 (3H, m), 7.59 (1H, dd, J=1.8, 8.4 Hz), 8.38 (1H, d, J=8.1 Hz). HPLC analysis (Agilent 1100 system): purity 99% (4.55 min). MS (ESI+): 520 (M+H), 522.

EXAMPLE 242

2-(benzo[1,3]dioxol-5-ylmethyl)-6-bromo-3-methoxymethyl-4-phenyl-2H-isoquinolin-1-one The present compound was synthesized by a method similar to that in Example 240 and using 2-(benzo[1,3]dioxol-5-ylmethyl)-6-bromo-3-hydroxymethyl-4-phenyl-2H-isoquinolin-1-one (250 mg) and methyl iodide. Colorless crystals (190 mg).

$^1$H-NMR (CDCl$_3$) δ: 3.21 (3H, s), 4.06 (2H, s), 5.53 (2H, s), 5.93 (2H, s), 6.65-6.78 (3H, m), 7.24 (1H, d, J=1.8 Hz), 7.26-7.34 (2H, m), 7.44-7.54 (3H, m), 7.60 (1H, dd, J=1.8, 8.7 Hz), 8.39 (1H, d, J=8.7 Hz). HPLC analysis (Agilent 1100 system): purity 98% (retention time: 4.06 min). MS (ESI+): 478 (M+H), 480.

EXAMPLE 243

2-(benzo[1,3]dioxol-5-ylmethyl)-6-bromo-3-(4-methoxybenzyloxymethyl)-4-phenyl-2H-isoquinolin-1-one The present compound was synthesized by a method similar to that in Example 240 and using 2-(benzo[1,3]dioxol-5-ylmethyl)-6-bromo-3-hydroxymethyl-4-phenyl-2H-isoquinolin-1-one (250 mg) and 4-methoxybenzylbromide. Colorless crystals (240 mg).

$^1$H-NMR (CDCl$_3$) δ: 3.82 (3H, s), 4.07 (2H, s), 4.28 (2H, s), 5.44 (2H, s), 5.90 (2H, s), 6.45 (1H, dd, J=1.8, 8.1 Hz), 6.55 (1H, d, J=1.8 Hz), 6.66 (1H, d, J=8.1 Hz), 6.89 (2H, d, J=9.0 Hz), 7.14 (2H, d, J=9.0 Hz), 7.22-7.34 (3H, m), 7.42-7.50 (3H, m), 7.59 (1H, dd, J=1.8, 8.7 Hz), 8.38 (1H, d, J=8.7 Hz). HPLC analysis (Agilent 1100 system): purity 96% (retention time: 4.35 min). MS (ESI+): 584 (M+H), 586.

EXAMPLE 244

2-(benzo[1,3]dioxol-5-ylmethyl)-6-bromo-4-phenyl-3-(pyridin-4-ylmethoxymethyl)-2H-isoquinolin-1-one The present compound was synthesized by a method similar to that in Example 240 and using 2-(benzo[1,3]dioxol-5-ylmethyl)-6-bromo-3-hydroxymethyl-4-phenyl-2H-isoquinolin-1-one (250 mg) and pyridin-4-ylmethanol. Colorless crystals (59 mg).

$^1$H-NMR (CDCl$_3$) δ: 4.21 (2H, s), 4.35 (2H, s), 5.54 (2H, s), 5.92 (2H, s), 6.60 (1H, dd, J=1.5, 7.8 Hz), 6.67 (1H, d, J=1.5 Hz), 6.73 (1H, d, J=7.8 Hz), 7.08 (2H, d, J=6.0 Hz), 7.22-7.32 (3H, m), 7.43-7.50 (3H, m), 7.62 (1H, dd, J=1.8, 8.4 Hz), 8.40 (1H, d, J=8.4 Hz), 8.53 (2H, d, J=6.0 Hz). HPLC analysis (Agilent 1100 system): purity 97% (retention time: 2.78 min). MS (ESI+): 555 (M+H), 557.

EXAMPLE 245

3-amino-2-(benzo[1,3]dioxol-5-ylmethyl)-6-bromo-4-phenyl-2H-isoquinolin-1-one

25% Hydrogen bromide-acetic acid solution (10.0 ml) was added to [2-(benzo[1,3]dioxol-5-ylmethyl)-6-bromo-1-oxo-4-phenyl-1,2-dihydroisoquinolin-3-yl]carbamic acid benzyl ester (3.6 g), and the mixture was stirred at room temperature for 1 hr. The precipitate was collected by filtration, washed with diethyl ether and dried to give the title compound (3.3 g) as a colorless powder.

$^1$H-NMR (DMSO-d$_6$) δ: 5.35 (2H, s), 5.98 (2H, s), 6.70-6.90 (4H, m), 7.20 (1H, dd, J=0.9, 8.7 Hz), 7.29 (2H, d, J=8.1 Hz), 7.46 (1H, m), 7.56 (2H, t, J=7.8 Hz), 8.00 (1H, d, J=8.7 Hz). Anal. Calcd for C$_{23}$H$_{17}$BrN$_2$O$_3$.HBr.0.4H$_2$O: C, 51.40; H, 3.53; N, 5.21. Found: C, 51.60; H, 3.48; N, 5.29.

EXAMPLE 246

3-[2-(benzo[1,3]dioxol-5-ylmethyl)-6-bromo-1-oxo-4-phenyl-1,2-dihydroisoquinolin-3-yl]acrylic acid methyl ester To a mixture of 2-(benzo[1,3]dioxol-5-ylmethyl)-6-bromo-3-hydroxymethyl-4-phenyl-2H-isoquinolin-1-one (780 mg), triethylamine (940 μl), DMSO (3.1 ml) and dichloromethane (3.1 ml) was added a solution of pyridine sulfur trioxide complex (1.1 g) in DMSO (3.1 ml) at 0° C. with stirring, and the mixture was stirred at room temperature for 2 hrs. Triethylamine (940 μl) and pyridine sulfur trioxide complex (1.1 g) were added, and the mixture was further stirred for 2 hrs., washed with water, dried and concentrated under reduced pressure to give aldehyde.

Then, to a solution (7.8 ml) of trimethoxyphosphonoacetate (300 μl) in THF was added sodium hydride (87 mg) at 0° C. with stirring, and the mixture was stirred at room temperature for 10 min. To this solution was added a solution (7.8 ml) of the above-mentioned aldehyde in THF, and the mixture was further stirred for 1 hr. The reaction mixture was diluted with ethyl acetate and washed with 1N hydrochloric acid. The organic layer was dried and concentrated under reduced pressure. The residue was purified by medium pressure preparative LC (hexane/ethyl acetate=9/1-1/1) to give the title compound (760 mg) as colorless crystals. $^1$H-NMR (CDCl$_3$) δ: 3.65 (3H, s), 5.29 (2H, s), 5.55 (1H, d, J=16.2 Hz), 5.94 (2H, s), 6.70-6.82 (3H, m), 7.14-7.24 (2H, m), 7.24-7.48 (5H, m), 7.62 (1H, dd, J=1.5, 8.4 Hz), 8.40 (1H, d, J=8.4 Hz). HPLC analysis: purity 95% (retention time: 4.91 min). MS (ESI+): 518 (M+H), 520.

EXAMPLE 247

3-[(2-(benzo[1,3]dioxol-5-ylmethyl)-6-bromo-1-oxo-4-phenyl-1,2-dihydroisoquinolin-3-yl)acrylic acid To a mixture of 3-[2-(benzo[1,3]dioxol-5-ylmethyl)-6-bromo-1-oxo-4-phenyl-1,2-dihydroisoquinolin-3-yl]acrylic acid methyl ester (100 mg), THF (4.0 ml) and methanol (4.0 ml) was added 1N sodium hydroxide (390 μl), and the mixture was stirred at room temperature for 1 hr. The reaction mixture was adjusted to pH 3 with 1N hydrochloric acid and concentrated under reduced pressure. The residue was partitioned between water and ethyl acetate, and the organic layer was dried over magnesium sulfate and concentrated under reduced pressure. The residue was purified by medium pressure preparative LC (hexane/ethyl acetate=3/1-1/1) to give the title compound (46 mg) as colorless crystals.
$^1$H-NMR (CDCl$_3$) δ: 5.28 (2H, s), 5.53 (1H, d, J=16.2 Hz), 5.94 (2H, s), 6.68-6.80 (3H, m), 7.15-7.21 (2H, m), 7.29 (1H, d, J=1.8 Hz), 7.34-7.50 (4H, m), 7.64 (1H, dd, J=1.8, 8.4 Hz), 8.40 (1H, d, J=8.4 Hz). HPLC analysis (Agilent 1100 system): purity 93% (retention time: 3.53 min). MS (ESI+): 504 (M+H), 506.

EXAMPLE 248

3-[2-(benzo[1,3]dioxol-5-ylmethyl)-1-oxo-4-phenyl-1,2-dihydroisoquinolin-3-yl]propionic acid methyl ester A mixture of 3-[2-(benzo[1,3]dioxol-5-ylmethyl)-6-bromo-1-oxo-4-phenyl-1,2-dihydroisoquinolin-3-yl]acrylic acid methyl ester (100 mg), Raney-nickel (suitable amount), methanol (2.0 ml) and THF (2.0 ml) was stirred at room temperature under a hydrogen atmosphere for 3 hrs. The catalyst was removed by filtration, and the filtrate was concentrated under reduced pressure. The residue was purified by medium pressure preparative LC (hexane/ethyl acetate=9/1-1/1) to give the title compound (55 mg) as a colorless powder.
$^1$H-NMR (CDCl$_3$) δ: 2.28-2.38 (2H, m), 2.78-2.87 (2H, m), 3.60 (3H, s), 5.43 (2H, br), 5.93 (2H, s), 6.68-6.77 (3H, m), 6.93 (1H, dd, J=1.5, 8.1 Hz), 7.20-7.28 (2H, m), 7.40-7.54 (5H, m), 8.51 (1H, m). HPLC analysis (Agilent 1100 system): purity 95% (retention time: 3.56 min). MS (ESI+): 442 (M+H).

EXAMPLE 249

2-(benzo[1,3]dioxol-5-ylmethyl)-6-bromo-1-oxo-4-phenyl-1,2-dihydroisoquinoline-3-carboxylic acid benzylamide 2-(Benzo[1,3]dioxol-5-ylmethyl)-6-bromo-1-oxo-4-phenyl-1,2-dihydroisoquinoline-3-carboxylic acid (200 mg) was dissolved in THF (6.0 ml) and oxalyl chloride (71 μl) and DMF (1 drop) were added at 0° C. with stirring, and the mixture was stirred at room temperature for 2 hrs. and concentrated under reduced pressure. Toluene was added to the residue and they were boiled together several times and dried to give 2-(benzo[1,3]dioxol-5-ylmethyl)-6-bromo-1-oxo-4-phenyl-1,2-dihydroisoquinoline-3-carbonyl chloride.
Then, to a mixture of this product, triethylamine (120 μl) and dichloromethane (2.1 ml) was added benzylamine (69 μl), and the mixture was stirred at room temperature for 2 hrs. The reaction mixture was washed with 5% potassium hydrogensulfate aqueous solution, and the organic layer was dried over magnesium sulfate and concentrated under reduced pressure. The residue was purified by medium pressure preparative LC (hexane/ethyl acetate=4/1-2/1) to give the title compound (150 mg) as colorless crystals.
$^1$H-NMR (CDCl$_3$) δ: 3.96 (2H, d, J=5.4 Hz), 5.20 (1H, d, J=5.4 Hz), 5.46 (2H, br), 5.90 (2H, s), 6.51-6.57 (2H, m), 6.71 (2H, d, J=8.1 Hz), 6.78 (1H, dd, J=1.5, 8.1 Hz), 6.83 (1H, d, J=1.5 Hz), 7.10-7.24 (3H, m), 7.28-7.37 (3H, m), 7.40-7.49 (3H, m), 7.63 (1H, dd, J=2.1, 8.7 Hz), 8.39 (1H, d, J=8.7 Hz). HPLC analysis: purity 100% (retention time: 4.79 min). MS (ESI+): 567 (M+H), 569.

EXAMPLE 250

2-(benzo[1,3]dioxol-5-ylmethyl)-6-bromo-1-oxo-4-phenyl-1,2-dihydroisoquinoline-3-carboxylic acid propylamide The present compound was synthesized by a method similar to that in Example 249 and using 2-(benzo[1,3]dioxol-5-ylmethyl)-6-bromo-1-oxo-4-phenyl-1,2-dihydroisoquinoline-3-carboxylic acid (200 mg) and propylamine. Colorless crystals (150 mg).
$^1$H-NMR (CDCl$_3$) δ: 0.51 (3H, t, J=7.5 Hz), 0.80-0.94 (2H, m), 2.78 (2H, q, J=7.5 Hz), 5.05 (1H, t, J=6.0 Hz), 5.42 (2H, s), 5.90 (2H, s), 6.70 (1H, d, J=7.8 Hz), 6.79 (1H, dd, J=1.8, 7.8 Hz), 6.86 (1H, d, J=1.8 Hz), 7.29-7.36 (2H, m), 7.37 (1H, d, J=1.8 Hz), 7.40-7.50 (3H, m), 7.64 (1H, dd, J=1.8, 8.7 Hz), 8.39 (1H, d, J=8.7 Hz). HPLC analysis: purity 99.59% (retention time: 4.597 min). MS (ESI+): 519.1 (M+H), 521.1.

EXAMPLE 251

2-(benzo[1,3]dioxol-5-ylmethyl)-6-bromo-4-phenyl-3-(piperidine-1-carbonyl)-2H-isoquinolin-1-one The present compound was synthesized by a method similar to that in Example 249 and using 2-(benzo[1,3]dioxol-5-ylmethyl)-6-bromo-1-oxo-4-phenyl-1,2-dihydroisoquinoline-3-carboxylic acid (200 mg) and piperidine. Colorless crystals (150 mg).
$^1$H-NMR (CDCl$_3$) δ: 0.52 (1H, m), 0.68 (1H, m), 0.88 (1H, m), 1.02-1.40 (3H, m), 2.02 (1H, m), 2.65 (1H, m), 2.93 (1H, m), 3.43 (1H, m), 4.82 (1H, d, J=15.3 Hz), 5.90 (1H, d, J=15.3 Hz), 5.91 (2H, s), 6.72 (1H, d, J=7.8 Hz), 6.78 (1H, d, J=7.8 Hz), 6.88 (1H, d, J=1.2 Hz), 7.29 (1H, m), 7.37-7.54 (5H, m), 7.64 (1H, dd, J=1.8, 8.7 Hz), 8.42 (1H, d, J=8.7 Hz). HPLC analysis: purity 100% (retention time: 4.93 min). MS (ESI+): 545 (M+H), 547.

EXAMPLE 252

2-(benzo[1,3]dioxol-5-ylmethyl)-6-bromo-1-oxo-4-phenyl-1,2-dihydroisoquinoline-3-carboxylic acid (2-dimethylaminoethyl)amide trifluoroacetate The present compound was synthesized, purified by preparative HPLC by a method similar to that in Example 249 and using 2-(benzo[1,3]dioxol-5-ylmethyl)-6-bromo-1-oxo-4-phenyl-1,2-dihydroisoquinoline-3-carboxylic acid (200 mg) and N',N'-dimethylethylenediamine and purified by preparative HPLC.
$^1$H-NMR (CDCl$_3$) δ: 2.32-2.44 (2H, m), 2.54 (6H, s), 3.14-3.26 (2H, m), 5.33 (2H, br), 5.89 (2H, s), 6.78-6.86 (2H, m), 6.77 (1H, m), 7.32 (1H, d, J=1.8 Hz), 7.36-7.52 (6H, m), 7.65 (1H, dd, J=1.8, 8.4 Hz), 8.39 (1H, d, J=8.4 Hz). A

EXAMPLE 253

2-(benzo[1,3]dioxol-5-ylmethyl)-6-bromo-1-oxo-4-phenyl-1,2-dihydroisoquinoline-3-carboxylic acid methylamide The present compound was synthesized by a method similar to that in Example 249 and using 2-(benzo[1,3]dioxol-5-ylmethyl)-6-bromo-1-oxo-4-phenyl-1,2-dihydroisoquinoline-3-carboxylic acid (200 mg) and monomethylamine THF solution. Colorless crystals (160 mg).
$^1$H-NMR (CDCl$_3$) δ: 2.35 (3H, d, J=4.8 Hz), 4.98 (1H, m), 5.41 (2H, s), 5.91 (2H, s), 6.69 (1H, d, J=8.1 Hz), 6.78 (1H, dd, J=1.8, 8.1 Hz), 6.84 (1H, d, J=1.8 Hz), 7.28-734 (2H, m), 7.37-7.50 (4H, m), 7.64 (1H, dd, J=2.1, 8.7 Hz), 8.39 (1H, d, J=8.7 Hz). HPLC analysis: purity 100% (retention time: 4.31 min). MS (ESI+): 491 (M+H), 493.

EXAMPLE 254

2-(benzo[1,3]dioxol-5-ylmethyl)-6-bromo-1-oxo-4-phenyl-1,2-dihydroisoquinoline-3-carboxylic acid dimethylamide The present compound was synthesized by a method similar to that in Example 249 and using 2-(benzo[1,3]dioxol-5-ylmethyl)-6-bromo-1-oxo-4-phenyl-1,2-dihydroisoquinoline-3-carboxylic acid (200 mg) and dimethylamine THF solution. Colorless crystals (160 mg).
$^1$H-NMR (CDCl$_3$) δ: 1.95 (3H, s), 2.49 (3H, s), 4.72 (1H, d, J=15.0 Hz), 5.91 (2H, d, J=6.3 Hz), 6.05 (1H, d, J=15.0 Hz), 6.70 (1H, d, J=7.8 Hz), 6.77 (1H, m), 6.90 (1H, d, J=1.8 Hz), 7.25 (1H, m), 7.38-7.49 (5H, m), 7.64 (1H, dd, J=1.8, 8.7 Hz), 8.43 (1H, d, J=8.7 Hz). HPLC analysis: purity 100% (retention time: 4.54 min). MS (ESI+): 505 (M+H), 507.

EXAMPLE 255

2-(benzo[1,3]dioxol-5-ylmethyl)-6-bromo-1-oxo-4-phenyl-1,2-dihydroisoquinoline-3-carboxylic acid cyclohexylamide The present compound was synthesized by a method similar to that in Example 249 and using 2-(benzo[1,3]dioxol-5-ylmethyl)-6-bromo-1-oxo-4-phenyl-1,2-dihydroisoquinoline-3-carboxylic acid (200 mg) and cyclohexylamine. Colorless crystals (130 mg).
$^1$H-NMR (CDCl$_3$) δ: 0.84-1.52 (10H, m), 3.34-3.50 (1H, m), 4.92 (1H, d, J=8.4 Hz), 5.44 (2H, s), 5.90 (2H, s), 6.70 (1H, d, J=7.6 Hz), 6.80 (1H, dd, J=1.8, 7.6 Hz), 6.87 (1H, d, J=1.8 Hz), 7.30-7.37 (3H, m), 7.42-7.51 (3H, m), 7.63 (1H, dd, J=2.1, 8.7 Hz), 8.39 (1H, d, J=8.7 Hz). HPLC analysis: purity 98% (retention time: 3.97 min), 559 (M+H), 561.

EXAMPLE 256

2-(benzo[1,3]dioxol-5-ylmethyl)-6-bromo-4-phenyl-3-(piperazine-1-carbonyl)-2H-isoquinolin-1-one trifluoroacetate The present compound was synthesized by a method similar to that in Example 249 and using 2-(benzo[1,3]dioxol-5-ylmethyl)-6-bromo-1-oxo-4-phenyl-1,2-dihydroisoquinoline-3-carboxylic acid (200 mg) and piperazine and purified by preparative HPLC. Colorless crystals (190 mg).
$^1$H-NMR (CDCl$_3$) δ: 1.68 (1H, m), 2.02-2.50 (5H, m), 2.76-2.82 (2H, m), 3.14 (1H, m), 3.77 (1H, m), 4.63 (1H, d, J=15.0 Hz), 5.90 (1H, d, J=1.2 Hz), 5.99 (1H, d, J=1.2 Hz), 6.13 (1H, d, J=15.0 Hz), 6.65-6.76 (2H, m), 6.78 (1H, m), 7.27 (1H, m), 7.41-7.52 (4H, m), 7.53 (1H, d, J=1.8 Hz), 7.70 (1H, dd, J=1.8, 8.7 Hz), 8.44 (1H, d, J=8.7 Hz). MS (ESI+): 546 (M+H), 548.

EXAMPLE 257

2-(benzo[1,3]dioxol-5-ylmethyl)-6-bromo-1-oxo-4-phenyl-1,2-dihydroisoquinoline-3-carboxylic acid (pyridin-4-ylmethyl)amide trifluoroacetate The present compound was synthesized by a method similar to that in Example 249 and using 2-(benzo[1,3]dioxol-5-ylmethyl)-6-bromo-1-oxo-4-phenyl-1,2-dihydroisoquinoline-3-carboxylic acid (200 mg) and picolylamine and purified by preparative HPLC. Colorless crystals (65 mg)
$^1$H-NMR (CDCl$_3$) δ: 4.10-4.24 (2H, m), 5.41 (2H, br), 5.94 (2H, s), 6.01 (1H, t, J=6.0 Hz), 6.70-6.80 (5H, m), 7.27 (1H, d, J=1.8 Hz), 7.34-7.40 (2H, m), 7.45-7.62 (3H, m), 7.67 (1H, dd, J=1.8, 8.4 Hz), 8.38 (1H, d, J=8.4 Hz), 8.49 (2H, d, J=6.6 Hz). HPLC analysis (Agilent 1100 system): purity 99% (retention time: 2.48 min). MS (ESI+): 568 (M+H), 570.

EXAMPLE 258

6-bromo-2-(4-hydroxybenzyl)-1-oxo-4-phenyl-1,2-dihydroisoquinoline-3-carboxylic acid methyl ester The present compound was synthesized by a method similar to that in Example 226 and using 6-chloro-1-oxo-4-phenyl-1H-isochromen-3-carboxylic acid (1.5 g) and 4-hydroxybenzylamine. A colorless powder (1.2 g).
$^1$H-NMR (CDCl$_3$) δ: 3.25 (3H, s), 5.20 (1H, s), 5.33 (2H, s), 6.72 (2H, d, J=8.7 Hz), 7.16 (2H, d, J=8.7 Hz), 7.25-7.30 (2H, m), 7.37 (1H, d, J=2.1 Hz), 7.40-7.49 (3H, m), 7.65 (1H, dd, J=2.1, 8.7 Hz), 8.39 (1H, d, J=8.7 Hz). HPLC analysis (Agilent 1100 system): purity 96% (retention time: 3.58 min). MS (ESI+): 464 (M+H), 466.

EXAMPLE 259

6-bromo-2-(4-ethoxybenzyl)-1-oxo-4-phenyl-1,2-dihydroisoquinoline-3-carboxylic acid methyl ester To a mixture of 6-bromo-2-(4-hydroxybenzyl)-1-oxo-4-phenyl-1,2-dihydroisoquinoline-3-carboxylic acid methyl ester (200 mg), potassium carbonate (89 mg) and DMF (4.0 ml) was added ethyl iodide (41 μl) at room temperature with stirring, and the mixture was stirred at room temperature for 12 hrs. The reaction mixture was concentrated, and the residue was partitioned between ethyl acetate and water. The organic layer was dried over magnesium sulfate and concentrated. The residue was purified by medium pressure preparative LC (hexane/ethyl acetate=9/1-1/1) to give the title compound (110 mg) as colorless crystals.
$^1$H-NMR (CDCl$_3$) δ: 1.38 (3H, t, J=6.9 Hz), 3.23 (3H, s), 3.98 (2H, q, J=6.9 Hz), 5.35 (2H, s), 6.80 (2H, d, J=8.7 Hz), 7.19 (2H, d, J=8.7 Hz), 7.24-7.30 (2H, m), 3.36 (1H, d, J=1.8 Hz), 7.39-7.48 (3H, m), 7.65 (1H, dd, J=1.8, 8.7 Hz), 8.40 (1H, d, J=8.7 Hz). HPLC analysis: purity 100% (retention time: 5.15 min). MS (ESI+): 492 (M+H), 494.

EXAMPLE 260

6-bromo-2-(4-methoxymethoxybenzyl)-1-oxo-4-phenyl-1,2-dihydroisoquinoline-3-carboxylic acid methyl ester To a mixture of 6-bromo-2-(4-hydroxybenzyl)-1-oxo-4-phenyl-1,2-dihydroisoquinoline-3-carboxylic acid methyl ester (200 mg), potassium carbonate (89 mg) and DMF (4.0 ml) was added methoxymethylchloride (39 μl) at room temperature with stirring, and the mixture was stirred at 50° C. for 12 hrs. After cooling the reaction mixture, the solvent was removed under reduced pressure. The residue was partitioned between ethyl acetate and water, and the organic layer was dried over magnesium sulfate and concentrated. The residue was purified by medium pressure preparative LC (hexane/ethyl acetate=9/1-1/1) to give the title compound (75 mg) as colorless crystals.

$^1$H-NMR (CDCl$_3$) δ: 3.25 (3H, s), 3.44 (3H, s), 5.13 (2H, s), 5.34 (2H, s), 6.95 (2H, d, J=8.7 Hz), 7.21 (2H, d, J=8.7 Hz), 7.24-7.32 (2H, m), 7.37 (1H, d, J=1.8 Hz), 7.40-7.49 (3H, m), 7.65 (1H, dd, J=1.8, 8.4 Hz), 8.39 (1H, d, J=8.4 Hz). HPLC analysis (Agilent 1100 system): purity 96% (retention time: 4.03 min). MS (ESI+): 508 (M+H), 510.

EXAMPLE 261

6-bromo-2-[4-(2-methoxyethoxymethoxy)benzyl]-1-oxo-4-phenyl-1,2-dihydroisoquinoline-3-carboxylic acid methyl ester The present compound was synthesized by a method similar to that in Example 260 and using 6-bromo-2-(4-hydroxybenzyl)-1-oxo-4-phenyl-1,2-dihydroisoquinoline-3-carboxylic acid methyl ester (200 mg) and methoxyethoxymethylchloride. Colorless crystals (28 mg).

$^1$H-NMR (CDCl$_3$) δ: 3.25 (3H, s), 3.35 (3H, s), 3.50-3.55 (2H, m) 3.75-3.81 (2H, m), 5.22 (2H, s), 5.34 (2H, s), 6.96 (2H, d, J=8.7 Hz), 7.20 (2H, d, J=8.7 Hz), 7.24-7.30 (2H, m), 7.37 (1H, d, J=1.8 Hz), 7.39-7.48 (3H, m), 7.65 (1H, dd, J=1.8, 8.7 Hz), 8.39 (1H, d, J=8.7 Hz). HPLC analysis: purity 100% (retention time: 4.90 min). MS (ESI+): 552 (M+H), 554.

EXAMPLE 262

6-bromo-2-(3-bromo-4-hydroxybenzyl)-1-oxo-4-phenyl-1,2-dihydroisoquinoline-3-carboxylic acid methyl ester To a mixture of 6-bromo-2-(4-hydroxybenzyl)-1-oxo-4-phenyl-1,2-dihydroisoquinoline-3-carboxylic acid methyl ester (290 mg), aluminum chloride (82 mg) and dichloromethane (5.7 ml) was added bromine (39 μl) at 0° C. with stirring, and the mixture was stirred for 1 hr. After the completion of the reaction, the reaction mixture was washed with water, dried and concentrated. The residue was purified by medium pressure preparative LC (hexane/ethyl acetate=4/1-1/1) to give the title compound (180 mg) as colorless crystals.

$^1$H-NMR (CDCl$_3$) δ: 3.27 (3H, s), 5.31 (2H, s), 5.49 (1H, s), 6.93 (1H, d, J=8.1 Hz), 7.17 (1H, dd, J=2.1, 8.1 Hz), 7.24-7.31 (2H, m), 7.37 (1H, d, J=2.1 Hz), 7.40-7.48 (4H, m), 7.66 (1H, dd, J=2.1, 8.7 Hz), 8.39 (1H, d, J=8.7 Hz). HPLC analysis: purity 100% (retention time: 4.80 min). MS (ESI+): 542 (M+H), 544, 546.

EXAMPLE 263

6-bromo-2-(3,5-dibromo-4-hydroxybenzyl)-1-oxo-4-phenyl-1,2-dihydroisoquinoline-3-carboxylic acid methyl ester In Example 262, the title compound was obtained as a reaction by-product. Colorless crystals (60 mg).

$^1$H-NMR (CDCl$_3$) δ: 3.31 (3H, s), 5.27 (2H, s), 5.86 (1H, s), 7.24-7.31 (3H, m), 7.38 (1H, d, J=1.8 Hz), 7.41-7.50 (4H, m), 7.68 (1H, dd, J=2.1, 8.7 Hz), 8.39 (1H, dd, J=0.6, 8.7 Hz). HPLC analysis: purity 100% (retention time: 5.06 min). MS (ESI+): 619 (M+H), 621, 623, 625.

EXAMPLE 264

3-amino-2-benzyl-6-bromo-4-phenyl-2-isoquinolin-1-one

To a mixture of 2-benzyl-6-bromo-1-oxo-4-phenyl-1,2-dihydroisoquinoline-3-carboxylic acid (300 mg), triethylamine (98 μl) and toluene (6.0 ml) was added diphenylphosphorylazide (257 μl) at room temperature with stirring, and the mixture was stirred at room temperature for 1 hr. and at 80° C. for 1 hr. After cooling the reaction mixture, benzyl alcohol (86 μl) was added, and the mixture was further stirred at 80° C. for 12 hrs. After cooling the reaction mixture, the solvent was evaporated and the residue was purified by medium pressure preparative LC (hexane/ethyl acetate=9/1-1/1) to give (2-benzyl-6-bromo-1-oxo-4-phenyl-1,2-dihydroisoquinolin-3-yl)carbamic acid benzyl ester as a colorless oil.

Then, to this product was added 25% hydrogen bromide-acetic acid solution (2.0 ml), and the mixture was stirred at room temperature for 1 hr. The reaction mixture was concentrated and the residue was diluted with ethyl acetate, and washed successively with water, saturated aqueous sodium hydrogen carbonate and saturated brine. The organic layer was dried over magnesium sulfate and concentrated under reduced pressure. The residue was purified by medium pressure preparative LC (hexane/ethyl acetate=4/1-1/1) to give the title compound (58 mg) as yellow powder.

$^1$H-NMR (CDCl$_3$) δ: 3.82 (2H, s), 5.52 (2H, s), 7.11 (1H, dd, J=0.3, 1.8 Hz), 7.24-7.55 (11H, m), 8.27 (1H, d, J=8.4 Hz). HPLC analysis: purity 97.66% (retention time: 4.78 min). HPLC analysis (Agilent 1100 system): purity 95% (retention time: 3.83 min). MS (ESI+): 405 (M+H), 407.

EXAMPLE 265

2-benzyl-6-bromo-1-oxo-4-phenyl-1,2-dihydroisoquinoline-3-carboxylic acid pyridin-3-ylmethyl ester The present compound was synthesized by a method similar to that in Example 200 and using 2-benzyl-6-bromo-1-oxo-4-phenyl-1,2-dihydroisoquinoline-3-carboxylic acid (200 mg) and 3-pyridinemethanol. A colorless powder (100 mg).

$^1$H-NMR (CDCl$_3$) δ: 4.50 (2H, s), 5.49 (2H, s), 6.93 (1H, m), 7.09 (1H, m), 7.17-7.40 (11H, m), 7.66 (1H, dd, J=1.8, 8.7 Hz), 7.99 (1H, d, J=1.8 Hz), 8.41 (1H, dd, J=0.6, 8.7 Hz), 8.49 (1H, dd, J=1.8, 4.8 Hz). HPLC analysis: purity 100% (retention time: 3.76 min). MS (ESI+): 525 (M+H), 527.

EXAMPLE 266

2-benzyl-6-bromo-1-oxo-4-phenyl-1,2-dihydroisoquinoline-3-carboxylic acid pyridin-4-ylmethyl ester The present compound was synthesized by a method similar to that in Example 200 and using 2-benzyl-6-bromo-1-oxo-4-phenyl-1,2-dihydroisoquinoline-3-carboxylic acid (200 mg) and 4-pyridinemethanol. A colorless powder (160 mg).
$^1$H-NMR (CDCl$_3$) δ: 4.49 (2H, s), 5.49 (2H, s), 6.52 (2H, d, J=6.0 Hz), 7.16-7.42 (11H, m), 7.68 (1H, dd, J=1.8, 8.4 Hz), 8.39 (2H, d, J=6.0 Hz), 8.43 (1H, d, J=8.4 Hz). HPLC analysis: purity 100% (retention time: 3.74 min). MS (ESI+): 525 (M+H), 527.

EXAMPLE 267

6-bromo-2-(4-methoxycarbonylmethoxybenzyl)-1-oxo-4-phenyl-1,2-dihydroisoquinoline-3-carboxylic acid methyl ester The present compound was synthesized by a method similar to that in Example 259 and using 6-bromo-2-(4-hydroxybenzyl)-1-oxo-4-phenyl-1,2-dihydroisoquinoline-3-carboxylic acid methyl ester (310 mg) and methyl bromoacetate. Colorless crystals (300 mg). $^1$H-NMR (CDCl$_3$) δ: 3.23 (3H, s), 3.78 (3H, s), 4.59 (2H, s), 5.34 (2H, s), 6.82 (2H, d, J=8.7 Hz), 7.22 (2H, d, J=8.7 Hz), 7.24-7.31 (2H, m), 7.37 (1H, d, J=1.8 Hz), 7.40-7.49 (3H, m), 7.65 (1H, dd, J=1.8, 8.7 Hz), 8.39 (1H, d, J=8.7 Hz). HPLC analysis: purity 100% (retention time: 4.80 min). MS (ESI+): 536 (M+H), 538.

EXAMPLE 268

6-bromo-2-(4-carboxymethoxybenzyl)-1-oxo-4-phenyl-1,2-dihydroisoquinoline-3-carboxylic acid methyl ester The present compound was synthesized by a method similar to that in Example 247 and using 6-bromo-2-(4-methoxycarbonylmethoxybenzyl)-1-oxo-4-phenyl-1,2-dihydroisoquinoline-3-carboxylic acid methyl ester (200 mg). Colorless crystals (120 mg).
$^1$H-NMR (CDCl$_3$) δ: 3.24 (3H, s), 4.62 (2H, s), 5.34 (2H, s), 6.84 (2H, d, J=9.0 Hz), 7.22-7.30 (4H, m), 7.37 (1H, dd, J=0.6, 1.8 Hz), 7.40-7.48 (3H, m), 7.65 (1H, dd, J=1.8, 8.7 Hz), 8.39 (1H, dd, J=0.6, 8.7 Hz). HPLC analysis: purity 99% (retention time: 4.45 min). MS (ESI+): 522 (M+H), 524.
Anal. Calcd for C$_{26}$H$_{20}$NO$_6$Br: C, 59.78; H, 3.86; N, 2.68. Found: C, 59.67; H, 3.88; N, 2.58.

EXAMPLE 269

2-benzyl-6-bromo-1-oxo-4-phenyl-1,2-dihydroisoquinoline-3-carboxylic acid benzylamide The present compound was synthesized by a method similar to that in Example 249 and using 2-benzyl-6-bromo-1-oxo-4-phenyl-1,2-dihydroisoquinoline-3-carboxylic acid (250 mg) and benzylamine. Colorless crystals (210 mg).
$^1$H-NMR (CDCl$_3$) δ: 3.89 (2H, d, J=5.4 Hz), 5.09 (1H, d, J=5.4 Hz), 5.57 (2H, s), 6.46 (2H, d, J=6.6 Hz), 7.06-7.18 (3H, m), 7.22-7.37 (8H, m), 7.39-7.48 (3H, m), 7.65 (1H, dd, J=1.8, 8.4 Hz), 8.41 (1H, dd, J=0.3, 8.4 Hz). HPLC analysis: purity 100% (retention time: 4.80 min). MS (ESI+): 523 (M+H), 525.

EXAMPLE 270

2-benzyl-6-bromo-1-oxo-4-phenyl-1,2-dihydroisoquinoline-3-carboxylic acid dimethylamide The present compound was synthesized by a method similar to that in Example 249 and using 2-benzyl-6-bromo-1-oxo-4-phenyl-1,2-dihydroisoquinoline-3-carboxylic acid (250 mg) and dimethylamine THF solution. Colorless crystals (180 mg).
$^1$H-NMR (CDCl$_3$) δ: 1.75 (3H, s), 2.42 (3H, s), 4.78 (1H, d, J=10.0 Hz), 6.22 (1H, d, J=10.0 Hz), 7.28-7.48 (11H, m), 7.65 (1H, dd, J=1.8, 8.4 Hz), 8.45 (1H, dd, J=0.3, 8.4 Hz). HPLC analysis: purity 99% (retention time: 4.61 min). MS (ESI+): 461 (M+H), 463.

EXAMPLE 271

2-benzyl-6-bromo-1-oxo-4-phenyl-1,2-dihydroisoquinoline-3-carboxylic acid(pyridin-4-ylmethyl) amide The present compound was synthesized by a method similar to that in Example 249 and using 2-benzyl-6-bromo-1-oxo-4-phenyl-1,2-dihydroisoquinoline-3-carboxylic acid (250 mg) and 4-picolylamine. Colorless crystals (17 mg).
$^1$H-NMR (CDCl$_3$) δ: 3.89 (2H, d, J=5.7 Hz), 5.27 (1H, t, J=5.7 Hz), 5.56 (2H, s), 6.31 (2H, d, J=6.0 Hz), 7.20-7.38 (8H, m), 740-7.52 (3H, m), 7.67 (1H, dd, J=1.8, 8.7 Hz), 8.29 (2H, d, J=6.0 Hz), 8.43 (1H, dd, J=0.3, 8.7 Hz). HPLC analysis: purity 99% (retention time: 3.39 min). MS (ESI+): 524 (M+H), 526.

EXAMPLE 272

2-benzyl-6-chloro-4-(4-fluorophenyl)-1-oxo-1,2-dihydroisoquinoline-3-carboxylic acid methyl ester A mixture of 2-benzyl-6-chloro-1-oxo-4-trifluoromethanesulfonyloxy-1,2-dihydroisoquinoline-3-carboxylic acid methyl ester (100 mg), sodium carbonate (45 mg), 4-fluorophenylboronic acid (35 mg), tetrakis(triphenylphosphine)palladium(0) (12 mg), toluene (2.0 ml), water (0.4 ml) and ethanol (0.4 ml) in a pear shape flask with dimroth was deaerated in a vacuum line, substituted with argon and stirred at 80° C. for 12 hrs. After cooling, the reaction mixture was partitioned between water and ethyl acetate. The organic layer was dried over magnesium sulfate and concentrated under reduced pressure. The residue was purified by preparative HPLC to give the title compound (52 mg) as a colorless powder.
$^1$H-NMR (CDCl$_3$) δ: 3.24 (3H, s), 5.41 (2H, s), 7.07-7.18 (3H, m), 7.19-7.34 (7H, m), 7.51 (1H, m), 8.49 (1H, m). HPLC analysis: purity 98% (retention time: 4.98 min). MS (ESI+): 422 (M+H), 424.

EXAMPLE 273

2-benzyl-6-chloro-4-(4-chlorophenyl)-1-oxo-1,2-dihydroisoquinoline-3-carboxylic acid methyl ester The present compound was synthesized by a method similar to that in Example 272 and using 2-benzyl-6-chloro-1-oxo-4-trifluoromethanesulfonyloxy-1,2-dihydroisoquinoline-3-carboxylic acid methyl ester (100 mg) and 4-chlorophenylboronic acid. Colorless crystals (55 mg).

¹H-NMR (CDCl₃) δ: 3.25 (3H, s), 5.41 (2H, s), 7.14 (1H, d, J=1.8 Hz), 7.19-7.34 (7H, m), 7.42 (2H, d, J=8.7 Hz), 7.51 (1H, dd, J=2.1, 8.7 Hz), 8.49 (1H, d, J=8.4 Hz). HPLC analysis: purity 96% (retention time: 5.22 min). MS (ESI+): 438 (M+H), 440.

EXAMPLE 274

2-benzyl-6-chloro-1-oxo-4-p-tolyl-1,2-dihydroisoquinoline-3-carboxylic acid methyl ester The present compound was synthesized by a method similar to that in Example 272 and using 2-benzyl-6-chloro-1-oxo-4-trifluoromethanesulfonyloxy-1,2-dihydroisoquinoline-3-carboxylic acid methyl ester (100 mg) and 4-methylphenylboronic acid. Colorless crystals (24 mg).
¹H-NMR (CDCl₃) δ: 2.41 (3H, s), 3.23 (3H, s), 5.40 (2H, s), 7.15 (2H, d, J=8.1 Hz), 7.19-7.33 (8H, m), 7.49 (1H, dd, J=2.1, 8.7 Hz), 8.48 (1H, dd, J=0.3, 8.7 Hz). HPLC analysis: purity 97% (retention time: 5.22 min). MS (ESI+): 418 (M+H), 420.

EXAMPLE 275

2-benzyl-6-chloro-4-(4-methoxyphenyl)-1-oxo-1,2-dihydroisoquinoline-3-carboxylic acid methyl ester The present compound was synthesized by a method similar to that in Example 272 and using 2-benzyl-6-chloro-1-oxo-4-trifluoromethanesulfonyloxy-1,2-dihydroisoquinoline-3-carboxylic acid methyl ester (100 mg) and 4-methoxyphenylboronic acid. beige powder (61 mg).
¹H-NMR (CDCl₃) δ: 3.26 (3H, s), 3.86 (3H, s), 5.42 (2H, s), 6.96 (2H, d, J=9.0 Hz), 7.16-7.34 (8H, m), 7.52 (1H, dd, J=2.1, 8.7 Hz), 8.48 (1H, dd, J=0.3, 8.7 Hz). HPLC analysis: purity 100% (retention time: 4.95 min). MS (ESI+): 434 (M+H), 436.

EXAMPLE 276

2-benzyl-6-chloro-4-(3-chloro-4-fluorophenyl)-1-oxo-1,2-dihydroisoquinoline-3-carboxylic acid methyl ester The present compound was synthesized by a method similar to that in Example 272 and using 2-benzyl-6-chloro-1-oxo-4-trifluoromethanesulfonyloxy-1,2-dihydroisoquinoline-3-carboxylic acid methyl ester (100 mg) and 3-chloro-4-fluorophenylboronic acid. A colorless powder (80 mg).
¹H-NMR (CDCl₃) δ: 3.29 (3H, s), 5.35 (1H, d, J=15.3 Hz), 5.46 (1H, d, J=15.3 Hz), 5.12 (1H, d, J=1.8 Hz), 7.13-7.40 (8H, m), 7.53 (1H, dd, J=1.8, 8.4 Hz), 8.49 (1H, dd, J=0.3, 8.4 Hz). HPLC analysis: purity 100% (retention time: 5.17 min). MS (ESI+): 456 (M+H), 458.

EXAMPLE 277

2-benzyl-6-chloro-4-(2,4-difluorophenyl)-1-oxo-1,2-dihydroisoquinoline-3-carboxylic acid methyl ester The present compound was synthesized by a method similar to that in Example 272 and using 2-benzyl-6-chloro-1-oxo-4-trifluoromethanesulfonyloxy-1,2-dihydroisoquinoline-3-carboxylic acid methyl ester (100 mg) and 2,4-difluorophenylboronic acid. A colorless powder (9 mg).
¹H-NMR (CDCl₃) δ: 3.28 (3H, s), 5.30 (1H, d, J=15.6 Hz), 5.54 (1H, d, J=15.6 Hz), 6.90-7.01 (2H, m), 7.04 (1H, m), 7.17-7.34 (6H, m), 7.52 (1H, dd, J=1.8, 8.4 Hz), 8.48 (1H, dd, J=0.3, 8.4 Hz). HPLC analysis: purity 99% (retention time: 4.88 min). MS (ESI+): 440 (M+H), 442.

EXAMPLE 278

2-benzyl-6-chloro-4-(4-methanesulfonylphenyl)-1-oxo-1,2-dihydroisoquinoline-3-carboxylic acid methyl ester The present compound was synthesized by a method similar to that in Example 272 and using 2-benzyl-6-chloro-1-oxo-4-trifluoromethanesulfonyloxy-1,2-dihydroisoquinoline-3-carboxylic acid methyl ester (100 mg) and 4-(methanesulfonyl)phenylboronic acid. A colorless powder (63 mg).
¹H-NMR (CDCl₃) δ: 3.15 (3H, s), 3.22 (3H, s), 5.43 (2H, s), 7.07 (1H, d, J=2.1 Hz), 7.20-7.34 (5H, m), 7.49-7.58 (3H, m), 8.04 (2H, d, J=8.7 Hz), 8.52 (1H, d, J=8.7 Hz). HPLC analysis: purity 100% (retention time: 4.33 min). MS (ESI+): 482 (M+H), 484.

EXAMPLE 279

2-benzyl-6-chloro-1-oxo-4-(m-tolyl)-1,2-dihydroisoquinoline-3-carboxylic acid methyl ester The present compound was synthesized by a method similar to that in Example 272 and using 2-benzyl-6-chloro-1-oxo-4-trifluoromethanesulfonyloxy-1,2-dihydroisoquinoline-3-carboxylic acid methyl ester (100 mg) and 3-methylphenylboronic acid. A colorless powder (63 mg).
¹H-NMR (CDCl₃) δ: 2.38 (3H, s), 3.22 (3H, s), 5.41 (2H, s), 7.04-7.10 (2H, m), 7.18-7.35 (8H, m), 7.50 (1H, dd, J=2.1, 8.7 Hz), 8.48 (1H, dd, J=0.3, 8.7 Hz). HPLC analysis: purity 100% (retention time: 5.19 min). MS (ESI+): 418 (M+H), 420.

EXAMPLE 280

2-benzyl-6-chloro-4-(4-formylphenyl)-1-oxo-1,2-dihydroisoquinoline-3-carboxylic acid methyl ester The present compound was synthesized by a method similar to that in Example 272 and using 2-benzyl-6-chloro-1-oxo-4-trifluoromethanesulfonyloxy-1,2-dihydroisoquinoline-3-carboxylic acid methyl ester (300 mg) and 4-formylphenylboronic acid. Colorless crystals (170 mg).
¹H-NMR (CDCl₃) δ: 3.20 (3H, s), 5.44 (2H, s), 7.11 (1H, d, J=1.8 Hz), 7.20-7.34 (5H, m), 7.48 (2H, d, J=8.1 Hz), 7.53 (1H, dd, J=2.1, 8.7 Hz), 7.97 (2H, d, J=8.1 Hz), 8.51 (1H, d, J=8.7 Hz), 10.9 (1H, s). HPLC analysis: purity 100% (retention time: 4.66 min). MS (ESI+): 432 (M+H), 434.

EXAMPLE 281

2-benzyl-6-chloro-4-(3-formylphenyl)-1-oxo-1,2-dihydroisoquinoline-3-carboxylic acid methyl ester The present compound was synthesized by a method similar to that in Example 272 and using 2-benzyl-6-chloro-1-oxo-4-trifluoromethanesulfonyloxy-1,2-dihydroisoquinoline-3-carboxylic acid methyl ester (300 mg) and 3-formylphenylboronic acid. Colorless crystals (140 mg).
¹H-NMR (CDCl₃) δ: 3.20 (3H, s), 5.37 (1H, d, J=15.6 Hz), 5.49 (1H, d, J=15.6 Hz), 7.08 (1H, d, J=1.8 Hz), 7.20-7.35 (5H, m), 7.50-7.68 (3H, m), 7.81 (1H, m), 7.97 (1H, dt, J=1.5, 7.5 Hz), 8.51 (1H, d, J=8.7 Hz), 10.06 (1H, s). HPLC analysis: purity 100.0% (retention time: 4.63 min). MS (ESI+): 432 (M+H), 434.

EXAMPLE 282

2-benzyl-4-(4-carboxyphenyl)-6-chloro-1-oxo-1,2-dihydroisoquinoline-3-carboxylic acid methyl ester To a mixture of 2-benzyl-6-chloro-4-(4-formylphenyl)-1-oxo-1,2-dihydroisoquinoline-3-carboxylic acid methyl ester (93 mg), sodium dihydrogenphosphate (26 mg), 2-methyl-2-butene (100 µl), THF (2.0 ml), butanol (1.0 ml) and water (2.0 ml) was added sodium chlorite (73 mg) at 0° C. with stirring, and the mixture was stirred for 1 hr. The solvent was removed and the residue was partitioned between 1N hydrochloric acid and ethyl acetate. The organic layer was dried over magnesium sulfate and concentrated. The residue was purified by preparative HPLC to give the title compound (33 mg) as a colorless powder.

$^1$H-NMR (CDCl$_3$) δ: 3.22 (3H, s), 5.45 (2H, s), 7.13 (1H, m), 7.20-7.34 (5H, m), 7.43 (2H, d, J=8.4 Hz), 7.53 (1H, dd, J=2.1, 8.7 Hz), 8.20 (2H, d, J=8.4 Hz), 8.51 (1H, d, J=8.7 Hz) HPLC analysis (Agilent 1100 system): purity 100% (retention time: 3.39 min). MS (ESI+): 448 (M+H), 450.

EXAMPLE 283

2-benzyl-6-chloro-4-(4-hydroxymethylphenyl)-1-oxo-1,2-dihydroisoquinoline-3-carboxylic acid methyl ester To a mixture of 2-benzyl-6-chloro-4-(4-formylphenyl)-1-oxo-1,2-dihydroisoquinoline-3-carboxylic acid methyl ester (66 mg), methanol (1.0 ml) and THF (1.0 ml) was added sodium borohydride (6 mg) at 0° C. with stirring, and the mixture was stirred for 1 hr. The reaction mixture was concentrated, and the residue was partitioned between 1N hydrochloric acid and ethyl acetate. The organic layer was dried over magnesium sulfate and concentrated. The residue was purified by preparative HPLC to give the title compound (30 mg) as a colorless powder.

$^1$H-NMR (CDCl$_3$) δ: 1.86 (1H, br), 3.23 (3H, s), 4.78 (2H, s), 5.41 (2H, s), 7.19 (1H, dd, J=0.6, 2.1 Hz), 7.20-7.35 (7H, m), 7.44 (2H, dd, J=0.6, 7.8 Hz), 7.50 (1H, dd, J=2.1, 8.7 Hz), 8.49 (1H, dd, J=0.3, 8.7 Hz).

EXAMPLE 284

2-benzyl-4-(3-carboxyphenyl)-6-chloro-1-oxo-1,2-dihydroisoquinoline-3-carboxylic acid methyl ester The present compound was synthesized by a method similar to that in Example 282 and using 2-benzyl-6-chloro-4-(3-formylphenyl)-1-oxo-1,2-dihydroisoquinoline-3-carboxylic acid methyl ester (90 mg). A colorless powder (32 mg).

$^1$H-NMR (CDCl$_3$) δ: 3.22 (3H, s), 5.37 (1H, d, J=15.3 Hz), 5.49 (1H, d, J=15.3 Hz), 7.10 (1H, dd, J=0.6, 1.8 Hz), 7.20-7.36 (5H, m), 7.50-7.62 (3H, m), 8.04 (1H, m), 8.17 (1H, dt, J=1.8, 8.7 Hz), 8.51 (1H, d, J=8.7 Hz). HPLC analysis (Agilent 1100 system): purity 99% (retention time: 3.38 min). MS (ESI+): 448 (M+H), 450.

EXAMPLE 285

2-benzyl-6-chloro-4-(3-hydroxymethylphenyl)-1-oxo-1,2-dihydroisoquinoline-3-carboxylic acid methyl ester The present compound was synthesized by a method similar to that in Example 283 and using 2-benzyl-6-chloro-4-(3-formylphenyl)-1-oxo-1,2-dihydroisoquinoline-3-carboxylic acid methyl ester (100 mg). A colorless powder (35 mg).

$^1$H-NMR (CDCl$_3$) δ: 1.79 (1H, br), 3.22 (3H, s), 4.75 (2H, s), 5.34-5.48 (2H, m), 7.17-7.34 (8H, m), 7.40-7.46 (2H, m), 7.50 (1H, dd, J=2.1, 8.7 Hz), 8.49 (1H, d, J=8.7 Hz).

EXAMPLE 286

2-benzyl-6-bromo-1-oxo-4-phenyl-1,2-dihydroisoquinoline-3-carboxylic acid 2-isobutoxycarbonylpyridin-4-ylmethyl ester The present compound was synthesized by a method similar to that in Example 200 and using 2-benzyl-6-bromo-1-oxo-4-phenyl-1,2-dihydroisoquinoline-3-carboxylic acid (600 mg) and 4-hydroxymethylpyridin-2-carboxylic acid isobutyl ester. A colorless powder (530 mg).

$^1$H-NMR (CDCl$_3$) δ: 1.03 (6H, d, J=6.9 Hz), 2.10-2.22 (1H, m), 4.21 (2H, d, J=6.0 Hz), 4.53 (2H, s), 5.52 (2H, s), 6.64 (1H, dd, J=1.5, 5.1 Hz), 7.17-7.37 (11H, m), 7.57 (1H, m), 7.69 (1H, dd, J=1.8, 8.7 Hz), 8.44 (1H, d, J=8.7 Hz), 8.57 (1H, d, J=5.1 Hz).

EXAMPLE 287

2-benzyl-6-bromo-1-oxo-4-phenyl-1,2-dihydroisoquinoline-3-carboxylic acid 2-carboxypyridin-4-ylmethyl ester hydrochloride The present compound was synthesized by a method similar to that in Example 247 and using 2-benzyl-6-bromo-1-oxo-4-phenyl-1,2-dihydroisoquinoline-3-carboxylic acid 2-isobutoxycarbonylpyridin-4-ylmethyl ester (860 mg). The present compound was purified with reversed-phase polystyrene resin (CHP-20P, Mitsubishi Chemical, eluent: 70-80% aqueous acetonitrile containing 0.01% HCl). A pale-yellow powder (540 mg).

$^1$H-NMR (CDCl$_3$) δ: 4.66 (2H, br), 5.53 (2H, s), 6.86 (1H, br), 7.14-7.50 (11H, m), 7.71 (1H, dd, J=1.8, 8.4 Hz), 7.79 (1H, br), 8.45 (1H, d, J=8.4 Hz), 8.62 (1H, br). Anal. Calcd for C$_{30}$H$_{21}$BrN$_2$O$_5$.HCl.2H$_2$O: C, 56.13; H, 4.08; N, 4.36. Found: C, 56.04; H, 3.87; N, 4.41.

EXAMPLE 288

2-benzyl-6-bromo-1-oxo-4-phenyl-1,2-dihydroisoquinoline-3-carboxylic acid 2-methoxycarbonylpyridin-4-ylmethyl ester To a solution (3.0 ml) of 2-benzyl-6-bromo-1-oxo-4-phenyl-1,2-dihydroisoquinoline-3-carboxylic acid 2-carboxypyridin-4-ylmethyl ester hydrochloride (120 mg) in methanol was added conc. sulfuric acid (0.3 ml) at 0° C. with stirring, and the mixture was stirred at 50° C. for 48 hrs. After cooling the mixture, the solvent was removed under reduced pressure. The residue was partitioned between ethyl acetate and saturated aqueous sodium hydrogen carbonate, and the organic layer was dried over magnesium sulfate and concentrated under reduced pressure. The residue was purified by medium pressure preparative LC (hexane/ethyl acetate=4/1-1/1) to give the title compound (73 mg) as colorless crystals.

$^1$H-NMR (CDCl$_3$) δ: 4.03 (3H, s), 4.50 (2H, s), 5.51 (2H, s), 6.63 (1H, dd, J=1.8, 4.8 Hz), 7.15-7.38 (11H, m), 7.54 (1H, m), 7.69 (1H, dd, J=1.8, 8.7 Hz), 8.43 (1H, d, J=8.7 Hz), 8.51 (1H, dd, J=0.6, 4.8 Hz).

EXAMPLE 289

6-chloro-2-(2-hydroxyethylamino)-1-oxo-4-(p-tolyl)-1,2-dihydroisoquinoline-3-carboxylic acid methyl ester To a solution (5.0 ml) of 6-chloro-1-oxo-4-(p-tolyl)-1H-isochromen-3-carboxylic acid methyl ester and 7-chloro-1-oxo-4-p-tolyl-1H-isochromen-3-carboxylic acid methyl ester (mixture, 250 mg) in methanol was added hydrazine ethanol (540 μl), and the mixture was heated under reflux for 2 hrs. After cooling the reaction mixture, conc. sulfuric acid (0.5 ml) was added to the reaction mixture, and the mixture was stirred at room temperature for 18 hrs. The solvent was removed under reduced pressure and the residue was partitioned between water and ethyl acetate. The organic layer was dried over magnesium sulfate and concentrated under reduced pressure. The residue was purified by medium pressure preparative LC (hexane/ethyl acetate=5/1-2/3) to give the title compound (50 mg) as colorless crystals.

IR (KBr) cm$^{-1}$: 1742, 1661, 1597, 1514, 1435, 1375, 1248, 1231, 1163. $^1$H-NMR (CDCl$_3$) δ: 2.43 (3H, s), 3.25-3.34 (2H, m), 3.50 (1H, t, J=6.6 Hz), 3.63 (3H, s), 3.59-3.68 (2H, m), 5.90 (1H, t, J=6.6 Hz), 7.18-7.31 (5H, m), 7.50 (1H, dd, J=2.4, 9.0 Hz), 8.42 (1H, d, J=9.0 Hz). HPLC analysis: purity 99% (4.04 min). MS (ESI+): 387 (M+H), 389.

EXAMPLE 290

6-chloro-2-(methoxycarbonylmethylamino)-1-oxo-4-(p-tolyl)-1,2-dihydroisoquinoline-3-carboxylic acid methyl ester To a solution (5.0 ml) of 6-chloro-1-oxo-4-(p-tolyl)-1H-isochromen-3-carboxylic acid methyl ester and 7-chloro-1-oxo-4-p-tolyl-1H-isochromen-3-carboxylic acid methyl ester (mixture, 270 mg) in methanol were added hydrazinoacetic acid ethyl ester hydrochloride (1.3 g) and sodium methoxide (0.44 g), and the mixture was heated under reflux for 2 hrs. After cooling the reaction mixture, conc. sulfuric acid (0.5 ml) was added to the reaction mixture, and the mixture was stirred at room temperature for 18 hrs. The solvent was removed under reduced pressure and the residue was partitioned between water and ethyl acetate. The organic layer was dried over magnesium sulfate and concentrated. The residue was purified by medium pressure preparative LC (hexane/ethyl acetate=8/1-3/2) to give the title compound (85 mg) as colorless crystals. IR (KBr) cm$^{-1}$: 1748, 1667, 1597, 1514, 1435, 1375, 1229. $^1$H-NMR (CDCl$_3$) δ: 2.43 (3H, s), 3.62 (3H, s), 3.79 (3H, s), 3.96 (2H, d, J=6.2 Hz), 5.99 (1H, t, J=6.4 Hz), 7.14-7.38 (5H, m), 7.48 (1H, dd, J=2.0, 8.4 Hz), 8.40 (1H, d, J=8.4 Hz). HPLC analysis: purity 97% (4.44 min). MS (APCI+): 415 (M+H), 417.

EXAMPLE 291

6-chloro-2-cyclohexylamino-1-oxo-4-(p-tolyl)-1,2-dihydroisoquinoline-3-carboxylic acid methyl ester A mixture of 6-chloro-1-oxo-4-(p-tolyl)-1H-isochromen-3-carboxylic acid (300 mg), cyclohexylhydrazine hydrochloride (360 mg), sodium methoxide (130 mg) and 1,3-dimethyl-2-imidazolidinone (4.0 ml) was stirred at 100° C. for 12 hrs. The reaction mixture was cooled and partitioned between 1N hydrochloric acid and ethyl acetate. The organic layer was dried over magnesium sulfate and concentrated under reduced pressure.

Then, to a mixture of this product, potassium carbonate (160 mg) and DMF (3.0 ml) was added methyl iodide (65 μl) at room temperature with stirring, and the mixture was stirred for 1 hr. The reaction mixture was concentrated under reduced pressure and the residue was partitioned between ethyl acetate and 1N hydrochloric acid. The organic layer was dried over magnesium sulfate and concentrated under reduced pressure. The residue was purified by medium pressure preparative LC (hexane/ethyl acetate=9/1-2/1) to give the title compound (33 mg) as colorless crystals.

IR (KBr) cm$^{-1}$: 2932, 2855, 1746, 1667, 1599, 1433, 1381, 1246, 1225. $^1$H-NMR (CDCl$_3$) δ: 1.04-1.34 (5H, m), 1.52-1.66 (1H, m), 1.68-1.88 (4H, m), 2.42 (3H, s), 3.28 (1H, m), 3.61 (3H, s), 5.48 (1H, d, J=4.2 Hz), 7.14-7.30 (5H, m), 7.47 (1H, dd, J=2.1, 8.4 Hz), 8.40 (1H, d, J=8.4 Hz). HPLC analysis: purity 97% (5.22 min). MS (APCI+): 425 (M+H), 427.

EXAMPLE 292

6-chloro-1-oxo-2-(pyridin-2-ylamino)-4-(p-tolyl)-1,2-dihydroisoquinoline-3-carboxylic acid methyl ester A mixture of 6-chloro-1-oxo-4-(p-tolyl)-1H-isochromen-3-carboxylic acid (300 mg), 2-pyridylhydrazine (260 mg) and 1,3-dimethyl-2-imidazolidinone (3.0 ml) was stirred at 100° C. for 12 hrs. The reaction mixture was cooled and partitioned between 1N hydrochloric acid and ethyl acetate. The organic layer was dried over magnesium sulfate and concentrated under reduced pressure.

Then, to a mixture of this product, potassium carbonate (160 mg) and DMF (3.0 ml) was added methyl iodide (65 μl) at room temperature with stirring, and the mixture was stirred for 1 hr. The reaction mixture was concentrated under reduced pressure and the residue was partitioned between ethyl acetate and 1N hydrochloric acid. The organic layer was dried over magnesium sulfate and concentrated under reduced pressure. The residue was purified by medium pressure preparative LC (hexane/ethyl acetate=9/1-2/1) to give the title compound (58 g) as colorless crystals.

IR (KBr) cm$^{-1}$: 1744, 1674, 1597, 1435, 1373, 1279, 1231, 1165, 959, 910, 777, 733. $^1$H-NMR (CDCl$_3$) δ: 2.44 (3H, s), 3.53 (3H, s), 6.68 (1H, d, J=8.4 Hz), 6.93 (1H, m), 7.20-7.40 (5H, m), 7.48 (1H, dd, J=2.1, 8.7 Hz), 7.58 (1H, m), 8.26 (1H, m), 8.37 (1H, d, J=8.4 Hz). HPLC analysis: purity 97% (3.64 min). MS (APCI+): 420 (M+H), 421.

EXAMPLE 293

2-(4-tert-butoxycarbonylbenzyl)-1-oxo-4-phenyl-1,2-dihydroisoquinoline-3,6-dicarboxylic acid dimethyl ester A mixture of 6-bromo-2-(4-tert-butoxycarbonylbenzyl)-1-oxo-4-phenyl-1,2-dihydroisoquinoline-3-carboxylic acid methyl ester (2.54 g), palladium(II) acetate (52 mg), 1,1'-bis(diphenylphosphino)ferrocene (125 mg), triethylamine (1.6 ml), DMF (13 ml) and methanol (13 ml) was stirred at 60° C. for 72 hrs. under 1 atm carbon monoxide. The reaction mixture was concentrated and water was added to the residue. The mixture was extracted with ethyl acetate. The organic layer was washed with water and saturated brine, dried over anhydrous sodium sulfate, and concentrated under reduced pressure. The obtained residue was purified by silica gel column chromatography (hexane-hexane:ethyl acetate=2:1) and recrystallized (ethyl acetate-hexane) to give the title compound (1.82 g).

$^1$H-NMR (CDCl$_3$) δ: 1.56 (9H, s), 3.22 (3H, s), 3.89 (3H, s), 5.47 (2H, s), 7.22-7.56 (7H, m), 7.86-8.00 (3H, m), 8.17 (1H, dd, J=1.4, 8.4 Hz), 8.61 (1H, d, J=8.4 Hz).

EXAMPLE 294

2-(4-carboxybenzyl)-1-oxo-4-phenyl-1,2-dihydroisoquinoline-3,6-dicarboxylic acid dimethyl ester To a 4N-hydrochloric acid ethyl acetate solution (4 ml) was added 2-(4-tert-butoxycarbonylbenzyl)-1-oxo-4-phenyl-1,2-dihydroisoquinoline-3,6-dicarboxylic acid dimethyl ester (200 mg), and the mixture was stirred at room temperature for 2 hrs. The reaction mixture was concentrated and crystals were washed with a mixture of ethyl acetate and hexane to give the title compound (160 mg).

$^1$H-NMR (CDCl$_3$) δ: 3.22 (3H, s), 3.89 (3H, s), 5.49 (2H, s), 7.22-7.54 (7H, m), 7.97 (1H, d, J=1.8 Hz), 8.03 (2H, d, J=8.0 Hz), 8.17 (1H, dd, J=1.8, 8.4 Hz), 8.62 (1H, d, J=8.4 Hz).

EXAMPLE 295

2-(4-tert-butoxycarbonylbenzyl)-1-oxo-4-phenyl-1,2-dihydroisoquinoline-3,6-dicarboxylic acid 3-methyl ester To a solution of 2-(4-tert-butoxycarbonylbenzyl)-1-oxo-4-phenyl-1,2-dihydroisoquinoline-3,6-dicarboxylic acid dimethyl ester (1.63 g) in THF (16 ml) were added methanol (16 ml) and 8N-aqueous sodium hydroxide solution (0.8 ml) at room temperature, and the mixture was stirred for 18 hrs. The reaction mixture was concentrated under reduced pressure and water and 1N-hydrochloric acid (7 ml) were added to the residue. The aqueous layer was acidified and extracted with ethyl acetate. The organic layer was washed with water and saturated brine, dried over anhydrous sodium sulfate, and concentrated under reduced pressure. Methylene chloride was added to the residue and insoluble material was removed from the mixture. The filtrate was concentrated and recrystallized (ethyl acetate-hexane) to give the title compound (1.16 g).

$^1$H-NMR (CDCl$_3$) δ: 1.56 (9H, s), 3.22 (3H, s), 5.48 (2H, s), 7.22-7.56 (7H, m), 7.92 (2H, d, J=8.4 Hz), 7.96-8.08 (1H, m), 8.20 (1H, dd, J=1.6, 8.4 Hz), 8.64 (1H, d, J=8.4 Hz).

EXAMPLE 296

2-(4-tert-butoxycarbonylbenzyl)-6-carbamoyl-1-oxo-4-phenyl-1,2-dihydroisoquinoline-3-carboxylic acid methyl ester To a solution of 2-(4-tert-butoxycarbonylbenzyl)-1-oxo-4-phenyl-1,2-dihydroisoquinoline-3,6-dicarboxylic acid 3-methyl ester (300 mg) in THF (6 ml) were added ammonium chloride (100 mg), 1-ethyl-3-(3-dimethylaminopropyl)carbodiimide hydrochloride (230 mg), 1-hydroxy-1H-benzotriazole monohydrate (180 mg) and triethylamine (1 ml) at room temperature. The reaction mixture was stirred at 40° C. for 12 hrs. Water and 1N-hydrochloric acid were added to acidify the aqueous layer and the mixture was extracted with ethyl acetate. The organic layer was washed with water, saturated aqueous sodium hydrogen carbonate solution, water and saturated brine, and dried over anhydrous sodium sulfate. The solvent was evaporated under reduced pressure, and the obtained crystals were washed with methanol to give the title compound (240 mg).

$^1$H-NMR (CDCl$_3$) δ: 1.56 (9H, s), 3.22 (3H, s), 5.40-6.20 (2H, m), 5.47 (2H, s), 7.22-7.54 (7H, m), 7.66-7.76 (1H, m), 7.86-8.00 (3H, m), 8.63 (1H, d, J=8.4 Hz).

EXAMPLE 297

6-carbamoyl-2-(4-carboxybenzyl)-1-oxo-4-phenyl-1,2-dihydroisoquinoline-3-carboxylic acid methyl ester To a 4N-hydrochloric acid dioxane solution (5 ml) was added 2-(4-tert-butoxycarbonylbenzyl)-6-carbamoyl-1-oxo-4-phenyl-1,2-dihydroisoquinoline-3-carboxylic acid methyl ester (140 mg), and the mixture was stirred at room temperature for 2 hrs. The reaction mixture was concentrated under reduced pressure, and the obtained crystals were washed with methanol to give the title compound (86 mg).

$^1$H-NMR (DMSO-d$_6$) δ: 3.27 (3H, s), 5.34 (2H, s), 7.24-7.42 (4H, m), 7.44-7.66 (3H, m), 7.59 (1H, s), 7.72 (1H, s), 7.89 (2H, d, J=8.0 Hz), 8.00-8.14 (1H, m), 8.19 (1H, s), 8.43 (1H, d, J=8.4 Hz).

EXAMPLE 298

2-(4-tert-butoxycarbonylbenzyl)-6-dimethylcarbamoyl-1-oxo-4-phenyl-1,2-dihydroisoquinoline-3-carboxylic acid methyl ester To a solution of 2-(4-tert-butoxycarbonylbenzyl)-1-oxo-4-phenyl-1,2-dihydroisoquinoline-3,6-dicarboxylic acid 3-methyl ester (300 mg) in THF (6 ml) were added methyl ammonium chloride (150 mg), 1-ethyl-3-(3-dimethylaminopropyl)carbodiimide hydrochloride (230 mg), 1-hydroxy-1H-benzotriazole monohydrate (180 mg) and triethylamine (1 ml) at room temperature. The reaction mixture was stirred at 40° C. for 12 hrs. Water and 1N-hydrochloric acid were added to acidify the aqueous layer and the mixture was extracted with ethyl acetate. The organic layer was washed with water, saturated aqueous sodium hydrogen carbonate solution, water and saturated brine, and dried over anhydrous sodium sulfate. The solvent was evaporated under reduced pressure, and the obtained residue was crystallized from methanol to give the title compound (160 mg).

$^1$H-NMR (CDCl$_3$) δ: 1.56 (9H, s), 2.87 (3H, s), 3.07 (3H, s)., 3.21 (3H, s), 5.47 (2H, s), 7.20-7.50 (8H, m), 7.56 (1H, dd, J=1.5, 8.2 Hz), 7.92 (2H, d, J=8.4 Hz), 8.58 (1H, d, J=8.2 Hz).

EXAMPLE 299

2-(4-carboxybenzyl)-6-dimethylcarbamoyl-1-oxo-4-phenyl-1,2-dihydroisoquinoline-3-carboxylic acid methyl ester To a 4N-hydrochloric acid ethyl acetate solution (4 ml) was added 2-(4-tert-butoxycarbonylbenzyl)-6-dimethylcarbamoyl-1-oxo-4-phenyl-1,2-dihydroisoquinoline-3-carboxylic acid methyl ester (140 mg), and the mixture was stirred at room temperature for 4 hrs. The reaction mixture was concentrated under reduced pressure, and the obtained residue was crystallized from methanol-diisopropyl ether to give the title compound (86 mg).

$^1$H-NMR (CDCl$_3$) δ: 2.87 (3H, s), 3.07 (3H, s), 3.21 (3H, s), 5.48 (2H, s), 7.20-7.54 (8H, m), 7.57 (1H, dd, J=1.4, 8.2 Hz), 8.02 (2H, d, J=8.0 Hz), 8.59 (1H, d, J=8.2 Hz).

EXAMPLE 300

2-(4-tert-butoxycarbonylbenzyl)-6-[4-(5-methyl-3-phenylisoxazol-4-yl)pyrimidin-2-ylamino]-1-oxo-4-phenyl-1,2-dihydroisoquinoline-3-carboxylic acid methyl ester To toluene (6 ml) were added palladium(II) acetate (4.1 mg) and rac-2,2'-bis(diphenylphosphino)-1,1'-binaphthyl (34 mg) at room temperature and the mixture was stirred for 5 min. under a nitrogen stream. To the reaction mixture were added 6-bromo-2-(4-tert-butoxycarbonylbenzyl)-1-oxo-4-phenyl-1,2-dihydroisoquinoline-3-carboxylic acid methyl ester (300 mg) and 4-(5-methyl-3-phenylisoxazol-4-yl)pyrimidin-2-ylamine (200 mg) at room temperature and the mixture was stirred for 10 min. under a nitrogen stream. Further, sodium tert-butoxide (70 mg) was added to the reaction mixture at room temperature, and the mixture was heated under reflux under a nitrogen atmosphere for 12 hrs. Water was added to the reaction mixture and the mixture was extracted with ethyl acetate. The organic layer was washed with water, saturated brine and dried over anhydrous sodium sulfate. The solvent was evaporated under reduced pressure and the obtained residue was purified by silica gel column chromatography (hexane-hexane:ethyl acetate=1:1), followed by recrystallization (ethyl acetate-hexane) to give the title compound (240 mg).

$^1$H-NMR (CDCl$_3$) δ: 1.56 (9H, s), 2.48 (3H, s), 3.20 (3H, s), 5.46 (2H, s), 6.40 (1H, d, J=5.1 Hz), 7.20-7.56 (12H, m), 7.62-7.76 (2H, m), 7.91 (2H, d, J=8.0 Hz), 8.22 (1H, d, J=5.1 Hz), 8.45 (1H, d, J=9.4 Hz).

EXAMPLE 301

6-bromo-2-{4-[4-(5-methyl-3-phenylisoxazol-4-yl)pyrimidin-2-ylcarbamoyl]benzyl}-1-oxo-4-phenyl-1,2-dihydroisoquinoline-3-carboxylic acid methyl ester To a solution of 6-bromo-2-(4-tert-butoxycarbonylbenzyl)-1-oxo-4-phenyl-1,2-dihydroisoquinoline-3-carboxylic acid methyl ester (300 mg) in THF (6 ml) was added DMF (0.03 ml), and then added dropwise oxalyl chloride (0.11 ml) at room temperature, and the mixture was stirred for 30 min. The reaction mixture was concentrated under reduced pressure and the obtained residue was added to a solution of 4-(5-methyl-3-phenylisoxazol-4-yl)pyrimidin-2-ylamine (200 mg) in pyridine (6 ml) at room temperature. The mixture was stirred for 6 hrs. and then at 40° C. for 2 hrs., at 60° C. for 2 hrs. and at 80° C. for 2 hrs., and concentrated under reduced pressure. Saturated aqueous sodium hydrogen carbonate solution was added to the residue, and the mixture was extracted with ethyl acetate. The organic layer was washed with water and saturated brine, and dried over anhydrous sodium sulfate. The solvent was evaporated under reduced pressure, and the obtained residue was purified by silica gel column chromatography (ethyl acetate) and basic silica gel column chromatography (ethyl acetate) and recrystallized (ethyl acetate-hexane) to give the title compound (95 mg).

$^1$H-NMR (CDCl$_3$) δ: 2.90 (3H, s), 3.25 (3H, s), 5.45 (2H, s), 6.63 (1H, d, J=5.1 Hz), 7.20-7.60 (13H, m), 7.68 (1H, dd, J=1.8, 8.8 Hz), 7.88 (2H, d, J=8.0 Hz), 8.40 (1H, d, J=8.8 Hz), 8.41 (1H, d, J=5.1 Hz), 8.55 (1H, s).

EXAMPLE 302

2-(4-carboxybenzyl)-6-[4-(5-methyl-3-phenylisoxazol-4-yl)pyrimidin-2-ylamino]-1-oxo-4-phenyl-1,2-dihydroisoquinoline-3-carboxylic acid methyl ester hydrochloride To 4N-hydrochloric acid ethyl acetate solution (4 ml) was added 2-(4-tert-butoxycarbonylbenzyl)-6-dimethylcarbamoyl-1-oxo-4-phenyl-1,2-dihydroisoquinoline-3-carboxylic acid methyl ester (170 mg), and the mixture was stirred at room temperature for 4 hrs. The reaction mixture was concentrated under reduced pressure, and the obtained crystals were washed with methanol-diisopropyl ether to give the title compound (150 mg).

$^1$H-NMR (DMSO-d$_6$) δ: 2.48 (3H, s), 3.26 (3H, s), 5.30 (2H, s), 6.56 (1H, d, J=5.1 Hz), 7.14-7.62 (11H, m), 7.64-8.00 (4H, m), 8.17 (2H, d, J=8.8 Hz), 8.38 (1H, d, J=5.1 Hz), 10.23 (1H, s).

EXAMPLE 303

6-benzylamino-2-(4-tert-butoxycarbonylbenzyl)-1-oxo-4-phenyl-1,2-dihydroisoquinoline-3-carboxylic acid methyl ester To toluene (40 ml) were added palladium(II) acetate (27 mg) and rac-2,2'-bis(diphenylphosphino)-1,1'-binaphthyl (240 mg) at room temperature, and the mixture was stirred for 5 min. under a nitrogen stream. To the reaction mixture were added 6-bromo-2-(4-tert-butoxycarbonylbenzyl)-1-oxo-4-phenyl-1,2-dihydroisoquinoline-3-carboxylic acid methyl ester (2.0 g) and benzylamine (0.6 ml) at room temperature and the mixture was stirred for 10 min. under a nitrogen stream. Further, to the reaction mixture was added sodium tert-butoxide (480 mg) at room temperature and the mixture was heated under reflux under a nitrogen atmosphere for 12 hr. Water was added to the reaction mixture, and the mixture was extracted with ethyl acetate. The organic layer was washed with water and saturated brine, and dried over anhydrous sodium sulfate. The solvent was evaporated under reduced pressure and the obtained residue was purified by silica gel column chromatography (hexane-hexane:ethyl acetate=1:1) to give the title compound (1.8 g).

$^1$H-NMR (CDCl$_3$) δ: 1.56 (9H, s), 3.16 (3H, s), 4.23 (2H, br. s), 4.61 (1H, br. s), 5.40 (2H, s), 6.19 (1H, d, J=2.3 Hz), 6.83 (1H, dd, J=2.3, 8.7 Hz), 7.12-7.42 (12H, m), 7.88 (2H, d, J=8.0 Hz), 8.32 (1H, d, J=8.7 Hz).

EXAMPLE 304

6-benzylamino-2-(4-carboxybenzyl)-1-oxo-4-phenyl-1,2-dihydroisoquinoline-3-carboxylic acid methyl ester hydrochloride To 4N-hydrochloric acid ethyl acetate solution (6 ml) was added 6-benzylamino-2-(4-tert-butoxycarbonylbenzyl)-1-oxo-4-phenyl-1,2-dihydroisoquinoline-3-carboxylic acid methyl ester (300 mg), and the mixture was stirred at room temperature for 6 hrs. Crystals were collected by filtration to give the title compound (260 mg).

$^1$H-NMR (CDCl$_3$) δ: 3.21 (3H, s), 4.15 (2H, s), 5.23 (2H, s), 6.11 (1H, d, J=2.2 Hz), 6.91 (1H, dd, J=2.2, 8.8 Hz), 6.98-7.60 (12H, m), 7.87 (2H, d, J=8.0 Hz), 8.04 (1H, d, J=8.8 Hz).

EXAMPLE 305

6-chloro-2-(4-methanesulfonylbenzyl)-1-oxo-4-phenyl-1,2-dihydroisoquinoline-3-carboxylic acid methyl ester A mixture of 6-chloro-1-oxo-4-phenyl-1H-isocoumarin-3-carboxylic acid methyl ester (200 mg), 4-methanesulfonyl-benzylamine (240 mg) and methanol (4 ml) was heated under reflux for 12 hr. Conc. sulfuric acid (0.4 ml) was added to the reaction mixture under ice-cooling and the mixture was heated under reflux for 2 hrs. The reaction mixture was concentrated under reduced pressure, and water was added. The mixture was extracted with ethyl acetate and the organic layer was washed with water, saturated aqueous sodium hydrogen carbonate solution, water and saturated brine, dried over anhydrous sodium sulfate, and concentrated under reduced pressure. The residue was purified by recrystallization (ethyl acetate-hexane) to give title compound (200 mg).

$^1$H-NMR (CDCl$_3$) δ: 3.02 (3H, s), 3.26 (3H, s), 5.42 (2H, s), 7.18-7.62 (9H, m), 7.89 (2H, d, J=8.4 Hz), 8.46 (1H, d, J=8.4 Hz).

EXAMPLE 306

6-fluoro-2-(4-methanesulfonylbenzyl)-1-oxo-4-phenyl-1,2-dihydroisoquinoline-3-carboxylic acid methyl ester In the same manner as in Example 305, the title compound was synthesized using 6-fluoro-1-oxo-4-phenyl-1H-isocoumarin-3-carboxylic acid methyl ester.

Crystals (ethyl acetate-hexane).

$^1$H-NMR (CDCl$_3$) δ: 3.02 (3H, s), 3.27 (3H, s), 5.42 (2H, s), 6.91 (1H, dd, J=2.6, 9.8 Hz), 7.20-7.58 (8H, m), 7.89 (2H, d, J=8.4 Hz), 8.54 (1H, dd, J=6.0, 8.8 Hz).

EXAMPLE 307

2-benzyl-6-bromo-1-oxo-4-phenyl-1,2-dihydroisoquinoline-3-carbaldehyde

Under a nitrogen stream, to a solution of oxalyl chloride (0.54 ml) in THF (28 ml) was added dropwise a solution of DMSO (0.58 ml) in THF (5 ml) at −70° C. or below and the mixture was stirred for 10 min. A solution of 2-benzyl-6-bromo-3-hydroxymethyl-4-phenyl-2H-isoquinolin-1-one (1.30 g) in THF (7 ml) was added dropwise at −70° C. or below and the mixture was stirred at −60° C. to −50° C. for 1 hr. To the reaction mixture was added dropwise triethylamine (3.1 ml) at 50° C. or below and the mixture was allowed to warm to room temperature and stirred for 30 min. To the reaction mixture was added water and the mixture was extracted with ethyl acetate. The organic layer was washed with water and saturated brine, and dried over anhydrous sodium sulfate. The solvent was evaporated under reduced pressure and the obtained residue was crystallized from ethyl acetate-hexane to give the title compound (810 mg).

$^1$H-NMR (CDCl$_3$) δ: 5.90 (2H, s), 7.10-7.70 (11H, m), 7.77 (1H, dd, J=1.8, 8.4 Hz), 8.46 (1H, d, J=8.4 Hz), 9.40 (1H, s).

EXAMPLE 308

2-benzyl-6-bromo-3-(1-hydroxyethyl)-4-phenyl-2H-isoquinolin-1-one

To a solution of 2-benzyl-6-bromo-1-oxo-4-phenyl-1,2-dihydroisoquinoline-3-carbaldehyde (500 mg) in THF (5 ml) was added dropwise a solution of methyl magnesium bromide in THF (3M, 0.5 ml) at room temperature, and the mixture was stirred for 10 min. To the reaction mixture was added water and the mixture was extracted with ethyl acetate. The organic layer was washed with water and saturated brine, and dried over anhydrous sodium sulfate. The solvent was evaporated under reduced pressure and the obtained residue was crystallized from ethyl acetate-hexane to give the title compound (470 mg).

$^1$H-NMR (CDCl$_3$) δ: 1.35 (3H, d, J=6.8 Hz), 2.07 (1H, d, J=4.0 Hz), 4.92-5.12 (1H, m), 5.71 (1H, d, J=16.1 Hz), 5.85 (1H, d, J=16.1 Hz), 6.96-7.62 (12H, m), 8.28 (1H, d, J=8.4 Hz).

EXAMPLE 309

3-acetyl-2-benzyl-6-bromo-4-phenyl-2H-isoquinolin-1-one

To a solution of 2-benzyl-6-bromo-3-(1-hydroxyethyl)-4-phenyl-2H-isoquinolin-1-one (250 mg) in THF (5 ml) was added manganese(IV) oxide (500 mg), and the mixture was heated under reflux for 1 hr. To the reaction mixture was add manganese(IV) oxide (500 mg) and the mixture was heated under reflux for 1 hr, manganese(IV) oxide (500 mg) was added and the mixture was heated under reflux for 1 hr, and manganese(IV) oxide (500 mg) was added and the mixture was heated under reflux for 12 hrs. The reaction mixture was filtered and the filtrate was concentrated. The obtained residue was purified by silica gel column chromatography (hexane-hexane:ethyl acetate=8:1) and recrystallized (ethyl acetate-hexane) to give the title compound (150 mg).

$^1$H-NMR (CDCl$_3$) δ: 1.19 (3H, s), 5.46 (2H, s), 7.00-7.60 (11H, m), 7.67 (1H, dd, J=2.0, 8.6 Hz), 8.44 (1H, d, J=8.6 Hz).

EXAMPLE 310

6-bromo-3-hydroxymethyl-2-(4-methanesulfonylbenzyl)-4-phenyl-2H-isoquinolin-1-one DMF (0.1 ml) was added to a suspension of 6-bromo-2-(4-methanesulfonylbenzyl)-1-oxo-4-phenyl-1,2-dihydroisoquinoline-3-carboxylic acid (5.5 g) in THF (55 ml), and oxalyl chloride (1.9 ml) was added dropwise under ice-cooling. The reaction mixture was allowed to warm to room temperature, stirred for 30 min., and concentrated under reduced pressure. The residue was suspended in a mixture of THF (90 ml) and 1,2-dimethoxyethane (90 ml), and under ice-cooling sodium borohydride (1.62 g) and methanol (3 ml) were added. The mixture was allowed to warm to room temperature and stirred for 1 hr. The reaction mixture was poured into water under ice-cooling. 10% Hydrochloric acid was added to acidify the aqueous layer, and THF and methanol were evaporated under reduced pressure. The residue was extracted with ethyl acetate and the organic layer was washed with water, saturated aqueous sodium hydrogen carbonate solution, water and saturated brine, and dried over anhydrous sodium sulfate. The solvent was evaporated under reduced pressure and the obtained residue was crystallized from diisopropyl ether to give the title compound (5.3 g).

$^1$H-NMR (CDCl$_3$) δ: 3.02 (3H, s), 4.27 (2H, s), 5.75 (2H, s), 7.20-7.60 (8H, m), 7.62 (1H, dd, J=1.8, 8.8 Hz), 7.89 (2H, d, J=8.6 Hz), 8.35 (1H, d, J=8.8 Hz). 1H unconfirmed.

EXAMPLE 311

6-bromo-2-(4-methanesulfonylbenzyl)-1-oxo-4-phenyl-1,2-dihydroisoquinoline-3-carbaldehyde To a solution of 6-bromo-3-hydroxymethyl-2-(4-methanesulfonylbenzyl)-4-phenyl-2H-isoquinolin-1-one (1.0 g) in DMSO (10 ml) was added triethylamine (4.4 ml), and pyridine sulfur trioxide complex (2.6 g) was added at room temperature, and the mixture was stirred for 1 hr. and the reaction mixture was added to water. 10% Hydrochloric acid was added to acidify the aqueous layer and the mixture was extracted with ethyl acetate. The organic layer was washed with water, saturated aqueous sodium hydrogen carbonate solution, water and saturated brine, and dried over anhydrous sodium sulfate. The solvent was evaporated under reduced pressure and the obtained residue was crystallized from diisopropyl ether to give the title compound (940 mg).

$^1$H-NMR (CDCl$_3$) δ: 3.02 (3H, s), 5.91 (2H, s), 7.26-7.66 (8H, m), 7.81 (1H, dd, J=2.2, 8.8 Hz), 7.87 (2H, d, J=8.4 Hz), 8.44 (1H, d, J=8.8 Hz), 9.44 (1H, s).

EXAMPLE 312

6-bromo-3-(1-hydroxyethyl)-2-(4-methanesulfonylbenzyl)-4-phenyl-2H-isoquinolin-1-one To a solution of 6-bromo-2-(4-methanesulfonylbenzyl)-1-oxo-4-phenyl-1,2-dihydroisoquinoline-3-carbaldehyde (500 mg) in THF (10 ml) was added dropwise a solution of methyl magnesium bromide in THF (3M, 0.4 ml) at room temperature, and the mixture was stirred for 10 min. The reaction mixture was added to water and the mixture was extracted with ethyl acetate. The organic layer was washed with water and saturated brine, and dried over anhydrous sodium sulfate. The solvent was evaporated under reduced pressure and the obtained residue was crystallized from diisopropyl ether to give the title compound (490 mg).

$^1$H-NMR (CDCl$_3$) δ: 1.38 (3H, d, J=7.0 Hz), 2.18-2.36 (1H, m), 3.02 (3H, s), 4.92-5.14 (1H, m), 5.75 (1H, d, J=16.4 Hz), 5.92 (1H, d, J=16.4 Hz), 7.10 (1H, d, J=1.8 Hz), 7.14-7.42 (4H, m), 7.44-7.64 (4H, m), 7.84 (2H, d, J=8.6 Hz), 8.25 (1H, d, J=8.4 Hz).

EXAMPLE 313

6-bromo-3-(1-hydroxypropyl)-2-(4-methanesulfonylbenzyl)-4-phenyl-2H-isoquinolin-1-one To a solution of 6-bromo-2-(4-methanesulfonylbenzyl)-1-oxo-4-phenyl-1,2-dihydroisoquinoline-3-carbaldehyde (500 mg) in THF (10 ml) was added dropwise a solution of ethyl magnesium chloride in THF (2M, 0.61 ml) and the mixture was stirred at room temperature for 10 min. The reaction mixture was added to water and extracted with ethyl acetate. The organic layer was washed with water and saturated brine, and dried over anhydrous sodium sulfate. The solvent was evaporated under reduced pressure and the obtained residue was purified by silica gel thin layer chromatography (hexane: ethyl acetate=1:2), followed by crystallization from ethyl acetate-hexane to give the title compound (250 mg).

$^1$H-NMR (CDCl$_3$) δ: 0.75 (3H, t, J=7.5 Hz), 1.48-1.88 (2H, m), 2.30 (1H, d, J=4.0 Hz), 3.02 (3H, s), 4.64-4.80 (1H, m), 5.72 (1H, d, J=16.6 Hz), 5.88 (1H, d, J=16.6 Hz), 7.12 (1H, d, J=1.8 Hz), 7.18-7.40 (4H, m), 7.44-7.64 (4H, m), 7.85 (2H, d, J=8.4 Hz), 8.26 (1H, d, J=8.6 Hz).

EXAMPLE 314

3-acetyl-6-bromo-2-(4-methanesulfonylbenzyl)-4-phenyl-2H-isoquinolin-1-one

In the same manner as in Example 311, the title compound was synthesized using 6-bromo-3-(1-hydroxyethyl)-2-(4-methanesulfonylbenzyl)-4-phenyl-2H-isoquinolin-1-one. Crystals (THF-diisopropyl ether).

$^1$H-NMR (CDCl$_3$) δ: 1.45 (3H, s), 3.02 (3H, s), 5.45 (2H, s), 7.18-7.62 (8H, m), 7.70 (1H, dd, J=1.8, 8.4 Hz), 7.90 (2H, d, J=8.4 Hz), 8.41 (1H, d, J=8.4 Hz).

EXAMPLE 315

6-bromo-2-(4-methanesulfonylbenzyl)-4-phenyl-3-propionyl-2H-isoquinolin-1-one

In the same manner as in Example 311, the title compound was synthesized using 6-bromo-3-(1-hydroxypropyl)-2-(4-methanesulfonylbenzyl)-4-phenyl-2H-isoquinolin-1-one. Crystals (THF-diisopropyl ether).

$^1$H-NMR (CDCl$_3$) δ: 0.51 (3H, t, J=7.0 Hz), 1.72 (2H, q, J=7.0 Hz), 3.02 (3H, s), 5.37 (2H, s), 7.18-7.60 (8H, m), 7.69 (1H, dd, J=2.0, 8.8 Hz), 7.89 (2H, d, J=8.4 Hz), 8.39 (1H, d, J=8.8 Hz).

EXAMPLE 316

6-chloro-2-(4-methanesulfonylbenzyl)-1-oxo-4-phenyl-1,2-dihydroisoquinoline-3-carboxylic acid A mixture of 6-chloro-1-oxo-4-phenyl-1H-isocoumarin-3-carboxylic acid (5.0 g), 4-methanesulfonylbenzylamine (6.2 g), triethylamine (5.0 ml) and methanol (50 ml) was heated under reflux for 48 hrs. The reaction mixture was concentrated under reduced pressure and 10% hydrochloric acid was added. The mixture was extracted with ethyl acetate. The organic layer was washed with water and saturated brine, dried over anhydrous sodium sulfate, and concentrated under reduced pressure. To the residue was added 4N-hydrochloric acid ethyl acetate solution (20 ml) at room temperature, and the mixture was stirred for 12 hrs. The reaction mixture was concentrated under reduced pressure, and the obtained crystals were washed with a mixture of diethyl ether and diisopropyl ether to give the title compound (6.0 g).

$^1$H-NMR (DMSO-d$_6$) δ: 3.19 (3H, s), 5.35 (2H, s), 7.04 (1H, d, J=2.0 Hz), 7.20-7.70 (7H, m), 7.65 (1H, dd, J=2.0, 8.8 Hz), 7.89 (2H, d, J=8.6 Hz), 8.34 (1H, d, J=8.8 Hz).

EXAMPLE 317

6-chloro-3-hydroxymethyl-2-(4-methanesulfonyl-benzyl)-4-phenyl-2H-isoquinolin-1-one In the same manner as in Example 310, the title compound was synthesized using 6-chloro-2-(4-methanesulfonylbenzyl)-1-oxo-4-phenyl-1,2-dihydroisoquinoline-3-carboxylic acid. Crystals (diisopropyl ether).
$^1$H-NMR (CDCl$_3$) δ: 3.02 (3H, s), 4.28 (2H, s), 5.75 (2H, s), 7.06 (1H, d, J=1.8 Hz), 7.20-7.64 (8H, m), 7.87 (2H, d, J=8.6 Hz), 8.42 (1H, d, J=8.4 Hz). 1H unconfirmed.

EXAMPLE 318

6-chloro-2-(4-methanesulfonylbenzyl)-1-oxo-4-phenyl-1,2-dihydroisoquinoline-3-carbaldehyde In the same manner as in Example 311, the title compound was synthesized using 6-chloro-3-hydroxymethyl-2-(4-methanesulfonylbenzyl)-4-phenyl-2H-isoquinolin-1-one. Crystals (methanol).
$^1$H-NMR (CDCl$_3$) δ: 3.02 (3H, s), 5.92 (2H, s), 7.16-7.74 (9H, m), 7.87 (2H, d, J=8.0 Hz), 8.52 (1H, d, J=8.4 Hz), 9.44 (1H, s).

EXAMPLE 319

6-chloro-3-(1-hydroxyethyl)-2-(4-methanesulfonyl-benzyl)-4-phenyl-2H-isoquinolin-1-one In the same manner as in Example 312, the title compound was synthesized using 6-chloro-2-(4-methanesulfonylbenzyl)-1-oxo-4-phenyl-1,2-dihydroisoquinoline-3-carbaldehyde. Crystals (diisopropyl ether).
$^1$H-NMR (CDCl$_3$) δ: 1.38 (3H, d, J=7.0 Hz), 2.13 (1H, d, J=4.0 Hz), 3.01 (3H, s), 4.94-5.14 (1H, m), 5.76 (1H, d, J=16.5 Hz), 5.92 (1H, d, J=16.5 Hz), 6.92 (1H, d, J=2.2 Hz), 7.16-7.66 (8H, m), 7.85 (2H, d, J=8.4 Hz), 8.34 (1H, d, J=8.4 Hz).

EXAMPLE 320

6-chloro-3-(1-hydroxypropyl)-2-(4-methanesulfonyl-benzyl)-4-phenyl-2H-isoquinolin-1-one In the same manner as in Example 313, the title compound was synthesized using 6-chloro-2-(4-methanesulfonylbenzyl)-1-oxo-4-phenyl-1,2-dihydroisoquinoline-3-carbaldehyde. Crystals (diisopropyl ether).
$^1$H-NMR (CDCl$_3$) δ: 0.75 (3H, t, J=7.5 Hz), 1.48-1.90 (2H, m), 2.30 (1H, d, J=4.4 Hz), 3.01 (3H, s), 4.64-4.82 (1H, m), 5.72 (1H, d, J=16.4 Hz), 5.87 (1H, d, J=16.4 Hz), 6.94 (1H, d, J=2.2 Hz), 7.14-7.64 (8H, m), 7.84 (2H, d, J=8.4 Hz), 8.33 (1H, d, J=8.6 Hz).

EXAMPLE 321

6-chloro-3-(1-hydroxybutyl)-2-(4-methanesulfonyl-benzyl)-4-phenyl-2H-isoquinolin-1-one In the same manner as in Example 313, the title compound was synthesized using 6-chloro-2-(4-methanesulfonylbenzyl)-1-oxo-4-phenyl-1,2-dihydroisoquinoline-3-carbaldehyde and a solution (2M) of propyl magnesium chloride in diethyl ether. Crystals (ethyl acetate-diisopropyl ether).
$^1$H-NMR (CDCl$_3$) δ: 0.63 (3H, t, J=7.3 Hz), 0.88-1.88 (4H, m), 2.10 (1H, d, J=4.4 Hz), 3.01 (3H, s), 4.74-4.92 (1H, m), 5.74 (1H, d, J=16.5 Hz), 5.87 (1H, d, J=16.5 Hz), 6.94 (1H, d, J=1.8 Hz), 7.18-7.66 (8H, m), 7.86 (2H, d, J=8.4 Hz), 8.35 (1H, d, J=8.4 Hz).

EXAMPLE 322

6-chloro-3-(1-hydroxypentyl)-2-(4-methanesulfonyl-benzyl)-4-phenyl-2H-isoquinolin-1-one In the same manner as in Example 313, the title compound was synthesized using 6-chloro-2-(4-methanesulfonylbenzyl)-1-oxo-4-phenyl-1,2-dihydroisoquinoline-3-carbaldehyde and a solution (2M) of n-butylmagnesium chloride in THF. Crystals (ethyl acetate-diisopropyl ether).
$^1$H-NMR (CDCl$_3$) δ: 0.71 (3H, t, J=6.6 Hz), 0.86-1.86 (6H, m), 2.07 (1H, d, J=4.4 Hz), 3.01 (3H, s), 4.72-4.92 (1H, m), 5.74 (1H, d, J=16.4 Hz), 5.88 (1H, d, J=16.4 Hz), 6.94 (1H, d, J=1.8 Hz), 7.16-7.66 (8H, m), 7.86 (2H, d, J=8.0 Hz), 8.35 (1H, d, J=8.6 Hz).

EXAMPLE 323

3-acetyl-6-chloro-2-(4-methanesulfonylbenzyl)-4-phenyl-2H-isoquinolin-1-one

In the same manner as in Example 311, the title compound was synthesized using 6-bromo-3-(1-hydroxyethyl)-2-(4-methanesulfonylbenzyl)-4-phenyl-2H-isoquinolin-1-one. Crystals (THF-diisopropyl ether).
$^1$H-NMR (CDCl$_3$) δ: 1.46 (3H, s), 3.02 (3H, s), 5.45 (2H, s), 7.18-7.66 (9H, m), 7.90 (2H, d, J=8.4 Hz), 8.49 (1H, d, J=8.8 Hz).

EXAMPLE 324

6-chloro-2-(4-methanesulfonylbenzyl)-4-phenyl-3-propionyl-2H-isoquinolin-1-one

In the same manner as in Example 311, the title compound was synthesized using 6-chloro-3-(1-hydroxypropyl)-2-(4-methanesulfonylbenzyl)-4-phenyl-2H-isoquinolin-1-one. Crystals (THF-diisopropyl ether).
$^1$H-NMR (CDCl$_3$) δ: 0.51 (3H, t, J=7.0 Hz), 1.73 (2H, q, J=7.0 Hz), 3.02 (3H, s), 5.38 (2H, s), 7.16-7.64 (9H, m), 7.89 (2H, d, J=8.4 Hz), 8.48 (1H, d, J=8.8 Hz).

EXAMPLE 325

3-butyryl-6-chloro-2-(4-methanesulfonylbenzyl)-4-phenyl-2H-isoquinolin-1-one

In the same manner as in Example 311, the title compound was synthesized using 6-chloro-3-(1-hydroxybutyl)-2-(4-methanesulfonylbenzyl)-4-phenyl-2H-isoquinolin-1-one. Crystals (methanol).
$^1$H-NMR (CDCl$_3$) δ: 0.41 (3H, t, J=7.6 Hz), 0.92-1.20 (2H, m), 1.73 (2H, t, J=7.2 Hz), 3.02 (3H, s), 5.36 (2H, s), 7.16-7.64 (9H, m), 7.89 (2H, d, J=8.4 Hz), 8.47 (1H, d, J=8.8 Hz).

EXAMPLE 326

6-chloro-2-(4-methanesulfonylbenzyl)-3-pentanoyl-4-phenyl-2H-isoquinolin-1-one

In the same manner as in Example 311, the title compound was synthesized using 6-chloro-3-(1-hydroxypentyl)-2-(4-methanesulfonylbenzyl)-4-phenyl-2H-isoquinolin-1-one. Crystals (methanol-diisopropyl ether).
$^1$H-NMR (CDCl$_3$) δ: 0.56 (3H, t, J=6.8 Hz), 0.64-1.16 (4H, m), 1.74 (2H, t, J=7.1 Hz), 3.01 (3H, s), 5.36 (2H, s), 7.18-7.64 (9H, m), 7.89 (2H, d, J=8.0 Hz), 8.47 (1H, d, J=8.4 Hz).

EXAMPLE 327

6-bromo-2-(4-methanesulfonylbenzyl)-1-oxo-4-phenyl-1,2-dihydroisoquinoline-3-carbonyl Chloride To a suspension of 6-bromo-2-(4-methanesulfonylbenzyl)-1-oxo-4-phenyl-1,2-dihydroisoquinoline-3-carboxylic acid (1.0 g) in THF (10 ml) was added DMF (0.1 ml), and oxalyl chloride (0.4 ml) was added dropwise under ice-cooling. The reaction mixture was allowed to warm to room temperature, stirred for 30 min., and concentrated under reduced pressure. The obtained crystals were washed with diisopropyl ether to give the title compound (1.0 g).
$^1$H-NMR (CDCl$_3$) δ: 3.02 (3H, s), 5.45 (2H, s), 7.20-7.64 (8H, m), 7.74 (1H, dd, J=1.8, 8.4 Hz), 7.91 (2H, d, J=8.4 Hz), 8.39 (1H, d, J=8.4 Hz).

EXAMPLE 328

6-bromo-2-(4-methanesulfonylbenzyl)-1-oxo-4-phenyl-1,2-dihydroisoquinoline-3-carbothionic acid-pyridin-2-yl ester To a solution of 6-bromo-2-(4-methanesulfonylbenzyl)-1-oxo-4-phenyl-1,2-dihydroisoquinoline-3-carbonyl chloride (200 mg) in THF (2 ml) was added 2-mercaptopyridine (42 mg) and the mixture was stirred at 40° C. for 12 hrs. The reaction mixture was concentrated under reduced pressure and the residue was purified by recrystallization (THF-diisopropyl ether) to give the title compound (220 mg).
$^1$H-NMR (CDCl$_3$) δ: 3.02 (3H, s), 5.49 (2H, s), 6.97 (1H, d, J=8.0 Hz), 7.30-7.62 (9H, m), 7.64-7.96 (4H, m), 8.39 (1H, d, J=8.4 Hz), 8.59 (1H, d, J=4.4 Hz).

EXAMPLE 329

6-bromo-2-(4-methanesulfonylbenzyl)-1-oxo-4-phenyl-1,2-dihydroisoquinoline-3-carboxylic acid N-methoxy-N-methylamide To a solution of 6-bromo-2-(4-methanesulfonylbenzyl)-1-oxo-4-phenyl-1,2-dihydroisoquinoline-3-carbonyl chloride (200 mg) in methylene chloride (4 ml) were added N,O-dimethylhydroxylamine hydrochloride (70 mg) and triethylamine (0.2 ml) and the mixture was stirred at room temperature for 12 hrs. The reaction mixture was concentrated under reduced pressure and water was added to the residue. The mixture was extracted with ethyl acetate. The organic layer was washed with water and saturated brine, and dried over anhydrous sodium sulfate. The solvent was evaporated under reduced pressure and crystallized from diisopropyl ether to give the title compound (180 mg).
$^1$H-NMR (CDCl$_3$) δ: 2.30 (3H×0.6, s), 2.88 (3H×0.4, s), 3.005 (3H×0.6, s), 3.011 (3H×0.4, s), 3.02 (3H×0.6, s), 3.26 (3H×0.4, s), 5.11 (1H, d, J=15.4 Hz), 5.46 (1H×0.4, d, J=15.4 Hz), 5.90 (1H×0.6, d, J=15.4 Hz), 7.20-7.80 (9H, m), 7.89 (2H×0.4, d, J=8.4 Hz), 7.90 (2H×0.6, d, J=8.2 Hz), 8.34 (1H×0.4, d, J=8.4 Hz), 8.42 (1H×0.6, d, J=8.4 Hz).

EXAMPLE 330

6-bromo-2-(4-methanesulfonylbenzyl)-1-oxo-4-phenyl-1,2-dihydroisoquinoline-3-carboxylic acid pyridin-2-ylamide In the same manner as in Example 329, the title compound was synthesized using 2-aminopyridine.
$^1$H-NMR (CDCl$_3$) δ: 2.92 (3H, s), 5.54 (2H, s), 6.92-7.06 (1H, m), 7.20-7.84 (12H, m), 7.90 (1H, d, J=8.6 Hz), 7.94-8.08 (1H, m), 8.40 (1H, d, J=8.8 Hz).

EXAMPLE 331

6-bromo-2-(4-methanesulfonylbenzyl)-1-oxo-4-phenyl-1,2-dihydroisoquinoline-3-carboxylic acid To a solution of 6-bromo-4-phenyl-3-isocoumarincarboxylic acid (1.25 g) in methanol (20 ml) were added 4-methanesulfonylbenzylamine hydrochloride (1.6 g) and triethylamine (2.5 ml), and the mixture was stirred at 50° C. for 18 hrs. The solvent was evaporated under reduced pressure, and the residue was diluted with ethyl acetate, washed with 1N hydrochloric acid, and dried. The solvent was evaporated under reduced pressure. 4N Hydrochloric acid ethyl acetate solution (10 ml) was added to the residue, and the mixture was stirred at room temperature for 18 hrs. The precipitate was collected by filtration, washed with diethyl ether and dried to give the title compound (1.43 g).
$^1$H-NMR (DMSO-d$_6$) δ: 3.20 (3H, s), 5.34 (2H, s), 7.20 (1H, d, J=2.1 Hz), 7.36-7.43 (2H, m), 7.45-7.58 (5H, m), 7.79 (1H, dd, J=2.1, 8.7 Hz), 7.88 (2H, d, J=8.4 Hz), 8.25 (1H, d, J=8.7 Hz).

EXAMPLE 332

6-bromo-2-(4-methanesulfonylbenzyl)-1-oxo-4-phenyl-1,2-dihydroisoquinoline-3-carboxylic acid 2-methoxycarbonylpyridin-4-ylmethyl ester The present compound was synthesized by a method similar to that in Example 200 and using 6-bromo-2-(4-methanesulfonylbenzyl)-1-oxo-4-phenyl-1,2-dihydroisoquinoline-3-carboxylic acid (330 mg) and 4-hydroxymethylpyridin-2-carboxylic acid methyl ester. A colorless powder (410 mg).
$^1$H-NMR (CDCl$_3$) δ: 3.00 (3H, s), 4.04 (3H, s), 4.66 (2H, s), 5.46 (2H, S), 6.79 (1H, dd, J=1.8, 4.8 Hz), 7.22-7.40 (6H, m), 7.46 (2H, d, J=8.7 Hz), 7.63 (1H, m), 7.70 (1H, dd, J=2.1, 8.7 Hz), 7.88 (2H, d, J=8.7 Hz), 8.39 (1H, dd, J=0.6, 8.7 Hz), 8.59 (1H, dd, J=0.6, 4.8 Hz). HPLC analysis: purity 99.7% (retention time: 4.28 min). MS (ESI+): 661 (M+H), 663.

EXAMPLE 333

6-chloro-4-(3-formylphenyl)-2-(4-methoxycarbonylbenzyl)-1-oxo-1,2-dihydroisoquinoline-3-carboxylic acid methyl ester The present compound was synthesized by a method similar to that in Example 272 and using 6-chloro-2-(4-methoxycarbonylbenzyl)-1-oxo-4-trifluoromethanesulfonyloxy-1,2-dihydroisoquinoline-3-carboxylic acid methyl ester and 3-formylphenylboronic acid.

¹H-NMR (CDCl₃) δ: 3.19 (3H, s), 3.90 (3H, s), 5.41 (1H, d, J=15.6 Hz), 5.51 (1H, d, J=15.6 Hz), 7.09 (1H, d, J=2.1 Hz), 7.31 (2H, d, J=8.4 Hz), 7.52-7.60 (2H, m), 7.65 (1H, t, J=7.5 Hz), 7.81 (1H, m), 7.94-8.02 (3H, m), 8.51 (1H, d, J=8.4 Hz), 10.06 (1H, s). HPLC analysis: purity 98.9% (retention time: 4.56 min). MS (ESI+): 490 (M+H), 492.

EXAMPLE 334

6-chloro-4-(3-hydroxymethylphenyl)-2-(4-methoxycarbonylbenzyl)-1-oxo-1,2-dihydroisoquinoline-3-carboxylic acid methyl ester The present compound was synthesized by a method similar to that in Example 283 and using 6-chloro-4-(3-formylphenyl)-2-(4-methoxycarbonylbenzyl)-1-oxo-1,2-dihydroisoquinoline-3-carboxylic acid methyl ester.
¹H-NMR (CDCl₃) δ: 1.80 (1H, br), 3.21 (3H, s), 3.89 (3H, s) 4.75 (2H, d, J=3.3 Hz), 5.37-5.52 (2H, m), 7.18-7.25 (2H, m), 7.25-7.35 (3H, m), 7.40-7.48 (2H, m), 7.52 (1H, dd, J=2.1, 8.7 Hz), 7.97 (2H, d, J=8.4 Hz), 8.48 (1H, d, J=8.7 Hz). HPLC analysis: purity 98.2% (retention time: 4.25 min). MS (ESI+): 492 (M+H), 494.

EXAMPLE 335

2-(4-carboxybenzyl)-6-chloro-4-(3-hydroxymethylphenyl)-1-oxo-1,2-dihydroisoquinoline-3-carboxylic acid methyl ester To a solution of 6-chloro-4-(3-hydroxymethylphenyl)-2-(4-methoxycarbonylbenzyl)-1-oxo-1,2-dihydroisoquinoline-3-carboxylic acid methyl ester (130 mg) in methanol (4.0 ml) was added 1N sodium hydroxide (390 μl), and the mixture was stirred at room temperature for 1 hr. The reaction mixture was adjusted to pH 3 with 1N hydrochloric acid and concentrated under reduced pressure. The residue was partitioned between water and ethyl acetate, and the organic layer was dried over magnesium sulfate and concentrated under reduced pressure. The residue was purified by silica gel column chromatography (ethyl acetate/methanol=10/1) to give the title compound (92 mg) as a colorless powder. ¹H-NMR (CDCl₃) δ: 3.23 (3H, s), 4.76 (2H, s), 5.41 (1H, d, J=15.6 Hz), 5.48 (1H, d, J=15.6 Hz), 7.18-7.30 (3H, m), 7.35 (2H, d, J=8.7 Hz), 7.42-7.47 (2H, m), 7.52 (1H, dd, J=2.1, 8.4 Hz), 8.02 (2H, d, J=8.7 Hz), 8.48 (1H, d, J=8.4 Hz). HPLC analysis: purity 97.9% (retention time: 3.84 min). MS (ESI+): 478 (M+H), 480.

EXAMPLE 336

6-bromo-2-(4-methanesulfonylbenzyl)-1-oxo-4-phenyl-1,2-dihydroisoquinoline-3-carboxylic acid pyridin-2-ylmethyl ester The present compound was synthesized by a method similar to that in Example 200 and using 6-bromo-2-(4-methanesulfonylbenzyl)-1-oxo-4-phenyl-1,2-dihydroisoquinoline-3-carboxylic acid and 2-pyridinemethanol.
¹H-NMR (CDCl₃) δ: 2.98 (3H, s), 4.81 (2H, s), 5.48 (2H, s), 6.58 (1H, d, J=7.8 Hz), 7.17 (1H, m), 7.26-7.34 (2H, m), 7.40-7.47 (6H, m), 7.52 (1H, dt, J=1.8, 7.8 Hz), 7.69 (1H, dd, J=2.1, 8.7 Hz), 7.83 (2H, d, J=8.4 Hz), 8.37 (1H, d, J=8.7 Hz), 8.43 (1H, m). HPLC analysis: purity 99.4% (retention time: 3.91 min). MS (ESI+): 603 (M+H), 605.

EXAMPLE 337

6-bromo-2-(4-methanesulfonylbenzyl)-1-oxo-4-phenyl-1,2-dihydroisoquinoline-3-carboxylic acid pyridin-4-ylmethyl ester The present compound was synthesized by a method similar to that in Example 200 and using 6-bromo-2-(4-methanesulfonylbenzyl)-1-oxo-4-phenyl-1,2-dihydroisoquinoline-3-carboxylic acid and 4-pyridinemethanol.
¹H-NMR (CDCl₃) δ: 3.00 (3H, s), 4.60 (2H, s), 5.45 (2H, s), 6.62 (2H, d, J=6.0 Hz), 7.24-7.30 (2H, m), 7.36-7.47 (6H, m), 7.70 (1H, dd, J=1.8, 8.4 Hz), 7.88 (2H, d, J=8.7 Hz), 8.39 (1H, d, J=8.4 Hz), 8.45 (2H, d, J=6.0 Hz). HPLC analysis: purity 100% (retention time: 3.49 min). MS (ESI+): 603 (M+H), 605.

EXAMPLE 338

2-(4-methanesulfonylbenzyl)-1-oxo-4-phenyl-1,2-dihydroisoquinoline-3-carboxylic acid methyl ester A mixture of 6-bromo-2-(4-methanesulfonylbenzyl)-1-oxo-4-phenyl-1,2-dihydroisoquinoline-3-carboxylic acid methyl ester (200 mg) obtained in Example 94, 10% palladium carbon (20 mg) and methanol (4 ml) was stirred under a hydrogen atmosphere for 1 hr. The catalyst was removed by filtration, and the filtrate was concentrated under reduced pressure to give the title compound (127 mg) as a colorless powder.
¹H-NMR (CDCl₃) δ: 3.02 (3H, s), 3.26 (3H, s), 5.45 (2H, s), 7.26-7.34 (3H, m), 7.41-7.52 (5H, m), 7.56-7.67 (2H, m), 7.89 (2H, d, J=8.4 Hz), 8.54 (1H, m). HPLC analysis: purity 99.8% (retention time: 4.14 min).

EXAMPLE 339

6-bromo-2-(4-methylsulfanylbenzyl)-1-oxo-4-phenyl-1,2-dihydroisoquinoline-3-carboxylic acid methyl ester The present compound was synthesized by a method similar to that in Example 83 and using 6-bromo-4-phenyl-3-isocoumarincarboxylic acid methyl ester and 4-(methylthio)benzylamine.
¹H-NMR (CDCl₃) δ: 2.43 (3H, s), 3.23 (3H, s), 5.34 (2H, s), 7.15 (2H, d, J=8.7 Hz), 7.19 (2H, d, J=8.7 Hz), 7.22-7.29 (2H, m), 7.36 (1H, d, J=1.8 Hz), 7.38-7.47 (3H, m), 7.64 (1H, dd, J=1.8, 8.4 Hz), 8.38 (1H, d, J=8.4 Hz). HPLC analysis: purity 99.3% (retention time: 5.19 min).

EXAMPLE 340

6-chloro-4-(3-formylphenyl)-2-(4-methanesulfonylbenzyl)-1-oxo-1,2-dihydroisoquinoline-3-carboxylic acid methyl ester The present compound was synthesized by a method similar to that in Example 272 and using 6-chloro-2-(4-methanesulfonylbenzyl)-1-oxo-4-trifluoromethanesulfonyloxy-1,2-dihydroisoquinoline-3-carboxylic acid methyl ester and 3-formylphenylboronic acid.
¹H-NMR (CDCl₃) δ: 3.02 (3H, s), 3.27 (3H, s), 5.41 (2H, d, J=2.4 Hz), 7.10 (1H, d, J=1.8 Hz), 7.47 (2H, d, J=8.7 Hz), 7.51-7.61 (2H, m), 7.66 (1H, t, J=7.5 Hz), 7.82 (1H, m), 7.89 (2H, d, J=8.7 Hz), 7.98 (1H, dt, J=1.8, 7.5 Hz), 8.47 (1H, d, J=9.0 Hz), 10.06 (1H, s). HPLC analysis: purity 92.5% (retention time: 4.17 min). MS (ESI+): 510 (M+H), 512.

EXAMPLE 341

6-chloro-4-(3-hydroxymethylphenyl)-2-(4-methanesulfonylbenzyl)-1-oxo-1,2-dihydroisoquinoline-3-carboxylic acid methyl ester The present compound was synthesized by a method similar to that in Example 283 and using 6-chloro-4-(3-formylphenyl)-2-(4-methanesulfonylbenzyl)-1-oxo-1,2-dihydroisoquinoline-3-carboxylic acid methyl ester. $^1$H-NMR (CDCl$_3$) δ: 1.82 (1H, t, J=5.4 Hz), 3.03 (3H, s), 3.29 (3H, s), 4.77 (2H, d, J=5.1 Hz), 5.38 (1H, d, J=16.5 Hz), 5.45 (1H, d, J=16.5 Hz), 7.18-7.36 (3H, m), 7.41-7.66 (5H, m), 7.89 (2H, d, J=8.4 Hz), 8.46 (1H, d, J=8.4 Hz). HPLC analysis: purity 93.7% (retention time: 3.88 min). MS (ESI+): 512 (M+H), 514.

EXAMPLE 342

6-chloro-4-[3-(1-hydroxyethyl)phenyl]-2-(4-methanesulfonylbenzyl)-1-oxo-1,2-dihydroisoquinoline-3-carboxylic acid methyl ester To a solution (2.6 ml) of 6-chloro-4-(3-formylphenyl)-2-(4-methanesulfonylbenzyl)-1-oxo-1,2-dihydroisoquinoline-3-carboxylic acid methyl ester (130 mg) in THF was added a solution (3 mol/l, 0.10 ml) of methyl magnesium bromide in THF at room temperature with stirring, and the mixture was stirred at room temperature for 1 hr. After the completion of the reaction, 5% aqueous potassium hydrogensulfate solution was added to the mixture, and the mixture was extracted with ethyl acetate. The ethyl acetate layer was dried over magnesium sulfate and concentrated under reduced pressure. The residue was purified by medium pressure preparative LC (hexane/ethyl acetate=1/2-ethyl acetate) to give the title compound (69 mg) as colorless crystals.
$^1$H-NMR (CDCl$_3$): 1.52 (3H, t, J=6.3 Hz), 1.88 (1H, t, J=4.2 Hz), 3.03 (3H, s), 3.27 (3H, s), 4.97 (1H, br), 5.42 (2H, s), 7.19-7.36 (3H, m), 7.41-7.58 (5H, m), 7.89 (2H, d, J=8.1 Hz), 8.46 (1H, d, J=8.7 Hz). HPLC analysis: purity 95.6% (retention time: 3.99 min). MS (ESI+): 526 (M+H), 528.

EXAMPLE 343

4-(3-carboxyphenyl)-6-chloro-2-(4-methanesulfonylbenzyl)-1-oxo-1,2-dihydroisoquinoline-3-carboxylic acid methyl ester The present compound was synthesized by a method similar to that in Example 282 and using 6-chloro-4-(3-formylphenyl)-2-(4-methanesulfonylbenzyl)-1-oxo-1,2-dihydroisoquinoline-3-carboxylic acid methyl ester.
$^1$H-NMR (CDCl$_3$) δ: 3.03 (3H, s), 3.30 (3H, s), 5.37 (1H, d, J=15.8 Hz), 5.48 (1H, d, J=15.8 Hz), 7.14 (1H, d, J=2.2 Hz), 7.46-7.68 (5H, m), 7.90 (2H, d, J=8.0 Hz), 8.06 (1H, m), 8.16-8.25 (1H, m), 8.48 (1H, d, J=8.8 Hz). HPLC analysis: purity 94.4% (retention time: 3.89 min). MS (ESI+): 526 (M+H), 528.

EXAMPLE 344

6-chloro-2-(4-methanesulfonylbenzyl)-4-[3-(3-morpholine-4-ylpropylcarbamoyl)phenyl]-1-oxo-1,2-dihydroisoquinoline-3-carboxylic acid methyl ester To a solution (2 ml) of 4-(3-carboxyphenyl)-6-chloro-2-(4-methanesulfonylbenzyl)-1-oxo-1,2-dihydroisoquinoline-3-carboxylic acid methyl ester (100 mg) and 3-morpholin-4-ylpropylamine (31 μl) in acetonitrile were added 1-ethyl-3-(3-dimethylaminopropyl)carbodiimide hydrochloride (69 mg) and 4-hydroxybenzotriazole monohydrate (38 mg) at room temperature with stirring and the mixture was stirred at room temperature for 12 hrs. The solvent was removed under reduced pressure and the residue was partitioned between ethyl acetate and 1N hydrochloric acid. The organic layer was dried and concentrated to dryness. The residue was purified by silica gel column chromatography (ethyl acetate/methanol=10/1) to give the title compound (93 mg) as colorless crystals.
$^1$H-NMR (CDCl$_3$)δ: 1.75-7.85 (2H, m), 2.39-2.51 (4H, m), 2.56 (2H, t, J=6.0 Hz), 3.03 (3H, s), 3.28 (3H, s), 3.49-3.63 (6H, m), 5.36 (1H, d, J=16.5 Hz), 5.49 (1H, d, J=16.5 Hz), 7.14 (1H, m), 7.42-7.51 (3H, m), 7.52-7.61 (2H, m), 7.75 (1H, t, J=1.5 Hz), 7.86-7.97 (3H, m), 8.16 (1H, m), 8.47 (1H, d, J=8.7 Hz). HPLC analysis: purity 99.6% (retention time: 3.18 min). MS (ESI+): 652 (M+H), 654.

EXAMPLE 345

6-chloro-4-[3-(2-dimethylaminoethylcarbamoyl)phenyl]-2-(4-methanesulfonylbenzyl)-1-oxo-1,2-dihydroisoquinoline-3-carboxylic acid methyl ester To a solution (2 ml) of 4-(3-carboxyphenyl)-6-chloro-2-(4-methanesulfonylbenzyl)-1-oxo-1,2-dihydroisoquinoline-3-carboxylic acid methyl ester (100 mg) and N,N-dimethylethylenediamine (23 μl) in acetonitrile were added 1-ethyl-3-(3-dimethylaminopropyl)carbodiimide hydrochloride (69 mg) and 4-hydroxybenzotriazole monohydrate (38 mg) at room temperature with stirring, and the mixture was stirred at room temperature for 12 hrs. The solvent was removed under reduced pressure and the residue was partitioned between ethyl acetate and 1N hydrochloric acid. The organic layer was dried and concentrated to dryness. The residue was purified by silica gel column chromatography (dichloromethane/methanol=10/1) to give the title compound (56 mg) as colorless crystals.
$^1$H-NMR (CDCl$_3$)δ: 2.27 (6H, s), 2.54 (2H, t, J=6.0 Hz), 3.03 (3H, s), 3.30 (3H, s), 3.50-3.58 (2H, m), 5.38 (1H, d, J=16.2 Hz), 5.45 (1H, d, J=16.2 Hz), 6.94 (1H, m), 7.17 (1H, m), 7.41-7.59 (5H, m), 7.77 (1H, t, J=1.5 Hz), 7.86-7.93 (3H, m), 8.47 (1H, d, J=8.7 Hz). HPLC analysis: purity 99.7% (retention time: 3.14 min). MS (ESI+): 596 (M+H), 598.

EXAMPLE 346

6-bromo-2-(4-methanesulfinylbenzyl)-1-oxo-4-phenyl-1,2-dihydroisoquinoline-3-carboxylic acid methyl ester To a solution (6.7 ml) of 6-bromo-2-(4-methylsulfanylbenzyl)-1-oxo-4-phenyl-1,2-dihydroisoquinoline-3-carboxylic acid methyl ester (334 mg) in dichloromethane was added m-chloro perbenzoic acid (200 mg) at 0° C. with stirring, and the mixture was stirred at room temperature for 2 hrs. The reaction mixture was washed with 1N sodium hydroxide and water, and the organic layer was dried and concentrated under reduced pressure. The residue was purified by silica gel column chromatography (hexane/ethyl acetate=1/1-1/4) to give the title compound (160 mg) as colorless crystals.

$^1$H-NMR (CDCl$_3$)δ: 2.69 (3H, s), 3.24 (3H, s), 5.42 (2H, s), 7.25-7.32 (2H, m), 7.38-7.51 (6H, m), 7.59 (2H, d, J=8.4 Hz), 7.68 (1H, dd, J=1.8, 8.4 Hz), 8.39 (1H, d, J=8.4 Hz). HPLC analysis: purity 99.8% (retention time: 4.24 min).

EXAMPLE 347

6-chloro-4-(4-formylphenyl)-2-(4-methanesulfonylbenzyl)-1-oxo-1,2-dihydroisoquinoline-3-carboxylic acid methyl ester The present compound was synthesized by a method similar to that in Example 272 and using 6-chloro-2-(4-methanesulfonylbenzyl)-1-oxo-4-trifluoromethanesulfonyloxy-1,2-dihydroisoquinoline-3-carboxylic acid methyl ester and 4-formylphenylboronic acid.

$^1$H-NMR (CDCl$_3$)δ: 3.02 (3H, s), 3.27 (3H, s), 5.42 (2H, s), 7.13 (1H, d, J=2.1 Hz), 7.44-7.52 (4H, m), 7.55 (1H, dd, J=2.1, 8.7 Hz), 7.89 (2H, d, J=8.7 Hz), 7.99 (2H, d, J=8.4 Hz), 8.47 (1H, d, J=8.7 Hz), 10.10 (1H, s). HPLC analysis: purity 92.9% (retention time: 4.19 min). MS (ESI+): 510 (M+H), 512.

EXAMPLE 348

6-chloro-4-(4-hydroxymethylphenyl)-2-(4-methanesulfonylbenzyl)-1-oxo-1,2-dihydroisoquinoline-3-carboxylic acid methyl ester The present compound was synthesized by a method similar to that in Example 283 and using 6-chloro-4-(4-formylphenyl)-2-(4-methanesulfonylbenzyl)-1-oxo-1,2-dihydroisoquinoline-3-carboxylic acid methyl ester.

$^1$H-NMR (CDCl$_3$): 1.84 (1H, t, J=5.7 Hz), 3.03 (3H, s), 3.30 (3H, s), 4.80 (2H, d, J=5.7 Hz), 5.41 (2H, s), 7.21-7.36 (3H, m), 7.43-7.57 (5H, m), 7.89 (2H, d, J=8.7 Hz), 8.45 (1H, d, J=8.7 Hz). HPLC analysis: purity 90.1% (retention time: 3.83 min). MS (ESI+): 512 (M+H), 514.

EXAMPLE 349

6-chloro-4-[4-(1-hydroxyethyl)phenyl]-2-(4-methanesulfonylbenzyl)-1-oxo-1,2-dihydroisoquinoline-3-carboxylic acid methyl ester To a solution (2.6 ml) of 6-chloro-4-(4-formylphenyl)-2-(4-methanesulfonylbenzyl)-1-oxo-1,2-dihydroisoquinoline-3-carboxylic acid methyl ester (130 mg) in THF was added a solution (3 mol/l, 0.10 ml) of methyl magnesium bromide in THF at room temperature with stirring, and the mixture was stirred at room temperature for 1 hr. After the completion of the reaction, 5% aqueous potassium hydrogensulfate solution was added to the mixture, and the mixture was extracted with ethyl acetate. The ethyl acetate layer was dried over magnesium sulfate and concentrated under reduced pressure. The residue was purified by medium pressure preparative LC (hexane/ethyl acetate=1/2-ethyl acetate) to give the title compound (72 mg) as colorless crystals.

$^1$H-NMR (CDCl$_3$)δ: 1.56 (3H, d, J=6.6 Hz), 3.03 (3H, s), 3.28 (3H, s), 4.95-5.05 (1H, m), 5.41 (2H, s), 7.23-7.33 (3H, m), 7.44-7.56 (5H, m), 7.89 (2H, d, J=8.7 Hz), 8.45 (1H, d, J=8.7 Hz). HPLC analysis: purity 92.6%
(retention time: 3.96 min). MS (ESI+): 526 (M+H), 528.

EXAMPLE 350

4-(4-carboxyphenyl)-6-chloro-2-(4-methanesulfonylbenzyl)-1-oxo-1,2-dihydroisoquinoline-3-carboxylic acid methyl ester The present compound was synthesized by a method similar to that in Example 282 and using 6-chloro-4-(4-formylphenyl)-2-(4-methanesulfonylbenzyl)-1-oxo-1,2-dihydroisoquinoline-3-carboxylic acid methyl ester.

$^1$H-NMR (CDCl$_3$)δ: 3.03 (3H, s), 3.30 (3H, s), 5.44 (2H, s), 7.17 (1H, d, J=2.1 Hz), 7.42-7.53 (4H, m), 7.56 (1H, dd, J=1.8, 8.7 Hz), 7.91 (2H, d, J=8.4 Hz), 8.23 (2H, d, J=8.7 Hz), 8.48 (1H, d, J=8.7 Hz). HPLC analysis: purity 92.6% (retention time: 3.87 min). MS (ESI+): 526 (M+H), 528.

EXAMPLE 351

6-chloro-2-(4-methanesulfonylbenzyl)-4-[4-(3-morpholine-4-ylpropylcarbamoyl)phenyl]-1-oxo-1,2-dihydroisoquinoline-3-carboxylic acid methyl ester To a solution (2 ml) of 4-(4-carboxyphenyl)-6-chloro-2-(4-methanesulfonylbenzyl)-1-oxo-1,2-dihydroisoquinoline-3-carboxylic acid methyl ester (100 mg) and 3-morpholin-4-ylpropylamine (31 μl) in acetonitrile were added 1-ethyl-3-(3-dimethylaminopropyl)carbodiimide hydrochloride (69 mg) and 4-hydroxybenzotriazole monohydrate (38 mg) at room temperature with stirring, and the mixture was stirred at room temperature for 12 hrs. The solvent was removed under reduced pressure, and the residue was partitioned between ethyl acetate and 1N hydrochloric acid. The organic layer was dried and concentrated to dryness. The residue was purified by silica gel column chromatography (ethyl acetate/methanol=10/1) to give the title compound (93 mg) as colorless crystals.

$^1$H-NMR (CDCl$_3$)δ: 1.78-1.89 (2H, m), 2.47-2.65 (6H, m), 3.03 (3H, s), 3.30 (3H, s), 3.57-3.75 (6H, m), 5.41 (2H, s), 7.14 (1H, d, J=1.8 Hz), 7.40 (2H, d, J=8.4 Hz), 7.48 (2H, d, J=8.7H), 7.54 (1H, dd, J=1.8, 8.7 Hz), 7.86-7.96 (4H, m), 8.15 (1H, m), 8.47 (1H, d, J=8.7 Hz). HPLC analysis: purity 99.2% (retention time: 3.16 min). MS (ESI+): 652 (M+H), 654.

EXAMPLE 352

6-chloro-2-(4-carboxybenzyl)-1-oxo-4-phenyl-1,2-dihydroisoquinoline-3-carboxylic acid methyl ester To a mixture of 6-chloro-2-(4-methoxycarbonylbenzyl)-1-oxo-4-phenyl-1,2-dihydroisoquinoline-3-carboxylic acid methyl ester (2.50 g), methanol (10 ml) and tetrahydrofuran (20 ml) was added 8N aqueous sodium hydroxide solution (1 ml) and the mixture was stirred at room temperature for 12 hrs. The solvent was evaporated under reduced pressure and water was added. The mixture was acidified with 1N hydrochloric acid and extracted with ethyl acetate. The extract was washed with saturated brine and dried by adding sodium sulfate. The solvent was evaporated under reduced pressure and the obtained residue was recrystallized from methanol to give the title compound (1.27 g, 52%).

$^1$H-NMR (CDCl$_3$) δ: 3.17 (3H, s), 5.42 (2H, s), 7.15-7.51 (9H, m), 7.98 (2H, d, J=8.6 Hz), 8.44 (1H, d, J=8.6 Hz)

EXAMPLE 353

6-bromo-2-[4-(4-ethoxycarbonylpiperidine-1-carbonyl)benzyl]-1-oxo-4-phenyl-1,2-dihydroisoquinoline-3-carboxylic acid methyl ester To a solution of 6-bromo-2-(4-carboxybenzyl)-1-oxo-4-phenyl-1,2-dihydroisoquinoline-3-carboxylic acid methyl ester (246 mg) in dichloromethane (10 ml) were added diethyl isonipecotate (0.085 ml), 1-hydroxy-1H-benzotriazole (92 mg) and triethylamine (0.1 ml) and then 1-ethyl-3-(3-dimethylaminopropyl)-carbodiimide (144 mg) was added at room temperature. The mixture was stirred at room temperature for 15 hrs. Dichloromethane was added, and the mixture was washed with 1N hydrochloric acid and saturated brine and dried by adding sodium sulfate. The solvent was evaporated under reduced pressure and the obtained residue was purified by silica gel column chromatography (n-hexane/ethyl acetate=3/2→1/4) to give the title compound (295 mg, 93%).

$^1$H-NMR (CDCl$_3$) δ: 1.22 (3H, t, J=7.2 Hz) 1.60-2.00 (4H, m), 2.53 (1H, m), 2.90-3.08 (2H, m), 3.20 (3H, s), 3.67 (1H, m), 4.47 (1H, m), 4.11 (2H, q, J=7.2 Hz), 5.38 (2H, s), 7.23-7.46 (10H, m), 7.63 (1H, dd, J=1.8, 8.4 Hz), 8.36 (1H, d, J=8.4 Hz).

In the same manner as in Example 353, the compounds of Examples 354-365 were synthesized by amidation of 6-bromo-2-(4-carboxybenzyl)-1-oxo-4-phenyl-1,2-dihydroisoquinoline-3-carboxylic acid methyl ester using various amines.

EXAMPLE 354

6-bromo-2-[4-(3-ethoxycarbonylphenylcarbamoyl)benzyl]-1-oxo-4-phenyl-1,2-dihydroisoquinoline-3-carboxylic acid methyl ester yield: 88%
$^1$H-NMR (CDCl$_3$) δ: 1.36 (3H, t, J=7.5 Hz), 3.23 (3H, s), 4.34 (2H, q, J=7.5 Hz), 5.41 (2H, s), 7.12 (1H, m), 7.25-7.49 (9H, m), 7.66 (1H, dd, J=1.8, 8.7 Hz), 7.80 (2H, d, J=8.4 Hz), 8.03 (1H, m), 8.11 (1H, s), 8.37 (1H, d, J=8.4 Hz).

EXAMPLE 355

6-bromo-2-(4-ethoxyaminocarbonylbenzyl)-1-oxo-4-phenyl-1,2-dihydroisoquinoline-3-carboxylic acid methyl ester yield: 70%
$^1$H-NMR (CDCl$_3$) δ: 1.30 (3H, t, J=7.2 Hz) 3.22 (3H, s), 4.06 (2H, q, J=7.2 Hz), 5.40 (2H, s), 7.26-7.31 (4H, m), 7.39-7.47 (4H, m), 7.65-7.70 (3H, m), 8.38 (1H, d, J=8.4 Hz), 8.95 (1H, s).

EXAMPLE 356

6-bromo-2-[4-(N',N'-diethylhydrazinocarbonyl)benzyl]-1-oxo-4-phenyl-1,2-dihydroisoquinoline-3-carboxylic acid methyl ester yield: 11%
$^1$H-NMR (CDCl$_3$) δ: 1.33 (6H, t, J=6.8 Hz) 2.63 (1H, s), 3.27 (3H, s), 3.37 (4H, q, J=6.8 Hz), 5.41 (2H, s), 7.27-7.47 (8H, m), 7.67 (1H, dd, J=1.8, 8.6 Hz), 7.81 (2H, d, J=8.4 Hz), 8.39 (1H, d, J=8.6 Hz).

EXAMPLE 357

6-bromo-2-[4-(4-methoxycarbonylbenzylcarbamoyl)benzyl]-1-oxo-4-phenyl-1,2-dihydroisoquinoline-3-carboxylic acid methyl ester yield: 83%
$^1$H-NMR (CDCl$_3$) δ: 3.22 (3H, s), 3.91 (3H, s), 4.68 (2H, d, J=6.0 Hz), 5.41 (2H, s), 6.52 (1H, t, J=6.0 Hz), 7.26-7.47 (10H, m), 7.66 (1H, dd, J=2.1, 8.4 Hz), 7.74 (2H, d, J=8.4 Hz), 8.00 (2H, d, J=8.4 Hz), 8.37 (1H, d, J=8.4 Hz).

EXAMPLE 358

6-bromo-2-{4-[(4-methoxycarbonylcyclohexylmethyl)carbamoyl]benzyl}-1-oxo-4-phenyl-1,2-dihydroisoquinoline-3-carboxylic acid methyl ester yield: 62%
$^1$H-NMR (CDCl$_3$) δ: 0.93-0.19 (2H, m), 1.30-1.64 (3H, m), 1.80-2.06 (4H, m), 2.23 (1H, m), 3.22 (3H, s), 3.23-3.30 (2H, m), 3.65 (3H, s), 5.41 (2H, s), 6.48 (1H, brs), 7.26-7.31 (4H, m), 7.39-7.49 (4H, m), 7.64-7.73 (3H, m), 8.37 (1H, d, J=8.7 Hz).

EXAMPLE 359

6-bromo-2-[4-(N'-tert-butoxycarbonylhydrazinocarbonyl)benzyl]-1-oxo-4-phenyl-1,2-dihydroisoquinoline-3-carboxylic acid methyl ester yield: 48%
$^1$H-NMR (CDCl$_3$) δ: 1.45 (9H, s), 3.18 (3H, s), 5.41 (2H, s), 6.87 (1H, brs), 7.25-7.29 (4H, m), 7.39-7.48 (4H, m), 7.66 (1H, m), 7.75 (1H, d, J=8.1 Hz), 8.37 (1H, d, J=8.7 Hz), 8.50 (1H, brs).

EXAMPLE 360

6-bromo-2-(4-cyclohexylcarbamoylbenzyl)-1-oxo-4-phenyl-1,2-dihydroisoquinoline-3-carboxylic acid methyl ester yield: 73%
$^1$H-NMR (CDCl$_3$) δ: 1.12-1.77 (8H, m), 1.95-2.06 (2H, m), 3.22 (3H, s), 5.42 (2H, s), 5.90 (1H, d, J=7.2 Hz), 7.23-7.47 (8H, m), 7.66-7.69 (3H, m), 8.39 (1H, d, J=8.7 Hz).

EXAMPLE 361

6-bromo-2-(4-isopropylcarbamoylbenzyl)-1-oxo-4-phenyl-1,2-dihydroisoquinoline-3-carboxylic acid methyl ester yield: 53%
$^1$H-NMR (CDCl$_3$) δ: 1.24 (6H, d, J=6.3 Hz), 3.21 (3H, s), 4.24 (1H, m), 5.43 (2H, s), 5.87 (1H, d, J=7.5 Hz), 7.24-7.47 (8H, m), 7.65-7.70 (3H, m), 8.39 (1H, d, J=8.7 Hz).

EXAMPLE 362

6-bromo-2-(4-cyclopropylcarbamoylbenzyl)-1-oxo-4-phenyl-1,2-dihydroisoquinoline-3-carboxylic acid methyl ester yield: 84%
$^1$H-NMR (CDCl$_3$) δ: 0.58-0.62 (2H, m), 0.82-0.89 (2H, m), 2.87 (1H, m), 3.20 (3H, s), 5.42 (2H, s), 6.19 (1H, brs), 7.25-7.44 (8H, m), 7.64-7.69 (3H, m), 8.39 (1H, d, J=8.7 Hz).

EXAMPLE 363

6-bromo-2-[4-(cyclohexylmethylcarbamoyl)benzyl]-1-oxo-4-phenyl-1,2-dihydroisoquinoline-3-carboxylic acid methyl ester yield: 88%
$^1$H-NMR (CDCl$_3$) δ: 0.90-1.30 (2H, m), 1.50-1.77 (6H, m), 3.22 (3H, s), 3.20-3.32 (2H, m), 5.42 (2H, s), 6.15 (1H, brs), 7.24-7.48 (8H, m), 7.63-7.70 (3H, m), 8.39 (1H, d, J=8.7 Hz).

EXAMPLE 364

6-bromo-2-(4-cyclopentylcarbamoylbenzyl)-1-oxo-4-phenyl-1,2-dihydroisoquinoline-3-carboxylic acid methyl ester yield: 48%
$^1$H-NMR (CDCl$_3$) δ: 1.42-1.71 (6H, m), 2.00-2.14 (2H, m), 3.21 (3H, s), 4.37 (1H, m), 5.42 (2H, s), 6.95 (1H, m), 7.25-7.47 (8H, m), 7.65-7.69 (3H, m), 8.39 (1H, d, J=8.7 Hz).

EXAMPLE 365

6-bromo-2-[4-(2-cyanoethylcarbamoyl)benzyl]-1-oxo-4-phenyl-1,2-dihydroisoquinoline-3-carboxylic acid methyl ester yield: 92%
$^1$H-NMR (CDCl$_3$) δ: 2.73 (2H, t, J=6.2 Hz), 3.22 (3H, s), 3.68 (2H, dt, J=5.8, 6.2 Hz), 5.43 (2H, s), 6.71 (1H, t, J=5.8 Hz), 7.25-7.48 (8H, m), 7.65-7.74 (3H, m), 8.39 (1H, d, J=8.7 Hz).

EXAMPLE 366

6-bromo-2-(4-phenylcarbamoylbenzyl)-1-oxo-4-phenyl-1,2-dihydroisoquinoline-3-carboxylic acid methyl ester To a solution of 6-bromo-2-(4-carboxybenzyl)-1-oxo-4-phenyl-1,2-dihydroisoquinoline-3-carboxylic acid methyl ester (97 mg) in tetrahydrofuran (5 ml) were added oxalyl chloride (0.03 ml) and dimethylformamide (1 drop), and the mixture was stirred at room temperature for 1 hr. The solvent was evaporated under reduced pressure, and the residue was dissolved in chloroform (5 ml) and aniline (0.055 ml) was added. The mixture was stirred at room temperature for 2 hrs. and extracted with dichloromethane. The extract was washed with saturated brine and dried by adding sodium sulfate. The solvent was evaporated under reduced pressure and the obtained residue was purified by silica gel column chromatography (n-hexane/ethyl acetate=4/1→1/1) to give the title compound (96 mg, 85%).

$^1$H-NMR (CDCl$_3$) δ: 3.24 (3H, s), 5.44 (2H, s), 7.15 (1H, m), 7.26-7.50 (9H, m), 7.60-7.63 (2H, m), 7.68 (1H, dd, J=1.8, 8.4 Hz), 7.79-7.83 (3H, m), 8.40 (1H, d, J=8.4 Hz).

In the same manner as in Example 366, 6-bromo-2-(4-carboxybenzyl)-1-oxo-4-phenyl-1,2-dihydroisoquinoline-3-carboxylic acid methyl ester was converted to acid chloride and reacted with various amines to give the compounds of Examples 367-371.

EXAMPLE 367

6-bromo-2-[4-(2-methoxycarbonylphenylcarbamoyl)benzyl]-1-oxo-4-phenyl-1,2-dihydroisoquinoline-3-carboxylic acid methyl ester yield: 2%
$^1$H-NMR (CDCl$_3$) δ: 3.23 (3H, s), 3.94 (3H, s), 5.47 (2H, s), 7.12 (1H, m), 7.27-7.32 (3H, m), 7.40-7.49 (5H, m), 7.60 (1H, m), 7.68 (1H, dd, J=1.8, 8.4 Hz), 7.99-8.02 (2H, m), 8.08 (1H, dd, J=1.2, 8.1 Hz), 8.41 (1H, d, J=8.1 Hz), 8.91 (1H, d, J=8.1 Hz).

EXAMPLE 368

6-bromo-2-[4-(4-methoxycarbonylphenylcarbamoyl)benzyl]-1-oxo-4-phenyl-1,2-dihydroisoquinoline-3-carboxylic acid methyl ester yield: 80%
$^1$H-NMR (CDCl$_3$) δ: 3.25 (3H, s), 3.91 (3H, s), 5.43 (2H, s), 7.26-7.47 (7H, m), 7.66-7.74 (3H, m), 7.82 (2H, d, J=8.4 Hz), 8.02-8.06 (3H, m), 8.39 (1H, d, J=8.4 Hz).

EXAMPLE 369

6-bromo-1-oxo-4-phenyl-2-[4-(pyridin-3-ylcarbamoyl)benzyl]-1,2-dihydroisoquinoline-3-carboxylic acid methyl ester yield: 53%
$^1$H-NMR (CDCl$_3$) δ: 3.25 (3H, s), 5.43 (2H, s), 7.24-7.47 (8H, m), 7.68 (1H, dd, J=1.8, 8.7 Hz), 7.83 (2H, d, J=8.4 Hz), 8.04 (1H, s), 8.28 (1H, m), 8.37-8.41 (2H, m), 8.65 (1H, d, J=2.7 Hz).

EXAMPLE 370

6-bromo-1-oxo-4-phenyl-2-[4-(pyridin-4-ylcarbamoyl)benzyl]-1,2-dihydroisoquinoline-3-carboxylic acid methyl ester yield: 63%
$^1$H-NMR (CDCl$_3$) δ: 3.25 (3H, s), 5.40 (2H, s), 7.25-7.49 (8H, m), 7.61 (2H, d, J=6.3 Hz), 7.68 (1H, d, J=1.8, 8.7 Hz), 7.80 (2H, d, J=8.1 Hz), 8.38 (1H, d, J=8.7 Hz), 8.44 (1H, s), 8.51 (2H, d, J=6.3 Hz).

EXAMPLE 371

6-bromo-1-oxo-4-phenyl-2-[4-(pyridin-2-ylcarbamoyl)benzyl]-1,2-dihydroisoquinoline-3-carboxylic acid methyl ester yield: 4%
$^1$H-NMR (CDCl$_3$) δ: 3.22 (3H, s), 5.46 (2H, s), 7.08 (1H, m), 7.26-7.30 (3H, m), 7.38-7.48 (5H, m), 7.68 (1H, d, J=1.8, 8.7 Hz), 7.76 (1H, m), 7.87 (2H, d, J=8.1 Hz), 8.30 (1H, m), 8.36 (1H, d, J=8.7 Hz), 8.41 (1H, d, J=6.3 Hz), 8.55 (1H, brs).

EXAMPLE 372

6-bromo-2-[4-(2-methoxycarbonylethyl)benzyl]-1-oxo-4-phenyl-1,2-dihydroisoquinoline-3-carboxylic acid methyl ester To a solution of 6-bromo-4-phenyl-3-isocoumarincarboxylic acid methyl ester (359 mg) in methanol (20 ml) was added 3-(4-aminomethylphenyl)propionic acid methyl ester (387 mg) and the mixture was stirred at room temperature for 18 hr. The solvent was evaporated under reduced pressure, 1N hydrochloric acid was added, and the mixture was extracted with ethyl acetate. The extract was washed with saturated brine and dried by adding sodium sulfate. The solvent was evaporated under reduced pressure and the obtained residue was dissolved in methanol (30 ml) and conc. sulfuric acid (3 ml) was added. The mixture was heated under reflux for 3 hrs. The solvent was evaporated under reduced pressure, water was added under ice-cooling and the mixture was neutralized with potassium carbonate. The solution was extracted with ethyl acetate. The extract was washed with saturated brine and dried by adding sodium sulfate. The obtained residue was purified by silica gel column chromatography (n-hexane/ethyl acetate=19/1→3/1) to give the title compound (425 mg, 80%).

$^1$H-NMR (CDCl$_3$) δ: 2.58 (2H, t, J=8.4 Hz), 2.90 (2H, t, J=8.4 Hz), 3.21 (3H, s), 3.64 (3H, s), 5.37 (2H, s), 7.12 (2H, d, J=8.4 Hz), 7.19 (2H, d, J=8.4 Hz), 7.26-7.30 (2H, m), 7.37-7.46 (4H, m), 7.65 (1H, dd, J=1.8, 8.4 Hz), 8.39 (1H, d, J=8.4 Hz).

EXAMPLE 373

6-bromo-2-(4-hydroxymethylbenzyl)-1-oxo-4-phenyl-1,2-dihydroisoquinoline-3-carboxylic acid methyl ester To a solution of 6-bromo-2-(4-carboxybenzyl)-1-oxo-4-phenyl-1,2-dihydroisoquinoline-3-carboxylic acid methyl ester (4.9 g) in tetrahydrofuran (20 ml) was added a solution (1M, 30 ml) of borane in tetrahydrofuran, and the mixture was stirred at room temperature for 3 hr. The solvent was evaporated under reduced pressure, 1N hydrochloric acid was added, and the mixture was extracted with ethyl acetate. The extract was washed with saturated brine and dried by adding sodium sulfate. The solvent was evaporated under reduced pressure and the obtained residue was purified by recrystallization from methanol to give the title compound (2.97 g, 62%).

$^1$H-NMR (CDCl$_3$) δ: 3.24 (3H, s), 4.65 (2H, s), 5.39 (2H, s), 7.25-7.45 (10H, m), 7.65 (1H, m), 8.39 (1H, d, J=8.8 Hz).

EXAMPLE 374

2-{4-[bis(methylsulfonyl)amino]benzyl}-6-bromo-1-oxo-4-phenyl-1,2-dihydroisoquinoline-3-carboxylic acid methyl ester To a solution of 2-(4-aminobenzyl)-6-bromo-1-oxo-4-phenyl-1,2-dihydroisoquinoline-3-carboxylic acid methyl ester (139 mg) in tetrahydrofuran (5 ml) was added triethylamine (0.48 ml), methanesulfonyl chloride (0.07 ml) was added and the mixture was stirred at room temperature for 3 hrs. The solvent was evaporated under reduced pressure, 1N hydrochloric acid was added, and the mixture was extracted with dichloromethane. The extract was washed with saturated brine and dried by adding sodium sulfate. The solvent was evaporated under reduced pressure, and the obtained residue was purified by silica gel column chromatography (n-hexane/ethyl acetate=3/1→2/3) to give the title compound (110 mg, 59%).

$^1$H-NMR (CDCl$_3$) δ: 3.19 (3H, s), 3.37 (6H, s), 5.42 (2H, s), 7.26-7.35 (4H, m), 7.36-7.47 (6H, m), 7.67 (1H, dd, J=1.8, 8.4 Hz), 8.38 (1H, d., J=8.4 Hz).

EXAMPLE 375

6-bromo-2-[4-(3-ethoxycarbonylacryloylamino)benzyl]-1-oxo-4-phenyl-1,2-dihydroisoquinoline-3-carboxylic acid methyl ester To a solution of 2-(4-aminobenzyl)-6-bromo-1-oxo-4-phenyl-1,2-dihydroisoquinoline-3-carboxylic acid methyl ester (232 mg) in chloroform (5 ml) was added triethylamine (0.2 ml) and then 3-chlorocarbonyl-acrylic acid ester (122 mg) was added. The mixture was stirred at room temperature for 3 hrs. Dichloromethane (30 ml) was added, and the mixture was washed with 1N hydrochloric acid and saturated brine and dried by adding sodium sulfate. The solvent was evaporated under reduced pressure and the obtained residue was purified by silica gel column chromatography (n-hexane/ethyl acetate=3/1→2/3) to give the title compound (53 mg, 56%).

$^1$H-NMR (CDCl$_3$) δ: 1.32 (3H, t, J=6.9 Hz), 3.25 (3H, s), 4.26 (4H, q, J=6.9 Hz), 5.37 (2H, s), 6.92 (1H, d, J=15.3 Hz), 7.07 (1H, t, J=15.3 Hz), 7.20-7.35 (4H, m), 7.38-7.58 (6H, m), 7.66 (1H, dd, J=1.8, 8.7 Hz), 8.39 (1H, d, J=8.7 Hz).

EXAMPLE 376

6-bromo-2-[4-(4-carboxy-butyrylamino)benzyl]-1-oxo-4-phenyl-1,2-dihydroisoquinoline-3-carboxylic acid methyl ester To a solution of 2-(4-aminobenzyl)-6-bromo-1-oxo-4-phenyl-1,2-dihydroisoquinoline-3-carboxylic acid methyl ester (139 mg) in tetrahydrofuran (5 ml) were added triethylamine (0.084 ml), glutaric anhydride (51 mg), and the mixture was stirred at room temperature for 24 hrs. The solvent was evaporated under reduced pressure, water was added and the mixture was extracted with ethyl acetate. The extract was washed with saturated brine and dried by adding sodium sulfate. The solvent was evaporated under reduced pressure and isopropyl ether was added to the obtained residue and the mixture was crystallized. The obtained crystals were collected by filtration and dried under reduced pressure at 50° C. to give the title compound (131 mg, 76%).

$^1$H-NMR (CDCl$_3$) δ: 1.98-2.08 (2H, m), 2.39-2.49 (4H, m), 3.24 (3H, s), 5.36 (2H, s), 7.19-7.28 (4H, m), 7.36-7.48 (6H, m), 7.64 (1H, dd, J=1.8, 8.4 Hz), 8.37 (1H, d, J=8.4 Hz).

EXAMPLE 377

6-bromo-2-(4-methanesulfonylaminobenzyl)-1-oxo-4-phenyl-1,2-dihydroisoquinoline-3-carboxylic acid methyl ester To a solution of 2-(4-aminobenzyl)-6-bromo-1-oxo-4-phenyl-1,2-dihydroisoquinoline-3-carboxylic acid methyl ester (139 mg) in tetrahydrofuran (5 ml) was added triethylamine (0.083 ml) and then methanesulfonyl chloride (0.028 ml) was added. The mixture was stirred at room temperature for 3 hrs. The solvent was evaporated under reduced pressure, 1N hydrochloric acid was added, and the mixture was extracted with dichloromethane. The extract was washed with saturated brine and dried by adding sodium sulfate. The solvent was evaporated under reduced pressure and the obtained residue was purified by silica gel column chromatography (n-hexane/ethyl acetate=3/1→2/3) to give the title compound (90 mg, 55%).

$^1$H-NMR (CDCl$_3$) δ: 2.97 (3H, s), 3.27 (3H, s), 5.34 (2H, s), 6.60 (1H, s), 7.14 (2H, d, J=8.7 Hz), 7.26-7.49 (8H, m), 7.66 (1H, dd, J=1.8, 8.4 Hz), 8.38 (1H, d, J=8.4 Hz).

In the same manner as in Example 377, the compounds of Examples 378-386 were synthesized using 2-(4-aminobenzyl)-6-bromo-1-oxo-4-phenyl-1,2-dihydroisoquinoline-3-carboxylic acid methyl ester and various sulfonyl chlorides.

EXAMPLE 378

2-(4-benzenesulfonylaminobenzyl)-6-bromo-1-oxo-4-phenyl-1,2-dihydroisoquinoline-3-carboxylic acid methyl ester yield: 57%
$^1$H-NMR (CDCl$_3$) δ: 3.15 (3H, s), 5.31 (2H, s), 6.89 (1H, s), 6.98 (2H, d, J=8.7 Hz), 7.12 (2H, d, J=8.7 Hz), 7.24-7.27 (2H, m), 7.37-7.54 (7H, m), 7.65 (1H, dd, J=1.8, 8.7 Hz), 7.74 (2H, d, J=8.7 Hz), 8.37 (1H, d, J=8.7 Hz).

EXAMPLE 379

6-bromo-2-[4-(3-carboxybenzenesulfonylamino)benzyl]-1-oxo-4-phenyl-1,2-dihydroisoquinoline-3-carboxylic acid methyl ester yield: 35%
$^1$H-NMR (DMSO-d$_6$) δ: 3.15 (3H, s), 5.26 (2H, s), 7.18-7.35 (5H, m), 7.44-7.51 (4H, m), 7.71-7.91 (5H, m), 8.21 (1H, s), 8.32 (1H, d, J=8.4 Hz).

EXAMPLE 380

6-bromo-2-[4-(4-carboxybenzenesulfonylamino)benzyl]-1-oxo-4-phenyl-1,2-dihydroisoquinoline-3-carboxylic acid methyl ester yield: 29%
$^1$H-NMR (DMSO-d$_6$) δ: 3.31 (3H, s), 5.26 (2H, s), 7.10-7.37 (5H, m), 7.40-7.55 (3H, m), 7.65-7.93 (7H, m), 8.31 (1H, d, J=8.4 Hz), 10.24 (1H, s).

EXAMPLE 381

6-bromo-2-[4-(4-methanesulfonylbenzenesulfonylamino)benzyl]-1-oxo-4-phenyl-1,2-dihydroisoquinoline-3-carboxylic acid methyl ester yield: 28%
$^1$H-NMR (CDCl$_3$) δ: 3.06 (3H, s), 3.26 (3H, s), 5.30 (2H, s), 6.96-7.00 (2H, m), 7.15-7.50 (8H, m), 7.66 (1H, dd, J=2.1, 8.4 Hz), 7.89-8.01 (4H, m), 8.36 (1H, d, J=8.4 Hz).

EXAMPLE 382

2-[4-(4-acetylbenzenesulfonylamino)benzyl]-6-bromo-1-oxo-4-phenyl-1,2-dihydroisoquinoline-3-carboxylic acid methyl ester yield: 28%
$^1$H-NMR (CDCl$_3$) δ: 2.60 (3H, s), 3.21 (3H, s), 5.30 (2H, s), 6.97 (2H, d, J=8.7 Hz), 7.08 (1H, s), 7.13 (2H, d, J=8.7 Hz), 7.25-7.49 (8H, m), 7.65 (1H, dd, J=1.8, 8.4 Hz), 7.80 (2H, d, J=8.7 Hz), 7.95 (2H, d, J=8.7 Hz), 8.36 (1H, d, J=8.4 Hz).

EXAMPLE 383

2-[4-(4-acetylaminobenzenesulfonylamino)benzyl]-6-bromo-1-oxo-4-phenyl-1,2-dihydroisoquinoline-3-carboxylic acid methyl ester yield: 29%
$^1$H-NMR (DMSO-d$_6$) δ: 2.05 (3H, s), 3.16 (3H, s), 5.15 (2H, s), 6.98-7.51 (10H, m), 7.60-7.70 (4H, m), 7.80 (1H, dd, J=1.8, 8.4 Hz), 8.27 (1H, d, J=8.4 Hz).

EXAMPLE 384

2-[4-(2-acetylamino-4-methylthiazol-5-sulfonylamino)benzyl]-6-bromo-1-oxo-4-phenyl-1,2-dihydroisoquinoline-3-carboxylic acid methyl ester yield: 17%
$^1$H-NMR (DMSO-d$_6$) δ: 2.12 (3H, s), 2.25 (3H, s), 3.20 (3H, s), 5.19 (2H, s), 7.05-7.29 (7H, m), 7.45-7.58 (3H, m), 7.82 (1H, dd, J=1.8, 8.4 Hz), 8.28 (1H, d, J=8.4 Hz).

EXAMPLE 385

6-bromo-2-[4-(4-fluorobenzenesulfonylamino)benzyl]-1-oxo-4-phenyl-1,2-dihydroisoquinoline-3-carboxylic acid methyl ester yield: 32%
$^1$H-NMR (CDCl$_3$) δ: 3.20 (3H, s), 5.32 (2H, s), 6.80 (1H, s), 6.95-7.15 (7H, m), 7.64-7.75 (3H, m), 8.37 (1H, d, J=8.7 Hz).

EXAMPLE 386

6-bromo-2-(4-{5-[(4-chlorobenzoylamino)methyl]thiophen-2-sulfonylamino}benzyl)-1-oxo-4-phenyl-1,2-dihydroisoquinoline-3-carboxylic acid methyl ester yield: 51%
$^1$H-NMR (DMSO-d$_6$) δ: 3.19 (3H, s), 4.58 (2H, d, J=5.8 Hz), 5.17 (2H, s), 6.97-7.53 (14H, m), 7.79-7.88 (3H, m), 8.27 (1H, d, J=8.6 Hz), 9.28 (1H, m).

EXAMPLE 387

6-bromo-2-[4-(4-methoxycarbonylbenzoylamino)benzyl]-1-oxo-4-phenyl-1,2-dihydroisoquinoline-3-carboxylic acid methyl ester To a solution of 2-(4-aminobenzyl)-6-bromo-1-oxo-4-phenyl-1,2-dihydroisoquinoline-3-carboxylic acid methyl ester (139 mg) in dichloromethane (5 ml) were added terephthalic acid monomethyl ester (65 mg), 1-hydroxy-1H-benzotriazole (64 mg) and dimethylpyridin-4-yl-amine (51 mg), and then 1-ethyl-3-(3-dimethylaminopropyl)carbodiimide (103 mg) was added at room temperature. The mixture was stirred at room temperature for 15 hrs. Dichloromethane was added, and the mixture was washed with 1N hydrochloric acid and saturated brine and dried by adding sodium sulfate. The solvent was evaporated under reduced pressure and the obtained residue was purified by silica gel column chromatography (ethyl acetate/methanol=1/0-+9/1) to give the title compound (103 mg, 55%).

$^1$H-NMR (CDCl$_3$) δ: 3.26 (3H, s), 3.95 (3H, s), 5.39 (2H, s), 7.25-7.67 (10H, m), 7.90 (2H, d, J=8.4 Hz), 7.99 (1H, s), 8.12 (2H, d, J=8.2 Hz), 8.37 (1H, d, J=8.4 Hz).

EXAMPLE 388

6-bromo-2-(4-hydrazinocarbonylbenzyl)-1-oxo-4-phenyl-1,2-dihydroisoquinoline-3-carboxylic acid methyl ester hydrochloride To 6-bromo-2-[4-(N'-tert-butoxycarbonylhydrazinocarbonyl)benzyl]-1-oxo-4-phenyl-1,2-dihydroisoquinoline-3-carboxylic acid methyl ester (158 mg) was added a solution (5 ml) of 4N hydrochloric acid ethyl acetate at room temperature and the mixture was stirred at room temperature for 1 hr. The solvent was evaporated under reduced pressure and the obtained residue was crystallized from diisopropyl ether to give the title compound (112 mg, 79%).

$^1$H-NMR (DMSO-d$_6$) δ: 3.30 (3H, s), 5.32 (2H, s), 7.26-7.53 (8H, m), 7.82-7.87 (3H, m), 8.30 (1H, d, J=8.8 Hz).

EXAMPLE 389

4-(3-acetyl-6-bromo-1-oxo-4-phenyl-1H-isoquinolin-2-ylmethyl)benzoic acid methyl ester

[Step 1] To an aqueous solution (180 ml) of sodium sulfite (9.7 g) and sodium hydrogen carbonate (11.8 g) was added 4-cyanobenzenesulfonyl chloride (14.1 g) at room temperature and the mixture was stirred at 70° C. for 4 hrs. The solvent was evaporated under reduced pressure and the obtained residue was purified by medium pressure preparative liquid chromatography (MCI GEL, CHP20P (75-150µ), eluant=water) to give sodium 4-cyanobenzenesulfinate (15.9 g, 99%).

$^1$H-NMR (DMSO-d$_6$) δ: 7.64-7.66 (2H, m), 7.73-7.78 (2H, m).

[Step 2] To a solution of sodium 4-cyanobenzenesulfate (946 mg) in dimethylformamide (10 ml) was added ethyl iodide (1.2 ml) and the mixture was stirred at 70° C. for 5 hrs. The solvent was evaporated under reduced pressure, and the residue was partitioned between water and ethyl acetate. The ethyl acetate layer was washed with 10% aqueous sodium sulfite solution and saturated brine and dried by adding sodium sulfate. The solvent was evaporated under reduced pressure and the obtained residue was purified by silica gel column chromatography (n-hexane/ethyl acetate=19/1→1/1) to give 4-ethanesulfonylbenzonitrile (709 mg, 73%).

$^1$H-NMR (CDCl$_3$) δ: 1.30 (3H, t, J=7.5 Hz), 3.16 (2H, q, J=7.5 Hz), 7.88 (2H, d, J=8.4 Hz), 8.04 (2H, d, J=8.4 Hz).

[Step 3] To a mixture of 4-ethanesulfonylbenzonitrile (500 mg) in methanol (6 ml) and tetrahydrofuran (2 ml) was added 28% aqueous ammonia (1 ml) and then Raney nickel (500 mg) was added. Under a hydrogen pressure (0.5 Mpa), the mixture was stirred at room temperature for 2 hrs., and undesired substances were removed by filtration. The filtrate was concentrated under reduced pressure to give 4-ethanesulfonylbenzylamine (408 mg, 82%).

$^1$H-NMR (CDCl$_3$) δ: 1.25 (3H, t, J=7.0 Hz), 3.11 (2H, q, J=7.0 Hz), 3.99 (2H, s), 7.54 (2H, d, J=8.4 Hz), 7.84 (2H, d, J=8.4 Hz).

[Step 4] To a solution of 6-bromo-1-oxo-4-phenyl-1H-isochromen-3-carboxylic acid methyl ester (359 mg) in methanol (20 ml) were added 4-ethanesulfonylbenzylamine (400 mg) and triethylamine (0.7 ml), and the mixture was stirred at room temperature for 72 hrs. The solvent was evaporated under reduced pressure, and the residue was partitioned between 1N hydrochloric acid and ethyl acetate. The ethyl acetate layer was washed with saturated brine and dried by adding sodium sulfate. The solvent was evaporated under reduced pressure, 4N hydrochloric acid ethyl acetate solution (5 ml) was added to the obtained residue, and the mixture was stirred at room temperature for 10 hrs. The solvent was evaporated under reduced pressure, water was added and the mixture was extracted with ethyl acetate. The extract was washed with saturated sodium hydrogen carbonate solution and saturated brine and dried by adding sodium sulfate. The obtained residue was purified by silica gel column chromatography (n-hexane/ethyl acetate=7/3→2/3) to give the title compound (297 mg, 55%).

$^1$H-NMR (CDCl$_3$) δ: 1.25 (3H, t, J=7.2 Hz), 3.88 (2H, q, J=7.2 Hz), 3.24 (3H, s), 5.44 (2H, s), 7.27-7.50 (8H, m), 7.68 (1H, dd, J=1.8, 8.4 Hz), 7.85 (2H, d, J=8.4 Hz), 8.39 (1H, d, J=8.4 Hz).

In the same manner as in Example 389, various benzylamines were synthesized from various alkylhalides and sodium 4-cyanobenzenesulfinate and reacted with 6-bromo-1-oxo-4-phenyl-1H-isochromen-3-carboxylic acid methyl ester to give the compounds of Examples 390-394.

EXAMPLE 390

6-bromo-1-oxo-4-phenyl-2-[4-(propan-2-sulfonyl-benzyl]-1,2-dihydroisoquinoline-3-carboxylic acid methyl ester

[Step 1] 4-(propan-2-sulfonyl)benzonitrile yield: 52%

$^1$H-NMR (CDCl$_3$) δ: 1.32 (6H, d, J=7.0 Hz), 3.24 (1H, m), 7.88 (2H, d, J=8.4 Hz), 8.03 (2H, d, J=8.4 Hz).

[Step 2] 4-(propan-2-sulfonyl)benzylamine yield: 78%

$^1$H-NMR (CDCl$_3$) δ: 1.27 (6H, d, J=6.6 Hz), 1.67 (2H, brs), 3.19 (1H, m), 3.99 (2H, s), 7.54 (2H, d, J=8.4 Hz), 7.81 (2H, d, J=8.4 Hz).

[Step 3] 6-bromo-1-oxo-4-phenyl-2-[4-(propan-2-sulfonylbenzyl)-1,2-dihydroisoquinoline-3-carboxylic acid methyl ester yield: 48%

$^1$H-NMR (CDCl$_3$) δ: 1.27 (6H, d, J=7.0 Hz), 3.15 (1H, m), 3.22 (3H, s), 5.45 (2H, s), 7.26-7.31 (2H, m), 7.40-7.49 (4H, m), 7.68 (1H, dd, J=1.8, 8.4 Hz), 7.82 (2H, d, J=8.4 Hz), 8.39 (1H, d, J=8.4 Hz).

EXAMPLE 391

6-bromo-2-[4-(2-methylpropan-1-sulfonyl)benzyl]-1-oxo-4-phenyl-1,2-dihydroisoquinoline-3-carboxylic acid methyl ester

[Step 1] 4-(2-methylpropan-1-sulfonyl)benzonitrile yield: 36%
$^1$H-NMR (CDCl$_3$) δ: 1.09 (6H, d, J=6.9 Hz), 2.25 (1H, m), 3.06 (2H, d, J=6.6 Hz), 7.91 (2H, d, J=8.4 Hz), 8.07 (2H, d, J=8.4 Hz).

[Step 2] 4-(2-methylpropan-1-sulfonyl)benzylamine yield: 83%
$^1$H-NMR (CDCl$_3$) δ: 1.06 (6H, d, J=7.0 Hz), 1.69 (2H, brs), 2.21 (1H, m), 3.00 (2H, d, J=6.6 Hz), 3.99 (2H, s), 7.55 (2H, d, J=8.0 Hz), 7.86 (2H, d, J=8.0 Hz).

[Step 3] 6-bromo-2-[4-(2-methylpropan-1-sulfonyl)benzyl]-1-oxo-4-phenyl-1,2-dihydroisoquinoline-3-carboxylic acid methyl ester yield: 27%
$^1$H-NMR (CDCl$_3$) δ: 1.04 (6H, d, J=7.0 Hz), 2.21 (1H, m), 2.95 (2H, d, J=6.6 Hz), 3.23 (3H, s), 5.44 (2H, s), 7.26-7.48 (8H, m), 7.68 (1H, dd, J=1.8, 8.6 Hz), 7.85 (2H, d, J=8.8 Hz), 8.38 (1H, d, J=8.6 Hz).

EXAMPLE 392

6-bromo-2-[4-(4-methoxycarbonyl-phenylmethanesulfonyl)benzyl]-1-oxo-4-phenyl-1,2-dihydroisoquinoline-3-carboxylic acid methyl ester

[Step 1] 4-(2-methylpropan-1-sulfonyl)benzonitrile yield: 93%
$^1$H-NMR (CDCl$_3$) δ: 3.93 (3H, s), 4.41 (2H, s), 7.18 (2H, d, J=8.6 Hz), 7.70-7.80 (4H, m), 7.96 (2H, d, J=8.6 Hz).

[Step 2] 4-(4-cyanobenzenesulfonylmethyl)benzoic acid methyl ester yield: 82%
$^1$H-NMR (CDCl$_3$) δ: 3.91 (3H, s), 4.00 (2H, s), 4.35 (2H, s), 7.16 (2H, d, J=8.4 Hz), 7.41 (2H, d, J=8.4 Hz), 7.57 (2H, d, J=8.4 Hz), 7.92 (2H, d, J=8.4 Hz).

[Step 3] 6-bromo-2-[4-(4-methoxycarbonylphenylmethanesulfonyl)benzyl]-1-oxo-4-phenyl-1,2-dihydroisoquinoline-3-carboxylic acid methyl ester yield: 41%
$^1$H-NMR (CDCl$_3$) δ: 3.23 (3H, s), 3.90 (3H, s), 4.33 (2H, s), 5.43 (2H, s), 7.15 (2H, d, J=8.1 Hz), 7.27-7.51 (10H, m), 7.57 (2H, d, J=8.1 Hz), 7.69 (1H, dd, J=1.8, 8.4 Hz), 7.92 (2H, d, J=8.1 Hz), 8.39 (1H, d, J=8.1 Hz).

EXAMPLE 393

6-bromo-2-[4-(3-methoxycarbonylpropan-1-sulfonyl)benzyl]-1-oxo-4-phenyl-1,2-dihydroisoquinoline-3-carboxylic acid methyl ester

[Step 1] 4-(4-cyanobenzenesulfonyl)butyric acid ethyl ester yield: 49%
$^1$H-NMR (CDCl$_3$) δ: 1.24 (3H, t, J=7.6 Hz), 1.95-2.10 (2H, m), 2.47 (2H, t, J=7.0 Hz), 3.23 (2H, t, J=7.0 Hz), 4.11 (2H, q, J=7.6 Hz), 7.90 (2H, d, J=8.8 Hz), 8.06 (2H, d, J=8.8 Hz).

[Step 2] 4-(4-aminomethylbenzenesulfonyl)butyric acid methyl ester yield: 72%
$^1$H-NMR (CDCl$_3$) δ: 1.65 (2H, brs), 1.93-2.10 (2H, m), 2.31-2.60 (2H, m), 3.08-3.30 (2H, m), 3.64 (3H, s), 3.98 (2H, s), 7.55 (2H, d, J=8.2 Hz), 7.84 (2H, d, J=8.2 Hz).

[Step 3] 6-bromo-2-[4-(3-methoxycarbonylpropan-1-sulfonyl)benzyl]-1-oxo-4-phenyl-1,2-dihydroisoquinoline-3-carboxylic acid methyl ester yield: 39%
$^1$H-NMR (CDCl$_3$) δ: 1.96-2.06 (2H, m), 2.46 (2H, t, J=7.2 Hz), 3.13-3.18 (2H, m), 3.25 (3H, s), 3.65 (3H, s), 5.43 (2H, s), 7.26-7.33 (2H, m), 7.39-7.55 (10H, m), 7.68 (1H, dd, J=2.1, 8.7 Hz), 7.86 (2H, d, J=8.4 Hz), 8.38 (1H, d, J=8.7 Hz).

EXAMPLE 394

6-bromo-2-[4-(4-methoxycarbonyl-butan-1-sulfonyl)benzyl]-1-oxo-4-phenyl-1,2-dihydroisoquinoline-3-carboxylic acid methyl ester

[Step 1] 5-(4-cyanobenzenesulfonyl)pentanic acid methyl ester yield: 44%
$^1$H-NMR (CDCl$_3$) δ: 1.63-1.94 (4H, m), 2.33 (2H, t, J=6.4 Hz), 3.14 (2H, t, J=6.4 Hz), 3.66 (3H, s), 7.89 (2H, d, J=8.4 Hz), 8.05 (2H, d, J=8.4 Hz).

[Step 2] 5-(4-aminomethylbenzenesulfonyl)pentanic acid methyl ester yield: 70%
$^1$H-NMR (CDCl$_3$) δ: 1.60-1.80 (4H, m), 1.63 (2H, brs), 2.25-2.40 (2H, m), 3.00-3.18 (2H, m), 3.64 (3H, s), 3.98 (2H, s), 7.54 (2H, d, J=8.0 Hz), 7.84 (2H, d, J=8.0 Hz).

[Step 3] 6-bromo-2-[4-(4-methoxycarbonylbutan-1-sulfonyl)benzyl]-1-oxo-4-phenyl-1,2-dihydroisoquinoline-3-carboxylic acid methyl ester Yield: 42%

$^1$H-NMR (CDCl$_3$) δ: 1.67-1.79 (4H, m), 2.30 (2H, t, J=6.9 Hz), 3.03-3.10 (2H, m), 3.25 (3H, s), 3.64 (3H, s), 5.43 (2H, s), 7.28-7.32 (2H, m), 7.40-7.51 (10H, m), 7.69 (1H, dd, J=2.1, 8.7 Hz), 7.85 (2H, d, J=8.4 Hz), 8.38 (1H, d, J=8.7 Hz).

EXAMPLE 395

6-bromo-2-[4-(4-methoxycarbonylphenylsulfanylmethyl)benzyl]-1-oxo-4-phenyl-1,2-dihydroisoquinoline-3-carboxylic acid methyl ester To a solution of 6-bromo-2-(4-hydroxymethylbenzyl)-1-oxo-4-phenyl-1,2-dihydroisoquinoline-3-carboxylic acid methyl ester (478 mg) in dichloromethane (10 ml) was added triethylamine (0.21 ml) and methanesulfonyl chloride (0.09 ml) was added under ice-cooling. The mixture was stirred under ice-cooling for 1 hr., diluted with dichloromethane, washed with saturated brine, and dried by adding sodium sulfate. The solvent was evaporated under reduced pressure and the residue was dissolved in dimethylformamide (5 ml). The solution was added to a mixed solution of 4-mercaptobenzoic acid methyl ester (817 mg) and potassium carbonate (415 mg) prepared separately. The mixture was stirred at room temperature for 2 hrs., and the solvent was evaporated under reduced pressure. The residue was partitioned between 1N hydrochloric acid and ethyl acetate. The ethyl acetate layer was washed with saturated aqueous sodium hydrogen carbonate solution and saturated brine and dried by adding sodium sulfate. The solvent was evaporated under reduced pressure and the obtained residue was purified by silica gel column chromatography (n-hexane/ethyl acetate=19/1→7/3) to give the title compound (529 mg, 83%).

$^1$H-NMR (CDCl$_3$) δ: 3.14 (3H, s), 3.87 (3H, s), 4.13 (2H, s), 5.37 (2H, s), 7.18-7.28 (8H, m), 7.35-7.45 (4H, m), 7.63 (1H, dd, J=1.8, 8.7 Hz), 7.86 (2H, d, J=8.4 Hz), 8.37 (1H, d, J=8.4 Hz).

EXAMPLE 396

6-bromo-2-[4-(4-methoxycarbonylbenzenesulfinylmethyl)benzyl]-1-oxo-4-phenyl-1,2-dihydroisoquinoline-3-carboxylic acid methyl ester To a solution of 6-bromo-2-[4-(4-methoxycarbonylphenylsulfanylmethyl)benzyl]-1-oxo-4-phenyl-1,2-dihydroisoquinoline-3-carboxylic acid methyl ester (189 mg) in dichloromethane (20 ml) was added 3-chloroperbenzoic acid (74 mg) under ice-cooling and the mixture was stirred under ice-cooling for 1 hr. The mixture was diluted with dichloromethane, washed with saturated aqueous sodium hydrogen carbonate solution and saturated brine and dried by adding sodium sulfate. The solvent was evaporated under reduced pressure and the obtained residue was purified by silica gel column chromatography (n-hexane/ethyl acetate=7/3→1/4) to give the title compound (95 mg, 49%).

$^1$H-NMR (CDCl$_3$) δ: 3.26 (3H, s), 3.92 (3H, s), 4.02 (2H, s), 5.39 (2H, s), 6.90 (2H, d, J=8.4 Hz), 7.16 (2H, d, J=8.4 Hz), 7.27-7.48 (8H, m), 7.66 (1H, dd, J=1.8, 8.4 Hz), 8.05 (2H, d, J=8.8 Hz), 8.39 (1H, d, J=8.4 Hz).

EXAMPLE 397

6-bromo-2-[4-(4-methoxycarbonylbenzenesulfonylmethyl)benzyl]-1-oxo-4-phenyl-1,2-dihydroisoquinoline-3-carboxylic acid methyl ester To a solution of 6-bromo-2-[4-(4-methoxycarbonylphenylsulfanylmethyl)benzyl]-1-oxo-4-phenyl-1,2-dihydroisoquinoline-3-carboxylic acid methyl ester (189 mg) in dichloromethane (20 ml) was added, 3-chloroperbenzoic acid (222 mg) under ice-cooling and the mixture was stirred at room temperature for 5 hrs. The mixture was diluted with dichloromethane, washed with 10% aqueous sodium sulfite solution, saturated aqueous sodium hydrogen carbonate solution and saturated brine and dried by adding sodium sulfate. The solvent was evaporated under reduced pressure and the obtained residue was purified by silica gel column chromatography (n-hexane/ethyl acetate=7/3→1/4) to give the title compound (179 mg, 90%).

$^1$H-NMR (CDCl$_3$) δ: 3.24 (3H, s), 3.94 (3H, s), 4.29 (2H, s), 5.40 (2H, s), 7.02 (2H, d, J=8.2 Hz), 7.17 (2H, d, J=8.2 Hz), 7.25-7.55 (5H, m), 7.60-7.70 (4H, m), 8.07 (2H, d, J=8.8 Hz), 8.39 (1H, d, J=8.8 Hz).

EXAMPLE 398

6-bromo-2-[4-(4-carboxypiperidine-1-carbonyl)benzyl]-1-oxo-4-phenyl-1,2-dihydroisoquinoline-3-carboxylic acid methyl ester To a mixture of 6-bromo-2-[4-(4-ethoxycarbonylpiperidine-1-carbonyl)benzyl]-1-oxo-4-phenyl-1,2-dihydroisoquinoline-3-carboxylic acid methyl ester (290 mg), methanol (5 ml) and tetrahydrofuran (5 ml) was added a solution (0.1 ml) of 8N aqueous sodium hydroxide and the mixture was stirred at room temperature for 12 hrs. The solvent was evaporated under reduced pressure, water was added and the mixture was acidified with 1N hydrochloric acid and extracted with ethyl acetate. The extract was washed with saturated brine and dried by adding sodium sulfate. The solvent was evaporated under reduced pressure and the obtained residue was purified by preparative liquid chromatography to give the title compound (72 mg, 26%).

$^1$H-NMR (CDCl$_3$) δ: 1.60-2.10 (4H, m), 2.60 (1H, m), 2.98-3.12 (2H, m), 3.23 (3H, s), 3.71 (1H, m), 4.46 (1H, m), 5.40 (2H, s), 7.26-7.49 (10H, m), 7.67 (1H, dd, J=1.8, 8.4 Hz), 8.39 (1H, d, J=8.4 Hz).

In the same manner as in Example 398, various ester derivatives were hydrolyzed to give carboxylic acid derivatives of Examples 399-410.

EXAMPLE 399

6-bromo-2-[4-(2-carboxyethyl)benzyl]-1-oxo-4-phenyl-1,2-dihydroisoquinoline-3-carboxylic acid methyl ester yield: 81%

$^1$H-NMR (CDCl$_3$) δ: 1.60-2.10 (4H, m), 2.60 (1H, m), 2.98-3.12 (2H, m), 3.23 (3H, s), 3.71 (1H, m), 4.46 (1H, m), 5.40 (2H, s), 7.26-7.49 (10H, m), 7.67 (1H, dd, J=1.8, 8.4 Hz), 8.39 (1H, d, J=8.4 Hz).

EXAMPLE 400

6-bromo-2-[4-(4-carboxybenzoylamino)benzyl]-1-oxo-4-phenyl-1,2-dihydroisoquinoline-3-carboxylic acid methyl ester yield: 88%

$^1$H-NMR (DMSO-d$_6$) δ: 3.80 (3H, s), 5.83 (2H, s), 7.70-7.83 (5H, m), 7.92-7.99 (3H, m), 8.21-8.28 (3H, m), 8.50-8.61 (4H, m), 8.84 (1H, d, J=8.8 Hz).

EXAMPLE 401

6-bromo-2-[4-(4-carboxybenzylcarbamoyl)benzyl]-1-oxo-4-phenyl-1,2-dihydroisoquinoline-3-carboxylic acid methyl ester yield: 97%
$^1$H-NMR (CDCl$_3$) δ: 3.23 (3H, s), 4.71 (2H, d, J=5.7 Hz), 5.42 (2H, s), 6.47 (1H, m), 7.26-7.45 (10H, m), 7.67 (1H, dd, J=1.8, 8.4 Hz), 7.74 (2H, d, J=8.4 Hz), 8.05 (2H, d, J=8.4 Hz), 8.39 (1H, d, J=8.4 Hz).

EXAMPLE 402

6-bromo-2-{4-[(4-carboxycyclohexylmethyl)carbamoyl]benzyl}-1-oxo-4-phenyl-1,2-dihydroisoquinoline-3-carboxylic acid methyl ester Yield: 97%

$^1$H-NMR (CDCl$_3$) δ: 1.00-1.13 (2H, m), 1.30-1.50 (3H, m), 1.73-2.11 (4H, m), 2.28 (1H, m), 3.24 (3H, s), 3.18-3.32 (2H, m), 5.42 (2H, s), 6.21 (1H, t, J=5.8 Hz), 7.26-7.46 (8H, m), 7.65-7.71 (3H, m), 8.39 (1H, d, J=8.4 Hz).

EXAMPLE 403

6-bromo-2-[4-(3-carboxyacryloylamino)benzyl]-1-oxo-4-phenyl-1,2-dihydroisoquinoline-3-carboxylic acid methyl ester yield: 22%
$^1$H-NMR (DMSO-d$_6$) δ: 3.45 (3H, s), 5.82 (2H, s), 7.73-8.00 (10H, m), 8.19 (1H, dd, J=1.8, 8.4 Hz), 8.44 (2H, d, J=7.8 Hz), 8.76 (1H, d, J=8.4 Hz).

EXAMPLE 404

6-bromo-2-[4-(carboxymethylcarbamoyl)benzyl]-1-oxo-4-phenyl-1,2-dihydroisoquinoline-3-carboxylic acid yield: 71%
$^1$H-NMR (DMSO-d$_6$) δ: 3.91 (2H, d, J=5.8 Hz), 5.33 (2H, s), 7.91 (1H, d, J=1.8 Hz), 7.25-7.52 (7H, m), 7.74-7.83 (3H, m), 8.27 (1H, d, J=8.4 Hz), 8.77 (1H, t, J=5.8 Hz).

EXAMPLE 405

6-bromo-2-[4-(4-carboxyphenylsulfanylmethyl)benzyl]-1-oxo-4-phenyl-1,2-dihydroisoquinoline-3-carboxylic acid methyl ester yield: 70%
$^1$H-NMR (CDCl$_3$) δ: 3.15 (3H, s), 4.17 (2H, s), 5.87 (2H, s), 7.19-7.48 (12H, m), 7.66 (1H, dd, J=1.8, 8.4 Hz), 7.93 (2H, d, J=8.4 Hz), 8.40 (1H, d, J=8.4 Hz).

EXAMPLE 406

6-bromo-2-[4-(4-carboxybenzenesulfonylmethyl)benzyl]-1-oxo-4-phenyl-1,2-dihydroisoquinoline-3-carboxylic acid methyl ester yield: 63%
$^1$H-NMR (DMSO-d$_6$) δ: 3.26 (3H, s), 4.71 (2H, s), 5.26 (2H, s), 7.08-7.20 (4H, m), 7.24 (1H, d, J=1.8 Hz), 7.29-7.35 (2H, m), 7.45-7.55 (3H, m), 7.77-7.86 (3H, m), 8.07 (2H, d, J=8.0 Hz), 8.30 (1H, d, J=8.4 Hz).

EXAMPLE 407

6-bromo-2-[4-(4-carboxybenzenesulfinylmethyl)benzyl]-1-oxo-4-phenyl-1,2-dihydroisoquinoline-3-carboxylic acid methyl ester yield: 80%
$^1$H-NMR (DMSO-d$_6$) δ: 3.28 (3H, s), 4.07 (1H, d, J=12.8 Hz), 4.07 (1H, d, J=12.8 Hz), 5.26 (2H, s), 7.02 (2H, d, J=8.4 Hz), 7.11 (2H, d, J=8.4 Hz), 7.23-7.38 (3H, m), 7.49-7.60 (5H, m), 7.83 (1H, dd, J=1.8, 8.4 Hz), 8.01 (2H, d, J=8.4 Hz), 8.31 (1H, d, J=8.4 Hz).

EXAMPLE 408

6-bromo-2-[4-(4-carboxyphenylmethanesulfonyl)benzyl]-1-oxo-4-phenyl-1,2-dihydroisoquinoline-3-carboxylic acid methyl ester yield: 70%
$^1$H-NMR (CDCl$_3$) δ: 3.24 (3H, s), 4.34 (2H, s), 5.43 (2H, s), 7.28 (2H, d, J=8.4 Hz), 7.26-7.48 (8H, m), 7.59 (2H, d, J=8.4 Hz), 7.69 (1H, dd, J=1.8, 8.8 Hz), 7.98 (2H, d, J=8.7 Hz), 8.39 (1H, d, J=8.8 Hz).

EXAMPLE 409

6-bromo-2-[4-(3-carboxypropan-1-sulfonyl)benzyl]-1-oxo-4-phenyl-1,2-dihydroisoquinoline-3-carboxylic acid methyl ester yield: 77%
$^1$H-NMR (CDCl$_3$) δ: 1.95-2.05 (2H, m), 2.47 (2H, t, J=6.6 Hz), 3.12-3.24 (2H, m), 3.27 (3H, s), 5.41 (2H, s), 7.26-7.50 (8H, m), 7.68 (1H, dd, J=1.8, 8.6 Hz), 7.85 (2H, d, J=8.6 Hz), 8.36 (1H, d, J=8.6 Hz).

EXAMPLE 410

6-bromo-2-[4-(4-carboxybutan-1-sulfonyl)benzyl]-1-oxo-4-phenyl-1,2-dihydroisoquinoline-3-carboxylic acid methyl ester yield: 60%
$^1$H-NMR (CDCl$_3$) δ: 1.60-1.80 (4H, m), 2.20-2.35 (2H, m), 3.00-3.16 (2H, m), 3.32 (3H, s), 5.37 (2H, s), 7.28-7.50 (8H, m), 7.68 (1H, dd, J=1.8, 8.4 Hz), 7.84 (2H, d, J=8.4 Hz), 8.35 (1H, d, J=8.4 Hz).

EXAMPLE 411

4-(3-acetyl-6-bromo-1-oxo-4-phenyl-1H-isoquinolin-2-ylmethyl)benzoic acid methyl ester

[Step 1] To a solution of 6-bromo-4-phenyl-3-isocoumarincarboxylic acid (10.3 g), 2,2-dimethyl-[1,3]dioxane-4,6-dione (4.76 g), dimethylpyridin-4-yl-amine (5.50 g) and triethylamine (6.3 ml) in dichloromethane (100 ml) was added 1-ethyl-3-(3-dimethylaminopropyl)-carbodiimide (8.6 g) at room temperature and the mixture was stirred at room temperature for 15 hrs. The mixture was diluted with dichloromethane, washed with 1N hydrochloric acid and saturated brine and dried by adding sodium sulfate. The solvent was evaporated under reduced pressure and the obtained residue dissolved in water (200 ml) and acetic acid (100 ml) and the mixture was heated under reflux for 10 hrs. The solvent was evaporated under reduced pressure, water was added and the mixture was extracted with ethyl acetate. The extract was washed with saturated sodium hydrogen carbonate solution and saturated brine and dried by adding sodium sulfate. The obtained residue was crystallized from diisopropyl ether to give 3-acetyl-6-bromo-4-phenyl-isochromen-1-one (8.29 g, 81%).

$^1$H-NMR (CDCl$_3$) δ: 2.44 (3H, s), 7.19-7.28 (3H, m), 7.48-7.58 (3H, m), 7.76 (1H, dd, J=1.8, 8.4 Hz), 8.27 (1H, d, J=8.4 Hz).

[Step 2] To a solution of 3-acetyl-6-bromo-4-phenyl-isochromen-1-one (1.03 g) in methanol (100 ml) were added 4-aminomethyl-benzoic acid methyl ester hydrochloride (3.02 g) and triethylamine (4.2 ml) and the mixture was stirred at room temperature for 18 hrs. The solvent was evaporated under reduced pressure, 1N hydrochloric acid was added, and the mixture was extracted with ethyl acetate. The extract was washed with saturated brine and dried by adding sodium sulfate. The solvent was evaporated under reduced pressure, 4N hydrochloric acid ethyl acetate solution (5 ml) was added to the obtained residue, and the mixture was stirred at room temperature for 10 hrs. The solvent was evaporated under reduced pressure, water was added and the mixture was extracted with ethyl acetate. The extract was washed with saturated sodium hydrogen carbonate solution and saturated brine and dried by adding sodium sulfate. The obtained residue was purified by silica gel column chromatography (n-hexane/ethyl acetate=19/1→3/1) to give the title compound (220 mg, 15%).

$^1$H-NMR (CDCl$_3$) δ: 1.25 (3H, s), 3.89 (3H, s), 3.64 (3H, s), 5.49 (2H, s), 7.20-7.29 (6H, m), 7.42-7.50 (4H, m), 7.69 (1H, dd, J=1.8, 8.4 Hz), 7.97 (2H, d, J=8.4 Hz), 8.39 (1H, d, J=8.4 Hz).

In the same manner as in Example 411, 3-acetyl-6-bromo-4-phenylisochromen-1-one was reacted with various amines to give the compounds of Examples 412-417.

EXAMPLE 412

3-acetyl-2-(4-aminobenzyl)-6-bromo-4-phenyl-2H-isoquinolin-1-one yield: 7%

$^1$H-NMR (CDCl$_3$) δ: 1.21 (3H, s), 3.64 (2H, s), 5.35 (2H, s), 6.58 (2H, d, J=8.4 Hz), 6.93 (2H, d, J=8.4 Hz), 7.22-7.25 (2H, m), 7.38-7.45 (4H, m), 7.65 (1H, dd, J=1.8, 8.4 Hz), 8.42 (1H, d, J=8.4 Hz).

EXAMPLE 413

3-acetyl-6-bromo-2-(4-methylsulfanylbenzyl)-4-phenyl-2H-isoquinolin-1-one yield: 28%

$^1$H-NMR (CDCl$_3$) δ: 1.26 (3H, s), 2.43 (3H, s), 5.39 (2H, s), 7.07-7.26 (6H, m), 7.40-7.46 (4H, m), 7.66 (1H, dd, J=1.8, 8.4 Hz), 8.42 (1H, d, J=8.4 Hz).

EXAMPLE 414

3-acetyl-6-bromo-2-(4-ethanesulfonylbenzyl)-4-phenyl-2H-isoquinolin-1-one yield: 4%

$^1$H-NMR (CDCl$_3$) δ: 1.24 (3H, t, J=7.6 Hz), 1.41 (3H, s), 3.08 (2H, q, J=7.6 Hz), 5.47 (2H, s), 7.26-7.50 (8H, m), 7.70 (1H, dd, J=1.8, 8.8 Hz), 7.85 (1H, d, J=8.4 Hz), 8.41 (1H, d, J=8.8 Hz).

EXAMPLE 415

3-acetyl-6-bromo-4-phenyl-2-(4-sulfamoylbenzyl)-2H-isoquinolin-1-one yield: 14%

$^1$H-NMR (DMSO-d$_6$) δ: 1.72 (3H, s), 5.25 (2H, s), 7.26-7.39 (7H, m), 7.50-7.56 (3H, m), 7.76-7.84 (3H, m), 8.29 (1H, d, J=8.4 Hz).

EXAMPLE 416

4-[4-(3-acetyl-6-bromo-1-oxo-4-phenyl-1H-isoquinolin-2-ylmethyl)benzenesulfonyl]butyric acid ethyl ester yield: 9%

$^1$H-NMR (CDCl$_3$) δ: 1.22 (3H, t, J=7.4 Hz), 1.42 (3H, s), 1.90-2.05 (2H, m), 2.43 (2H, t, J=7.0 Hz), 3.11-3.18 (2H, m), 4.09 (2H, q, J=7.4 Hz), 5.47 (2H, s), 7.26-7.51 (8H, m), 7.70 (1H, dd, J=1.8, 8.4 Hz), 7.86 (1H, d, J=8.4 Hz), 8.41 (1H, d, J=8.4 Hz).

EXAMPLE 417

5-[4-(3-acetyl-6-bromo-1-oxo-4-phenyl-1H-isoquinolin-2-ylmethyl)benzenesulfonyl]pentanic acid ethyl ester yield: 13%

$^1$H-NMR (CDCl$_3$) δ: 1.23 (3H, t, J=7.0 Hz), 1.42 (3H, s), 1.58-1.82 (4H, m), 2.08-2.38 (2H, m), 2.95-3.19 (2H, m), 4.09 (2H, q, J=7.4 Hz), 5.46 (2H, s), 7.26-7.60 (8H, m), 7.68-7.86 (3H, m), 8.41 (1H, d, J=8.4 Hz).

EXAMPLE 418

1-[4-(3-acetyl-6-bromo-1-oxo-4-phenyl-1H-isoquinolin-2-ylmethyl)benzenesulfonyl]piperidine-4-carboxylic acid ethyl ester

[Step 1] To a solution of ethyl isonipecotate (1.2 g) in tetrahydrofuran (10 ml) was added triethylamine (2.1 ml) at room temperature, 4-cyanobenzenesulfonyl (1.0 g) was added and the mixture was stirred at room temperature for 4 hrs. The solvent was evaporated under reduced pressure, and partitioned between water and ethyl acetate. The ethyl acetate layer was washed with 1N hydrochloric acid, saturated aqueous sodium hydrogen carbonate solution and saturated brine and dried by adding sodium sulfate. The solvent was evaporated under reduced pressure to give 1-(4-cyanobenzenesulfonyl)piperidine-4-carboxylic acid ethyl ester (1.36 g, 84%).

$^1$H-NMR (CDCl$_3$) δ: 1.23 (3H, t, J=7.4 Hz), 1.78-2.04 (4H, m), 2.30 (1H, m), 2.52-2.65 (2H, m), 3.58-3.68 (2H, m), 4.12 (2H, q, J=7.4 Hz), 7.13-7.91 (4H, m).

[Step 2] To a mixture of 1-(4-cyanobenzenesulfonyl)piperidine-4-carboxylic acid ethyl ester (1.36 g) in ethanol (84 ml) and tetrahydrofuran (14 ml) was added 28% aqueous ammonia (3 ml) and then Raney nickel (500 mg) was added. Under a hydrogen pressure (0.5 Mpa), the mixture was stirred at room temperature for 2 hrs., and undesired substances were removed by filtration. The filtrate was concentrated under reduced pressure to give 1-(4-aminomethylbenzenesulfonyl) piperidine-4-carboxylic acid ethyl ester (1.05 g, 77%).

¹H-NMR (DMSO-d₆)δ: 1.15 (3H, t, J=7.6 Hz), 1.48-1.60 (2H, m), 1.82-1.99 (2H, m), 2.15-2.58 (3H, m), 3.42-3.60 (2H, m), 4.03 (2H, q, J=7.6 Hz), 4.14 (2H, s), 7.60-7.95 (4H, m).

[Step 3] To a solution of 3-acetyl-6-bromo-4-phenylisochromen-1-one (343 mg) in methanol (20 ml) were added 1-(4-aminomethylbenzenesulfonyl)piperidine-4-carboxylic acid ethyl ester (979 mg) and triethylamine (1.4 ml), and the mixture was stirred at room temperature for 72 hrs. The solvent was evaporated under reduced pressure, and partitioned between 1N hydrochloric acid and ethyl acetate. The ethyl acetate layer was washed with saturated brine and dried by adding sodium sulfate. The solvent was evaporated under reduced pressure, 4N hydrochloric acid ethyl acetate solution (5 ml) was added to the obtained residue, and the mixture was stirred at room temperature for 10 hrs. The solvent was evaporated under reduced pressure, water was added and the mixture was extracted with ethyl acetate. The extract was washed with saturated sodium hydrogen carbonate solution and saturated brine and dried by adding sodium sulfate. The obtained residue was purified by silica gel column chromatography (n-hexane/ethyl acetate=7/3→2/3) to give the title compound (91 mg, 14%). ¹H-NMR (CDCl₃) δ: 1.21 (3H, t, J=7.0 Hz), 1.37 (3H, s), 1.65-2.01 (4H, m), 2.11 (1H, m), 2.38-2.56 (2H, m), 3.50-3.66 (2H, m), 4.09 (2H, q, J=7.0 Hz), 5.47 (2H, s), 7.24-7.50 (8H, m), 7.67-7.76 (3H, m), 8.41 (1H, d, J=8.4 Hz).

In the same manner as in Example 418, various benzylamines were synthesized from 4-cyanobenzenesulfonyl and various amines and reacted with 3-acetyl-6-bromo-4-phenylisochromen-1-one to give the compounds of Examples 419 and 420.

EXAMPLE 419

3-[4-(3-acetyl-6-bromo-1-oxo-4-phenyl-1H-isoquinolin-2-ylmethyl)benzenesulfonylamino]propionic acid ethyl ester

[Step 1] 3-(4-cyanobenzenesulfonylamino)propionic acid ethyl ester yield: 77%
¹H-NMR (CDCl₃) δ: 1.26 (3H, t, J=7.2 Hz), 2.56 (2H, t, J=6.3 Hz), 3.20-3.26 (2H, m), 4.13 (2H, q, J=7.2 Hz), 5.43 (1H, t, J=6.0 Hz), 7.82 (2H, d, J=8.7 Hz), 7.98 (2H, d, J=8.7 Hz).

[Step 2] 3-(4-aminomethylbenzenesulfonylamino)propionic acid ethyl ester yield: 87%
¹H-NMR (DMSO-d₆)δ: 1.67 (3H, t, J=7.4 Hz), 2.44 (2H, d, J=6.6 Hz), 2.90-3.00 (2H, m), 4.03 (2H, q, J=6.6 Hz), 4.12 (2H, s), 4.23 (1H, s), 7.71-7.89 (4H, m).

[Step 3] 3-[4-(3-acetyl-6-bromo-1-oxo-4-phenyl-1H-isoquinolin-2-ylmethyl)benzenesulfonylamino]propionic acid ethyl ester
yield: 18%
¹H-NMR (CDCl₃) δ: 1.22 (3H, t, J=7.2 Hz), 1.39 (3H, s), 2.50 (2H, t, J=5.7 Hz), 3.11-3.17 (2H, m), 4.09 (2H, q, J=7.2 Hz), 5.30 (1H, t, J=6.3 Hz), 5.45 (2H, s), 7.26-7.48 (8H, m), 7.68 (1H, dd, J=1.8, 8.7 Hz), 7.79 (2H, d, J=8.1 Hz), 8.40 (1H, d, J=8.7 Hz).

EXAMPLE 420

4-[4-(3-acetyl-6-bromo-1-oxo-4-phenyl-1H-isoquinolin-2-ylmethyl)benzenesulfonylamino]butyric acid methyl ester

[Step 1] 4-(4-cyanobenzenesulfonylamino)butyric acid methyl ester yield: 89%
¹H-NMR (CDCl₃) δ: 1.76-1.89 (2H, m), 2.39 (2H, t, J=6.6 Hz), 3.02-3.12 (2H, m), 3.67 (3H, s), 5.04 (1H, t, J=6.2 Hz), 7.83 (2H, d, J=8.4 Hz), 7.98 (2H, d, J=8.4 Hz).

[Step 2] 4-(4-aminomethylbenzenesulfonylamino)butyric acid methyl ester yield: 74%
¹H-NMR (DMSO-d₆)δ: 1.55-1.78 (2H, m), 2.32 (2H, t, J=7.4 Hz), 2.69-2.80 (2H, m), 3.56 (3H, s), 4.11 (2H, s), 4.21 (1H, s), 7.71-7.88 (4H, m).

[Step 3] 4-[4-(3-acetyl-6-bromo-1-oxo-4-phenyl-1H-isoquinolin-2-ylmethyl)benzenesulfonylamino]butyric acid methyl ester yield: 38%
¹H-NMR (CDCl₃) δ: 1.39 (3H, s), 1.74-1.81 (2H, m), 2.34 (2H, t, J=7.2 Hz), 2.92-2.98 (2H, m), 3.63 (3H, s), 4.97 (1H, t, J=6.3 Hz), 5.44 (2H, s), 7.25-7.28 (2H, m), 7.34 (2H, d, J=8.4 Hz), 7.43-7.48 (4H, m), 7.68 (1H, dd, J=2.1, 8.7 Hz), 7.77 (2H, d, J=8.4 Hz), 8.40 (1H, d, J=8.7 Hz).

EXAMPLE 421

4-[4-(3-acetyl-6-bromo-1-oxo-4-phenyl-1H-isoquinolin-2-ylmethyl)phenylsulfamoyl]benzoic acid In the same manner as in Example 377, 3-acetyl-2-(4-aminobenzyl)-6-bromo-4-phenyl-2H-isoquinolin-1-one was reacted with 4-carboxybenzenesulfonyl chloride to give the title compound. yield: 45 mg (26%)
¹H-NMR (CDCl₃) δ: 1.17 (3H, s), 5.34 (2H, s), 6.68 (1H, s), 6.95-8.10 (15H, m), 8.39 (1H, d, J=6.6 Hz).

EXAMPLE 422

4-(3-acetyl-6-bromo-1-oxo-4-phenyl-1H-isoquinolin-2-ylmethyl)benzoic acid

To a mixture of methyl 4-(3-acetyl-6-bromo-1-oxo-4-phenyl-1H-isoquinolin-2-ylmethyl)benzoate (510 mg) in methanol (5 ml) and tetrahydrofuran (5 ml) was added 1N aqueous sodium hydroxide solution (4 ml) and the mixture was stirred at room temperature for 12 hrs. The solvent was evaporated under reduced pressure and water was added. The mixture was acidified with 1N hydrochloric acid and extracted with ethyl acetate. The extract was washed with saturated brine and dried by adding sodium sulfate. The solvent was evaporated under reduced pressure and the obtained residue was recrystallized from methanol to give the title compound (467 mg, 94%).
¹H-NMR (CDCl₃) δ: 1.31 (3H, s), 5.49 (2H, s), 7.22-7.33 (5H, m), 7.41-7.50 (3H, m), 7.69 (1H, dd, J=1.8, 8.4 Hz), 8.03 (2H, d, J=8.4 Hz), 8.43 (1H, d, J=8.4 Hz).

EXAMPLE 423

4-(3-acetyl-6-bromo-1-oxo-4-phenyl-1H-isoquinolin-2-ylmethyl)-N-methoxy-N-methylbenzamide To a solution of 4-(3-acetyl-6-bromo-1-oxo-4-phenyl-1H-isoquinolin-2-ylmethyl)benzoic acid (476 mg) in dichloromethane (10 ml) were added O,N-dimethylhydroxylamine hydrochloride (117 mg), 1-hydroxy-1H-benzotriazole (184 mg) and triethylamine (0.21 ml) and then 1-ethyl-3-(3-dimethylaminopropyl)carbodiimide (287 mg) was added at room temperature, and the mixture was stirred at room temperature for 15 hrs. Dichloromethane was added, and the mixture was washed with saturated aqueous sodium hydrogen carbonate solution and saturated brine and sodium sulfate was added to dry the mixture. The solvent was evaporated under reduced pressure and the obtained residue was purified by silica gel column chromatography (n-hexane/ethyl acetate=1/1→1/9) to give the title compound (407 mg, 78%).

$^1$H-NMR (CDCl$_3$) δ: 1.25 (3H, s), 3.33 (3H, s), 3.47 (3H, s), 5.49 (2H, s), 7.20-7.35 (4H, m), 7.42-7.52 (4H, m), 7.60-7.74 (3H, m), 8.44 (1H, d, J=8.4 Hz).

EXAMPLE 424

3-acetyl-2-(4-acetylbenzyl)-6-bromo-4-phenyl-2H-isoquinolin-1-one

To a solution of 4-(3-acetyl-6-bromo-1-oxo-4-phenyl-1H-isoquinolin-2-ylmethyl)-N-methoxy-N-methylbenzamide (330 mg) in tetrahydrofuran (10 ml) was added methyl magnesium bromide (3M tetrahydrofuran solution, 0.64 ml) under ice-cooling and the mixture was stirred for 2 hrs. under ice-cooling. The reaction solution was poured into saturated aqueous ammonium chloride solution, extracted with ethyl acetate, washed with saturated brine and dried by adding sodium sulfate. The solvent was evaporated under reduced pressure and the obtained residue was purified by silica gel column chromatography (n-hexane/ethyl acetate=19/1→7/3) to give the title compound (259 mg, 87%).

$^1$H-NMR (CDCl$_3$) δ: 1.31 (3H, s), 2.57 (3H, s), 5.48 (2H, s), 7.23-7.32 (4H, m), 7.40-7.50 (4H, m), 7.69 (1H, dd, J=2.0, 8.4 Hz), 7.90 (2H, d, J=8.6 Hz), 8.44 (1H, d, J=8.4 Hz).

EXAMPLE 425

3-acetyl-6-bromo-2-[4-(1-hydroxyiminoethyl)benzyl]-4-phenyl-2H-isoquinolin-1-one To a solution of 3-acetyl-2-(4-acetylbenzyl)-6-bromo-4-phenyl-2H-isoquinolin-1-one (95 mg) in ethanol (10 ml) were added hydroxylamine hydrochloride (17 mg) and sodium acetate (29 mg) at room temperature and the mixture was heated under reflux for 6 hrs. The solvent was evaporated under reduced pressure and the residue was partitioned between ethyl acetate and saturated aqueous sodium hydrogen carbonate solution, washed with saturated brine and dried by adding sodium sulfate. The solvent was evaporated under reduced pressure and the obtained residue was purified by silica gel column chromatography (n-hexane/ethyl acetate=4/1→3/2) to give the title compound (84 mg, 86%).

$^1$H-NMR (CDCl$_3$) δ: 1.25 (3H, s), 2.22 (3H, s), 5.46 (2H, s), 7.16-7.28 (4H, m), 7.42-7.47 (4H, m), 7.56 (2H, d, J=8.0 Hz), 7.68 (1H, dd, J=1.8, 8.4 Hz), 7.90 (1H, brs), 8.44 (1H, d, J=8.4 Hz).

EXAMPLE 426

3-acetyl-6-bromo-2-[4-(1E-methoxyiminomethyl)benzyl]-4-phenyl-2H-isoquinolin-1-one The title compound (88 mg, 87%) was synthesized by a method similar to that in Example 425 and using O-methylhydroxylamine.

$^1$H-NMR (CDCl$_3$) δ: 1.25 (3H, s), 2.22 (3H, s), 3.96 (3H, s), 5.46 (2H, s), 7.17 (2H, d, J=8.4 Hz), 7.19-7.29 (2H, m), 7.40-7.50 (4H, m), 7.58 (2H, d, J=8.4 Hz), 7.68 (1H, dd, J=1.8, 8.4 Hz), 8.44 (1H, d, J=8.4 Hz).

EXAMPLE 427

3-acetyl-6-bromo-2-(4-hydroxymethyl-benzyl)-4-phenyl-2H-isoquinolin-1-one

By a method similar to that in Example 373, 4-(3-acetyl-6-bromo-1-oxo-4-phenyl-1H-isoquinolin-2-ylmethyl)benzoic acid was reduced to give the title compound (388 mg, 89%).

$^1$H-NMR (CDCl$_3$) δ: 1.25 (3H, s), 4.65 (2H, d, J=5.8 Hz), 5.44 (2H, s), 7.15-7.32 (2H, m), 7.40-7.47 (4H, m), 7.68 (1H, dd, J=1.8, 8.4 Hz), 8.44 (1H, d, J=8.4 Hz).

EXAMPLE 428

3-acetyl-6-bromo-2-(4-methylsulfanylmethylbenzyl)-4-phenyl-2H-isoquinolin-1-one

By a method similar to that in Example 395, 3-acetyl-6-bromo-2-(4-hydroxymethylbenzyl)-4-phenyl-2H-isoquinolin-1-one was converted to mesylate and reacted with sodium thiomethoxide to give the title compound (239 mg, 64%).

$^1$H-NMR (CDCl$_3$) δ: 1.20 (3H, s), 1.91 (3H, s), 3.61 (2H, s), 5.45 (2H, s), 7.11 (2H, d, J=8.0 Hz), 7.21-7.29 (4H, m), 7.40-7.50 (4H, m), 7.68 (1H, dd, J=1.8, 8.4 Hz), 8.44 (1H, d, J=8.4 Hz).

EXAMPLE 429

3-acetyl-6-bromo-2-(4-methanesulfonylmethylbenzyl)-4-phenyl-2H-isoquinolin-1-one By a method similar to that in Example 397, 3-acetyl-6-bromo-2-(4-hydroxymethyl-benzyl)-4-phenyl-2H-isoquinolin-1-one was oxidized to give the title compound (186 mg, 58%).

$^1$H-NMR (CDCl$_3$) δ: 1.31 (3H, s), 2.73 (3H, s), 4.20 (2H, s), 5.45 (2H, s), 7.21-7.50 (10H, m), 7.68 (1H, dd, J=2.0, 8.4 Hz), 8.42 (1H, d, J=8.4 Hz).

By a method similar to that in Example 423, 4-(3-acetyl-6-bromo-1-oxo-4-phenyl-1H-isoquinolin-2-ylmethyl)benzoic acid was condensed with various amines to give the compounds of Examples 430-432.

EXAMPLE 430

4-(3-acetyl-6-bromo-1-oxo-4-phenyl-1H-isoquinolin-2-ylmethyl)-N-(2-cyanoethyl) benzamide yield: 52%

$^1$H-NMR (CDCl$_3$) δ: 1.31 (3H, s), 2.73 (2H, t, J=6.2 Hz), 3.69 (2H, m), 5.47 (2H, s), 6.76 (1H, m), 7.24-7.31 (4H, m), 7.43-7.49 (4H, m), 7.65-7.75 (3H., m), 8.43 (1H, d, J=8.8 Hz).

EXAMPLE 431

4-(3-acetyl-6-bromo-1-oxo-4-phenyl-1H-isoquinolin-2-ylmethyl)benzamide yield: 14%

$^1$H-NMR (CDCl$_3$) δ: 1.33 (3H, s), 5.45 (2H, s), 6.38 (2H, brs), 7.24-7.29 (4H, m), 7.43-7.49 (4H, m), 7.68 (1H, dd, J=1.8, 8.8 Hz), 7.76 (2H, d, J=8.0 Hz), 8.41 (1H, d, J=8.8 Hz).

EXAMPLE 432

4-(3-acetyl-6-bromo-1-oxo-4-phenyl-1H-isoquinolin-2-ylmethyl)benzoic acid N'-pyridin-2-ylhydrazide yield: 30%

$^1$H-NMR (CDCl$_3$) δ: 1.34 (3H, s), 5.47 (2H, s), 6.34-6.85 (3H, m), 7.26-7.56 (8H, m), 7.69 (1H, dd, J=1.8, 8.4 Hz), 7.81 (2H, d, J=8.4 Hz), 8.13 (1H, m), 8.42 (1H, d, J=8.4 Hz).

By a method similar to that in Example 422, various ester derivatives were hydrolyzed to synthesize Examples 433-437.

EXAMPLE 433

1-[4-(3-acetyl-6-bromo-1-oxo-4-phenyl-1H-isoquinolin-2-ylmethyl)benzenesulfonyl]piperidine-4-carboxylic acid yield: 75%

$^1$H-NMR (CDCl$_3$) δ: 1.39 (3H, s), 1.70-2.00 (4H, m), 2.29 (1H, m), 2.28-2.62 (2H, m), 3.50-3.63 (2H, m), 5.46 (2H, s), 7.26-7.50 (9H, m), 7.43-7.49 (4H, m), 7.69 (2H, d, J=8.4 Hz), 8.41 (1H, d, J=8.8 Hz).

EXAMPLE 434

3-[4-(3-acetyl-6-bromo-1-oxo-4-phenyl-1H-isoquinolin-2-ylmethyl)benzenesulfonylamino]propionic acid yield: 21%

$^1$H-NMR (CDCl$_3$) δ: 1.44 (3H, s), 2.55 (2H, t, J=5.8 Hz), 3.08-3.14 (2H, m), 5.44 (2H, s), 5.85 (1H, m), 7.23-7.60 (8H, m), 7.70 (1H, dd, J=1.8, 8.8 Hz), 7.80 (2H, d, J=8.4 Hz), 8.39 (1H, d, J=8.8 Hz).

EXAMPLE 435

4-[4-(3-acetyl-6-bromo-1-oxo-4-phenyl-1H-isoquinolin-2-ylmethyl)benzenesulfonylamino]butyric acid yield: 41%

$^1$H-NMR (CDCl$_3$) δ: 1.47 (3H, s), 1.72-1.81 (2H, m), 2.34 (2H, t, J=7.0 Hz), 2.96 (2H, t, J=6.6 Hz), 5.41 (2H, s), 6.00 (1H, m), 7.20-7.64 (8H, m), 7.69 (1H, dd, J=1.8, 8.4 Hz), 7.78 (2H, d, J=8.4 Hz), 8.38 (1H, d, J=8.4 Hz).

EXAMPLE 436

4-[4-(3-acetyl-6-bromo-1-oxo-4-phenyl-1H-isoquinolin-2-ylmethyl)benzenesulfonyl]butyric acid yield: 34%

$^1$H-NMR (CDCl$_3$) δ: 1.46 (3H, s), 1.90-1.10 (2H, m), 2.49 (2H, t, J=7.0 Hz), 3.17 (2H, t, J=7.8 Hz), 5.45 (2H, s), 7.25-7.60 (8H, m), 7.71 (1H, dd, J=1.8, 8.4 Hz), 7.86 (2H, d, J=8.4 Hz), 8.38 (1H, d, J=8.4 Hz).

EXAMPLE 437

5-[4-(3-acetyl-6-bromo-1-oxo-4-phenyl-1H-isoquinolin-2-ylmethyl)benzenesulfonyl]pentanoic acid yield: 29%

$^1$H-NMR (CDCl$_3$) δ: 1.47 (3H, s), 1.50-1.78 (4H, m), 2.26 (2H, t, J=6.2 Hz), 3.03 (2H, t, J=7.4 Hz), 5.37 (2H, s), 7.22-7.60 (8H, m), 7.66 (1H, dd, J=1.8, 8.4 Hz), 7.80 (2H, d, J=8.2 Hz), 8.38 (1H, d, J=8.4 Hz).

EXAMPLE 438

6-bromo-1-oxo-4-phenyl-2-(4-[1,2,3]thiadiazole-4-ylbenzyl)-1,2-dihydroisoquinoline-3-carboxylic acid methyl ester To a solution of 6-bromo-1-oxo-4-phenyl-1H-isochromen-3-carboxylic acid methyl ester (359 mg) in methanol (20 ml) were added 4-[1,2,3]thiadiazol-4-ylbenzylamine (956 mg) and triethylamine (1.4 ml) and the mixture was stirred at room temperature for 72 hrs. The solvent was evaporated under reduced pressure, and the residue was partitioned between 1N hydrochloric acid and ethyl acetate. The ethyl acetate layer was washed with saturated brine and dried by adding sodium sulfate. The solvent was evaporated under reduced pressure, 4N hydrochloric acid ethyl acetate solution (5 ml) was added to the obtained residue, and the mixture was stirred at room temperature for 10 hrs. The solvent was evaporated under reduced pressure, water was added and the mixture was extracted with ethyl acetate. The extract was washed with saturated sodium hydrogen carbonate solution and saturated brine and dried by adding sodium sulfate. The obtained residue was purified by silica gel column chromatography (n-hexane/ethyl acetate=3/1→1/1) to give the title compound (80 mg, 15%).

$^1$H-NMR (CDCl$_3$) δ: 3.24 (3H, s), 5.47 (2H, s), 7.26-7.46 (8H, m), 7.67 (1H, dd, J=2.0, 8.8 Hz), 7.99 (2H, d, J=8.0 Hz), 8.42 (1H, d, J=8.8 Hz), 8.61 (1H, s).

EXAMPLE 439

6-bromo-1-oxo-4-phenyl-2-(4-sulfamoylbenzyl)-1,2-dihydroisoquinoline-3-carboxylic acid The title compound (3.64 g, 71%) was synthesized by a method similar to that in Example 331 and using 6-bromo-1-oxo-4-phenyl-1H-isochromen-3-carboxylic acid and 4-sulfamoylbenzylamine hydrochloride.

$^1$H-NMR (CDCl$_3$) δ: 5.32 (2H, s), 7.35-7.60 (8H, m), 7.70-7.82 (3H, m), 8.26 (1H, d, J=8.4 Hz).

EXAMPLE 440

3-acetyl-6-bromo-2-(3-fluorobenzyl)-4-phenyl-2H-isoquinolin-1-one

In the same manner as in Example 411, the title compound was synthesized from 3-fluorobenzylamine and 3-acetyl-6-bromo-4-phenylisochromen-1-one.

yield: 74 mg (64%)

$^1$H-NMR (CDCl$_3$) δ: 1.32 (3H, s), 5.42 (2H, s), 6.88-6.96 (3H, m), 7.22-7.29 (3H, m), 7.41-7.48 (4H, m), 7.67 (1H, dd, J=1.8, 8.4 Hz), 8.41 (1H, d, J=8.4 Hz).

EXAMPLE 441

3-acetyl-6-bromo-2-[4-(1Z-methoxyiminoethyl)benzyl]-4-phenyl-2H-isoquinolin-1-one The by-product obtained during synthesis of Example 426 was purified by silica gel column chromatography (n-hexane/ethyl acetate=19/1→4/1) to give the title compound.

yield: 12 mg (12%)

$^1$H-NMR (CDCl$_3$) δ: 1.31 (3H, s), 2.14 (3H, s), 3.79 (3H, s), 5.43 (2H, s), 7.21-7.49 (10H, m), 7.67 (1H, dd, J=1.8, 8.4 Hz), 8.42 (1H, d, J=8.4 Hz).

EXAMPLE 442

1-[4-(3-acetyl-6-bromo-1-oxo-4-phenyl-1H-isoquinolin-2-ylmethyl)benzoyl]piperidine-4-carboxylic acid ethyl ester In the same manner as in Example 423, the title compound was synthesized from 4-(3-acetyl-6-bromo-1-oxo-4-phenyl-1H-isoquinolin-2-ylmethyl)benzoic acid and piperidine-4-carboxylic acid ethyl ester.

yield: 309 mg (99%)

$^1$H-NMR (CDCl$_3$) δ: 1.26 (3H, t, J=7.4 Hz), 1.34 (3H, s), 1.50-2.10 (4H, m), 2.55 (1H, m), 2.93-3.09 (2H, m), 3.65 (1H, m), 4.15 (2H, q, J=7.4 Hz), 4.47 (1H, m), 5.45 (2H, s), 7.20-7.50 (10H, m), 7.68 (1H, dd, J=1.8, 8.6 Hz), 8.43 (1H, d, J=8.6 Hz)

EXAMPLE 443

3-acetyl-6-bromo-2-[4-(1-hydroxy-1-methylethyl)benzyl]-4-phenyl-2H-isoquinolin-1-one To a solution of 3-acetyl-2-(4-acetylbenzyl)-6-bromo-4-phenyl-2H-isoquinolin-1-one (297 mg) in THF (10 ml) was added methyl magnesium bromide (1M tetrahydrofuran solution, 1.89 ml) under ice-cooling and the mixture was stirred under ice-cooling for 1 hr. The reaction solution was poured into saturated aqueous ammonium chloride solution, extracted with ethyl acetate, washed with brine and dried by adding sodium sulfate. The solvent was evaporated under reduced pressure and the obtained residue was purified by silica gel column chromatography (n-hexane/ethyl acetate=9/1→3/2) to give the title compound (258 mg, 83%).

$^1$H-NMR (CDCl$_3$) δ: 1.22 (3H, s), 1.52 (6H, s), 1.74 (1H, s), 5.43 (2H, s), 7.14 (2H, d, J=8.7 Hz), 7.20-7.30 (2H, m), 7.35-7.50 (6H, m), 7.67 (1H, dd, J=2.1, 8.4 Hz), 8.43 (1H, d, J=8.4 Hz).

EXAMPLE 444

[4-(3-acetyl-6-bromo-1-oxo-4-phenyl-1H-isoquinolin-2-ylmethyl)benzyl]carbamic acid tert-butyl ester

[Step 1] 3-acetyl-2-(4-azidemethylbenzyl)-6-bromo-4-phenyl-2H-isoquinolin-1-one

To a solution of 3-acetyl-6-bromo-2-(4-hydroxymethylbenzyl)-4-phenyl-2H-isoquinolin-1-one (1.72 g) in dichloromethane (50 ml) was added triethylamine (0.34 ml), and then methanesulfonyl chloride (0.77 ml) was added under ice-cooling, and the mixture was stirred at the same temperature for 1 hr. Water was added and the mixture was partitioned. The dichloromethane layer was washed with saturated brine and dried by adding sodium sulfate. The solvent was evaporated under reduced pressure and the obtained residue was dissolved in DMF (30 ml). Sodium azide (289 mg) was added, and the mixture was stirred at room temperature for 3 hrs. The solvent was evaporated under reduced pressure and the obtained residue was partitioned between dichloromethane and 1N hydrochloric acid. The dichloromethane layer was washed with aqueous sodium hydrogen carbonate and brine and dried by adding sodium sulfate. The solvent was evaporated under reduced pressure, diisopropyl ether was added to the obtained residue and the mixture was crystallized to give the title compound (1.61 g, 89%).

$^1$H-NMR (CDCl$_3$) δ: 1.23 (3H, s), 4.27 (2H, s), 5.46 (2H, s), 7.18-7.28 (6H, m), 7.40-7.51 (4H, m), 7.67 (1H, m) 8.42 (1H, d, J=8.7 Hz).

[Step 2] [4-(3-acetyl-6-bromo-1-oxo-4-phenyl-1H-isoquinolin-2-ylmethyl)benzyl]carbamic acid tert-butyl ester To a solution of 3-acetyl-2-(4-azidemethylbenzyl)-6-bromo-4-phenyl-2H-isoquinolin-1-one (572 mg) and triphenylphosphine (338 mg) in THF (10 ml) was added water (0.32 ml) and the mixture was stirred at room temperature for 15 hrs. A 1N aqueous sodium hydroxide solution was added and the reaction mixture was basified and di-t-butyl carbonate (384 mg) was added. The mixture was stirred at room temperature for 2 hrs. The solvent was evaporated under reduced pressure and partitioned between water and ethyl acetate. The ethyl acetate layer was washed with brine and dried by adding sodium sulfate. The solvent was evaporated under reduced pressure and the obtained residue was purified by silica gel column chromatography (n-hexane/ethyl acetate=9/1→3/2) to give the title compound (599 mg, 91%).

$^1$H-NMR (CDCl$_3$) δ: 1.23 (3H, s), 1.43 (9H, s), 4.25 (2H, d, J=5.8 Hz), 4.81 (1H, brs), 5.43 (2H, s), 7.11-7.30 (6H, m), 7.41-7.49 (4H, m), 7.67 (1H, dd, J=1.8, 8.6 Hz), 8.43 (1H, d, J=8.6 Hz).

EXAMPLE 445

3-acetyl-2-(4-aminomethylbenzyl)-6-bromo-4-phenyl-2H-isoquinolin-1-one hydrochloride To [4-(3-acetyl-6-bromo-1-oxo-4-phenyl-1H-isoquinolin-2-ylmethyl)benzyl]carbamic acid tert-butyl ester (561 mg) was added 4N hydrochloric acid ethyl acetate solution (5 ml) and the mixture was stirred at room temperature for 30 min. The solvent was evaporated under reduced pressure and toluene was added. The solvent was evaporated again under reduced pressure. To the obtained residue was added diisopropyl ether and the mixture was crystallized to give the title compound (410 mg, 82%).

¹H-NMR (CDCl₃) δ: 1.40 (3H, s), 4.03 (2H, s), 5.43 (2H, s), 7.22-7.52 (10H, m), 7.71 (1H, dd, J=1.8, 8.4 Hz), 8.38 (1H, d, J=8.4 Hz).

EXAMPLE 446

N-[4-(3-acetyl-6-bromo-1-oxo-4-phenyl-1H-isoquinolin-2-ylmethyl)benzyl]acetamide To a solution of 3-acetyl-2-(4-aminomethylbenzyl)-6-bromo-4-phenyl-2H-isoquinolin-1-one hydrochloride (100 mg) and triethylamine (0.09 ml) and 4-dimethylaminopyridine (24 mg) in THF (5 ml) was added acetic anhydride (0.08 ml) and the mixture was stirred at room temperature for 12 hrs. The solvent was evaporated under reduced pressure, and partitioned between water and ethyl acetate. The ethyl acetate layer was washed with 1N hydrochloric acid, aqueous sodium hydrogen carbonate and brine and dried by adding sodium sulfate. The solvent was evaporated under reduced pressure and the obtained residue was purified by silica gel column chromatography (n-hexane/ethyl acetate=1/1→1/9) to give the title compound (93 mg, 92%).

¹H-NMR (CDCl₃) δ: 1.29 (3H, s), 1.99 (3H, s), 4.37 (2H, d, J=6.0 Hz), 5.39 (2H, s), 5.83 (1H, brs), 7.12-7.28 (6H, m), 7.40-7.49 (4H, m), 7.67 (1H, dd, J=1.8, 8.4 Hz), 8.41 (1H, d, J=8.4 Hz).

In the same manner as in Example 446, the compounds of Examples 447-448 were synthesized from 3-acetyl-2-(4-aminomethylbenzyl)-6-bromo-4-phenyl-2H-isoquinolin-1-one hydrochloride and the corresponding sulfonyl chloride.

EXAMPLE 447

N-[4-(3-acetyl-6-bromo-1-oxo-4-phenyl-1H-isoquinolin-2-ylmethyl)benzyl]methanesulfonamide yield: 58 mg (54%)

¹H-NMR (CDCl₃) δ: 1.30 (3H, s), 2.86 (3H, s), 4.27 (2H, d, J=6.0 Hz), 4.63 (1H, t, J=6.0 Hz), 5.41 (2H, s), 7.19 (2H, d, J=8.1 Hz), 7.25-7.30 (4H, m), 7.42-7.50 (4H, m), 7.68 (1H, dd, J=1.8, 8.7 Hz), 8.42 (1H, d, J=8.7 Hz).

EXAMPLE 448

4-[4-(3-acetyl-6-bromo-1-oxo-4-phenyl-1H-isoquinolin-2-ylmethyl)benzylsulfamoyl]benzoic acid yield: 5 mg (4%).
LCMS (ESI+): 90% (2.45 min); 646 (M+1), 648. (A)

EXAMPLE 449

1-[4-(3-acetyl-6-bromo-1-oxo-4-phenyl-1H-isoquinolin-2-lmethyl)benzoyl]piperidine-4-carboxylic acid In the same manner as in Example 102, the title compound was synthesized from 1-[4-(3-acetyl-6-bromo-1-oxo-4-phenyl-1H-isoquinolin-2-ylmethyl)benzoyl]piperidine-4-carboxylic acid ethyl ester.

Yield: 35 mg (15%)

¹H-NMR (CDCl₃) δ: 1.43 (3H, s), 1.55-2.15 (4H, m), 2.59 (1H, m) 2.97-3.20 (2H, m), 3.70 (1H, m), 4.45 (1H, m), 5.45 (2H, s), 7.20-7.53 (10H, m), 7.69 (1H, dd, J=1.8, 8.4 Hz), 8.42 (1H, d, J=8.4 Hz).

EXAMPLE 450

6-bromo-2-(4-methylsulfanylbenzyl)-4-phenyl-3-propionyl-2H-isoquinolin-1-one To a solution of 1-(4-methylsulfanylbenzylamino)butan-2-ol (8.5 g) and 2-benzoyl-4-bromobenzoic acid (14.7 g) and 1-hydroxy-1H-benzotriazole (7.4 g) in DMF (100 ml) was added triethylamine (8.4 ml) and then WSC (11.5 g) was added at room temperature. The mixture was stirred at room temperature for 4 days. The solvent was evaporated under reduced pressure, and the residue was partitioned between dichloromethane and water, washed with 1N hydrochloric acid, aqueous sodium hydrogen carbonate and brine and dried by adding sodium sulfate. The solvent was evaporated under reduced pressure and the obtained residue was purified by silica gel column chromatography (n-hexane/ethyl acetate=4/1-+13/7). The resulting colorless amorphous form was dissolved in dimethyl sulfoxide (100 ml) and triethylamine (25.3 ml) was added. Under ice-cooling, pyridine sulfur trioxide complex (14.5 g) was added, and the mixture was stirred at room temperature for 8 hrs. Water (300 ml) was added, and the mixture was extracted with ethyl acetate and washed with 1N hydrochloric acid, aqueous sodium hydrogen carbonate and brine. Sodium sulfate was added to dry the mixture. The solvent was evaporated under reduced pressure and the obtained residue was purified by silica gel column chromatography (n-hexane/ethyl acetate=4/1→2/3). The obtained colorless amorphous form was dissolved in 0.1N potassium hydroxide-ethanol solution (75 ml) and heated under reflux for 12 hrs. 1N Hydrochloric acid (7.5 ml) was added and the mixture was stirred under ice-cooling for 1 hr. The crystals were collected by filtration and washed with 70% ethanol-water to give the title compound (6.58 g, 34%).

¹H-NMR (CDCl₃) δ: 0.44 (3H, t, J=7.2 Hz), 1.52 (2H, q, J=7.2 Hz), 2.43 (3H, s), 5.34 (2H, s), 7.10 (2H, d, J=8.4 Hz), 7.16 (2H, d, J=8.4 Hz), 7.24-7.28 (4H, m), 7.42-7.48 (4H, m), 7.66 (1H, dd, J=1.8, 8.4 Hz), 8.42 (1H, d, J=8.4 Hz).

EXAMPLE 451

6-bromo-2-(4-methanesulfinylbenzyl)-4-phenyl-3-propionyl-2H-isoquinolin-1-one To a solution of 1-(4-methylsulfanylbenzylamino)butan-2-ol (1.60 g) in dichloromethane (40 ml) was added dropwise a solution of 3-chloroperbenzoic acid (1.20 g) in dichloromethane (10 ml) at −78° C. and the mixture was stirred at the same temperature for 3 hrs. The reaction solution was poured into 10% aqueous sodium sulfite solution and the mixture was stirred at room temperature for 1 hr., extracted with dichloromethane, washed with aqueous sodium hydrogen carbonate and brine and dried by adding sodium sulfate. The solvent was evaporated under reduced pressure and the obtained residue was purified by silica gel column chromatography (n-hexane/ethyl acetate=1/1→1/9) to give the title compound (1.27 g, 74%).

¹H-NMR (CDCl₃) δ: 0.46 (3H, t, J=7.0 Hz), 1.62 (2H, q, J=7.0 Hz), 2.67 (3H, s), 5.40 (2H, s), 7.20-7.35 (2H, m), 7.36-7.50 (6H, m), 7.59 (2H, d, J=8.4 Hz), 7.68 (1H, dd, J=1.8, 8.8 Hz), 8.41 (1H, d, J=8.8 Hz).

EXAMPLE 452

4-(6-bromo-1-oxo-4-phenyl-3-propionyl-1H-iso-quinolin-2-ylmethyl)benzenesulfonamide

[Step 1]
4-[(2-hydroxybutylamino)methyl]benzenesulfonamide hydrochloride

To a mixed suspension of 4-aminomethylbenzenesulfonamide hydrochloride (4.45 g), methanol (20 ml) and THF (10 ml) was added N-ethyldiisopropylamine (5.2 ml) and then 1,2-epoxybutane (2.58 ml) was added, and the mixture was heated under reflux for 12 hrs. A 1N aqueous sodium hydroxide solution was added and the reaction mixture was basified and di-t-butyl carbonate (6.55 g) was added. The mixture was stirred at room temperature for 2 hrs. The solvent was evaporated under reduced pressure, and the residue was partitioned between water and ethyl acetate. The ethyl acetate layer was washed with 1N hydrochloric acid, aqueous sodium hydrogen carbonate and brine and dried by adding sodium sulfate. The solvent was evaporated under reduced pressure and the obtained residue was purified by silica gel column chromatography (n-hexane/ethyl acetate=7/3→1/1). To the obtained colorless amorphous form was added 4N hydrochloric acid ethyl acetate solution (10 ml), and the mixture was stirred at room temperature for 30 min. The solvent was evaporated under reduced pressure, toluene was added and the solvent was again evaporated under reduced pressure. Diisopropyl ether was added to the obtained residue and the mixture was crystallized to give the title compound (2.58 g, 46%).

$^1$H-NMR (DMSO-$d_6$) δ: 0.87 (3H, t, J=7.4 Hz), 1.30-1.50 (2H, m), 2.71 (1H, m), 2.94 (1H, m), 3.72 (1H, m), 4.23 (2H, s), 5.33 (1H, d, J=5.6 Hz), 7.72 (2H, d, J=8.4 Hz), 7.87 (2H, d, J=8.4 Hz), 9.15 (2H, brs).

[Step 2] 4-(6-bromo-1-oxo-4-phenyl-3-propionyl-1H-isoquinolin-2-ylmethyl)benzenesulfonamide To a solution of 4-[(2-hydroxybutylamino)methyl]benzenesulfonamide hydrochloride (842 mg) and 2-benzoyl-4-bromobenzoic acid (915 mg) and 1-hydroxy-1H-benzotriazole (643 mg) in DMF (20 ml) was added triethylamine (1.25 ml) and then WSC (1.03 g) was added at room temperature, and the mixture was stirred at room temperature for 15 hrs. The solvent was evaporated under reduced pressure, and the residue was partitioned between dichloromethane and water, washed with 1N hydrochloric acid, aqueous sodium hydrogen carbonate and brine and dried by adding sodium sulfate. The solvent was evaporated under reduced pressure and the obtained residue was purified by silica gel column chromatography (n-hexane/ethyl acetate=1/1→1/9). The obtained colorless amorphous form was dissolved in dichloromethane (20 ml) and 4-methylmorpholine N-oxide (612 mg) and molecular sieves 4A (500 mg) were added. Under ice-cooling, tetra-n-propylammonium perruthenate (31 mg) was added, and the mixture was stirred at room temperature for 3 hrs. The molecular sieves 4A was removed from the reaction solution by filtration. The solvent was evaporated under reduced pressure and the obtained residue was purified by silica gel column chromatography (n-hexane/ethyl acetate=7/3→1/1). The obtained colorless amorphous form was dissolved in ethanol (20 ml) and 1,8-diazabicyclo[5.4.0]-7-undecene (0.84 ml) was added. The mixture was heated under reflux for 12 hrs. The solvent was evaporated under reduced pressure, and the residue was partitioned between ethyl acetate and 1N hydrochloric acid, washed with aqueous sodium hydrogen carbonate and brine and sodium sulfate was added to dry the mixture. The solvent was evaporated under reduced pressure and the obtained residue was purified by silica gel column chromatography (n-hexane/ethyl acetate=7/3→1/1) to give the title compound (267 mg, 17%).

$^1$H-NMR (CDCl$_3$) δ: 0.51 (3H, t, J=7.2 Hz), 1.72 (2H, q, J=7.2 Hz), 4.85 (2H, s), 5.36 (2H, s), 7.26-7.49 (8H, m), 7.68 (1H, d, J=8.8 Hz), 7.86 (2H, d, J=7.0 Hz), 8.39 (1H, d, J=8.8 Hz).

EXAMPLE 453

4-(6-chloro-1-oxo-4-phenyl-3-propionyl-1H-isoquinolin-2-ylmethyl)benzenesulfonamide In the same manner as in Example 452, Step 2, the title compound was synthesized from 4-[(2-hydroxybutylamino)methyl]benzenesulfonamide hydrochloride and 2-benzoyl-4-chlorobenzoic acid.

yield: 220 mg (15%)

$^1$H-NMR (CDCl$_3$) δ: 0.50 (3H, t, J=7.2 Hz), 1.77 (2H, q, J=7.2 Hz), 5.33 (2H, s), 5.37 (2H, s), 7.25-7.35 (5H, m), 7.43-7.54 (4H, m), 7.82 (2H, d, J=8.4 Hz), 8.44 (1H, d, J=8.8 Hz).

EXAMPLE 454

4-(6-bromo-3-butyryl-1-oxo-4-phenyl-1H-isoquinolin-2-ylmethyl)benzenesulfonamide

[Step 1]
4-[(2-hydroxypentylamino)methyl]benzenesulfonamide hydrochloride

In the same manner as in Example 452, Step 1, the title compound was synthesized from 4-aminomethylbenzenesulfonamide hydrochloride and 1,2-epoxypentane.

yield: 3.24 g (53%)

$^1$H-NMR (DMSO-$d_6$) δ: 0.87 (3H, t, J=6.9 Hz), 1.23-1.43 (4H, m), 2.69 (1H, m), 2.93 (1H, m), 3.85 (1H, m), 4.22 (2H, s), 5.32 (1H, d, J=5.4 Hz), 7.75 (2H, d, J=7.8 Hz), 7.85 (2H, d, J=7.8 Hz), 9.32 (2H, brs).

[Step 2] 4-(6-bromo-3-butyryl-1-oxo-4-phenyl-1H-isoquinolin-2-ylmethyl)benzenesulfonamide In the same manner as in Example 452, Step 2, the title compound was synthesized from 4-[(2-hydroxypentylamino)methyl]benzenesulfonamide hydrochloride and 2-benzoyl-4-bromobenzoic acid.

yield: 291 mg (18%)

$^1$H-NMR (CDCl$_3$) δ: 0.41 (3H, t, J=7.5 Hz), 1.00-1.10 (2H, m), 1.71 (2H, t, J=7.2 Hz), 4.88 (2H, s), 5.34 (2H, s), 7.24-7.32 (2H, m), 7.38 (2H, d, J=8.4 Hz), 7.44-7.51 (4H, m), 7.68 (1H, dd, J=1.8, 8.4 Hz), 7.86 (2H, d, J=8.4 Hz), 8.38 (1H, d, J=8.4 Hz).

EXAMPLE 455

4-(6-chloro-3-butyryl-1-oxo-4-phenyl-1H-isoquinolin-2-ylmethyl)benzenesulfonamide In the same manner as in Example 452, Step 2, the title compound was synthesized from 4-[(2-hydroxypentylamino)

methyl]benzenesulfonamide hydrochloride and 2-benzoyl-4-chlorobenzoic acid.

yield: 204 mg (14%)

$^1$H-NMR (CDCl$_3$) δ: 0.41 (3H, t, J=7.2 Hz), 1.00-1.10 (2H, m), 1.72 (2H, t, J=7.2 Hz), 5.00 (2H, s), 5.32 (2H, s), 7.24-7.28 (3H, m), 7.35 (2H, d, J=8.7 Hz), 7.45-7.52 (4H, m), 7.84 (2H, d, J=8.7 Hz), 8.45 (1H, d, J=8.7 Hz).

EXAMPLE 456

4-(6-bromo-1-oxo-3-pentanoyl-4-phenyl-1H-isoquinolin-2-ylmethyl)benzenesulfonamide

[Step 1] 4-[(2-hydroxyhexylamino)methyl]benzenesulfonamide hydrochloride

In the same manner as in Example 452, Step 1, the title compound was synthesized from 4-aminomethylbenzenesulfonamide hydrochloride and 1,2-epoxyhexane.

yield: 4.46 g (69%)

$^1$H-NMR (CDCl$_3$) δ: 0.88 (3H, t, J=6.9 Hz), 1.20-1.60 (6H, m), 3.00-3.40 (2H, m), 3.79 (1H, m), 4.56 (2H, s), 5.17 (3H, brs), 7.35 (2H, d, J=8.4 Hz), 7.86 (2H, d, J=8.4 Hz).

[Step 2] 4-(6-bromo-1-oxo-3-pentanoyl-4-phenyl-1H-isoquinolin-2-ylmethyl)benzenesulfonamide In the same manner as in Example 452, Step 2, the title compound was synthesized from 4-[(2-hydroxyhexylamino)methyl]benzenesulfonamide hydrochloride and 2-benzoyl-4-bromobenzoic acid.

yield: 210 mg (13%)

$^1$H-NMR (CDCl$_3$) δ: 0.56 (3H, t, J=7.5 Hz), 0.73-0.85 (2H, m), 0.92-1.02 (2H, m), 1.72 (2H, t, J=7.2 Hz), 4.95 (2H, s), 5.34 (2H, s), 7.26-7.29 (2H, m), 7.37 (2H, d, J=8.4 Hz), 7.45-7.49 (4H, m), 7.68 (1H, dd, J=1.8, 8.7 Hz), 7.86 (2H, d, J=8.4 Hz), 8.38 (1H, d, J=8.4 Hz).

EXAMPLE 457

4-(6-chloro-3-pentanoyl-1-oxo-4-phenyl-1H-isoquinolin-2-ylmethyl)benzenesulfonamide In the same manner as in Example 452, Step 2, the title compound was synthesized from 4-[(2-hydroxyhexylamino)methyl]benzenesulfonamide hydrochloride and 2-benzoyl-4-chlorobenzoic acid.

yield: 92 mg (6%)

$^1$H-NMR (CDCl$_3$) δ: 0.56 (3H, t, J=7.2 Hz), 0.70-0.85 (2H, m), 0.93-1.05 (2H, m), 1.73 (2H, t, J=7.2 Hz), 4.85 (2H, s), 5.35 (2H, s), 7.26-7.29 (2H, m), 7.38 (2H, d, J=8.4 Hz), 7.45-7.54 (5H, m), 7.86 (2H, d, J=8.4 Hz), 8.47 (1H, d, J=8.7 Hz).

EXAMPLE 458

4-(6-bromo-1-oxo-4-phenyl-3-propionyl-1H-isoquinolin-2-ylmethyl)benzoic acid methyl ester

[Step 1] 4-[(2-hydroxybutylamino)methyl]benzoic acid methyl ester hydrochloride

To a solution of 1-aminobutan-2-ol (10.7 g) in THF (50 ml) was added triethylamine (20.9 ml) and then a solution of 4-bromomethylbenzoic acid methyl ester (22.9 g) in THF (100 ml) was added dropwise. The mixture was stirred at room temperature for 12 hrs. and 1N aqueous sodium hydroxide solution was added. The reaction mixture was basified and di-t-butyl carbonate (32.7 g) was added. The mixture was stirred at room temperature for 2 hrs. The solvent was evaporated under reduced pressure, and the residue was partitioned between water and ethyl acetate. The ethyl acetate layer was washed with 1N hydrochloric acid, aqueous sodium hydrogen carbonate and brine and dried by adding sodium sulfate. The solvent was evaporated under reduced pressure, 4N hydrochloric acid ethyl acetate solution (10 ml) was added to the obtained residue, and the mixture was stirred at room temperature for 30 min. The solvent was evaporated under reduced pressure, toluene was added and the solvent was again evaporated under reduced pressure. To the obtained residue was added diisopropyl ether and the mixture was crystallized to give the title compound (19.0 g, 70%).

$^1$H-NMR (DMSO-d$_6$) δ: 0.86 (3H, t, J=7.6 Hz), 1.25-1.48 (2H, m), 2.73 (1H, m), 2.94 (1H, m), 3.76 (1H, m), 3.87 (3H, s), 4.18-4.32 (2H, m), 7.73 (2H, d, J=8.4 Hz), 8.00 (2H, d, J=8.4 Hz), 9.17 (2H, brs).

[Step 2] 4-(6-bromo-1-oxo-4-phenyl-3-propionyl-1H-isoquinolin-2-ylmethyl)benzoic acid methyl ester To a suspension of 2-benzoyl-4-bromobenzoic acid (21.4 g) in toluene (300 ml) was added DMF (0.4 ml) and then sulfonyl chloride (6.1 ml) was added under ice-cooling, and the mixture was stirred at 60° C. for 3 hrs. The solvent was evaporated under reduced pressure, toluene (50 ml) was added and the mixture was re-concentrated. The obtained residue was suspended in toluene (250 ml) and N-ethyldiisopropylamine (36.6 ml) was added. Then, 4-[(2-hydroxybutylamino)methyl]benzoic acid methyl ester hydrochloride (24.9 g) was added. The mixture was stirred at 90° C. for 5 hrs. Under ice-cooling, 1N hydrochloric acid was added and the mixture was acidified and partitioned. The organic layer was washed with aqueous sodium hydrogen carbonate and brine and dried by adding sodium sulfate. The solvent was evaporated under reduced pressure and the obtained residue was dissolved in dimethyl sulfoxide (250 ml) and triethylamine (78 ml) was added. Under ice-cooling, pyridine sulfur trioxide complex (44.6 g) was added, and the mixture was stirred at room temperature for 8 hrs. Water (500 ml) was added, and the mixture was extracted with ethyl acetate, washed with 1N hydrochloric acid, aqueous sodium hydrogen carbonate and brine and dried by adding sodium sulfate. The solvent was evaporated under reduced pressure and the obtained residue was suspended in methanol, crystallized and filtered. The obtained colorless amorphous was dissolved in methanol (200 ml) and THF (100 ml) and 1,8-diazabicyclo[5.4.0]-7-undecene (28.1 ml) was added. The mixture was heated under reflux for 30 hrs. After standing still at room temperature for 12 hrs., the precipitated crystals were collected by filtration to give the title compound (7.72 g, 22%).

$^1$H-NMR (CDCl$_3$) δ: 0.41 (3H, t, J=7.0 Hz), 1.52 (2H, q, J=7.0 Hz), 3.89 (3H, s), 5.43 (2H, s), 7.20-7.32 (4H, m), 7.40-7.48 (4H, m), 7.68 (1H, dd, J=1.8, 8.4 Hz), 7.96 (2H, d, J=8.4 Hz), 8.43 (1H, d, J=8.4 Hz).

EXAMPLE 459

4-(6-chloro-1-oxo-4-phenyl-3-propionyl-1H-isoquinolin-2-ylmethyl)benzoic acid methyl ester In the same manner as in Example 458, Step 2, the title compound was synthesized from 4-[(2-hydroxybutylamino)

methyl]benzoic acid methyl ester hydrochloride and 2-benzoyl-4-chlorobenzoic acid.

yield: 19.6 g (61%)
$^1$H-NMR (CDCl$_3$) δ: 0.41 (3H, t, J=7.2 Hz), 1.53 (2H, q, J=7.2 Hz), 3.88 (3H, s), 5.42 (2H, s), 7.20-7.28 (5H, m), 7.42-7.56 (4H, m), 7.95 (2H, d, J=8.4 Hz), 8.49 (1H, d, J=8.7 Hz).

EXAMPLE 460

4-(6-bromo-3-butyryl-1-oxo-4-phenyl-1H-isoquinolin-2-ylmethyl)benzoic acid methyl ester

[Step 1] 1-aminopentan-2-ol

An aqueous ammonia solution (28%)(1000 ml) was added to 1,2-epoxypentane (30 g) and the mixture was stirred at room temperature for 18 hrs. The solvent was evaporated under reduced pressure, toluene (100 ml) was added and the mixture was re-concentrated to give the title compound (32.1 g, 89%).
$^1$H-NMR (CDCl$_3$) δ: 0.94 (3H, t, J=7.2 Hz), 1.40 (2H, q, J=7.2 Hz), 1.86 (3H, brs), 2.50 (1H, dd, J=8.1, 12.6 Hz), 2.84 (1H, dd, J=3.0, 12.6 Hz), 3.51 (1H, m).

[Step 2] 4-[(2-hydroxypentylamino)methyl]benzoic acid methyl ester hydrochloride In the same manner as in Example 458, Step 1, the title compound was synthesized from 4-bromomethylbenzoic acid methyl ester and 1-aminopentan-2-ol.

yield: 13.1 g (46%)
$^1$H-NMR (DMSO-d$_6$) δ: 0.84 (3H, t, J=6.9 Hz), 1.19-1.44 (4H, m), 2.73 (1H, m), 2.94 (1H, m), 3.85 (3H, s), 3.92 (2H, s), 4.39-4.65 (2H, m), 7.73 (2H, d, J=8.1 Hz), 7.96 (2H, d, J=8.1 Hz), 9.27 (1H, brs), 9.65 (1H, brs).

[Step 3] 4-(6-bromo-3-butyryl-1-oxo-4-phenyl-1H-isoquinolin-2-ylmethyl)benzoic acid methyl ester In the same manner as in Example 458, Step 2, the title compound was synthesized from 4-[(2-hydroxypentylamino)methyl]benzoic acid methyl ester hydrochloride and 2-benzoyl-4-bromobenzoic acid.

yield: 1.70 g (16%)
$^1$H-NMR (CDCl$_3$) δ: 0.34 (3H, t, J=7.2 Hz), 0.92-1.03 (2H, m), 1.53 (2H, t, J=6.9 Hz), 3.88 (3H, s), 5.40 (2H, s), 7.24-7.27 (4H, m), 7.43-7.46 (4H, m), 7.66 (1H, dd, J=1.8, 8.7 Hz), 7.95 (2H, d, J=8.4 Hz), 8.41 (1H, d, J=8.7 Hz).

EXAMPLE 461

4-(6-chloro-1-oxo-4-phenyl-3-butyryl-1H-isoquinolin-2-ylmethyl)benzoic acid methyl ester In the same manner as in Example 458, Step 2, the title compound was synthesized from 4-[(2-hydroxypentylamino)methyl]benzoic acid methyl ester hydrochloride and 2-benzoyl-4-chlorobenzoic acid.

yield: 961 mg (7%)
$^1$H-NMR (CDCl$_3$) δ: 0.34 (3H, t, J=7.2 Hz), 0.92-1.02 (2H, m), 1.54 (2H, t, J=7.2 Hz), 3.88 (3H, s), 5.40 (2H, s), 7.24-7.27 (5H, m), 7.43-7.47 (3H, m), 7.51 (1H, dd, J=1.8, 8.7 Hz), 7.95 (2H, d, J=8.4 Hz), 8.49 (1H, d, J=8.7 Hz).

In the same manner as in Example 102, various ester derivatives were hydrolyzed and the compounds of Example 462-Example 465 were synthesized.

EXAMPLE 462

4-(6-bromo-1-oxo-4-phenyl-3-propionyl-1H-isoquinolin-2-ylmethyl)benzoic acid yield: 375 mg (67%)
$^1$H-NMR (CDCl$_3$) δ: 0.44 (3H, t, J=7.2 Hz), 1.57 (2H, q, J=7.2 Hz), 5.43 (2H, s), 7.24-7.31 (4H, m), 7.42-7.50 (4H, m), 7.67 (1H, dd, J=1.8, 8.7 Hz), 8.01 (2H, d, J=8.4 Hz), 8.42 (1H, d, J=8.7 Hz).

EXAMPLE 463

4-(6-chloro-1-oxo-4-phenyl-3-propionyl-1H-isoquinolin-2-ylmethyl)benzoic acid yield: 674 mg (69%)
$^1$H-NMR (CDCl$_3$) δ: 0.44 (3H, t, J=7.2 Hz), 1.58 (2H, q, J=7.2 Hz), 5.43 (2H, s), 7.24-7.30 (5H, m), 7.43-7.55 (4H, m), 8.01 (2H, d, J=7.8 Hz), 8.50 (1H, d, J=8.4 Hz).

EXAMPLE 464

4-(6-bromo-1-oxo-4-phenyl-3-butyryl-1H-isoquinolin-2-ylmethyl)benzoic acid yield: 920 mg (61%)
$^1$H-NMR (CDCl$_3$) δ: 0.34 (3H, t, J=7.2 Hz), 0.92-1.05 (2H, m), 1.57 (2H, t, J=6.9 Hz), 5.39 (2H, s), 7.20-7.35 (4H, m), 7.38-7.50 (4H, m), 7.66 (1H, d, J=8.4 Hz), 7.99 (2H, d, J=8.4 Hz), 8.40 (1H, d, J=8.4 Hz).

EXAMPLE 465

4-(6-chloro-1-oxo-4-phenyl-3-butyryl-1H-isoquinolin-2-ylmethyl)benzoic acid yield: 254 mg (29%)
$^1$H-NMR (CDCl$_3$) δ: 0.34 (3H, t, J=7.2 Hz), 0.92-1.05 (2H, m), 1.50-1.66 (2H, m), 5.39 (2H, s), 7.25-7.35 (5H, m), 7.37-7.55 (4H, m), 7.99 (2H, d, J=7.5 Hz), 8.48 (1H, d, J=8.7 Hz).

In the same manner as in Example 423, the compounds of Example 466-Example 471 were synthesized using 4-(6-bromo-1-oxo-4-phenyl-3-propionyl-1H-isoquinolin-2-ylmethyl)benzoic acid and the corresponding various amines.

EXAMPLE 466

1-[4-(6-bromo-1-oxo-4-phenyl-3-propionyl-1H-isoquinolin-2-ylmethyl)benzoyl]piperidine-4-carboxylic acid ethyl ester yield: 47 mg (25%)
$^1$H-NMR (CDCl$_3$) δ: 0.44 (3H, t, J=7.2 Hz), 1.26 (3H, t, J=7.2 Hz), 1.52-2.12 (6H, m), 2.55 (1H, m), 2.94-3.07 (2H, m), 3.63 (1H, m), 4.15 (2H, q, J=7.2 Hz), 4.45 (1H, m), 5.39 (2H, s), 7.20-7.35 (6H, m), 7.43-7.50 (4H, m), 7.67 (1H, dd, J=1.8, 8.7 Hz), 8.42 (1H, d, J=8.7 Hz).

EXAMPLE 467

4-[4-(6-bromo-1-oxo-4-phenyl-3-propionyl-1H-isoquinolin-2-ylmethyl)benzoyl]piperazine-1-carboxylic acid tert-butyl ester yield: 2.97 g (91%)
$^1$H-NMR (CDCl$_3$) δ: 0.45 (3H, t, J=7.2 Hz), 1.46 (9H, s), 1.61 (2H, q, J=7.2 Hz), 3.19-3.83 (8H, m), 5.38 (2H, s), 7.24-7.29 (4H, m), 7.34 (2H, d, J=8.4 Hz), 7.43-7.51 (4H, m), 7.68 (1H, dd, J=1.8, 8.4 Hz), 8.41 (1H, d, J=8.4 Hz).

EXAMPLE 468

6-bromo-4-phenyl-2-[4-(piperidine-1-carbonyl)benzyl]-3-propionyl-2H-isoquinolin-1-one yield: 115 mg (52%)
$^1$H-NMR (CDCl$_3$) δ: 0.43 (3H, t, J=7.2 Hz), 1.40-1.73 (8H, m), 3.19-3.37 (2H, m), 3.58-3.75 (2H, m), 5.40 (2H, s), 7.18-7.29 (4H, m), 7.33 (2H, d, J=8.1 Hz), 7.41-7.50 (4H, m), 7.67 (1H, dd, J=1.8, 8.4 Hz), 8.42 (1H, d, J=8.4 Hz).

EXAMPLE 469

2-[4-(4-benzyl-piperazine-1-carbonyl)benzyl]-6-bromo-4-phenyl-3-propionyl-2H-isoquinolin-1-one yield: 185 mg (71%)
$^1$H-NMR (CDCl$_3$) δ: 0.43 (3H, t, J=7.2 Hz), 1.58 (2H, q, J=7.2 Hz), 2.25-2.59 (4H, m), 3.27-3.45 (2H, m), 3.51 (2H, s), 3.67-3.84 (2H, m), 5.38 (2H, s), 7.17-7.37 (11H, m), 7.41-7.50 (4H, m), 7.67 (1H, dd, J=1.8, 8.4 Hz), 8.41 (1H, d, J=8.4 Hz).

EXAMPLE 470

6-bromo-2-[4-[4-(2-hydroxyethyl)piperazine-1-carbonyl]benzyl]-4-phenyl-3-propionyl-2H-isoquinolin-1-one yield: 187 mg (78%)
$^1$H-NMR (CDCl$_3$) δ: 0.45 (3H, t, J=7.2 Hz), 1.61 (2H, q, J=7.2 Hz), 2.34-2.66 (6H, m), 3.34-3.50 (2H, m), 3.63 (2H, t, J=5.4 Hz), 3.65-3.86 (2H, m), 5.38 (2H, s), 7.20-7.30 (4H, m), 7.34 (2H, d, J=8.1 Hz), 7.42-7.49 (4H, m), 7.68 (1H, dd, J=1.8, 8.7 Hz), 8.42 (1H, d, J=8.7 Hz).

EXAMPLE 471

4-(6-bromo-1-oxo-4-phenyl-3-propionyl-1H-isoquinolin-2-ylmethyl)-N-methoxy-N-methylbenzamide yield: 2.17 g (82%)
$^1$H-NMR (CDCl$_3$) δ: 0.41 (3H, t, J=7.2 Hz), 1.51 (2H, q, J=7.2 Hz), 3.32 (3H, s), 3.48 (3H, s), 5.43 (2H, s), 7.20-7.29 (4H, m), 7.41-7.50 (4H, m), 7.63 (2H, d, J=8.1 Hz), 7.68 (1H, dd, J=1.8, 8.4 Hz), 8.43 (1H, d, J=8.4 Hz).

EXAMPLE 472

1-[4-(6-bromo-1-oxo-4-phenyl-3-propionyl-1H-isoquinolin-2-ylmethyl)benzoyl]piperidine-4-carboxylic acid In the same manner as in Example 102, the title compound was synthesized from 1-[4-(6-bromo-1-oxo-4-phenyl-3-propionyl-1H-isoquinolin-2-ylmethyl)benzoyl]piperidine-4-carboxylic acid ethyl ester.

yield: 33 mg (92%)
$^1$H-NMR (CDCl$_3$) δ: 1.44 (3H, t, J=7.2 Hz), 1.45-2.06 (6H, m), 2.59 (1H, m), 2.92-3.15 (2H, m), 3.65 (1H, m), 4.46 (1H, m), 5.39 (1H, m), 7.20-7.37 (6H, m), 7.41-7.50 (4H, m), 7.67 (1H, dd, J=1.8, 8.4 Hz), 8.42 (1H, d, J=8.4 Hz).

EXAMPLE 473

6-bromo-4-phenyl-2-[4-(piperazine-1-carbonyl)benzyl]-3-propionyl-2H-isoquinolin-1-one hydrochloride In the same manner as in Example 444, the title compound was synthesized from 4-[4-(6-bromo-1-oxo-4-phenyl-3-propionyl-1H-isoquinolin-2-ylmethyl)benzoyl]piperazine-1-carboxylic acid tert-butyl ester.

yield: 2.95 g (quant.)
$^1$H-NMR (CDCl$_3$) δ: 0.48 (3H, t, J=7.2 Hz), 1.69 (2H, q, J=7.2 Hz), 3.10-3.31 (4H, m), 3.78-4.08 (4H, m), 5.35 (2H, s), 7.26-7.37 (6H, m), 7.44-7.51 (4H, m), 7.68 (1H, dd, J=1.8, 8.4 Hz), 8.40 (1H, d, J=8.4 Hz), 10.10 (1H, brs).

In the same manner as in Example 112, the compounds of Example 474-Example 485 were synthesized using 6-bromo-4-phenyl-2-[4-(piperazine-1-carbonyl)benzyl]-3-propionyl-2H-isoquinolin-1-one hydrochloride and the corresponding various acid anhydrides, acyl chlorides, sulfonyl chlorides, isocyanic acid esters, chloroformic acid esters and alkyl halides.

EXAMPLE 474

6-bromo-2-[4-(4-methanesulfonylpiperazine-1-carbonyl)benzyl]-4-phenyl-3-propionyl-2H-isoquinolin-1-one yield: 32 mg (50%)
$^1$H-NMR (CDCl$_3$) δ: 0.47 (3H, t, J=7.2 Hz), 1.66 (2H, q, J=7.2 Hz), 2.79 (3H, s), 3.08-3.38 (4H, m), 3.42-4.09 (4H, m), 5.37 (2H, s), 7.25-7.32 (4H, m), 7.36 (2H, d, J=8.1 Hz), 7.42-7.51 (4H, m), 7.68 (1H, dd, J=1.8, 8.4 Hz), 8.41 (1H, d, J=8.4 Hz).

EXAMPLE 475

6-bromo-2-[4-(4-ethanesulfonylpiperazine-1-carbonyl)benzyl]-4-phenyl-3-propionyl-2H-isoquinolin-1-one yield: 141 mg (72%)
$^1$H-NMR (CDCl$_3$) δ: 0.47 (3H, t, J=7.2 Hz), 1.37 (3H, t, J=7.2 Hz), 1.64 (2H, q, J=7.2 Hz), 2.96 (2H, q, J=7.2 Hz), 3.13-4.02 (8H, m), 5.37 (2H, s), 7.26-7.31 (4H, m), 7.35 (2H, d, J=8.1 z), 7.44-7.51 (4H, m), 7.68 (1H, dd, J=1.8, 8.7 Hz), 8.41 (1H, d, J=8.7 Hz).

EXAMPLE 476

6-bromo-4-phenyl-2-[4-[4-(propan-1-sulfonyl)piperazine-1-carbonyl]benzyl]-3-propionyl-2H-isoquinolin-1-one yield: 163 mg (82%)
$^1$H-NMR (CDCl$_3$) δ: 0.47 (3H, t, J=7.2 Hz), 1.06 (3H, t, J=7.2 Hz), 1.64 (2H, q, J=7.2 Hz), 1.77-1.92 (2H, m), 2.88 (2H, q, J=7.8 Hz), 3.12-3.91 (8H, m), 5.37 (2H, s), 7.21-7.39 (6H, m), 7.42-7.54 (4H, m), 7.68 (1H, dd, J=1.8, 8.7 Hz), 8.41 (1H, d, J=8.7 Hz).

EXAMPLE 477

2-[4-(4-benzenesulfonylpiperazine-1-carbonyl)benzyl]-6-bromo-4-phenyl-3-propionyl-2H-isoquinolin-1-one yield: 99 mg (47%)
$^1$H-NMR (CDCl$_3$) δ: 0.45 (3H, t, J=7.2 Hz), 1.63 (2H, q, J=7.2 Hz), 2.83-3.17 (4H, m), 3.39-3.92 (4H, m), 5.33 (2H, s), 7.20-7.31 (5H, m), 7.42-7.78 (11H, m), 8.39 (1H, d, J=8.4 Hz).

EXAMPLE 478

2-[4-(4-acetylpiperazine-1-carbonyl)benzyl]-6-bromo-4-phenyl-3-propionyl-2H-isoquinolin-1-one yield: 134 mg (74%)
$^1$H-NMR (CDCl$_3$) δ: 0.47 (3H, t, J=7.4 Hz), 1.65 (2H, q, J=7.4 Hz), 2.12 (3H, s), 3.20-3.85 (8H, m), 5.38 (2H, s), 7.24-7.51 (10H, m), 7.67 (1H, dd, J=1.8, 8.4 Hz), 8.41 (1H, d, J=8.4 Hz).

EXAMPLE 479

2-[4-(4-benzoylpiperazine-1-carbonyl)benzyl]-6-bromo-4-phenyl-3-propionyl-2H-isoquinolin-1-one yield: 149 mg (75%)
$^1$H-NMR (CDCl$_3$) δ: 0.46 (3H, t, J=7.2 Hz), 1.63 (2H, q, J=7.2 Hz), 3.20-4.00 (8H, m), 5.37 (2H, s), 7.20-7.55 (15H, m), 7.67 (1H, dd, J=1.8, 8.7 Hz), 8.41 (1H, d, J=8.7 Hz).

EXAMPLE 480

4-[4-(6-bromo-1-oxo-4-phenyl-3-propionyl-1H-isoquinolin-2-ylmethyl)benzoyl]piperazine-1-carboxylic acid methylamide yield: 87 mg (47%)
$^1$H-NMR (CDCl$_3$) δ: 0.46 (3H, t, J=7.2 Hz), 1.62 (2H, q, J=7.2 Hz), 2.82 (3H, d, J=4.8 Hz), 3.19-3.89 (8H, m), 4.33 (1H, m), 5.38 (2H, s), 7.24-7.50 (10H, m), 7.68 (1H, dd, J=1.8, 8.7 Hz), 8.41 (1H, d, J=8.7 Hz).

EXAMPLE 481

4-[4-(6-bromo-1-oxo-4-phenyl-3-propionyl-1H-isoquinolin-2-ylmethyl)benzoyl]piperazine-1-carboxylic acid ethylamide yield: 132 mg (70%)
$^1$H-NMR (CDCl$_3$) δ: 0.46 (3H, t, J=7.2 Hz), 1.15 (3H, t, J=7.2 Hz), 1.62 (2H, q, J=7.2 Hz), 3.16-3.86 (10H, m), 4.33 (1H, brs), 5.38 (2H, s), 7.23-7.30 (4H, m), 7.35 (2H, d, J=8.4 Hz), 7.42-7.52 (4H, m), 7.68 (1H, dd, J=1.8, 8.7 Hz), 8.41 (1H, d, J=8.7 Hz).

EXAMPLE 482

4-[4-(6-bromo-1-oxo-4-phenyl-3-propionyl-1H-isoquinolin-2-ylmethyl)benzoyl]piperazine-1-carboxylic acid methyl ester yield: 31 mg (17%)
$^1$H-NMR (CDCl$_3$) δ: 0.46 (3H, t, J=7.2 Hz), 1.62 (2H, q, J=7.2 Hz), 3.21-3.79 (8H, m), 3.72 (3H, s), 5.38 (2H, s), 7.25-7.28 (4H, m), 7.35 (2H, d, J=8.4 Hz), 7.44-7.51 (4H, m), 7.67 (1H, dd, J=1.8, 8.7 Hz), 8.41 (1H, d, J=8.7 Hz).

EXAMPLE 483

4-[4-(6-bromo-1-oxo-4-phenyl-3-propionyl-1H-isoquinolin-2-ylmethyl)benzoyl]piperazine-1-carboxylic acid ethyl ester yield: 164 mg (87%)
$^1$H-NMR (CDCl$_3$) δ: 0.46 (3H, t, J=7.2 Hz), 1.27 (3H, t, J=7.2 Hz), 1.62 (2H, q, J=7.2 Hz), 3.24-3.85 (8H, m), 4.16 (2H, q, J=7.2 Hz), 5.38 (2H, s), 7.25-7.30 (4H, m), 7.35 (2H, d, J=8.1 Hz), 7.45-7.51 (4H, m), 7.68 (1H, dd, J=1.8, 8.7 Hz), 8.41 (1H, d, J=8.7 Hz).

EXAMPLE 484

4-[4-(6-bromo-1-oxo-4-phenyl-3-propionyl-1H-isoquinolin-2-ylmethyl)benzoyl]piperazine-1-carboxylic acid benzyl ester yield: 105 mg (50%)
$^1$H-NMR (CDCl$_3$) δ: 0.45 (3H, t, J=7.2 Hz), 1.62 (2H, q, J=7.2 Hz), 3.20-3.85 (8H, m), 5.14 (2H, s), 5.38 (2H, s), 7.24-7.58 (15H, m), 7.67 (1H, dd, J=1.8, 8.7 Hz), 8.41 (1H, d, J=8.7 Hz).

EXAMPLE 485

6-bromo-2-[4-(4-ethylpiperazine-1-carbonyl)benzyl]-4-phenyl-3-propionyl-2H-isoquinolin-1-one yield: 99 mg (56%)
$^1$H-NMR (CDCl$_3$) δ: 0.44 (3H, t, J=7' 2 Hz), 1.08 (3H, t, J=7.2 Hz), 1.60 (2H, q, J=7.2 Hz), 2.26-2.58 (6H, m), 3.30-3.49 (2H, m), 3.66-3.87 (2H, m), 5.39 (2H, s), 7.20-7.30 (4H, m), 7.35 (2H, d, J=8.4 Hz), 7.43-7.49 (4H, m), 7.67 (1H, dd, J=1.8, 8.4 Hz), 8.41 (1H, d, J=8.4 Hz).

In the same manner as in Example 123, the compounds of Example 486-Example 488 were synthesized using 4-(6-chloro-1-oxo-4-phenyl-3-propionyl-1H-isoquinolin-2-ylmethyl)benzoic acid and the corresponding various amines and sulfonamides.

EXAMPLE 486

4-(6-chloro-1-oxo-4-phenyl-3-propionyl-1H-isoquinolin-2-ylmethyl)benzamide yield: 222 mg (Quant.)
$^1$H-NMR (CDCl$_3$) δ: 0.44 (3H, t, J=7.2 Hz), 1.58 (2H, q, J=7.2 Hz), 5.41 (2H, s), 5.73 (1H, brs), 6.08 (1H, brs), 7.23-

7.33 (5H, m), 7.43-7.50 (3H, m), 7.52 (1H, dd, J=1.8, 8.7 Hz), 7.75 (2H, d, J=8.1 Hz), 8.50 (1H, d, J=8.7 Hz).

EXAMPLE 487

N-[4-(6-chloro-1-oxo-4-phenyl-3-propionyl-1H-isoquinolin-2-ylmethyl)benzoyl]methanesulfonamide yield: 228 mg (87%)
$^1$H-NMR (CDCl$_3$) δ: 0.47 (3H, t, J=7.2 Hz), 1.65 (2H, q, J=7.2 Hz), 3.41 (3H, s), 5.38 (2H, s), 7.17-7.38 (5H, m), 7.43-7.55 (4H, m), 7.78 (2H, d, J=8.4 Hz), 8.49 (1H, d, J=8.7 Hz), 8.60 (1H, brs)

EXAMPLE 488

N-[4-(6-chloro-1-oxo-4-phenyl-3-propionyl-1H-isoquinolin-2-ylmethyl)benzoyl]benzenesulfonamide yield: 255 mg (87%)
$^1$H-NMR (CDCl$_3$) δ: 0.44 (3H, t, J=7.2 Hz), 1.61 (2H, q, J=7.2 Hz), 5.32 (2H, s), 7.20-7.31 (4H, m), 7.42-7.69 (8H, m), 7.74 (2H, d, J=8.4 Hz), 8.13 (2H, d, J=7.2 Hz), 8.49 (1H, d, J=8.7 Hz), 9.29 (1H, brs).

In the same manner as in Example 424, the compounds of Example 489 and Example 490 were synthesized using 4-(6-bromo-1-oxo-4-phenyl-3-propionyl-1H-isoquinolin-2-ylmethyl)-N-methoxy-N-methylbenzamide and the corresponding various Grignard reagents.

EXAMPLE 489

2-(4-acetylbenzyl)-6-bromo-4-phenyl-3-propionyl-2H-isoquinolin-1-one yield: 863 mg (88%)
$^1$H-NMR (CDCl$_3$) δ: 0.44 (3H, t, J=7.2 Hz), 1.59 (2H, q, J=7.2 Hz), 2.56 (3H, s), 5.41 (2H, s), 7.25-7.31 (4H, m), 7.43-7.50 (4H, m), 7.68 (1H, dd, J=1.8, 8.4 Hz), 7.89 (2H, d, J=8.4 Hz), 8.42 (1H, d, J=8.4 Hz).

EXAMPLE 490

6-bromo-4-phenyl-3-propionyl-2-(4-propionylbenzyl)-2H-isoquinolin-1-one yield: 115 mg (46%)
$^1$H-NMR (CDCl$_3$) δ: 0.43 (3H, t, J=7.2 Hz), 1.19 (3H, t, J=7.2 Hz), 1.57 (2H, q, J=7.2 Hz), 2.95 (2H, q, J=7.2 Hz), 5.41 (2H, s), 7.24-7.30 (4H, m), 7.45-7.50 (4H, m), 7.68 (1H, dd, J=1.8, 8.4 Hz), 7.89 (2H, d, J=8.4 Hz), 8.42 (1H, d, J=8.4 Hz).

EXAMPLE 491

6-bromo-2-[4-(1-hydroxy-1-methylethyl)benzyl]-4-phenyl-3-propionyl-2H-isoquinolin-1-one The present compound was synthesized by a method similar to that in Example 443 and using 2-(4-acetylbenzyl)-6-bromo-4-phenyl-3-propionyl-2H-isoquinolin-1-one as a starting material.
yield: 90 mg (22%)
$^1$H-NMR (CDCl$_3$) δ: 0.40 (3H, t, J=7.4 Hz), 1.45 (2H, q, J=7.4 Hz), 1.52 (6H, s), 1.73 (1H, s), 5.38 (2H, s), 7.15 (2H, d, J=8.1 Hz), 7.21-7.29 (2H, m), 7.37-7.48 (6H, m), 7.66 (1H, dd, J=2.1, 8.7 Hz), 8.43 (1H, d, J=8.7 Hz).

EXAMPLE 492

6-bromo-2-(4-hydroxymethylbenzyl)-4-phenyl-3-propionyl-2H-isoquinolin-1-one

The present compound was synthesized by a method similar to that in Example 373 and reduction of 4-(6-bromo-1-oxo-4-phenyl-3-propionyl-1H-isoquinolin-2-ylmethyl)benzoic acid.

yield: 8.73 g (89%)
$^1$H-NMR (CDCl$_3$) δ: 0.42 (3H, t, J=7.2 Hz), 1.51 (2H, q, J=7.2 Hz), 1.80 (1H, s), 4.65 (2H, s), 5.38 (2H, s), 7.17 (2H, d, J=8.1 Hz), 7.24-7.32 (5H, m), 7.41-7.58 (4H, m), 8.50 (1H, d, J=8.7 Hz).

EXAMPLE 493

4-(6-bromo-1-oxo-4-phenyl-3-propionyl-1H-isoquinolin-2-ylmethyl)benzonitrile

[Step 1] 4-[(2-hydroxybutylamino)methyl]benzonitrile hydrochloride

In the same manner as in Example 458, Step 1, the title compound was synthesized from 4-bromomethylbenzonitrile and 1-aminobutan-2-ol.

yield: 9.90 g (82%)
$^1$H-NMR (DMSO-d$_6$) δ: 0.90 (3H, t, J=7.8 Hz), 1.35-1.50 (2H, m), 2.70-2.97 (2H, m), 4.02 (1H, m), 4.23-4.36 (2H, m), 7.72 (2H, d, J=8.4 Hz), 7.81 (2H, d, J=8.4 Hz), 9.26 (1H, brs).

[Step 2] 4-(6-bromo-3-butyryl-1-oxo-4-phenyl-1H-isoquinolin-2-ylmethyl)benzoic acid methyl ester In the same manner as in Example 458, Step 2, the title compound was synthesized from 4-[(2-hydroxybutylamino)methyl]benzonitrile hydrochloride and 2-benzoyl-4-bromobenzoic acid.

yield: 2.48 g (26%)
$^1$H-NMR (CDCl$_3$) δ: 0.50 (3H, t, J=7.2 Hz), 1.69 (2H, q, J=7.2 Hz), 5.35 (2H, s), 7.26-7.30 (2H, m), 7.35 (2H, d, J=8.4 Hz), 7.45-7.51 (4H, m), 7.60 (2H, d, J=8.4 Hz), 7.68 (1H, dd, J=1.8, 8.7 Hz), 8.39 (1H, d, J=8.7 Hz).

EXAMPLE 494

4-(6-chloro-1-oxo-4-phenyl-3-propionyl-1H-isoquinolin-2-ylmethyl)benzonitrile

In the same manner as in Example 458, Step 2, the title compound was synthesized from 4-[(2-hydroxybutylamino)methyl]benzonitrile hydrochloride and 2-benzoyl-4-chlorobenzoic acid.

yield: 4.54 g (27%)
$^1$H-NMR (CDCl$_3$) δ: 0.50 (3H, t, J=7.4 Hz), 1.70 (2H, q, J=7.4 Hz), 5.35 (2H, s), 7.25-7.63 (11H, m), 8.48 (1H, d, J=8.4 Hz).

EXAMPLE 495

6-bromo-4-phenyl-3-propionyl-2-[4-(1H-tetrazol-5-yl)benzyl]-2H-isoquinolin-1-one To a suspension of 4-(6-bromo-1-oxo-4-phenyl-3-propionyl-1H-isoquinolin-2-ylmethyl)benzonitrile (1.89 g) in toluene (80 ml) was added trimethyltin azide (2.47 g) and the mixture was stirred at 110° C. for 4 days. Water (50 ml) and methanol (50 ml) were added at room temperature, and the precipitated crystals were collected by filtration to give the title compound (1.19 g, 58%).

$^1$H-NMR (DMSO-$d_6$) δ: 0.35 (3H, t, J=7.4 Hz), 1.69 (2H, q, J=7.4 Hz), 5.26 (2H, s), 7.14 (2H, d, J=8.0 Hz), 7.24-7.38 (3H, m), 7.42-7.56 (3H, m), 7.82 (1H, dd, J=1.8, 8.4 Hz), 7.91 (2H, d, J=8.0 Hz), 8.30 (1H, s), 8.35 (1H, d, J=8.4 Hz).

EXAMPLE 496

6-bromo-4-phenyl-3-propionyl-2-[4-(1H-tetrazol-5-yl)benzyl]-2H-isoquinolin-1-one Potassium Salt To a suspension of 6-bromo-4-phenyl-3-propionyl-2-[4-(1H-tetrazol-5-yl)benzyl]-2H-isoquinolin-1-one (113 mg) in methanol (30 ml) was added 0.1N potassium hydroxide-ethanol solution (2 ml) and the mixture was stirred at room temperature for 2 days. Undesired materials were removed by filtration, and the filtrate was concentrated under reduced pressure. Ethyl acetate was added to the obtained residue and the mixture was crystallized to give the title compound (119 mg, quant.).

$^1$H-NMR (CD$_3$OD)δ: 0.42 (3H, t, J=6.0 Hz), 0.50-0.73 (2H, m), 5.43 (2H, s), 7.23-7.58 (8H, m), 7.77 (1H, dd, J=1.8, 8.4 Hz), 7.99 (2H, d, J=8.0 Hz), 8.39 (1H, d, J=8.4 Hz).

EXAMPLE 497

4-(6-bromo-1-oxo-4-phenyl-3-propionyl-1H-isoquinolin-2-ylmethyl)-N-hydroxybenzamidine To a solution of hydroxylamine hydrochloride (737 mg) in DMSO (10 ml) was added triethylamine (1.51 ml) and the mixture was stirred at room temperature for 30 min. The precipitated white undesired materials were removed by filtration and washed with THF. After concentrated under reduced pressure, THF was removed from the filtrate and 4-(6-bromo-1-oxo-4-phenyl-3-propionyl-1H-isoquinolin-2-ylmethyl)benzonitrile (1.00 g) was added, and the mixture was stirred at 75° C. for 18 hrs. Water was added and the mixture was extracted with ethyl acetate. The organic layer was washed with brine and dried by adding sodium sulfate. The solvent was evaporated under reduced pressure and diisopropyl ether was added to the obtained residue, and the mixture was crystallized to give the title compound (1.05 g, 98%).

$^1$H-NMR (CDCl$_3$) δ: 0.42 (3H, t, J=7.2 Hz), 1.52 (2H, q, J=7.2 Hz), 4.80 (2H, s), 5.40 (2H, s), 7.21-7.30 (5H, m), 7.43-7.48 (3H, m), 7.56 (2H, d, J=8.0 Hz), 7.67 (1H, dd, J=2.0, 8.4 Hz), 8.43 (1H, d, J=8.4 Hz).

EXAMPLE 498

4-(6-chloro-1-oxo-4-phenyl-3-propionyl-1H-isoquinolin-2-ylmethyl)-N-hydroxybenzamidine In the same manner as in Example 497, the title compound was synthesized from 4-(6-bromo-1-oxo-4-phenyl-3-propionyl-1H-isoquinolin-2-ylmethyl)benzonitrile.

yield: 4.19 g (91%)

$^1$H-NMR (DMSO-$d_6$) δ: 0.42 (3H, t, J=7.0 Hz), 1.86 (2H, q, J=7.0 Hz), 5.20 (2H, s), 5.79 (2H, s), 7.11-7.18 (3H, m), 7.30-7.35 (2H, m), 7.50-7.56 (3H, m), 7.62 (2H, d, J=8.4 Hz), 7.69 (1H, dd, J=1.8, 8.4 Hz), 8.39 (1H, d, J=8.4 Hz), 9.63 (1H, s).

EXAMPLE 499

6-bromo-2-[4-(5-oxo-4,5-dihydro-[1,2,4]oxadiazol-3-yl)benzyl]-4-phenyl-3-propionyl-2H-isoquinolin-1-one To a suspension of 4-(6-bromo-1-oxo-4-phenyl-3-propionyl-1H-isoquinolin-2-ylmethyl)-N-hydroxybenzamidine (230 mg) in THF (10 ml) was added 1,1'-carbodiimidazole (89 mg) and then 1,8-diazabicyclo[5.4.0]-7-undecene (0.08 ml) was added and the mixture was stirred at 40° C. for 15 hrs. The residue was partitioned between 1N hydrochloric acid and ethyl acetate. The organic layer was washed with brine and dried by adding sodium sulfate. The solvent was evaporated under reduced pressure and the obtained residue was purified by silica gel column chromatography (n-hexane/ethyl acetate=1/1-+1/4) to give the title compound (102 mg, 48%).

$^1$H-NMR (CDCl$_3$) δ: 0.51 (3H, t, J=7.0 Hz), 1.73 (2H, q, J=7.0 Hz), 5.34 (2H, s), 7.20-7.40 (6H, m), 7.42-7.65 (3H, m), 7.69-7.73 (2H, m), 8.42 (1H, d, J=8.8 Hz).

EXAMPLE 500

6-chloro-2-[4-(5-oxo-4,5-dihydro-[1,2,4]oxadiazol-3-yl)benzyl]-4-phenyl-3-propionyl-2H-isoquinolin-1-one In the same manner as in Example 499, the title compound was synthesized from (6-chloro-1-oxo-4-phenyl-3-propionyl-1H-isoquinolin-2-ylmethyl)-N-hydroxybenzamidine.

yield: 132 mg (54%)

$^1$H-NMR (CDCl$_3$) δ: 0.51 (3H, t, J=7.2 Hz), 1.76 (2H, q, J=7.2 Hz), 5.34 (2H, s), 7.20-7.33 (4H, m), 7.45-7.55 (5H, m), 7.70 (2H, d, J=8.4 Hz), 8.49 (1H, d, J=8.4 Hz).

EXAMPLE 501

6-chloro-4-phenyl-3-propionyl-2-[4-(5-thioxo-4,5-dihydro-[1,2,4]oxadiazol-3-yl)benzyl]-2H-isoquinolin-1-one To a suspension of 4-(6-chloro-1-oxo-4-phenyl-3-propionyl-1H-isoquinolin-2-ylmethyl)-N-hydroxybenzamidine (230 mg) in THF (10 ml) was added 1,1'-thiocarbodiimidazole (109 mg) and then 1,8-diazabicyclo[5.4.0]-7-undecene (0.3 ml) was added and the mixture was stirred at 40° C. for 15 hrs. The residue was partitioned between 1N hydrochloric acid and ethyl acetate. The organic layer was washed with brine and dried by adding sodium sulfate. The solvent was evaporated under reduced pressure and the obtained residue was purified by silica gel column chromatography (n-hexane/ethyl acetate=1/1→0/1) to give the title compound (61 mg, 24%).

$^1$H-NMR (DMSO-$d_6$) δ: 0.45 (3H, t, J=7.2 Hz), 2.01 (2H, q, J=7.2 Hz), 5.20 (2H, s), 7.11 (1H, d, J=2.1 Hz), 7.32-7.40 (4H, m), 7.45-7.54 (3H, m), 7.67 (1H, dd, J=1.8, 8.4 Hz), 7.83 (2H, d, J=8.4 Hz), 8.36 (1H, d, J=8.4 Hz).

EXAMPLE 502

6-chloro-2-[4-(5-oxo-4,5-dihydro-[1,2,4]thiadiazol-3-yl)benzyl]-4-phenyl-3-propionyl-2H-isoquinolin-1-one To a suspension of 4-(6-chloro-1-oxo-4-phenyl-3-propionyl-1H-isoquinolin-2-ylmethyl)-N-hydroxybenzamidine (230 mg) in THF (15 ml) was added 1,1'-thiocarbodiimidazole (119 mg) and the mixture was stirred at 40° C. for 15 hrs. The residue was partitioned between water and ethyl acetate. The organic layer was washed with brine and dried by adding sodium sulfate. The solvent was evaporated under reduced pressure and the obtained residue was dissolved in THF (10 ml), boron trifluoride-diethyl ether complex (0.32 ml) was added, and the mixture was stirred at room temperature for 1 hr. The residue was partitioned between 1N hydrochloric acid and ethyl acetate. The organic layer was washed with brine and dried by adding sodium sulfate. The solvent was evaporated under reduced pressure and the obtained residue was purified by silica gel column chromatography (n-hexane/ethyl acetate=3/2->2/3) to give the title compound (107 mg, 43%).

$^1$H-NMR (DMSO-$d_6$) δ: 0.43 (3H, t, J=7.2 Hz), 1.96 (2H, q, J=7.2 Hz), 5.20 (2H, s), 7.10 (1H, d, J=2.1 Hz), 7.30-7.35 (4H, m), 7.47-7.55 (3H, m), 7.67 (1H, dd, J=2.1, 8.4 Hz), 7.88 (2H, d, J=8.4 Hz), 8.36 (1H, d, J=8.4 Hz), 13.42 (1H, brs).

EXAMPLE 503

6-chloro-2-[4-(2-oxo-2,3-dihydro-214-[1,2,3,5]oxathiadiazol-4-yl)benzyl]-4-phenyl-3-propionyl-2H-isoquinolin-1-one To a suspension of 4-(6-chloro-1-oxo-4-phenyl-3-propionyl-1H-isoquinolin-2-ylmethyl)-N-hydroxybenzamidine (230 mg) in THF (15 ml) was added pyridine (0.081 ml). Under ice-cooling, a solution of thionyl chloride (0.04 ml) in dichloromethane (3 ml) was added dropwise and the mixture was stirred under ice-cooling for 1 hr. The residue was partitioned between 1N hydrochloric acid and ethyl acetate. The organic layer was washed with brine and dried by adding sodium sulfate. The solvent was evaporated under reduced pressure and the obtained residue was purified by silica gel column chromatography (n-hexane/ethyl acetate=3/2→2/3) to give the title compound (46 mg, 17%).

$^1$H-NMR (CDCl$_3$) δ: 0.50 (3H, t, J=7.2 Hz), 1.72 (2H, q, J=7.2 Hz), 5.31 (2H, s), 7.23-7.31 (3H, m), 7.32 (1H, d, J=2.1 Hz), 7.44-7.52 (3H, m), 7.56 (1H, dd, J=2.1, 8.7 Hz), 7.67 (2H, d, J=8.4 Hz), 8.50 (1H, d, J=8.7 Hz), 9.61 (1H, brs).

EXAMPLE 504

4-(6-chloro-1-oxo-4-phenyl-3-propionyl-1,2-dihydronaphthalen-2-ylmethyl)benzaldehyde To a solution of 6-bromo-2-(4-hydroxymethylbenzyl)-4-phenyl-3-propionyl-2H-isoquinolin-1-one in dichloromethane (100 ml) were added 4-methylmorpholine N-oxide (7.03 g) and molecular sieves 4A (4 g). Tetra-n-propylammonium perruthenate (351 mg) was added under ice-cooling and the mixture was stirred under ice-cooling for 3 hrs. The molecular sieves 4A were removed from the reaction solution by filtration, the solvent was evaporated under reduced pressure and the obtained residue was purified by silica gel column chromatography (n-hexane/ethyl acetate=19/1→7/3) to give the title compound (2.01 g, 23%).

$^1$H-NMR (CDCl$_3$) δ: 0.45 (3H, t, J=7.2 Hz), 1.60 (2H, q, J=7.2 Hz), 5.43 (2H, s), 7.23-7.32 (3H, m), 7.38 (1H, d, J=8.1 Hz), 7.42-7.50 (3H, m), 7.53 (1H, dd, J=2.0, 8.6 Hz), 7.82 (2H, d, J=8.1 Hz), 8.50 (1H, d, J=8.6 Hz), 9.97 (1H, s).

EXAMPLE 505

4-(6-chloro-1-oxo-4-phenyl-3-propionyl-1,2-dihydronaphthalen-2-ylmethyl)phenyl]hydroxyacetonitrile To a solution of 4-(6-chloro-1-oxo-4-phenyl-3-propionyl-1,2-dihydronaphthalen-2-ylmethyl)benzaldehyde in dichloromethane (20 ml) was added zinc iodide (13 mg). Under ice-cooling, trimethylsilylnitrile (1.60 ml) was added, and the mixture was stirred at room temperature for 15 hrs. Dichloromethane was added to the reaction solution, and the mixture was washed with aqueous sodium hydrogen carbonate and brine and sodium sulfate was added to dry the mixture. The solvent was evaporated under reduced pressure and the obtained residue was dissolved in 1,3-dioxolane (20 ml) and 2N hydrochloric acid (20 ml) was added. The mixture was stirred at room temperature for 2 hrs. The reaction solution was extracted with ethyl acetate, washed with brine and dried by adding sodium sulfate. The solvent was evaporated under reduced pressure and the obtained residue was purified by silica gel column chromatography (n-hexane/ethyl acetate=7/3→1/1) to give the title compound (1.83 g, Quant.).

$^1$H-NMR (CDCl$_3$) δ: 0.46 (3H, t, J=7.1 Hz), 1.60 (2H, q, J=7.1 Hz), 3.43 (1H, d, J=7.4 Hz), 5.32 (2H, s), 5.50 (1H, d, J=7.4 Hz), 7.21-7.29 (5H, m), 7.43-7.49 (3H, m), 7.53 (1H, dd, J=2.0, 8.7 Hz), 8.47 (1H, d, J=8.7 Hz).

EXAMPLE 506

5-[4-(6-chloro-1-oxo-4-phenyl-3-propionyl-1H-isoquinolin-2-ylmethyl)phenyl]thiazolidine-2,4-dione To a solution of 4-(6-chloro-1-oxo-4-phenyl-3-propionyl-1,2-dihydronaphthalen-2-ylmethyl)phenyl]hydroxyacetonitrile in chloroform (40 ml) was added DMF (2 drops) and then thionyl chloride (0.16 ml) was added. The mixture was heated under reflux for 30 min. The reaction solution was partitioned between chloroform and water. The organic layer was washed with brine and dried by adding sodium sulfate. The solvent was evaporated under reduced pressure and the obtained residue was dissolved in ethanol (20 ml). Thiourea (183 mg) was added, and the mixture was heated under reflux for 4 hrs. 5N Hydrochloric acid (10 ml) was added and the mixture was heated under reflux for 20 hrs. Water was added, and the mixture was extracted with ethyl acetate, washed with brine and dried by adding sodium sulfate. The solvent was evaporated under reduced pressure and the obtained residue was purified by silica gel column chromatography (n-hexane/ethyl acetate=4/1→1/1) and recrystallized from ethanol to give the title compound (137 mg, 13%).

$^1$H-NMR (CDCl$_3$) δ: 0.44 (3H, t, J=7.1 Hz), 1.57 (2H, q, J=7.1 Hz), 5.32 (1H, s), 5.32-7.37 (2H, m), 7.22-7.30 (5H, m), 7.32-7.37 (2H, m), 7.42-7.48 (3H, m), 7.51 (1H, dd, J=2.1, 8.5 Hz), 8.45 (1H, s), 8.47 (1H, d, J=8.5 Hz).

Using various Grignard reagents, the compounds of Example 507 and Example 508 were synthesized from 4-(6-chloro-1-oxo-4-phenyl-3-propionyl-1,2-dihydronaphthalen-2-ylmethyl)benzaldehyde by a method similar to that in Example 443.

EXAMPLE 507

6-chloro-2-[4-(1-hydroxyethyl)benzyl]-4-phenyl-3-propionyl-2H-isoquinolin-1-one yield: 126 mg (57%)
$^1$H-NMR (CDCl$_3$) δ: 0.41 (3H, t, J=7.1 Hz), 1.43 (3H, t, J=6.6 Hz), 1.49 (2H, q, J=7.1 Hz), 1.75 (1H, d, J=3.6 Hz), 4.86 (1H, m), 5.38 (2H, s), 7.17 (2H, d, J=8.1 Hz), 7.23-7.31 (5H, m), 7.41-7.48 (3H, m), 7.51 (2H, dd, J=2.1, 8.5 Hz), 8.51 (1H, d, J=8.5 Hz).

EXAMPLE 508

6-chloro-2-[4-(1-hydroxypropyl)benzyl]-4-phenyl-3-propionyl-2H-isoquinolin-1-one yield: 36 mg (16%)
$^1$H-NMR (CDCl$_3$) δ: 0.39 (3H, t, J=7.1 Hz), 0.83 (3H, t, J=7.4 Hz), 1.44 (2H, q, J=7.1 Hz), 1.64-1.79 (3H, m), 4.56 (1H, m), 5.40 (2H, s), 7.16 (2H, d, J=8.1 Hz), 7.22-7.28 (5H, m), 7.39-7.47 (3H, m), 7.51 (2H, dd, J=2.1, 8.7 Hz), 8.51 (1H, d, J=8.7 Hz)

EXAMPLE 509

4-(4-bromophenyl)-6-chloro-2-(4-methanesulfonyl-benzyl)-3-propionyl-2H-isoquinolin-1-one

[Step 1] To a mixture of 4-chlorophthalic acid anhydride (25.3 g) and bromobenzene (200 ml) was added aluminum chloride (37.1 g) at room temperature with stirring and the mixture was stirred at the same temperature for 1 hr. and then stirred at 100° C. for 30 min. After cooling the reaction mixture, the mixture was diluted with ethyl acetate and was added to ice water. To this mixture, conc. hydrochloric acid (20 ml) was added and the mixture was stirred at room temperature for 1 hr. and the organic layer was partitioned. The organic layer was washed successively with 4N hydrochloric acid, water and saturated brine and dried over magnesium sulfate. The organic layer was concentrated until crystals precipitated, the precipitated crystals were collected by filtration, and recrystallization from toluene was repeated to give 2-(4-bromobenzoyl)-4-chlorobenzoic acid (12 g) as colorless crystals.

[Step 2] To a mixture of 2-(4-bromobenzoyl)-4-chlorobenzoic acid (7.1 g), 1-(4-methanesulfonylbenzylamino)butan-2-ol (5.4 g) and acetonitrile (140 ml) were added 1-hydroxy-1H-benzotriazole monohydrate (3.5 g) and 1-ethyl-3-(3-dimethylaminopropyl)carbodiimide hydrochloride (5.2 g) at room temperature and the mixture was stirred at the same temperature for 18 hrs. The solvent was evaporated under reduced pressure, and the residue was diluted with ethyl acetate. This solution was washed with 1N hydrochloric acid and saturated aqueous sodium hydrogen carbonate solution, dried over magnesium sulfate, and concentrated under reduced pressure. The residue was purified by silica gel chromatography (hexane/ethyl acetate=2/1→1/4) to give 2-(4-bromobenzoyl)-4-chloro-N-(2-hydroxybutyl)-N-(4-methanesulfonylbenzyl)benzamide (5.2 g) as a colorless powder.

[Step 3] To a mixture of 2-(4-bromobenzoyl)-4-chloro-N-(2-hydroxybutyl)-N-(4-methanesulfonylbenzyl)benzamide (5.2 g), triethylamine (20 ml) and DMSO (52 ml) was added dropwise gently pyridine sulfur trioxide complex (11.5 g) in DMSO (10 ml) at room temperature with stirring, and the mixture was stirred at room temperature for 2 hrs. After confirmation of the completion of the reaction, the mixture was diluted with ethyl acetate and washed with water. The organic layer was dried over magnesium sulfate and concentrated under reduced pressure. Then, the residue was dissolved in toluene (52 ml) 1,8-diazabicyclo[5.4.0]-7-undecene (2.7 ml) was added, and the mixture was stirred at 80° C. for 18 hrs. The mixture was diluted with ethyl acetate, washed with 1N hydrochloric acid, dried (MgSO$_4$) and concentrated under reduced pressure. The residue was purified by medium pressure preparative LC (hexane/ethyl acetate=2/1-1/2), and crystallized from methanol to give the title compound (3.2 g) in beige crystals. $^1$H NMR (CDCl$_3$) δ: 0.59 (3H, t, J=7.2 Hz), 1.80 (2H, q, J=7.2 Hz), 3.02 (3H, s), 5.34 (2H, s), 7.17 (2H, d, J=8.4 Hz) 7.23 (1H, d, J=1.8 Hz), 7.44 (2H, d, J=8.1 Hz), 7.54 (1H, dd, J=1.8, 8.7 Hz),7.63 (2H, d, J=8.4 Hz), 7.89 (2H, d, J=8.1 Hz), 8.47 (1H, d, J=8.7 Hz). HPLC analysis: purity 97.0% (retention time: 4.86 min).

EXAMPLE 510

4-[6-chloro-2-(4-methanesulfonylbenzyl)-1-oxo-3-propionyl-1,2-dihydroisoquinolin-4-yl]benzoic acid methyl ester Into a mixture of 4-(4-bromophenyl)-6-chloro-2-(4-methanesulfonylbenzyl)-3-propionyl-2H-isoquinolin-1-one (1.6 g), triethylamine (0.79 ml), 1,3-bis(diphenylphosphino)propane (64 mg), palladium (0) acetate (12 mg), methanol (30 ml) and DMSO (30 ml) in a pear shape flask with dimroth condenser was blown carbon monoxide gas at room temperature for 5 min. and the mixture was stirred at 90° C. for 18 hrs. After cooling the reaction mixture, methanol was evaporated under reduced pressure, the residue was diluted with ethyl acetate, and washed with 1N hydrochloric acid. The organic layer was dried (MgSO$_4$) and concentrated under reduced pressure. The residue was purified by medium pressure preparative LC (hexane/ethyl acetate=3/2-1/2), and crystallized from hexane/ethyl acetate=4/1 to give the title compound (0.85 g) in pale-pink crystals. $^1$H NMR (CDCl$_3$) δ: 0.54 (3H, t, J=6.9 Hz), 1.76 (2H, q, J=6.9 Hz), 3.02 (3H, s), 3.97 (3H, s), 5.36 (2H, s), 7.21 (1H, d, J=2.1 Hz), 7.39 (2H, d, J=8.4 Hz), 7.45 (2H, d, J=8.4 Hz), 7.55 (1H, dd, J=2.1, 8.7 Hz), 7.90 (2H, d, J=8.4 Hz), 8.16 (2H, d, J=8.4 Hz), 8.48 (1H, d, J=8.7 Hz). HPLC analysis: purity 99.8% (retention time: 4.46 min). MS (ESI+): 538.3 (M+H), 540.3.

EXAMPLE 511

2-(4-methanesulfonylbenzyl)-4-(4-methoxycarbonylphenyl)-1-oxo-3-propionyl-1,2-dihydroisoquinoline-6-carboxylic acid methyl ester The present compound was obtained (0.48 g) in Example 510 as a by-product. $^1$H NMR (CDCl$_3$) δ: 0.54 (3H, t, J=6.9 Hz), 1.76 (2H, q, J=6.9 Hz), 3.02 (3H, s), 3.98 (3H, s), 5.39 (2H, s), 7.41 (2H, d, J=8.4 Hz), 7.46 (2H, d, J=8.4 Hz), 7.86-7.97 (3H, m), 8.13-8.24 (3H, m), 8.62 (1H, d, J=8.4 Hz). HPLC analysis: purity 97.4% (retention time: 4.18 min). MS (ESI+): 562.3 (M+H).

EXAMPLE 512

4-[6-chloro-2-(4-methanesulfonylbenzyl)-1-oxo-3-propionyl-1,2-dihydroisoquinolin-4-yl]benzoic acid To a solution (2.0 ml) of 4-[6-chloro-2-(4-methanesulfonylbenzyl)-1-oxo-3-propionyl-1,2-dihydroisoquinolin-4-yl] benzoic acid methyl ester (100 mg) in methanol was added 1N sodium hydroxide (0.28 ml) at room temperature with stirring, and the mixture was stirred for 18 hrs. at the same temperature. The reaction mixture was neutralized with 1N hydrochloric acid and concentrated under reduced pressure. The residue was purified by preparative HPLC, and crystallized from methanol to give the title compound (42 mg) in beige crystals. $^1$H NMR (CDCl$_3$) δ: 0.56 (3H, t, J=6.9 Hz), 1.79 (2H, q, J=6.9 Hz), 3.02 (3H, s), 5.36 (2H, s), 7.22 (1H, d, J=2.1 Hz), 7.40-7.49 (4H, m), 7.56 (1H, dd, J=2.1, 8.7 Hz), 7.91 (2H, d, J=8.7 Hz), 8.24 (2H, d, J=8.7 Hz), 8.50 (1H, d, J=8.7 Hz). HPLC analysis: purity 99.9% (retention time: 3.92 min). MS (ESI+): 524.0 (M+H), 526.0.

EXAMPLE 513

4-(4-acetylphenyl)-6-chloro-2-(4-methanesulfonylbenzyl)-3-propionyl-2H-isoquinolin-1-one To a solution (2.0 ml) of 4-[6-chloro-2-(4-methanesulfonylbenzyl)-1-oxo-3-propionyl-1,2-dihydroisoquinolin-4-yl] benzoic acid methyl ester (100 mg) in THF was added dropwise gently a methyl lithium diethyl ether solution (1.1 mol/l, 0.25 ml) at −50° C. with stirring, and the mixture was allowed to warm to room temperature and stirred for 18 hrs. The reaction mixture was diluted with dichloromethane, washed with 1N hydrochloric acid, and the organic layer was dried over magnesium sulfate and concentrated under reduced pressure. The residue was purified by preparative HPLC to give the title compound (9 mg) in beige crystals. $^1$H NMR (CDCl$_3$) δ: 0.54 (3H, t, J=7.2 Hz), 1.78 (2H, q, J=7.2 Hz), 2.67 (3H, s), 3.02 (3H, s), 5.35 (2H, s), 7.19 (1H, d, J=2.1 Hz), 7.37-7.47 (4H, m), 7.54 (1H, dd, J=2.1 Hz), 7.89 (2H, d, J=8.7 Hz), 8.06 (2H, d, J=8.7 Hz), 8.47 (1H, d, J=8.7 Hz). HPLC analysis: purity 97.7% (retention time: 4.29 min). MS (ESI+): 522.0 (M+H), 524.0.

EXAMPLE 514

4-[3-acetyl-2-(4-methanesulfonylbenzyl)-1-oxo-1,2-dihydroisoquinolin-4-yl]benzoic acid The present compound was synthesized by a method similar to the method that afforded 4-[6-chloro-2-(4-methanesulfonylbenzyl)-1-oxo-3-propionyl-1,2-dihydroisoquinolin-4-yl]benzoic acid. A pink powder. $^1$H NMR (CDCl$_3$) δ: 1.53 (3H, s), 3.03 (3H, s), 5.47 (2H, s), 7.22-7.30 (2H, m), 7.42-7.50 (3H, m), 7.60-7.72 (2H, m), 7.91 (2H, d, J=8.4 Hz), 8.22 (2H, d, J=8.4 Hz), 8.58 (1H, m). HPLC analysis: purity 98.2%. MS (ESI+): 476 (M+H).

EXAMPLE 515

[4-[(6-bromo-1-oxo-4-phenyl-3-propionyl-2(1H)-isoquinolinyl)methyl]phenyl]sulfonylcarbamic acid tert-butyl ester To a mixture of 4-(6-bromo-1-oxo-4-phenyl-3-propionyl-1H-isoquinolin-2-ylmethyl)benzenesulfonamide (2.0 g), triethylamine (1.1 ml), 4-dimethylaminopyridine (0.23 g) and methylene chloride (40 ml) was added di-t-butyl carbonate (1.1 ml) at room temperature with stirring, and the mixture was stirred at the same temperature for 1 hr. After the completion of the reaction, the reaction mixture was washed with 1N hydrochloric acid, and the organic layer was dried over magnesium sulfate and concentrated under reduced pressure. The residue was purified by medium pressure preparative LC (hexane/ethyl acetate=3/1-1/1), crystallized from hexane/ethyl acetate=3/1 to give the title compound (2.0 g) in pale-pink crystals. $^1$H NMR (CDCl$_3$) δ: 0.46 (3H, t, J=6.9 Hz), 1.37 (9H, s), 1.62 (2H, q, J=6.9 Hz), 5.42 (2H, s), 7.14 (1H, br), 7.24-7.30 (2H, m), 7.39 (2H, d, J=8.4 Hz), 7.29-7.51 (4H, m), 7.69 (1H, dd, J=1.8, 8.4 Hz), 7.95 (2H, d, J=8.4 Hz), 8.41 (1H, d, J=8.4 Hz).
HPLC analysis: purity 99.8% (retention time: 4.94 min).

EXAMPLE 516

N-[[4-[(6-bromo-1-oxo-4-phenyl-3-propionyl-2(1H)-isoquinolinyl)methyl]phenyl]sulfonyl]-2,2,2-trifluoroacetamide The present compound was synthesized by a method similar to that in Example 515 and using trifluoroacetic anhydride and 4-(6-bromo-1-oxo-4-phenyl-3-propionyl-1H-isoquinolin-2-ylmethyl)benzenesulfonamide. $^1$H NMR (DMSO-d$_6$) δ: 0.37 (3H, t, J=6.9 Hz), 1.79 (2H, q, J=6.9 Hz), 5.21 (2H, s), 7.21 (2H, d, J=8.4 Hz), 7.26 (1H, d, J=1.8 Hz), 7.28-7.38 (2H, m), 7.44-7.58 (3H, m), 7.70 (2H, d, J=8.4 Hz), 7.81 (1H, dd, J=1.8, 8.7 Hz), 8.30 (1H, d, J=8.7 Hz). HPLC analysis: purity 85.5% (retention time: 4.72 min). MS (ESI+): 621 (M+H), 623.

EXAMPLE 517

N-[[4-[(6-bromo-1-oxo-4-phenyl-3-propionyl-2(1H)-isoquinolinyl)methyl]phenyl]sulfonyl]acetamide The present compound was synthesized by a method similar to that in Example 515 and using acetic anhydride and 4-(6-bromo-1-oxo-4-phenyl-3-propionyl-1H-isoquinolin-2-ylmethyl)benzenesulfonamide. $^1$H NMR (CDCl$_3$) δ: 0.49 (3H, t, J=7.2 Hz), 1.71 (2H, q, J=7.2 Hz), 2.00 (3H, s), 5.36 (2H, s), 7.23-7.30 (2H, m), 7.39 (2H, d, J=8.4 Hz), 7.43-7.52 (4H, m), 7.68 (1H, dd, J=2.1, 8.7 Hz), 7.96 (2H, d, J=8.4 Hz), 8.38 (1H, d, J=8.7 Hz). HPLC analysis: purity 99.4% (retention time: 4.50 min). MS (ESI+): 567 (M+H), 569.

EXAMPLE 518 methyl [4-[(6-bromo-1-oxo-4-phenyl-3-propionyl-2(1H)-isoquinolinyl)methyl]phenyl]sulfonylcarbamate To a mixture of 4-(6-bromo-1-oxo-4-phenyl-3-propionyl-1H-isoquinolin-2-ylmethyl)benzenesulfonamide (0.2 g), triethylamine (0.11 ml), 4-dimethylaminopyridine (23 mg) and methylene chloride (2.0 ml) was added methyl chlorocarbonate (35 μl) at room temperature with stirring, and the mixture was stirred at the same temperature for 1 hr. After the completion of the reaction, the reaction mixture was washed with 1N hydrochloric acid, and the organic layer was dried over magnesium sulfate and concentrated under reduced pressure. The residue was purified by medium pressure preparative LC (hexane/ethyl acetate=3/1-1/1), crystallized from hexane/ethyl acetate=3/2 to give the title compound (0.15 g) as colorless crystals. $^1$H NMR (CDCl$_3$) δ: 0.48 (3H, t, J=6.9 Hz), 1.69 (2H, q, J=6.9 Hz), 3.68 (3H, s), 5.38 (2H, s), 7.23-7.32

(2H, m), 7.41 (2H, d, J=8.7 Hz), 7.44-7.53 (5H, m), 7.69 (1H, dd, J=2.1, 8.4 Hz) 7.98 (2H, d, J=8.7 Hz), 8.40 (1H, d, J=8.4 Hz).

HPLC analysis: purity 100% (retention time: 4.60 min). MS (ESI+): 583.3 (M+H), 585.3.

The compounds of Examples 519-523 were synthesized by a method similar to that in Example 518 and using the corresponding acid chloride and 4-(6-bromo-1-oxo-4-phenyl-3-propionyl-1H-isoquinolin-2-ylmethyl)benzenesulfonamide.

EXAMPLE 519

4-(6-bromo-1-oxo-4-phenyl-3-propionyl-1H-isoquinolin-2-ylmethyl)-N-(furan-2-carbonyl)benzenesulfonamide $^1$H NMR (CDCl$_3$) δ: 0.44 (3H, t, J=7.2 Hz), 1.66 (2H, q, J=7.2 Hz), 5.38 (2H, s), 6.54 (1H, m), 7.20 (1H, m), 7.27 (1H, m), 7.42 (2H, d, J=8.7 Hz), 7.44-7.52 (6H, m), 7.68 (1H, dd, J=1.8, 8.4 Hz), 8.08 (2H, d, J=8.7 Hz), 8.38 (1H, d, J=8.4 Hz), 8.61 (1H, br).

HPLC analysis: purity 96.6% (retention time: 4.71 min). MS (ESI+): 619 (M+H), 621.

EXAMPLE 520

4-(6-bromo-1-oxo-4-phenyl-3-propionyl-1H-isoquinolin-2-ylmethyl)-N-(thiophen-2-carbonyl)benzenesulfonamide $^1$H NMR (CDCl$_3$) δ: 0.44 (3H, t, J=6.9 Hz), 1.65 (2H, q, J=6.9 Hz), 5.38 (2H, s), 7.09 (1H, dd, J=3.9, 4.8 Hz), 7.23-7.31 (2H, m), 7.41 (2H, d, J=8.4 Hz), 7.43-7.52 (4H, m), 7.55-7.63 (2H, m), 7.68 (1H, dd, J=1.8, 8.7 Hz), 8.07 (2H, d, J=8.4 Hz), 8.39 (1H, d, J=8.7 Hz), 8.63 (1H, br).

HPLC analysis: purity 98.89% (retention time: 4.86 min). MS (ESI+): 635 (M+H), 637.

EXAMPLE 521 ethyl[4-[(6-bromo-1-oxo-4-phenyl-3-propionyl-2(1H)-isoquinolinyl)methyl]phenyl]sulfonylcarbamate $^1$H NMR (CDCl$_3$) δ: 0.48 (3H, t, J=6.9 Hz), 1.20 (3H, t, J=7.2 Hz), 1.68 (2H, q, J=6.9 Hz), 4.11 (2H, q, J=7.2 Hz), 5.39 (2H, s), 7.25-7.31 (2H, m), 7.36-7.53 (7H, m), 7.69 (1H, dd, J=1.8, 8.4 Hz), 7.98 (2H, d, J=8.4 Hz), 8.40 (1H, d, J=8.4 Hz).

HPLC analysis: purity 99.8% (retention time: 4.76 min). MS (ESI+): 597 (M+H), 599.

EXAMPLE 522

4-[(6-bromo-1-oxo-4-phenyl-3-propionyl-2(1H)-isoquinolinyl)methyl]-N-(methylsulfonyl)benzenesulfonamide $^1$H NMR (CDCl$_3$) δ: 0.48 (3H, t, J=6.9 Hz), 1.65 (2H, q, J=6.9 Hz), 3.33 (3H, s), 5.41 (2H, s), 7.23-7.30 (2H, m), 7.38 (2H, d, J=8.4 Hz), 7.43-7.52 (4H, m), 7.70 (1H, dd, J=1.8, 8.4 Hz), 7.90 (2H, d, J=8.4 Hz), 8.44 (1H, d, J=8.4 Hz). HPLC analysis: purity 98.0% (retention time: 4.13 min). MS (ESI+): 603 (M+H), 605.

EXAMPLE 523

4-[(6-bromo-1-oxo-4-phenyl-3-propionyl-2(1H)-isoquinolinyl)methyl]-N-[(trifluoromethyl)sulfonyl]benzenesulfonamide $^1$H NMR (DMSO-d$_6$) δ: 0.40 (3H, t, J=6.9 Hz), 1.84 (2H, q, J=6.9 Hz), 5.22 (2H, s), 7.22-7.29 (3H, m), 7.29-7.36 (2H, m), 7.45-7.57 (3H, m), 7.68 (2H, d, J=8.1 Hz), 7.81 (1H, dd, J=1.8, 8.4 Hz), 8.30 (1H, d, J=8.4 Hz). HPLC analysis: purity 95.3% (retention time: 5.00 min). MS (ESI+): 657 (M+H), 659.

EXAMPLE 524

4-(6-bromo-1-oxo-4-phenyl-3-propionyl-1H-isoquinolin-2-ylmethyl)-N-methylbenzenesulfonamide To a mixture of [4-[(6-bromo-1-oxo-4-phenyl-3-propionyl-2(1H)-isoquinolinyl)methyl]phenyl]sulfonylcarbamic acid tert-butyl ester (0.15 g), methanol (19 μl), triphenylphosphine (0.13 g) and THF (4.0 ml) was added diethyl azodicarboxylate (190 μl) at 0° C. with stirring, and the mixture was stirred at room temperature for 2 hrs. The reaction mixture was concentrated under reduced pressure and the residue was purified by medium pressure preparative LC (hexane/ethyl acetate=3/1-1/1) to give tert-butyl [[4-[(6-bromo-1-oxo-4-phenyl-3-propionylisoquinolin-2(1H)-yl)methyl]phenyl]sulfonyl]methylcarbamate. Then this product was dissolved in trifluoroacetic acid (2.0 ml) and the mixture was stirred at room temperature for 1 hr. and concentrated under reduced pressure. The residue was purified by medium pressure preparative LC (hexane/ethyl acetate=3/1-1/2) to give the title compound (86 mg) as colorless crystals. $^1$H NMR (CDCl$_3$) δ: 0.48 (3H, t, J=6.9 Hz), 1.66 (2H, q, J=6.9 Hz), 2.63 (3H, d, J=5.4 Hz), 4.25 (1H, q, J=5.4 Hz), 5.38 (2H, s), 7.22-7.30 (2H, m), 7.37 (2H, d, J=8.1 Hz), 7.42-7.51 (4H, m), 7.67 (1H, m), 7.78 (2H, d, J=8.1 Hz), 8.39 (1H, d, J=8.4 Hz). HPLC analysis: purity 99.4% (retention time: 4.64 min). MS (ESI+): 539.2 (M+H), 541.2.

The compounds of Examples 525-531 were synthesized by a method similar to that in Example 524 and using [4-[(6-bromo-1-oxo-4-phenyl-3-propionyl-2(1H)-isoquinolinyl)methyl]phenyl]sulfonylcarbamic acid tert-butyl ester and the corresponding alcohol.

EXAMPLE 525

4-(6-bromo-1-oxo-4-phenyl-3-propionyl-1H-isoquinolin-2-ylmethyl)-N-butylbenzenesulfonamide $^1$H NMR (CDCl$_3$) δ: 0.47 (3H, t, J=6.9 Hz), 0.85 (3H, t, J=7.2 Hz), 1.20-1.34 (2H, m), 1.36-1.48 (2H, m), 1.63 (3H, q, J=6.9 Hz), 2.91 (2H, q, J=6.6 Hz), 4.26 (1H, t, J=6.3 Hz), 5.40 (2H, s), 7.23-7.31 (2H, m), 7.36 (2H, d, J=8.4 Hz) 7.44-7.53 (4H, m), 7.69 (1H, dd, J=2.1, 8.4 Hz), 7.79 (2H, d, J=8.4 Hz), 8.41 (1H, d, J=8.4 Hz).

HPLC analysis: purity 100% (retention time: 5.05 min). MS (ESI+): 581.3 (M+H), 583.3.

EXAMPLE 526

4-(6-bromo-1-oxo-4-phenyl-3-propionyl-1H-iso-quinolin-2-ylmethyl)-N-(2-hydroxyethyl)benzene-sulfonamide $^1$H NMR (CDCl$_3$) δ: 0.48 (3H, t, J=7.2 Hz), 1.57-1.74 (3H, m), 3.09 (2H, q, J=6.0 Hz), 3.71 (2H, t, J=5.7 Hz), 4.95 (1H, t, J=6.0 Hz), 5.38 (2H, s), 7.23-7.31 (2H, m), 7.37 (2H, d, J=8.4 Hz), 7.43-7.53 (4H, m), 7.69 (1H, dd, J=2.1, 8.7 Hz), 7.80 (2H, d, J=8.4 Hz), 8.41 (1H, d, J=8.7 Hz).

HPLC analysis: purity 99.8% (retention time: 4.34 min). MS (ESI+): 569.3 (M+H), 571.3.

EXAMPLE 527

4-(6-bromo-1-oxo-4-phenyl-3-propionyl-1H-iso-quinolin-2-ylmethyl)-N-(2-methoxyethyl)benzene-sulfonamide $^1$H NMR (CDCl$_3$) δ: 0.47 (3H, t, J=6.9 Hz), 1.64 (2H, q, J=6.9 Hz), 3.03-3.12 (2H, m), 3.26 (3H, s), 3.35-3.42 (2H, m), 4.78 (1H, t, J=6.0 Hz), 5.39 (2H, s), 7.24-7.31 (2H, m), 7.37 (2H, d, J=8.4 Hz), 7.44-7.53 (4H, m), 7.69 (1H, dd, J=1.8, 8.4 Hz), 7.79 (2H, d, J=8.4 Hz), 8.41 (1H, d, J=8.4 Hz). HPLC analysis: purity 99.4% (retention time: 4.67 min). MS (ESI+): 583.3 (M+H), 585.3.

EXAMPLE 528

4-(6-bromo-1-oxo-4-phenyl-3-propionyl-1H-iso-quinolin-2-ylmethyl)-N-pyridin-2-ylmethylbenzene-sulfonamide $^1$H NMR (CDCl$_3$) δ: 0.43 (3H, t, J=7.2 Hz), 1.60 (2H, q, J=7.2 Hz), 4.22 (2H, d, J=5.1 Hz), 5.35 (2H, s), 5.93 (1H, t, J=5.1 Hz), 7.10-7.20 (2H, m), 7.22-7.34 (4H, m), 7.43-7.53 (4H, m), 7.61 (1H, m), 7.68 (1H, dd, J=1.8, 8.7 Hz), 7.80 (2H, d, J=8.4 Hz), 8.40 (1H, d, J=8.7 Hz), 8.44 (1H, d, J=4.5 Hz). HPLC analysis: purity 99.7% (retention time: 3.85 min). MS (ESI+): 616.3 (M+H), 618.3.

EXAMPLE 529

4-(6-bromo-1-oxo-4-phenyl-3-propionyl-1H-iso-quinolin-2-ylmethyl)-N-(3-hydroxypropyl)benzene-sulfonamide $^1$H NMR (CDCl$_3$) δ: 0.49 (3H, t, J=7.2 Hz), 1.68 (2H, q, J=7.2 Hz), 1.75 (1H, t, J=5.1 Hz), 3.03-3.11 (2H, m), 3.49 (2H, d, J=4.2 Hz), 3.64-3.72 (2H, m), 4.84 (1H, t, J=6.0 Hz), 5.38 (2H, s), 7.23-7.31 (2H, m), 7.38 (2H, d, J=8.4 Hz), 7.43-7.53 (4H, m), 7.69 (1H, dd, J=1.8, 8.7 Hz), 7.81 (2H, d, J=8.4 Hz), 8.40 (1H, d, J=8.7 Hz). HPLC analysis: purity 97.7% (retention time: 4.36 min). MS (ESI+): 583 (M+H), 585.

EXAMPLE 530

4-(6-bromo-1-oxo-4-phenyl-3-propionyl-1H-iso-quinolin-2-ylmethyl)-N-(2-methanesulfonylethyl)benzenesulfonamide $^1$H NMR (CDCl$_3$) δ: 0.52 (3H, t, J=6.9 Hz), 1.74 (2H, q, J=6.9 Hz), 2.96 (3H, s), 3.18-3.25 (2H, m), 3.41-3.50 (2H, m), 5.29 (1H, t, J=6.3 Hz), 5.36 (2H, s), 7.23-7.32 (2H, m), 7.41 (2H, d, J=8.7 Hz), 7.44-7.53 (4H, m), 7.69 (1H, dd, J=2.1, 8.7 Hz), 7.81 (2H, d, J=8.7 Hz), 8.39 (1H, d, J=8.7 Hz). HPLC analysis: purity 99.9% (retention time: 4.45 min). MS (ESI+): 631.2 (M+H), 633.2.

EXAMPLE 531

[4-(6-bromo-1-oxo-4-phenyl-3-propionyl-1H-iso-quinolin-2-ylmethyl)benzenesulfonylamino]acetic acid methyl ester $^1$H NMR (CDCl$_3$) δ: 0.49 (3H, t, J=6.9 Hz), 1.68 (2H, q, J=6.9 Hz), 3.65 (3H, s), 3.76 (2H, d, J=5.4 Hz), 5.01 (1H, t, J=5.4 Hz), 5.37 (2H, s), 7.24-7.31 (2H, m), 7.37 (2H, d, J=8.4 Hz), 7.44-7.53 (4H, m), 7.68 (1H, dd, J=1.8, 8.4 Hz), 7.80 (2H, d, J=8.4 Hz), 8.39 (1H, d, J=8.4 Hz). HPLC analysis: purity 99.7% (retention time: 4.65 min). MS (ESI+): 597 (M+H), 599.

EXAMPLE 532

[4-(6-bromo-1-oxo-4-phenyl-3-propionyl-1H-iso-quinolin-2-ylmethyl)benzenesulfonylamino]acetic acid To a mixture of [4-(6-bromo-1-oxo-4-phenyl-3-propionyl-1H-isoquinolin-2-ylmethyl)benzenesulfonylamino]acetic acid methyl ester (70 mg), methanol (2.0 ml) and THF (2.0 ml) was added 1N sodium hydroxide (0.23 ml) at room temperature with stirring, and the mixture was stirred at the same temperature for 18 hrs. The reaction mixture was neutralized with 1N hydrochloric acid and concentrated under reduced pressure. The residue was purified by preparative HPLC to give the title compound (33 mg) in beige crystals. $^1$H NMR (CDCl$_3$) δ: 0.52 (3H, t, J=6.9 Hz), 1.78 (2H, q, J=6.9 Hz), 3.82 (2H, d, J=6.0 Hz), 5.25-5.36 (3H, m), 7.23-7.31 (2H, m), 7.33 (2H, d, J=8.4 Hz), 7.44-7.55 (4H, m), 7.70 (1H, dd, J=1.8, 8.4 Hz), 7.80 (2H, d, J=8.4 Hz), 8.37 (1H, d, J=8.4 Hz). HPLC analysis: purity 95.2% (retention time: 4.38 min). MS (ESI+): 583 (M+H), 585.

EXAMPLE 533

4-(6-bromo-1-oxo-4-phenyl-3-propionyl-1H-iso-quinolin-2-ylmethyl)-N,N-dimethylbenzenesulfona-mide A mixture of 4-(6-bromo-1-oxo-4-phenyl-3-propionyl-1H-isoquinolin-2-ylmethyl)benzenesulfonamide (0.19 g), potassium carbonate (0.11 g), methyl iodide (23 μl) and DMF (2.0 ml) was stirred at room temperature for 1 hr. After the completion of the reaction, the reaction mixture was concentrated, and the residue was diluted with dichloromethane. Then, this solution was washed with 1N hydrochloric acid, dried over magnesium sulfate, and concentrated under reduced pressure. The residue was purified by medium pressure preparative LC (hexane/ethyl acetate=4/1-1/1), and crystallized from methanol to give the title compound (32 mg) as colorless crystals. $^1$H NMR (CDCl$_3$) δ: 0.46 (3H, t, J=6.9 Hz), 1.61 (2H, q, J=6.9 Hz), 2.66 (6H, s), 5.42 (2H, s), 7.24-7.31 (2H, m), 7.39 (2H, d, J=8.4 Hz), 7.44-7.53 (4H, m), 7.66-7.74 (3H, m), 8.42 (1H, d, J=8.7 Hz).

HPLC analysis: purity 99.5% (retention time: 4.87 min). MS (ESI+): 553 (M+H), 555.

EXAMPLE 534

4-(6-bromo-1-oxo-4-phenyl-3-propionyl-1H-isoquinolin-2-ylmethyl)-N-(piperidine-1-carbonyl)benzenesulfonamide A mixture of 4-(6-bromo-1-oxo-4-phenyl-3-propionyl-1H-isoquinolin-2-ylmethyl)benzenesulfonamide (0.10 g), potassium carbonate (0.11 mg), 1-piperidinecarbonyl chloride (29 µl) and DMF (2.0 ml) was stirred at 50° C. for 18 hrs. After the completion of the reaction, the reaction mixture was concentrated, and the residue was diluted with dichloromethane. Then, this solution was washed with 1N hydrochloric acid, dried over magnesium sulfate, and concentrated under reduced pressure. The residue was purified by medium pressure preparative LC (hexane/ethyl acetate=4/1-1/1) to give the title compound (38 mg) as a colorless powder. HPLC analysis: purity 91.6% (retention time: 4.78 min). MS (ESI+): 636 (M+H), 638.

EXAMPLE 535

6-bromo-2-(4-methoxybenzyl)-4-phenyl-3-propionyl-2H-isoquinolin-1-one

[Step 1] To a solution of 1-amino-2-butanol (3.9 g) in methanol (50 ml) was added anisaldehyde (5.0 g) under ice-cooling. The mixture was stirred at the same temperature for 1 hr., and a solution of sodium borohydride (1.1 g) in 1N sodium hydroxide (17 ml) was added dropwise. The mixture was stirred at 0° C. for 30 min, 2N hydrochloric acid (68 ml) was added dropwise and diisopropyl ether was added to allow partitioning. The aqueous layer was alkalified with potassium carbonate (12.1 g) and ethyl acetate was added to allow partitioning. The ethyl acetate layer was washed with saturated brine, dried over magnesium sulfate, and concentrated under reduced pressure to give 1-(4-methoxybenzylamino)butan-2-ol (5.4 g) as a brown oil.

[Step 2] To a mixture of 2-benzoyl-4-bromobenzoic acid (7.5 g), 1-(4-methoxybenzylamino)butan-2-ol (5.4 g) and acetonitrile (100 ml) were added 1-hydroxy-1H-benzotriazole monohydrate (4.3 g) and 1-ethyl-3-(3-dimethylaminopropyl)carbodiimide hydrochloride (5.9 g) at room temperature and the mixture was stirred at the same temperature for 18 hrs. The solvent was evaporated under reduced pressure, and the residue was diluted with ethyl acetate. This solution was washed with 1N hydrochloric acid and saturated aqueous sodium hydrogen carbonate solution, dried over magnesium sulfate and concentrated under reduced pressure. The residue was purified by silica gel chromatography (hexane/ethyl acetate=5/1-2/3) to give 2-benzoyl-4-bromo-N-(2-hydroxybutyl)-N-(4-methoxybenzyl)benzamide (3.2 g) as a colorless powder.

[Step 3] To a mixture of 2-benzoyl-4-bromo-N-(2-hydroxybutyl)-N-(4-methoxybenzyl)benzamide (3.2 g), 4-methylmorpholine N-oxide (2.3 g), molecular sieves 4A powder (1.6 g) and dichloromethane (50 ml) was added tetra-n-propylammonium perruthenate (0.23 g) under ice-cooling, and the mixture was stirred at room temperature for 3 hrs. After the completion of the reaction, molecular sieves 4 A was removed by filtration and the filtrate was concentrated under reduced pressure. The residue was purified by silica gel column chromatography (hexane/ethyl acetate=3/2) to give 2-benzoyl-4-bromo-N-(4-methoxybenzyl)-N-(2-oxobutyl)benzamide (2.6 g).

[Step 4] To a solution of 2-benzoyl-4-bromo-N-(4-methoxybenzyl)-N-(2-oxobutyl)benzamide (2.6 g) in ethanol (52 ml) was added 1,8-diazabicyclo[5.4.0]-7-undecene (2.7 ml) and the mixture was stirred at 90° C. for 18 hrs. After cooling the reaction mixture, the solvent was evaporated under reduced pressure, ethyl acetate was added to the residue, and the mixture was washed with 1N hydrochloric acid. The organic layer was dried over magnesium sulfate and concentrated under reduced pressure. The residue was purified by medium pressure preparative LC (hexane/ethyl acetate=5/1-1/1), and crystallized from hexane/ethyl acetate=3/1 to give the title compound (1.6 g) as colorless crystals. $^1$H NMR (CDCl$_3$) δ: 0.43 (3H, t, J=6.9 Hz), 1.46 (2H, q, J=6.9 Hz), 3.75 (3H, s), 5.34 (2H, s), 6.80 (2H, d, J=8.7 Hz), 7.11 (2H, d, J=8.7 Hz), 7.22-7.28 (2H, m), 7.40-7.48 (4H, m), 7.66 (1H, dd, J=1.8, 8.4 Hz), 8.43 (1H, d, J=8.4 Hz). HPLC analysis: purity 99.2% (retention time: 5.16 min). MS (ESI+): 476 (M+H), 478.

EXAMPLE 536

6-bromo-2-(4-methanesulfonylbenzyl)-4-phenyl-3-(2,2,2-trifluoro-1-hydroxyethyl)-2H-isoquinolin-1-one To a solution (5 ml) of 6-bromo-2-(4-methanesulfonylbenzyl)-1-oxo-4-phenyl-1,2-dihydroisoquinoline-3-carbaldehyde (500 mg) and (trifluoromethyl)trimethylsilane (170 mg) in THF was added a solution of tetra-N-butylammonium fluoride (1M, 0.03 ml) in THF at room temperature, and the mixture was stirred for 30 min. Then a solution (1M, 2 ml) of tetra-N-butylammonium fluoride in THF was added, and the mixture was stirred for 30 min. The reaction mixture was concentrated under reduced pressure and the residue was diluted with ethyl acetate. The organic layer was washed with saturated aqueous sodium hydrogen carbonate, water and saturated brine, and dried over anhydrous sodium sulfate. The solvent was evaporated under reduced pressure and the obtained residue was purified by silica gel column chromatography (THF) and basic silica gel column chromatography (THF) and the crystals were washed with a mixture of ethyl acetate and diisopropyl ether, and recrystallized (MeOH-hexane) to give the title compound (290 mg).

$^1$H-NMR (CDCl$_3$) δ: 2.97 (3H, s), 4.08-4.24 (1H, m), 5.28-5.46 (1H, m), 5.66 (2H, s), 7.08 (1H, d, J=1.8 Hz), 7.20-7.40 (4H, m), 7.42-7.66 (4H, m), 7.74 (2H, d, J=8.4 Hz), 8.20 (1H, d, J=8.7 Hz).

EXAMPLE 537

6-bromo-3-(1-hydroxy-2-phenylethyl)-2-(4-ethanesulfonylbenzyl)-4-phenyl-2H-isoquinolin-1-one To a solution (5 ml) of 6-bromo-2-(4-methanesulfonylbenzyl)-1-oxo-4-phenyl-1,2-dihydroisoquinoline-3-carbaldehyde (500 mg) in THF was added dropwise a solution (1M, 1.2 ml) of benzylmagnesium chloride in THF at room temperature, and the mixture was stirred for 10 min. Water was added to the reaction mixture and the mixture was extracted with ethyl acetate. The organic layer was washed with water and saturated brine, and dried over anhydrous sodium sulfate. The solvent was evaporated under reduced pressure and the obtained residue was crystallized from diisopropyl ether to give the title compound (400 mg).

$^1$H-NMR (CDCl$_3$) δ: 1.96-2.10 (1H, m), 2.94 (2H, d, J=7.6 Hz), 3.02 (3H, s), 4.90-5.06 (1H, m), 5.93 (2H, s), 6.70-7.70 (14H, m), 7.88 (2H, d, J=8.6 Hz), 8.29 (1H, d, J=8.6 Hz).

EXAMPLE 538

6-bromo-3-(1-hydroxy-2-pyridin-2-ylethyl)-2-(4-methanesulfonylbenzyl)-4-phenyl-2H-isoquinolin-1-one Under a nitrogen stream, a solution (1.61M, 15.8 ml) of n-butyllithium in hexane was added to THF (15 ml) at −50° C. or below, and a solution (2.5 ml) of 2-methylpyridine (2.5 g) in THF was added dropwise at −50° C. or below. The reaction mixture was allowed to warm to −20° C. and stirred for 10 min. and then cooled to −50° C. and magnesium bromide (2.5 g) was added. The reaction mixture was allowed to warm to room temperature, stirred for 30 min. and bromo(pyridin-2-ylmethyl)magnesium was prepared. The obtained suspension (4 ml) of bromo(pyridin-2-ylmethyl)magnesium was added to a solution of 6-bromo-2-(4-methanesulfonylbenzyl)-1-oxo-4-phenyl-1,2-dihydroisoquinoline-3-carbaldehyde (500 mg) in THF (5 ml), and the mixture was stirred at room temperature for 10 min. To the reaction mixture were added water and saturated aqueous sodium hydrogen carbonate, and the mixture was extracted with ethyl acetate. The organic layer was washed with water and saturated brine, and dried over anhydrous sodium sulfate. The solvent was evaporated under reduced pressure and the obtained residue was purified by silica gel column chromatography (ethyl acetate) to give the title compound (400 mg).

$^1$H-NMR (CDCl$_3$) δ: 2.74-2.96 (1H, m), 3.02 (3H, s), 3.08-3.36 (1H, m), 5.18-5.36 (1H, m), 6.07 (2H, s), 6.91 (1H, d, J=7.8 Hz), 7.02-7.72 (11H, m), 7.87 (2H, d, J=8.6 Hz), 8.28 (1H, d, J=8.8 Hz), 8.34 (1H, d, J=5.0 Hz), 1H unconfirmed.

EXAMPLE 539

6-bromo-3-butyryl-2-(4-methanesulfonylbenzyl)-4-phenyl-2H-isoquinolin-1-one

[Step 1] To a solution (20 ml) of 2-benzoyl-4-bromobenzoic acid (2.0 g) in THF were added 1-(4-methanesulfonylbenzylamino)pentan-2-ol (1.8 g), 1-ethyl-3-(3-dimethylaminopropyl)carbodiimide hydrochloride (1.9 g), 1-hydroxy-1H-benzotriazole monohydrate (1.0 g), acetonitrile (20 ml) and triethylamine (5 ml) at room temperature. The reaction mixture was stirred at room temperature for 12 hrs. and concentrated under reduced pressure. To the residue was added saturated aqueous sodium hydrogen carbonate and the mixture was extracted with ethyl acetate. The organic layer was washed with water, 1N-hydrochloric acid, water, saturated aqueous sodium hydrogen carbonate, water and saturated brine, and dried over anhydrous sodium sulfate. The solvent was evaporated under reduced pressure, and the obtained crystals were washed with diisopropyl ether to give 2-benzoyl-4-bromo-N-(2-hydroxypentyl)-N-(4-methanesulfonylbenzyl)benzamide (3.0 g).

$^1$H-NMR (CDCl$_3$) δ: 0.74-0.98 (3H, m), 1.00-1.60 (4H, m), 2.94-3.16 (1H×0.5, m), 3.05 (3H×0.5, s), 3.07 (3H×0.5, s), 3.18-3.32 (1H×0.5, m), 3.34-3.52 (1H×0.5, m), 3.58-3.74 (1H×0.5, m), 3.76-3.90 (1H×0.5, m), 4.02-4.18 (1H×0.5, m), 4.69 (1H×0.5, d, J=17.3 Hz), 4.72 (1H×0.5, d, J=15.3 Hz), 4.83 (1H×0.5, d, J=17.3 Hz), 5.03 (1H×0.5, d, J=15.3 Hz), 7.10-8.00 (12H, m), 1H unconfirmed.

[Step 2] To a solution of 2-benzoyl-4-bromo-N-(2-hydroxypentyl)-N-(4-methanesulfonylbenzyl)benzamide (2.7 g) in DMSO (27 ml) was added triethylamine (11 ml), and pyridine sulfur trioxide complex (6.2 g) was added to the mixture at room temperature. The mixture was stirred for 1 hr. and added to water. 10% Hydrochloric acid was added to acidify the aqueous layer and the mixture was extracted with ethyl acetate. The organic layer was washed with water, saturated aqueous sodium hydrogen carbonate, water and saturated brine, and dried over anhydrous sodium sulfate. The solvent was evaporated under reduced pressure to give 2-benzoyl-4-bromo-N-(4-methanesulfonylbenzyl)-N-(2-oxopentyl)benzamide (2.2 g).

$^1$H-NMR (CDCl$_3$) δ: 0.83 (3H×0.5, t, J=7.5 Hz), 0.88 (3H×0.5, t, J=7.2 Hz), 1.42-1.72 (2H, m), 2.16 (2H×0.5, t, J=7.4 Hz), 2.36 (2H×0.5, t, J=7.4 Hz), 3.05 (3H, s), 4.05 (2H×0.5, s), 4.10 (2H×0.5, br. s), 4.68 (2H×0.5, s), 4.77 (2H×0.5, br. s), 6.80-8.10 (12H, m).

[Step 3] To a solution (40 ml) of 2-benzoyl-4-bromo-N-(4-methanesulfonylbenzyl)-N-(2-oxopentyl)benzamide (2.0 g) in toluene was added 1,8-diazabicyclo[5.4.0]undeca-7-ene (1.1 g), and the mixture was heated under reflux for 48 hrs. The reaction mixture was concentrated under reduced pressure. To the residue were added water and 10% hydrochloric acid, and the mixture was extracted with ethyl acetate. The organic layer was washed with water, saturated aqueous sodium hydrogen carbonate, water and saturated brine, and dried over anhydrous sodium sulfate. The solvent was evaporated under reduced pressure, and the residue was purified by recrystallization (THF-diisopropyl ether) to give the title compound (1.4 g).

$^1$H-NMR (CDCl$_3$) δ: 0.41 (3H, t, J=7.2 Hz), 1.06 (2H, sextet, J=7.2 Hz), 1.73 (2H, t, J=7.2 Hz), 3.02 (3H, s), 5.36 (2H, s), 7.22-7.34 (3H, m), 7.36-7.56 (5H, m), 7.68 (1H, dd, J=1.8, 8.7 Hz), 7.89 (2H, d, J=8.4 Hz), 8.39 (1H, d, J=8.7 Hz).

EXAMPLE 540

6-bromo-2-(4-methanesulfonylbenzyl)-3-pentanoyl-4-phenyl-2H-isoquinolin-1-one

[Step 1] To a solution (20 ml) of 2-benzoyl-4-bromobenzoic acid (2.0 g) in THF were added 1-(4-methanesulfonylbenzylamino)hexan-2-ol (1.9 g), 1-ethyl-3-(3-dimethylaminopropyl)carbodiimide hydrochloride (1.9 g), 1-hydroxy-1H-benzotriazole monohydrate (1.0 g), acetonitrile (20 ml) and triethylamine (5 ml) at room temperature. The mixture was stirred at room temperature for 12 hrs. and concentrated under reduced pressure. Saturated aqueous sodium hydrogen carbonate was added to the residue and the mixture was extracted with ethyl acetate. The organic layer was washed with water, 1N-hydrochloric acid, water, saturated aqueous sodium hydrogen carbonate, water and saturated brine, and dried over anhydrous sodium sulfate. The solvent was evaporated under reduced pressure. The residue was purified by silica gel column chromatography (hexane-hexane:ethyl acetate=1:1) to give 2-benzoyl-4-bromo-N-(2-hydroxyhexyl)-N-(4-methanesulfonylbenzyl) benzamide (2.57 g).

$^1$H-NMR (CDCl$_3$) δ: 0.70-0.96 (3H, m), 1.00-1.54 (6H, s), 2.94-3.18 (1H×0.5, m), 3.06 (3H×0.5, s), 3.07 (3H×0.5, s), 3.20-3.32 (1H×0.5, m), 3.34-3.50 (1H×0.5, m), 3.56-3.88 (2H×0.5, m), 4.02-4.18 (1H×0.5, m), 4.69 (1H×0.5, d, J=17.4 Hz), 4.74 (1H×0.5, d, J=15.6 Hz), 4.83 (1H×0.5, d, J=17.4 Hz), 5.02 (1H×0.5, d, J=15.6 Hz), 7.12-8.06 (12H, m), 1H unconfirmed.

[Step 2] To a solution (25 ml) of 2-benzoyl-4-bromo-N-(2-hydroxyhexyl)-N-(4-methanesulfonylbenzyl)benzamide (2.3 g) in DMSO was added triethylamine (9 ml), and pyridine sulfur trioxide complex (5.2 g) was added at room temperature. The mixture was stirred for 1 hr. and added to water.

10% Hydrochloric acid was added to acidify the aqueous layer and the mixture was extracted with ethyl acetate. The organic layer was washed with water, saturated aqueous sodium hydrogen carbonate, water and saturated brine, and dried over anhydrous sodium sulfate. The solvent was evaporated under reduced pressure to give 2-benzoyl-4-bromo-N-(4-methanesulfonylbenzyl)-N-(2-oxohexyl)benzamide (1.75 g).

$^1$H-NMR (CDCl$_3$) δ: 0.80-0.90 (3H, m), 1.10-1.64 (4H, m), 2.17 (2H×0.5, t, J=7.5 Hz), 2.37 (2H×0.5, t, J=7.5 Hz), 3.05 (3H, s), 4.05 (2H×0.5, s), 4.10 (2H×0.5, br. s), 4.68 (2H×0.5, s), 4.77 (2H×0.5, br. s), 6.80-8.10 (12H, m).

[Step 3] In the same manner as in Example 539, [Step 3], the title compound was synthesized using 2-benzoyl-4-bromo-N-(4-methanesulfonylbenzyl)-N-(2-oxohexyl)benzamide. Crystals (THF-diisopropyl ether).

$^1$H-NMR (CDCl$_3$) δ: 0.56 (3H, t, J=7.1 Hz), 0.68-0.88 (2H, m), 0.92-1.10 (2H, m), 1.73 (2H, t, J=7.2 Hz), 3.01 (3H, s), 5.36 (2H, s), 7.20-7.56 (8H, m), 7.68 (1H, dd, J=1.8, 8.7 Hz), 7.89 (2H, d, J=8.4 Hz), 8.39 (1H, d, J=8.7 Hz).

EXAMPLE 541

6-bromo-2-(4-methanesulfonylbenzyl)-4-phenyl-3-phenylacetyl-2H-isoquinolin-1-one

[Step 1] 2-Benzoyl-4-bromobenzoic acid (1.0 g) and 1-(4-methanesulfonylbenzylamino)-3-phenylpropan-2-ol (1.1 g) were dissolved in a mixture of THF (10 ml) and acetonitrile (10 ml), and 1-ethyl-3-(3-dimethylaminopropyl)carbodiimide hydrochloride (1.0 g), 1-hydroxy-1H-benzotriazole monohydrate (0.5 g) and triethylamine (3 ml) were added at room temperature. The reaction mixture was stirred at room temperature for 12 hrs. and concentrated under reduced pressure. Saturated aqueous sodium hydrogen carbonate was added to the residue and the mixture was extracted with ethyl acetate. The organic layer was washed with water, 1N-hydrochloric acid, water, saturated aqueous sodium hydrogen carbonate, water and saturated brine, and dried over anhydrous sodium sulfate. The solvent was evaporated under reduced pressure, and the residue was purified by silica gel column chromatography (hexane:ethyl acetate=10:1-hexane:ethyl acetate=1:2) to give 2-benzoyl-4-bromo-N-(2-hydroxy-3-phenylpropyl)-N-(4-methanesulfonylbenzyl)benzamide (1.25 g).

$^1$H-NMR (CDCl$_3$) δ: 2.45 (1H×0.5, dd, J=7.5, 13.5 Hz), 2.64-2.84 (3H×0.5, s), 3.04 (3H×0.5, s), 3.06 (3H×0.5, s), 3.12-3.46 (3H×0.5, m), 3.66 (1H×0.5, d, J=13.5 Hz), 4.02-4.18 (1H×0.5, m), 4.20-4.36 (1H×0.5, m), 4.58 (1H×0.5, d, J=15.3 Hz), 4.60 (1H×0.5, d, J=17.0 Hz), 4.76 (1H×0.5, d, J=17.0 Hz), 5.00 (1H×0.5, d, J=15.3 Hz), 6.90-8.00 (17H, m), 1H unconfirmed.

[Step 2] To a solution (10 ml) of 2-benzoyl-4-bromo-N-(2-hydroxy-3-phenylpropyl)-N-(4-methanesulfonylbenzyl)benzamide (1.0 g) in DMSO was added triethylamine (2 ml), and pyridine sulfur trioxide complex (1.1 g) was added at room temperature. The mixture was stirred for 1 hr. and the reaction mixture was added to water. 10% Hydrochloric acid was added to acidify the aqueous layer, and the mixture was extracted with ethyl acetate. The organic layer was washed with water, saturated aqueous sodium hydrogen carbonate, water and saturated brine, and dried over anhydrous sodium sulfate. The solvent was evaporated under reduced pressure, and the residue was purified by silica gel column chromatography (hexane-hexane:ethyl acetate=1:2) to give 2-benzoyl-4-bromo-N-(4-methanesulfonylbenzyl)-N-(2-oxo-3-phenylpropyl)benzamide (0.72 g).

[Step 3] To a solution (6 ml) of 2-benzoyl-4-bromo-N-(4-methanesulfonylbenzyl)-N-(2-oxo-3-phenylpropyl)benzamide (0.3 g) in ethanol was added 1,8-diazabicyclo[5.4.0]undeca-7-ene (0.15 g), and the mixture was stirred at 80° C. for 12 hrs. The reaction mixture was concentrated under reduced pressure, water and 10% hydrochloric acid were added to the residue and the mixture was extracted with ethyl acetate. The organic layer was washed with water, saturated aqueous sodium hydrogen carbonate, water and saturated brine, and dried over anhydrous sodium sulfate. The solvent was evaporated under reduced pressure and the obtained residue was purified by silica gel thin layer chromatography (hexane:ethyl acetate=2:1) and recrystallized (ethyl acetate-hexane) to give the title compound (4 mg).

$^1$H-NMR (CDCl$_3$) δ: 3.01 (3H, s), 3.13 (2H, s), 5.10 (2H, s) 6.42-6.58 (2H, m), 7.00-7.66 (11H, m), 7.71 (1H, dd, J=2.0, 8.6 Hz), 7.88 (2H, d, J=8.4 Hz), 8.39 (1H, d, J=8.6 Hz).

EXAMPLE 542

4-[(3-acetyl-6-chloro-1-oxo-4-phenyl-1H-isoquinolin-2-yl)methyl]benzoic acid methyl ester

[Step 1] To a solution (100 ml) of 2-benzoyl-4-chlorobenzoic acid (7.0 g) in THF were added 4-[(2-hydroxypropylamino) methyl]benzoic acid methyl ester (6.0 g), 1-ethyl-3-(3-dimethylaminopropyl)carbodiimide hydrochloride (7.7 g), 1-hydroxy-1H-benzotriazole monohydrate (4.1 g), acetonitrile (100 ml) and triethylamine (20 ml) at room temperature. The reaction mixture was stirred at room temperature for 12 hrs. and concentrated under reduced pressure. Saturated aqueous sodium hydrogen carbonate was added to the residue and the mixture was extracted with ethyl acetate. The organic layer was washed with water, 1N-hydrochloric acid, water, saturated aqueous sodium hydrogen carbonate, water and saturated brine, and dried over anhydrous sodium sulfate. The solvent was evaporated under reduced pressure and the obtained residue was purified by silica gel column chromatography (hexane:ethyl acetate=10:1-hexane:ethyl acetate=1:2) to give 4-[[(2-benzoyl-4-chlorobenzoyl)(2-hydroxypropyl)amino]methyl]benzoic acid methyl ester (6.7 g).

[Step 2] To a solution (64 ml) of 4-[[(2-benzoyl-4-chlorobenzoyl)(2-hydroxypropyl)amino]methyl]benzoic acid methyl ester (6.4 g) in DMSO was added triethylamine (16 ml), and pyridine sulfur trioxide complex (8.7 g) was added at room temperature. The mixture was stirred for 1 hr. and added to water. 10% Hydrochloric acid was added to acidify the aqueous layer and the mixture was extracted with ethyl acetate. The organic layer was washed with water, saturated aqueous sodium hydrogen carbonate, water and saturated brine, and dried over anhydrous sodium sulfate. The solvent was evaporated under reduced pressure and the obtained residue was purified by silica gel column chromatography (hexane:ethyl acetate=10:1-hexane:ethyl acetate=1:2) to give 4-[[(2-benzoyl-4-chlorobenzoyl)(2-oxopropyl)amino]methyl]benzoic acid methyl ester (5.8 g).

[Step 3] To a solution (60 ml) of 4-[[(2-benzoyl-4-chlorobenzoyl)(2-oxopropyl)amino]methyl]benzoic acid methyl ester (5.6 g) in THF were added methanol (60 ml) and 1,8-diazabicyclo[5.4.0]undeca-7-ene (3.7 g), and the mixture was heated under reflux for 72 hrs. The reaction mixture was concentrated under reduced pressure, and the residue was diluted with ethyl acetate. The organic layer was washed with 1N-hydrochloric acid, water, saturated aqueous sodium hydrogen carbonate, water and saturated brine, and dried over anhydrous sodium sulfate. The solvent was evaporated under reduced pressure, and the obtained crystals were washed with methanol to give the title compound (3.1 g).

$^1$H-NMR (CDCl$_3$) δ: 1.27 (3H, s), 3.88 (3H, s), 5.49 (2H, s), 7.16-7.34 (5H, m), 7.40-7.50 (3H, m), 7.52 (1H, dd, J=2.1, 8.7 Hz), 7.96 (2H, d, J=8.4 Hz), 8.50 (1H, d, J=8.7 Hz).

EXAMPLE 543

4-[(3-acetyl-6-chloro-1-oxo-4-phenyl-1H-isoquinolin-2-yl)methyl]benzoic acid

To a solution of 4-[(3-acetyl-6-chloro-1-oxo-4-phenyl-1H-isoquinolin-2-yl)methyl]benzoic acid methyl ester (1.5 g) in THF (15 ml) were added methanol (15 ml) and 8N-aqueous sodium hydroxide solution (0.8 ml) at room temperature, and the mixture was stirred for 12 hrs. The reaction mixture was concentrated under reduced pressure, water and 10% hydrochloric acid were added to the residue. The aqueous layer was acidified and extracted with ethyl acetate. The organic layer was washed with water and saturated brine and dried over anhydrous sodium sulfate. The solvent was evaporated under reduced pressure, and the residue was purified by recrystallization (ethyl acetate-hexane) to give the title compound (1.2 g).

$^1$H-NMR (CDCl$_3$) δ: 1.32 (3H, s), 5.49 (2H, s), 7.16-7.36 (5H, m), 7.38-7.56 (3H, m), 7.52 (1H, dd, J=2.1, 8.7 Hz), 8.02 (2H, d, J=8.4 Hz), 8.50 (1H, d, J=8.7 Hz), 1H unconfirmed.

EXAMPLE 544

6-bromo-3-(2-bromoacetyl)-2-(4-methanesulfonylbenzyl)-4-phenyl-2H-isoquinolin-1-one A mixture of 3-acetyl-6-bromo-2-(4-methanesulfonylbenzyl)-4-phenyl-2H-isoquinolin-1-one (300 mg), copper(II) bromide (260 mg) and ethyl acetate (6 ml) was heated under reflux under a nitrogen atmosphere for 12 hrs. The reaction mixture was filtered, and the filtrate was concentrated under reduced pressure. The residue was purified by recrystallization (ethyl acetate-hexane) to give the title compound (290 mg).

$^1$H-NMR (CDCl$_3$) δ: 3.02 (3H, s), 3.16 (2H, s), 5.35 (2H, s), 7.20-7.50 (8H, m), 7.73 (1H, dd, J=2.2, 8.8 Hz), 7.90 (2H, d, J=8.4 Hz), 8.41 (1H, d, J=8.8 Hz).

EXAMPLE 545

4-[[3-(2-bromoacetyl)-6-chloro-1-oxo-4-phenyl-1H-isoquinolin-2-yl]methyl]benzoic acid

[Step 1] A mixture of 4-[(3-acetyl-6-chloro-1-oxo-4-phenyl-1H-isoquinolin-2-yl)methyl]benzoic acid methyl ester (100 mg), copper(II) bromide (125 mg) and ethyl acetate (3 ml) was heated under reflux under a nitrogen atmosphere for 12 hrs. The reaction mixture was filtered and the filtrate was concentrated under reduced pressure to give a crude product of 4-[[3-(2-bromoacetyl)-6-chloro-1-oxo-4-phenyl-1H-isoquinolin-2-yl]methyl]benzoic acid methyl ester.

$^1$H-NMR (CDCl$_3$) δ: 3.00 (2H, s), 3.89 (3H, s), 5.40 (2H, s), 7.14-7.64 (9H, m), 7.97 (2H, d, J=8.4 Hz), 8.50 (1H, d, J=8.7 Hz).

[Step 2] The crude product of 4-[[3-(2-bromoacetyl)-6-chloro-1-oxo-4-phenyl-1H-isoquinolin-2-yl]methyl]benzoic acid methyl ester obtained in the above-mentioned Step 1 was dissolved in THF (1 ml), and methanol (1 ml) and 8N-aqueous sodium hydroxide solution (0.06 ml) were added at room temperature. The mixture was stirred for 12 hrs. and concentrated under reduced pressure. To the residue were added water and 10% hydrochloric acid to acidify the aqueous layer and the mixture was extracted with ethyl acetate. The organic layer was washed with water and saturated brine, and dried over anhydrous sodium sulfate. The solvent was evaporated under reduced pressure, and the obtained crystals were washed with diisopropyl ether to give the title compound (66 mg).

$^1$H-NMR (CDCl$_3$) δ: 3.05 (2H, s), 5.40 (2H, s), 7.14-7.64 (9H, m), 8.03 (2H, d, J=8.4 Hz), 8.50 (1H, d, J=8.7 Hz), 1H unconfirmed.

EXAMPLE 546

3-[(2Z)-3-aminobut-2-enoyl]-6-bromo-2-(4-methanesulfonylbenzyl)-4-phenyl-2H-isoquinolin-1-one To a solution (44 ml) of 6-bromo-3-(2-bromoacetyl)-2-(4-methanesulfonylbenzyl)-4-phenyl-2H-isoquinolin-1-one (4.41 g) in DMF was added thioacetamide (1.1 g) and the mixture was stirred at 70° C. for 24 hrs. Water and saturated aqueous sodium hydrogen carbonate were added to the reaction mixture, and the mixture was extracted with ethyl acetate. The organic layer was washed with water and saturated brine, and dried over anhydrous sodium sulfate. The solvent was evaporated under reduced pressure. The obtained crystals were washed with methanol and recrystallized (ethyl acetate) to give the title compound (1.31 g).

$^1$H-NMR (CDCl$_3$) δ: 1.61 (3H, s), 3.01 (3H, s), 4.54 (1H, d, J=1.6 Hz), 5.20 (1H, d, J=5.3 Hz), 5.44 (2H, s), 7.20-7.44 (6H, m), 7.50 (2H, d, J=8.6 Hz), 7.60 (1H, dd, J=1.9, 8.6 Hz), 7.83 (2H, d, J=8.6 Hz), 8.34 (1H, d, J=8.6 Hz), 9.74 (1H, d, J=5.3 Hz).

EXAMPLE 547

3-[(2Z)-3-aminopent-2-enoyl]-6-bromo-2-(4-methanesulfonylbenzyl)-4-phenyl-2H-isoquinolin-1-one A mixture of 6-bromo-3-(2-bromoacetyl)-2-(4-methanesulfonylbenzyl)-4-phenyl-2H-isoquinolin-1-one (300 mg), thiopropionamide (70 mg), THF (3 ml) and ethanol (3 ml) was stirred at 80° C. for 12 hrs. The reaction mixture was concentrated under reduced pressure and saturated aqueous sodium hydrogen carbonate was added to the residue. The mixture was extracted with ethyl acetate. The organic layer was washed with water and saturated brine, and dried over anhydrous sodium sulfate. The solvent was evaporated under reduced pressure. The residue was purified by silica gel column chromatography (hexane:ethyl acetate=9:1-hexane:ethyl acetate=1:2) and recrystallized (ethyl acetate-hexane) to give the title compound (100 mg).

$^1$H-NMR (CDCl$_3$) δ: 0.75 (3H, t, J=7.5 Hz), 1.83 (2H, q, J=7.5 Hz), 3.00 (3H, s), 4.54 (1H, d, J=1.8 Hz), 5.45 (2H, s), 5.51 (1H, d, J=5.8 Hz), 7.20-7.44 (6H, m), 7.51 (2H, d, J=8.6 Hz), 7.60 (1H, dd, J=2.0, 8.6 Hz), 7.82 (2H, d, J=8.6 Hz), 8.33 (1H, d, J=8.6 Hz), 9.78 (1H, d, J=5.8 Hz).

EXAMPLE 548

3-[(2Z)-3-amino-4-methylpent-2-enoyl]-6-bromo-2-(4-methanesulfonylbenzyl)-4-phenyl-2H-isoquinolin-1-one In the same manner as in Example 546, the title compound was synthesized using thioisobutylamide.

Crystals (ethyl acetate-hexane).

$^1$H-NMR (CDCl$_3$) δ: 0.75 (6H, d, J=6.9 Hz), 1.95 (1H, septet, J=6.9 Hz), 3.00 (3H, s), 4.51 (1H, d, J=1.8 Hz), 5.25 (1H, d, J=5.1 Hz), 5.48 (2H, s), 7.20-7.46 (6H, m), 7.51 (2H, d, J=8.6 Hz), 7.61 (1H, dd, J=1.8, 8.6 Hz), 7.82 (2H, d, J=8.6 Hz), 8.35 (1H, d, J=8.6 Hz), 9.90 (1H, d, J=5.1 Hz).

EXAMPLE 549

3-[(2Z)-3-aminooct-2-enoyl]-6-bromo-2-(4-methanesulfonylbenzyl)-4-phenyl-2H-isoquinolin-1-one In the same manner as in Example 546, the title compound was synthesized using hexanethioacid amide.

Crystals (ethyl acetate-hexane).

$^1$H-NMR (CDCl$_3$) δ: 0.85 (3H, t, J=7.2 Hz), 0.92-1.34 (6H, m), 1.79 (2H, t, J=7.5 Hz), 3.00 (3H, s), 4.56 (1H, d, J=1.8 Hz), 5.21 (1H, d, J=5.0 Hz), 5.44 (2H, s), 7.20-7.44 (6H, m), 7.50 (2H, d, J=8.6 Hz), 7.59 (1H, dd, J=2.0, 8.6 Hz), 7.81 (2H, d, J=8.6 Hz), 8.33 (1H, d, J=8.6 Hz), 9.83 (1H, d, J=5.0 Hz).

EXAMPLE 550

(2Z)-2-amino-4-[6-bromo-2-(4-methanesulfonylbenzyl)-1-oxo-4-phenyl-1,2-dihydroisoquinolin-3-yl]-4-oxobuta-2-enoic acid ethyl ester In the same manner as in Example 546, the title compound was synthesized using ethyl thioxamate.

Crystals (ethyl acetate).

$^1$H-NMR (CDCl$_3$) δ: 1.23 (3H, t, J=7.1 Hz), 2.99 (3H, s), 4.17 (2H, q, J=7.1 Hz), 5.32 (1H, s), 5.42 (2H, s), 5.99 (1H, br s), 7.16-7.54 (8H, m), 7.64 (1H, dd, J=1.5, 8.4 Hz), 7.81 (2H, d, J=8.1 Hz), 8.36 (1H, d, J=8.4 Hz), 8.94 (1H, br s).

EXAMPLE 551

4-[[3-[(2Z)-3-aminobut-2-enoyl]-6-chloro-1-oxo-4-phenyl-1H-isoquinolin-2-yl]methyl]benzoic acid To a solution (6 ml) of 4-[[3-(2-bromoacetyl)-6-chloro-1-oxo-4-phenyl-1H-isoquinolin-2-yl]methyl]benzoic acid (570 mg) in DMF was added thioacetamide (170 mg), and the mixture was stirred at 70° C. for 24 hrs. Water was added to the reaction mixture, and the mixture was extracted with ethyl acetate. The organic layer was washed with water and saturated brine, dried over anhydrous sodium sulfate, and the solvent was evaporated under reduced pressure. The residue was crystallized from ethyl acetate to give the title compound (270 mg).

$^1$H-NMR (DMSO-d$_6$) δ: 1.55 (3H, s), 4.60 (1H, s), 5.27 (2H, s), 7.01 (1H, d, J=1.8 Hz), 7.20-7.50 (7H, m), 7.57 (1H, dd, J=1.8, 8.7 Hz), 7.83 (2H, d, J=8.4 Hz), 7.96-8.12 (1H, m), 8.30 (1H, d, J=8.7 Hz), 9.45 (1H, d, J=4.8 Hz), 12.8 (1H, s).

EXAMPLE 552

6-bromo-4-phenyl-3-propionyl-2-[4-[3-(tetrahydropyran-2-yloxy)propylsulfanyl]benzyl]-2H-isoquinolin-1-one To a solution of 6-bromo-2-(4-methanesulfinylbenzyl)-4-phenyl-3-propionyl-2H-isoquinolin-1-one (254 mg) in THF (5 ml) was added trifluoroacetic anhydride (0.2 ml), and the mixture was stirred at 60° C. for 3 hrs. The solvent was evaporated under reduced pressure and the residue was dissolved in methanol (10 ml). 2-(3-Bromopropoxy) tetrahydropyran (0.13 ml) was added and then triethylamine (10 ml) was added. The mixture was stirred at room temperature for 2 hrs. and the solvent was evaporated under reduced pressure. The residue was partitioned between ethyl acetate and saturated aqueous ammonium chloride solution. The organic layer was washed with brine and dried by adding sodium sulfate. The solvent was evaporated under reduced pressure and the obtained residue was purified by silica gel column chromatography (n-hexane/ethyl acetate=19/1→7/3) to give the title compound (178 mg, 57%).

$^1$H-NMR (CDCl$_3$) δ: 0.42 (3H, t, J=7.1 Hz), 1.45-1.91 (10H, m), 2.98 (2H, t, J=6.8 Hz), 3.41-3.52 (2H, m), 3.76-3.86 (2H, m), 4.55 (1H, t, J=3.5 Hz), 5.35 (2H, s), 7.10 (2H, d, J=8.3 Hz), 7.22-7.28 (4H, m), 7.42-7.49 (4H, m), 7.66 (1H, dd, J=2.0, 8.5 Hz), 8.42 (1H, d, J=8.5 Hz).

EXAMPLE 553

6-bromo-4-phenyl-3-propionyl-2-[4-[3-(tetrahydropyran-2-yloxy)propan-1-sulfonyl]benzyl]-2H-isoquinolin-1-one In the same manner as in Example 397, the title compound (115 mg, 61%) was synthesized from 6-bromo-4-phenyl-3-propionyl-2-[4-[3-(tetrahydropyran-2-yloxy)propylsulfanyl]benzyl]-2H-isoquinolin-1-onyl acetate using 3-chloroperbenzoic acid.

$^1$H-NMR (CDCl$_3$) δ: 0.49 (3H, t, J=7.1 Hz), 1.42-2.00 (10H, m), 3.12-3.25 (2H, m), 3.44-3.75 (2H, m), 3.69-3.80 (2H, m), 4.50 (1H, m), 5.39 (2H, s), 77.24-7.32 (2H, m), 7.40-7.51 (6H, m), 7.69 (1H, dd, J=1.8, 8.7 Hz), 7.85 (2H, d, J=8.5 Hz), 8.40 (1H, d, J=8.7 Hz).

EXAMPLE 554

6-bromo-2-[4-(3-hydroxypropan-1-sulfonyl)benzyl]-4-phenyl-3-propionyl-2H-isoquinolin-1-one To a solution of 6-bromo-4-phenyl-3-propionyl-2-[4-[3-(tetrahydropyran-2-yloxy)propan-1-sulfonyl]benzyl]-2H-isoquinolin-1-one (110 mg) in methanol (10 ml) was added p-toluenesulfonic acid monohydrate (49 mg), and the mixture was stirred at room temperature for 1 hr. The solvent was evaporated under reduced pressure and the residue was partitioned between ethyl acetate and 1N aqueous sodium hydroxide solution. The organic layer was washed with brine and dried by adding sodium sulfate. The solvent was evaporated under reduced pressure and the obtained residue was purified by silica gel column chromatography (n-hexane/ethyl acetate=3/2-+1/9) to give the title compound (95 mg, 98%).

$^1$H-NMR (CDCl$_3$) δ: 0.50 (3H, t, J=7.2 Hz), 1.62 (1H, m), 1.70 (2H, q, J=7.2 Hz), 1.90-1.99 (2H, m), 3.17-3.23 (2H, m), 3.72 (1H, dd, J=5.7, 5.7 Hz), 5.38 (2H, s), 7.25-7.30 (2H, m), 7.41-7.50 (6H, m), 7.69 (1H, dd, J=1.9, 8.5 Hz), 7.86 (2H, d, J=8.5 Hz), 8.40 (1H, d, J=8.5 Hz).

EXAMPLE 555 acetic acid 4-(6-bromo-1-oxo-4-phenyl-3-propionyl-1H-isoquinolin-2-ylmethyl)phenylsulfanylmethyl ester In the same manner as in Example 552, the title compound (190 mg, 69%) was obtained from 6-bromo-2-(4-methanesulfinylbenzyl)-4-phenyl-3-propionyl-2H-isoquinolin-1-one and acetic acid bromomethyl ester.

$^1$H-NMR (CDCl$_3$) δ: 0.45 (3H, t, J=7.1 Hz), 1.57 (2H, q, J=7.1 Hz), 2.07 (3H, s), 5.35 (4H, s), 7.16 (2H, d, J=8.5 Hz), 7.23-7.29 (2H, m), 7.38 (2H, d, J=8.5 Hz), 7.43-7.49 (4H, m), 7.67 (1H, dd, J=1.9, 8.5 Hz), 8.42 (1H, d, J=8.5 Hz).

EXAMPLE 556 acetic acid 4-(6-bromo-1-oxo-4-phenyl-3-propionyl-1H-isoquinolin-2-ylmethyl)benzenesulfonylmethyl ester In the same manner as in Example 397, the title compound (209 mg, 92%) was synthesized from acetic acid 4-(6-bromo-1-oxo-4-phenyl-3-propionyl-1H-isoquinolin-2-ylmethyl) phenylsulfanylmethyl ester using 3-chloroperbenzoic acid.

$^1$H-NMR (CDCl$_3$) δ: 0.49 (3H, t, J=7.1 Hz), 1.69 (2H, q, J=7.1 Hz), 2.07 (3H, s), 5.11 (2H, s), 5.40 (2H, s), 7.25-7.30 (2H, m), 7.43-7.51 (6H, m), 7.69 (1H, dd, J=1.9, 8.7 Hz), 7.87 (2H, d, J=8.5 Hz), 8.40 (1H, d, J=8.7 Hz).

FORMULATION EXAMPLE 1

The JNK inhibitors of the present invention, which contains a compound represented by the formula (I) or a salt thereof as an active ingredient, such as a therapeutic agent for chronic or acute cardiac failure, cardiac hypertrophy, post-myocardial infarction, myocarditis, chronic rheumatoid arthritis, osteoarthritis, inflammatory bowel disease, asthma, ischemia reperfusion injury, organ failure, cerebral apolexy, cerebrovascular disorder, and the like can be produced according to, for example, the following formulations.

In the following formulations, for the components (additives) other than the active ingredient, products meeting the standards of the Japan Pharmacopoeia, the standards of drugs listed in the Pharmacopoeia of Japan, the standards of Pharmaceutical Product Additives and the like can be used.

1. Capsule

| | |
|---|---|
| (1) Compound obtained in Example 24 | 40 mg |
| (2) Lactose | 70 mg |
| (3) Microcrystalline cellulose | 9 mg |
| (4) Magnesium stearate | 1 mg |
| 1 capsule | 120.0 mg |

(1), (2), (3) and ½ of (4) are admixed and granulated. The rest of (4) is added and the entire mixture is sealed in a gelatin capsule.

2. Capsule

| | |
|---|---|
| (1) Compound obtained in Example 94 | 40 mg |
| (2) Lactose | 70 mg |
| (3) Microcrystalline cellulose | 9 mg |
| (4) Magnesium stearate | 1 mg |
| 1 capsule | 120.0 mg |

(1), (2), (3) and ½ of (4) are admixed and granulated. The rest of (4) is added and the entire mixture is sealed in a gelatin capsule.

3. Capsule

| | |
|---|---|
| (1) Compound obtained in Example 102 | 40 mg |
| (2) Lactose | 70 mg |
| (3) Microcrystalline cellulose | 9 mg |
| (4) Magnesium stearate | 1 mg |
| 1 capsule | 120.0 mg |

(1), (2), (3) and ½ of (4) are admixed and granulated. The rest of (4) is added and the entire mixture is sealed in a gelatin capsule.

4. Capsule

| | |
|---|---|
| (1) Compound obtained in Example 315 | 40 mg |
| (2) Lactose | 70 mg |
| (3) Microcrystalline cellulose | 9 mg |
| (4) Magnesium stearate | 1 mg |
| 1 capsule | 120.0 mg |

(1), (2), (3) and ½ of (4) are admixed and granulated. The rest of (4) is added and the entire mixture is sealed in a gelatin capsule.

5. Tablet

| | |
|---|---|
| (1) Compound obtained in Example 24 | 40 mg |
| (2) Lactose | 58 mg |
| (3) Cornstarch | 18 mg |
| (4) Microcrystalline cellulose | 3.5 mg |
| (5) Magnesium stearate | 0.5 mg |
| 1 tablet | 120.0 mg |

(1), (2), (3), 2/3 of (4) and ½ of (5) are admixed and granulated. The rest of (4) and (5) is added and compression formed into a tablet.

6. Tablet

| | |
|---|---|
| (1) Compound obtained in Example 94 | 40 mg |
| (2) Lactose | 58 mg |
| (3) Cornstarch | 18 mg |
| (4) Microcrystalline cellulose | 3.5 mg |
| (5) Magnesium stearate | 0.5 mg |
| 1 tablet | 120.0 mg |

(1), (2), (3), 2/3 of (4) and ½ of (5) are admixed and granulated. The rest of (4) and (5) is added and compression formed into a tablet.

7. Tablet

| | |
|---|---|
| (1) Compound obtained in Example 102 | 40 mg |
| (2) Lactose | 58 mg |
| (3) Cornstarch | 18 mg |
| (4) Microcrystalline cellulose | 3.5 mg |
| (5) Magnesium stearate | 0.5 mg |
| 1 tablet | 120.0 mg |

(1), (2), (3), ⅔ of (4) and ½ of (5) are admixed and granulated. The rest of (4) and (5) is added and compression formed into a tablet.

8. Tablet

| | |
|---|---|
| (1) Compound obtained in Example 315 | 40 mg |
| (2) Lactose | 58 mg |
| (3) Cornstarch | 18 mg |
| (4) Microcrystalline cellulose | 3.5 mg |
| (5) Magnesium stearate | 0.5 mg |
| 1 tablet | 120.0 mg |

(1), (2), (3), 2/3 of (4) and ½ of (5) are admixed and granulated. The rest of (4) and (5) is added and compression formed into a tablet.

FORMULATION EXAMPLE 2

The compound (50 mg) obtained in Example 141 is dissolved in the Japan Pharmacopoeia distilled water for injection (50 ml) and the Japan Pharmacopoeia distilled water for injection is added to make 100 ml. This solution is filtered under sterile conditions, and this solution (1 ml) is taken and filled in a vial for injection under sterile conditions, which is vial freeze-dried and sealed.

EXPERIMENTAL EXAMPLE 1

Genetic manipulation methods described in Reference Example below are based on methods described in Maniatis et al., *Molecular Cloning*, Cold Spring Harbor Laboratory, 1989, and the appended reagent protocol.

(1) Cloning of Human JNK1 Kinase Gene and Preparation of Recombinant Baculovirus Cloning of human JNK1 kinase gene was conducted by a PCR method using primer set JNK1-U: 5-ACAACTC-GAGATAACATATGGCTCATCATCATCAT-CATCATAGCAGAAGCAAGCGTGACAAC-3 [SEQ ID No. 1] and JNK1-L:
5'-TCCCGGGTACCTCACTGCTGCACCTGTGCTAA-3', [SEQ ID No. 2] prepared referring to the nucleotide sequence of JNK1 gene reported by Derijard, B. et al (Cell, 76, 1025-1037 (1994)), utilizing kidney cDNA (QUICK-Clone cDNA, manufactured by Toyobo Co., Ltd.) as a template.

A PCR reaction was performed according to Hot Start method using AmpliWax PCR Gem 100 (Takara Shuzo Co., Ltd.). For preparing the lower layer of the mixed liquid, 2 μL of 10×LA PCR Buffer, 3 μL of 2.5 mM dNTP solution, each 2.5 μL of 12.5 μM primer solution, 2 μl of 25 mM MgCl$_2$ solution and 8 μL of sterile distilled water were mixed. For preparing the upper layer of the mixed liquid, 1 μL of human kidney cDNA (1 ng/mL) as a template, 3 μL of 10×LA PCR Buffer, 5 μL of 2.5 mM dNTP solution, 3 μl of 25 mM MgCl$_2$ solution, 0.5 μL of TaKaRa LA Taq DNA polymerase (Takara Shuzo Co., Ltd.) and 17.5 μL of sterile distilled water were mixed. To the prepared lower mixed liquid layer was added one AmpliWax PCR Gem 100 (Takara Shuzo Co., Ltd.), treated at 70° C. for 5 minutes and in ice for 5 minutes, then, the upper mixed liquid layer was added to prepare a reaction solution for PCR. A tube filled with the reaction solution was set on Thermal Cycler (Perkin Elmer), then, treated at 95° C. for 2 minutes.

Further, a cycle including 15 seconds at 95° C. and 2 minutes at 68° C. was repeated 35 times, then, treated for 8 minutes at 72° C. The resulted PCR product was subjected to agarose gel (1%) electrophoresis, a 1.2 kb DNA fragment containing a JNK-1 gene was recovered from the gel, then, digested with restriction enzyme KpnI, XhoI, and inserted into 4.8 kb XhoI-KpnI fragment of plasmid pFASTBAC1 (GIBCO BRL) to prepare a plasmid pFBJNK1. Using plasmid pFBJNK1 and BAC-TO-BAC Baculovirus Expression System (GIBCO BRL), a virus stock BAC-HJNK1 of recombinant baculovirus was prepared.

(2) Cloning of Human MKK7 Gene and Preparation of Recombinant Baculovirus

Cloning of human MKK7 gene was conducted by a PCR method using primer set MKK7-U:
5'-ACCAGAATTCATAACATATGGCTCAT-CATCATCATCATCATGCGGCGTCCTC-CCTGGAACAG-3' [SEQ ID No. 3]

MKK7-L:
5'-ACCCTCTAGACAAGCAGCTACCTGAAGAAGG-3' [SEQ ID No. 4]

prepared referring to the nucleotide sequence of MKK7 gene reported by Foltz, I. N. et al (*J. Biol. Chem.*, 273 (15), 9344-9351 (1998)), utilizing pancreas cDNA (QUICK-Clone cDNA, manufactured by Toyobo Co., Ltd.) as a template. A PCR reaction was performed according to Hot Start method using AmpliWax PCR Gem 100 (Takara Shuzo Co., Ltd.). For preparing the lower layer of the mixed liquid, 2 μL of 10×LA PCR Buffer, 3 μL of 2.5 mM dNTP solution, each 2.5 μL of 12.5 μM primer solution, 2 μl of 25 mM MgCl$_2$ solution and 8 μL of sterile distilled water were mixed. For preparing the upper layer of the mixed liquid, 1 μL of human pancreatic cDNA (1 ng/mL) as a template, 3 μL of 10×LA PCR Buffer, 5 μL of 2.5 mM dNTP solution, 3 μl of 25 mM MgCl$_2$ solution, 0.5 μL of TaKaRa LA Taq DNA polymerase (Takara Shuzo Co., Ltd.) and 17.5 μL of sterile distilled water were mixed. To the prepared lower mixed liquid layer was added one AmpliWax PCR Gem 100 (Takara Shuzo Co., Ltd.), treated at 70° C. for 5 minutes and in ice for 5 minutes, then, the upper mixed liquid layer was added to prepare a reaction solution for PCR. A tube filled with the reaction solution was set on Thermal Cycler (Perkin Elmer), then, treated at 95° C. for 2 minutes. Further, a cycle including 15 seconds at 95° C. and 2 minutes at 68° C. was repeated 35 times, then, treated for 8 minutes at 72° C. The resulted PCR product was subjected to agarose gel (1%) electrophoresis, a 1.3 kb DNA fragment containing a MKK7 gene was recovered from the gel, then inserted into pT7Blue-T vector (Novagen) to prepare a plasmid pHMKK7.

For the preparation of constitutive active MKK7 (271st Ser to Asp, 275th Thr to Asp) reported by Wang, Y. et al (*J. Biol. Chem.*, 273 (10), 5423-5426, 1998), primer set CAM7-U:
5'-GGCCGCCTGGTGGACGACAAAGCCAAG-
   GACCGGAGCGCCGGCTG-3'
[SEQ ID No. 5]

CAM7-L:
5'-CAGCCGGCGCTCCGGTCCTTG-
   GCTTTGTCGTCCACCAGGCGGCC-3'
[SEQ ID No. 6]

and QuikChange Site-Directed Mutagenesis Kit (Stratagene) were used to introduce mutation, whereby pcaMKK7 was obtained.

A 4.8 kb EcoRI-XbaI fragment of plasmid pFASTBAC1 (GIBCO BRL) and a 1.3 kb EcoRI-XbaI fragment of the above-mentioned plasmid pcaMKK7 were ligated to give a plasmid pFBcaMKK7. Using the plasmid pFBcaMKK7 and BAC-TO-BAC Baculovirus Expression System (GIBCO BRL), a recombinant baculovirus virus stock BAC-caMKK7 was prepared.

(3) Cloning of Human cJUN gene

For cloning of human cJUN gene, a gene encoding 79 amino acids of N-terminal was amplified by a PCR method using primer set cJUN-U:
5'-AAAAGAATTCATGACTGCAAAGATG-
   GAAACGACC-3'
[SEQ ID No. 7]

CJUN-L:
5'-AAAAGCGGCCGCTCACAGGCGCTC-
   CAGCTCGGGCGACGC-3'
[SEQ ID No. 8]

prepared referring to the nucleotide sequence of cJUN gene reported by Hattori, K. et al (*Proc. Natl. Acad. Sci. U.S.A.*, 85 (23), 9148-9152 (1988)), utilizing skeletal muscle cDNA (QUICK-Clone cDNA, manufactured by Toyobo Co., Ltd.) as a template.

A PCR reaction was performed according to Hot Start method using AmpliWax PCR Gem 100 (Takara Shuzo Co., Ltd.). For preparing the lower layer of the mixed liquid, 2 µL of 10× Pyrobest PCR Buffer, 3 µL of 2.5 mM dNTP solution, each 2.5 µL of 12.5 µM primer solution and 10 µL of sterile distilled water were mixed. For preparing the upper layer of the mixed liquid, 1 µL of human skeletal muscle cDNA (1 ng/mL) as a template, 3 µL of 10× Pyrobest PCR Buffer, 2 µL of 2.5 mM dNTP solution, 0.5 µL of TaKaRa Pyrobest DNA polymerase (Takara Shuzo Co., Ltd.) and 24.5 µL of sterile distilled water were mixed. To the prepared lower mixed liquid layer was added one AmpliWax PCR Gem 100 (Takara Shuzo Co., Ltd.), treated at 70° C. for 5 minutes and in ice for 5 minutes, then, the upper mixed liquid layer was added to prepare a reaction solution for PCR. A tube filled with the reaction solution was set on Thermal Cycler (Perkin Elmer), then, treated at 95° C. for 2 minutes. Further, a cycle including 15 seconds at 95° C. and 30 seconds at 68° C. was repeated 35 times, then, treated for 8 minutes at 72° C. The resulted PCR product was subjected to agarose gel (1%) electrophoresis, a 240 bp DNA fragment containing a cJUN gene was recovered from the gel, then, digested with restriction enzymes EcoRI, NotI and inserted into 4.9 kb EcoRI-NotI fragment of plasmid pGEX6P-1 (Amersham-Pharmacia Biotech) to prepare a plasmid pGEJUN.

(4) Preparation of Active JNK1

Sf-21 cells were seeded to achieve $1 \times 10^6$ cells/ml in 100 ml of Sf-900 II SFM medium (GIBCO BRL) containing 10% fetal calf serum and cultured at 27° C. for 24 hrs. The recombinant baculovirus virus stock BAC-HJNK1 and BAC-caMKK7 were added by 0.2 ml each, and the cells were further cultured for 60 hrs. The cells were separated from the culture solution by centrifugation (3000 rpm, 10 min.) and washed twice with PBS. The cells were suspended in 10 ml of Lysis buffer (25 mM HEPES (pH 7.5), 1% Triton X, 130 mM NaCl, 1 mM EDTA, 1 mM DTT, 25 mM β-glycerophosphate, 20 µM leupeptin, 1 mM APMSF, 1 mM sodium orthovanadate) and ruptured by 4 times of treatment with a homogenizer (POLYTRON) at 20000 rpm, 30 seconds each. Active JNK1 was purified from a supernatant obtained by centrifugal separation (40000 rpm, 45 min.) by the use of Anti-FLAG M2 Affinity Gel (Sigma).

(5) Preparation of Recombinant cJUN

*Escherichia coli* JM109 (Toyobo Co., Ltd.) was transformed with a plasmid pGEJUN to give ampicillin resistant pGEJUN/JM109. The pGEJUN/JM109 strain was cultured overnight in 150 ml of LB medium (10 g/l tripton, 5 g/l yeast extract, 10 g/l sodium chloride) containing 50 µg/ml ampicillin at 200 rpm, 37° C. The culture solution (15 ml) was added to a fresh LB medium (150 ml) and cultured at 37° C. for 2 hrs. at 200 rpm. 1 mM IPTG (Wako Pure Chemical Industries, Ltd.) was added and the cells were further cultured for 6 hrs. The culture solution was centrifuged at 8000 rpm for 10 min. and bacterial cells were recovered, washed with PBS and frozen at −80° C. The cells were suspended in 20 ml of lysis buffer (B-PER bacterial protein extraction reagent (Pierce), Protease inhibitor Complete (Boehringer)) and shaken at room temperature for 10 min. After centrifugal separation (14000 rpm, 15 min., 4° C.), and GST-cJUN fused protein was purified from the supernatant using Redipack GST Purification Module (Amersham-Pharmacia Biotech).

(6) Measurement of JNK Inhibitory Activity

A reaction solution (37.5 µl, 25 mM HEPES (pH 7.5), 10 mM magnesium acetate, 1 mM DTT) containing 50 ng of active JNK1 and 1 µg of cJUN was dissolved in DMSO. The test compound (2.5 µl) was added and the mixture was incubated at 30° C. for 5 min. ATP solution (2.5 µM ATP, 0.01 µCi [γ-$^{32}$P]ATP) was added by 10 µl to start the reaction. After reacting at 30° C. for 60 min., 50 µl of 20% TCA solution was added to stop the reaction. The reaction solution was left standing at 0° C. for 20 min. and an acid-insoluble fraction was transferred onto a GF/C filter (Packard Japan) using Cell Harvester (Packard Japan), and washed with 250 mM phosphoric acid. After drying at 45° C. for 60 min., 40 µl of Microscint 0 (Packard Japan) was added and the radioactivity was measured on TopCount (Packard Japan). The concentration ($IC_{50}$ value) of the test compound necessary for 50% inhibition of the uptake of $^{32}$P by the acid-insoluble fraction was calculated by PRISM 2.01 (Graphpad Software).

EXPERIMENTAL EXAMPLE 2

Measurement of TNF α Production Inhibitory Activity

THP-1 cells cultured in RPMI1640 medium (GIBCO BRL) containing 1% inactivated fetal calf serum and 10 mM HEPES (pH 7.5) were seeded in a 96 well plate at $1 \times 10^5$ cells/well and 1 µl of a test compound dissolved in DMSO was added.

After culture in a $CO_2$ incubator at 37° C. for 1 hr., LPS (Wako Pure Chemical Industries, Ltd.) was added at a final concentration of 5 µg/ml. After culture in a $CO_2$ incubator at separation. The TNF-α concentration of the supernatant was measured with ELISA kit (DIACLONE). The concentration ($IC_{50}$ value) of the test compound necessary for 50% inhibition of TNF-α production was calculated by PRISM 2.01 (Graphpad Software).

EXPERIMENTAL EXAMPLE 3

Measurement of TNF-α after LPS Administration (Rat)

(1) Oral administration:

9 to 10-weeks-old male Jcl:Wistar rats were used. LPS (SIGMA, derived from *E. coli*) (dissolved in physiological saline) was intraperitoneally administered at 5 mg/kg. The compound was suspended in 0.5% methyl cellulose and given 60 min. before LPS administration. To a control group, 0.5% methyl cellulose alone was administered similarly. At 90 min. after LPS administration, blood was drawn under pentobarbital (50 mg/kg, intraperitoneal administration) anesthesia from the abdominal aorta with a syringe containing aprotinin with EDTA and centrifuged at 3000 rpm, 4° C. for 10 min. to give plasma. TNFα in the plasma was measured using ELISA Kit (GENZYME).

(2) Intravenous Administration:

9 to 10-week-old male Jcl:Wistar rats were used. LPS (SIGMA, derived from *E. coli*) (dissolved in physiological saline) was intravenously administered at 5 mg/kg. The compound was dissolved in DMAA/PEG400 (1:1) and given 10 min. before LPS administration. To a control group, DMAA/PEG400 (1:1) alone was administered similarly. At 90 min. after LPS administration, blood was drawn under pentobarbital (50 mg/kg, intraperitoneal administration) anesthesia from the abdominal aorta with a syringe containing aprotinin with EDTA and centrifuged at 3000 rpm, 4° C. for 10 min. to give plasma. TNFα in the plasma was measured using ELISA Kit (GENZYME).

EXPERIMENTAL EXAMPLE 4

Measurement of Heart Phosphorylated c-Jun after LPS Administration (Rat)

9 to 10-week-old male Jcl:Wistar rats were used. LPS (SIGMA, derived from *E. coli*) (dissolved in physiological saline) was intraperitoneally administered at 5 mg/kg. The compound was orally or intravenously administered according to the method described in (1-1) or (1-2). The heart was removed at 90 min. after LPS administration. The heartbeat was stopped in ice-cooled TBS buffer (50 mM Tris-HCl pH 7.4, 150 mM NaCl) and the left ventricle was harvested. The left ventricle was homogenized in 5.0 ml of ice-cooled lysis buffer (20 mM Tris-HCl pH 7.4, 1% NP40, 0.1% SDS, 150 mM NaCl, 1 mM EDTA, 0.1 mg/ml PMSF, 0.3 TIU aprotinin, 1 mM sodium orthovanadate), and centrifuged at 12000 rpm (15800 g), 4° C. for 30 min. After centrifugation, the supernatant was recovered and used as a tissue extract solution. The protein amount was measured by the Bradford method (BIO-RAD: Protein assay). The tissue extract solution containing 10 mg of protein were added 8 μg of anti-c-Jun rabbit polyclonal antibody (H79: SANTA CRUZ) and 20 μl of Protein A-Agarose (SANTA CRUZ), and the mixture was stirred overnight at 4° C. The mixture was centrifuged at 2500 rpm, 4° C. for 5 min, and after removal of supernatant, washed 3 times with TBS buffer (50 mM Tris-HCl pH 7.4, 150 mM NaCl, 0.1 mg/ml PMSF, 0.3 TIU aprotinin, 1 mM sodium orthovanadate), and dissolved in 60 μl of Laemmli sample buffer (BIORAD). The dissolved sample was loaded at 10 μl on a 10% separation gel (BIORAD) and electrophoresed at 150 V for 60 min. The protein on the gel was transferred onto PVDF membrane (BIORAD) after methanol treatment by wet blotting at 100 V for 1 hr. The membrane was washed with TBS-T (0.05% Tween 20), blocked with 5% skim milk/TBS-T (blocking buffer) at room temperature for 1 hr. and reacted with anti-phosphorylated c-Jun (ser63) mouse monoclonal antibody (KM-1: SANTA CRUZ; diluted 250-fold with blocking buffer) at room temperature for 1.5 hrs. The membrane was washed with TBS-T (5 min., 2 times), reacted with HRP labeled-anti mouse IgG secondary antibody (Amersham) diluted 2000-fold with blocking buffer at room temperature for 1 hr. and washed with TBS-T (5 min., 3 times) and TBS. The membrane was reacted with 2 ml of ECL reactive solution (ECL Plus: Amersham) for 5 min., exposed to X-ray film for 1 min., and the film was immersed in a developing solution for 90 seconds, washed with water and immersed in a fixing solution to develop the film. The developed X-ray film was scanned by DeskscanII, automatically corrected, and further automatically corrected by Photoshop to reverse the color tone. The density of the band seen at the objective molecular weight was digitalized on the histogram of Photoshop.

Experiment Results

Table 1 shows inhibitory action of human JNK1, p38α and ERK1.

TABLE 1

| Example No. | JNK1 IC$_{50}$ (μM) | P38α % of Inhibition at 10 μM | ERK1 % of Inhibition at 10 μM |
|---|---|---|---|
| 24 | 0.018 | 18 | 39 |
| 93 | 0.014 | 20 | 0 |
| 94 | 0.030 | 2 | 0 |
| 102 | 0.020 | 0 | 0 |
| 112 | 3 | 0 | 0.095 |
| 122 | 0.0092 | 0 | 0 |
| 141 | 0.037 | 10 | 4 |
| 156 | 0.028 | 10 | 16 |
| 315 | 0.046 | 0 | 1 |
| 356 | 0.0075 | 0 | 0 |
| 415 | 0.039 | 0 | 0 |
| 455 | 0.034 | 0 | 0 |
| 462 | 0.0091 | 0 | 13 |
| 463 | 0.016 | 0 | 22 |
| 495 | 0.0067 | 0 | 37 |
| 546 | 0.032 | 0 | 5 |

From the results of Table 1, it is clear that Compound (I) and a salt thereof of the present invention have superior JNK specific inhibitory activity.

EXPERIMENTAL EXAMPLE 5

Preparation of the Model of Pressure Overloaded Cardiac Hypertrophy Induced by an Abdominal Aortic Stenosis (Rat)

Male wistar rats (body weight 260-300 g, CLEA Japan, Inc) were used. Under xylazine (10 mg/kg, i.p.) and ketamine (50 mg/kg, i.p.) anesthesia, abdominal aorta was exposed by median laparotomy. The left and right renal arteries were detached from the back, a 22G injection needle was put along the artery and it was ligated together with the aorta using a 2-0 silk thread just below the right renal artery. Then, the injection needle was removed to make a stenosis in the abdominal aorta. The abdomen was closed and the rats were housed commonly. For a sham group, the abdomen was closed without ligation (no stenosis) with a silk thread. A compound was suspended in a 0.5% methyl cellulose solution (2 ml/kg) and orally administered at a dose of 10 mg/kg 1 hr. before aortic stenosis and once a day from day 1 (the next day of stricture)

to day 7 after operation. Vehicle (0.5% methyl cellulose solution) was administered instead of the compound to the sham group and control group. At day 7 after the preparation of aortic stenosis, the body weight was measured, and the heart was removed and then extracted under pentobarbital (50 mg/kg, i.p.) anesthesia. The right and left artium and right ventricle were excised from the heart and the wet weight of the left ventricle was measured. The left ventricle weight to body weight ratio of each rat was calculated and an increase from the average value of the sham group was calculated. Inhibitory rate of each group to a cardiac hypertrophy was calculated based on the control group as 100%. The experiment results are shown in Table 2.

TABLE 2

| Compound, Example No. | Left ventricular weight/body weight ratio (mg/g) | |
|---|---|---|
| | value | amount of increase from sham group |
| sham group (n = 9) | 1.90 ± 0.03 | — |
| control group (n = 18) | 2.42 ± 0.05 | 0.53 ± 0.05 |
| Compound 94 (10 mg/kg, p.o., n = 14) | 2.21 ± 0.06* | 0.31 ± 0.06 (Inhibitory rate 40%) |

TABLE 2-continued

| Compound, Example No. | Left ventricular weight/body weight ratio (mg/g) | |
|---|---|---|
| | value | amount of increase from sham group |
| Compound 315 (10 mg/kg, p.o., n = 14) | 2.19 ± 0.05* | 0.29 ± 0.05 (Inhibitory rate 44%) |

*:p < 0.05 vs control group

From the results of Table 2, it is clear that Compound (I) and a salt thereof of the present invention are useful as agents for the prevention or treatment of JNK-related clinically pathological conditions or diseases.

INDUSTRIAL APPLICABILITY

Since Compound (I) and a salt thereof of the present invention have superior JNK specific inhibitory action and show superior oral absorbability, they can be advantageously used as safe and effective pharmaceutical agents for the prophylaxis or treatment of JNK-related clinical conditions or diseases.

The invention claimed is:

1. A compound represented by the formula

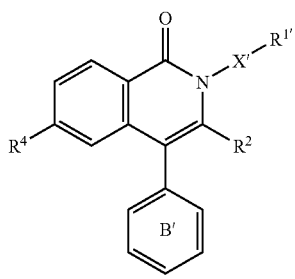

wherein ring B' is a benzene ring optionally having not more than two substituent(s);

X' is —$CH_2$—:

$R^{1'}$ is
 a phenyl group optionally substituted by substituent(s) selected from substituent group B or
 a heterocyclic group bonded via a ring-constituting carbon atom and optionally substituted by substituent(s) selected from the substituent group B;

$R^2$ is
 a hydrocarbon group optionally having substituent(s) selected from the group consisting of a hydroxy group optionally substituted by a substituent selected from substituent group C,
 a thiol group optionally substituted by a substituent selected from the substituent group C, a sulfinyl group substituted by a substituent selected from the group consisting of
  1) a hydroxy group optionally substituted by a substituent selected from the substituent group C,
  2) an amino optionally N-mono- or N,N-di-substituted by substituent(s) selected from the substituent group C,
  3) a 3 to 8-membered cyclic amino group,
  4) a hydrocarbon group optionally substituted by substituent(s) selected from the substituent group B, and
  5) a heterocyclic group optionally substituted by substituent(s) selected from the substituent group B,
a sulfonyl group substituted by a substituent selected from the group consisting of
  1) a hydroxy group optionally substituted by a substituent selected from the substituent group C,
  2) an amino optionally N-mono- or N,N-di-substituted by substituent(s) selected from the substituent group C,
  3) a 3 to 8-membered cyclic amino group,
  4) a hydrocarbon group optionally substituted by substituent(s) selected from the substituent group B, and
  5) a heterocyclic group optionally substituted by substituent(s) selected from the substituent group B,
and
an optionally esterified carboxyl group,
$R^A CO$ wherein $R^A$ is a hydrogen atom, a hydrocarbon group optionally substituted by substituent(s) selected from the substituent group B or a heterocyclic group optionally substituted by substituent(s) selected from the substituent group B,
$R^A SO_2$ wherein $R^A$ is as defined above,
$R^A SO$ wherein $R^A$ is as defined above,
$R^A OPO(OR^B)$ wherein $R^A$ is as defined above and $R^B$ is a hydrogen atom or a hydrocarbon group optionally substituted by substituent(s) selected from the substituent group B,
an optionally esterified or thioesterified carboxyl group,
a carbamoyl group optionally N-mono- or N,N-di-substituted by subsuituent(s) selected from the group consisting of
  i) a hydrocarbon group optionally substituted by substituent(s) selected from substituent group B,
  ii) $R^A CO$ wherein wherein $R^A$ is as defined above,
  iii) $R^A SO_2$ wherein $R^A$ is as defined above,
  iv) $R^A SO$ wherein $R^A$ is as defined above,
  v) $R^A OPO(OR^B)$ wherein each symbol is as defined above,
  vi) an alkoxycarbonyl optionally substituted by substituent(s) selected from substituent group A,
  vii) a carbamoyl optionally N-mono- or N,N-di-substituted by 1 or 2 substituent(s) selected from the group consisting of a lower($C_{1-6}$)alkyl group and phenyl group,
  viii) a 3 to 8-membered cyclic aminocarbonyl,
  ix) a heterocyclic group optionally substituted by substituent(s) selected from the substituent group B,
  x) an amino optionally N-mono- or N,N-di-substituted by substituent(s) selected from the substituent group C,
  xi) a 3 to 8-membered cyclic amino group, and
  xii) a hydroxy group optionally substituted by a substituent selected from the substituent group C,
a 3 to 8-membered cyclic aminocarbonyl,
an amino group optionally N-mono- or N,N-di-substituted by substituent(s) selected from the substituent group C, or
a 3to 8-membered cyclic amino group;
$R^4$ is
a hydrogen atom,
a halogen atom,
a cyano group,
a hydrocarbon group optionally substituted by substituent(s) selected from the substituent group B,
a heterocyclic group optionally substituted by substituent(s) selected from the substituent group B,
a hydroxy group optionally substituted by a substituent selected from the substituent group C,
a thiol group optionally substituted by a substituent selected from the substituent group C,
a sulfinyl group substituted by a substituent selected from the group consisting of
  1) a hydroxy group optionally substituted by a substituent selected from the substituent group C,
  2) an amino optionally N-mono- or N,N-di-substituted by substituent(s) selected from the subsutuent group C,
  3) a 3 to 8-membered cyclic amino group,
  4) a hydrocarbon group optionally substituted by substituent(s) selected from the substituent group B, and
  5) a heterocyclic group optionally substituted by substituent(s) selected from the substituent group B,
a sulfonyl group substituted by a substituent selected from the group consisting of
  1) a hydroxy group optionally substituted by a substituent selected from the substituent group C,
  2) an amino optionally N-mono- or N,N-di-substituted by substituent(s) selected from the substituent group C,
  3) a 3 to 8-membered cyclic amino group,
  4) a hydrocarbon group optionally substituted by substituent(s) selected from the substituent group B, and
  5) a heterocyclic group optionally substituted by substituent(s) selected from the substituent group B,
an amino group optionally N-mono- or N,N-di-substituted by substituent(s) selected from the substituent group C,
a 3 to 8-membered cyclic amino group,
a carbamoyl group optionally N-mono- or N,N-di-substituted by substituent(s) selected from the group consisting of
  i) a hydrocarbon group optionally substituted by substituent(s) selected from the substituent group B,
  ii) $R^A CO$ wherein wherein $R^A$ is as defined above,
  iii) $R^A SO$, wherein $R^A$ is as defined above,
  iv) $R^A SO$ wherein $R^A$ is as defined above,
  v) $R^A OPO(OR^B)$ wherein each symbol is as defined above,
  vi) an alkoxycarbonyl optionally substituted by substituent(s) selected from the substituent group A,
  vii) a carbamoyl optionally substituted by 1 or 2 substituent(s) selected from the group consisting of a lower($C_{1-6}$)alkyl group and phenyl group,
  viii) a 3 to 8-membered cyclic aminocarbonyl,
  ix) a heterocyclic group optionally substituted by substituent(s) selected from the substituent group B, x) an amino optionally N-mono- or N,N-di-substituted by substituent(s) selected from the substituent group C, xi) a 3 to 8-membered cyclic amino group, and xii) a hydroxy group optionally substituted by a substituent selected from the substituent group C, a 3 to 8-membered cyclic aminocarbonyl, or an optionally esterified carboxyl group;

the substituent group A consists of (1) a nitro group,
(2) a hydroxy group,
(3) an oxo group,
(4) a cyano group,
(5) a carbamoyl group,
(6) a mono- or di-$C_{1-4}$ alkyl-carbamoyl group,
(7) a mono- or di-$C_{2-4}$ alkenyl-carbamoyl group,
(8) a mono- or di-phenyl-carbamoyl group,
(9) a mono- or di-benzyl-carbamoyl group,
(10) a $C_{1-4}$ alkoxy-carbonyl-carbamoyl group,
(11) a $C_{1-4}$ alkylsulfonyl-carbamoyl group,
(12) a $C_{1-4}$ alkoxy-carbamoyl group,
(13) an amino-carbamoyl group,
(14) a mono- or di-$C_{1-4}$ alkylamino-carbamoyl group,
(15) a mono- or di-phenylamino-carbamoyl group,
(16) a carboxyl group,
(17) a $C_{1-4}$ alkoxy-carbonyl group,
(18) a sulfo group,
(19) a halogen atom,
(20) an optionally halogenated $C_{1-4}$ alkoxy group,
(21) a $C_{1-4}$ alkoxy group optionally substituted by hydroxy group,
(22) a $C_{1-4}$ alkoxy group optionally substituted by carboxyl group,
(23) a $C_{1-4}$ alkoxy group optionally substituted by $C_{1-4}$ alkoxy-carbonyl group,
(24) a $C_{1-4}$ alkoxy-$C_{1-4}$ alkoxy group,
(25) a $C_{1-4}$ alkoxy-$C_{1-4}$ alkoxy-$C_{1-4}$ alkoxy group,
(26) a phenoxy group,
(27) a phenoxy-$C_{1-4}$ alkyl group,
(28) a phenoxy-$C_{1-4}$ alkoxy group,
(29) a $C_{1-4}$ alkylcarbonyl-oxy group,
(30) a carbamoyloxy group,
(31) a mono- or di-$C_{1-4}$ alkyl-carbamoyloxy group,
(32) an optionally halogenated phenyl group,
(33) an optionally hatogenated phenyl-$C_{1-4}$ alkyl group,
(34) an optionally halogenated phenyl-$C_{2-4}$ alkenyl group,
(35) an optionally halogenated phenoxy group,
(36) a pyridyloxy group,
(37) a $C_{3-10}$ cycloalkyl group,
(38) a $C_{3-10}$ cycloalkyl-$C_{1-4}$ alkoxy group,
(39) a $C_{3-10}$ cycloalkyl-$C_{1-4}$ alkyl group,
(40) an optionally halogenated $C_{1-4}$ alkyl group,
(41) an optionally halogenated $C_{2-6}$ alkenyl group,
(42) an optionally halogenated $C_{1-4}$ alkylthio group,
(43) a $C_{1-4}$ alkyl group optionally substituted by hydroxy group,
(44) a $C_{1-4}$ alkylthio group optionally substituted by hydroxy group,
(45) a mercapto group,
(46) a thioxo group,
(47) a benzyloxy group or benzylthio group optionally substituted by a substituent(s) selected from a halogen atom, carboxyl group and $C_{1-4}$ alkoxy-carbonyl group,
(48) an optionally halogenated phenylthio group,
(49) a pyridylthio group,
(50) a phenylthio-$C_{1-4}$ alkyl group,
(51) a pyridylthio $C_{1-4}$ alkyl group,
(52) an optionally halogenated $C_{1-4}$ alkylsulfinyl group,
(53) a phenylsulfinyl group,
(54) a phenylsulfinyl-$C_{1-4}$ alkyl group,
(55) an optionally halogenated $C_{1-4}$ alkylsulfonyl group,
(56) a phenylsulfonyl group,
(57) a phenylsulfonyl-$C_{1-4}$ alkyl group,
(58) an amino group,
(59) an arninosulfonyl group,
(60) a mono- or di-$C_{1-4}$ alkylaminosulfonyl group wherein said alkyl group is optionally substituted by halogen atom, hydroxy group or $C_{1-4}$ alkoxy group,
(61) a $C_{1-6}$ alkanoylamino wherein said $C_{1-6}$ alkanoyl is optionally substituted by halogen atom, hydroxy group or carboxyl group,
(62) a benzoylamino wherein said benzoyl is optionally substituted by halogen atom, hydroxy group, carboxyl group,
(63) a $C_{1-6}$ alkylsulfonylamino wherein said $C_{1-6}$ alkylsulfonyl is optionally substituted by halogen atom, hydroxy group or carboxyl group,
(64) a $C_{6-10}$ arylsulfonylamino wherein said $C_{6-10}$ arylsulfonyl is optionally substituted by halogen atom, hydroxy group or carboxyl group,
(65) a benzyloxycarbonylamino,
(66) an optionally halogenated $C_{1-6}$ alkoxycarbonylamino,
(67) a carbamoylamino group,
(68) a mono- or di-$C_{1-4}$ alkylcarbamoylamino group,
(69) a mono- or di-$C_{1-4}$ alkylamino group wherein said alkyl group is optionally substituted by halogen atom, hydroxy group or $C_{1-4}$ alkoxy group and the like,
(70) phenylamino,
(71) benzylamino,
(72) a 4 to 6-membered cyclic amino group,
(73) a 4 to 6-membered cyclic amino-carbonyl group,
(74) a 4 to 6-membered cyclic amino-carbonyl-oxy group,
(75) a 4 to 6-membered cyclic amino-carbonyl-amino group,
(76) a 4 to 6-membered cyclic amino-sulfonyl group,
(77) a 4 to 6-membered cyclic amino-$C_{1-4}$ alkyl group,
(78) a formyl,
(79) a $C_{2-6}$ alkanoyl group optionally substituted by a substituent(s) selected from halogen atom, carboxyl group and $C_{1-4}$ alkoxy-carbonyl group,
(80) a benzoyl group,
(81) a benzoyl group optionally substituted by halogen atom,
(82) a 5 to 10-membered heterocyclic group wherein said heterocyclic group is optionally substituted by $C_{1-4}$ alkyl group,
(83) a 5 to 10-membered heterocycle-carbonyl group wherein said heterocyclic group is optionally substituted by $C_{1-4}$ alkyl group,
(84) a hydroxyimino group,
(85) a $C_{1-4}$ alkoxyimino group,
(86) an aryl group, and
(87) an optionally halogenated linear or branched $C_{1-4}$ alkylenedioxy group; the substituent group B consists of
(1) the substituent group A,
(2) a $C_{1-10}$ alkyl group,
(3) a $C_{2-10}$ alkenyl group,
(4) a phenyl-$C_{2-4}$ alkenyl group,
(5) a mono- or di-$C_{1-6}$ alkenyl-carbamoyl group,
(6) a $C_{6-14}$ aryl group,
(7) a $C_{7-20}$ aralkyl group, and
(8) a styryl group; and
the substituent group C consists of (1) a hydrocarbon group optionally substituted by substituent(s) selected from the substituent group B,
(2) $R^A CO$ wherein $R^A$ is as defined above,
(3) $R^A SO_2$ wherein $R^A$ is as defined above,
(4) $R^A SO$ wherein $R^A$ is as defined above,
(5) $R^A OPO(OR^B)$ wherein each symbol is as defined above,
(6) an alkoxycarbonyl optionally substituted by substituent(s) selected from the substituent group A,
(7) a carbamoyl optionally N-mono- or N,N-di-substituted by substituent(s) selected from the group consisting of
  i) a hydrocarbon group optionally substituted by substituent(s) selected from the substituent group B,
  ii) $R^A CO$ wherein wherein $R^A$ is as defined above,
  iii) $R^A SO_2$ wherein $R^A$ is as defined above,
  iv) $R^A SO$ wherein $R^A$ is as defined above,
  v) $R^A OPO(OR^B)$ wherein each symbol is as defined above,
  vi) an alkoxycarbonyl optionally substituted by substituent(s) selected from the substituent group A,
  vii) a carbamoyl optionally N-mono- or N,N-di-substituted by 1 or 2 substituent(s) selected from the group consisting of a lower($C_{1-6}$)alkyl group and phenyl group,
  viii) a 3 to 8-membered cyclic aminocarbonyl,
  ix) a heterocyclic group optionally substituted by substituent(s) selected from the substituent group B,
  x) an amino optionally N-mono- or N,N-di-substituted by substituent(s) selected from the substituent group C,
  xi) a 3 to 8-membered cyclic amino group, and
  xii) a hydroxy group optionally substituted by a substituent selected from the substituent group C,
(8) a 3 to 8-membered cyclic aminocarbonyl, and
(9) a heterocyclic group optionally substituted by substituent(s) selected from the substituent group B;
or a salt thereof,
provided that 2-benzyl-1-oxo-4-phenyl-1,2-dihydro-isociuinoline-3-carboxamide is excluded.

2. The compound of claim 1, wherein $R^4$ is not a hydrogen atom.

3. The compound of claim 1, wherein $R^4$ is
a halogen atom,
an alkyl group optionally substituted by substituent(s) selected from the substituent group A,
an amino group optionally N-mono- or N,N-di-substituted by substituent(s) selected from the substituent group C. or
a 3 to 8-membered cyclic amino group; and
the substituent groups A and C are as defined in claim 1.

4. The compound of claim 1, wherein $R^4$ is a halogen atom or a $C_{1-4}$ alkyl group.

5. The compound of claim 1, wherein the ring B' is a benzene ring optionally having substituent(s) at a meta and/or para position(s).

6. The compound of claim 1, wherein the ring B' is a non-substituted benzene ring.

7. The compound of claim 1, wherein $R^2$ is
a hydrocarbon group substituted by a hydroxy group optionally substituted by a substituent selected from the substituent group C,
an optionally esterified or thioesterified carboxyl group,
a carbamoyl group optionally N-mono- or N,N-di-substituted by substituent(s) selected from the group consisting of
  i) a hydrocarbon group optionally substituted by substituent(s) selected from the substituent group B,
  ii) $R^A CO$ wherein wherein $R^A$ is as defined above,
  iii) $R^A SO_2$ wherein $R^A$ is as defined above,
  iv) $R^A SO$ wherein $R^A$ is as defined above,
  v) $R^A OPO(OR^B)$ wherein each symbol is as defined above,
  vi) an alkoxycarbonyl optionally substituted by substituent(s) selected from the substituent group A,
  vii) a carbamoyl optionally N-mono- or N,N-di-substituted by 1 or 2 substituent(s) selected from the group consisting of a lower($C_{1-6}$)alkyl group and phenyl group,
  viii) a 3 to 8-membered cyclic aminocarbonyl,
  ix) a heterocyclic group optionally substituted by substituent(s) selected from the substituent group B,
  x) an amino optionally N-mono- or N,N-di-substituted by substituent(s) selected from the substituent group C,
  xi) a 3 to 8-membered cyclic amino group, and
  xii) a hydroxy group optionally substituted by a substituent selected from the substituent group C,
a 3 to 8-membered cyclic aminocarbonyl,
an amino group optionally N-mono- or N,N-di-substituted by substituent(s) selected from the substituent group C,
a 3 to 8-membered cyclic amino group,
$R^A CO$ wherein $R^A$ is a hydrogen atom, a hydrocarbon group optionally substituted by substituent(s) selected from the substituent group B or a heterocyclic group optionally substituted by substituent(s) selected from the substituent group B,
$R^A SO_2$ wherein $R^A$ is as defined above,
$R^A SO$ wherein $R^A$ is as defined above, or
$R_A OPO(OR^B)$ wherein $R^A$ is as defined above and $R^B$ is a hydrogen atom or a hydrocarbon group optionally substituted by substituent(s) selected from the substituent group B; and
the substituent groups A, B and C are as defined in claim 1.

8. The compound of claim 1, wherein $R^2$ is
a lower alkyl group substituted by a hydroxy group,
an optionally esterified or thioesterified carboxyl group,
a carbamoyl group optionally substituted by a lower alkyl group,
an amino group optionally substituted by a lower alkyl group,
$R^A CO$ wherein $R^A$ is a hydrogen atom, a hydrocarbon group optionally substituted by substituent(s) selected from the substituent group B or a heterocyclic group optionally substituted by substituent(s) selected from the substituent group B,
$R^A SO_2$ wherein $R^A$ is as defined above,
$R^A SO$ wherein $R^A$ is as defined above, or
$R^A OPO(OR^B)$ wherein $R^A$ is as defined above and $R^B$ is a hydrogen atom or a hydrocarbon group optionally substituted by substituent(s) selected from the substituent group B; and
the substituent group B is as defined in claim 1.

9. The compound of claim 1, wherein $R^2$ is an optionally esterified or thioesterified carboxyl group.

10. The compound of claim 1, wherein $R^2$ is
a carboxyl group optionally esterified by an alkyl optionally substituted by substituent(s) selected from a phenyl group optionally substituted by substituent(s) selected from the substituent group B and a pyridyl group optionally substituted by substituent(s) selected from the substituent group B, or optionally thioesterified by a pyridyl group optionally substituted by substituent(s) selected from the substituent group B; and the substituent group B is as defined in claim 1.

11. The compound of claim 1, wherein $R^2$ is
$R^A CO$ wherein $R^A$ is a hydrogen atom, a hydrocarbon group optionally substituted by substituent(s) selected from the substituent group B or a heterocyclic group optionally substituted by substituent(s) selected from the substituent group B,
$R^A SO_2$ wherein $R^A$ is as defined above,
$R^A SO$ wherein $R^A$ is as defined above, or
$R^A OPO(OR^B)$ wherein $R^A$ is as defined above and $R^B$ is a hydrogen atom or a hydrocarbon group optionally substituted by substituent(s) selected from the substituent group B; and
the substituent group B is as defined in claim 1.

12. The compound of claim 1, wherein $R^2$ is $R^A CO$, where $R^A$ is a hydrogen atom, an optionally subgtitutcd a hydrocarbon group optionally substituted by substituent(s) selected from the substituent group B or a heterocyclic group optionally substituted by substituent(s) selected from the substituent group B; and
the substituent group B is as defined in claim 1.

13. The compound of claim 12, wherein $R^A$ is a $C_{1-7}$ alkyl group or a group represented by the formula

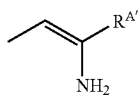

wherein $R^A$ is a $C_{1-5}$ alkyl group or an optionally esterified carboxyl group.

14. The compound of claim 1, wherein $R^2$ is a methoxycarbonyl group, a pyridylmethyloxycarbonyl group, a dimethylcarbamoyl group, a pyridylmethylcarbamoyl group, a hydroxymethyl group, a pyridylthiocarbonyl group, an amino group, an acetyl group, a propionyl group, a butyryl group, a valeryl group or a (2Z)-3-aminobut-2-enoyl group.

15. The compound of claim 1, wherein $R^1$ is a phenyl group having substituent(s) at the meta and/or para position(s).

16. The compound of claim 1, wherein $R^{1'}$ is an optionally zubztituted a nitrogen-containing heterocyclic group bonded via a ring-constituting carbon atom and optionally substituted by substituent(s) selected from the substituent group B; and
the substituent group B is as defined in claim 1.

17. The compound of claim 16, wherein the nitrogen-containing heterocyclic group is a nitrogen-containing heterocyclic group comprising carbon atom(s) and nitrogen atom(s).

18. The compound of claim 16, wherein the nitrogen-containing heterocyclic group is an aromatic nitrogen-containing heterocyclic group.

19. The compound of claim 16, wherein the nitrogen-containing heterocyclic group is a 2-, 3- or 4-piperidinyl group.

20. The compound of claim 16, wherein the nitrogen-containing heterocyclic group is a 4-piperidinyl group.

21. The compound of claim 1, wherein $R^{1'}$ is a 4-piperidinyl group substituted by an acyl group.

22. A compound selected from the group consisting of 2-(benzo[1,3]dioxol-5-ylmethyl)-6-bromo-1-oxo-4-phenyl-1,2-dihydroisoquinoline-3-carboxylic acid methyl ester, 6-bromo-1-oxo-4-phenyl-2-(4-sulfamoylbenzyl)-1,2-dihydroisoquinoline-3-carboxylic acid methyl ester, 6-bromo-2-(4-methanesulfonylbenzyl)-1-oxo-4-phenyl-1,2-dihydroisoquinoline-3-carboxylic acid methyl ester, 6-bromo-2-(2,3-dihydrobenzofuran-5-ylmethyl)-1-oxo-4-phenyl-1,2-dihydroisoquinoline-3-carboxylic acid methyl ester, 6-bromo-2-(4-carboxybenzyl)-1-oxo-4-phenyl-1,2-dihydroisoquinoline-3-carboxylic acid methyl ester, 2-(1-acetylpiperidine-4-ylmethyl)-6-bromo-1-oxo-4-phenyl-1,2-dihydroisoquinoline-3-carboxylic acid methyl ester, 6-bromo-2-[4-(3-carboxypropionylamino)benzyl]-1-oxo-4-phenyl-1,2-dihydroisoquinoline-3-carboxylic acid methyl ester, 6-bromo-2-(4-carbamoylbenzyl)-1-oxo-4-phenyl-1,2-dihydroisoquinoline-3-carboxylic acid methyl ester, 2-(benzo[1,3]dioxol-5-ylmethyl)-6-methyl-1-oxo-4-phenyl-1,2-dihydroisoquinoline-3-carboxylic acid methyl ester, 6-amino-2-(benzo[1,3]dioxol-5-ylmethyl)-1-oxo-4-phenyl-1,2-dihydroisoquinoline-3-carboxylic acid methyl ester, 2-(benzo[1,3]dioxol-5-ylmethyl)-6-bromo-1-oxo-4-phenyl-1,2-dihydroisoquinoline-3-carboxylic acid pyridin-3-ylmethyl ester, N,N-dimethyl-2-(benzo[1,3]dioxol-5-ylmethyl)-6-bromo-1-oxo-4-phenyl-1,2-dihydroisoquinoline-3-carboxamide, 6-bromo-2-(4-methanesulfonylbenzyl)-4-phenyl-3-propionyl-2H-isoquinolin-1-one, 3-butyryl-6-chloro-2-(4-methanesulfonylbenzyl)-4-phenyl-2H-isoquinolin-1-one, 2-(4-carboxybenzyl)-6-chloro-4-(3-hydroxymethylphenyl)-1-oxo-1,2-dihydroisoqu inoline-3-carboxylic acid methyl ester, 6-bromo-2-[4-(N',N'-diethylhydrazinocarbonyl)benzyl]-1-oxo-4-phenyl-1,2-dihydroisoquinol ine-3-carboxylic acid methyl ester, 4-(6-chloro-3-butyryl-1-oxo-4-phenyl-1H-isoquinolin-2-ylmethyl)benzenesulfonamide, 4-(6-bromo-1-oxo-4-phenyl-3-propionyl-1H-isoquinolin-2-ylmethyl)benzoic acid, 4-(6-chloro-1-oxo-4-phenyl-3-propionyl-1H-isoquinolin-2-ylmethyl)benzoic acid, 6-bromo-4-phenyl-3-propionyl-2-[4-(1H-tetrazol-5-yl)benzyl]-2H-isoquinolin-1-one, 3-[(2Z)-3-aminobut-2-enoyl]-6-bromo-2-(4-methanesulfonylbenzyl)-4-phenyl-2H-isoquinolin-1-one, 3-[(2Z)-3-aminopent-2-enoyl]-6-bromo-2-(4-methanesulfonylbenzyl)-4-phenyl-2H-isoquinolin-1-one, 3-amino-2-(benzo[1,3]dioxol-5-ylmethyl)-6-bromo-4-phenyl-2H-isoquinolin-1-one, and 6-bromo-2-(4-methanesulfonylbenzyl)-1-oxo-4-phenyl-1,2-dihydroisoquinoline-3-carbothioic acid S-pyridin-2-yl ester, or a salt thereof.

23. A pharmaceutical preparation comprising a compound of claim 1 and a pharmaceutically acceptable carrier, excipient or diluent.

24. The pharmaceutical preparation of claim 23, which is a JNK inhibitor.

25. The pharmaceutical preparation of claim 23, which is an agent for the prophylaxis or treatment of chronic or acute cardiac failure, cardiac hypertrophy, dilated, hypertrophic or restrictive cardiomyopathy, acute myocardial infarction, post-myocardial infarction, acute or chronic myocarditis, diastolic dysfunction of the left ventricle, systolic dysfunction of the left ventricle, hypertension and nephropathy and nephritis as complications thereof, endothelial dysfunction, arteriosclerosis or post-angioplasty restenosis.

26. The pharmaceutical preparation of claim 23, which is an agent for the prophylaxis or treatment of chronic rheumatoid arthritis, osteoarthritis, gout, chronic obstructive pulmonary disease, asthma, bronchitis, cystic fibrosis, inflammatory bowel disease, irritable colon syndrome, mucous colitis, ulcerative colitis, Crohn's disease, gastritis, esophagitis, multiple sclerosis, eczema, dermatitis, hepatitis, glomerulonephritis, diabetes, diabetic nephropathy, diabetic retinopathy, diabetic neuropathy, obesity, psoriasis or cancer.

27. The pharmaceutical preparation of claim 23, which is an agent for the prophylaxis or treatment of Alzheimer's disease, Huntington's chorea, Parkinson's syndrome, epilepsy, amyotrophic lateral sclerosis, peripheral neuropathy, neurodegenerative disease or spinal injury.

28. The pharmaceutical preparation of claim 23, which is an agent for the prophylaxis or treatment of cerebral apolexy, cerebrovascular disorder, an ischemic disorder of an organ selected from the heart, kidney, liver and brain, ischemia-reperfusion injury, organ failure, endotoxin shock or rejection in transplantation.

29. A production method of a compound represented by the formula wherein
ring B' is a benzene ring optionally having not more than two substituent(s):
X' is —$CH_2$—;
$R^{1'}$ is
a phenyl group optionally substituted by substituent(s) selected from the substituent group B or
a heterocyclic group bonded via a ring-constituting carbon atom and optionally substituted by substituent(s) selected from substituent group B;
$R^2$ is
a hydrocarbon group optionally having substituent(s) selected from the group consisting of
  a hydroxy group optionally substituted by a substituent selected from substituent group C,
  a thiol group optionally substituted by a substituent selected from the substituent group C,
  a sulfinyl group substituted by a substituent selected from the group consisting of
    1) a hydroxy group optionally substituted by a substituent selected from the substituent group C,
    2) an amino optionally N-mono- or N,N-di-substituted by substituent(s) selected from the substituent group C,
    3) a 3 to 8-membered cyclic amino group,
    4) a hydrocarbon group optionally substituted by substituent(s) selected from the substituent group B, and
    5) a heterocyclic group optionally substituted by substituent(s) selected from the substituent group B,
  a sulfonyl group substituted by a substituent selected from the group consisting of
    1) a hydroxy group optionally substituted by a substituent selected from the substituent group C,
    2) an amino optionally N-mono- or N,N-di-substituted by substituent(s) selected from the substituent group C,
    3) a 3 to 8-membered cyclic amino group,
    4) a hydrocarbon group optionally substituted by substituent(s) selected from the substituent group B, and
    5) a heterocyclic group optionally substituted by substituent(s) selected from the substituent group B, and
an optionally esterified carboxyl group,
$R^A$CO wherein $R^A$ is a hydrogen atom, a hydrocarbon group optionally substituted by substituent(s) selected from the substituent group B or a heterocyclic group optionally substituted by substituent(s) selected from the substituent group B,
$R^A SO_2$ wherein $R^A$ is as defined above,
$R^A$SO wherein $R^A$ is as defined above,
$R^A OPO(OR^B)$ wherein $R^A$ is as defined above and $R^B$ is a hydrogen atom or a hydrocarbon group optionally substituted by substituent(s) selected from the substituent group B,
an optionally esterified or thioesterified carboxyl group,
a carbamoyl group optionally N-mono- or N,N-di-substituted by substituent(s) selected from the group consisting of
  i) a hydrocarbon group optionally substituted by substituent(s) selected from the substituent group B,
  ii) $R^A$CO wherein wherein $R^A$ is as defined above,
  iii) $R^A SO_2$ wherein $R^A$ is as defined above,
  iv) $R^A$SO wherein $R^A$ is as defined above,
  v) $R^A OPO(OR^B)$ wherein each symbol is as defined above,
  vi) an alkoxycarbonyl optionally substituted by substituent(s) selected from substituent group A,
  vii) a carbamoyl optionally N-mono- or N,N-di-substituted by 1 or 2 substituent(s) selected from the group consisting of a lower($C_{1-6}$)alkyl group and phenyl group,
  viii) a 3 to 8-membered cyclic aminocarbonyl,
  ix) a heterocyclic group optionally substituted by substituent(s) selected from the substituent group B,
  x) an amino optionally N-mono- or N,N-di-substituted by substituent(s) selected from the substituent group C,
  xi) a 3 to 8-membered cyclic amino group, and
  xii) a hydroxy group optionally substituted by a substituent selected from the substituent group C,
a 3 to 8-membered cyclic aminocarbonyl,
an amino group optionally N-mono- or N,N-di-substituted by substituent(s) selected from the substituent group C, or
a 3 to 8-membered cyclic amino group;
$R^4$ is
a hydrogen atom,
a halogen atom,
a cyano group,
a hydrocarbon group optionally substituted by substituent(s) selected from the substituent group B,
a heterocyclic group optionally substituted by substituent(s) selected from the substituent group B,
a hydroxy group optionally substituted by a substituent selected from the substituent group C,
a thiol group optionally substituted by a substituent selected from the substituent group C,
a sulfinyl group substituted by a substituent selected from the group consisting of
  1) a hydroxy group optionally substituted by a substituent selected from the substituent group C,
  2) an amino optionally N-mono- or N,N-di-substituted by substituent(s) selected from the substituent group C,
  3) a 3 to 8-membered cyclic amino group,
  4) a hydrocarbon group optionally substituted by substituent(s) selected from the substituent group B, and
  5) a heterocyclic group optionally substituted by substituent(s) selected from the substituent group B, a sulfonyl group substituted by a substituent selected from the group consisting of
1) a hydroxy group optionally substituted by a substituent selected from the substituent group C,
2) an amino optionally N-mono- or N,N-di-substituted by substituent(s) selected from the substituent group C,
3) a 3 to 8-membered cyclic amino group,
4) a hydrocarbon group optionally substituted by substituent(s) selected from the substituent group B, and
5) a heterocyclic group optionally substituted by substituent(s) selected from the substituent group B,
an amino group optionally N-mono- or N,N-di-substituted by substituent(s) selected from the substituent group C,
a 3 to 8-membered cyclic amino group,
a carbamoyl group optionally N-mono- or N,N-di-substituted by substituent(s) selected from the group consisting of
i) a hydrocarbon group optionally substituted by substituent(s) selected from the substituent group B,
ii) $R^A CO$ wherein wherein $R^A$ is as defined above,
iii) $R^A SO_2$ wherein $R^A$ is as defined above,
iv) $R^A SO$ wherein $R^A$ is as defined above,
v) $R^A OPO(OR^B)$ wherein each symbol is as defined above,
vi) an alkoxycarbonyl optionally substituted by substituent(s) selected from the substituent group A,
vii) a carbamoyl optionally substituted by 1 or 2 substituent(s) selected from the group consisting of a lower($C_{1-6}$)alkyl group and phenyl group,
viii) a 3 to 8-membered cyclic aminocarbonyl,
ix) a heterocyclic group optionally substituted by substituent(s) selected from the substituent group B,
x) an amino optionally N-mono- or N,N-di-substituted by substituent(s) selected from the substituent group C,
xi) a 3 to 8-membered cyclic amino group, and
xii) a hydroxy group optionally substituted by a substituent selected from the substituent group C,
a 3 to 8-membered cyclic aminocarbonyl, or
an optionally esterified carboxyl group, or a salt thereof, which comprises (1) reacting a compound represented by the formula

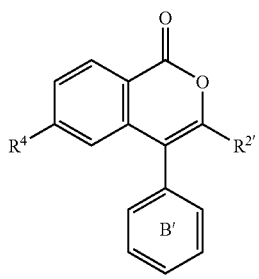

wherein $R^{2'}$ is
an optionally esterified carboxyl group or
$R^A CO$ wherein $R^A$ is a hydrogen atom, a hydrocarbon group optionally substituted by substituent(s) selected from the substituent group B or a heterocyclic group optionally substituted by substituent(s) selected from the substituent group B,
$R^A SO_2$ wherein $R^A$ is as defined above,
$R^A SO$ wherein $R^A$ is as defined above, or
$R^A OPO(OR^B)$ wherein $R^A$ is as defined above and $R^B$ is a hydrogen atom or a hydrocarbon group optionally substituted by substituent(s) selected from the substituent group B,
and other symbols are as defined above, or a salt thereof with an amino compound represented by the formula
$H_2N-X'-R^{1'}$ wherein the symbols in the formula are as defined above, or a salt thereof, or
(2) reacting a compound represented by the formula

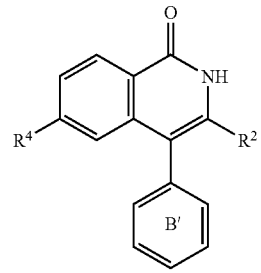

wherein the symbols in the formula are as defined above, or a salt thereof with a compound represented by the formula
$L-X'-R^{1'}$ wherein L is a leaving group, and other symbols are as defined above, or a salt thereof, or
(3) subjecting a compound represented by the formula

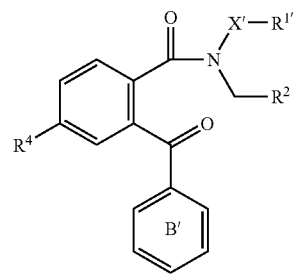

wherein the symbols in the formula are as defined above, or a salt thereof to an intramolecular cyclization reaction, or
(4) reacting a compound represented by the formula

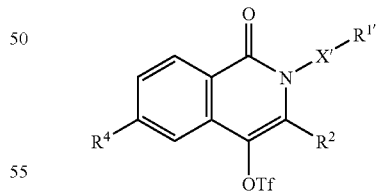

wherein OTf is a triflate group and other symbols are as defined above, or a salt thereof with a compound represented by the formula

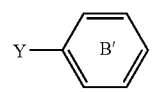

wherein Y is an atomic group capable of a crosscoupling reaction and other symbols are as defined above, or a salt thereof, wherein the substituent group A consists of
(1) a nitro group,
(2) a hydroxy group,
(3) an oxo group,
(4) a cyano group,
(5) a carbamoyl group,
(6) a mono- or di-$C_{1-4}$ alkyl-carbamoyl group,
(7) a mono- or di-$C_{2-4}$ alkenyl-carbamoyl group,
(8) a mono- or di-phenyl-carbamoyl group,
(9) a mono- or di-benzyl-carbamoyl group,
(10) a $C_{1-4}$ alkoxy-carbonyl-carbamoyl group,
(11) a $C_{1-4}$ alkylsulfonyl-carbamoyl group,
(12) a $C_{1-4}$ alkoxy-carbamoyl group,
(13) an amino-carbamoyl group,
(14) a mono- or di-$C_{1-4}$ alkylamino-carbamoyl group,
(15) a mono- or di-phenylamino-carbamoyl group,
(16) a carboxyl group,
(17) a $C_{1-4}$ alkoxy-carbonyl group,
(18) a sulfo group,
(19) a halogen atom,
(20) an optionally halogenated $C_{1-4}$ alkoxy group,
(21) a $C_{1-4}$ alkoxy group optionally substituted by hydroxy group, (22) a $C_{1-4}$ alkoxy group optionally substituted by carboxyl group,
(23) a $C_{1-4}$ alkoxy group optionally substituted by $C_{1-4}$ alkoxy-carbonyl group,
(24) a $C_{1-4}$ alkoxy-$C_{1-4}$ alkoxy group,
(25) a $C_{1-4}$ alkoxy-$C_{1-4}$ alkoxy-$C_{1-4}$ alkoxy group,
(26) a phenoxy group,
(27) a phenoxy-$C_{1-4}$ alkyl group,
(28) a phenoxy-$C_{1-4}$ alkoxy group,
(29) a $C_{1-4}$ alkylcarbonyl-oxy group,
(30) a carbamoyloxy group,
(31) a mono- or di-$C_{1-4}$ alkyl-carbamoyloxy group,
(32) an optionally halogenated phenyl group,
(33) an optionally halo genated phenyl-$C_{1-4}$ alkyl group,
(34) an optionally halogenated phenyl-$C_{1-4}$ alkenyl group,
(35) an optionally halogenated phenoxy group,
(36) a pyridyloxy group,
(37) a $C_{3-10}$ cycloalkyl group,
(38) a $C_{3-10}$ cycloalkyl-$C_{1-4}$ alkoxy group,
(39) a $C_{3-10}$ cycloalkyl-$C_{1-4}$ alkyl group,
(40) an optionally halogenated $C_{1-4}$ alkyl group,
(41) an optionally halogenated $C_{2-6}$ alkenyl group,
(42) an optionally halogenated $C_{1-4}$ alkylthio group,
(43) a $C_{1-4}$ alkyl group optionally substituted by hydroxy group,
(44) a $C_{1-4}$ alkylthio group optionally substituted by hydroxy group,
(45) a mercapto group,
(46) a thioxo group,
(47) a benzyloxy group or benzylthio group optionally substituted by a substituent(s) selected from a halogen atom, carboxyl group and $C_{1-4}$ alkoxy-carbonyl group,
(48) an optionally halogenated phenylthio group,
(49) a pyridylthio group,
(50) a phenyhhio-$C_{1-4}$ alkyl group,
(51) a pyridylthio $C_{1-4}$ alkyl group,
(52) an optionally halogenated $C_{1-4}$ alkylsulfinyl group,
(53) a phenylsulfinyl group,
(54) a phenylsulfinyl-$C_{1-4}$ alkyl group,
(55) an optionally halogenated $C_{1-4}$ alkylsulfonyl group,
(56) a phenylsulfonyl group,
(57) a phenylsulfonyl-$C_{1-4}$ alkyl group,
(58) an amino group,
(59) an aminosulfonyl group,
(60) a mono- or di-$C_{1-4}$ alkylaminosulfonyl group wherein said alkyl group is optionally substituted by halogen atom, hydroxy group or $C_{1-4}$ alkoxy group,
(61) a $C_{1-6}$ alkanoylamino wherein said $C_{1-6}$ alkanoyl is optionally substituted by halogen atom, hydroxy group or carboxyl group,
(62) a benzoylamino wherein said benzoyl is optionally substituted by halogen atom, hydroxy group, carboxyl group,
(63) a $C_{1-6}$ alkylsulfonylamino wherein said $C_{1-6}$ alkylsulfonyl is optionally substituted by halogen atom, hydroxy group or carboxyl group,
(64) a $C_{6-10}$ aiylsulfonylamino wherein said $C_{6-10}$ arylsulfonyl is optionally substituted by halogen atom, hydroxy group or carboxyl group,
(65) a benzyloxycarbonylamino,
(66) an optionally halogenated $C_{1-6}$ alkoxycarbonylamino,
(67) a carbamoylamino group,
(68) a mono- or di-$C_{1-4}$ alkylcarbamoylamino group,
(69) a mono- or di-$C_{1-4}$ alkylamino group wherein said alkyl group is optionally substituted by halogen atom, hydroxy group or $C_{1-4}$ alkoxy group and the like,
(70) phenylamino,
(71) benzylamino,
(72) a 4 to 6-membered cyclic amino group,
(73) a 4 to 6-membered cyclic amino-carbonyl group,
(74) a 4 to 6-membered cyclic amino-carbonyl-oxy group,
(75) a 4 to 6-membered cyclic amino-carbonyl-amino group,
(76) a 4 to 6-membered cyclic amino-sulfonyl group,
(77) a 4 to 6-membered cyclic amino-$C_{1-4}$ alkyl group,
(78) a formyl,
(79) a $C_{2-6}$ alkanoyl gruop opionally substituted by a substituent(s) selected from halogen atom, carboxyl group and $C_{1-4}$ alkoxy-carbonyl group,
(80) a benzoyl group,
(81) a benzoyl group optionally substituted by halogen atom,
(82) a 5 to 10-membered heterocyclic group wherein said heterocyclic group is optionally substituted by $C_{1-4}$ alkyl group,
(83) a 5 to 10-membered heterocycle-carbonyl group wherein said heterocyclic group is optionally substituted by $C_{1-4}$ alkyl group,
(84) a hydroxyimino group,
(85) a $C_{1-4}$ alkoxyirnino group,
(86) an aryl group, and
(87) an optionally halogenated linear or branched $C_{1-4}$ alkylenedioxy group;

the substituent group B consists of
(1) the substituent group A,
(2) a $C_{1-10}$ alkyl group,
(3) a $C_{2-10}$ alkenyl group,
(4) a phenyl-$C_{2-4}$ alkenyl group,
(5) a mono- or di-$C_{1-6}$ alkenyl-carbamoyl group,
(6) a $C_{6-14}$ aryl group,
(7) a $C_{7-20}$ aralkyl group, and
(8) a styryl group; and the substituent group C consists of
(1) a hydrocarbon group optionally substituted by substituent(s) selected from the substituent group B,
(2) $R^A CO$ wherein wherein $R^A$ is as defined above,
(3) $R^A SO_2$ wherein $R^A$ is as defined above,
(4) $R^A SO$ wherein $R^A$ is as defined above, (5) $R^A OPO(OR^B)$ wherein each symbol is as defined above,
(6) an alkoxycarbonyl optionally substituted by substituent(s) selected from the substituent group A,
(7) a carbamoyl optionally N-mono- or N,N-di-substituted by substituent(s) selected from the group consisting of
    a hydrocarbon group optionally substituted by substituent(s) selected from the substituent group B,
    ii) $R^A CO$ wherein wherein $R^A$ is as defined above,
    iii) $R^A SO_2$ wherein $R^A$ is as defined above,
    iv) $R^A SO$ wherein $R^A$ is as defined above,
    v) $R^A OPO(OR^B)$ wherein each symbol is as defined above,
    vi) an alkoxycarbonyl optionally substituted by substituent(s) selected from the substituent group A,
    vii) a carbamoyl optionally N-mono- or N,N-di-substituted by 1 or 2 substituent(s) selected from the group consisting of a lower($C_{1-6}$)alkyl group and phenyl group,
    viii) a 3 to 8-membered cyclic aminocarbonyl,
    ix) a heterocyclic group optionally substituted by substituent(s) selected from the substituent group B,
    x) an amino opionally N-mono- or N,N-disubstitued by substituent(s) selected from the substituent group C,
    xi) a 3 to 8-membered cyclic amino group, and
    xii) a hydroxy group optionally substituted by a substituent selected from the substituent group C,
(8) a 3 to 8-membered cyclic aminocarbonyl, and
(9) a heterocyclic group optionally substituted by substituent(s) selected from the substituent group B.

\* \* \* \* \*